(12) United States Patent
Walker et al.

(10) Patent No.: US 8,993,727 B2
(45) Date of Patent: Mar. 31, 2015

(54) CARRIER IMMUNOGLOBULINS AND USES THEREOF

(75) Inventors: Kenneth W. Walker, Newbury Park, CA (US); Frederick W. Jacobsen, Newbury Park, CA (US); Taruna Arora, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 131 days.

(21) Appl. No.: 13/825,547

(22) PCT Filed: Sep. 22, 2011

(86) PCT No.: PCT/US2011/052841
§ 371 (c)(1),
(2), (4) Date: Mar. 21, 2013

(87) PCT Pub. No.: WO2012/040518
PCT Pub. Date: Mar. 29, 2012

(65) Prior Publication Data
US 2013/0189283 A1 Jul. 25, 2013

Related U.S. Application Data

(60) Provisional application No. 61/385,460, filed on Sep. 22, 2010.

(51) Int. Cl.
*C07K 16/18* (2006.01)
*C07K 16/28* (2006.01)
*A61K 39/395* (2006.01)
*A61K 39/00* (2006.01)

(52) U.S. Cl.
CPC ............ *C07K 16/2878* (2013.01); *C07K 16/18* (2013.01); *C07K 16/2866* (2013.01); *C07K 16/2875* (2013.01); *A61K 2039/6056* (2013.01); *C07K 2317/565* (2013.01); *C07K 2317/92* (2013.01); *C07K 2319/30* (2013.01)
USPC .............. 530/387.3; 530/387.9; 530/388.22; 530/389.1; 530/391.7; 424/143.1; 424/178.1; 424/192.1

(58) Field of Classification Search
None
See application file for complete search history.

(56) References Cited

U.S. PATENT DOCUMENTS

| | | | |
|---|---|---|---|
| 6,072,037 A | 6/2000 | Yao et al. |
| 6,932,969 B1 | 8/2005 | Bourel et al. |
| 7,067,131 B2 | 6/2006 | Gudas et al. |
| 7,326,414 B2 | 2/2008 | Bedian et al. |
| 7,521,048 B2 | 4/2009 | Gliniak et al. |
| 2006/0140948 A1 | 6/2006 | Foltz et al. |
| 2006/0246071 A1 | 11/2006 | Green et al. |
| 2007/0148180 A1 | 6/2007 | Fischer et al. |
| 2007/0166308 A1 | 7/2007 | Pullen et al. |
| 2007/0269369 A1 | 11/2007 | Gegg et al. |
| 2008/0152587 A1 | 6/2008 | Zhou et al. |
| 2008/0268462 A1 | 10/2008 | Kosmeder et al. |
| 2009/0155275 A1 | 6/2009 | Wu et al. |

FOREIGN PATENT DOCUMENTS

| | | |
|---|---|---|
| WO | WO 00/09730 | 2/2000 |
| WO | WO 01/62931 A2 | 8/2001 |
| WO | WO 03/080672 | 10/2003 |
| WO | WO 2004/096271 A1 | 11/2004 |
| WO | WO 2005/037235 A2 | 4/2005 |
| WO | WO 2005/040229 A2 | 5/2005 |
| WO | WO 2006/055689 A2 | 5/2006 |
| WO | WO 2006/127040 A2 | 11/2006 |
| WO | WO 2007/027713 A2 | 3/2007 |
| WO | WO 2007/045463 A1 | 4/2007 |
| WO | WO 2008/054603 C2 | 5/2008 |
| WO | WO 2008/088422 A2 | 7/2008 |
| WO | WO 2009/086411 A2 | 7/2009 |
| WO | WO 2010/054007 A1 | 5/2010 |
| WO | WO 2010/088522 A2 | 8/2010 |
| WO | WO 2010/108153 A2 | 9/2010 |
| WO | WO 2010/108153 A3 | 9/2010 |
| WO | WO 2010/108154 A2 | 9/2010 |
| WO | WO 2010/108154 A3 | 9/2010 |
| WO | WO 2011/094593 A2 | 8/2011 |
| WO | WO 2012/040518 A2 | 3/2012 |
| WO | WO 2012/040518 A3 | 3/2012 |

OTHER PUBLICATIONS

Davies, et al., "Structural Basis of Antibody Function", *Ann. Rev. Immunol*, 1: 87-117 (1983).

Dougan, et al., "Effects of substitutions in binding surface of an antibody on antigen affinity", *Protein Engineering*, 11(1): 65-74 (1998).

Fagerstam, et al., "Detection of Antigen-Antibody Interactions by Surface Plasmon Resonance, Application to Epitope Mapping", *J of Molecular Recognition*, 3(5/6): 208-214 (1990).

He, et al., "Effects of mutation at the D-$J_H$ junction on affinity, specificity, and idiotypy of anti-progesterone antibody DB3", *Protein Science* 15: 2141-2148 (2006).

Igawa, et al., "Reduced elimination of IgG antibodies by engineering the variable region", *Protein Engineering, Design & Selection*, 23(5): 385-392 (2010).

Parhami-Seren, et al., "Structural Analysis of Mutants of High-Affinity and Low-Affinity p-Azophenylarsonal-Specific Antibodies Generalted by Alanine Scanning of Heavy Chain Complementarity-Determining Region 2", *J of Immunol*, 167: 5129-5135 (2001).

(Continued)

*Primary Examiner* — Phuong Huynh
(74) *Attorney, Agent, or Firm* — Thomas J. Wrona

(57) ABSTRACT

Disclosed is an isolated immunoglobulin. Also disclosed are pharmaceutical compositions and medicaments comprising the immunoglobulin, isolated nucleic acid encoding it, vectors, host cells, useful in methods of making it. In some embodiments the immunoglobulin comprises one to twenty-four pharmacologically active chemical moieties conjugated thereto, such as a pharmacologically active polypeptide.

16 Claims, 56 Drawing Sheets

(56) References Cited

OTHER PUBLICATIONS

Probes Product Information Sheet, entitled "Anti-Dinitrophenyl-KLH Antibodies", downloaded from the interne on Sep. 8, 2013 from the URL: http://probes.invitrogen.com/media/pis/mp06423.pdf>, 2 pgs.

Yang, et al., "Preparation and Identification of anti-2, 4-dinitrophenyl monoclonal antibodies", *J of Immunol Methods*, 313: 20-28 (2006).

Zoon, FDA Document, "Points to Consider in the Manufacture and Testing of Monoclonal Antibody Products for Human Use", *U.S. Department of Health & Human Services, Food and Drug Administration, Center for Biologics Evaluation and Research*, 50 pgs, (1997).

Weiner et al., "Tunable antibodies," Nat Biotechnol (2005) 23(5):556-557.

Schildbach et al., "Modulation of antibody affinity by a non-contact residue," Protein Sci (1993) 2(2):206-214.

Schildbach et al., "Contribution of a single heavy chain residue to specificity of anti-digoxin monoclonal antibody," Protein Sci (1994) 3(5):737-749.

Park et al., "A human scFv antibody against TRAIL Receptor 2 induces autophagic cell death in both TRAIL-sensitive and TRAIL-resistant cancer cells," Cancer Res (2007) 67(15):7327-7334.

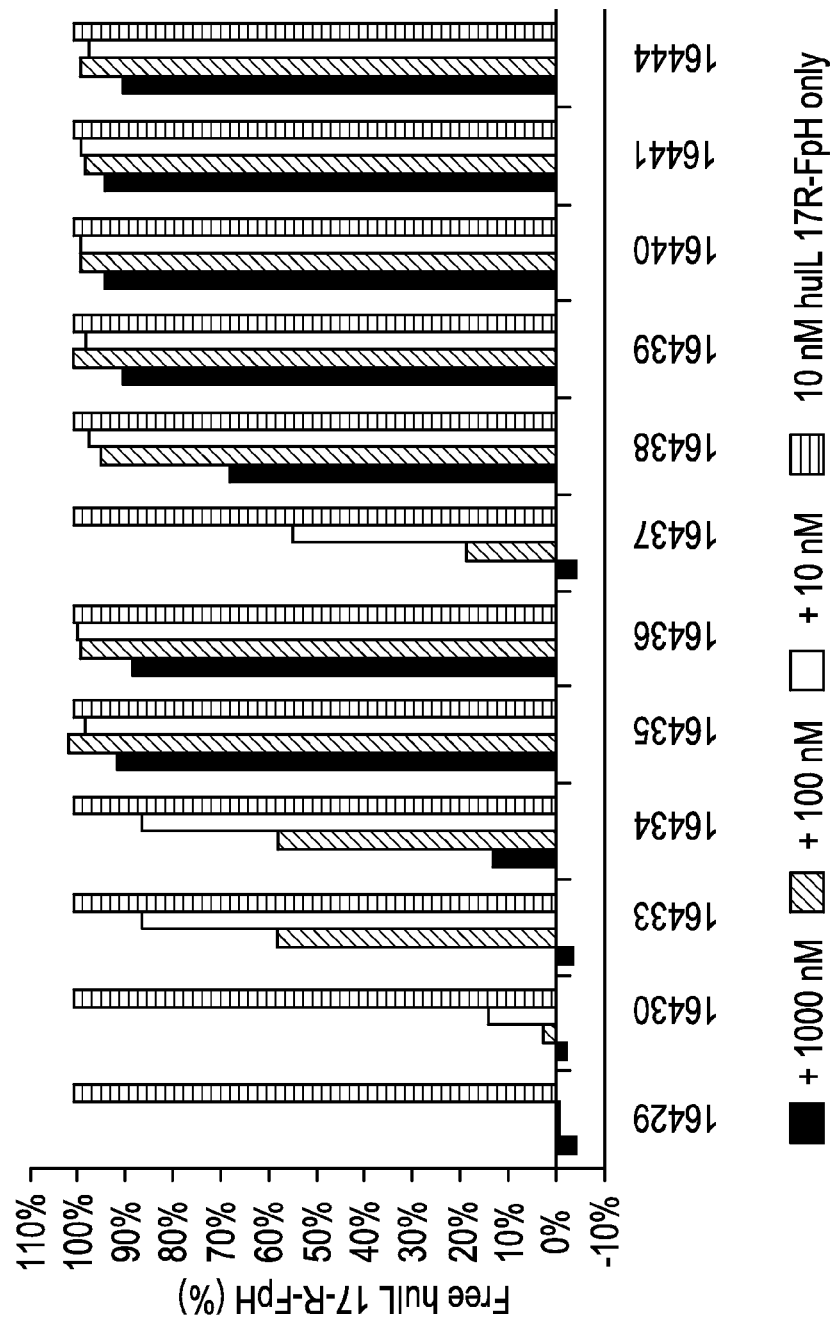

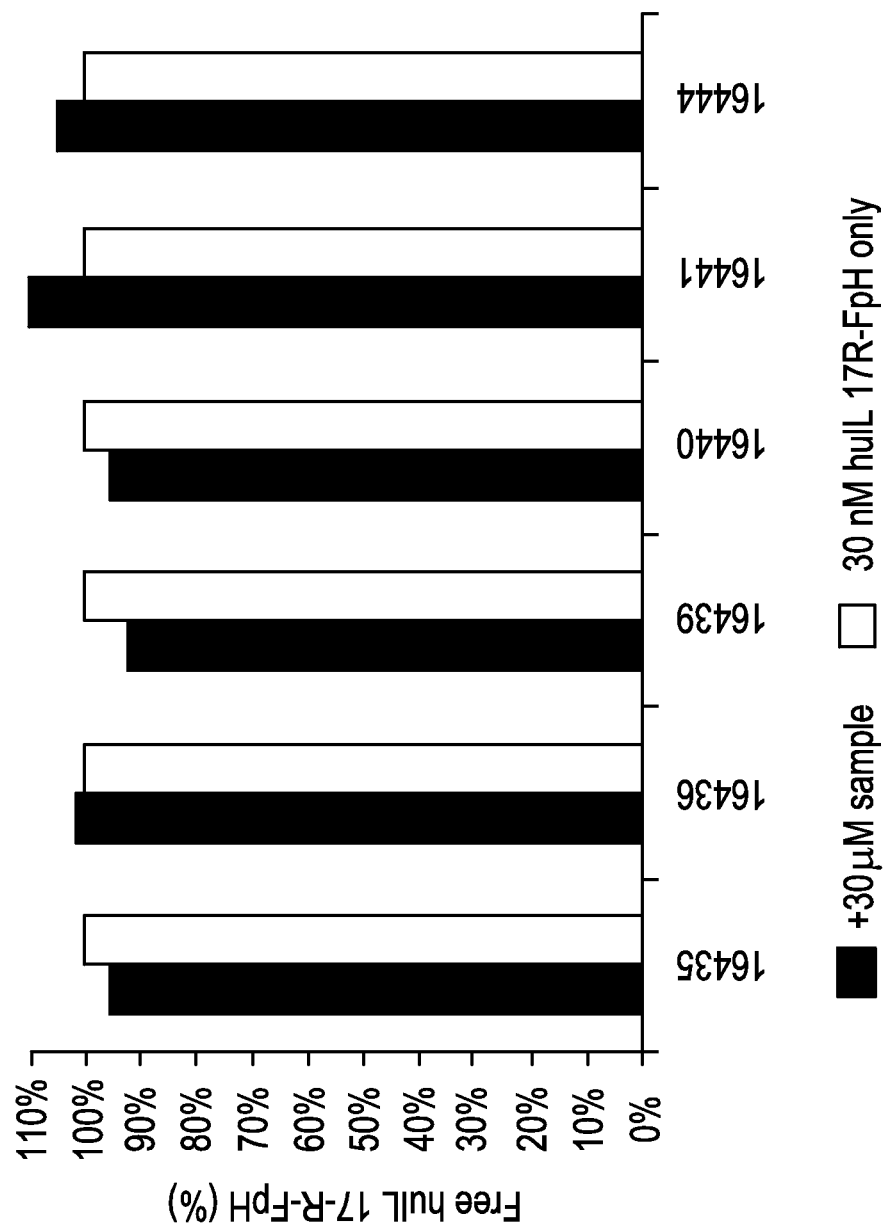

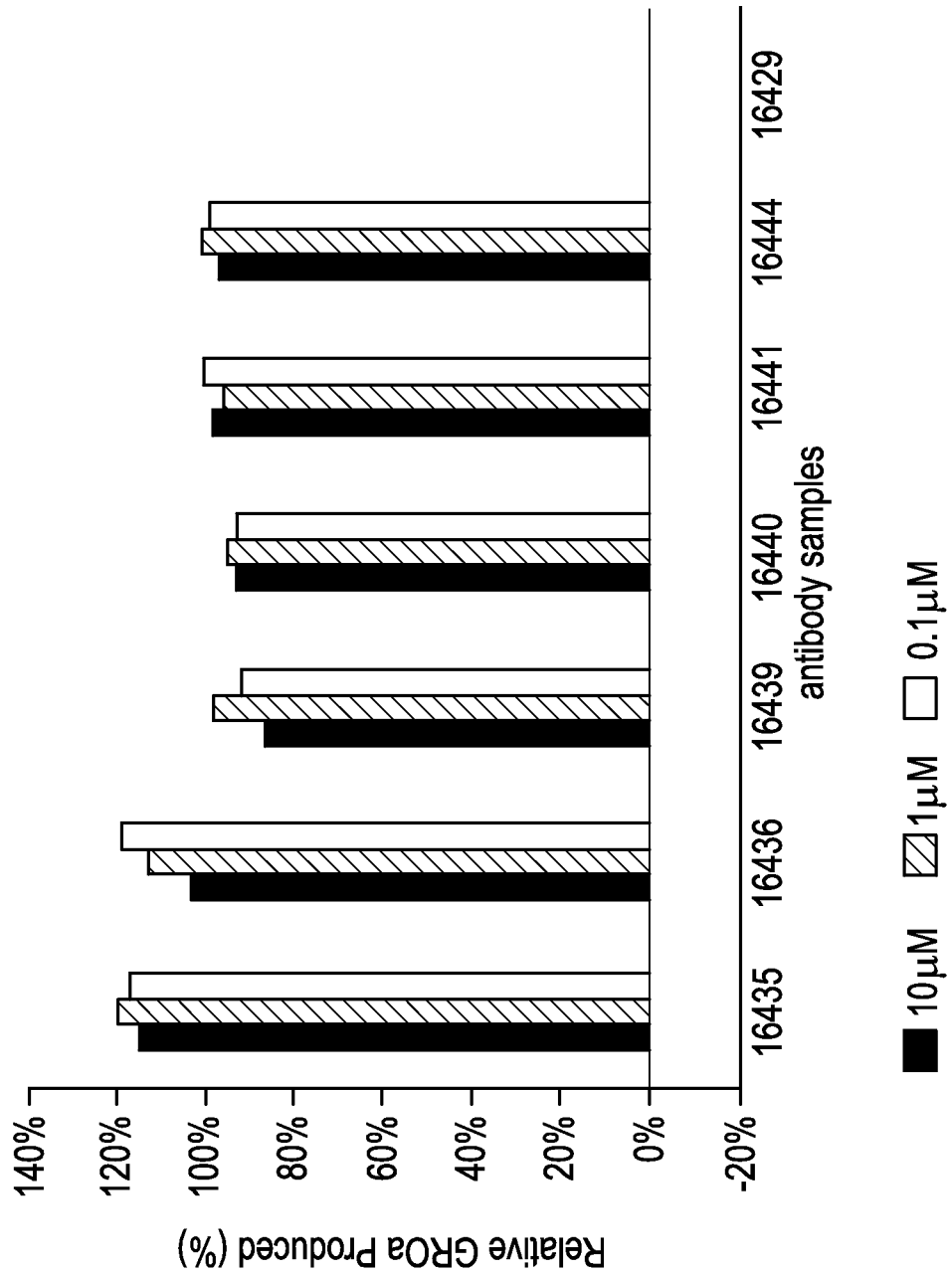

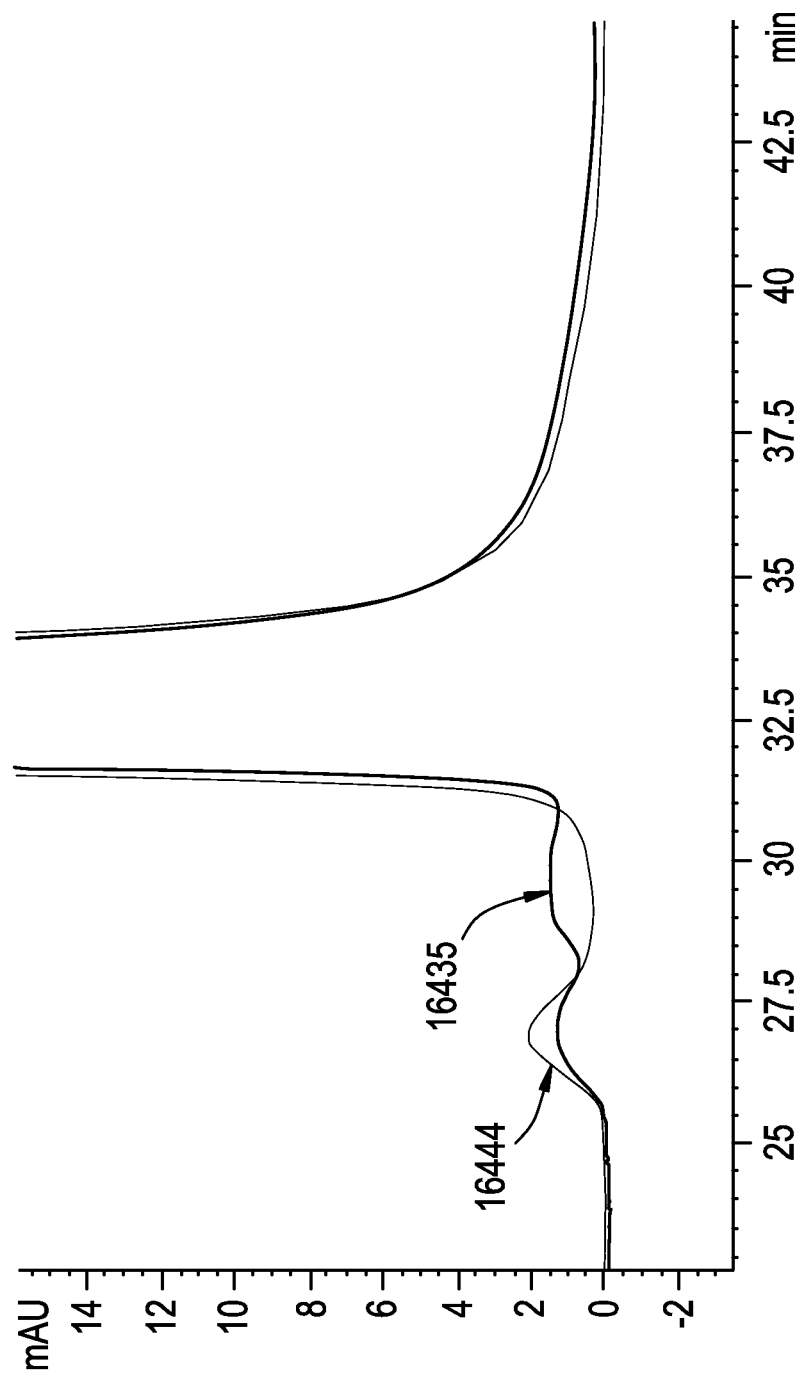

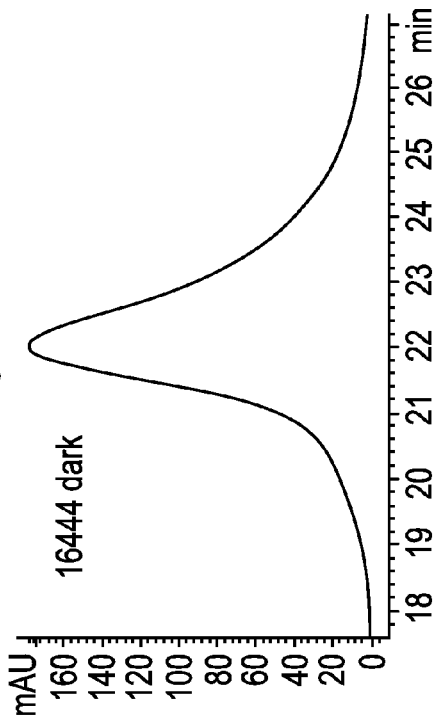
FIG. 14A
FIG. 14B
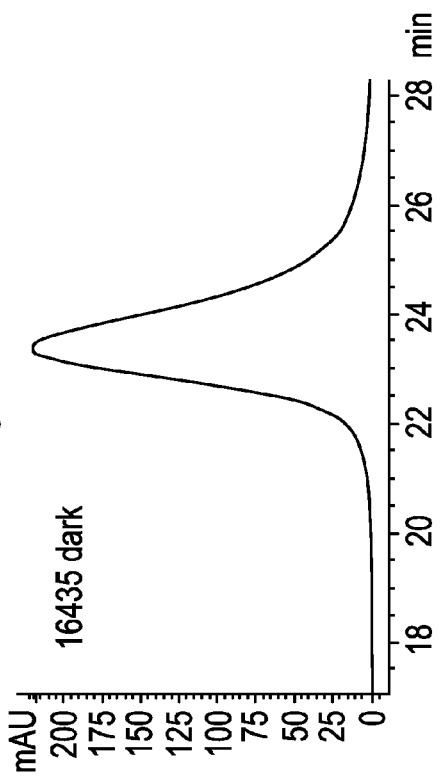
FIG. 14C
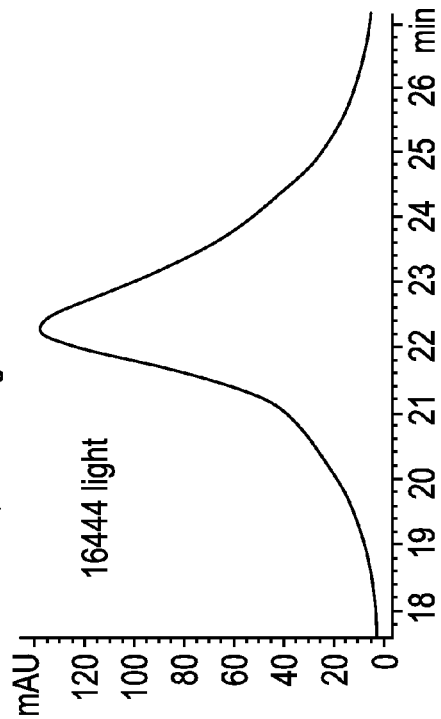
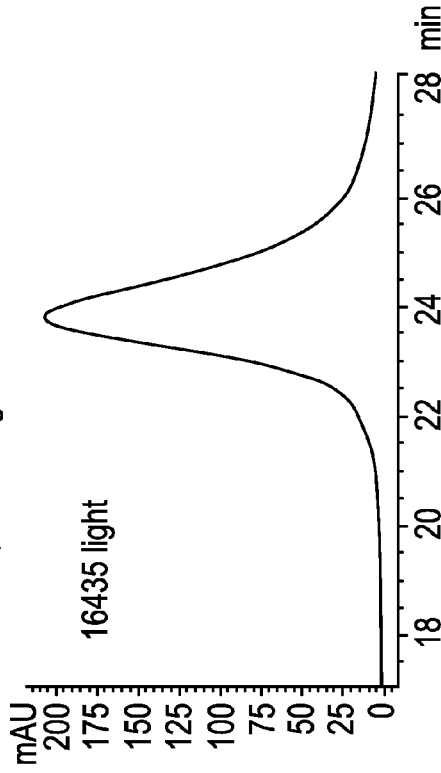
FIG. 14D

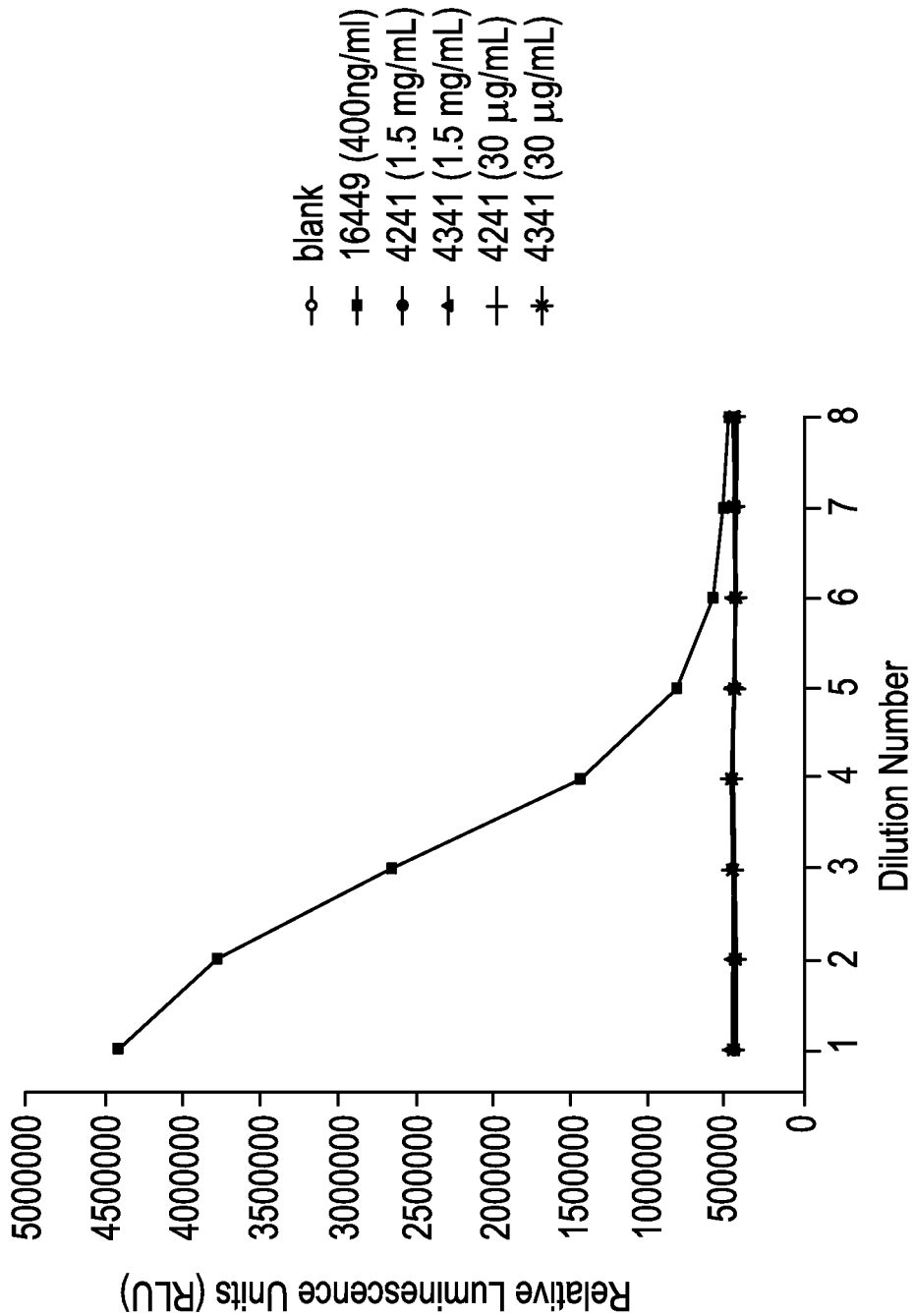

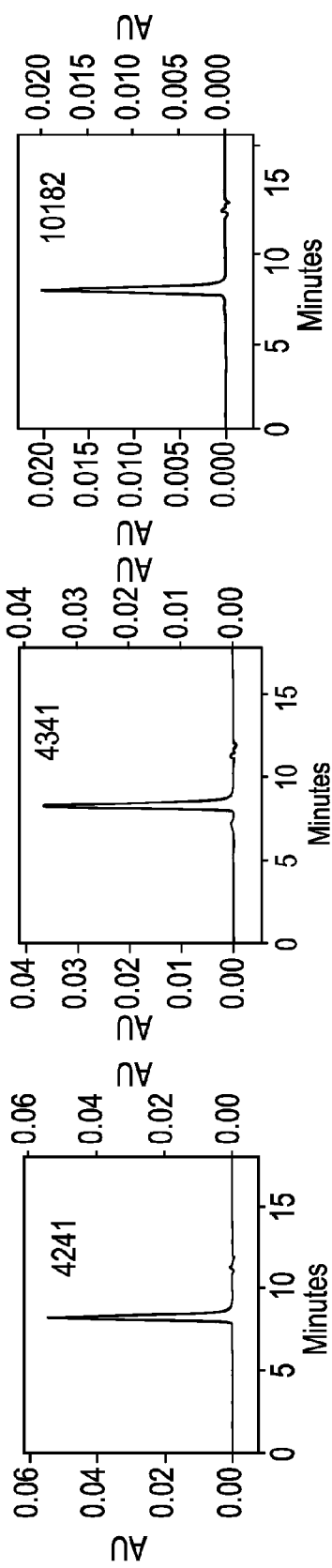
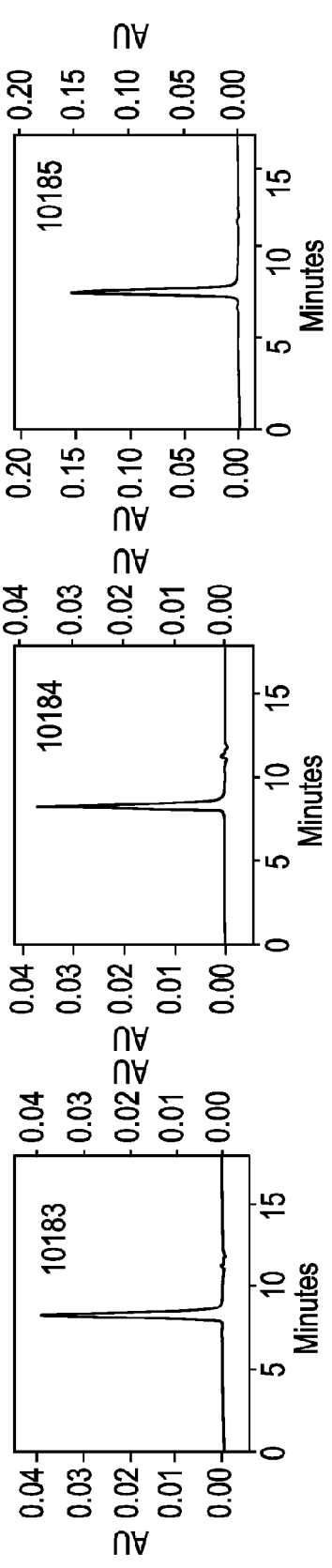

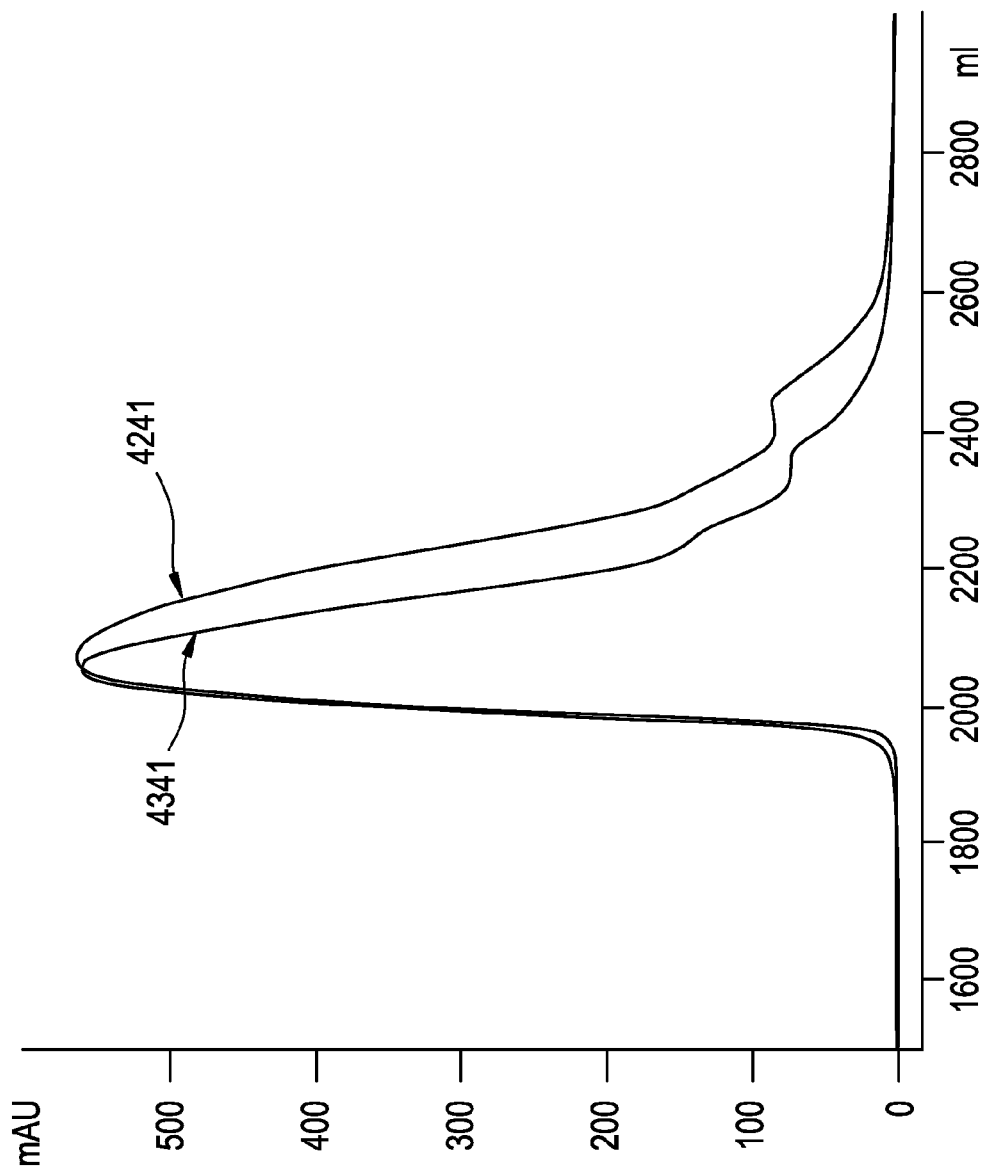

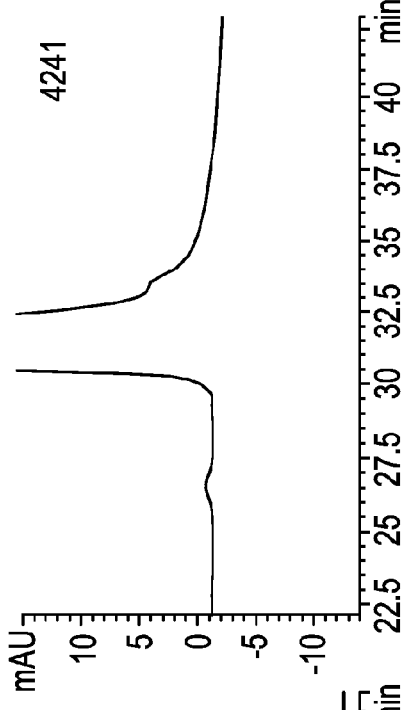
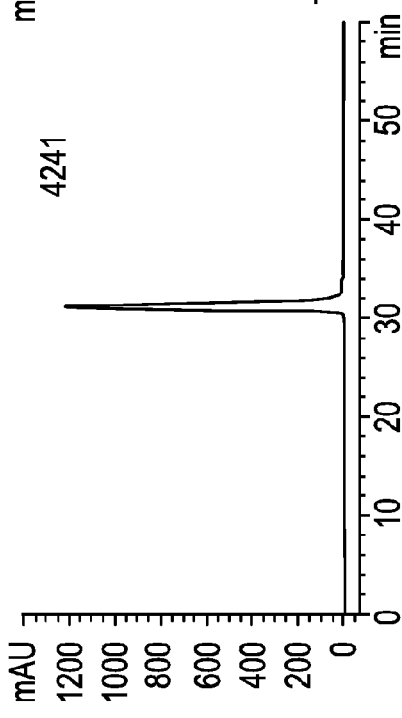
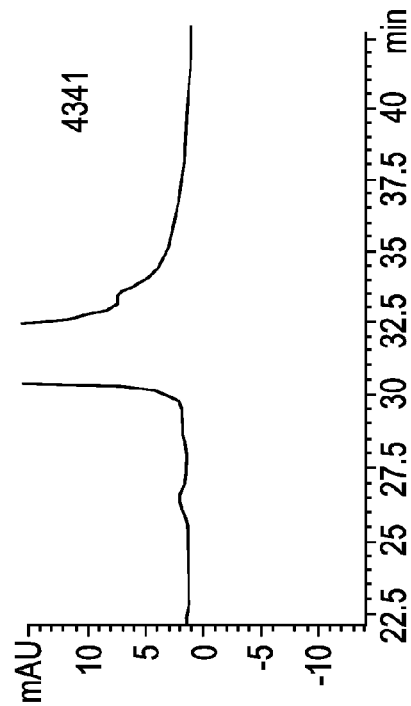
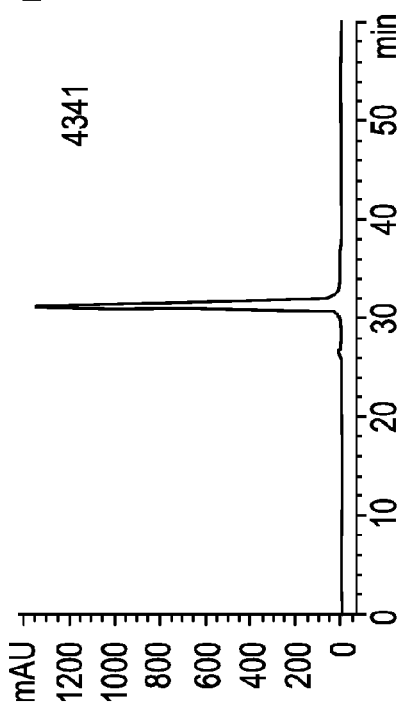
FIG. 27A
FIG. 27B

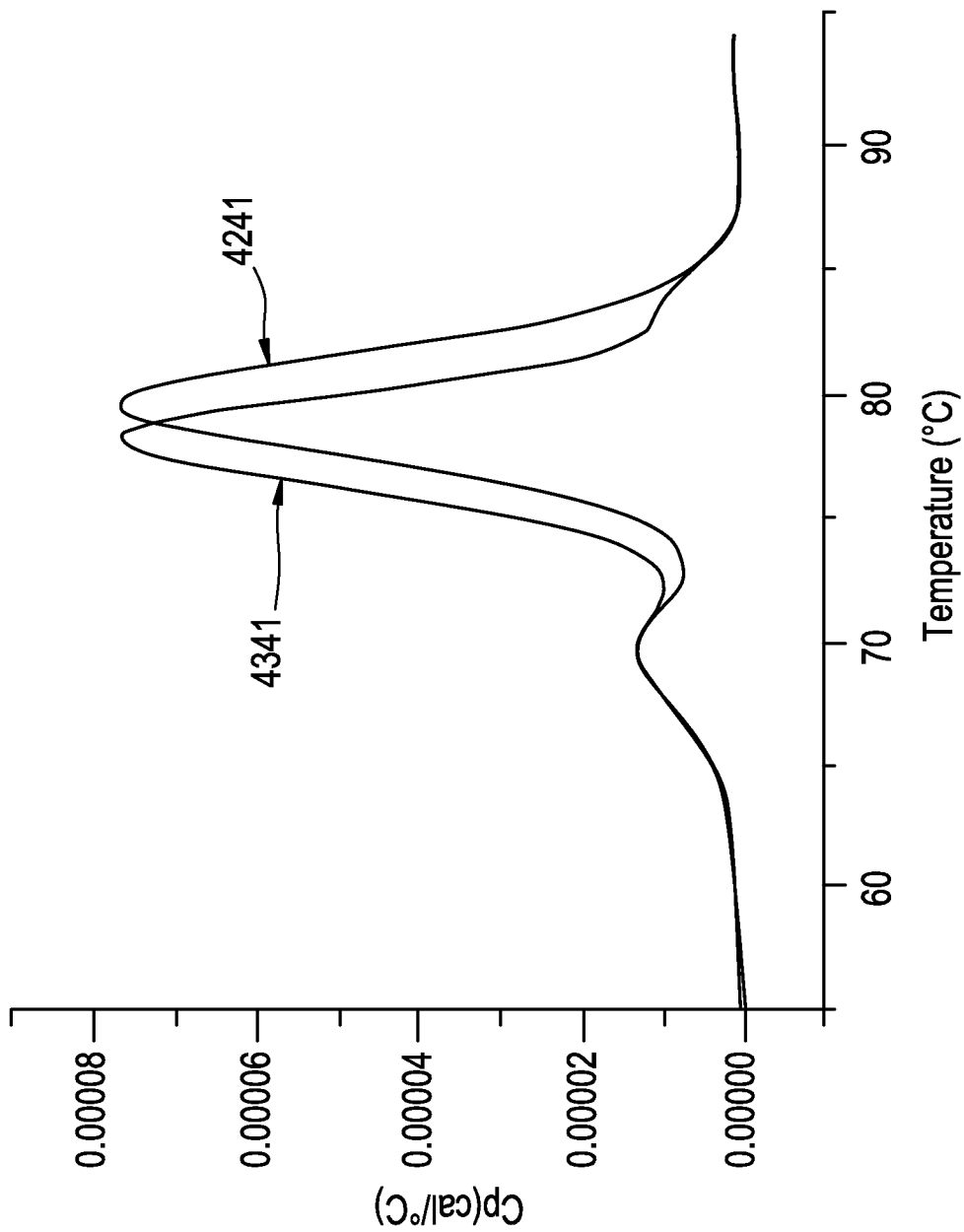

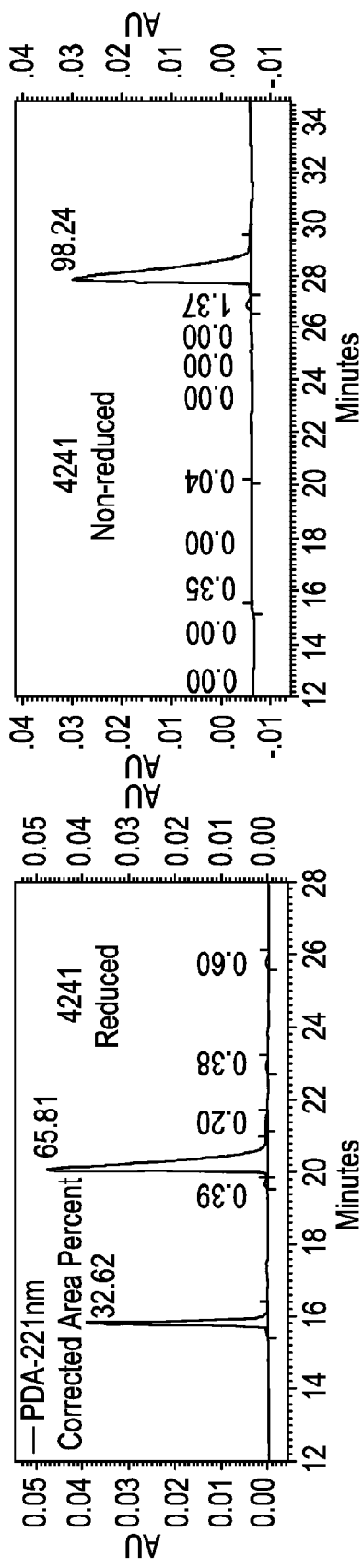

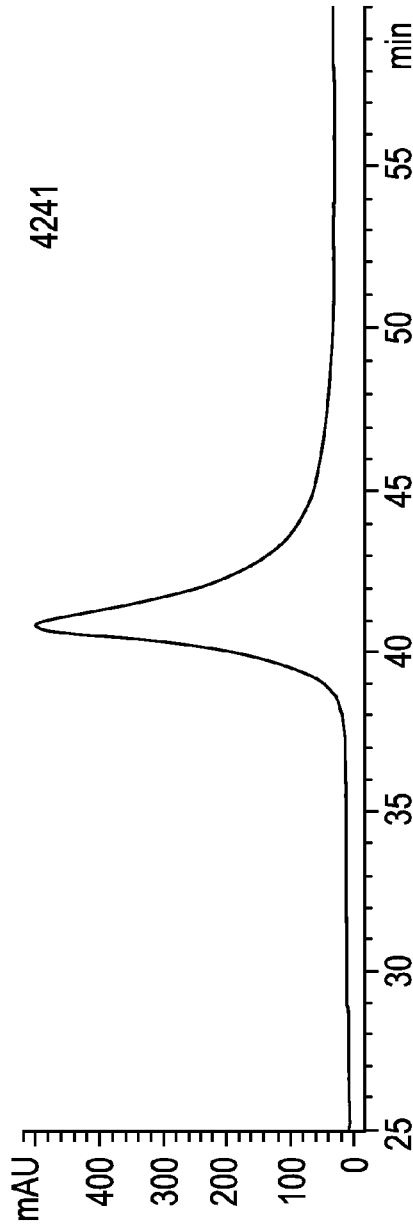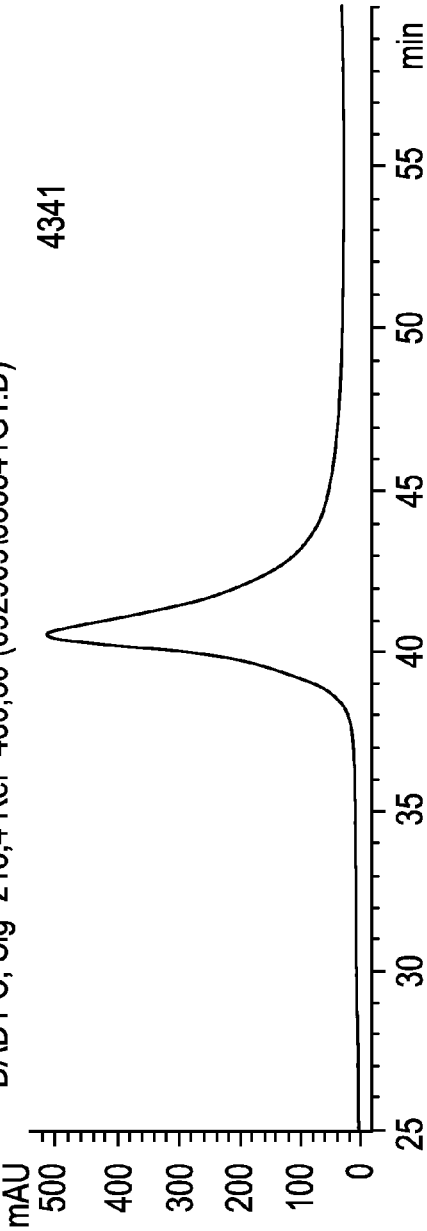
FIG. 30

FIG. 31A
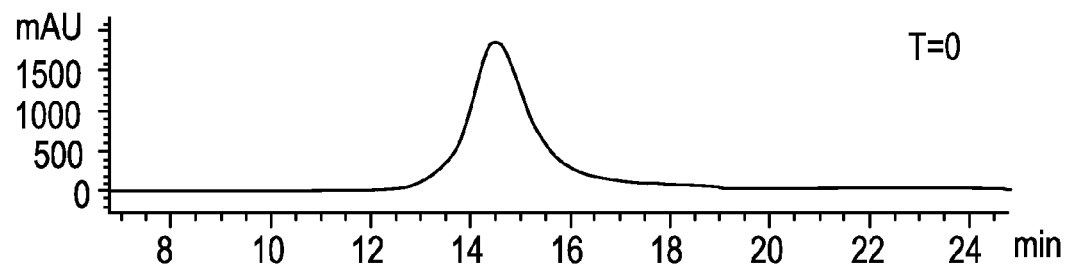
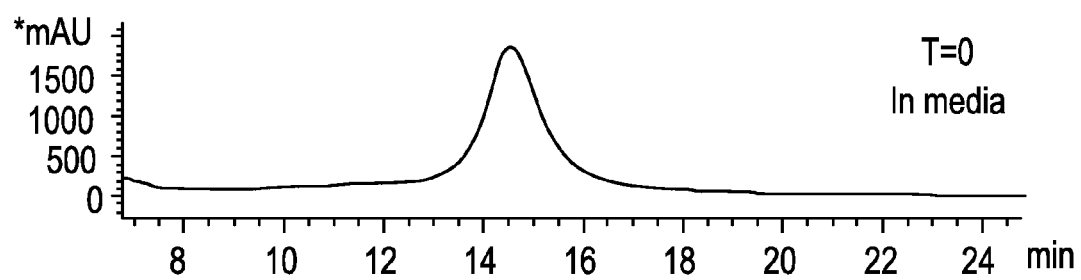
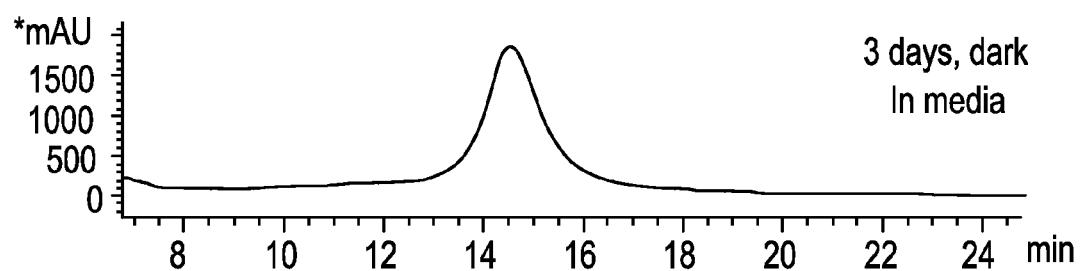
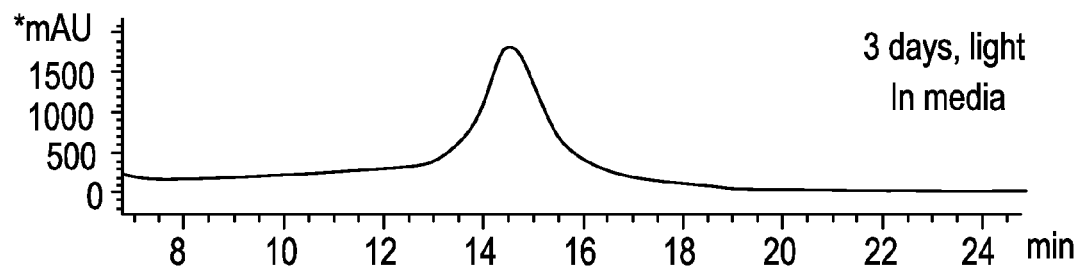

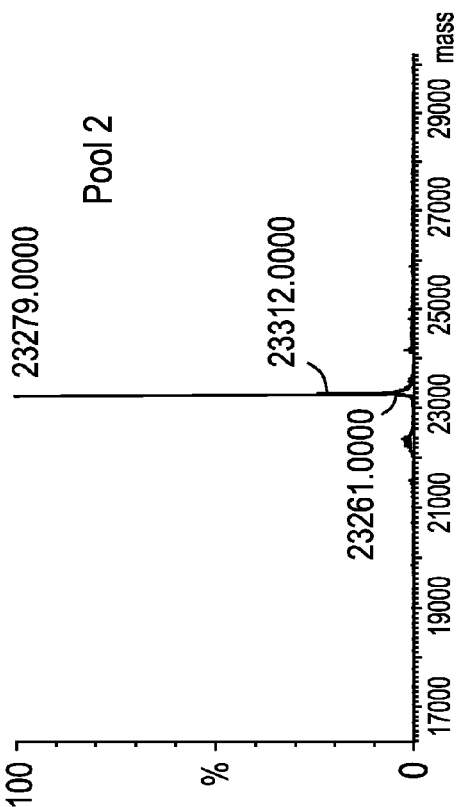
FIG. 37A — Pool 1
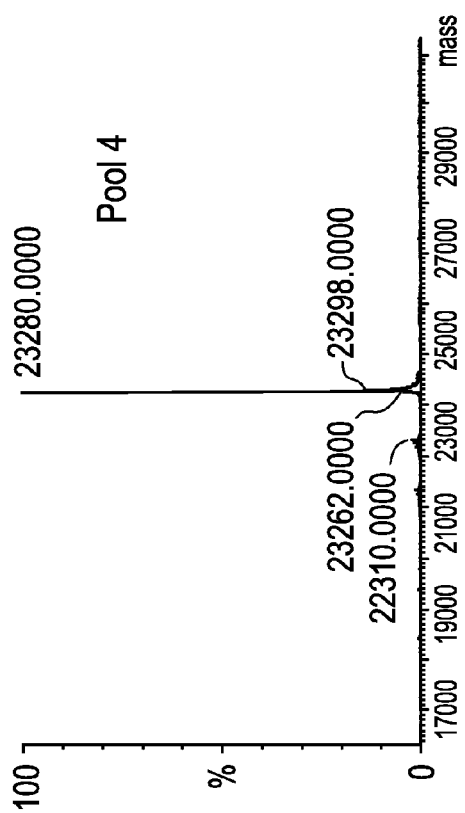
FIG. 37B — Pool 2
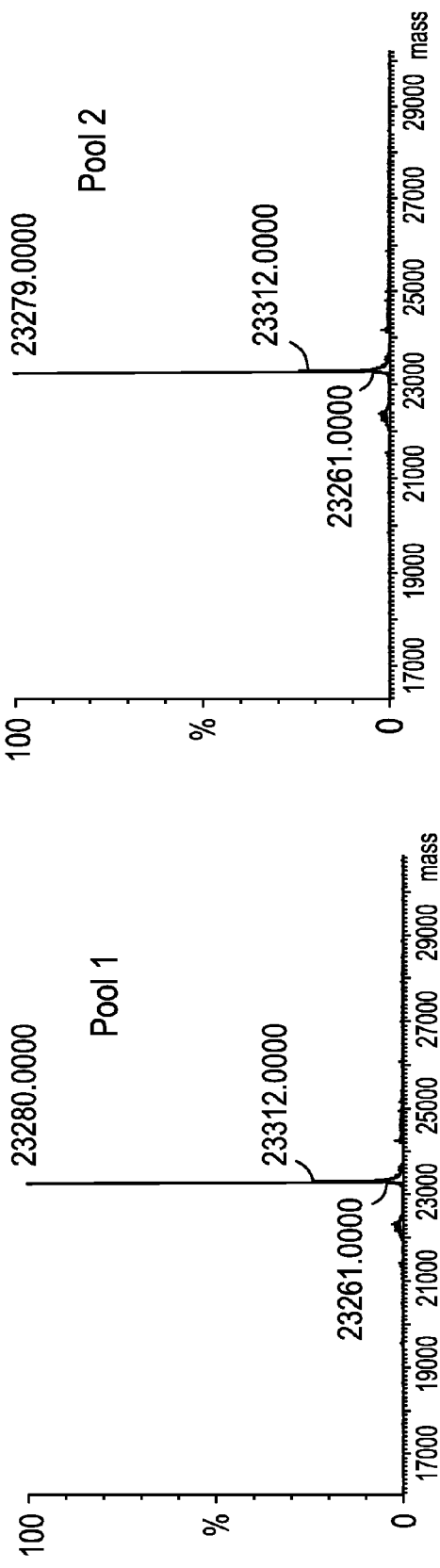
FIG. 37C — Pool 3
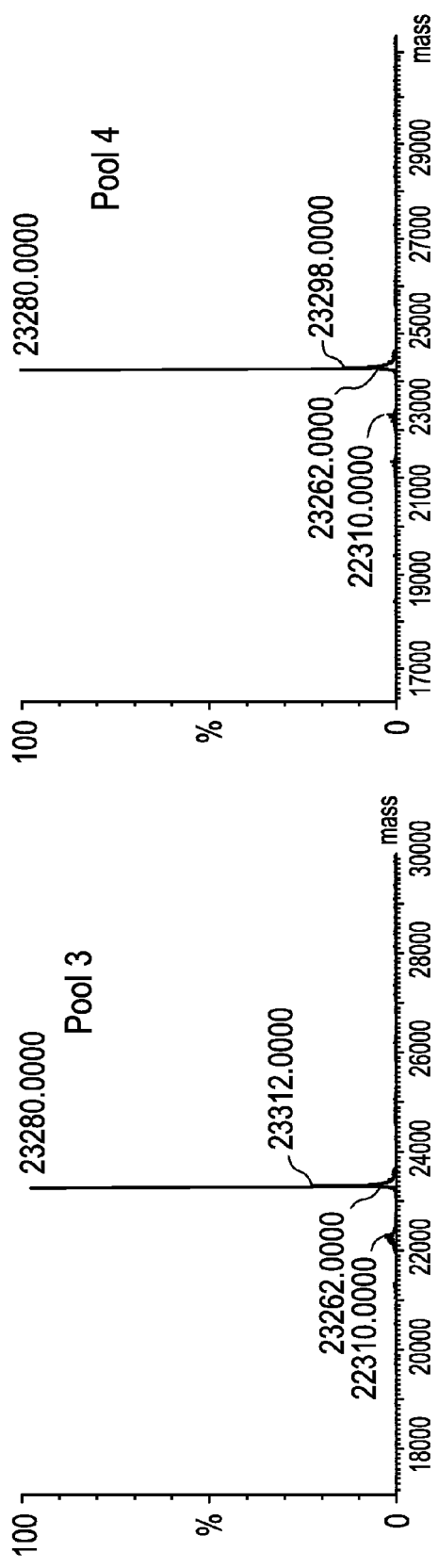
FIG. 37D — Pool 4

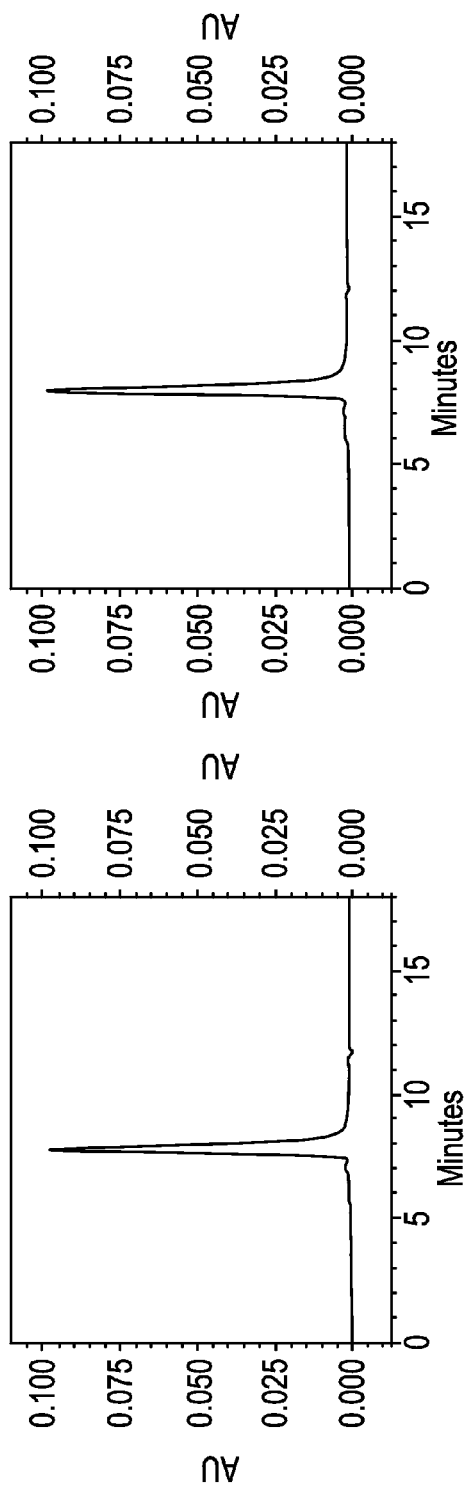
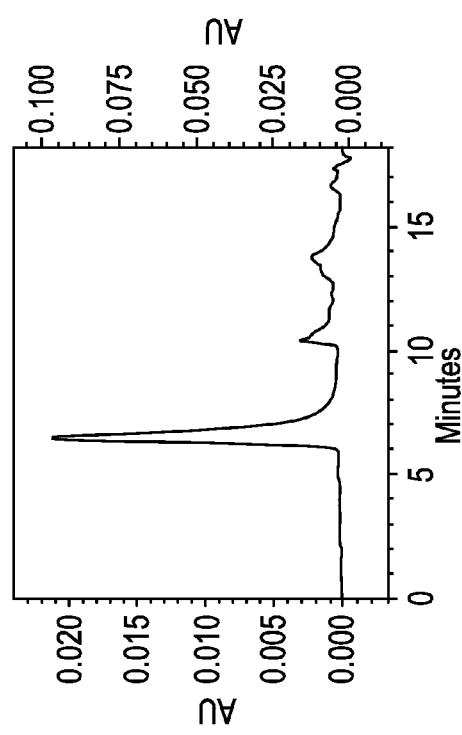
FIG. 40A
FIG. 40B
FIG. 40C

+ESI Scan (7.398-8.398 min, 61 Scans) Frag=225.0V

+ESI Scan (8.583-9.767 min, 72 Scans) Frag=225.0V

+ESI Scan (8.909-11.443 min, 153 Scans) Frag=225.0V

SEQUENCE LISTING

```
<160> NUMBER OF SEQ ID NOS: 392

<210> SEQ ID NO 1
<211> LENGTH: 245
<212> TYPE: PRT
<213> ORGANISM: Homo sapiens
<220> FEATURE:
<221> NAME/KEY: MISC_FEATURE
<223> OTHER INFORMATION: Immunoglobulin Fc domain of human IgG2

<400> SEQUENCE: 1

Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
```

```
              115                 120                 125
Pro Ile Glu Lys Thr Ile Ser Lys Thr Lys Gly Gln Pro Arg Glu Pro
        130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
            165                 170                 175

Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
        210                 215                 220

Val Met His Glu Ala Leu His Asn His Tyr Thr Gln Lys Ser Leu Ser
225                 230                 235                 240

Leu Ser Pro Gly Lys
            245

<210> SEQ ID NO 2
<211> LENGTH: 19
<212> TYPE: PRT
<213> ORGANISM: ARTIFICIAL SEQUENCE
<220> FEATURE:
<223> OTHER INFORMATION: modifed VH21 signal peptide

<400> SEQUENCE: 2

Met Glu Trp Ser Trp Val Phe Leu Phe Phe Leu Ser Val Thr Thr Gly
1               5                   10                  15

Val His Ser

<210> SEQ ID NO 3
<211> LENGTH: 30
<212> TYPE: DNA
<213> ORGANISM: ARTIFICIAL SEQUENCE
<220> FEATURE:
<223> OTHER INFORMATION: Primer sequence

<400> SEQUENCE: 3
catgaattcc ccaccatgga atggagctgg                                         30

<210> SEQ ID NO 4
<211> LENGTH: 38
<212> TYPE: DNA
<213> ORGANISM: ARTIFICIAL SEQUENCE
<220> FEATURE:
<223> OTHER INFORMATION: Primer sequence

<400> SEQUENCE: 4
cacggtgggc actcgacttt gcgctcggag tggacacc                                38

<210> SEQ ID NO 5
<211> LENGTH: 132
<212> TYPE: DNA
<213> ORGANISM: ARTIFICIAL SEQUENCE
<220> FEATURE:
<223> OTHER INFORMATION: ShK[2-35] with N-terminal linker extension

<400> SEQUENCE: 5
ggaggaggag gatccggagg aggaggaagc agctgcatcg acaccatccc caagagccgc        60
tgcaccgcct tccagtgcaa gcacagcatg aagtaccgcc tgagcttctg ccgcaagacc       120
tgcggcacct gc                                                          132
```

<210> SEQ ID NO 6
<211> LENGTH: 44
<212> TYPE: PRT
<213> ORGANISM: ARTIFICIAL SEQUENCE
<220> FEATURE:
<223> OTHER INFORMATION: ShK[2-35] with N-terminal linker extension

<400> SEQUENCE: 6

Gly Gly Gly Gly Ser Gly Gly Gly Ser Ser Cys Ile Asp Thr Ile
1               5                   10                  15

Pro Lys Ser Arg Cys Thr Ala Phe Gln Cys Lys His Ser Met Lys Tyr
            20                  25                  30

Arg Leu Ser Phe Cys Arg Lys Thr Cys Gly Thr Cys
        35                  40

<210> SEQ ID NO 7
<211> LENGTH: 37
<212> TYPE: DNA
<213> ORGANISM: ARTIFICIAL SEQUENCE
<220> FEATURE:
<223> OTHER INFORMATION: Primer sequence

<400> SEQUENCE: 7
gtccactccg agcgcaaagt cgagtgccca ccgtgcc                              37

<210> SEQ ID NO 8
<211> LENGTH: 30
<212> TYPE: DNA
<213> ORGANISM: ARTIFICIAL SEQUENCE
<220> FEATURE:
<223> OTHER INFORMATION: Primer sequence

<400> SEQUENCE: 8
tcctcctcct ttacccggag acagggagag                                      30

<210> SEQ ID NO 9
<211> LENGTH: 29
<212> TYPE: DNA
<213> ORGANISM: ARTIFICIAL SEQUENCE
<220> FEATURE:
<223> OTHER INFORMATION: Primer sequence

<400> SEQUENCE: 9
gctgcaccgc cttcaagtgc aagcacagc                                       29

<210> SEQ ID NO 10
<211> LENGTH: 29
<212> TYPE: DNA
<213> ORGANISM: ARTIFICIAL SEQUENCE
<220> FEATURE:
<223> OTHER INFORMATION: Primer sequence

<400> SEQUENCE: 10
gctgtgcttg cacttgaagg cggtgcagc                                       29

<210> SEQ ID NO 11
<211> LENGTH: 132
<212> TYPE: DNA
<213> ORGANISM: ARTIFICIAL SEQUENCE
<220> FEATURE:
<223> OTHER INFORMATION: ShK[2-35, K16] with N-terminal linker extension

<400> SEQUENCE: 11
ggaggaggag gatccggagg aggaggaagc agctgcatcg acaccatccc caagagccgc     60

```
tgcaccgcct tcaagtgcaa gcacagcatg aagtaccgcc tgagcttctg ccgcaagacc    120
tgcggcacct gc                                                        132
```

```
<210> SEQ ID NO 12
<211> LENGTH: 44
<212> TYPE: PRT
<213> ORGANISM: ARTIFICIAL SEQUENCE
<220> FEATURE:
<223> OTHER INFORMATION: ShK[2-35, Q16K] with N-terminal linker
      extension

<400> SEQUENCE: 12
```

Gly Gly Gly Gly Ser Gly Gly Gly Ser Ser Cys Ile Asp Thr Ile
1               5                   10                  15

Pro Lys Ser Arg Cys Thr Ala Phe Lys Cys Lys His Ser Met Lys Tyr
            20                  25                  30

Arg Leu Ser Phe Cys Arg Lys Thr Cys Gly Thr Cys
        35                  40

```
<210> SEQ ID NO 13
<211> LENGTH: 28
<212> TYPE: DNA
<213> ORGANISM: ARTIFICIAL SEQUENCE
<220> FEATURE:
<223> OTHER INFORMATION: Primer sequence

<400> SEQUENCE: 13
ccgggtaaag gaggaggagg atccggag                                       28

<210> SEQ ID NO 14
<211> LENGTH: 24
<212> TYPE: DNA
<213> ORGANISM: ARTIFICIAL SEQUENCE
<220> FEATURE:
<223> OTHER INFORMATION: Primer sequence

<400> SEQUENCE: 14
catgcggccg ctcattagca ggtg                                           24

<210> SEQ ID NO 15
<211> LENGTH: 648
<212> TYPE: DNA
<213> ORGANISM: Homo sapiens
<220> FEATURE:
<221> NAME/KEY: misc_feature
<223> OTHER INFORMATION: Coding sequence of fragment of immunoglobulin
      Fc domain of human IgG2
<220> FEATURE:
<221> NAME/KEY: CDS
<222> LOCATION: (1)..(648)

<400> SEQUENCE: 15
``` gca cca cct gtg gca gga ccg tca gtc ttc ctc ttc ccc cca aaa ccc     48
Ala Pro Pro Val Ala Gly Pro Ser Val Phe Leu Phe Pro Pro Lys Pro
1               5                   10                  15 aag gac acc ctc atg atc tcc cgg acc cct gag gtc acg tgc gtg gtg    96
Lys Asp Thr Leu Met Ile Ser Arg Thr Pro Glu Val Thr Cys Val Val
            20                  25                  30 gtg gac gtg agc cac gaa gac ccc gag gtc cag ttc aac tgg tac gtg    144
Val Asp Val Ser His Glu Asp Pro Glu Val Gln Phe Asn Trp Tyr Val
        35                  40                  45 gac ggc gtg gag gtg cat aat gcc aag aca aag cca cgg gag gag cag    192
Asp Gly Val Glu Val His Asn Ala Lys Thr Lys Pro Arg Glu Glu Gln
    50                  55                  60 ttc aac agc acg ttc cgt gtg gtc agc gtc ctc acc gtt gtg cac cag    240

```
                gac tgg ctg aac ggc aag gag tac aag tgc aag gtc tcc aac aaa ggc    288
                Asp Trp Leu Asn Gly Lys Glu Tyr Lys Cys Lys Val Ser Asn Lys Gly
                                85                  90                  95 ctc cca gcc ccc atc gag aaa acc atc tcc aaa acc aaa ggg cag ccc    336
                Leu Pro Ala Pro Ile Glu Lys Thr Ile Ser Lys Thr Lys Gly Gln Pro
                            100                 105                 110 cga gaa cca cag gtg tac acc ctg ccc cca tcc cgg gag gag atg acc    384
                Arg Glu Pro Gln Val Tyr Thr Leu Pro Pro Ser Arg Glu Glu Met Thr
                        115                 120                 125 aag aac cag gtc agc ctg acc tgc ctg gtc aaa ggc ttc tac ccc agc    432
                Lys Asn Gln Val Ser Leu Thr Cys Leu Val Lys Gly Phe Tyr Pro Ser
                    130                 135                 140 gac atc gcc gtg gag tgg gag agc aat ggg cag ccg gag aac aac tac    480
                Asp Ile Ala Val Glu Trp Glu Ser Asn Gly Gln Pro Glu Asn Asn Tyr
                145                 150                 155                 160 aag acc aca cct ccc atg ctg gac tcc gac ggc tcc ttc ttc ctc tac    528
                Lys Thr Thr Pro Pro Met Leu Asp Ser Asp Gly Ser Phe Phe Leu Tyr
                                165                 170                 175 agc aag ctc acc gtg gac aag agc agg tgg cag cag ggg aac gtc ttc    576
                Ser Lys Leu Thr Val Asp Lys Ser Arg Trp Gln Gln Gly Asn Val Phe
                            180                 185                 190 tca tgc tcc gtg atg cat gag gct ctg cac aac cac tac acg cag aag    624
                Ser Cys Ser Val Met His Glu Ala Leu His Asn His Tyr Thr Gln Lys
                        195                 200                 205 agc ctc tcc ctg tct ccg ggt aaa                                    648
                Ser Leu Ser Leu Ser Pro Gly Lys
                    210                 215

<210> SEQ ID NO 16
<211> LENGTH: 216
<212> TYPE: PRT
<213> ORGANISM: Homo sapiens

<400> SEQUENCE: 16

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175
```

```
Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 17
<211> LENGTH: 289
<212> TYPE: PRT
<213> ORGANISM: ARTIFICIAL SEQUENCE
<220> FEATURE:
<223> OTHER INFORMATION: VH21SP-IgG2-Fc-L10-ShK(2-35, Q16K) Fusion
      polypeptide

<400> SEQUENCE: 17

Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys Gly Gly Gly Gly Ser Gly Gly Gly Gly Ser Ser
                245                 250                 255

Cys Ile Asp Thr Ile Pro Lys Ser Arg Cys Thr Ala Phe Gln Cys Lys
            260                 265                 270

His Ser Met Lys Tyr Arg Leu Ser Phe Cys Arg Lys Thr Cys Gly Thr
        275                 280                 285

Cys

<210> SEQ ID NO 18
<211> LENGTH: 289
<212> TYPE: PRT
```

<213> ORGANISM: ARTIFICIAL SEQUENCE
<220> FEATURE:
<223> OTHER INFORMATION: VH21SP-IgG2-Fc-L10-ShK(2-35, Q16K) Fusion polypeptide

<400> SEQUENCE: 18

```
Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys Gly Gly Gly Gly Ser Gly Gly Gly Gly Ser Ser
                245                 250                 255

Cys Ile Asp Thr Ile Pro Lys Ser Arg Cys Thr Ala Phe Lys Cys Lys
            260                 265                 270

His Ser Met Lys Tyr Arg Leu Ser Phe Cys Arg Lys Thr Cys Gly Thr
        275                 280                 285

Cys
```

<210> SEQ ID NO 19
<211> LENGTH: 290
<212> TYPE: PRT
<213> ORGANISM: ARTIFICIAL SEQUENCE
<220> FEATURE:
<223> OTHER INFORMATION: VH21SP-IgG2-Fc-L10-ShK(1-35, Q16K) Fusion polypeptide

<400> SEQUENCE: 19

```
Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30
```

Val Ala Gly Pro Ser Val Phe Leu Phe Pro Pro Lys Pro Lys Asp Thr
         35                  40                  45
Leu Met Ile Ser Arg Thr Pro Glu Val Thr Cys Val Val Val Asp Val
 50                  55                  60
Ser His Glu Asp Pro Glu Val Gln Phe Asn Trp Tyr Val Asp Gly Val
 65                  70                  75                  80
Glu Val His Asn Ala Lys Thr Lys Pro Arg Glu Glu Gln Phe Asn Ser
                 85                  90                  95
Thr Phe Arg Val Val Ser Val Leu Thr Val Val His Gln Asp Trp Leu
            100                 105                 110
Asn Gly Lys Glu Tyr Lys Cys Lys Val Ser Asn Lys Gly Leu Pro Ala
        115                 120                 125
Pro Ile Glu Lys Thr Ile Ser Lys Thr Lys Gly Gln Pro Arg Glu Pro
    130                 135                 140
Gln Val Tyr Thr Leu Pro Pro Ser Arg Glu Glu Met Thr Lys Asn Gln
145                 150                 155                 160
Val Ser Leu Thr Cys Leu Val Lys Gly Phe Tyr Pro Ser Asp Ile Ala
                165                 170                 175
Val Glu Trp Glu Ser Asn Gly Gln Pro Glu Asn Asn Tyr Lys Thr Thr
            180                 185                 190
Pro Pro Met Leu Asp Ser Asp Gly Ser Phe Phe Leu Tyr Ser Lys Leu
        195                 200                 205
Thr Val Asp Lys Ser Arg Trp Gln Gln Gly Asn Val Phe Ser Cys Ser
    210                 215                 220
Val Met His Glu Ala Leu His Asn His Tyr Thr Gln Lys Ser Leu Ser
225                 230                 235                 240
Leu Ser Pro Gly Lys Gly Gly Gly Ser Gly Gly Gly Ser Arg
                245                 250                 255
Ser Cys Ile Asp Thr Ile Pro Lys Ser Arg Cys Thr Ala Phe Gln Cys
            260                 265                 270
Lys His Ser Met Lys Tyr Arg Leu Ser Phe Cys Arg Lys Thr Cys Gly
        275                 280                 285
Thr Cys
    290

<210> SEQ ID NO 20
<211> LENGTH: 30
<212> TYPE: DNA
<213> ORGANISM: ARTIFICIAL SEQUENCE
<220> FEATURE:
<223> OTHER INFORMATION: Primer sequence

<400> SEQUENCE: 20
cataagcttc ccaccatgga atggagctgg                                       30

<210> SEQ ID NO 21
<211> LENGTH: 31
<212> TYPE: DNA
<213> ORGANISM: ARTIFICIAL SEQUENCE
<220> FEATURE:
<223> OTHER INFORMATION: Primer sequence

<400> SEQUENCE: 21
catggatcct catttacccg gagacaggga g                                     31

<210> SEQ ID NO 22
<211> LENGTH: 163
<212> TYPE: DNA
<213> ORGANISM: ARTIFICIAL SEQUENCE

<220> FEATURE:
<223> OTHER INFORMATION: Coding sequence ShK{1-35, Q16K) with an
      N-terminal linker
<220> FEATURE:
<221> NAME/KEY: CDS
<222> LOCATION: (1)..(126)

<400> SEQUENCE: 22

```
gga tcc gga gga gga gga agc cgc agc tgc atc gac acc atc ccc aag     48
Gly Ser Gly Gly Gly Gly Ser Arg Ser Cys Ile Asp Thr Ile Pro Lys
1               5                   10                  15 agc cgc tgc acc gcc ttc aag tgc aag cac agc atg aag tac cgc ctg     96
Ser Arg Cys Thr Ala Phe Lys Cys Lys His Ser Met Lys Tyr Arg Leu
            20                  25                  30 agc ttc tgc cgc aag acc tgc ggc acc tgc taatgagcgg ccgctcgagg      146
Ser Phe Cys Arg Lys Thr Cys Gly Thr Cys
        35                  40 ccggcaaggc cggatcc                                                  163
```

<210> SEQ ID NO 23
<211> LENGTH: 42
<212> TYPE: PRT
<213> ORGANISM: ARTIFICIAL SEQUENCE
<220> FEATURE:
<223> OTHER INFORMATION: Synthetic Construct

<400> SEQUENCE: 23

```
Gly Ser Gly Gly Gly Gly Ser Arg Ser Cys Ile Asp Thr Ile Pro Lys
1               5                   10                  15

Ser Arg Cys Thr Ala Phe Lys Cys Lys His Ser Met Lys Tyr Arg Leu
            20                  25                  30

Ser Phe Cys Arg Lys Thr Cys Gly Thr Cys
        35                  40
```

<210> SEQ ID NO 24
<211> LENGTH: 744
<212> TYPE: DNA
<213> ORGANISM: ARTIFICIAL SEQUENCE
<220> FEATURE:
<223> OTHER INFORMATION: Coding sequence - IgG2 fragment
<220> FEATURE:
<221> NAME/KEY: CDS
<222> LOCATION: (1)..(744)

<400> SEQUENCE: 24

```
atg gaa tgg agc tgg gtc ttt ctc ttc ttc ctg tca gta acg act ggt     48
Met Glu Trp Ser Trp Val Phe Leu Phe Phe Leu Ser Val Thr Thr Gly
1               5                   10                  15 gtc cac tcc gag cgc aaa gtc gag tgc cca ccg tgc cca gca cca cct     96
Val His Ser Glu Arg Lys Val Glu Cys Pro Pro Cys Pro Ala Pro Pro
            20                  25                  30 gtg gca gga ccg tca gtc ttc ctc ttc ccc cca aaa ccc aag gac acc    144
Val Ala Gly Pro Ser Val Phe Leu Phe Pro Pro Lys Pro Lys Asp Thr
        35                  40                  45 ctc atg atc tcc cgg acc cct gag gtc acg tgc gtg gtg gtg gac gtg    192
Leu Met Ile Ser Arg Thr Pro Glu Val Thr Cys Val Val Val Asp Val
50                  55                  60 agc cac gaa gac ccc gag gtc cag ttc aac tgg tac gtg gac ggc gtg    240
Ser His Glu Asp Pro Glu Val Gln Phe Asn Trp Tyr Val Asp Gly Val
65                  70                  75                  80 gag gtg cat aat gcc aag aca aag cca cgg gag gag cag ttc aac agc    288
Glu Val His Asn Ala Lys Thr Lys Pro Arg Glu Glu Gln Phe Asn Ser
                85                  90                  95 acg ttc cgt gtg gtc agc gtc ctc acc gtt gtg cac cag gac tgg ctg    336
```

```
                Thr Phe Arg Val Val Ser Val Leu Thr Val Val His Gln Asp Trp Leu
                                100                 105                 110 aac ggc aag gag tac aag tgc aag gtc tcc aac aaa ggc ctc cca gcc        384
Asn Gly Lys Glu Tyr Lys Cys Lys Val Ser Asn Lys Gly Leu Pro Ala
            115                 120                 125 ccc atc gag aaa acc atc tcc aaa acc aaa ggg cag ccc cga gaa cca        432
Pro Ile Glu Lys Thr Ile Ser Lys Thr Lys Gly Gln Pro Arg Glu Pro
    130                 135                 140 cag gtg tac acc ctg ccc cca tcc cgg gag gag atg acc aag aac cag        480
Gln Val Tyr Thr Leu Pro Pro Ser Arg Glu Glu Met Thr Lys Asn Gln
145                 150                 155                 160 gtc agc ctg acc tgc ctg gtc aaa ggc ttc tac ccc agc gac atc gcc        528
Val Ser Leu Thr Cys Leu Val Lys Gly Phe Tyr Pro Ser Asp Ile Ala
                165                 170                 175 gtg gag tgg gag agc aat ggg cag ccg gag aac aac tac aag acc aca        576
Val Glu Trp Glu Ser Asn Gly Gln Pro Glu Asn Asn Tyr Lys Thr Thr
            180                 185                 190 cct ccc atg ctg gac tcc gac ggc tcc ttc ttc ctc tac agc aag ctc        624
Pro Pro Met Leu Asp Ser Asp Gly Ser Phe Phe Leu Tyr Ser Lys Leu
    195                 200                 205 acc gtg gac aag agc agg tgg cag cag ggg aac gtc ttc tca tgc tcc        672
Thr Val Asp Lys Ser Arg Trp Gln Gln Gly Asn Val Phe Ser Cys Ser
210                 215                 220 gtg atg cat gag gct ctg cac aac cac tac acg cag aag agc ctc tcc        720
Val Met His Glu Ala Leu His Asn His Tyr Thr Gln Lys Ser Leu Ser
225                 230                 235                 240 ctg tct ccg ggt aaa gga gga gga                                        744
Leu Ser Pro Gly Lys Gly Gly Gly
                245

<210> SEQ ID NO 25
<211> LENGTH: 248
<212> TYPE: PRT
<213> ORGANISM: ARTIFICIAL SEQUENCE
<220> FEATURE:
<223> OTHER INFORMATION: Synthetic Construct

<400> SEQUENCE: 25

Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
```

```
                    165                 170                 175
Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
        210                 215                 220

Val Met His Glu Ala Leu His Asn His Tyr Thr Gln Lys Ser Leu Ser
225                 230                 235                 240

Leu Ser Pro Gly Lys Gly Gly Gly
                245

<210> SEQ ID NO 26
<211> LENGTH: 290
<212> TYPE: PRT
<213> ORGANISM: ARTIFICIAL SEQUENCE
<220> FEATURE:
<223> OTHER INFORMATION: IgG2 Fc-L10-ShK(1-35, Q16K) fusion protein

<400> SEQUENCE: 26

Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys Gly Gly Gly Gly Ser Gly Gly Gly Gly Ser Arg
                245                 250                 255

Ser Cys Ile Asp Thr Ile Pro Lys Ser Arg Cys Thr Ala Phe Lys Cys
            260                 265                 270

Lys His Ser Met Lys Tyr Arg Leu Ser Phe Cys Arg Lys Thr Cys Gly
        275                 280                 285
```

<210> SEQ ID NO 27
<211> LENGTH: 35
<212> TYPE: PRT
<213> ORGANISM: ARTIFICIAL SEQUENCE
<220> FEATURE:
<223> OTHER INFORMATION: ShK

<400> SEQUENCE: 27

```
Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

<210> SEQ ID NO 28

<400> SEQUENCE: 28

000

<210> SEQ ID NO 29

<400> SEQUENCE: 29

000

<210> SEQ ID NO 30
<211> LENGTH: 290
<212> TYPE: PRT
<213> ORGANISM: ARTIFICIAL SEQUENCE
<220> FEATURE:
<223> OTHER INFORMATION: IgG2 Fc-L10-ShK(1-35)

<400> SEQUENCE: 30

```
Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175
```

-continued

```
Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
            195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys Gly Gly Gly Ser Gly Gly Gly Ser Arg
                245                 250                 255

Ser Cys Ile Asp Thr Ile Pro Lys Ser Arg Cys Thr Ala Phe Gln Cys
            260                 265                 270

Lys His Ser Met Lys Tyr Arg Leu Ser Phe Cys Arg Lys Thr Cys Gly
            275                 280                 285

Thr Cys
    290

<210> SEQ ID NO 31
<211> LENGTH: 42
<212> TYPE: DNA
<213> ORGANISM: ARTIFICIAL SEQUENCE
<220> FEATURE:
<223> OTHER INFORMATION: Forward primer sequence 4661-03

<400> SEQUENCE: 31
aagctcgagg tcgactagac caccatggaa gccccagcgc ag                    42

<210> SEQ ID NO 32
<211> LENGTH: 33
<212> TYPE: DNA
<213> ORGANISM: ARTIFICIAL SEQUENCE
<220> FEATURE:
<223> OTHER INFORMATION: Reverse primer sequence 5140-51

<400> SEQUENCE: 32
gaaagtgagc ggagcgttat catactgctg aca                              33

<210> SEQ ID NO 33
<211> LENGTH: 33
<212> TYPE: DNA
<213> ORGANISM: ARTIFICIAL SEQUENCE
<220> FEATURE:
<223> OTHER INFORMATION: Forward primer sequence 5140-50

<400> SEQUENCE: 33
tgtcagcagt atgataacgc tccgctcact ttc                              33

<210> SEQ ID NO 34
<211> LENGTH: 41
<212> TYPE: DNA
<213> ORGANISM: ARTIFICIAL SEQUENCE
<220> FEATURE:
<223> OTHER INFORMATION: Reverse primer sequence 3250-80

<400> SEQUENCE: 34
aaccgtttaa acgcggccgc tcaacactct cccctgttga a                     41

<210> SEQ ID NO 35
<211> LENGTH: 51
<212> TYPE: DNA
<213> ORGANISM: ARTIFICIAL SEQUENCE
<220> FEATURE:
<223> OTHER INFORMATION: Primer sequence 5143-27
```

-continued

<400> SEQUENCE: 35
aagctcgagg tcgactagac caccatggag tggacctgga gggtccttttt c    51

<210> SEQ ID NO 36
<211> LENGTH: 41
<212> TYPE: DNA
<213> ORGANISM: ARTIFICIAL SEQUENCE
<220> FEATURE:
<223> OTHER INFORMATION: Primer sequence 3250-79

<400> SEQUENCE: 36
aaccgtttaa acgcggccgc tcatttaccc ggagacaggg a    41

<210> SEQ ID NO 37
<211> LENGTH: 45
<212> TYPE: DNA
<213> ORGANISM: ARTIFICIAL SEQUENCE
<220> FEATURE:
<223> OTHER INFORMATION: Primer sequence 5135-89

<400> SEQUENCE: 37
gccccagtag tcaaagtaaa gctgagctct cgcacagtaa tacac    45

<210> SEQ ID NO 38
<211> LENGTH: 45
<212> TYPE: DNA
<213> ORGANISM: ARTIFICIAL SEQUENCE
<220> FEATURE:
<223> OTHER INFORMATION: Primer sequence 5135-88

<400> SEQUENCE: 38
gtgtattact gtgcgagagc tcagctttac tttgactact ggggc    45

<210> SEQ ID NO 39
<211> LENGTH: 45
<212> TYPE: DNA
<213> ORGANISM: ARTIFICIAL SEQUENCE
<220> FEATURE:
<223> OTHER INFORMATION: Primer sequence 5135-95

<400> SEQUENCE: 39
gccccagtag tcaaagtact gctgccgtct cgcacagtaa tacac    45

<210> SEQ ID NO 40
<211> LENGTH: 45
<212> TYPE: DNA
<213> ORGANISM: ARTIFICIAL SEQUENCE
<220> FEATURE:
<223> OTHER INFORMATION: Primer sequence 5135-94

<400> SEQUENCE: 40
gtgtattact gtgcgagacg gcagcagtac tttgactact ggggc    45

<210> SEQ ID NO 41
<211> LENGTH: 45
<212> TYPE: DNA
<213> ORGANISM: ARTIFICIAL SEQUENCE
<220> FEATURE:
<223> OTHER INFORMATION: Primer sequence 5154-92

<400> SEQUENCE: 41
gccccagtag tcaaagtact gctgagctct cgcacagtaa tacac    45

<210> SEQ ID NO 42
<211> LENGTH: 45
<212> TYPE: DNA

-continued

<213> ORGANISM: ARTIFICIAL SEQUENCE
<220> FEATURE:
<223> OTHER INFORMATION: Primer sequence 5154-91

<400> SEQUENCE: 42
gtgtattact gtgcgagagc tcagcagtac tttgactact ggggc        45

<210> SEQ ID NO 43
<211> LENGTH: 36
<212> TYPE: DNA
<213> ORGANISM: ARTIFICIAL SEQUENCE
<220> FEATURE:
<223> OTHER INFORMATION: Primer sequence 5141-27

<400> SEQUENCE: 43
gtccatacca tagtagtagg cacccccctcg atctct        36

<210> SEQ ID NO 44
<211> LENGTH: 36
<212> TYPE: DNA
<213> ORGANISM: ARTIFICIAL SEQUENCE
<220> FEATURE:
<223> OTHER INFORMATION: Primer sequence 5141-26

<400> SEQUENCE: 44
agagatcgag ggggtgccta ctactatggt atggac        36

<210> SEQ ID NO 45
<211> LENGTH: 36
<212> TYPE: DNA
<213> ORGANISM: ARTIFICIAL SEQUENCE
<220> FEATURE:
<223> OTHER INFORMATION: Primer sequence 5141-29

<400> SEQUENCE: 45
gtccatacca tagtaggcgt cacccccctcg atctct        36

<210> SEQ ID NO 46
<211> LENGTH: 36
<212> TYPE: DNA
<213> ORGANISM: ARTIFICIAL SEQUENCE
<220> FEATURE:
<223> OTHER INFORMATION: Primer sequence 5141-28

<400> SEQUENCE: 46
agagatcgag ggggtgacgc ctactatggt atggac        36

<210> SEQ ID NO 47
<211> LENGTH: 34
<212> TYPE: DNA
<213> ORGANISM: ARTIFICIAL SEQUENCE
<220> FEATURE:
<223> OTHER INFORMATION: Primer sequence

<400> SEQUENCE: 47
tccctgtctc cgggtggagg aggaggatcc ggag        34

<210> SEQ ID NO 48
<211> LENGTH: 511
<212> TYPE: PRT
<213> ORGANISM: ARTIFICIAL SEQUENCE
<220> FEATURE:
<223> OTHER INFORMATION: IgG2-HC-L10-ShK[1-35] fusion polypeptide

<400> SEQUENCE: 48

Met Asp Met Arg Val Pro Ala Gln Leu Leu Gly Leu Leu Leu Leu Trp
1               5                   10                  15

-continued

```
Leu Arg Gly Ala Arg Cys Gln Val Gln Leu Val Gln Ser Gly Ala Glu
                20                  25                  30
Val Lys Lys Pro Gly Ala Ser Val Lys Val Ser Cys Lys Ala Ser Gly
            35                  40                  45
Tyr Thr Phe Thr Gly Tyr His Met His Trp Val Arg Gln Ala Pro Gly
        50                  55                  60
Gln Gly Leu Glu Trp Met Gly Trp Ile Asn Pro Asn Ser Gly Gly Thr
65                  70                  75                  80
Asn Tyr Ala Gln Lys Phe Gln Gly Arg Val Thr Met Thr Arg Asp Thr
                85                  90                  95
Ser Ile Ser Thr Ala Tyr Met Glu Leu Ser Arg Leu Arg Ser Asp Asp
            100                 105                 110
Thr Ala Val Tyr Tyr Cys Ala Arg Asp Arg Gly Ser Tyr Tyr Trp Phe
        115                 120                 125
Asp Pro Trp Gly Gln Gly Thr Leu Val Thr Val Ser Ser Ala Ser Thr
    130                 135                 140
Lys Gly Pro Ser Val Phe Pro Leu Ala Pro Cys Ser Arg Ser Thr Ser
145                 150                 155                 160
Glu Ser Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
        195                 200                 205
Val Val Thr Val Pro Ser Ser Asn Phe Gly Thr Gln Thr Tyr Thr Cys
    210                 215                 220
Asn Val Asp His Lys Pro Ser Asn Thr Lys Val Asp Lys Thr Val Glu
225                 230                 235                 240
Arg Lys Cys Cys Val Glu Cys Pro Pro Cys Pro Ala Pro Pro Val Ala
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Gln Phe Asn Trp Tyr Val Asp Gly Val Glu Val
    290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
            340                 345                 350
Glu Lys Thr Ile Ser Lys Thr Lys Gly Gln Pro Arg Glu Pro Gln Val
        355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
```

```
                 435             440             445
His Glu Ala Leu His Asn His Tyr Thr Gln Lys Ser Leu Ser Leu Ser
            450                 455                 460

Pro Gly Gly Gly Gly Ser Gly Gly Gly Ser Arg Ser Cys Ile
465             470                 475                 480

Asp Thr Ile Pro Lys Ser Arg Cys Thr Ala Phe Gln Cys Lys His Ser
                485                 490                 495

Met Lys Tyr Arg Leu Ser Phe Cys Arg Lys Thr Cys Gly Thr Cys
            500                 505                 510

<210> SEQ ID NO 49
<211> LENGTH: 511
<212> TYPE: PRT
<213> ORGANISM: ARTIFICIAL SEQUENCE
<220> FEATURE:
<223> OTHER INFORMATION: IgG2-HC-L10-ShK[1-35, Q16K] fusion polypeptide

<400> SEQUENCE: 49

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300
```

```
His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
            325                 330                 335

Lys Glu Tyr Lys Cys Lys Val Ser Asn Lys Gly Leu Pro Ala Pro Ile
        340                 345                 350

Glu Lys Thr Ile Ser Lys Thr Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Gly Gly Ser Gly Gly Gly Ser Arg Ser Cys Ile
465                 470                 475                 480

Asp Thr Ile Pro Lys Ser Arg Cys Thr Ala Phe Lys Cys Lys His Ser
                485                 490                 495

Met Lys Tyr Arg Leu Ser Phe Cys Arg Lys Thr Cys Gly Thr Cys
            500                 505                 510

<210> SEQ ID NO 50
<211> LENGTH: 1407
<212> TYPE: DNA
<213> ORGANISM: ARTIFICIAL SEQUENCE
<220> FEATURE:
<223> OTHER INFORMATION: Coding sequence
<220> FEATURE:
<221> NAME/KEY: CDS
<222> LOCATION: (1)..(1407)

<400> SEQUENCE: 50 atg gac atg agg gtg ccc gct cag ctc ctg ggg ctc ctg ctg ctg tgg    48
Met Asp Met Arg Val Pro Ala Gln Leu Leu Gly Leu Leu Leu Leu Trp
1               5                   10                  15 ctg aga ggt gcc aga tgt cag gtg cag ctg gtg cag tct ggg gct gag    96
Leu Arg Gly Ala Arg Cys Gln Val Gln Leu Val Gln Ser Gly Ala Glu
            20                  25                  30 gtg aag aag cct ggg gcc tca gtg aag gtc tcc tgc aag gct tct gga   144
Val Lys Lys Pro Gly Ala Ser Val Lys Val Ser Cys Lys Ala Ser Gly
        35                  40                  45 tac acc ttc acc ggc tac cac atg cac tgg gtg cga cag gcc cct gga   192
Tyr Thr Phe Thr Gly Tyr His Met His Trp Val Arg Gln Ala Pro Gly
    50                  55                  60 caa ggg ctt gag tgg atg gga tgg atc aac cct aac agt ggt ggc aca   240
Gln Gly Leu Glu Trp Met Gly Trp Ile Asn Pro Asn Ser Gly Gly Thr
65                  70                  75                  80 aac tat gca cag aag ttt cag ggc agg gtc acc atg acc agg gac acg   288
Asn Tyr Ala Gln Lys Phe Gln Gly Arg Val Thr Met Thr Arg Asp Thr
                85                  90                  95 tcc atc agc aca gcc tac atg gag ctg agc agg ctg aga tct gac gac   336
Ser Ile Ser Thr Ala Tyr Met Glu Leu Ser Arg Leu Arg Ser Asp Asp
            100                 105                 110
```

-continued

| | | |
|---|---|---|
| acg gcc gtg tat tac tgt gcg aga gat cgt ggg agc tac tac tgg ttc<br>Thr Ala Val Tyr Tyr Cys Ala Arg Asp Arg Gly Ser Tyr Tyr Trp Phe<br>        115                  120                125 | | 384 |
| gac ccc tgg ggc cag gga acc ctg gtc acc gtc tcc tca gcc tcc acc<br>Asp Pro Trp Gly Gln Gly Thr Leu Val Thr Val Ser Ser Ala Ser Thr<br>130                  135                  140 | | 432 |
| aag ggc cca tcg gtc ttc ccc ctg gcg ccc tgc tcc agg agc acc tcc<br>Lys Gly Pro Ser Val Phe Pro Leu Ala Pro Cys Ser Arg Ser Thr Ser<br>145                  150                155              160 | | 480 |
| gag agc aca gcg gcc ctg ggc tgc ctg gtc aag gac tac ttc ccc gaa<br>Glu Ser Thr Ala Ala Leu Gly Cys Leu Val Lys Asp Tyr Phe Pro Glu<br>        165                  170                175 | | 528 |
| ccg gtg acg gtg tcg tgg aac tca ggc gct ctg acc agc ggc gtg cac<br>Pro Val Thr Val Ser Trp Asn Ser Gly Ala Leu Thr Ser Gly Val His<br>              180                185              190 | | 576 |
| acc ttc cca gct gtc cta cag tcc tca gga ctc tac tcc ctc agc agc<br>Thr Phe Pro Ala Val Leu Gln Ser Ser Gly Leu Tyr Ser Leu Ser Ser<br>           195                200              205 | | 624 |
| gtg gtg acc gtg ccc tcc agc aac ttc ggc acc cag acc tac acc tgc<br>Val Val Thr Val Pro Ser Ser Asn Phe Gly Thr Gln Thr Tyr Thr Cys<br>        210                  215                220 | | 672 |
| aac gta gat cac aag ccc agc aac acc aag gtg gac aag aca gtt gag<br>Asn Val Asp His Lys Pro Ser Asn Thr Lys Val Asp Lys Thr Val Glu<br>225                  230                235              240 | | 720 |
| cgc aaa tgt tgt gtc gag tgc cca ccg tgc cca gca cca cct gtg gca<br>Arg Lys Cys Cys Val Glu Cys Pro Pro Cys Pro Ala Pro Pro Val Ala<br>                      245                250              255 | | 768 |
| gga ccg tca gtc ttc ctc ttc ccc cca aaa ccc aag gac acc ctc atg<br>Gly Pro Ser Val Phe Leu Phe Pro Pro Lys Pro Lys Asp Thr Leu Met<br>                260                265              270 | | 816 |
| atc tcc cgg acc cct gag gtc acg tgc gtg gtg gtg gac gtg agc cac<br>Ile Ser Arg Thr Pro Glu Val Thr Cys Val Val Val Asp Val Ser His<br>           275                280              285 | | 864 |
| gaa gac ccc gag gtc cag ttc aac tgg tac gtg gac ggc gtg gag gtg<br>Glu Asp Pro Glu Val Gln Phe Asn Trp Tyr Val Asp Gly Val Glu Val<br>        290                  295              300 | | 912 |
| cat aat gcc aag aca aag cca cgg gag gag cag ttc aac agc acg ttc<br>His Asn Ala Lys Thr Lys Pro Arg Glu Glu Gln Phe Asn Ser Thr Phe<br>305                  310                315              320 | | 960 |
| cgt gtg gtc agc gtc ctc acc gtt gtg cac cag gac tgg ctg aac ggc<br>Arg Val Val Ser Val Leu Thr Val Val His Gln Asp Trp Leu Asn Gly<br>                      325                330              335 | | 1008 |
| aag gag tac aag tgc aag gtc tcc aac aaa ggc ctc cca gcc ccc atc<br>Lys Glu Tyr Lys Cys Lys Val Ser Asn Lys Gly Leu Pro Ala Pro Ile<br>                340                345              350 | | 1056 |
| gag aaa acc atc tcc aaa acc aaa ggg cag ccc cga gaa cca cag gtg<br>Glu Lys Thr Ile Ser Lys Thr Lys Gly Gln Pro Arg Glu Pro Gln Val<br>           355                360              365 | | 1104 |
| tac acc ctg ccc cca tcc cgg gag gag atg acc aag aac cag gtc agc<br>Tyr Thr Leu Pro Pro Ser Arg Glu Glu Met Thr Lys Asn Gln Val Ser<br>        370                  375              380 | | 1152 |
| ctg acc tgc ctg gtc aaa ggc ttc tac ccc agc gac atc gcc gtg gag<br>Leu Thr Cys Leu Val Lys Gly Phe Tyr Pro Ser Asp Ile Ala Val Glu<br>385                  390                395              400 | | 1200 |
| tgg gag agc aat ggg cag ccg gag aac aac tac aag acc aca cct ccc<br>Trp Glu Ser Asn Gly Gln Pro Glu Asn Asn Tyr Lys Thr Thr Pro Pro<br>                      405                410              415 | | 1248 |
| atg ctg gac tcc gac ggc tcc ttc ttc ctc tac agc aag ctc acc gtg<br>Met Leu Asp Ser Asp Gly Ser Phe Phe Leu Tyr Ser Lys Leu Thr Val<br>           420                425              430 | | 1296 |

-continued

```
gac aag agc agg tgg cag cag ggg aac gtc ttc tca tgc tcc gtg atg    1344
Asp Lys Ser Arg Trp Gln Gln Gly Asn Val Phe Ser Cys Ser Val Met
        435                 440                 445 cat gag gct ctg cac aac cac tac acg cag aag agc ctc tcc ctg tct    1392
His Glu Ala Leu His Asn His Tyr Thr Gln Lys Ser Leu Ser Leu Ser
450                 455                 460 ccg ggt gga gga gga                                                 1407
Pro Gly Gly Gly Gly
465

<210> SEQ ID NO 51
<211> LENGTH: 469
<212> TYPE: PRT
<213> ORGANISM: ARTIFICIAL SEQUENCE
<220> FEATURE:
<223> OTHER INFORMATION: Synthetic Construct

<400> SEQUENCE: 51
```

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

```
His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
            325                 330                 335

Lys Glu Tyr Lys Cys Lys Val Ser Asn Lys Gly Leu Pro Ala Pro Ile
        340                 345                 350

Glu Lys Thr Ile Ser Lys Thr Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Met Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Gly Gly Gly
465

<210> SEQ ID NO 52
<211> LENGTH: 129
<212> TYPE: DNA
<213> ORGANISM: ARTIFICIAL SEQUENCE
<220> FEATURE:
<223> OTHER INFORMATION: Coding sequence
<220> FEATURE:
<221> NAME/KEY: CDS
<222> LOCATION: (1)..(129)

<400> SEQUENCE: 52 gga tcc gga gga gga gga agc agc tgc atc gac acc atc ccc aag agc      48
Gly Ser Gly Gly Gly Gly Ser Ser Cys Ile Asp Thr Ile Pro Lys Ser
1               5                   10                  15 cgc tgc acc gcc ttc aag tgc aag cac agc atg aag tac cgc ctg agc      96
Arg Cys Thr Ala Phe Lys Cys Lys His Ser Met Lys Tyr Arg Leu Ser
            20                  25                  30 ttc tgc cgc aag acc tgc ggc acc tgc taa tga                         129
Phe Cys Arg Lys Thr Cys Gly Thr Cys
        35                  40

<210> SEQ ID NO 53
<211> LENGTH: 41
<212> TYPE: PRT
<213> ORGANISM: ARTIFICIAL SEQUENCE
<220> FEATURE:
<223> OTHER INFORMATION: Synthetic Construct

<400> SEQUENCE: 53

Gly Ser Gly Gly Gly Gly Ser Ser Cys Ile Asp Thr Ile Pro Lys Ser
1               5                   10                  15

Arg Cys Thr Ala Phe Lys Cys Lys His Ser Met Lys Tyr Arg Leu Ser
            20                  25                  30

Phe Cys Arg Lys Thr Cys Gly Thr Cys
        35                  40

<210> SEQ ID NO 54
<211> LENGTH: 510
```

-continued

```
<212> TYPE: PRT
<213> ORGANISM: ARTIFICIAL SEQUENCE
<220> FEATURE:
<223> OTHER INFORMATION: IgG2 HC-L10-ShK[2-35,Q16K] fusion polypeptide

<400> SEQUENCE: 54

Met Asp Met Arg Val Pro Ala Gln Leu Leu Gly Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
```

```
                385                 390                 395                 400

Trp Glu Ser Asn Gly Gln Pro Glu Asn Tyr Lys Thr Thr Pro Pro
                    405                 410                 415

Met Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Gly Gly Gly Ser Gly Gly Gly Ser Ser Cys Ile Asp
465                 470                 475                 480

Thr Ile Pro Lys Ser Arg Cys Thr Ala Phe Lys Cys Lys His Ser Met
                485                 490                 495

Lys Tyr Arg Leu Ser Phe Cys Arg Lys Thr Cys Gly Thr Cys
                500                 505                 510

<210> SEQ ID NO 55
<211> LENGTH: 127
<212> TYPE: DNA
<213> ORGANISM: ARTIFICIAL SEQUENCE
<220> FEATURE:
<223> OTHER INFORMATION: Forward primer
<220> FEATURE:
<221> NAME/KEY: misc_feature
<222> LOCATION: (6)..(11)
<223> OTHER INFORMATION: HINDIII Site

<400> SEQUENCE: 55
tgcagaagct tctagaccac catggaatgg agctgggtct ttctcttctt cctgtcagta      60
acgactggtg tccactcccg cagctgcatc gacaccatcc ccaagagccg ctgcaccgcc     120
ttccagt                                                                127

<210> SEQ ID NO 56
<211> LENGTH: 115
<212> TYPE: DNA
<213> ORGANISM: ARTIFICIAL SEQUENCE
<220> FEATURE:
<223> OTHER INFORMATION: Reverse primer
<220> FEATURE:
<221> NAME/KEY: misc_feature
<222> LOCATION: (5)..(10)
<223> OTHER INFORMATION: BAMHI Site

<400> SEQUENCE: 56
ctccggatcc tcctcctccg caggtgccgc aggtcttgcg gcagaagctc aggcggtact      60
tcatgctgtg cttgcactgg aaggcggtgc agcggctctt ggggatggtg tcgat          115

<210> SEQ ID NO 57
<211> LENGTH: 38
<212> TYPE: DNA
<213> ORGANISM: ARTIFICIAL SEQUENCE
<220> FEATURE:
<223> OTHER INFORMATION: Forward primer
<220> FEATURE:
<221> NAME/KEY: misc_feature
<222> LOCATION: (4)..(9)
<223> OTHER INFORMATION: BAMHI Site

<400> SEQUENCE: 57
gtaggatccg gaggaggagg aagcgacaaa actcacac                              38

<210> SEQ ID NO 58
<211> LENGTH: 35
```

<210> SEQ ID NO 59
<211> LENGTH: 879
<212> TYPE: DNA
<213> ORGANISM: ARTIFICIAL SEQUENCE
<220> FEATURE:
<223> OTHER INFORMATION: Reverse primer
<220> FEATURE:
<221> NAME/KEY: misc_feature
<222> LOCATION: (4)..(11)
<223> OTHER INFORMATION: NOTI Site

<400> SEQUENCE: 58
cgagcggccg cttactattt acccggagac aggga                               35

<210> SEQ ID NO 59
<211> LENGTH: 879
<212> TYPE: DNA
<213> ORGANISM: ARTIFICIAL SEQUENCE
<220> FEATURE:
<223> OTHER INFORMATION: VH21 SP-ShK(1-35)-L10-IgG1 Fc coding sequence
<220> FEATURE:
<221> NAME/KEY: CDS
<222> LOCATION: (1)..(879)

<400> SEQUENCE: 59

| atg | gaa | tgg | agc | tgg | gtc | ttt | ctc | ttc | ttc | ctg | tca | gta | acg | act | ggt | 48 |
| Met | Glu | Trp | Ser | Trp | Val | Phe | Leu | Phe | Phe | Leu | Ser | Val | Thr | Thr | Gly | |
| 1 | | | | 5 | | | | | 10 | | | | | 15 | | |

| gtc | cac | tcc | cgc | agc | tgc | atc | gac | acc | atc | ccc | aag | agc | cgc | tgc | acc | 96 |
| Val | His | Ser | Arg | Ser | Cys | Ile | Asp | Thr | Ile | Pro | Lys | Ser | Arg | Cys | Thr | |
| | | | 20 | | | | | 25 | | | | | 30 | | | |

| gcc | ttc | cag | tgc | aag | cac | agc | atg | aag | tac | cgc | ctg | agc | ttc | tgc | cgc | 144 |
| Ala | Phe | Gln | Cys | Lys | His | Ser | Met | Lys | Tyr | Arg | Leu | Ser | Phe | Cys | Arg | |
| | | 35 | | | | | 40 | | | | | 45 | | | | |

| aag | acc | tgc | ggc | acc | tgc | gga | gga | gga | gga | tcc | gga | gga | gga | gga | agc | 192 |
| Lys | Thr | Cys | Gly | Thr | Cys | Gly | Gly | Gly | Gly | Ser | Gly | Gly | Gly | Gly | Ser | |
| 50 | | | | | 55 | | | | | 60 | | | | | | |

| gac | aaa | act | cac | aca | tgc | cca | ccg | tgc | cca | gca | cct | gaa | ctc | ctg | ggg | 240 |
| Asp | Lys | Thr | His | Thr | Cys | Pro | Pro | Cys | Pro | Ala | Pro | Glu | Leu | Leu | Gly | |
| 65 | | | | 70 | | | | | 75 | | | | | 80 | | |

| gga | ccg | tca | gtc | ttc | ctc | ttc | ccc | cca | aaa | ccc | aag | gac | acc | ctc | atg | 288 |
| Gly | Pro | Ser | Val | Phe | Leu | Phe | Pro | Pro | Lys | Pro | Lys | Asp | Thr | Leu | Met | |
| | | | | 85 | | | | | 90 | | | | | 95 | | |

| atc | tcc | cgg | acc | cct | gag | gtc | aca | tgc | gtg | gtg | gtg | gac | gtg | agc | cac | 336 |
| Ile | Ser | Arg | Thr | Pro | Glu | Val | Thr | Cys | Val | Val | Val | Asp | Val | Ser | His | |
| | | | 100 | | | | | 105 | | | | | 110 | | | |

| gaa | gac | cct | gag | gtc | aag | ttc | aac | tgg | tac | gtg | gac | ggc | gtg | gag | gtg | 384 |
| Glu | Asp | Pro | Glu | Val | Lys | Phe | Asn | Trp | Tyr | Val | Asp | Gly | Val | Glu | Val | |
| | | 115 | | | | | 120 | | | | | 125 | | | | |

| cat | aat | gcc | aag | aca | aag | ccg | cgg | gag | gag | cag | tac | aac | agc | acg | tac | 432 |
| His | Asn | Ala | Lys | Thr | Lys | Pro | Arg | Glu | Glu | Gln | Tyr | Asn | Ser | Thr | Tyr | |
| | 130 | | | | | 135 | | | | | 140 | | | | | |

| cgt | gtg | gtc | agc | gtc | ctc | acc | gtc | ctg | cac | cag | gac | tgg | ctg | aat | ggc | 480 |
| Arg | Val | Val | Ser | Val | Leu | Thr | Val | Leu | His | Gln | Asp | Trp | Leu | Asn | Gly | |
| 145 | | | | | 150 | | | | | 155 | | | | | 160 | |

| aag | gag | tac | aag | tgc | aag | gtc | tcc | aac | aaa | gcc | ctc | cca | gcc | ccc | atc | 528 |
| Lys | Glu | Tyr | Lys | Cys | Lys | Val | Ser | Asn | Lys | Ala | Leu | Pro | Ala | Pro | Ile | |
| | | | | 165 | | | | | 170 | | | | | 175 | | |

| gag | aaa | acc | atc | tcc | aaa | gcc | aaa | ggg | cag | ccc | cga | gaa | cca | cag | gtg | 576 |
| Glu | Lys | Thr | Ile | Ser | Lys | Ala | Lys | Gly | Gln | Pro | Arg | Glu | Pro | Gln | Val | |
| | | | 180 | | | | | 185 | | | | | 190 | | | |

| tac | acc | ctg | ccc | cca | tcc | cgg | gat | gag | ctg | acc | aag | aac | cag | gtc | agc | 624 |
| Tyr | Thr | Leu | Pro | Pro | Ser | Arg | Asp | Glu | Leu | Thr | Lys | Asn | Gln | Val | Ser | |
| | | 195 | | | | | 200 | | | | | 205 | | | | |

| ctg | acc | tgc | ctg | gtc | aaa | ggc | ttc | tat | ccc | agc | gac | atc | gcc | gtg | gag | 672 |
| Leu | Thr | Cys | Leu | Val | Lys | Gly | Phe | Tyr | Pro | Ser | Asp | Ile | Ala | Val | Glu | |

```
                                                  210                 215                 220
tgg gag agc aat ggg cag ccg gag aac aac tac aag acc acg cct ccc       720
Trp Glu Ser Asn Gly Gln Pro Glu Asn Asn Tyr Lys Thr Thr Pro Pro
225                 230                 235                 240 gtg ctg gac tcc gac ggc tcc ttc ttc ctc tac agc aag ctc acc gtg       768
Val Leu Asp Ser Asp Gly Ser Phe Phe Leu Tyr Ser Lys Leu Thr Val
                245                 250                 255 gac aag agc agg tgg cag cag ggg aac gtc ttc tca tgc tcc gtg atg       816
Asp Lys Ser Arg Trp Gln Gln Gly Asn Val Phe Ser Cys Ser Val Met
            260                 265                 270 cat gag gct ctg cac aac cac tac acg cag aag agc ctc tcc ctg tct       864
His Glu Ala Leu His Asn His Tyr Thr Gln Lys Ser Leu Ser Leu Ser
        275                 280                 285 ccg ggt aaa tag taa                                                   879
Pro Gly Lys
    290
```

<210> SEQ ID NO 60
<211> LENGTH: 291
<212> TYPE: PRT
<213> ORGANISM: ARTIFICIAL SEQUENCE
<220> FEATURE:
<223> OTHER INFORMATION: Synthetic Construct

<400> SEQUENCE: 60

```
Met Glu Trp Ser Trp Val Phe Leu Phe Phe Leu Ser Val Thr Thr Gly
1               5                   10                  15

Val His Ser Arg Ser Cys Ile Asp Thr Ile Pro Lys Ser Arg Cys Thr
            20                  25                  30

Ala Phe Gln Cys Lys His Ser Met Lys Tyr Arg Leu Ser Phe Cys Arg
        35                  40                  45

Lys Thr Cys Gly Thr Cys Gly Gly Gly Ser Gly Gly Gly Gly Ser
    50                  55                  60

Asp Lys Thr His Thr Cys Pro Pro Cys Pro Ala Pro Glu Leu Leu Gly
65                  70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser His
            100                 105                 110

Glu Asp Pro Glu Val Lys Phe Asn Trp Tyr Val Asp Gly Val Glu Val
        115                 120                 125

His Asn Ala Lys Thr Lys Pro Arg Glu Glu Gln Tyr Asn Ser Thr Tyr
    130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Ala Leu Pro Ala Pro Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Arg Asp Glu Leu Thr Lys Asn Gln Val Ser
        195                 200                 205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Lys Leu Thr Val
                245                 250                 255
```

```
Asp Lys Ser Arg Trp Gln Gln Gly Asn Val Phe Ser Cys Ser Val Met
            260                 265                 270

His Glu Ala Leu His Asn His Tyr Thr Gln Lys Ser Leu Ser Leu Ser
            275                 280                 285

Pro Gly Lys
    290

<210> SEQ ID NO 61
<211> LENGTH: 291
<212> TYPE: PRT
<213> ORGANISM: ARTIFICIAL SEQUENCE
<220> FEATURE:
<223> OTHER INFORMATION: VH21 SP-ShK(1-35, Q16K)-L10-IgG1 Fc

<400> SEQUENCE: 61

Met Glu Trp Ser Trp Val Phe Leu Phe Leu Ser Val Thr Thr Gly
1               5                   10                  15

Val His Ser Arg Ser Cys Ile Asp Thr Ile Pro Lys Ser Arg Cys Thr
            20                  25                  30

Ala Phe Lys Cys Lys His Ser Met Lys Tyr Arg Leu Ser Phe Cys Arg
            35                  40                  45

Lys Thr Cys Gly Thr Cys Gly Gly Gly Ser Gly Gly Gly Gly Ser
    50                  55                  60

Asp Lys Thr His Thr Cys Pro Pro Cys Pro Ala Pro Glu Leu Leu Gly
65                  70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser His
            100                 105                 110

Glu Asp Pro Glu Val Lys Phe Asn Trp Tyr Val Asp Gly Val Glu Val
            115                 120                 125

His Asn Ala Lys Thr Lys Pro Arg Glu Glu Gln Tyr Asn Ser Thr Tyr
        130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Ala Leu Pro Ala Pro Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Arg Asp Glu Leu Thr Lys Asn Gln Val Ser
            195                 200                 205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Lys Leu Thr Val
                245                 250                 255

Asp Lys Ser Arg Trp Gln Gln Gly Asn Val Phe Ser Cys Ser Val Met
            260                 265                 270

His Glu Ala Leu His Asn His Tyr Thr Gln Lys Ser Leu Ser Leu Ser
            275                 280                 285

Pro Gly Lys
    290

<210> SEQ ID NO 62
<211> LENGTH: 23
<212> TYPE: DNA
```

<213> ORGANISM: ARTIFICIAL SEQUENCE
<220> FEATURE:
<223> OTHER INFORMATION: Primer sequence

<400> SEQUENCE: 62
cattctagac caccatggaa tgg 23

<210> SEQ ID NO 63
<211> LENGTH: 29
<212> TYPE: DNA
<213> ORGANISM: ARTIFICIAL SEQUENCE
<220> FEATURE:
<223> OTHER INFORMATION: Primer sequence

<400> SEQUENCE: 63
cagctgcacc tggcttcctc ctcctccgg 29

<210> SEQ ID NO 64
<211> LENGTH: 192
<212> TYPE: DNA
<213> ORGANISM: ARTIFICIAL SEQUENCE
<220> FEATURE:
<223> OTHER INFORMATION: VH21 SP-ShK(1-35, Q16K)-L10 coding sequence
<220> FEATURE:
<221> NAME/KEY: CDS
<222> LOCATION: (1)..(192)

<400> SEQUENCE: 64

```
atg gaa tgg agc tgg gtc ttt ctc ttc ttc ctg tca gta acg act ggt    48
Met Glu Trp Ser Trp Val Phe Leu Phe Phe Leu Ser Val Thr Thr Gly
1               5                   10                  15 gtc cac tcc cgc agc tgc atc gac acc atc ccc aag agc cgc tgc acc    96
Val His Ser Arg Ser Cys Ile Asp Thr Ile Pro Lys Ser Arg Cys Thr
                20                  25                  30 gcc ttc aag tgc aag cac agc atg aag tac cgc ctg agc ttc tgc cgc   144
Ala Phe Lys Cys Lys His Ser Met Lys Tyr Arg Leu Ser Phe Cys Arg
            35                  40                  45 aag acc tgc ggc acc tgc gga gga gga gga tcc gga gga gga gga agc   192
Lys Thr Cys Gly Thr Cys Gly Gly Gly Gly Ser Gly Gly Gly Gly Ser
        50                  55                  60
```

<210> SEQ ID NO 65
<211> LENGTH: 64
<212> TYPE: PRT
<213> ORGANISM: ARTIFICIAL SEQUENCE
<220> FEATURE:
<223> OTHER INFORMATION: Synthetic Construct

<400> SEQUENCE: 65

Met Glu Trp Ser Trp Val Phe Leu Phe Phe Leu Ser Val Thr Thr Gly
1               5                   10                  15

Val His Ser Arg Ser Cys Ile Asp Thr Ile Pro Lys Ser Arg Cys Thr
                20                  25                  30

Ala Phe Lys Cys Lys His Ser Met Lys Tyr Arg Leu Ser Phe Cys Arg
            35                  40                  45

Lys Thr Cys Gly Thr Cys Gly Gly Gly Gly Ser Gly Gly Gly Gly Ser
        50                  55                  60

<210> SEQ ID NO 66
<211> LENGTH: 30
<212> TYPE: DNA
<213> ORGANISM: ARTIFICIAL SEQUENCE
<220> FEATURE:
<223> OTHER INFORMATION: Primer sequence

<400> SEQUENCE: 66

```
ggaggaggaa gccaggtgca gctggtgcag                                    30

<210> SEQ ID NO 67
<211> LENGTH: 21
<212> TYPE: DNA
<213> ORGANISM: ARTIFICIAL SEQUENCE
<220> FEATURE:
<223> OTHER INFORMATION: Primer sequence

<400> SEQUENCE: 67
catgcggccg ctcatttacc c                                             21

<210> SEQ ID NO 68
<211> LENGTH: 1338
<212> TYPE: DNA
<213> ORGANISM: ARTIFICIAL SEQUENCE
<220> FEATURE:
<223> OTHER INFORMATION: aKLH 120.6-HC coding sequence
<220> FEATURE:
<221> NAME/KEY: CDS
<222> LOCATION: (1)..(1338)

<400> SEQUENCE: 68 cag gtg cag ctg gtg cag tct ggg gct gag gtg aag aag cct ggg gcc     48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac     96
Ser Val Lys Val Ser Cys Lys Ala Ser Gly Tyr Thr Phe Thr Gly Tyr
            20                  25                  30 cac atg cac tgg gtg cga cag gcc cct gga caa ggg ctt gag tgg atg    144
His Met His Trp Val Arg Gln Ala Pro Gly Gln Gly Leu Glu Trp Met
        35                  40                  45 gga tgg atc aac cct aac agt ggt ggc aca aac tat gca cag aag ttt    192
Gly Trp Ile Asn Pro Asn Ser Gly Gly Thr Asn Tyr Ala Gln Lys Phe
    50                  55                  60 cag ggc agg gtc acc atg acc agg gac acg tcc atc agc aca gcc tac    240
Gln Gly Arg Val Thr Met Thr Arg Asp Thr Ser Ile Ser Thr Ala Tyr
65                  70                  75                  80 atg gag ctg agc agg ctg aga tct gac gac acg gcc gtg tat tac tgt    288
Met Glu Leu Ser Arg Leu Arg Ser Asp Asp Thr Ala Val Tyr Tyr Cys
                85                  90                  95 gcg aga gat cgt ggg agc tac tac tgg ttc gac ccc tgg ggc cag gga    336
Ala Arg Asp Arg Gly Ser Tyr Tyr Trp Phe Asp Pro Trp Gly Gln Gly
            100                 105                 110 acc ctg gtc acc gtc tcc tca gcc tcc acc aag ggc cca tcg gtc ttc    384
Thr Leu Val Thr Val Ser Ser Ala Ser Thr Lys Gly Pro Ser Val Phe
        115                 120                 125 ccc ctg gcg ccc tgc tcc agg agc acc tcc gag agc aca gcg gcc ctg    432
Pro Leu Ala Pro Cys Ser Arg Ser Thr Ser Glu Ser Thr Ala Ala Leu
    130                 135                 140 ggc tgc ctg gtc aag gac tac ttc ccc gaa ccg gtg acg gtg tcg tgg    480
Gly Cys Leu Val Lys Asp Tyr Phe Pro Glu Pro Val Thr Val Ser Trp
145                 150                 155                 160 aac tca ggc gct ctg acc agc ggc gtg cac acc ttc cca gct gtc cta    528
Asn Ser Gly Ala Leu Thr Ser Gly Val His Thr Phe Pro Ala Val Leu
                165                 170                 175 cag tcc tca gga ctc tac tcc ctc agc agc gtg gtg acc gtg ccc tcc    576
Gln Ser Ser Gly Leu Tyr Ser Leu Ser Ser Val Val Thr Val Pro Ser
            180                 185                 190 agc aac ttc ggc acc cag acc tac acc tgc aac gta gat cac aag ccc    624
Ser Asn Phe Gly Thr Gln Thr Tyr Thr Cys Asn Val Asp His Lys Pro
        195                 200                 205
```

```
agc aac acc aag gtg gac aag aca gtt gag cgc aaa tgt tgt gtc gag      672
Ser Asn Thr Lys Val Asp Lys Thr Val Glu Arg Lys Cys Cys Val Glu
    210                 215                 220 tgc cca ccg tgc cca gca cca cct gtg gca gga ccg tca gtc ttc ctc      720
Cys Pro Pro Cys Pro Ala Pro Pro Val Ala Gly Pro Ser Val Phe Leu
225                 230                 235                 240 ttc ccc cca aaa ccc aag gac acc ctc atg atc tcc cgg acc cct gag      768
Phe Pro Pro Lys Pro Lys Asp Thr Leu Met Ile Ser Arg Thr Pro Glu
                245                 250                 255 gtc acg tgc gtg gtg gtg gac gtg agc cac gaa gac ccc gag gtc cag      816
Val Thr Cys Val Val Val Asp Val Ser His Glu Asp Pro Glu Val Gln
            260                 265                 270 ttc aac tgg tac gtg gac ggc gtg gag gtg cat aat gcc aag aca aag      864
Phe Asn Trp Tyr Val Asp Gly Val Glu Val His Asn Ala Lys Thr Lys
        275                 280                 285 cca cgg gag gag cag ttc aac agc acg ttc cgt gtg gtc agc gtc ctc      912
Pro Arg Glu Glu Gln Phe Asn Ser Thr Phe Arg Val Val Ser Val Leu
    290                 295                 300 acc gtt gtg cac cag gac tgg ctg aac ggc aag gag tac aag tgc aag      960
Thr Val Val His Gln Asp Trp Leu Asn Gly Lys Glu Tyr Lys Cys Lys
305                 310                 315                 320 gtc tcc aac aaa ggc ctc cca gcc ccc atc gag aaa acc atc tcc aaa     1008
Val Ser Asn Lys Gly Leu Pro Ala Pro Ile Glu Lys Thr Ile Ser Lys
                325                 330                 335 acc aaa ggg cag ccc cga gaa cca cag gtg tac acc ctg ccc cca tcc     1056
Thr Lys Gly Gln Pro Arg Glu Pro Gln Val Tyr Thr Leu Pro Pro Ser
            340                 345                 350 cgg gag gag atg acc aag aac cag gtc agc ctg acc tgc ctg gtc aaa     1104
Arg Glu Glu Met Thr Lys Asn Gln Val Ser Leu Thr Cys Leu Val Lys
        355                 360                 365 ggc ttc tac ccc agc gac atc gcc gtg gag tgg gag agc aat ggg cag     1152
Gly Phe Tyr Pro Ser Asp Ile Ala Val Glu Trp Glu Ser Asn Gly Gln
    370                 375                 380 ccg gag aac aac tac aag acc aca cct ccc atg ctg gac tcc gac ggc     1200
Pro Glu Asn Asn Tyr Lys Thr Thr Pro Pro Met Leu Asp Ser Asp Gly
385                 390                 395                 400 tcc ttc ttc ctc tac agc aag ctc acc gtg gac aag agc agg tgg cag     1248
Ser Phe Phe Leu Tyr Ser Lys Leu Thr Val Asp Lys Ser Arg Trp Gln
                405                 410                 415 cag ggg aac gtc ttc tca tgc tcc gtg atg cat gag gct ctg cac aac     1296
Gln Gly Asn Val Phe Ser Cys Ser Val Met His Glu Ala Leu His Asn
            420                 425                 430 cac tac acg cag aag agc ctc tcc ctg tct ccg ggt aaa tga             1338
His Tyr Thr Gln Lys Ser Leu Ser Leu Ser Pro Gly Lys
        435                 440                 445

<210> SEQ ID NO 69
<211> LENGTH: 445
<212> TYPE: PRT
<213> ORGANISM: ARTIFICIAL SEQUENCE
<220> FEATURE:
<223> OTHER INFORMATION: Synthetic Construct

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
```

```
              50                  55                  60
Gln Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Asp Arg Gly Ser Tyr Tyr Trp Phe Asp Pro Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Asn Phe Gly Thr Gln Thr Tyr Thr Cys Asn Val Asp His Lys Pro
                195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
                260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 70
<211> LENGTH: 509
<212> TYPE: PRT
<213> ORGANISM: ARTIFICIAL SEQUENCE
<220> FEATURE:
```

<223> OTHER INFORMATION: VH21 SP-ShK[1-35, Q16K]-L10-aKLH120.6-HC fusion polypeptide

<400> SEQUENCE: 70

```
Met Glu Trp Ser Trp Val Phe Leu Phe Phe Leu Ser Val Thr Thr Gly
1               5                   10                  15

Val His Ser Arg Ser Cys Ile Asp Thr Ile Pro Lys Ser Arg Cys Thr
            20                  25                  30

Ala Phe Lys Cys Lys His Ser Met Lys Tyr Arg Leu Ser Phe Cys Arg
        35                  40                  45

Lys Thr Cys Gly Thr Cys Gly Gly Gly Ser Gly Gly Gly Ser
    50                  55                  60

Gln Val Gln Leu Val Gln Ser Gly Ala Glu Val Lys Lys Pro Gly Ala
65                  70                  75                  80

Ser Val Lys Val Ser Cys Lys Ala Ser Gly Tyr Thr Phe Thr Gly Tyr
                85                  90                  95

His Met His Trp Val Arg Gln Ala Pro Gly Gln Gly Leu Glu Trp Met
            100                 105                 110

Gly Trp Ile Asn Pro Asn Ser Gly Gly Thr Asn Tyr Ala Gln Lys Phe
        115                 120                 125

Gln Gly Arg Val Thr Met Thr Arg Asp Thr Ser Ile Ser Thr Ala Tyr
    130                 135                 140

Met Glu Leu Ser Arg Leu Arg Ser Asp Asp Thr Ala Val Tyr Tyr Cys
145                 150                 155                 160

Ala Arg Asp Arg Gly Ser Tyr Tyr Trp Phe Asp Pro Trp Gly Gln Gly
                165                 170                 175

Thr Leu Val Thr Val Ser Ser Ala Ser Thr Lys Gly Pro Ser Val Phe
            180                 185                 190

Pro Leu Ala Pro Cys Ser Arg Ser Thr Ser Glu Ser Thr Ala Ala Leu
        195                 200                 205

Gly Cys Leu Val Lys Asp Tyr Phe Pro Glu Pro Val Thr Val Ser Trp
    210                 215                 220

Asn Ser Gly Ala Leu Thr Ser Gly Val His Thr Phe Pro Ala Val Leu
225                 230                 235                 240

Gln Ser Ser Gly Leu Tyr Ser Leu Ser Ser Val Val Thr Val Pro Ser
                245                 250                 255

Ser Asn Phe Gly Thr Gln Thr Tyr Thr Cys Asn Val Asp His Lys Pro
            260                 265                 270

Ser Asn Thr Lys Val Asp Lys Thr Val Glu Arg Lys Cys Cys Val Glu
        275                 280                 285

Cys Pro Pro Cys Pro Ala Pro Pro Val Ala Gly Pro Ser Val Phe Leu
    290                 295                 300

Phe Pro Pro Lys Pro Lys Asp Thr Leu Met Ile Ser Arg Thr Pro Glu
305                 310                 315                 320

Val Thr Cys Val Val Val Asp Val Ser His Glu Asp Pro Glu Val Gln
                325                 330                 335

Phe Asn Trp Tyr Val Asp Gly Val Glu Val His Asn Ala Lys Thr Lys
            340                 345                 350

Pro Arg Glu Glu Gln Phe Asn Ser Thr Phe Arg Val Val Ser Val Leu
        355                 360                 365

Thr Val Val His Gln Asp Trp Leu Asn Gly Lys Glu Tyr Lys Cys Lys
    370                 375                 380

Val Ser Asn Lys Gly Leu Pro Ala Pro Ile Glu Lys Thr Ile Ser Lys
385                 390                 395                 400
```

-continued

| | | | | | | | | | | | |
|---|---|---|---|---|---|---|---|---|---|---|---|
|Thr|Lys|Gly|Gln|Pro|Arg|Glu|Pro|Gln|Val|Tyr|Thr|Leu|Pro|Pro|Ser|
| | | |405| | | |410| | | |415|

Arg Glu Glu Met Thr Lys Asn Gln Val Ser Leu Thr Cys Leu Val Lys
                 420                425             430

Gly Phe Tyr Pro Ser Asp Ile Ala Val Glu Trp Glu Ser Asn Gly Gln
         435                 440                   445

Pro Glu Asn Asn Tyr Lys Thr Thr Pro Pro Met Leu Asp Ser Asp Gly
450                   455                   460

Ser Phe Phe Leu Tyr Ser Lys Leu Thr Val Asp Lys Ser Arg Trp Gln
465              470               475            480

Gln Gly Asn Val Phe Ser Cys Ser Val Met His Glu Ala Leu His Asn
         485                 490                  495

His Tyr Thr Gln Lys Ser Leu Ser Leu Ser Pro Gly Lys
         500                 505

<210> SEQ ID NO 71
<211> LENGTH: 29
<212> TYPE: DNA
<213> ORGANISM: ARTIFICIAL SEQUENCE
<220> FEATURE:
<223> OTHER INFORMATION: Primer sequence

<400> SEQUENCE: 71
catctggatg tcgcttcctc ctcctccgg                                          29

<210> SEQ ID NO 72
<211> LENGTH: 32
<212> TYPE: DNA
<213> ORGANISM: ARTIFICIAL SEQUENCE
<220> FEATURE:
<223> OTHER INFORMATION: Primer sequence

<400> SEQUENCE: 72
ggaggaggaa gcgacatcca gatgacccag tc                                 32

<210> SEQ ID NO 73
<211> LENGTH: 21
<212> TYPE: DNA
<213> ORGANISM: ARTIFICIAL SEQUENCE
<220> FEATURE:
<223> OTHER INFORMATION: Primer sequence

<400> SEQUENCE: 73
catctcgagc ggccgctcaa c                                                       21

<210> SEQ ID NO 74
<211> LENGTH: 1476
<212> TYPE: DNA
<213> ORGANISM: ARTIFICIAL SEQUENCE
<220> FEATURE:
<223> OTHER INFORMATION: 10164 HC(Y125A)-ShK(1-35, Q16K) coding sequence
<220> FEATURE:
<221> NAME/KEY: CDS
<222> LOCATION: (1)..(1476)

<400> SEQUENCE: 74 cag gtg cag ctg cag gag tcg ggc cca gga ctg gtg aag cct tca cag      48
Gln Val Gln Leu Gln Glu Ser Gly Pro Gly Leu Val Lys Pro Ser Gln
1              5                 10                15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
              20                25                30 gat tac ttc tgg agc tgg atc cgc cag ctc cca ggg aag ggc ctg gag    144
Asp Tyr Phe Trp Ser Trp Ile Arg Gln Leu Pro Gly Lys Gly Leu Glu

```
                    35                  40                  45
tgg att ggg cac atc cat aac agt ggg acc acc tac tac aat ccg tcc    192
Trp Ile Gly His Ile His Asn Ser Gly Thr Thr Tyr Tyr Asn Pro Ser
 50                  55                  60 ctc aag agt cga gtt acc ata tca gta gac acg tct aag aag cag ttc    240
Leu Lys Ser Arg Val Thr Ile Ser Val Asp Thr Ser Lys Lys Gln Phe
 65                  70                  75                  80 tcc ctg agg ctg agt tct gtg act gcc gcg gac acg gcc gta tat tac    288
Ser Leu Arg Leu Ser Ser Val Thr Ala Ala Asp Thr Ala Val Tyr Tyr
                     85                  90                  95 tgt gcg aga gat cga ggg ggt gac tac gct tat ggt atg gac gtc tgg    336
Cys Ala Arg Asp Arg Gly Gly Asp Tyr Ala Tyr Gly Met Asp Val Trp
                100                 105                 110 ggc caa ggg acc acg gtc acc gtc tcc tca gct agc acc aag ggc cca    384
Gly Gln Gly Thr Thr Val Thr Val Ser Ser Ala Ser Thr Lys Gly Pro
            115                 120                 125 tcg gtc ttc ccc ctg gcg ccc tgc tcc agg agc acc tcc gag agc aca    432
Ser Val Phe Pro Leu Ala Pro Cys Ser Arg Ser Thr Ser Glu Ser Thr
        130                 135                 140 gcg gcc ctg ggc tgc ctg gtc aag gac tac ttc ccc gaa ccg gtg acg    480
Ala Ala Leu Gly Cys Leu Val Lys Asp Tyr Phe Pro Glu Pro Val Thr
145                 150                 155                 160 gtg tcg tgg aac tca ggc gct ctg acc agc ggc gtg cac acc ttc cca    528
Val Ser Trp Asn Ser Gly Ala Leu Thr Ser Gly Val His Thr Phe Pro
                165                 170                 175 gct gtc cta cag tcc tca gga ctc tac tcc ctc agc agc gtg gtg acc    576
Ala Val Leu Gln Ser Ser Gly Leu Tyr Ser Leu Ser Ser Val Val Thr
            180                 185                 190 gtg ccc tcc agc aac ttc ggc acc cag acc tac acc tgc aac gta gat    624
Val Pro Ser Ser Asn Phe Gly Thr Gln Thr Tyr Thr Cys Asn Val Asp
        195                 200                 205 cac aag ccc agc aac acc aag gtg gac aag aca gtt gag cgc aaa tgt    672
His Lys Pro Ser Asn Thr Lys Val Asp Lys Thr Val Glu Arg Lys Cys
    210                 215                 220 tgt gtc gag tgc cca ccg tgc cca gca cca cct gtg gca gga ccg tca    720
Cys Val Glu Cys Pro Pro Cys Pro Ala Pro Pro Val Ala Gly Pro Ser
225                 230                 235                 240 gtc ttc ctc ttc ccc cca aaa ccc aag gac acc ctc atg atc tcc cgg    768
Val Phe Leu Phe Pro Pro Lys Pro Lys Asp Thr Leu Met Ile Ser Arg
                245                 250                 255 acc cct gag gtc acg tgc gtg gtg gtg gac gtg agc cac gaa gac ccc    816
Thr Pro Glu Val Thr Cys Val Val Val Asp Val Ser His Glu Asp Pro
            260                 265                 270 gag gtc cag ttc aac tgg tac gtg gac ggc gtg gag gtg cat aat gcc    864
Glu Val Gln Phe Asn Trp Tyr Val Asp Gly Val Glu Val His Asn Ala
        275                 280                 285 aag aca aag cca cgg gag gag cag ttc aac agc acg ttc cgt gtg gtc    912
Lys Thr Lys Pro Arg Glu Glu Gln Phe Asn Ser Thr Phe Arg Val Val
    290                 295                 300 agc gtc ctc acc gtt gtg cac cag gac tgg ctg aac ggc aag gag tac    960
Ser Val Leu Thr Val Val His Gln Asp Trp Leu Asn Gly Lys Glu Tyr
305                 310                 315                 320 aag tgc aag gtc tcc aac aaa ggc ctc cca gcc ccc atc gag aaa acc   1008
Lys Cys Lys Val Ser Asn Lys Gly Leu Pro Ala Pro Ile Glu Lys Thr
                325                 330                 335 atc tcc aaa acc aaa ggg cag ccc cga gaa cca cag gtg tac acc ctg   1056
Ile Ser Lys Thr Lys Gly Gln Pro Arg Glu Pro Gln Val Tyr Thr Leu
            340                 345                 350 ccc cca tcc cgg gag gag atg acc aag aac cag gtc agc ctg acc tgc   1104
Pro Pro Ser Arg Glu Glu Met Thr Lys Asn Gln Val Ser Leu Thr Cys
```

```
                355                 360                 365
ctg gtc aaa ggc ttc tac ccc agc gac atc gcc gtg gag tgg gag agc        1152
Leu Val Lys Gly Phe Tyr Pro Ser Asp Ile Ala Val Glu Trp Glu Ser
    370                 375                 380 aat ggg cag ccg gag aac aac tac aag acc aca cct ccc atg ctg gac        1200
Asn Gly Gln Pro Glu Asn Asn Tyr Lys Thr Thr Pro Pro Met Leu Asp
385                 390                 395                 400 tcc gac ggc tcc ttc ttc ctc tac agc aag ctc acc gtg gac aag agc        1248
Ser Asp Gly Ser Phe Phe Leu Tyr Ser Lys Leu Thr Val Asp Lys Ser
                405                 410                 415 agg tgg cag cag ggg aac gtc ttc tca tgc tcc gtg atg cat gag gct        1296
Arg Trp Gln Gln Gly Asn Val Phe Ser Cys Ser Val Met His Glu Ala
    420                 425                 430 ctg cac aac cac tac acg cag aag agc ctc tcc ctg tct ccg ggt gga        1344
Leu His Asn His Tyr Thr Gln Lys Ser Leu Ser Leu Ser Pro Gly Gly
        435                 440                 445 gga gga gga tcc gga gga gga gga agc cgc agc tgc atc gac acc atc        1392
Gly Gly Gly Ser Gly Gly Gly Gly Ser Arg Ser Cys Ile Asp Thr Ile
450                 455                 460 ccc aag agc cgc tgc acc gcc ttc aag tgc aag cac agc atg aag tac        1440
Pro Lys Ser Arg Cys Thr Ala Phe Lys Cys Lys His Ser Met Lys Tyr
465                 470                 475                 480 cgc ctg agc ttc tgc cgc aag acc tgc ggc acc tgc                         1476
Arg Leu Ser Phe Cys Arg Lys Thr Cys Gly Thr Cys
                485                 490

<210> SEQ ID NO 75
<211> LENGTH: 492
<212> TYPE: PRT
<213> ORGANISM: ARTIFICIAL SEQUENCE
<220> FEATURE:
<223> OTHER INFORMATION: Synthetic Construct

<400> SEQUENCE: 75

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Ala Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

-continued

Val Pro Ser Ser Asn Phe Gly Thr Gln Thr Tyr Thr Cys Asn Val Asp
                195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Phe Arg Val Val
290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Gly
                435                 440                 445

Gly Gly Gly Ser Gly Gly Gly Gly Ser Arg Ser Cys Ile Asp Thr Ile
    450                 455                 460

Pro Lys Ser Arg Cys Thr Ala Phe Lys Cys Lys His Ser Met Lys Tyr
465                 470                 475                 480

Arg Leu Ser Phe Cys Arg Lys Thr Cys Gly Thr Cys
                485                 490

<210> SEQ ID NO 76
<211> LENGTH: 35
<212> TYPE: PRT
<213> ORGANISM: ARTIFICIAL SEQUENCE
<220> FEATURE:
<223> OTHER INFORMATION: ShK[1-35, Q16K] polypeptide sequence

<400> SEQUENCE: 76

Arg Ser Cys Ile Asp Thr Ile Pro Lys Ser Arg Cys Thr Ala Phe Lys
1               5                   10                  15

Cys Lys His Ser Met Lys Tyr Arg Leu Ser Phe Cys Arg Lys Thr Cys
                20                  25                  30

Gly Thr Cys
        35

<210> SEQ ID NO 77

<400> SEQUENCE: 77

000

<210> SEQ ID NO 78
<211> LENGTH: 1098
<212> TYPE: DNA
<213> ORGANISM: ARTIFICIAL SEQUENCE
<220> FEATURE:
<223> OTHER INFORMATION: Coding sequence
<220> FEATURE:
<221> NAME/KEY: CDS
<222> LOCATION: (1)..(1098)

<400> SEQUENCE: 78

```
atg gac atg agg gtg ccc gct cag ctc ctg ggg ctc ctg ctg ctg tgg      48
Met Asp Met Arg Val Pro Ala Gln Leu Leu Gly Leu Leu Leu Leu Trp
1               5                  10                  15 ctg aga ggt gcg atg gac atg agg gtg ccc gct cag ctc ctg ggg ctc      96
Leu Arg Gly Ala Met Asp Met Arg Val Pro Ala Gln Leu Leu Gly Leu
            20                  25                  30 ctg ctg ctg tgg ctg aga ggt gcg cgc tgt cag gtg cag ctg gtg gag     144
Leu Leu Leu Trp Leu Arg Gly Ala Arg Cys Gln Val Gln Leu Val Glu
        35                  40                  45 tct ggg gga ggc gtg gtc cag cct ggg agg tcc ctg aga ctc tcc tgt     192
Ser Gly Gly Gly Val Val Gln Pro Gly Arg Ser Leu Arg Leu Ser Cys
50                  55                  60 gca gcg tct gga ttc acc ttc agt agc tat ggc atg cac tgg gtc cgc     240
Ala Ala Ser Gly Phe Thr Phe Ser Ser Tyr Gly Met His Trp Val Arg
65                  70                  75                  80 cag gct cca ggc aag ggg ctg gag tgg gtg gca gtt ata tgg tat gat     288
Gln Ala Pro Gly Lys Gly Leu Glu Trp Val Ala Val Ile Trp Tyr Asp
                85                  90                  95 gga agt aat aaa tac tat gca gac tcc gtg aag ggc cga ttc act atc     336
Gly Ser Asn Lys Tyr Tyr Ala Asp Ser Val Lys Gly Arg Phe Thr Ile
            100                 105                 110 tcc aga gac aat tcc aag aac acg ctg tat ctg caa atg aac agc ctg     384
Ser Arg Asp Asn Ser Lys Asn Thr Leu Tyr Leu Gln Met Asn Ser Leu
        115                 120                 125 aga gcc gag gac acg gct gtg tat tac tgt gcg agg tat aac ttc aac     432
Arg Ala Glu Asp Thr Ala Val Tyr Tyr Cys Ala Arg Tyr Asn Phe Asn
    130                 135                 140 tac ggt atg gac gtc tgg ggc caa ggg acc acg gtc acc gtc tct agt     480
Tyr Gly Met Asp Val Trp Gly Gln Gly Thr Thr Val Thr Val Ser Ser
145                 150                 155                 160 gcc tcc acc aag ggc cca tcg gtc ttc ccc ctg gcg ccc tgc tcc agg     528
Ala Ser Thr Lys Gly Pro Ser Val Phe Pro Leu Ala Pro Cys Ser Arg
                165                 170                 175 agc acc tcc gag agc aca gcg gcc ctg ggc tgc ctg gtc aag gac tac     576
Ser Thr Ser Glu Ser Thr Ala Ala Leu Gly Cys Leu Val Lys Asp Tyr
            180                 185                 190 ttc ccc gaa ccg gtg acg gtg tcg tgg aac tca ggc gct ctg acc agc     624
Phe Pro Glu Pro Val Thr Val Ser Trp Asn Ser Gly Ala Leu Thr Ser
        195                 200                 205 ggc gtg cac acc ttc cca gct gtc cta cag tcc tca gga ctc tac tcc     672
Gly Val His Thr Phe Pro Ala Val Leu Gln Ser Ser Gly Leu Tyr Ser
    210                 215                 220 ctc agc agc gtg gtg acc gtg ccc tcc agc aac ttc ggc acc cag acc     720
Leu Ser Ser Val Val Thr Val Pro Ser Ser Asn Phe Gly Thr Gln Thr
225                 230                 235                 240 tac acc tgc aac gta gat cac aag ccc agc aac acc aag gtg gac aag     768
Tyr Thr Cys Asn Val Asp His Lys Pro Ser Asn Thr Lys Val Asp Lys
                245                 250                 255
```

-continued

```
aca gtt gag cgc aaa tgt tgt gtc gag tgc cca ccg tgc cca gca cca       816
Thr Val Glu Arg Lys Cys Cys Val Glu Cys Pro Pro Cys Pro Ala Pro
        260                 265                 270 cct gtg gca gga ccg tca gtc ttc ctc ttc ccc cca aaa ccc aag gac       864
Pro Val Ala Gly Pro Ser Val Phe Leu Phe Pro Pro Lys Pro Lys Asp
    275                 280                 285 acc ctc atg atc tcc cgg acc cct gag gtc acg tgc gtg gtg gtg gac       912
Thr Leu Met Ile Ser Arg Thr Pro Glu Val Thr Cys Val Val Val Asp
290                 295                 300 gtg agc cac gaa gac ccc gag gtc cag ttc aac tgg tac gtg gac ggc       960
Val Ser His Glu Asp Pro Glu Val Gln Phe Asn Trp Tyr Val Asp Gly
305                 310                 315                 320 gtg gag gtg cat aat gcc aag aca aag cca cgg gag gag cag ttc aac      1008
Val Glu Val His Asn Ala Lys Thr Lys Pro Arg Glu Glu Gln Phe Asn
            325                 330                 335 agc acg ttc cgt gtg gtc agc gtc ctc acc gtt gtg cac cag gac tgg      1056
Ser Thr Phe Arg Val Val Ser Val Leu Thr Val Val His Gln Asp Trp
        340                 345                 350 ctg aac ggc aag gag tac aag tgc aag gtc tcc aac aaa ggc              1098
Leu Asn Gly Lys Glu Tyr Lys Cys Lys Val Ser Asn Lys Gly
    355                 360                 365

<210> SEQ ID NO 79
<211> LENGTH: 366
<212> TYPE: PRT
<213> ORGANISM: ARTIFICIAL SEQUENCE
<220> FEATURE:
<223> OTHER INFORMATION: Synthetic Construct

<400> SEQUENCE: 79

Met Asp Met Arg Val Pro Ala Gln Leu Leu Gly Leu Leu Leu Leu Trp
1               5                   10                  15

Leu Arg Gly Ala Met Asp Met Arg Val Pro Ala Gln Leu Leu Gly Leu
                20                  25                  30

Leu Leu Leu Trp Leu Arg Gly Ala Arg Cys Gln Val Gln Leu Val Glu
            35                  40                  45

Ser Gly Gly Gly Val Val Gln Pro Gly Arg Ser Leu Arg Leu Ser Cys
        50                  55                  60

Ala Ala Ser Gly Phe Thr Phe Ser Ser Tyr Gly Met His Trp Val Arg
65                  70                  75                  80

Gln Ala Pro Gly Lys Gly Leu Glu Trp Val Ala Val Ile Trp Tyr Asp
                85                  90                  95

Gly Ser Asn Lys Tyr Tyr Ala Asp Ser Val Lys Gly Arg Phe Thr Ile
                100                 105                 110

Ser Arg Asp Asn Ser Lys Asn Thr Leu Tyr Leu Gln Met Asn Ser Leu
            115                 120                 125

Arg Ala Glu Asp Thr Ala Val Tyr Tyr Cys Ala Arg Tyr Asn Phe Asn
        130                 135                 140

Tyr Gly Met Asp Val Trp Gly Gln Gly Thr Thr Val Thr Val Ser Ser
145                 150                 155                 160

Ala Ser Thr Lys Gly Pro Ser Val Phe Pro Leu Ala Pro Cys Ser Arg
                165                 170                 175

Ser Thr Ser Glu Ser Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220
```

```
Leu Ser Ser Val Val Thr Val Pro Ser Ser Asn Phe Gly Thr Gln Thr
225                 230                 235                 240

Tyr Thr Cys Asn Val Asp His Lys Pro Ser Asn Thr Lys Val Asp Lys
                245                 250                 255

Thr Val Glu Arg Lys Cys Cys Val Glu Cys Pro Pro Cys Pro Ala Pro
            260                 265                 270

Pro Val Ala Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Phe Arg Val Val Ser Val Leu Thr Val Val His Gln Asp Trp
            340                 345                 350

Leu Asn Gly Lys Glu Tyr Lys Cys Lys Val Ser Asn Lys Gly
        355                 360                 365

<210> SEQ ID NO 80
<211> LENGTH: 501
<212> TYPE: DNA
<213> ORGANISM: ARTIFICIAL SEQUENCE
<220> FEATURE:
<223> OTHER INFORMATION: truncated IgG2 Fc-L10-ShK(1-35, Q16K) coding
      sequence
<220> FEATURE:
<221> NAME/KEY: CDS
<222> LOCATION: (1)..(501)

<400> SEQUENCE: 80 ctc cca gcc ccc atc gag aaa acc atc tcc aaa acc aaa ggg cag ccc      48
Leu Pro Ala Pro Ile Glu Lys Thr Ile Ser Lys Thr Lys Gly Gln Pro
1               5                   10                  15 cga gaa cca cag gtg tac acc ctg ccc cca tcc cgg gag gag atg acc      96
Arg Glu Pro Gln Val Tyr Thr Leu Pro Pro Ser Arg Glu Glu Met Thr
            20                  25                  30 aag aac cag gtc agc ctg acc tgc ctg gtc aaa ggc ttc tac ccc agc     144
Lys Asn Gln Val Ser Leu Thr Cys Leu Val Lys Gly Phe Tyr Pro Ser
        35                  40                  45 gac atc gcc gtg gag tgg gag agc aat ggg cag ccg gag aac aac tac     192
Asp Ile Ala Val Glu Trp Glu Ser Asn Gly Gln Pro Glu Asn Asn Tyr
    50                  55                  60 aag acc aca cct ccc atg ctg gac tcc gac ggc tcc ttc ttc ctc tac     240
Lys Thr Thr Pro Pro Met Leu Asp Ser Asp Gly Ser Phe Phe Leu Tyr
65                  70                  75                  80 agc aag ctc acc gtg gac aag agc agg tgg cag cag ggg aac gtc ttc     288
Ser Lys Leu Thr Val Asp Lys Ser Arg Trp Gln Gln Gly Asn Val Phe
                85                  90                  95 tca tgc tcc gtg atg cat gag gct ctg cac aac cac tac acg cag aag     336
Ser Cys Ser Val Met His Glu Ala Leu His Asn His Tyr Thr Gln Lys
            100                 105                 110 agc ctc tcc ctg tct ccg ggt aaa gga gga gga tcc gga gga             384
Ser Leu Ser Leu Ser Pro Gly Lys Gly Gly Gly Gly Ser Gly Gly Gly
        115                 120                 125 gga agc cgc agc tgc atc gac acc atc ccc aag agc cgc tgc acc gcc     432
Gly Ser Arg Ser Cys Ile Asp Thr Ile Pro Lys Ser Arg Cys Thr Ala
    130                 135                 140 ttc aag tgc aag cac agc atg aag tac cgc ctg agc ttc tgc cgc aag     480
Phe Lys Cys Lys His Ser Met Lys Tyr Arg Leu Ser Phe Cys Arg Lys
145                 150                 155                 160
```

```
acc tgc ggc acc tgc taa tga                                      501
Thr Cys Gly Thr Cys
            165
```

<210> SEQ ID NO 81
<211> LENGTH: 165
<212> TYPE: PRT
<213> ORGANISM: ARTIFICIAL SEQUENCE
<220> FEATURE:
<223> OTHER INFORMATION: Synthetic Construct

<400> SEQUENCE: 81

Leu Pro Ala Pro Ile Glu Lys Thr Ile Ser Lys Thr Lys Gly Gln Pro
1               5                   10                  15

Arg Glu Pro Gln Val Tyr Thr Leu Pro Pro Ser Arg Glu Glu Met Thr
            20                  25                  30

Lys Asn Gln Val Ser Leu Thr Cys Leu Val Lys Gly Phe Tyr Pro Ser
        35                  40                  45

Asp Ile Ala Val Glu Trp Glu Ser Asn Gly Gln Pro Glu Asn Asn Tyr
    50                  55                  60

Lys Thr Thr Pro Pro Met Leu Asp Ser Asp Gly Ser Phe Phe Leu Tyr
65                  70                  75                  80

Ser Lys Leu Thr Val Asp Lys Ser Arg Trp Gln Gln Gly Asn Val Phe
                85                  90                  95

Ser Cys Ser Val Met His Glu Ala Leu His Asn His Tyr Thr Gln Lys
            100                 105                 110

Ser Leu Ser Leu Ser Pro Gly Lys Gly Gly Gly Ser Gly Gly Gly
        115                 120                 125

Gly Ser Arg Ser Cys Ile Asp Thr Ile Pro Lys Ser Arg Cys Thr Ala
130                 135                 140

Phe Lys Cys Lys His Ser Met Lys Tyr Arg Leu Ser Phe Cys Arg Lys
145                 150                 155                 160

Thr Cys Gly Thr Cys
            165

<210> SEQ ID NO 82
<211> LENGTH: 441
<212> TYPE: PRT
<213> ORGANISM: ARTIFICIAL SEQUENCE
<220> FEATURE:
<223> OTHER INFORMATION: huTR2 long-huFc ( IgG1) fusion protein

<400> SEQUENCE: 82

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro

```
            115                 120                 125
Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
        195                 200                 205

Cys Ser Leu Ser Gly Val Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 83
<211> LENGTH: 37
<212> TYPE: DNA
<213> ORGANISM: ARTIFICIAL SEQUENCE
<220> FEATURE:
<223> OTHER INFORMATION: Forward primer

<400> SEQUENCE: 83 tttttttgc gcgctgtgac atccagatga cccagtc                              37

<210> SEQ ID NO 84
<211> LENGTH: 32
<212> TYPE: DNA
<213> ORGANISM: ARTIFICIAL SEQUENCE
<220> FEATURE:
```

<223> OTHER INFORMATION: Reverse primer

<400> SEQUENCE: 84
aaaaaacgta cgtttgatat ccactttggt cc                          32

<210> SEQ ID NO 85
<211> LENGTH: 978
<212> TYPE: DNA
<213> ORGANISM: Homo sapiens
<220> FEATURE:
<221> NAME/KEY: misc_feature
<223> OTHER INFORMATION: DNA encoding IgG2 heavy chain (HC) constant
    domain
<220> FEATURE:
<221> NAME/KEY: CDS
<222> LOCATION: (1)..(978)

<400> SEQUENCE: 85

| | | | | | | | | | | | | | | | | |
|---|---|---|---|---|---|---|---|---|---|---|---|---|---|---|---|---|---|
| gct | agc | acc | aag | ggc | cca | tcg | gtc | ttc | ccc | ctg | gcg | ccc | tgc | tcc | agg | | 48 |
| Ala | Ser | Thr | Lys | Gly | Pro | Ser | Val | Phe | Pro | Leu | Ala | Pro | Cys | Ser | Arg | | |
| 1 | | | | 5 | | | | | 10 | | | | | 15 | | | |
| agc | acc | tcc | gag | agc | aca | gcg | gcc | ctg | ggc | tgc | ctg | gtc | aag | gac | tac | | 96 |
| Ser | Thr | Ser | Glu | Ser | Thr | Ala | Ala | Leu | Gly | Cys | Leu | Val | Lys | Asp | Tyr | | |
| | | | 20 | | | | | 25 | | | | | 30 | | | | |
| ttc | ccc | gaa | ccg | gtg | acg | gtg | tcg | tgg | aac | tca | ggc | gct | ctg | acc | agc | | 144 |
| Phe | Pro | Glu | Pro | Val | Thr | Val | Ser | Trp | Asn | Ser | Gly | Ala | Leu | Thr | Ser | | |
| | | | | 35 | | | | | 40 | | | | | 45 | | | |
| ggc | gtg | cac | acc | ttc | cca | gct | gtc | cta | cag | tcc | tca | gga | ctc | tac | tcc | | 192 |
| Gly | Val | His | Thr | Phe | Pro | Ala | Val | Leu | Gln | Ser | Ser | Gly | Leu | Tyr | Ser | | |
| | | 50 | | | | | 55 | | | | | 60 | | | | | |
| ctc | agc | agc | gtg | gtg | acc | gtg | ccc | tcc | agc | aac | ttc | ggc | acc | cag | acc | | 240 |
| Leu | Ser | Ser | Val | Val | Thr | Val | Pro | Ser | Ser | Asn | Phe | Gly | Thr | Gln | Thr | | |
| 65 | | | | | 70 | | | | | 75 | | | | | 80 | | |
| tac | acc | tgc | aac | gta | gat | cac | aag | ccc | agc | aac | acc | aag | gtg | gac | aag | | 288 |
| Tyr | Thr | Cys | Asn | Val | Asp | His | Lys | Pro | Ser | Asn | Thr | Lys | Val | Asp | Lys | | |
| | | | | 85 | | | | | 90 | | | | | 95 | | | |
| aca | gtt | gag | cgc | aaa | tgt | tgt | gtc | gag | tgc | cca | ccg | tgc | cca | gca | cca | | 336 |
| Thr | Val | Glu | Arg | Lys | Cys | Cys | Val | Glu | Cys | Pro | Pro | Cys | Pro | Ala | Pro | | |
| | | | 100 | | | | | 105 | | | | | 110 | | | | |
| cct | gtg | gca | gga | ccg | tca | gtc | ttc | ctc | ttc | ccc | cca | aaa | ccc | aag | gac | | 384 |
| Pro | Val | Ala | Gly | Pro | Ser | Val | Phe | Leu | Phe | Pro | Pro | Lys | Pro | Lys | Asp | | |
| | | 115 | | | | | 120 | | | | | 125 | | | | | |
| acc | ctc | atg | atc | tcc | cgg | acc | cct | gag | gtc | acg | tgc | gtg | gtg | gtg | gac | | 432 |
| Thr | Leu | Met | Ile | Ser | Arg | Thr | Pro | Glu | Val | Thr | Cys | Val | Val | Val | Asp | | |
| | 130 | | | | | 135 | | | | | 140 | | | | | | |
| gtg | agc | cac | gaa | gac | ccc | gag | gtc | cag | ttc | aac | tgg | tac | gtg | gac | ggc | | 480 |
| Val | Ser | His | Glu | Asp | Pro | Glu | Val | Gln | Phe | Asn | Trp | Tyr | Val | Asp | Gly | | |
| 145 | | | | | 150 | | | | | 155 | | | | | 160 | | |
| gtg | gag | gtg | cat | aat | gcc | aag | aca | aag | cca | cgg | gag | gag | cag | ttc | aac | | 528 |
| Val | Glu | Val | His | Asn | Ala | Lys | Thr | Lys | Pro | Arg | Glu | Glu | Gln | Phe | Asn | | |
| | | | | 165 | | | | | 170 | | | | | 175 | | | |
| agc | acg | ttc | cgt | gtg | gtc | agc | gtc | ctc | acc | gtt | gtg | cac | cag | gac | tgg | | 576 |
| Ser | Thr | Phe | Arg | Val | Val | Ser | Val | Leu | Thr | Val | Val | His | Gln | Asp | Trp | | |
| | | | 180 | | | | | 185 | | | | | 190 | | | | |
| ctg | aac | ggc | aag | gag | tac | aag | tgc | aag | gtc | tcc | aac | aaa | ggc | ctc | cca | | 624 |
| Leu | Asn | Gly | Lys | Glu | Tyr | Lys | Cys | Lys | Val | Ser | Asn | Lys | Gly | Leu | Pro | | |
| | | 195 | | | | | 200 | | | | | 205 | | | | | |
| gcc | ccc | atc | gag | aaa | acc | atc | tcc | aaa | acc | aaa | ggg | cag | ccc | cga | gaa | | 672 |
| Ala | Pro | Ile | Glu | Lys | Thr | Ile | Ser | Lys | Thr | Lys | Gly | Gln | Pro | Arg | Glu | | |
| | 210 | | | | | 215 | | | | | 220 | | | | | | |
| cca | cag | gtg | tac | acc | ctg | ccc | cca | tcc | cgg | gag | gag | atg | acc | aag | aac | | 720 |
| Pro | Gln | Val | Tyr | Thr | Leu | Pro | Pro | Ser | Arg | Glu | Glu | Met | Thr | Lys | Asn | | |
| 225 | | | | | 230 | | | | | 235 | | | | | 240 | | |

```
cag gtc agc ctg acc tgc ctg gtc aaa ggc ttc tac ccc agc gac atc      768
Gln Val Ser Leu Thr Cys Leu Val Lys Gly Phe Tyr Pro Ser Asp Ile
            245                 250                 255 gcc gtg gag tgg gag agc aat ggg cag ccg gag aac aac tac aag acc      816
Ala Val Glu Trp Glu Ser Asn Gly Gln Pro Glu Asn Asn Tyr Lys Thr
        260                 265                 270 aca cct ccc atg ctg gac tcc gac ggc tcc ttc ttc ctc tac agc aag      864
Thr Pro Pro Met Leu Asp Ser Asp Gly Ser Phe Phe Leu Tyr Ser Lys
    275                 280                 285 ctc acc gtg gac aag agc agg tgg cag cag ggg aac gtc ttc tca tgc      912
Leu Thr Val Asp Lys Ser Arg Trp Gln Gln Gly Asn Val Phe Ser Cys
290                 295                 300 tcc gtg atg cat gag gct ctg cac aac cac tac acg cag aag agc ctc      960
Ser Val Met His Glu Ala Leu His Asn His Tyr Thr Gln Lys Ser Leu
305                 310                 315                 320 tcc ctg tct ccg ggt aaa                                              978
Ser Leu Ser Pro Gly Lys
                325
```

<210> SEQ ID NO 86
<211> LENGTH: 326
<212> TYPE: PRT
<213> ORGANISM: Homo sapiens

<400> SEQUENCE: 86

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 87
<211> LENGTH: 330
<212> TYPE: PRT
<213> ORGANISM: Homo sapiens
<220> FEATURE:
<221> NAME/KEY: MISC_FEATURE
<223> OTHER INFORMATION: hIgG1z heavy chain (HC) constant domain

<400> SEQUENCE: 87

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 88
<211> LENGTH: 330
<212> TYPE: PRT
<213> ORGANISM: Homo sapiens
<220> FEATURE:
<221> NAME/KEY: MISC_FEATURE
<223> OTHER INFORMATION: hIgG1za heavy chain (HC) constant domain

<400> SEQUENCE: 88

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
            325                 330

<210> SEQ ID NO 89
<211> LENGTH: 312
<212> TYPE: PRT
<213> ORGANISM: Homo sapiens
<220> FEATURE:
<221> NAME/KEY: MISC_FEATURE
<223> OTHER INFORMATION: huIL-17R-FpH

<400> SEQUENCE: 89

Leu Arg Leu Leu Asp His Arg Ala Leu Val Cys Ser Gln Pro Gly Leu
1               5                   10                  15

Asn Cys Thr Val Lys Asn Ser Thr Cys Leu Asp Asp Ser Trp Ile His
            20                  25                  30

Pro Arg Asn Leu Thr Pro Ser Ser Pro Lys Asp Leu Gln Ile Gln Leu
            35                  40                  45

His Phe Ala His Thr Gln Gln Gly Asp Leu Phe Pro Val Ala His Ile
    50                  55                  60

Glu Trp Thr Leu Gln Thr Asp Ala Ser Ile Leu Tyr Leu Glu Gly Ala
65                  70                  75                  80

Glu Leu Ser Val Leu Gln Leu Asn Thr Asn Glu Arg Leu Cys Val Arg
                85                  90                  95

Phe Glu Phe Leu Ser Lys Leu Arg His His Arg Arg Trp Arg Phe
            100                 105                 110

Thr Phe Ser His Phe Val Val Asp Pro Asp Gln Glu Tyr Glu Val Thr
    115                 120                 125

Val His His Leu Pro Lys Pro Ile Pro Asp Gly Asp Pro Asn His Gln
130                 135                 140

Ser Lys Asn Phe Leu Val Pro Asp Cys Glu His Ala Arg Met Lys Val
145                 150                 155                 160

Thr Thr Pro Cys Met Ser Ser Gly Ser Leu Trp Asp Pro Asn Ile Thr
                165                 170                 175

Val Glu Thr Leu Glu Ala His Gln Leu Arg Val Ser Phe Thr Leu Trp
            180                 185                 190

Asn Glu Ser Thr His Tyr Gln Ile Leu Leu Thr Ser Phe Pro His Met
    195                 200                 205

Glu Asn His Ser Cys Phe Glu His Met His His Ile Pro Ala Pro Arg
210                 215                 220

Pro Glu Glu Phe His Gln Arg Ser Asn Val Thr Leu Thr Leu Arg Asn
225                 230                 235                 240

Leu Lys Gly Cys Cys Arg His Gln Val Gln Ile Gln Pro Phe Phe Ser
                245                 250                 255

Ser Cys Leu Asn Asp Cys Leu Arg His Ser Ala Thr Val Ser Cys Pro
            260                 265                 270

Glu Met Pro Asp Thr Pro Glu Pro Ile Pro Asp Tyr Met Pro Leu Trp
    275                 280                 285

Glu Pro Arg Ser Gly Ser Ser Asp Tyr Lys Asp Asp Asp Lys Gly
290                 295                 300

Ser Ser His His His His His His
305                 310

<210> SEQ ID NO 90
<211> LENGTH: 330
<212> TYPE: PRT
<213> ORGANISM: Homo sapiens
```

```
<220> FEATURE:
<221> NAME/KEY: MISC_FEATURE
<223> OTHER INFORMATION: hIgG1fa heavy chain (HC) constant domain

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 91
<211> LENGTH: 106
<212> TYPE: PRT
<213> ORGANISM: Homo sapiens
<220> FEATURE:
<221> NAME/KEY: MISC_FEATURE
<223> OTHER INFORMATION: CL-1 human immunoglobulin light chain (LC)
      constant region

<400> SEQUENCE: 91
```

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 92
<211> LENGTH: 106
<212> TYPE: PRT
<213> ORGANISM: Homo sapiens
<220> FEATURE:
<221> NAME/KEY: MISC_FEATURE
<223> OTHER INFORMATION: CL-2 human immunoglobulin light chain (LC)
      constant region

<400> SEQUENCE: 92

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 93
<211> LENGTH: 106
<212> TYPE: PRT
<213> ORGANISM: Homo sapiens
<220> FEATURE:
<221> NAME/KEY: MISC_FEATURE
<223> OTHER INFORMATION: CL-3 human immunoglobulin light chain (LC)
      constant region

<400> SEQUENCE: 93

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys

```
                65                  70                  75                  80
Ser His Lys Ser Tyr Ser Cys Gln Val Thr His Glu Gly Ser Thr Val
                    85                  90                  95

Glu Lys Thr Val Ala Pro Thr Glu Cys Ser
                100                 105

<210> SEQ ID NO 94
<211> LENGTH: 106
<212> TYPE: PRT
<213> ORGANISM: Homo sapiens
<220> FEATURE:
<221> NAME/KEY: MISC_FEATURE
<223> OTHER INFORMATION: CL-7 human immunoglobulin light chain (LC)
      constant region

<400> SEQUENCE: 94

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
                20                  25                  30

Phe Tyr Pro Gly Ala Val Thr Val Ala Trp Lys Ala Asp Gly Ser Pro
            35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                    85                  90                  95

Glu Lys Thr Val Ala Pro Ala Glu Cys Ser
                100                 105

<210> SEQ ID NO 95
<211> LENGTH: 19
<212> TYPE: PRT
<213> ORGANISM: ARTIFICIAL SEQUENCE
<220> FEATURE:
<223> OTHER INFORMATION: VH21 SP

<400> SEQUENCE: 95

Met Glu Trp Ser Trp Val Phe Leu Phe Phe Leu Ser Val Thr Thr Gly
1               5                   10                  15

Val His Ser

<210> SEQ ID NO 96
<211> LENGTH: 705
<212> TYPE: DNA
<213> ORGANISM: ARTIFICIAL SEQUENCE
<220> FEATURE:
<223> OTHER INFORMATION: 4241 (LC: Y53A) coding sequence
<220> FEATURE:
<221> NAME/KEY: CDS
<222> LOCATION: (1)..(705)

<400> SEQUENCE: 96 atg gaa acc cca gcg cag ctt ctc ttc ctc ctg cta ctc tgg ctc cca      48
Met Glu Thr Pro Ala Gln Leu Leu Phe Leu Leu Leu Leu Trp Leu Pro
1               5                   10                  15 gat acc acc gga gaa att gtg ttg acg cag tct cca ggc acc ctg tct      96
Asp Thr Thr Gly Glu Ile Val Leu Thr Gln Ser Pro Gly Thr Leu Ser
                20                  25                  30 ttg tct cca ggg gaa aga gcc acc ctc tcc tgc agg gcc agt cag ggt     144
Leu Ser Pro Gly Glu Arg Ala Thr Leu Ser Cys Arg Ala Ser Gln Gly
            35                  40                  45
```

| | | |
|---|---|---|
| att agt aga agc gct tta gcc tgg tac cag cag aaa cct ggc cag gct<br>Ile Ser Arg Ser Ala Leu Ala Trp Tyr Gln Gln Lys Pro Gly Gln Ala<br>50 55 60 | | 192 |
| ccc agc ctc ctc atc tat ggt gca tcc agc agg gcc act ggc atc cca<br>Pro Ser Leu Leu Ile Tyr Gly Ala Ser Ser Arg Ala Thr Gly Ile Pro<br>65 70 75 80 | | 240 |
| gac agg ttc agt ggc agt ggg tct ggg aca gac ttc act ctc acc atc<br>Asp Arg Phe Ser Gly Ser Gly Ser Gly Thr Asp Phe Thr Leu Thr Ile<br>85 90 95 | | 288 |
| agc aga ctg gag cct gaa gat ttt gca gtg tat tac tgt caa caa ttt<br>Ser Arg Leu Glu Pro Glu Asp Phe Ala Val Tyr Tyr Cys Gln Gln Phe<br>100 105 110 | | 336 |
| ggt agt tca ccg tgg acg ttc ggc caa ggg acc aag gtg gaa atc aaa<br>Gly Ser Ser Pro Trp Thr Phe Gly Gln Gly Thr Lys Val Glu Ile Lys<br>115 120 125 | | 384 |
| cga act gtg gct gca cca tct gtc ttc atc ttc ccg cca tct gat gag<br>Arg Thr Val Ala Ala Pro Ser Val Phe Ile Phe Pro Pro Ser Asp Glu<br>130 135 140 | | 432 |
| cag ttg aaa tct gga act gct agc gtt gtg tgc ctg ctg aat aac ttc<br>Gln Leu Lys Ser Gly Thr Ala Ser Val Val Cys Leu Leu Asn Asn Phe<br>145 150 155 160 | | 480 |
| tat ccc aga gag gcc aaa gta cag tgg aag gtg gat aac gcc ctc caa<br>Tyr Pro Arg Glu Ala Lys Val Gln Trp Lys Val Asp Asn Ala Leu Gln<br>165 170 175 | | 528 |
| tcg ggt aac tcc cag gag agt gtc aca gag cag gac agc aag gac agc<br>Ser Gly Asn Ser Gln Glu Ser Val Thr Glu Gln Asp Ser Lys Asp Ser<br>180 185 190 | | 576 |
| acc tac agc ctc agc agc acc ctg acg ctg agc aaa gca gac tac gag<br>Thr Tyr Ser Leu Ser Ser Thr Leu Thr Leu Ser Lys Ala Asp Tyr Glu<br>195 200 205 | | 624 |
| aaa cac aaa gtc tac gcc tgc gaa gtc acc cat cag ggc ctg agc tcg<br>Lys His Lys Val Tyr Ala Cys Glu Val Thr His Gln Gly Leu Ser Ser<br>210 215 220 | | 672 |
| ccc gtc aca aag agc ttc aac agg gga gag tgt<br>Pro Val Thr Lys Ser Phe Asn Arg Gly Glu Cys<br>225 230 235 | | 705 |

<210> SEQ ID NO 97
<211> LENGTH: 235
<212> TYPE: PRT
<213> ORGANISM: ARTIFICIAL SEQUENCE
<220> FEATURE:
<223> OTHER INFORMATION: Synthetic Construct

<400> SEQUENCE: 97

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Gly
        35                  40                  45

Ile Ser Arg Ser Ala Leu Ala Trp Tyr Gln Gln Lys Pro Gly Gln Ala
    50                  55                  60

Pro Ser Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Phe
            100                 105                 110

Gly Ser Ser Pro Trp Thr Phe Gly Gln Gly Thr Lys Val Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 98
<211> LENGTH: 215
<212> TYPE: PRT
<213> ORGANISM: ARTIFICIAL SEQUENCE
<220> FEATURE:
<223> OTHER INFORMATION: 4241 (LC: Y53A)

<400> SEQUENCE: 98

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Ala Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 99
<211> LENGTH: 1413
<212> TYPE: DNA

<213> ORGANISM: ARTIFICIAL SEQUENCE
<220> FEATURE:
<223> OTHER INFORMATION: 4241 (HC: Y125E) coding sequence
<220> FEATURE:
<221> NAME/KEY: CDS
<222> LOCATION: (1)..(1413)

<400> SEQUENCE: 99

| | | | | | | | | | | | | | | | | |
|---|---|---|---|---|---|---|---|---|---|---|---|---|---|---|---|---|
| atg | aag | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |
| gtc | ctg | tcc | cag | gtg | cag | ctg | cag | gag | tcg | ggc | cca | gga | ctg | gtg | aag | 96 |
| Val | Leu | Ser | Gln | Val | Gln | Leu | Gln | Glu | Ser | Gly | Pro | Gly | Leu | Val | Lys | |
| | | | 20 | | | | | 25 | | | | | 30 | | | |
| cct | tca | cag | acc | ctg | tcc | ctc | acc | tgc | act | gtc | tct | ggt | ggc | tcc | atc | 144 |
| Pro | Ser | Gln | Thr | Leu | Ser | Leu | Thr | Cys | Thr | Val | Ser | Gly | Gly | Ser | Ile | |
| | | 35 | | | | | 40 | | | | | 45 | | | | |
| agc | agt | ggt | gat | tac | ttc | tgg | agc | tgg | atc | cgc | cag | ctc | cca | ggg | aag | 192 |
| Ser | Ser | Gly | Asp | Tyr | Phe | Trp | Ser | Trp | Ile | Arg | Gln | Leu | Pro | Gly | Lys | |
| 50 | | | | | 55 | | | | | 60 | | | | | | |
| ggc | ctg | gag | tgg | att | ggg | cac | atc | cat | aac | agt | ggg | acc | acc | tac | tac | 240 |
| Gly | Leu | Glu | Trp | Ile | Gly | His | Ile | His | Asn | Ser | Gly | Thr | Thr | Tyr | Tyr | |
| 65 | | | | 70 | | | | | 75 | | | | | 80 | | |
| aat | ccg | tcc | ctc | aag | agt | cga | gtt | acc | ata | tca | gta | gac | acg | tct | aag | 288 |
| Asn | Pro | Ser | Leu | Lys | Ser | Arg | Val | Thr | Ile | Ser | Val | Asp | Thr | Ser | Lys | |
| | | | | 85 | | | | | 90 | | | | | 95 | | |
| aag | cag | ttc | tcc | ctg | agg | ctg | agt | tct | gtg | act | gcc | gcg | gac | acg | gcc | 336 |
| Lys | Gln | Phe | Ser | Leu | Arg | Leu | Ser | Ser | Val | Thr | Ala | Ala | Asp | Thr | Ala | |
| | | | 100 | | | | | 105 | | | | | 110 | | | |
| gta | tat | tac | tgt | gcg | aga | gat | cga | ggg | ggt | gac | tac | gaa | tat | ggt | atg | 384 |
| Val | Tyr | Tyr | Cys | Ala | Arg | Asp | Arg | Gly | Gly | Asp | Tyr | Glu | Tyr | Gly | Met | |
| | | 115 | | | | | 120 | | | | | 125 | | | | |
| gac | gtc | tgg | ggc | caa | ggg | acc | acg | gtc | acc | gtc | tcc | tca | gcc | tcc | acc | 432 |
| Asp | Val | Trp | Gly | Gln | Gly | Thr | Thr | Val | Thr | Val | Ser | Ser | Ala | Ser | Thr | |
| | 130 | | | | | 135 | | | | | 140 | | | | | |
| aag | ggc | cca | tcc | gtc | ttc | ccc | ctg | gca | ccc | tcc | tcc | aag | agc | acc | tct | 480 |
| Lys | Gly | Pro | Ser | Val | Phe | Pro | Leu | Ala | Pro | Ser | Ser | Lys | Ser | Thr | Ser | |
| 145 | | | | | 150 | | | | | 155 | | | | | 160 | |
| ggg | ggc | aca | gcg | gcc | ctg | ggc | tgc | ctg | gtc | aag | gac | tac | ttc | ccc | gaa | 528 |
| Gly | Gly | Thr | Ala | Ala | Leu | Gly | Cys | Leu | Val | Lys | Asp | Tyr | Phe | Pro | Glu | |
| | | | | 165 | | | | | 170 | | | | | 175 | | |
| ccg | gtg | acg | gtg | tcg | tgg | aac | tca | ggc | gcc | ctg | acc | agc | ggc | gtg | cac | 576 |
| Pro | Val | Thr | Val | Ser | Trp | Asn | Ser | Gly | Ala | Leu | Thr | Ser | Gly | Val | His | |
| | | | 180 | | | | | 185 | | | | | 190 | | | |
| acc | ttc | ccg | gct | gtc | cta | cag | tcc | tca | gga | ctc | tac | tcc | ctc | agc | agc | 624 |
| Thr | Phe | Pro | Ala | Val | Leu | Gln | Ser | Ser | Gly | Leu | Tyr | Ser | Leu | Ser | Ser | |
| | | 195 | | | | | 200 | | | | | 205 | | | | |
| gtg | gtg | acc | gtg | ccc | tcc | agc | agc | ttg | ggc | acc | cag | acc | tac | atc | tgc | 672 |
| Val | Val | Thr | Val | Pro | Ser | Ser | Ser | Leu | Gly | Thr | Gln | Thr | Tyr | Ile | Cys | |
| 210 | | | | | 215 | | | | | 220 | | | | | | |
| aac | gtg | aat | cac | aag | ccc | agc | aac | acc | aag | gtg | gac | aag | aga | gtt | gag | 720 |
| Asn | Val | Asn | His | Lys | Pro | Ser | Asn | Thr | Lys | Val | Asp | Lys | Arg | Val | Glu | |
| 225 | | | | 230 | | | | | 235 | | | | | 240 | | |
| ccc | aaa | tct | tgt | gac | aaa | act | cac | aca | tgc | cca | ccg | tgc | cca | gca | cct | 768 |
| Pro | Lys | Ser | Cys | Asp | Lys | Thr | His | Thr | Cys | Pro | Pro | Cys | Pro | Ala | Pro | |
| | | | 245 | | | | | 250 | | | | | 255 | | | |
| gaa | ctc | ctg | ggg | gga | ccg | tca | gtc | ttc | ctc | ttc | ccc | cca | aaa | ccc | aag | 816 |
| Glu | Leu | Leu | Gly | Gly | Pro | Ser | Val | Phe | Leu | Phe | Pro | Pro | Lys | Pro | Lys | |
| | | 260 | | | | | 265 | | | | | 270 | | | | |
| gac | acc | ctc | atg | atc | tcc | cgg | acc | cct | gag | gtc | aca | tgc | gtg | gtg | gtg | 864 |
| Asp | Thr | Leu | Met | Ile | Ser | Arg | Thr | Pro | Glu | Val | Thr | Cys | Val | Val | Val | |
| | 275 | | | | | 280 | | | | | 285 | | | | | |

| | | | | | | | | | | | | | | | |
|---|---|---|---|---|---|---|---|---|---|---|---|---|---|---|---|
| gac | gtg | agc | cac | gaa | gac | cct | gag | gtc | aag | ttc | aac | tgg | tac | gtg | gac | 912 |
| Asp | Val | Ser | His | Glu | Asp | Pro | Glu | Val | Lys | Phe | Asn | Trp | Tyr | Val | Asp |
| | 290 | | | | 295 | | | | | 300 | | | | | |
| ggc | gtg | gag | gtg | cat | aat | gcc | aag | aca | aag | ccg | cgg | gag | gag | cag | tac | 960 |
| Gly | Val | Glu | Val | His | Asn | Ala | Lys | Thr | Lys | Pro | Arg | Glu | Glu | Gln | Tyr |
| 305 | | | | | 310 | | | | | 315 | | | | | 320 |
| aac | agc | acg | tac | cgt | gtg | gtc | agc | gtc | ctc | acc | gtc | ctg | cac | cag | gac | 1008 |
| Asn | Ser | Thr | Tyr | Arg | Val | Val | Ser | Val | Leu | Thr | Val | Leu | His | Gln | Asp |
| | | | | 325 | | | | | 330 | | | | | 335 | |
| tgg | ctg | aat | ggc | aag | gag | tac | aag | tgc | aag | gtc | tcc | aac | aaa | gcc | ctc | 1056 |
| Trp | Leu | Asn | Gly | Lys | Glu | Tyr | Lys | Cys | Lys | Val | Ser | Asn | Lys | Ala | Leu |
| | | | 340 | | | | | 345 | | | | | 350 | | |
| cca | gcc | ccc | atc | gag | aaa | acc | atc | tcc | aaa | gcc | aaa | ggg | cag | ccc | cga | 1104 |
| Pro | Ala | Pro | Ile | Glu | Lys | Thr | Ile | Ser | Lys | Ala | Lys | Gly | Gln | Pro | Arg |
| | | 355 | | | | | 360 | | | | | 365 | | | |
| gaa | cca | cag | gtg | tac | acc | ctg | ccc | cca | tcc | cgg | gag | gag | atg | acc | aag | 1152 |
| Glu | Pro | Gln | Val | Tyr | Thr | Leu | Pro | Pro | Ser | Arg | Glu | Glu | Met | Thr | Lys |
| | 370 | | | | | 375 | | | | | 380 | | | | |
| aac | cag | gtc | agc | ctg | acc | tgc | ctg | gtc | aaa | ggc | ttc | tat | ccc | agc | gac | 1200 |
| Asn | Gln | Val | Ser | Leu | Thr | Cys | Leu | Val | Lys | Gly | Phe | Tyr | Pro | Ser | Asp |
| 385 | | | | | 390 | | | | | 395 | | | | | 400 |
| atc | gcc | gtg | gag | tgg | gag | agc | aat | ggg | cag | ccg | gag | aac | aac | tac | aag | 1248 |
| Ile | Ala | Val | Glu | Trp | Glu | Ser | Asn | Gly | Gln | Pro | Glu | Asn | Asn | Tyr | Lys |
| | | | | 405 | | | | | 410 | | | | | 415 | |
| acc | acg | cct | ccc | gtg | ctg | gac | tcc | gac | ggc | tcc | ttc | ttc | ctc | tat | agc | 1296 |
| Thr | Thr | Pro | Pro | Val | Leu | Asp | Ser | Asp | Gly | Ser | Phe | Phe | Leu | Tyr | Ser |
| | | | 420 | | | | | 425 | | | | | 430 | | |
| aag | ctc | acc | gtg | gac | aag | agc | agg | tgg | cag | cag | ggg | aac | gtc | ttc | tca | 1344 |
| Lys | Leu | Thr | Val | Asp | Lys | Ser | Arg | Trp | Gln | Gln | Gly | Asn | Val | Phe | Ser |
| | | 435 | | | | | 440 | | | | | 445 | | | |
| tgc | tcc | gtg | atg | cat | gag | gct | ctg | cac | aac | cac | tac | acg | cag | aag | agc | 1392 |
| Cys | Ser | Val | Met | His | Glu | Ala | Leu | His | Asn | His | Tyr | Thr | Gln | Lys | Ser |
| | 450 | | | | | 455 | | | | | 460 | | | | |
| ctc | tcc | ctg | tct | ccg | ggt | aaa | | | | | | | | | | 1413 |
| Leu | Ser | Leu | Ser | Pro | Gly | Lys |
| 465 | | | | 470 | | |

<210> SEQ ID NO 100
<211> LENGTH: 471
<212> TYPE: PRT
<213> ORGANISM: ARTIFICIAL SEQUENCE
<220> FEATURE:
<223> OTHER INFORMATION: Synthetic Construct

<400> SEQUENCE: 100

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Ser Gly Asp Tyr Phe Trp Ser Trp Ile Arg Gln Leu Pro Gly Lys
    50                  55                  60

Gly Leu Glu Trp Ile Gly His Ile His Asn Ser Gly Thr Thr Tyr Tyr
65                  70                  75                  80

Asn Pro Ser Leu Lys Ser Arg Val Thr Ile Ser Val Asp Thr Ser Lys
                85                  90                  95

Lys Gln Phe Ser Leu Arg Leu Ser Ser Val Thr Ala Ala Asp Thr Ala
            100                 105                 110

Val Tyr Tyr Cys Ala Arg Asp Arg Gly Gly Asp Tyr Glu Tyr Gly Met
            115                 120                 125

Asp Val Trp Gly Gln Gly Thr Thr Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 101
<211> LENGTH: 452
<212> TYPE: PRT
<213> ORGANISM: ARTIFICIAL SEQUENCE
<220> FEATURE:
<223> OTHER INFORMATION: 4241 (HC: Y125E)

<400> SEQUENCE: 101

Gln Val Gln Leu Gln Glu Ser Gly Pro Gly Leu Val Lys Pro Ser Gln

-continued

```
              1               5                   10                  15
        Thr Leu Ser Leu Thr Cys Thr Val Ser Gly Gly Ser Ile Ser Ser Gly
                        20                  25                  30

Asp Tyr Phe Trp Ser Trp Ile Arg Gln Leu Pro Gly Lys Gly Leu Glu
                        35                  40                  45

Trp Ile Gly His Ile His Asn Ser Gly Thr Thr Tyr Tyr Asn Pro Ser
                        50                  55                  60

Leu Lys Ser Arg Val Thr Ile Ser Val Asp Thr Ser Lys Lys Gln Phe
        65                  70                  75                  80

Ser Leu Arg Leu Ser Ser Val Thr Ala Ala Asp Thr Ala Val Tyr Tyr
                        85                  90                  95

Cys Ala Arg Asp Arg Gly Gly Asp Tyr Glu Tyr Gly Met Asp Val Trp
                        100                 105                 110

Gly Gln Gly Thr Thr Val Thr Val Ser Ser Ala Ser Thr Lys Gly Pro
                        115                 120                 125

Ser Val Phe Pro Leu Ala Pro Ser Ser Lys Ser Thr Ser Gly Gly Thr
                        130                 135                 140

Ala Ala Leu Gly Cys Leu Val Lys Asp Tyr Phe Pro Glu Pro Val Thr
        145                 150                 155                 160

Val Ser Trp Asn Ser Gly Ala Leu Thr Ser Gly Val His Thr Phe Pro
                        165                 170                 175

Ala Val Leu Gln Ser Ser Gly Leu Tyr Ser Leu Ser Ser Val Val Thr
                        180                 185                 190

Val Pro Ser Ser Ser Leu Gly Thr Gln Thr Tyr Ile Cys Asn Val Asn
                        195                 200                 205

His Lys Pro Ser Asn Thr Lys Val Asp Lys Arg Val Glu Pro Lys Ser
                        210                 215                 220

Cys Asp Lys Thr His Thr Cys Pro Pro Cys Pro Ala Pro Glu Leu Leu
        225                 230                 235                 240

Gly Gly Pro Ser Val Phe Leu Phe Pro Pro Lys Pro Lys Asp Thr Leu
                        245                 250                 255

Met Ile Ser Arg Thr Pro Glu Val Thr Cys Val Val Val Asp Val Ser
                        260                 265                 270

His Glu Asp Pro Glu Val Lys Phe Asn Trp Tyr Val Asp Gly Val Glu
                        275                 280                 285

Val His Asn Ala Lys Thr Lys Pro Arg Glu Glu Gln Tyr Asn Ser Thr
                        290                 295                 300

Tyr Arg Val Val Ser Val Leu Thr Val Leu His Gln Asp Trp Leu Asn
        305                 310                 315                 320

Gly Lys Glu Tyr Lys Cys Lys Val Ser Asn Lys Ala Leu Pro Ala Pro
                        325                 330                 335

Ile Glu Lys Thr Ile Ser Lys Ala Lys Gly Gln Pro Arg Glu Pro Gln
                        340                 345                 350

Val Tyr Thr Leu Pro Pro Ser Arg Glu Glu Met Thr Lys Asn Gln Val
                        355                 360                 365

Ser Leu Thr Cys Leu Val Lys Gly Phe Tyr Pro Ser Asp Ile Ala Val
                        370                 375                 380

Glu Trp Glu Ser Asn Gly Gln Pro Glu Asn Asn Tyr Lys Thr Thr Pro
        385                 390                 395                 400

Pro Val Leu Asp Ser Asp Gly Ser Phe Phe Leu Tyr Ser Lys Leu Thr
                        405                 410                 415

Val Asp Lys Ser Arg Trp Gln Gln Gly Asn Val Phe Ser Cys Ser Val
                        420                 425                 430
```

Met His Glu Ala Leu His Asn His Tyr Thr Gln Lys Ser Leu Ser Leu
            435                 440                 445

Ser Pro Gly Lys
    450

<210> SEQ ID NO 102
<211> LENGTH: 66
<212> TYPE: DNA
<213> ORGANISM: ARTIFICIAL SEQUENCE
<220> FEATURE:
<223> OTHER INFORMATION: VK-1 SP signal peptide coding sequence
<220> FEATURE:
<221> NAME/KEY: CDS
<222> LOCATION: (1)..(66)

<400> SEQUENCE: 102 atg gac atg agg gtg ccc gct cag ctc ctg ggg ctc ctg ctg ctg tgg      48
Met Asp Met Arg Val Pro Ala Gln Leu Leu Gly Leu Leu Leu Leu Trp
1               5                   10                  15 ctg aga ggt gcg cgc tgt                                              66
Leu Arg Gly Ala Arg Cys
            20

<210> SEQ ID NO 103
<211> LENGTH: 22
<212> TYPE: PRT
<213> ORGANISM: ARTIFICIAL SEQUENCE
<220> FEATURE:
<223> OTHER INFORMATION: Synthetic Construct

<400> SEQUENCE: 103

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 104
<211> LENGTH: 20
<212> TYPE: PRT
<213> ORGANISM: ARTIFICIAL SEQUENCE
<220> FEATURE:
<223> OTHER INFORMATION: Signal peptide

<400> SEQUENCE: 104

Met Glu Ala Pro Ala Gln Leu Leu Phe Leu Leu Leu Leu Trp Leu Pro
1               5                   10                  15

Asp Thr Thr Gly
            20

<210> SEQ ID NO 105
<211> LENGTH: 19
<212> TYPE: PRT
<213> ORGANISM: ARTIFICIAL SEQUENCE
<220> FEATURE:
<223> OTHER INFORMATION: Signal peptide

<400> SEQUENCE: 105

Met Glu Trp Thr Trp Arg Val Leu Phe Leu Val Ala Ala Ala Thr Gly
1               5                   10                  15

Ala His Ser

<210> SEQ ID NO 106
<211> LENGTH: 20
<212> TYPE: PRT
<213> ORGANISM: ARTIFICIAL SEQUENCE
<220> FEATURE:

-continued

<223> OTHER INFORMATION: Signal peptide

<400> SEQUENCE: 106

Met Glu Thr Pro Ala Gln Leu Leu Phe Leu Leu Leu Trp Leu Pro
1               5                   10                  15

Asp Thr Thr Gly
            20

<210> SEQ ID NO 107
<211> LENGTH: 19
<212> TYPE: PRT
<213> ORGANISM: ARTIFICIAL SEQUENCE
<220> FEATURE:
<223> OTHER INFORMATION: Signal peptide

<400> SEQUENCE: 107

Met Lys His Leu Trp Phe Phe Leu Leu Leu Val Ala Ala Pro Arg Trp
1               5                   10                  15

Val Leu Ser

<210> SEQ ID NO 108
<211> LENGTH: 702
<212> TYPE: DNA
<213> ORGANISM: ARTIFICIAL SEQUENCE
<220> FEATURE:
<223> OTHER INFORMATION: 16435 (LC: P66L, D90E) coding sequence
<220> FEATURE:
<221> NAME/KEY: CDS
<222> LOCATION: (1)..(702)

<400> SEQUENCE: 108

```
atg gaa gcg ccg gcg cag ctt ctc ttc ctg cta ctc tgg ctc cca      48
Met Glu Ala Pro Ala Gln Leu Leu Phe Leu Leu Leu Trp Leu Pro
1               5                   10                  15 gat acc act gga gaa ata gtg atg acg cag tct cca gcc acc ctg tct  96
Asp Thr Thr Gly Glu Ile Val Met Thr Gln Ser Pro Ala Thr Leu Ser
                20                  25                  30 gtg tct cct ggg gaa aga gcc acc ctc tcc tgc agg gcc agt cag agt 144
Val Ser Pro Gly Glu Arg Ala Thr Leu Ser Cys Arg Ala Ser Gln Ser
        35                  40                  45 gtt agc agc aac tta gcc tgg ttc cag cag aaa cct ggc cag gct ccc 192
Val Ser Ser Asn Leu Ala Trp Phe Gln Gln Lys Pro Gly Gln Ala Pro
    50                  55                  60 agg ctc ctc atc tat gat gca tcc acc agg gcc act ggt gtc cca gcc 240
Arg Leu Leu Ile Tyr Asp Ala Ser Thr Arg Ala Thr Gly Val Pro Ala
65                  70                  75                  80 agg ttc agt ggc agt ggg tct ggg aca gaa ttc act ctc acc atc agc 288
Arg Phe Ser Gly Ser Gly Ser Gly Thr Glu Phe Thr Leu Thr Ile Ser
                85                  90                  95 agc ctg cag tct gaa gat ttt gca gtt tat tac tgt cag cag tat gat 336
Ser Leu Gln Ser Glu Asp Phe Ala Val Tyr Tyr Cys Gln Gln Tyr Asp
                100                 105                 110 aac tgg ccg ctc act ttc ggc gga ggg acc aag gtg gag atc aaa cgt 384
Asn Trp Pro Leu Thr Phe Gly Gly Gly Thr Lys Val Glu Ile Lys Arg
            115                 120                 125 acg gtg gct gca cca tct gtc ttc atc ttc ccg cca tct gat gag cag 432
Thr Val Ala Ala Pro Ser Val Phe Ile Phe Pro Pro Ser Asp Glu Gln
        130                 135                 140 ttg aaa tct gga act gcc tct gtt gtg tgc ctg ctg aat aac ttc tat 480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg 528
Pro Arg Glu Ala Lys Val Gln Trp Lys Val Asp Asn Ala Leu Gln Ser
```

```
                    165                 170                 175
ggt aac tcc cag gag agt gtc aca gag cag gac agc aag gac agc acc      576
Gly Asn Ser Gln Glu Ser Val Thr Glu Gln Asp Ser Lys Asp Ser Thr
            180                 185                 190 tac agc ctc agc agc acc ctg acg ctg agc aaa gca gac tac gag aaa      624
Tyr Ser Leu Ser Ser Thr Leu Thr Leu Ser Lys Ala Asp Tyr Glu Lys
        195                 200                 205 cac aaa gtc tac gcc tgc gaa gtc acc cat cag ggc ctg agc tcg ccc      672
His Lys Val Tyr Ala Cys Glu Val Thr His Gln Gly Leu Ser Ser Pro
    210                 215                 220 gtc aca aag agc ttc aac agg gga gag tgt                              702
Val Thr Lys Ser Phe Asn Arg Gly Glu Cys
225                 230

<210> SEQ ID NO 109
<211> LENGTH: 234
<212> TYPE: PRT
<213> ORGANISM: ARTIFICIAL SEQUENCE
<220> FEATURE:
<223> OTHER INFORMATION: Synthetic Construct

<400> SEQUENCE: 109

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Phe Gln Gln Lys Pro Gly Gln Ala Pro
    50                  55                  60

Arg Leu Leu Ile Tyr Asp Ala Ser Thr Arg Ala Thr Gly Val Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asp
            100                 105                 110

Asn Trp Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 110
<211> LENGTH: 214
<212> TYPE: PRT
<213> ORGANISM: ARTIFICIAL SEQUENCE
<220> FEATURE:
<223> OTHER INFORMATION: 16435 (LC: P66L, D90E)
```

<400> SEQUENCE: 110

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Leu Leu Ile
        35                  40                  45

Tyr Asp Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 111
<211> LENGTH: 1383
<212> TYPE: DNA
<213> ORGANISM: ARTIFICIAL SEQUENCE
<220> FEATURE:
<223> OTHER INFORMATION: 16435 (HC: R118A) coding sequence
<220> FEATURE:
<221> NAME/KEY: CDS
<222> LOCATION: (1)..(1383)

<400> SEQUENCE: 111

```
atg gag tgg acc tgg agg gtc ctt ttc ttg gtg gca gca gca aca ggt    48
Met Glu Trp Thr Trp Arg Val Leu Phe Leu Val Ala Ala Ala Thr Gly
1               5                   10                  15 gcc cac tcc cag gtt cag ctg gtg cag tct gga gct gag gtg aag aag    96
Ala His Ser Gln Val Gln Leu Val Gln Ser Gly Ala Glu Val Lys Lys
            20                  25                  30 cct ggg gcc tca gtg aag gtc tcc tgc aag gct tct ggt tac acc ttt   144
Pro Gly Ala Ser Val Lys Val Ser Cys Lys Ala Ser Gly Tyr Thr Phe
        35                  40                  45 acc aga tat ggt atc agc tgg gtg cga cag gcc cct gga caa ggg ctt   192
Thr Arg Tyr Gly Ile Ser Trp Val Arg Gln Ala Pro Gly Gln Gly Leu
    50                  55                  60 gag tgg atg gga tgg atc agc act tac agt ggt aac aca aac tat gca   240
Glu Trp Met Gly Trp Ile Ser Thr Tyr Ser Gly Asn Thr Asn Tyr Ala
65                  70                  75                  80 cag aag ctc cag ggc aga gtc acc atg acc aca gac aca tcc acg agc   288
Gln Lys Leu Gln Gly Arg Val Thr Met Thr Thr Asp Thr Ser Thr Ser
```

```
                85                  90                  95
aca gcc tac atg gag ctg agg agc ctg aga tct gac gac acg gcc gtg     336
Thr Ala Tyr Met Glu Leu Arg Ser Leu Arg Ser Asp Asp Thr Ala Val
            100                 105                 110 tat tac tgt gcg aga gct cag ctt tac ttt gac tac tgg ggc cag gga     384
Tyr Tyr Cys Ala Arg Ala Gln Leu Tyr Phe Asp Tyr Trp Gly Gln Gly
        115                 120                 125 acc ctg gtc acc gtc tcc tca gct agc acc aag ggc cca tcg gtc ttc     432
Thr Leu Val Thr Val Ser Ser Ala Ser Thr Lys Gly Pro Ser Val Phe
130                 135                 140 ccc ctg gcg ccc tgc tcc agg agc acc tcc gag agc aca gcg gcc ctg     480
Pro Leu Ala Pro Cys Ser Arg Ser Thr Ser Glu Ser Thr Ala Ala Leu
145                 150                 155                 160 ggc tgc ctg gtc aag gac tac ttc ccc gaa ccg gtg acg gtg tcg tgg     528
Gly Cys Leu Val Lys Asp Tyr Phe Pro Glu Pro Val Thr Val Ser Trp
            165                 170                 175 aac tca ggc gct ctg acc agc ggc gtg cac acc ttc cca gct gtc cta     576
Asn Ser Gly Ala Leu Thr Ser Gly Val His Thr Phe Pro Ala Val Leu
        180                 185                 190 cag tcc tca gga ctc tac tcc ctc agc agc gtg gtg acc gtg ccc tcc     624
Gln Ser Ser Gly Leu Tyr Ser Leu Ser Ser Val Val Thr Val Pro Ser
    195                 200                 205 agc aac ttc ggc acc cag acc tac acc tgc aac gta gat cac aag ccc     672
Ser Asn Phe Gly Thr Gln Thr Tyr Thr Cys Asn Val Asp His Lys Pro
210                 215                 220 agc aac acc aag gtg gac aag aca gtt gag cgc aaa tgt tgt gtc gag     720
Ser Asn Thr Lys Val Asp Lys Thr Val Glu Arg Lys Cys Cys Val Glu
225                 230                 235                 240 tgc cca ccg tgc cca gca cca cct gtg gca gga ccg tca gtc ttc ctc     768
Cys Pro Pro Cys Pro Ala Pro Pro Val Ala Gly Pro Ser Val Phe Leu
            245                 250                 255 ttc ccc cca aaa ccc aag gac acc ctc atg atc tcc cgg acc cct gag     816
Phe Pro Pro Lys Pro Lys Asp Thr Leu Met Ile Ser Arg Thr Pro Glu
        260                 265                 270 gtc acg tgc gtg gtg gtg gac gtg agc cac gaa gac ccc gag gtc cag     864
Val Thr Cys Val Val Val Asp Val Ser His Glu Asp Pro Glu Val Gln
    275                 280                 285 ttc aac tgg tac gtg gac ggc gtg gag gtg cat aat gcc aag aca aag     912
Phe Asn Trp Tyr Val Asp Gly Val Glu Val His Asn Ala Lys Thr Lys
290                 295                 300 cca cgg gag gag cag ttc aac agc acg ttc cgt gtg gtc agc gtc ctc     960
Pro Arg Glu Glu Gln Phe Asn Ser Thr Phe Arg Val Val Ser Val Leu
305                 310                 315                 320 acc gtt gtg cac cag gac tgg ctg aac ggc aag gag tac aag tgc aag     1008
Thr Val Val His Gln Asp Trp Leu Asn Gly Lys Glu Tyr Lys Cys Lys
            325                 330                 335 gtc tcc aac aaa ggc ctc cca gcc ccc atc gag aaa acc atc tcc aaa     1056
Val Ser Asn Lys Gly Leu Pro Ala Pro Ile Glu Lys Thr Ile Ser Lys
        340                 345                 350 acc aaa ggg cag ccc cga gaa cca cag gtg tac acc ctg ccc cca tcc     1104
Thr Lys Gly Gln Pro Arg Glu Pro Gln Val Tyr Thr Leu Pro Pro Ser
    355                 360                 365 cgg gag gag atg acc aag aac cag gtc agc ctg acc tgc ctg gtc aaa     1152
Arg Glu Glu Met Thr Lys Asn Gln Val Ser Leu Thr Cys Leu Val Lys
370                 375                 380 ggc ttc tac ccc agc gac atc gcc gtg gag tgg gag agc aat ggg cag     1200
Gly Phe Tyr Pro Ser Asp Ile Ala Val Glu Trp Glu Ser Asn Gly Gln
385                 390                 395                 400 ccg gag aac aac tac aag acc aca cct ccc atg ctg gac tcc gac ggc     1248
Pro Glu Asn Asn Tyr Lys Thr Thr Pro Pro Met Leu Asp Ser Asp Gly
```

```
                        405                 410                 415
tcc ttc ttc ctc tac agc aag ctc acc gtg gac aag agc agg tgg cag      1296
Ser Phe Phe Leu Tyr Ser Lys Leu Thr Val Asp Lys Ser Arg Trp Gln
        420                 425                 430 cag ggg aac gtc ttc tca tgc tcc gtg atg cat gag gct ctg cac aac      1344
Gln Gly Asn Val Phe Ser Cys Ser Val Met His Glu Ala Leu His Asn
            435                 440                 445 cac tac acg cag aag agc ctc tcc ctg tct ccg ggt aaa                  1383
His Tyr Thr Gln Lys Ser Leu Ser Leu Ser Pro Gly Lys
        450                 455                 460

<210> SEQ ID NO 112
<211> LENGTH: 461
<212> TYPE: PRT
<213> ORGANISM: ARTIFICIAL SEQUENCE
<220> FEATURE:
<223> OTHER INFORMATION: Synthetic Construct

<400> SEQUENCE: 112

Met Glu Trp Thr Trp Arg Val Leu Phe Leu Val Ala Ala Thr Gly
 1               5                  10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Arg Tyr Gly Ile Ser Trp Val Arg Gln Ala Pro Gly Gln Gly Leu
        50                  55                  60

Glu Trp Met Gly Trp Ile Ser Thr Tyr Ser Gly Asn Thr Asn Tyr Ala
 65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
                100                 105                 110

Tyr Tyr Cys Ala Arg Ala Gln Leu Tyr Phe Asp Tyr Trp Gly Gln Gly
            115                 120                 125

Thr Leu Val Thr Val Ser Ser Ala Ser Thr Lys Gly Pro Ser Val Phe
        130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300
```

```
Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 113
<211> LENGTH: 442
<212> TYPE: PRT
<213> ORGANISM: ARTIFICIAL SEQUENCE
<220> FEATURE:
<223> OTHER INFORMATION: 16435 (HC: R118A)

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Gln Leu Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205
```

```
Lys Val Asp Lys Thr Val Glu Arg Lys Cys Cys Val Glu Cys Pro Pro
            210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 114
<211> LENGTH: 705
<212> TYPE: DNA
<213> ORGANISM: ARTIFICIAL SEQUENCE
<220> FEATURE:
<223> OTHER INFORMATION: 4341 (LC: Y53E) coding sequence
<220> FEATURE:
<221> NAME/KEY: CDS
<222> LOCATION: (1)..(705)

<400> SEQUENCE: 114 atg gaa acc cca gcg cag ctt ctc ttc ctc ctg cta ctc tgg ctc cca      48
Met Glu Thr Pro Ala Gln Leu Leu Phe Leu Leu Leu Leu Trp Leu Pro
1               5                   10                  15 gat acc acc gga gaa att gtg ttg acg cag tct cca ggc acc ctg tct      96
Asp Thr Thr Gly Glu Ile Val Leu Thr Gln Ser Pro Gly Thr Leu Ser
            20                  25                  30 ttg tct cca ggg gaa aga gcc acc ctc tcc tgc agg gcc agt cag ggt     144
Leu Ser Pro Gly Glu Arg Ala Thr Leu Ser Cys Arg Ala Ser Gln Gly
        35                  40                  45 att agt aga agc gaa tta gcc tgg tac cag cag aaa cct ggc cag gct     192
Ile Ser Arg Ser Glu Leu Ala Trp Tyr Gln Gln Lys Pro Gly Gln Ala
    50                  55                  60 ccc agc ctc ctc atc tat ggt gca tcc agc agg gcc act ggc atc cca     240
Pro Ser Leu Leu Ile Tyr Gly Ala Ser Ser Arg Ala Thr Gly Ile Pro
65                  70                  75                  80 gac agg ttc agt ggc agt ggg tct ggg aca gac ttc act ctc acc atc     288
Asp Arg Phe Ser Gly Ser Gly Ser Gly Thr Asp Phe Thr Leu Thr Ile
```

|  |  |  |  |  |  |  |  |  |  |  |  |  |  |  |  |
|---|---|---|---|---|---|---|---|---|---|---|---|---|---|---|---|
|  |  |  |  | 85 |  |  |  | 90 |  |  |  | 95 |  |  |  |

```
agc aga ctg gag cct gaa gat ttt gca gtg tat tac tgt caa caa ttt    336
Ser Arg Leu Glu Pro Glu Asp Phe Ala Val Tyr Tyr Cys Gln Gln Phe
        100                 105                 110 ggt agt tca ccg tgg acg ttc ggc caa ggg acc aag gtg gaa atc aaa    384
Gly Ser Ser Pro Trp Thr Phe Gly Gln Gly Thr Lys Val Glu Ile Lys
            115                 120                 125 cga act gtg gct gca cca tct gtc ttc atc ttc ccg cca tct gat gag    432
Arg Thr Val Ala Ala Pro Ser Val Phe Ile Phe Pro Pro Ser Asp Glu
        130                 135                 140 cag ttg aaa tct gga act gct agc gtt gtg tgc ctg ctg aat aac ttc    480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa    528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc    576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag    624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg    672
Lys His Lys Val Tyr Ala Cys Glu Val Thr His Gln Gly Leu Ser Ser
210                 215                 220 ccc gtc aca aag agc ttc aac agg gga gag tgt                        705
Pro Val Thr Lys Ser Phe Asn Arg Gly Glu Cys
225                 230                 235
```

<210> SEQ ID NO 115
<211> LENGTH: 235
<212> TYPE: PRT
<213> ORGANISM: ARTIFICIAL SEQUENCE
<220> FEATURE:
<223> OTHER INFORMATION: Synthetic Construct

<400> SEQUENCE: 115

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Gly
        35                  40                  45

Ile Ser Arg Ser Glu Leu Ala Trp Tyr Gln Gln Lys Pro Gly Gln Ala
    50                  55                  60

Pro Ser Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Phe
            100                 105                 110

Gly Ser Ser Pro Trp Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175
```

```
Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 116
<211> LENGTH: 215
<212> TYPE: PRT
<213> ORGANISM: ARTIFICIAL SEQUENCE
<220> FEATURE:
<223> OTHER INFORMATION: 4341 (LC: Y53E)

<400> SEQUENCE: 116

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Glu Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 117
<211> LENGTH: 1413
<212> TYPE: DNA
<213> ORGANISM: ARTIFICIAL SEQUENCE
<220> FEATURE:
<223> OTHER INFORMATION: 4341 (HC: Y125A) coding sequence
<220> FEATURE:
<221> NAME/KEY: CDS
<222> LOCATION: (1)..(1413)

<400> SEQUENCE: 117 atg aag cac ctg tgg ttc ttc ctc ctg ctg gtg gca gct ccc aga tgg      48
Met Lys His Leu Trp Phe Phe Leu Leu Leu Val Ala Ala Pro Arg Trp
```

```
        1               5                   10                  15
gtc ctg tcc cag gtg cag ctg cag gag tcg ggc cca gga ctg gtg aag        96
Val Leu Ser Gln Val Gln Leu Gln Glu Ser Gly Pro Gly Leu Val Lys
             20                  25                  30 cct tca cag acc ctg tcc ctc acc tgc act gtc tct ggt ggc tcc atc       144
Pro Ser Gln Thr Leu Ser Leu Thr Cys Thr Val Ser Gly Gly Ser Ile
             35                  40                  45 agc agt ggt gat tac ttc tgg agc tgg atc cgc cag ctc cca ggg aag       192
Ser Ser Gly Asp Tyr Phe Trp Ser Trp Ile Arg Gln Leu Pro Gly Lys
    50                  55                  60 ggc ctg gag tgg att ggg cac atc cat aac agt ggg acc acc tac tac       240
Gly Leu Glu Trp Ile Gly His Ile His Asn Ser Gly Thr Thr Tyr Tyr
65                  70                  75                  80 aat ccg tcc ctc aag agt cga gtt acc ata tca gta gac acg tct aag       288
Asn Pro Ser Leu Lys Ser Arg Val Thr Ile Ser Val Asp Thr Ser Lys
                 85                  90                  95 aag cag ttc tcc ctg agg ctg agt tct gtg act gcc gcg gac acg gcc       336
Lys Gln Phe Ser Leu Arg Leu Ser Ser Val Thr Ala Ala Asp Thr Ala
                100                 105                 110 gta tat tac tgt gcg aga gat cga ggg ggt gac tac gct tat ggt atg       384
Val Tyr Tyr Cys Ala Arg Asp Arg Gly Gly Asp Tyr Ala Tyr Gly Met
            115                 120                 125 gac gtc tgg ggc caa ggg acc acg gtc acc gtc tcc tca gcc tcc acc       432
Asp Val Trp Gly Gln Gly Thr Thr Val Thr Val Ser Ser Ala Ser Thr
    130                 135                 140 aag ggc cca tcc gtc ttc ccc ctg gca ccc tcc tcc aag agc acc tct       480
Lys Gly Pro Ser Val Phe Pro Leu Ala Pro Ser Ser Lys Ser Thr Ser
145                 150                 155                 160 ggg ggc aca gcg gcc ctg ggc tgc ctg gtc aag gac tac ttc ccc gaa       528
Gly Gly Thr Ala Ala Leu Gly Cys Leu Val Lys Asp Tyr Phe Pro Glu
                165                 170                 175 ccg gtg acg gtg tcg tgg aac tca ggc gcc ctg acc agc ggc gtg cac       576
Pro Val Thr Val Ser Trp Asn Ser Gly Ala Leu Thr Ser Gly Val His
            180                 185                 190 acc ttc ccg gct gtc cta cag tcc tca gga ctc tac tcc ctc agc agc       624
Thr Phe Pro Ala Val Leu Gln Ser Ser Gly Leu Tyr Ser Leu Ser Ser
    195                 200                 205 gtg gtg acc gtg ccc tcc agc agc ttg ggc acc cag acc tac atc tgc       672
Val Val Thr Val Pro Ser Ser Ser Leu Gly Thr Gln Thr Tyr Ile Cys
210                 215                 220 aac gtg aat cac aag ccc agc aac acc aag gtg gac aag aga gtt gag       720
Asn Val Asn His Lys Pro Ser Asn Thr Lys Val Asp Lys Arg Val Glu
225                 230                 235                 240 ccc aaa tct tgt gac aaa act cac aca tgc cca ccg tgc cca gca cct       768
Pro Lys Ser Cys Asp Lys Thr His Thr Cys Pro Pro Cys Pro Ala Pro
                245                 250                 255 gaa ctc ctg ggg gga ccg tca gtc ttc ctc ttc ccc cca aaa ccc aag       816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg       864
Asp Thr Leu Met Ile Ser Arg Thr Pro Glu Val Thr Cys Val Val Val
    275                 280                 285 gac gtg agc cac gaa gac cct gag gtc aag ttc aac tgg tac gtg gac       912
Asp Val Ser His Glu Asp Pro Glu Val Lys Phe Asn Trp Tyr Val Asp
    290                 295                 300 ggc gtg gag gtg cat aat gcc aag aca aag ccg cgg gag gag cag tac       960
Gly Val Glu Val His Asn Ala Lys Thr Lys Pro Arg Glu Glu Gln Tyr
305                 310                 315                 320 aac agc acg tac cgt gtg gtc agc gtc ctc acc gtc ctg cac cag gac      1008
Asn Ser Thr Tyr Arg Val Val Ser Val Leu Thr Val Leu His Gln Asp
```

```
tgg ctg aat ggc aag gag tac aag tgc aag gtc tcc aac aaa gcc ctc    1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggg cag ccc cga    1104
Pro Ala Pro Ile Glu Lys Thr Ile Ser Lys Ala Lys Gly Gln Pro Arg
            355                 360                 365 gaa cca cag gtg tac acc ctg ccc cca tcc cgg gag gag atg acc aag    1152
Glu Pro Gln Val Tyr Thr Leu Pro Pro Ser Arg Glu Glu Met Thr Lys
370                 375                 380 aac cag gtc agc ctg acc tgc ctg gtc aaa ggc ttc tat ccc agc gac    1200
Asn Gln Val Ser Leu Thr Cys Leu Val Lys Gly Phe Tyr Pro Ser Asp
385                 390                 395                 400 atc gcc gtg gag tgg gag agc aat ggg cag ccg gag aac aac tac aag    1248
Ile Ala Val Glu Trp Glu Ser Asn Gly Gln Pro Glu Asn Asn Tyr Lys
            405                 410                 415 acc acg cct ccc gtg ctg gac tcc gac ggc tcc ttc ttc ctc tat agc    1296
Thr Thr Pro Pro Val Leu Asp Ser Asp Gly Ser Phe Phe Leu Tyr Ser
            420                 425                 430 aag ctc acc gtg gac aag agc agg tgg cag cag ggg aac gtc ttc tca    1344
Lys Leu Thr Val Asp Lys Ser Arg Trp Gln Gln Gly Asn Val Phe Ser
            435                 440                 445 tgc tcc gtg atg cat gag gct ctg cac aac cac tac acg cag aag agc    1392
Cys Ser Val Met His Glu Ala Leu His Asn His Tyr Thr Gln Lys Ser
450                 455                 460 ctc tcc ctg tct ccg ggt aaa                                        1413
Leu Ser Leu Ser Pro Gly Lys
465                 470

<210> SEQ ID NO 118
<211> LENGTH: 471
<212> TYPE: PRT
<213> ORGANISM: ARTIFICIAL SEQUENCE
<220> FEATURE:
<223> OTHER INFORMATION: Synthetic Construct

<400> SEQUENCE: 118

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Ser Gly Asp Tyr Phe Trp Ser Trp Ile Arg Gln Leu Pro Gly Lys
    50                  55                  60

Gly Leu Glu Trp Ile Gly His Ile His Asn Ser Gly Thr Thr Tyr Tyr
65                  70                  75                  80

Asn Pro Ser Leu Lys Ser Arg Val Thr Ile Ser Val Asp Thr Ser Lys
                85                  90                  95

Lys Gln Phe Ser Leu Arg Leu Ser Ser Val Thr Ala Ala Asp Thr Ala
            100                 105                 110

Val Tyr Tyr Cys Ala Arg Asp Arg Gly Asp Tyr Ala Tyr Gly Met Asp
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175
```

```
Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
            325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 119
<211> LENGTH: 452
<212> TYPE: PRT
<213> ORGANISM: ARTIFICIAL SEQUENCE
<220> FEATURE:
<223> OTHER INFORMATION: 4341 (HC: Y125A)

<400> SEQUENCE: 119

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
            35                  40                  45

Trp Ile Gly His Ile His Asn Ser Gly Thr Thr Tyr Tyr Asn Pro Ser
        50                  55                  60
```

-continued

Leu Lys Ser Arg Val Thr Ile Ser Val Asp Thr Ser Lys Lys Gln Phe
 65                  70                  75                  80

Ser Leu Arg Leu Ser Ser Val Thr Ala Ala Asp Thr Ala Val Tyr Tyr
                 85                  90                  95

Cys Ala Arg Asp Arg Gly Gly Asp Tyr Ala Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 120
<211> LENGTH: 702
<212> TYPE: DNA
<213> ORGANISM: ARTIFICIAL SEQUENCE

<220> FEATURE:
<223> OTHER INFORMATION: 16444 (LC: P66L, D90E, W 114A) Coding sequence
<220> FEATURE:
<221> NAME/KEY: CDS
<222> LOCATION: (1)..(702)

<400> SEQUENCE: 120

```
atg gaa gcc cca gcg cag ctt ctc ttc ctg cta ctc tgg ctc cca       48
Met Glu Ala Pro Ala Gln Leu Leu Phe Leu Leu Leu Trp Leu Pro
1               5                   10                  15 gat acc act gga gaa ata gtg atg acg cag tct cca gcc acc ctg tct   96
Asp Thr Thr Gly Glu Ile Val Met Thr Gln Ser Pro Ala Thr Leu Ser
            20                  25                  30 gtg tct cct ggg gaa aga gcc acc ctc tcc tgc agg gcc agt cag agt   144
Val Ser Pro Gly Glu Arg Ala Thr Leu Ser Cys Arg Ala Ser Gln Ser
        35                  40                  45 gtt agc agc aac tta gcc tgg ttc cag cag aaa cct ggc cag gct ccc   192
Val Ser Ser Asn Leu Ala Trp Phe Gln Gln Lys Pro Gly Gln Ala Pro
    50                  55                  60 agg ctc ctc atc tat gat gca tcc acc agg gcc act ggt gtc cca gcc   240
Arg Leu Leu Ile Tyr Asp Ala Ser Thr Arg Ala Thr Gly Val Pro Ala
65                  70                  75                  80 agg ttc agt ggc agt ggg tct ggg aca gaa ttc act ctc acc atc agc   288
Arg Phe Ser Gly Ser Gly Ser Gly Thr Glu Phe Thr Leu Thr Ile Ser
                85                  90                  95 agc ctg cag tct gaa gat ttt gca gtt tat tac tgt cag cag tat gat   336
Ser Leu Gln Ser Glu Asp Phe Ala Val Tyr Tyr Cys Gln Gln Tyr Asp
            100                 105                 110 aac gct ccg ctc act ttc ggc gga ggg acc aag gtg gag atc aaa cgt   384
Asn Ala Pro Leu Thr Phe Gly Gly Gly Thr Lys Val Glu Ile Lys Arg
        115                 120                 125 acg gtg gct gca cca tct gtc ttc atc ttc ccg cca tct gat gag cag   432
Thr Val Ala Ala Pro Ser Val Phe Ile Phe Pro Pro Ser Asp Glu Gln
    130                 135                 140 ttg aaa tct gga act gcc tct gtt gtg tgc ctg ctg aat aac ttc tat   480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg   528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc   576
Gly Asn Ser Gln Glu Ser Val Thr Glu Gln Asp Ser Lys Asp Ser Thr
            180                 185                 190 tac agc ctc agc agc acc ctg acg ctg agc aaa gca gac tac gag aaa   624
Tyr Ser Leu Ser Ser Thr Leu Thr Leu Ser Lys Ala Asp Tyr Glu Lys
        195                 200                 205 cac aaa gtc tac gcc tgc gaa gtc acc cat cag ggc ctg agc tcg ccc   672
His Lys Val Tyr Ala Cys Glu Val Thr His Gln Gly Leu Ser Ser Pro
    210                 215                 220 gtc aca aag agc ttc aac agg gga gag tgt                           702
Val Thr Lys Ser Phe Asn Arg Gly Glu Cys
225                 230
```

<210> SEQ ID NO 121
<211> LENGTH: 234
<212> TYPE: PRT
<213> ORGANISM: ARTIFICIAL SEQUENCE
<220> FEATURE:
<223> OTHER INFORMATION: Synthetic Construct

<400> SEQUENCE: 121

```
Met Glu Ala Pro Ala Gln Leu Leu Phe Leu Leu Leu Trp Leu Pro
1               5                   10                  15
```

```
Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Phe Gln Gln Lys Pro Gly Gln Ala Pro
    50                  55                  60

Arg Leu Leu Ile Tyr Asp Ala Ser Thr Arg Ala Thr Gly Val Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asp
            100                 105                 110

Asn Ala Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 122
<211> LENGTH: 214
<212> TYPE: PRT
<213> ORGANISM: ARTIFICIAL SEQUENCE
<220> FEATURE:
<223> OTHER INFORMATION: 16444 (LC: P66L, D90E, W114A)

<400> SEQUENCE: 122

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Leu Leu Ile
        35                  40                  45

Tyr Asp Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asn Ala Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 123
<211> LENGTH: 1383
<212> TYPE: DNA
<213> ORGANISM: ARTIFICIAL SEQUENCE
<220> FEATURE:
<223> OTHER INFORMATION: 16444 (HC: R118A, L120Q) coding sequence
<220> FEATURE:
<221> NAME/KEY: CDS
<222> LOCATION: (1)..(1383)

<400> SEQUENCE: 123 atg gag tgg acc tgg agg gtc ctt ttc ttg gtg gca gca aca ggt        48
Met Glu Trp Thr Trp Arg Val Leu Phe Leu Val Ala Ala Ala Thr Gly
1               5                   10                  15 gcc cac tcc cag gtt cag ctg gtg cag tct gga gct gag gtg aag aag    96
Ala His Ser Gln Val Gln Leu Val Gln Ser Gly Ala Glu Val Lys Lys
            20                  25                  30 cct ggg gcc tca gtg aag gtc tcc tgc aag gct tct ggt tac acc ttt   144
Pro Gly Ala Ser Val Lys Val Ser Cys Lys Ala Ser Gly Tyr Thr Phe
        35                  40                  45 acc aga tat ggt atc agc tgg gtg cga cag gcc cct gga caa ggg ctt   192
Thr Arg Tyr Gly Ile Ser Trp Val Arg Gln Ala Pro Gly Gln Gly Leu
    50                  55                  60 gag tgg atg gga tgg atc agc act tac agt ggt aac aca aac tat gca   240
Glu Trp Met Gly Trp Ile Ser Thr Tyr Ser Gly Asn Thr Asn Tyr Ala
65                  70                  75                  80 cag aag ctc cag ggc aga gtc acc atg acc aca gac aca tcc acg agc   288
Gln Lys Leu Gln Gly Arg Val Thr Met Thr Thr Asp Thr Ser Thr Ser
                85                  90                  95 aca gcc tac atg gag ctg agg agc ctg aga tct gac gac acg gcc gtg   336
Thr Ala Tyr Met Glu Leu Arg Ser Leu Arg Ser Asp Asp Thr Ala Val
            100                 105                 110 tat tac tgt gcg aga gct cag cag tac ttt gac tac tgg ggc cag gga   384
Tyr Tyr Cys Ala Arg Ala Gln Gln Tyr Phe Asp Tyr Trp Gly Gln Gly
        115                 120                 125 acc ctg gtc acc gtc tcc tca gct agc acc aag ggc cca tcg gtc ttc   432
Thr Leu Val Thr Val Ser Ser Ala Ser Thr Lys Gly Pro Ser Val Phe
    130                 135                 140 ccc ctg gcg ccc tgc tcc agg agc acc tcc gag agc aca gcg gcc ctg   480
Pro Leu Ala Pro Cys Ser Arg Ser Thr Ser Glu Ser Thr Ala Ala Leu
145                 150                 155                 160 ggc tgc ctg gtc aag gac tac ttc ccc gaa ccg gtg acg gtg tcg tgg   528
Gly Cys Leu Val Lys Asp Tyr Phe Pro Glu Pro Val Thr Val Ser Trp
                165                 170                 175 aac tca ggc gct ctg acc agc ggc gtg cac acc ttc cca gct gtc cta   576
Asn Ser Gly Ala Leu Thr Ser Gly Val His Thr Phe Pro Ala Val Leu
            180                 185                 190 cag tcc tca gga ctc tac tcc ctc agc agc gtg gtg acc gtg ccc tcc   624
Gln Ser Ser Gly Leu Tyr Ser Leu Ser Ser Val Val Thr Val Pro Ser
        195                 200                 205
```

| | | | | | | | | | | | | | | | | |
|---|---|---|---|---|---|---|---|---|---|---|---|---|---|---|---|---|
| agc | aac | ttc | ggc | acc | cag | acc | tac | acc | tgc | aac | gta | gat | cac | aag | ccc | 672 |
| Ser | Asn | Phe | Gly | Thr | Gln | Thr | Tyr | Thr | Cys | Asn | Val | Asp | His | Lys | Pro | |
| | 210 | | | | 215 | | | | | 220 | | | | | | |

| | | | | | | | | | | | | | | | | |
|---|---|---|---|---|---|---|---|---|---|---|---|---|---|---|---|---|
| agc | aac | acc | aag | gtg | gac | aag | aca | gtt | gag | cgc | aaa | tgt | tgt | gtc | gag | 720 |
| Ser | Asn | Thr | Lys | Val | Asp | Lys | Thr | Val | Glu | Arg | Lys | Cys | Cys | Val | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tgc | cca | ccg | tgc | cca | gca | cca | cct | gtg | gca | gga | ccg | tca | gtc | ttc | ctc | 768 |
| Cys | Pro | Pro | Cys | Pro | Ala | Pro | Pro | Val | Ala | Gly | Pro | Ser | Val | Phe | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| ttc | ccc | cca | aaa | ccc | aag | gac | acc | ctc | atg | atc | tcc | cgg | acc | cct | gag | 816 |
| Phe | Pro | Pro | Lys | Pro | Lys | Asp | Thr | Leu | Met | Ile | Ser | Arg | Thr | Pro | Glu | |
| | | | 260 | | | | | 265 | | | | | 270 | | | |

| | | | | | | | | | | | | | | | | |
|---|---|---|---|---|---|---|---|---|---|---|---|---|---|---|---|---|
| gtc | acg | tgc | gtg | gtg | gtg | gac | gtg | agc | cac | gaa | gac | ccc | gag | gtc | cag | 864 |
| Val | Thr | Cys | Val | Val | Val | Asp | Val | Ser | His | Glu | Asp | Pro | Glu | Val | Gln | |
| | | 275 | | | | | 280 | | | | | 285 | | | | |

| | | | | | | | | | | | | | | | | |
|---|---|---|---|---|---|---|---|---|---|---|---|---|---|---|---|---|
| ttc | aac | tgg | tac | gtg | gac | ggc | gtg | gag | gtg | cat | aat | gcc | aag | aca | aag | 912 |
| Phe | Asn | Trp | Tyr | Val | Asp | Gly | Val | Glu | Val | His | Asn | Ala | Lys | Thr | Lys | |
| | 290 | | | | | 295 | | | | | 300 | | | | | |

| | | | | | | | | | | | | | | | | |
|---|---|---|---|---|---|---|---|---|---|---|---|---|---|---|---|---|
| cca | cgg | gag | gag | cag | ttc | aac | agc | acg | ttc | cgt | gtg | gtc | agc | gtc | ctc | 960 |
| Pro | Arg | Glu | Glu | Gln | Phe | Asn | Ser | Thr | Phe | Arg | Val | Val | Ser | Val | Leu | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| acc | gtt | gtg | cac | cag | gac | tgg | ctg | aac | ggc | aag | gag | tac | aag | tgc | aag | 1008 |
| Thr | Val | Val | His | Gln | Asp | Trp | Leu | Asn | Gly | Lys | Glu | Tyr | Lys | Cys | Lys | |
| | | | | 325 | | | | | 330 | | | | | 335 | | |

| | | | | | | | | | | | | | | | | |
|---|---|---|---|---|---|---|---|---|---|---|---|---|---|---|---|---|
| gtc | tcc | aac | aaa | ggc | ctc | cca | gcc | ccc | atc | gag | aaa | acc | atc | tcc | aaa | 1056 |
| Val | Ser | Asn | Lys | Gly | Leu | Pro | Ala | Pro | Ile | Glu | Lys | Thr | Ile | Ser | Lys | |
| | | | 340 | | | | | 345 | | | | | 350 | | | |

| | | | | | | | | | | | | | | | | |
|---|---|---|---|---|---|---|---|---|---|---|---|---|---|---|---|---|
| acc | aaa | ggg | cag | ccc | cga | gaa | cca | cag | gtg | tac | acc | ctg | ccc | cca | tcc | 1104 |
| Thr | Lys | Gly | Gln | Pro | Arg | Glu | Pro | Gln | Val | Tyr | Thr | Leu | Pro | Pro | Ser | |
| | | 355 | | | | | 360 | | | | | 365 | | | | |

| | | | | | | | | | | | | | | | | |
|---|---|---|---|---|---|---|---|---|---|---|---|---|---|---|---|---|
| cgg | gag | gag | atg | acc | aag | aac | cag | gtc | agc | ctg | acc | tgc | ctg | gtc | aaa | 1152 |
| Arg | Glu | Glu | Met | Thr | Lys | Asn | Gln | Val | Ser | Leu | Thr | Cys | Leu | Val | Lys | |
| | 370 | | | | | 375 | | | | | 380 | | | | | |

| | | | | | | | | | | | | | | | | |
|---|---|---|---|---|---|---|---|---|---|---|---|---|---|---|---|---|
| ggc | ttc | tac | ccc | agc | gac | atc | gcc | gtg | gag | tgg | gag | agc | aat | ggg | cag | 1200 |
| Gly | Phe | Tyr | Pro | Ser | Asp | Ile | Ala | Val | Glu | Trp | Glu | Ser | Asn | Gly | Gln | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| ccg | gag | aac | aac | tac | aag | acc | aca | cct | ccc | atg | ctg | gac | tcc | gac | ggc | 1248 |
| Pro | Glu | Asn | Asn | Tyr | Lys | Thr | Thr | Pro | Pro | Met | Leu | Asp | Ser | Asp | Gly | |
| | | | | 405 | | | | | 410 | | | | | 415 | | |

| | | | | | | | | | | | | | | | | |
|---|---|---|---|---|---|---|---|---|---|---|---|---|---|---|---|---|
| tcc | ttc | ttc | ctc | tac | agc | aag | ctc | acc | gtg | gac | aag | agc | agg | tgg | cag | 1296 |
| Ser | Phe | Phe | Leu | Tyr | Ser | Lys | Leu | Thr | Val | Asp | Lys | Ser | Arg | Trp | Gln | |
| | | | 420 | | | | | 425 | | | | | 430 | | | |

| | | | | | | | | | | | | | | | | |
|---|---|---|---|---|---|---|---|---|---|---|---|---|---|---|---|---|
| cag | ggg | aac | gtc | ttc | tca | tgc | tcc | gtg | atg | cat | gag | gct | ctg | cac | aac | 1344 |
| Gln | Gly | Asn | Val | Phe | Ser | Cys | Ser | Val | Met | His | Glu | Ala | Leu | His | Asn | |
| | | 435 | | | | | 440 | | | | | 445 | | | | |

| | | | | | | | | | | | | |
|---|---|---|---|---|---|---|---|---|---|---|---|---|
| cac | tac | acg | cag | aag | agc | ctc | tcc | ctg | tct | ccg | ggt | aaa | 1383 |
| His | Tyr | Thr | Gln | Lys | Ser | Leu | Ser | Leu | Ser | Pro | Gly | Lys | |
| | 450 | | | | | 455 | | | | | 460 | | |

<210> SEQ ID NO 124
<211> LENGTH: 461
<212> TYPE: PRT
<213> ORGANISM: ARTIFICIAL SEQUENCE
<220> FEATURE:
<223> OTHER INFORMATION: Synthetic Construct

<400> SEQUENCE: 124

Met Glu Trp Thr Trp Arg Val Leu Phe Leu Val Ala Ala Thr Gly
1               5                   10                  15

Ala His Ser Gln Val Gln Leu Val Gln Ser Gly Ala Glu Val Lys Lys
            20                  25                  30

```
Pro Gly Ala Ser Val Lys Val Ser Cys Lys Ala Ser Gly Tyr Thr Phe
            35                  40                  45

Thr Arg Tyr Gly Ile Ser Trp Val Arg Gln Ala Pro Gly Gln Gly Leu
 50                  55                  60

Glu Trp Met Gly Trp Ile Ser Thr Tyr Ser Gly Asn Thr Asn Tyr Ala
 65                  70                  75                  80

Gln Lys Leu Gln Gly Arg Val Thr Met Thr Thr Asp Thr Ser Thr Ser
                 85                  90                  95

Thr Ala Tyr Met Glu Leu Arg Ser Leu Arg Ser Asp Asp Thr Ala Val
                100                 105                 110

Tyr Tyr Cys Ala Arg Ala Gln Gln Tyr Phe Asp Tyr Trp Gly Gln Gly
            115                 120                 125

Thr Leu Val Thr Val Ser Ser Ala Ser Thr Lys Gly Pro Ser Val Phe
        130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
450                 455                 460
```

<210> SEQ ID NO 125
<211> LENGTH: 442
<212> TYPE: PRT
<213> ORGANISM: ARTIFICIAL SEQUENCE
<220> FEATURE:
<223> OTHER INFORMATION: 16444 (HC: R118A, L120Q)

<400> SEQUENCE: 125

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Gln Gln Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365
```

```
Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly Lys
            435                 440

<210> SEQ ID NO 126
<211> LENGTH: 990
<212> TYPE: DNA
<213> ORGANISM: Homo sapiens
<220> FEATURE:
<221> NAME/KEY: CDS
<222> LOCATION: (1)..(990)

<400> SEQUENCE: 126
```

| | | | | | | | | | | | | | | | | |
|---|---|---|---|---|---|---|---|---|---|---|---|---|---|---|---|---|
| gcc | tcc | acc | aag | ggc | cca | tcc | gtc | ttc | ccc | ctg | gca | ccc | tcc | tcc | aag | 48 |
| Ala | Ser | Thr | Lys | Gly | Pro | Ser | Val | Phe | Pro | Leu | Ala | Pro | Ser | Ser | Lys | |
| 1 | | | | 5 | | | | | 10 | | | | | 15 | | |
| agc | acc | tct | ggg | ggc | aca | gcg | gcc | ctg | ggc | tgc | ctg | gtc | aag | gac | tac | 96 |
| Ser | Thr | Ser | Gly | Gly | Thr | Ala | Ala | Leu | Gly | Cys | Leu | Val | Lys | Asp | Tyr | |
| | | | 20 | | | | | 25 | | | | | 30 | | | |
| ttc | ccc | gaa | ccg | gtg | acg | gtg | tcg | tgg | aac | tca | ggc | gcc | ctg | acc | agc | 144 |
| Phe | Pro | Glu | Pro | Val | Thr | Val | Ser | Trp | Asn | Ser | Gly | Ala | Leu | Thr | Ser | |
| | 35 | | | | | 40 | | | | | 45 | | | | | |
| ggc | gtg | cac | acc | ttc | ccg | gct | gtc | cta | cag | tcc | tca | gga | ctc | tac | tcc | 192 |
| Gly | Val | His | Thr | Phe | Pro | Ala | Val | Leu | Gln | Ser | Ser | Gly | Leu | Tyr | Ser | |
| 50 | | | | | 55 | | | | | 60 | | | | | | |
| ctc | agc | agc | gtg | gtg | acc | gtg | ccc | tcc | agc | agc | ttg | ggc | acc | cag | acc | 240 |
| Leu | Ser | Ser | Val | Val | Thr | Val | Pro | Ser | Ser | Ser | Leu | Gly | Thr | Gln | Thr | |
| 65 | | | | 70 | | | | | 75 | | | | | 80 | | |
| tac | atc | tgc | aac | gtg | aat | cac | aag | ccc | agc | aac | acc | aag | gtg | gac | aag | 288 |
| Tyr | Ile | Cys | Asn | Val | Asn | His | Lys | Pro | Ser | Asn | Thr | Lys | Val | Asp | Lys | |
| | | | 85 | | | | | 90 | | | | | 95 | | | |
| aga | gtt | gag | ccc | aaa | tct | tgt | gac | aaa | act | cac | aca | tgc | cca | ccg | tgc | 336 |
| Arg | Val | Glu | Pro | Lys | Ser | Cys | Asp | Lys | Thr | His | Thr | Cys | Pro | Pro | Cys | |
| | | 100 | | | | | 105 | | | | | 110 | | | | |
| cca | gca | cct | gaa | ctc | ctg | ggg | gga | ccg | tca | gtc | ttc | ctc | ttc | ccc | cca | 384 |
| Pro | Ala | Pro | Glu | Leu | Leu | Gly | Gly | Pro | Ser | Val | Phe | Leu | Phe | Pro | Pro | |
| | 115 | | | | | 120 | | | | | 125 | | | | | |
| aaa | ccc | aag | gac | acc | ctc | atg | atc | tcc | cgg | acc | cct | gag | gtc | aca | tgc | 432 |
| Lys | Pro | Lys | Asp | Thr | Leu | Met | Ile | Ser | Arg | Thr | Pro | Glu | Val | Thr | Cys | |
| 130 | | | | | 135 | | | | | 140 | | | | | | |
| gtg | gtg | gtg | gac | gtg | agc | cac | gaa | gac | cct | gag | gtc | aag | ttc | aac | tgg | 480 |
| Val | Val | Val | Asp | Val | Ser | His | Glu | Asp | Pro | Glu | Val | Lys | Phe | Asn | Trp | |
| 145 | | | | 150 | | | | | 155 | | | | | 160 | | |
| tac | gtg | gac | ggc | gtg | gag | gtg | cat | aat | gcc | aag | aca | aag | ccg | cgg | gag | 528 |
| Tyr | Val | Asp | Gly | Val | Glu | Val | His | Asn | Ala | Lys | Thr | Lys | Pro | Arg | Glu | |
| | | | 165 | | | | | 170 | | | | | 175 | | | |
| gag | cag | tac | aac | agc | acg | tac | cgt | gtg | gtc | agc | gtc | ctc | acc | gtc | ctg | 576 |
| Glu | Gln | Tyr | Asn | Ser | Thr | Tyr | Arg | Val | Val | Ser | Val | Leu | Thr | Val | Leu | |
| | | 180 | | | | | 185 | | | | | 190 | | | | |
| cac | cag | gac | tgg | ctg | aat | ggc | aag | gag | tac | aag | tgc | aag | gtc | tcc | aac | 624 |
| His | Gln | Asp | Trp | Leu | Asn | Gly | Lys | Glu | Tyr | Lys | Cys | Lys | Val | Ser | Asn | |
| | 195 | | | | | 200 | | | | | 205 | | | | | |
| aaa | gcc | ctc | cca | gcc | ccc | atc | gag | aaa | acc | atc | tcc | aaa | gcc | aaa | ggg | 672 |
| Lys | Ala | Leu | Pro | Ala | Pro | Ile | Glu | Lys | Thr | Ile | Ser | Lys | Ala | Lys | Gly | |

```
                       210                 215                 220
cag ccc cga gaa cca cag gtg tac acc ctg ccc cca tcc cgg gag gag          720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat          768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac          816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc          864
Asn Tyr Lys Thr Thr Pro Pro Val Leu Asp Ser Asp Gly Ser Phe Phe
        275                 280                 285 ctc tat agc aag ctc acc gtg gac aag agc agg tgg cag cag ggg aac          912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg          960
Val Phe Ser Cys Ser Val Met His Glu Ala Leu His Asn His Tyr Thr
305                 310                 315                 320 cag aag agc ctc tcc ctg tct ccg ggt aaa                                  990
Gln Lys Ser Leu Ser Leu Ser Pro Gly Lys
                325                 330

<210> SEQ ID NO 127
<211> LENGTH: 330
<212> TYPE: PRT
<213> ORGANISM: Homo sapiens

<400> SEQUENCE: 127

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 128
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 128 cga act gtg gct gca cca tct gtc ttc atc ttc ccg cca tct gat gag     48
Arg Thr Val Ala Ala Pro Ser Val Phe Ile Phe Pro Pro Ser Asp Glu
1               5                   10                  15 cag ttg aaa tct gga act gct agc gtt gtg tgc ctg ctg aat aac ttc     96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa    144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc    192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag    240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg    288
Lys His Lys Val Tyr Ala Cys Glu Val Thr His Gln Gly Leu Ser Ser
                85                  90                  95 ccc gtc aca aag agc ttc aac agg gga gag tgt                        321
Pro Val Thr Lys Ser Phe Asn Arg Gly Glu Cys
            100                 105

<210> SEQ ID NO 129
<211> LENGTH: 107
<212> TYPE: PRT
<213> ORGANISM: Homo sapiens

<400> SEQUENCE: 129

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 130
<211> LENGTH: 1989
<212> TYPE: DNA
<213> ORGANISM: ARTIFICIAL SEQUENCE
<220> FEATURE:
<223> OTHER INFORMATION: aKLH120.6-IgG2-HC-L15-huFGF21 [1-181]
<220> FEATURE:
<221> NAME/KEY: CDS
<222> LOCATION: (1)..(1989)

<400> SEQUENCE: 130
```

| | | | | | | | | | | | | | | | | |
|---|---|---|---|---|---|---|---|---|---|---|---|---|---|---|---|---|
| atg | atg | agg | gtg | ccc | gct | cag | ctc | ctg | ggg | ctc | ctg | ctg | ctg | tgg | | 48 |
| Met | Asp | Met | Arg | Val | Pro | Ala | Gln | Leu | Leu | Gly | Leu | Leu | Leu | Leu | Trp | |
| 1 | | | | 5 | | | | | 10 | | | | | 15 | | |
| ctg | aga | ggt | gcc | aga | tgt | cag | gtg | cag | ctg | gtg | cag | tct | ggg | gct | gag | 96 |
| Leu | Arg | Gly | Ala | Arg | Cys | Gln | Val | Gln | Leu | Val | Gln | Ser | Gly | Ala | Glu | |
| | | | 20 | | | | | 25 | | | | | 30 | | | |
| gtg | aag | aag | cct | ggg | gcc | tca | gtg | aag | gtc | tcc | tgc | aag | gct | tct | gga | 144 |
| Val | Lys | Lys | Pro | Gly | Ala | Ser | Val | Lys | Val | Ser | Cys | Lys | Ala | Ser | Gly | |
| | | 35 | | | | | 40 | | | | | 45 | | | | |
| tac | acc | ttc | acc | ggc | tac | cac | atg | cac | tgg | gtg | cga | cag | gcc | cct | gga | 192 |
| Tyr | Thr | Phe | Thr | Gly | Tyr | His | Met | His | Trp | Val | Arg | Gln | Ala | Pro | Gly | |
| | 50 | | | | | 55 | | | | | 60 | | | | | |
| caa | ggg | ctt | gag | tgg | atg | gga | tgg | atc | aac | cct | aac | agt | ggt | ggc | aca | 240 |
| Gln | Gly | Leu | Glu | Trp | Met | Gly | Trp | Ile | Asn | Pro | Asn | Ser | Gly | Gly | Thr | |
| 65 | | | | 70 | | | | | 75 | | | | | 80 | | |
| aac | tat | gca | cag | aag | ttt | cag | ggc | agg | gtc | acc | atg | acc | agg | gac | acg | 288 |
| Asn | Tyr | Ala | Gln | Lys | Phe | Gln | Gly | Arg | Val | Thr | Met | Thr | Arg | Asp | Thr | |
| | | | 85 | | | | | 90 | | | | | 95 | | | |
| tcc | atc | agc | aca | gcc | tac | atg | gag | ctg | agc | agg | ctg | aga | tct | gac | gac | 336 |
| Ser | Ile | Ser | Thr | Ala | Tyr | Met | Glu | Leu | Ser | Arg | Leu | Arg | Ser | Asp | Asp | |
| | | 100 | | | | | 105 | | | | | 110 | | | | |
| acg | gcc | gtg | tat | tac | tgt | gcg | aga | gat | cgt | ggg | agc | tac | tac | tgg | ttc | 384 |
| Thr | Ala | Val | Tyr | Tyr | Cys | Ala | Arg | Asp | Arg | Gly | Ser | Tyr | Tyr | Trp | Phe | |
| | 115 | | | | | 120 | | | | | 125 | | | | | |
| gac | ccc | tgg | ggc | cag | gga | acc | ctg | gtc | acc | gtc | tcc | tca | gcc | tcc | acc | 432 |
| Asp | Pro | Trp | Gly | Gln | Gly | Thr | Leu | Val | Thr | Val | Ser | Ser | Ala | Ser | Thr | |
| 130 | | | | | 135 | | | | | 140 | | | | | | |
| aag | ggc | cca | tcg | gtc | ttc | ccc | ctg | gcg | ccc | tgc | tcc | agg | agc | acc | tcc | 480 |
| Lys | Gly | Pro | Ser | Val | Phe | Pro | Leu | Ala | Pro | Cys | Ser | Arg | Ser | Thr | Ser | |
| 145 | | | | | 150 | | | | | 155 | | | | | 160 | |
| gag | agc | aca | gcg | gcc | ctg | ggc | tgc | ctg | gtc | aag | gac | tac | ttc | ccc | gaa | 528 |
| Glu | Ser | Thr | Ala | Ala | Leu | Gly | Cys | Leu | Val | Lys | Asp | Tyr | Phe | Pro | Glu | |
| | | | | 165 | | | | | 170 | | | | | 175 | | |
| ccg | gtg | acg | gtg | tcg | tgg | aac | tca | ggc | gct | ctg | acc | agc | ggc | gtg | cac | 576 |
| Pro | Val | Thr | Val | Ser | Trp | Asn | Ser | Gly | Ala | Leu | Thr | Ser | Gly | Val | His | |
| | | | 180 | | | | | 185 | | | | | 190 | | | |
| acc | ttc | cca | gct | gtc | cta | cag | tcc | tca | gga | ctc | tac | tcc | ctc | agc | agc | 624 |
| Thr | Phe | Pro | Ala | Val | Leu | Gln | Ser | Ser | Gly | Leu | Tyr | Ser | Leu | Ser | Ser | |
| | | 195 | | | | | 200 | | | | | 205 | | | | |
| gtg | gtg | acc | gtg | ccc | tcc | agc | aac | ttc | ggc | acc | cag | acc | tac | acc | tgc | 672 |
| Val | Val | Thr | Val | Pro | Ser | Ser | Asn | Phe | Gly | Thr | Gln | Thr | Tyr | Thr | Cys | |
| | 210 | | | | | 215 | | | | | 220 | | | | | |
| aac | gta | gat | cac | aag | ccc | agc | aac | acc | aag | gtg | gac | aag | aca | gtt | gag | 720 |
| Asn | Val | Asp | His | Lys | Pro | Ser | Asn | Thr | Lys | Val | Asp | Lys | Thr | Val | Glu | |

```
                225                 230                 235                 240
cgc aaa tgt tgt gtc gag tgc cca ccg tgc cca gca cca cct gtg gca          768
Arg Lys Cys Cys Val Glu Cys Pro Pro Cys Pro Ala Pro Pro Val Ala
                    245                 250                 255 gga ccg tca gtc ttc ctc ttc ccc cca aaa ccc aag gac acc ctc atg          816
Gly Pro Ser Val Phe Leu Phe Pro Pro Lys Pro Lys Asp Thr Leu Met
                260                 265                 270 atc tcc cgg acc cct gag gtc acg tgc gtg gtg gtg gac gtg agc cac          864
Ile Ser Arg Thr Pro Glu Val Thr Cys Val Val Val Asp Val Ser His
            275                 280                 285 gaa gac ccc gag gtc cag ttc aac tgg tac gtg gac ggc gtg gag gtg          912
Glu Asp Pro Glu Val Gln Phe Asn Trp Tyr Val Asp Gly Val Glu Val
        290                 295                 300 cat aat gcc aag aca aag cca cgg gag gag cag ttc aac agc acg ttc          960
His Asn Ala Lys Thr Lys Pro Arg Glu Glu Gln Phe Asn Ser Thr Phe
305                 310                 315                 320 cgt gtg gtc agc gtc ctc acc gtt gtg cac cag gac tgg ctg aac ggc         1008
Arg Val Val Ser Val Leu Thr Val Val His Gln Asp Trp Leu Asn Gly
                325                 330                 335 aag gag tac aag tgc aag gtc tcc aac aaa ggc ctc cca gcc ccc atc         1056
Lys Glu Tyr Lys Cys Lys Val Ser Asn Lys Gly Leu Pro Ala Pro Ile
            340                 345                 350 gag aaa acc atc tcc aaa acc aaa ggg cag ccc cga gaa cca cag gtg         1104
Glu Lys Thr Ile Ser Lys Thr Lys Gly Gln Pro Arg Glu Pro Gln Val
        355                 360                 365 tac acc ctg ccc cca tcc cgg gag gag atg acc aag aac cag gtc agc         1152
Tyr Thr Leu Pro Pro Ser Arg Glu Glu Met Thr Lys Asn Gln Val Ser
    370                 375                 380 ctg acc tgc ctg gtc aaa ggc ttc tac ccc agc gac atc gcc gtg gag         1200
Leu Thr Cys Leu Val Lys Gly Phe Tyr Pro Ser Asp Ile Ala Val Glu
385                 390                 395                 400 tgg gag agc aat ggg cag ccg gag aac aac tac aag acc aca cct ccc         1248
Trp Glu Ser Asn Gly Gln Pro Glu Asn Asn Tyr Lys Thr Thr Pro Pro
                405                 410                 415 atg ctg gac tcc gac ggc tcc ttc ttc ctc tac agc aag ctc acc gtg         1296
Met Leu Asp Ser Asp Gly Ser Phe Phe Leu Tyr Ser Lys Leu Thr Val
            420                 425                 430 gac aag agc agg tgg cag cag ggg aac gtc ttc tca tgc tcc gtg atg         1344
Asp Lys Ser Arg Trp Gln Gln Gly Asn Val Phe Ser Cys Ser Val Met
        435                 440                 445 cat gag gct ctg cac aac cac tac acg cag aag agc ctc tcc ctg tct         1392
His Glu Ala Leu His Asn His Tyr Thr Gln Lys Ser Leu Ser Leu Ser
    450                 455                 460 ccg ggt ggt gga ggt ggt ggt tct ggt ggt ggt agc gga ggc ggc ggt         1440
Pro Gly Gly Gly Gly Gly Gly Ser Gly Gly Gly Ser Gly Gly Gly Gly
465                 470                 475                 480 tcc cac ccc atc cct gac tcc tct cca ctc ctg caa ttc ggg ggc caa         1488
Ser His Pro Ile Pro Asp Ser Ser Pro Leu Leu Gln Phe Gly Gly Gln
                485                 490                 495 gtc cgg cag cgg tac ctc tac aca gat gat gcc cag cag aca gaa gcc         1536
Val Arg Gln Arg Tyr Leu Tyr Thr Asp Asp Ala Gln Gln Thr Glu Ala
            500                 505                 510 cac ctg gag atc agg gag gat ggg acg gtg ggg ggc gct gct gac cag         1584
His Leu Glu Ile Arg Glu Asp Gly Thr Val Gly Gly Ala Ala Asp Gln
        515                 520                 525 agc ccc gaa agt ctc ctg cag ctg aaa gcc ttg aag ccg gga gtt att         1632
Ser Pro Glu Ser Leu Leu Gln Leu Lys Ala Leu Lys Pro Gly Val Ile
    530                 535                 540 caa atc ttg gga gtc aag aca tcc agg ttc ctg tgc cag cgg cca gat         1680
Gln Ile Leu Gly Val Lys Thr Ser Arg Phe Leu Cys Gln Arg Pro Asp
```

```
                545                 550                 555                 560
ggg gcc ctg tat gga tcg ctc cac ttt gac cct gag gcc tgc agc ttc    1728
Gly Ala Leu Tyr Gly Ser Leu His Phe Asp Pro Glu Ala Cys Ser Phe
                565                 570                 575 cgg gag ctg ctt ctt gag gac gga tac aat gtt tac cag tcc gaa gcc    1776
Arg Glu Leu Leu Leu Glu Asp Gly Tyr Asn Val Tyr Gln Ser Glu Ala
                580                 585                 590 cac ggc ctc ccg ctg cac ctg cca ggg aac aag tcc cca cac cgg gac    1824
His Gly Leu Pro Leu His Leu Pro Gly Asn Lys Ser Pro His Arg Asp
                595                 600                 605 cct gca ccc cga gga cca gct cgc ttc ctg cca cta cca ggc ctg cca    1872
Pro Ala Pro Arg Gly Pro Ala Arg Phe Leu Pro Leu Pro Gly Leu Pro
                610                 615                 620 ccc gca ccc ccg gag cca ccc gga atc ctg gcc ccc cag ccc ccc gat    1920
Pro Ala Pro Pro Glu Pro Pro Gly Ile Leu Ala Pro Gln Pro Pro Asp
625                 630                 635                 640 gtg ggc tcc tcg gac cct ctg agc atg gtg gga cct tcc cag ggc cga    1968
Val Gly Ser Ser Asp Pro Leu Ser Met Val Gly Pro Ser Gln Gly Arg
                645                 650                 655 agc ccc agc tac gct tcc tga                                        1989
Ser Pro Ser Tyr Ala Ser
                660

<210> SEQ ID NO 131
<211> LENGTH: 662
<212> TYPE: PRT
<213> ORGANISM: ARTIFICIAL SEQUENCE
<220> FEATURE:
<223> OTHER INFORMATION: Synthetic Construct

<400> SEQUENCE: 131

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Thr Gly Tyr His Met His Trp Val Arg Gln Ala Pro Gly
        50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
```

```
            210                 215                 220
Asn Val Asp His Lys Pro Ser Asn Thr Lys Val Asp Lys Thr Val Glu
225                 230                 235                 240
Arg Lys Cys Cys Val Glu Cys Pro Pro Cys Pro Ala Pro Pro Val Ala
                    245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Asp Val Ser His
                275                 280                 285
Glu Asp Pro Glu Val Gln Phe Asn Trp Tyr Val Asp Gly Val Glu Val
            290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
                340                 345                 350
Glu Lys Thr Ile Ser Lys Thr Lys Gly Gln Pro Arg Glu Pro Gln Val
                355                 360                 365
Tyr Thr Leu Pro Pro Ser Arg Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
                420                 425                 430
Asp Lys Ser Arg Trp Gln Gln Gly Asn Val Phe Ser Cys Ser Val Met
                435                 440                 445
His Glu Ala Leu His Asn His Tyr Thr Gln Lys Ser Leu Ser Leu Ser
            450                 455                 460
Pro Gly Gly Gly Gly Gly Ser Gly Gly Gly Ser Gly Gly Gly Gly
465                 470                 475                 480
Ser His Pro Ile Pro Asp Ser Ser Pro Leu Leu Gln Phe Gly Gly Gln
                485                 490                 495
Val Arg Gln Arg Tyr Leu Tyr Thr Asp Asp Ala Gln Gln Thr Glu Ala
                500                 505                 510
His Leu Glu Ile Arg Glu Asp Gly Thr Val Gly Gly Ala Ala Asp Gln
            515                 520                 525
Ser Pro Glu Ser Leu Leu Gln Leu Lys Ala Leu Lys Pro Gly Val Ile
            530                 535                 540
Gln Ile Leu Gly Val Lys Thr Ser Arg Phe Leu Cys Gln Arg Pro Asp
545                 550                 555                 560
Gly Ala Leu Tyr Gly Ser Leu His Phe Asp Pro Glu Ala Cys Ser Phe
                565                 570                 575
Arg Glu Leu Leu Leu Glu Asp Gly Tyr Asn Val Tyr Gln Ser Glu Ala
                580                 585                 590
His Gly Leu Pro Leu His Leu Pro Gly Asn Lys Ser Pro His Arg Asp
            595                 600                 605
Pro Ala Pro Arg Gly Pro Ala Arg Phe Leu Pro Leu Pro Gly Leu Pro
            610                 615                 620
Pro Ala Pro Pro Glu Pro Pro Gly Ile Leu Ala Pro Gln Pro Pro Asp
625                 630                 635                 640
```

Val Gly Ser Ser Asp Pro Leu Ser Met Val Gly Pro Ser Gln Gly Arg
            645                 650                 655

Ser Pro Ser Tyr Ala Ser
            660

<210> SEQ ID NO 132
<211> LENGTH: 45
<212> TYPE: DNA
<213> ORGANISM: ARTIFICIAL SEQUENCE
<220> FEATURE:
<223> OTHER INFORMATION: 5172-62 primer sequence

<400> SEQUENCE: 132
gtaccaggct aagtagctac tactaacact ctgactggcc ctgca                    45

<210> SEQ ID NO 133
<211> LENGTH: 45
<212> TYPE: DNA
<213> ORGANISM: ARTIFICIAL SEQUENCE
<220> FEATURE:
<223> OTHER INFORMATION: 5172-61 primer sequence

<400> SEQUENCE: 133
tgcagggcca gtcagagtgt tagtagtagc tacttagcct ggtac                    45

<210> SEQ ID NO 134
<211> LENGTH: 36
<212> TYPE: DNA
<213> ORGANISM: ARTIFICIAL SEQUENCE
<220> FEATURE:
<223> OTHER INFORMATION: 5172-64 primer sequence

<400> SEQUENCE: 134
cgtccacggt gaactaccat attgttgaca gtaata                              36

<210> SEQ ID NO 135
<211> LENGTH: 36
<212> TYPE: DNA
<213> ORGANISM: ARTIFICIAL SEQUENCE
<220> FEATURE:
<223> OTHER INFORMATION: 5172-63 primer sequence

<400> SEQUENCE: 135
tattactgtc aacaatatgg tagttcaccg tggacg                              36

<210> SEQ ID NO 136
<211> LENGTH: 27
<212> TYPE: DNA
<213> ORGANISM: ARTIFICIAL SEQUENCE
<220> FEATURE:
<223> OTHER INFORMATION: 5172-66 primer sequence

<400> SEQUENCE: 136
gatccagctc cagtagtaat caccact                                        27

<210> SEQ ID NO 137
<211> LENGTH: 27
<212> TYPE: DNA
<213> ORGANISM: ARTIFICIAL SEQUENCE
<220> FEATURE:
<223> OTHER INFORMATION: 5172-65 primer sequence

<400> SEQUENCE: 137
agtggtgatt actactggag ctggatc                                        27

<210> SEQ ID NO 138

-continued

```
<211> LENGTH: 48
<212> TYPE: DNA
<213> ORGANISM: ARTIFICIAL SEQUENCE
<220> FEATURE:
<223> OTHER INFORMATION: 5172-68 primer sequence

<400> SEQUENCE: 138
attgtagtag gtggacccac tgtaatagat gtacccaatc cactccag          48

<210> SEQ ID NO 139
<211> LENGTH: 48
<212> TYPE: DNA
<213> ORGANISM: ARTIFICIAL SEQUENCE
<220> FEATURE:
<223> OTHER INFORMATION: 5172-67 primer sequence

<400> SEQUENCE: 139
ctggagtgga ttgggtacat ctattacagt gggtccacct actacaat          48

<210> SEQ ID NO 140
<211> LENGTH: 54
<212> TYPE: DNA
<213> ORGANISM: ARTIFICIAL SEQUENCE
<220> FEATURE:
<223> OTHER INFORMATION: 5172-70 primer sequence

<400> SEQUENCE: 140
cataccatag tagtagtaat agtagtcccc ataatctctc gcacagtaat atac    54

<210> SEQ ID NO 141
<211> LENGTH: 54
<212> TYPE: DNA
<213> ORGANISM: ARTIFICIAL SEQUENCE
<220> FEATURE:
<223> OTHER INFORMATION: 5172-69 primer sequence

<400> SEQUENCE: 141
gtatattact gtgcgagaga ttatggggac tactattact actactatgg tatg    54

<210> SEQ ID NO 142
<211> LENGTH: 36
<212> TYPE: DNA
<213> ORGANISM: ARTIFICIAL SEQUENCE
<220> FEATURE:
<223> OTHER INFORMATION: 5245-83 primer sequence

<400> SEQUENCE: 142
ctggtaccag gctaattcgc ttctactaat accctg                        36

<210> SEQ ID NO 143
<211> LENGTH: 36
<212> TYPE: DNA
<213> ORGANISM: ARTIFICIAL SEQUENCE
<220> FEATURE:
<223> OTHER INFORMATION: 5245-82 primer sequence

<400> SEQUENCE: 143
cagggtatta gtagaagcga attagcctgg taccag                        36

<210> SEQ ID NO 144
<211> LENGTH: 36
<212> TYPE: DNA
<213> ORGANISM: ARTIFICIAL SEQUENCE
<220> FEATURE:
<223> OTHER INFORMATION: 5245-85 primer sequence

<400> SEQUENCE: 144
```

-continued

```
ctggtaccag gctaatctgc ttctactaat accctg                               36
```

<210> SEQ ID NO 145
<211> LENGTH: 36
<212> TYPE: DNA
<213> ORGANISM: ARTIFICIAL SEQUENCE
<220> FEATURE:
<223> OTHER INFORMATION: 5245 -84 primer sequence

<400> SEQUENCE: 145

```
cagggtatta gtagaagcag attagcctgg taccag                               36
```

<210> SEQ ID NO 146
<211> LENGTH: 25
<212> TYPE: PRT
<213> ORGANISM: ARTIFICIAL SEQUENCE
<220> FEATURE:
<223> OTHER INFORMATION: Linker sequence

<400> SEQUENCE: 146

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 147
<211> LENGTH: 20
<212> TYPE: PRT
<213> ORGANISM: ARTIFICIAL SEQUENCE
<220> FEATURE:
<223> OTHER INFORMATION: Linker sequence

<400> SEQUENCE: 147

Gly Gly Gly Gly Ser Gly Gly Gly Gly Ser Gly Gly Gly Gly Ser Gly
1               5                   10                  15

Gly Gly Gly Ser
            20

<210> SEQ ID NO 148
<211> LENGTH: 6
<212> TYPE: PRT
<213> ORGANISM: ARTIFICIAL SEQUENCE
<220> FEATURE:
<223> OTHER INFORMATION: Linker sequence
<220> FEATURE:
<221> NAME/KEY: MISC_FEATURE
<222> LOCATION: (1)..(2)
<223> OTHER INFORMATION: Independently any amino acid residue
<220> FEATURE:
<221> NAME/KEY: MISC_FEATURE
<222> LOCATION: (4)..(5)
<223> OTHER INFORMATION: Independently any amino acid residue

<400> SEQUENCE: 148

Xaa Xaa Asn Xaa Xaa Gly
1               5

<210> SEQ ID NO 149
<211> LENGTH: 4
<212> TYPE: PRT
<213> ORGANISM: ARTIFICIAL SEQUENCE
<220> FEATURE:
<223> OTHER INFORMATION: Linker sequence

<400> SEQUENCE: 149

Gly Gly Gly Gly
1

```
<210> SEQ ID NO 150
<211> LENGTH: 5
<212> TYPE: PRT
<213> ORGANISM: ARTIFICIAL SEQUENCE
<220> FEATURE:
<223> OTHER INFORMATION: Linker sequence

<400> SEQUENCE: 150

Gly Gly Gly Gly Gly
1               5

<210> SEQ ID NO 151
<211> LENGTH: 7
<212> TYPE: PRT
<213> ORGANISM: ARTIFICIAL SEQUENCE
<220> FEATURE:
<223> OTHER INFORMATION: Linker sequence

<400> SEQUENCE: 151

Gly Gly Gly Gly Gly Gly Gly
1               5

<210> SEQ ID NO 152
<211> LENGTH: 5
<212> TYPE: PRT
<213> ORGANISM: ARTIFICIAL SEQUENCE
<220> FEATURE:
<223> OTHER INFORMATION: Linker sequence "L5"

<400> SEQUENCE: 152

Gly Gly Gly Gly Ser
1               5

<210> SEQ ID NO 153
<211> LENGTH: 10
<212> TYPE: PRT
<213> ORGANISM: ARTIFICIAL SEQUENCE
<220> FEATURE:
<223> OTHER INFORMATION: Linker sequence "L10"

<400> SEQUENCE: 153

Gly Gly Gly Gly Ser Gly Gly Gly Gly Ser
1               5                   10

<210> SEQ ID NO 154
<211> LENGTH: 6
<212> TYPE: PRT
<213> ORGANISM: ARTIFICIAL SEQUENCE
<220> FEATURE:
<223> OTHER INFORMATION: Linker sequence

<400> SEQUENCE: 154

Gly Gly Gly Gly Gly Lys
1               5

<210> SEQ ID NO 155
<211> LENGTH: 7
<212> TYPE: PRT
<213> ORGANISM: ARTIFICIAL SEQUENCE
<220> FEATURE:
<223> OTHER INFORMATION: Linker sequence

<400> SEQUENCE: 155

Gly Gly Gly Gly Gly Lys Arg
1               5

<210> SEQ ID NO 156
```

```
<211> LENGTH: 8
<212> TYPE: PRT
<213> ORGANISM: ARTIFICIAL SEQUENCE
<220> FEATURE:
<223> OTHER INFORMATION: Linker sequence

<400> SEQUENCE: 156

Gly Gly Gly Asn Gly Ser Gly Gly
1               5

<210> SEQ ID NO 157
<211> LENGTH: 8
<212> TYPE: PRT
<213> ORGANISM: ARTIFICIAL SEQUENCE
<220> FEATURE:
<223> OTHER INFORMATION: Linker sequence

<400> SEQUENCE: 157

Gly Gly Gly Cys Gly Gly Gly Gly
1               5

<210> SEQ ID NO 158
<211> LENGTH: 5
<212> TYPE: PRT
<213> ORGANISM: ARTIFICIAL SEQUENCE
<220> FEATURE:
<223> OTHER INFORMATION: Linker sequence

<400> SEQUENCE: 158

Gly Pro Asn Gly Gly
1               5

<210> SEQ ID NO 159
<211> LENGTH: 8
<212> TYPE: PRT
<213> ORGANISM: ARTIFICIAL SEQUENCE
<220> FEATURE:
<223> OTHER INFORMATION: Linker sequence

<400> SEQUENCE: 159

Gly Gly Gly Lys Gly Gly Gly Gly
1               5

<210> SEQ ID NO 160
<211> LENGTH: 6
<212> TYPE: PRT
<213> ORGANISM: ARTIFICIAL SEQUENCE
<220> FEATURE:
<223> OTHER INFORMATION: Linker sequence

<400> SEQUENCE: 160

Gly Gly Glu Gly Gly Gly
1               5

<210> SEQ ID NO 161
<211> LENGTH: 8
<212> TYPE: PRT
<213> ORGANISM: ARTIFICIAL SEQUENCE
<220> FEATURE:
<223> OTHER INFORMATION: Linker sequence

<400> SEQUENCE: 161

Gly Gly Glu Glu Glu Gly Gly Gly
1               5

<210> SEQ ID NO 162
<211> LENGTH: 5
<212> TYPE: PRT
```

```
<213> ORGANISM: ARTIFICIAL SEQUENCE
<220> FEATURE:
<223> OTHER INFORMATION: Linker sequence

<400> SEQUENCE: 162

Gly Glu Glu Glu Gly
1               5

<210> SEQ ID NO 163
<211> LENGTH: 4
<212> TYPE: PRT
<213> ORGANISM: ARTIFICIAL SEQUENCE
<220> FEATURE:
<223> OTHER INFORMATION: Linker sequence

<400> SEQUENCE: 163

Gly Glu Glu Glu
1

<210> SEQ ID NO 164
<211> LENGTH: 6
<212> TYPE: PRT
<213> ORGANISM: ARTIFICIAL SEQUENCE
<220> FEATURE:
<223> OTHER INFORMATION: Linker sequence

<400> SEQUENCE: 164

Gly Gly Asp Gly Gly Gly
1               5

<210> SEQ ID NO 165
<211> LENGTH: 7
<212> TYPE: PRT
<213> ORGANISM: ARTIFICIAL SEQUENCE
<220> FEATURE:
<223> OTHER INFORMATION: Linker sequence

<400> SEQUENCE: 165

Gly Gly Asp Asp Asp Gly Gly
1               5

<210> SEQ ID NO 166
<211> LENGTH: 5
<212> TYPE: PRT
<213> ORGANISM: ARTIFICIAL SEQUENCE
<220> FEATURE:
<223> OTHER INFORMATION: Linker sequence

<400> SEQUENCE: 166

Gly Asp Asp Asp Gly
1               5

<210> SEQ ID NO 167
<211> LENGTH: 4
<212> TYPE: PRT
<213> ORGANISM: ARTIFICIAL SEQUENCE
<220> FEATURE:
<223> OTHER INFORMATION: Linker sequence

<400> SEQUENCE: 167

Gly Asp Asp Asp
1

<210> SEQ ID NO 168
<211> LENGTH: 21
<212> TYPE: PRT
<213> ORGANISM: ARTIFICIAL SEQUENCE
<220> FEATURE:
```

<223> OTHER INFORMATION: Linker sequence

<400> SEQUENCE: 168

Gly Gly Gly Gly Ser Asp Asp Ser Asp Glu Gly Ser Asp Gly Glu Asp
1               5                   10                  15

Gly Gly Gly Gly Ser
            20

<210> SEQ ID NO 169
<211> LENGTH: 5
<212> TYPE: PRT
<213> ORGANISM: ARTIFICIAL SEQUENCE
<220> FEATURE:
<223> OTHER INFORMATION: Linker sequence

<400> SEQUENCE: 169

Trp Glu Trp Glu Trp
1               5

<210> SEQ ID NO 170
<211> LENGTH: 5
<212> TYPE: PRT
<213> ORGANISM: ARTIFICIAL SEQUENCE
<220> FEATURE:
<223> OTHER INFORMATION: Linker sequence

<400> SEQUENCE: 170

Phe Glu Phe Glu Phe
1               5

<210> SEQ ID NO 171
<211> LENGTH: 6
<212> TYPE: PRT
<213> ORGANISM: ARTIFICIAL SEQUENCE
<220> FEATURE:
<223> OTHER INFORMATION: Linker sequence

<400> SEQUENCE: 171

Glu Glu Glu Trp Trp Trp
1               5

<210> SEQ ID NO 172
<211> LENGTH: 6
<212> TYPE: PRT
<213> ORGANISM: ARTIFICIAL SEQUENCE
<220> FEATURE:
<223> OTHER INFORMATION: Linker sequence

<400> SEQUENCE: 172

Glu Glu Glu Phe Phe Phe
1               5

<210> SEQ ID NO 173
<211> LENGTH: 7
<212> TYPE: PRT
<213> ORGANISM: ARTIFICIAL SEQUENCE
<220> FEATURE:
<223> OTHER INFORMATION: Linker sequence

<400> SEQUENCE: 173

Trp Trp Glu Glu Glu Trp Trp
1               5

<210> SEQ ID NO 174
<211> LENGTH: 7
<212> TYPE: PRT
<213> ORGANISM: ARTIFICIAL SEQUENCE

```
<220> FEATURE:
<223> OTHER INFORMATION: Linker sequence

<400> SEQUENCE: 174

Phe Phe Glu Glu Glu Phe Phe
1               5

<210> SEQ ID NO 175
<211> LENGTH: 6
<212> TYPE: PRT
<213> ORGANISM: ARTIFICIAL SEQUENCE
<220> FEATURE:
<223> OTHER INFORMATION: Linker sequence
<220> FEATURE:
<221> NAME/KEY: MISC_FEATURE
<222> LOCATION: (1)..(2)
<223> OTHER INFORMATION: Independently any amino acid residue
<220> FEATURE:
<221> NAME/KEY: MISC_FEATURE
<222> LOCATION: (4)..(5)
<223> OTHER INFORMATION: Independently any amino acid residue

<400> SEQUENCE: 175

Xaa Xaa Tyr Xaa Xaa Gly
1               5

<210> SEQ ID NO 176
<211> LENGTH: 6
<212> TYPE: PRT
<213> ORGANISM: ARTIFICIAL SEQUENCE
<220> FEATURE:
<223> OTHER INFORMATION: Linker sequence
<220> FEATURE:
<221> NAME/KEY: MISC_FEATURE
<222> LOCATION: (1)..(2)
<223> OTHER INFORMATION: Independently any amino acid residue
<220> FEATURE:
<221> NAME/KEY: MISC_FEATURE
<222> LOCATION: (4)..(5)
<223> OTHER INFORMATION: Independently any amino acid residue

<400> SEQUENCE: 176

Xaa Xaa Ser Xaa Xaa Gly
1               5

<210> SEQ ID NO 177
<211> LENGTH: 6
<212> TYPE: PRT
<213> ORGANISM: ARTIFICIAL SEQUENCE
<220> FEATURE:
<223> OTHER INFORMATION: Linker sequence
<220> FEATURE:
<221> NAME/KEY: MISC_FEATURE
<222> LOCATION: (1)..(2)
<223> OTHER INFORMATION: Independently any amino acid residue
<220> FEATURE:
<221> NAME/KEY: MISC_FEATURE
<222> LOCATION: (4)..(5)
<223> OTHER INFORMATION: Independently any amino acid residue

<400> SEQUENCE: 177

Xaa Xaa Thr Xaa Xaa Gly
1               5

<210> SEQ ID NO 178
<211> LENGTH: 22
<212> TYPE: PRT
<213> ORGANISM: ARTIFICIAL SEQUENCE
<220> FEATURE:
<223> OTHER INFORMATION: Linker sequence

<400> SEQUENCE: 178
```

```
Gly Ser Gly Ser Ala Thr Gly Gly Ser Gly Ser Thr Ala Ser Ser Gly
1               5                   10                  15

Ser Gly Ser Ala Thr His
            20
```

<210> SEQ ID NO 179
<211> LENGTH: 22
<212> TYPE: PRT
<213> ORGANISM: ARTIFICIAL SEQUENCE
<220> FEATURE:
<223> OTHER INFORMATION: Linker sequence

<400> SEQUENCE: 179

```
His Gly Ser Gly Ser Ala Thr Gly Gly Ser Gly Ser Thr Ala Ser Ser
1               5                   10                  15

Gly Ser Gly Ser Ala Thr
            20
```

<210> SEQ ID NO 180
<211> LENGTH: 19
<212> TYPE: PRT
<213> ORGANISM: ARTIFICIAL SEQUENCE
<220> FEATURE:
<223> OTHER INFORMATION: Linker sequence

<400> SEQUENCE: 180

```
Ala Glu Ala Ala Ala Lys Glu Ala Ala Ala Lys Glu Ala Ala Ala Lys
1               5                   10                  15

Ala Gly Gly
```

<210> SEQ ID NO 181
<211> LENGTH: 321
<212> TYPE: DNA
<213> ORGANISM: ARTIFICIAL SEQUENCE
<220> FEATURE:
<223> OTHER INFORMATION: VL1 coding sequence
<220> FEATURE:
<221> NAME/KEY: CDS
<222> LOCATION: (1)..(321)

<400> SEQUENCE: 181

```
gaa ata gtg atg acg cag tct cca gcc acc ctg tct gtg tct cct ggg     48
Glu Ile Val Met Thr Gln Ser Pro Ala Thr Leu Ser Val Ser Pro Gly
1               5                   10                  15 gaa aga gcc acc ctc tcc tgc agg gcc agt cag agt gtt agc agc aac     96
Glu Arg Ala Thr Leu Ser Cys Arg Ala Ser Gln Ser Val Ser Ser Asn
            20                  25                  30 tta gcc tgg ttc cag cag aaa cct ggc cag gct ccc agg ccc ctc atc    144
Leu Ala Trp Phe Gln Gln Lys Pro Gly Gln Ala Pro Arg Pro Leu Ile
        35                  40                  45 tat gat gca tcc acc agg gcc act ggt gtc cca gcc agg ttc agt ggc    192
Tyr Asp Ala Ser Thr Arg Ala Thr Gly Val Pro Ala Arg Phe Ser Gly
    50                  55                  60 agt ggg tct ggg aca gac ttc act ctc acc atc agc agc ctg cag tct    240
Ser Gly Ser Gly Thr Asp Phe Thr Leu Thr Ile Ser Ser Leu Gln Ser
65                  70                  75                  80 gaa gat ttt gca gtt tat tac tgt cag cag tat gat aac tgg ccg ctc    288
Glu Asp Phe Ala Val Tyr Tyr Cys Gln Gln Tyr Asp Asn Trp Pro Leu
                85                  90                  95 act ttc ggc gga ggg acc aag gtg gag atc aaa                        321
Thr Phe Gly Gly Gly Thr Lys Val Glu Ile Lys
            100                 105
```

```
<210> SEQ ID NO 182
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 182

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Pro Leu Ile
        35                  40                  45

Tyr Asp Ala Ser Thr Arg Ala Thr Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Leu
                85                  90                  95

Thr Phe Gly Gly Gly Thr Lys Val Glu Ile Lys
            100                 105

<210> SEQ ID NO 183
<211> LENGTH: 321
<212> TYPE: DNA
<213> ORGANISM: ARTIFICIAL SEQUENCE
<220> FEATURE:
<223> OTHER INFORMATION: VL2 coding sequence
<220> FEATURE:
<221> NAME/KEY: CDS
<222> LOCATION: (1)..(321)

<400> SEQUENCE: 183 gaa ata gtg atg acg cag tct cca gcc acc ctg tct gtg tct cct ggg        48
Glu Ile Val Met Thr Gln Ser Pro Ala Thr Leu Ser Val Ser Pro Gly
1               5                   10                  15 gaa aga gcc acc ctc tcc tgc agg gcc agt cag agt gtt agc agc aac        96
Glu Arg Ala Thr Leu Ser Cys Arg Ala Ser Gln Ser Val Ser Ser Asn
            20                  25                  30 tta gcc tgg ttc cag cag aaa cct ggc cag gct ccc agg ccc ctc atc       144
Leu Ala Trp Phe Gln Gln Lys Pro Gly Gln Ala Pro Arg Pro Leu Ile
        35                  40                  45 tat gat gca tcc acc agg gcc act ggt gtc cca gcc agg ttc agt ggc       192
Tyr Asp Ala Ser Thr Arg Ala Thr Gly Val Pro Ala Arg Phe Ser Gly
    50                  55                  60 agt ggg tct ggg aca gac ttc act ctc acc atc agc agc ctg cag tct       240
Ser Gly Ser Gly Thr Asp Phe Thr Leu Thr Ile Ser Ser Leu Gln Ser
65                  70                  75                  80 gaa gat ttt gca gtt tat tac tgt cag cag tat gat aac gct ccg ctc       288
Glu Asp Phe Ala Val Tyr Tyr Cys Gln Gln Tyr Asp Asn Ala Pro Leu
                85                  90                  95 act ttc ggc gga ggg acc aag gtg gag atc aaa                            321
Thr Phe Gly Gly Gly Thr Lys Val Glu Ile Lys
            100                 105

<210> SEQ ID NO 184
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 184
```

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Pro Leu Ile
        35                  40                  45

Tyr Asp Ala Ser Thr Arg Ala Thr Gly Val Pro Ala Arg Phe Ser Gly
    50                  55                  60

Ser Gly Ser Gly Thr Asp Phe Thr Leu Thr Ile Ser Ser Leu Gln Ser
65              70                  75                  80

Glu Asp Phe Ala Val Tyr Tyr Cys Gln Gln Tyr Asp Asn Ala Pro Leu
                85                  90                  95

Thr Phe Gly Gly Gly Thr Lys Val Glu Ile Lys
            100                 105

<210> SEQ ID NO 185
<211> LENGTH: 321
<212> TYPE: DNA
<213> ORGANISM: ARTIFICIAL SEQUENCE
<220> FEATURE:
<223> OTHER INFORMATION: VL3 coding sequence
<220> FEATURE:
<221> NAME/KEY: CDS
<222> LOCATION: (1)..(321)

<400> SEQUENCE: 185 gaa ata gtg atg acg cag tct cca gcc acc ctg tct gtg tct cct ggg    48
Glu Ile Val Met Thr Gln Ser Pro Ala Thr Leu Ser Val Ser Pro Gly
1               5                   10                  15 gaa aga gcc acc ctc tcc tgc agg gcc agt cag agt gtt agc agc aac    96
Glu Arg Ala Thr Leu Ser Cys Arg Ala Ser Gln Ser Val Ser Ser Asn
            20                  25                  30 tta gcc tgg ttc cag cag aaa cct ggc cag gct ccc agg ccc ctc atc   144
Leu Ala Trp Phe Gln Gln Lys Pro Gly Gln Ala Pro Arg Pro Leu Ile
        35                  40                  45 tat gat gca tcc acc agg gcc act ggt gtc cca gcc agg ttc agt ggc   192
Tyr Asp Ala Ser Thr Arg Ala Thr Gly Val Pro Ala Arg Phe Ser Gly
    50                  55                  60 agt ggg tct ggg aca gac ttc act ctc acc atc agc agc ctg cag tct   240
Ser Gly Ser Gly Thr Asp Phe Thr Leu Thr Ile Ser Ser Leu Gln Ser
65              70                  75                  80 gaa gat ttt gca gtt tat tac tgt cag cag gct gat aac tgg ccg ctc   288
Glu Asp Phe Ala Val Tyr Tyr Cys Gln Gln Ala Asp Asn Trp Pro Leu
                85                  90                  95 act ttc ggc gga ggg acc aag gtg gag atc aaa                        321
Thr Phe Gly Gly Gly Thr Lys Val Glu Ile Lys
            100                 105

<210> SEQ ID NO 186
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 186

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Pro Leu Ile
```

```
                    35                  40                  45
Tyr Asp Ala Ser Thr Arg Ala Thr Gly Val Pro Ala Arg Phe Ser Gly
         50                  55                  60
Ser Gly Ser Gly Thr Asp Phe Thr Leu Thr Ile Ser Ser Leu Gln Ser
 65                  70                  75                  80
Glu Asp Phe Ala Val Tyr Tyr Cys Gln Gln Ala Asp Asn Trp Pro Leu
                 85                  90                  95
Thr Phe Gly Gly Gly Thr Lys Val Glu Ile Lys
                100                 105
```

<210> SEQ ID NO 187
<211> LENGTH: 321
<212> TYPE: DNA
<213> ORGANISM: ARTIFICIAL SEQUENCE
<220> FEATURE:
<223> OTHER INFORMATION: VL4 coding sequence
<220> FEATURE:
<221> NAME/KEY: CDS
<222> LOCATION: (1)..(321)

<400> SEQUENCE: 187

```
gaa ata gtg atg acg cag tct cca gcc acc ctg tct gtg tct cct ggg    48
Glu Ile Val Met Thr Gln Ser Pro Ala Thr Leu Ser Val Ser Pro Gly
 1               5                  10                  15 gaa aga gcc acc ctc tcc tgc agg gcc agt cag agt gtt agc agc aac    96
Glu Arg Ala Thr Leu Ser Cys Arg Ala Ser Gln Ser Val Ser Ser Asn
                20                  25                  30 tta gcc tgg ttc cag cag aaa cct ggc cag gct ccc agg ctc ctc atc   144
Leu Ala Trp Phe Gln Gln Lys Pro Gly Gln Ala Pro Arg Leu Leu Ile
         35                  40                  45 tat gat gca tcc acc agg gcc act ggt gtc cca gcc agg ttc agt ggc   192
Tyr Asp Ala Ser Thr Arg Ala Thr Gly Val Pro Ala Arg Phe Ser Gly
 50                  55                  60 agt ggg tct ggg aca gaa ttc act ctc acc atc agc agc ctg cag tct   240
Ser Gly Ser Gly Thr Glu Phe Thr Leu Thr Ile Ser Ser Leu Gln Ser
 65                  70                  75                  80 gaa gat ttt gca gtt tat tac tgt cag cag tat gat aac tgg ccg ctc   288
Glu Asp Phe Ala Val Tyr Tyr Cys Gln Gln Tyr Asp Asn Trp Pro Leu
                 85                  90                  95 act ttc ggc gga ggg acc aag gtg gag atc aaa                       321
Thr Phe Gly Gly Gly Thr Lys Val Glu Ile Lys
                100                 105
```

<210> SEQ ID NO 188
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 188

```
Glu Ile Val Met Thr Gln Ser Pro Ala Thr Leu Ser Val Ser Pro Gly
 1               5                  10                  15
Glu Arg Ala Thr Leu Ser Cys Arg Ala Ser Gln Ser Val Ser Ser Asn
                20                  25                  30
Leu Ala Trp Phe Gln Gln Lys Pro Gly Gln Ala Pro Arg Leu Leu Ile
         35                  40                  45
Tyr Asp Ala Ser Thr Arg Ala Thr Gly Val Pro Ala Arg Phe Ser Gly
 50                  55                  60
Ser Gly Ser Gly Thr Glu Phe Thr Leu Thr Ile Ser Ser Leu Gln Ser
 65                  70                  75                  80
```

-continued

```
Glu Asp Phe Ala Val Tyr Tyr Cys Gln Gln Tyr Asp Asn Trp Pro Leu
                85                  90                  95
Thr Phe Gly Gly Gly Thr Lys Val Glu Ile Lys
            100                 105

<210> SEQ ID NO 189
<211> LENGTH: 321
<212> TYPE: DNA
<213> ORGANISM: ARTIFICIAL SEQUENCE
<220> FEATURE:
<223> OTHER INFORMATION: VL5 coding sequence
<220> FEATURE:
<221> NAME/KEY: CDS
<222> LOCATION: (1)..(321)

<400> SEQUENCE: 189 gaa ata gtg atg acg cag tct cca gcc acc ctg tct gtg tct cct ggg      48
Glu Ile Val Met Thr Gln Ser Pro Ala Thr Leu Ser Val Ser Pro Gly
1               5                   10                  15 gaa aga gcc acc ctc tcc tgc agg gcc agt cag agt gtt agc agc aac      96
Glu Arg Ala Thr Leu Ser Cys Arg Ala Ser Gln Ser Val Ser Ser Asn
            20                  25                  30 tta gcc tgg ttc cag cag aaa cct ggc cag gct ccc agg ctc ctc atc     144
Leu Ala Trp Phe Gln Gln Lys Pro Gly Gln Ala Pro Arg Leu Leu Ile
        35                  40                  45 tat gat gca tcc acc agg gcc act ggt gtc cca gcc agg ttc agt ggc     192
Tyr Asp Ala Ser Thr Arg Ala Thr Gly Val Pro Ala Arg Phe Ser Gly
    50                  55                  60 agt ggg tct ggg aca gaa ttc act ctc acc atc agc agc ctg cag tct     240
Ser Gly Ser Gly Thr Glu Phe Thr Leu Thr Ile Ser Ser Leu Gln Ser
65                  70                  75                  80 gaa gat ttt gca gtt tat tac tgt cag cag tat gat aac gct ccg ctc     288
Glu Asp Phe Ala Val Tyr Tyr Cys Gln Gln Tyr Asp Asn Ala Pro Leu
                85                  90                  95 act ttc ggc gga ggg acc aag gtg gag atc aaa                         321
Thr Phe Gly Gly Gly Thr Lys Val Glu Ile Lys
            100                 105

<210> SEQ ID NO 190
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 190

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Leu Leu Ile
        35                  40                  45

Tyr Asp Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asn Ala Pro Leu
                85                  90                  95

Thr Phe Gly Gly Gly Thr Lys Val Glu Ile Lys
            100                 105

<210> SEQ ID NO 191
```

```
<211> LENGTH: 324
<212> TYPE: DNA
<213> ORGANISM: ARTIFICIAL SEQUENCE
<220> FEATURE:
<223> OTHER INFORMATION: VL6 coding sequence
<220> FEATURE:
<221> NAME/KEY: CDS
<222> LOCATION: (1)..(324)

<400> SEQUENCE: 191 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag ggt att agt aga agc      96
Glu Arg Ala Thr Leu Ser Cys Arg Ala Ser Gln Gly Ile Ser Arg Ser
            20                  25                  30 tac tta gcc tgg tac cag cag aaa cct ggc cag gct ccc agc ctc ctc     144
Tyr Leu Ala Trp Tyr Gln Gln Lys Pro Gly Gln Ala Pro Ser Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt caa caa ttt ggt agt tca ccg     288
Pro Glu Asp Phe Ala Val Tyr Tyr Cys Gln Gln Phe Gly Ser Ser Pro
                85                  90                  95 tgg acg ttc ggc caa ggg acc aag gtg gaa atc aaa                     324
Trp Thr Phe Gly Gln Gly Thr Lys Val Glu Ile Lys
            100                 105

<210> SEQ ID NO 192
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 192

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys
            100                 105

<210> SEQ ID NO 193
<211> LENGTH: 324
<212> TYPE: DNA
<213> ORGANISM: ARTIFICIAL SEQUENCE
<220> FEATURE:
<223> OTHER INFORMATION: VL7 coding sequence
<220> FEATURE:
<221> NAME/KEY: CDS
<222> LOCATION: (1)..(324)
```

<400> SEQUENCE: 193

```
gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag ggt att agt aga agc      96
Glu Arg Ala Thr Leu Ser Cys Arg Ala Ser Gln Gly Ile Ser Arg Ser
            20                  25                  30 tac tta gcc tgg tac cag cag aaa cct ggc cag gct ccc agc ctc ctc     144
Tyr Leu Ala Trp Tyr Gln Gln Lys Pro Gly Gln Ala Pro Ser Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt caa caa gct ggt agt tca ccg     288
Pro Glu Asp Phe Ala Val Tyr Tyr Cys Gln Gln Ala Gly Ser Ser Pro
                85                  90                  95 tgg acg ttc ggc caa ggg acc aag gtg gaa atc aaa                     324
Trp Thr Phe Gly Gln Gly Thr Lys Val Glu Ile Lys
            100                 105
```

<210> SEQ ID NO 194
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 194

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Ser Ser Pro
                85                  90                  95

Trp Thr Phe Gly Gln Gly Thr Lys Val Glu Ile Lys
            100                 105
```

<210> SEQ ID NO 195
<211> LENGTH: 324
<212> TYPE: DNA
<213> ORGANISM: ARTIFICIAL SEQUENCE
<220> FEATURE:
<223> OTHER INFORMATION: VL8 coding sequence
<220> FEATURE:
<221> NAME/KEY: CDS
<222> LOCATION: (1)..(324)

<400> SEQUENCE: 195

```
gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag ggt att agt aga agc      96
```

```
                Glu Arg Ala Thr Leu Ser Cys Arg Ala Ser Gln Gly Ile Ser Arg Ser
                                20                  25                  30 gct tta gcc tgg tac cag cag aaa cct ggc cag gct ccc agc ctc ctc         144
Ala Leu Ala Trp Tyr Gln Gln Lys Pro Gly Gln Ala Pro Ser Leu Leu
         35                  40                  45 atc tat ggt gca tcc agc agg gcc act ggc atc cca gac agg ttc agt         192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag         240
Gly Ser Gly Ser Gly Thr Asp Phe Thr Leu Thr Ile Ser Arg Leu Glu
 65                  70                  75                  80 cct gaa gat ttt gca gtg tat tac tgt caa caa ttt ggt agt tca ccg         288
Pro Glu Asp Phe Ala Val Tyr Tyr Cys Gln Gln Phe Gly Ser Ser Pro
                 85                  90                  95 tgg acg ttc ggc caa ggg acc aag gtg gaa atc aaa                         324
Trp Thr Phe Gly Gln Gly Thr Lys Val Glu Ile Lys
             100                 105

<210> SEQ ID NO 196
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 196

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Gly Ile Ser Arg Ser
                 20                  25                  30

Ala Leu Ala Trp Tyr Gln Gln Lys Pro Gly Gln Ala Pro Ser Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Pro
                 85                  90                  95

Trp Thr Phe Gly Gln Gly Thr Lys Val Glu Ile Lys
             100                 105

<210> SEQ ID NO 197
<211> LENGTH: 324
<212> TYPE: DNA
<213> ORGANISM: ARTIFICIAL SEQUENCE
<220> FEATURE:
<223> OTHER INFORMATION: VL9 coding sequence
<220> FEATURE:
<221> NAME/KEY: CDS
<222> LOCATION: (1)..(324)

<400> SEQUENCE: 197 gaa att gtg ttg acg cag tct cca ggc acc ctg tct ttg tct cca ggg          48
Glu Ile Val Leu Thr Gln Ser Pro Gly Thr Leu Ser Leu Ser Pro Gly
  1               5                  10                  15 gaa aga gcc acc ctc tcc tgc agg gcc agt cag ggt att agt aga agc          96
Glu Arg Ala Thr Leu Ser Cys Arg Ala Ser Gln Gly Ile Ser Arg Ser
                 20                  25                  30 tac tta gcc tgg tac cag cag aaa cct ggc cag gct ccc agc ctc ctc         144
Tyr Leu Ala Trp Tyr Gln Gln Lys Pro Gly Gln Ala Pro Ser Leu Leu
         35                  40                  45 atc tat ggt gca tcc agc agg gcc act ggc atc cca gac agg ttc agt         192
```

```
Ile Tyr Gly Ala Ser Ser Arg Ala Thr Gly Ile Pro Asp Arg Phe Ser
 50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
 65                  70                  75                  80 cct gaa gat ttt gca gtg tat tac tgt caa caa ttt ggt agt tca ccg      288
Pro Glu Asp Phe Ala Val Tyr Tyr Cys Gln Gln Phe Gly Ser Ser Pro
                 85                  90                  95 gct acg ttc ggc caa ggg acc aag gtg gaa atc aaa                      324
Ala Thr Phe Gly Gln Gly Thr Lys Val Glu Ile Lys
            100                 105

<210> SEQ ID NO 198
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 198

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Gly Ile Ser Arg Ser
             20                  25                  30

Tyr Leu Ala Trp Tyr Gln Gln Lys Pro Gly Gln Ala Pro Ser Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Pro
                 85                  90                  95

Ala Thr Phe Gly Gln Gly Thr Lys Val Glu Ile Lys
            100                 105

<210> SEQ ID NO 199
<211> LENGTH: 324
<212> TYPE: DNA
<213> ORGANISM: ARTIFICIAL SEQUENCE
<220> FEATURE:
<223> OTHER INFORMATION: VL10 coding sequence
<220> FEATURE:
<221> NAME/KEY: CDS
<222> LOCATION: (1)..(324)

<400> SEQUENCE: 199 gaa att gtg ttg acg cag tct cca ggc acc ctg tct ttg tct cca ggg       48
Glu Ile Val Leu Thr Gln Ser Pro Gly Thr Leu Ser Leu Ser Pro Gly
 1               5                  10                  15 gaa aga gcc acc ctc tcc tgc agg gcc agt cag ggt att agt aga agc       96
Glu Arg Ala Thr Leu Ser Cys Arg Ala Ser Gln Gly Ile Ser Arg Ser
             20                  25                  30 tac tta gcc tgg tac cag cag aaa cct ggc cag gct ccc agc ctc ctc      144
Tyr Leu Ala Trp Tyr Gln Gln Lys Pro Gly Gln Ala Pro Ser Leu Leu
         35                  40                  45 atc tat ggt gca tcc agc agg gcc act ggc atc cca gac agg ttc agt      192
Ile Tyr Gly Ala Ser Ser Arg Ala Thr Gly Ile Pro Asp Arg Phe Ser
 50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
 65                  70                  75                  80 cct gaa gat ttt gca gtg tat tac tgt caa caa tat ggt agt tca ccg      288
Pro Glu Asp Phe Ala Val Tyr Tyr Cys Gln Gln Tyr Gly Ser Ser Pro
```

```
Pro Glu Asp Phe Ala Val Tyr Tyr Cys Gln Gln Tyr Gly Ser Ser Pro
            85                  90                  95 tgg acg ttc ggc caa ggg acc aag gtg gaa atc aaa                     324
Trp Thr Phe Gly Gln Gly Thr Lys Val Glu Ile Lys
            100                 105

<210> SEQ ID NO 200
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 200

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

Trp Thr Phe Gly Gln Gly Thr Lys Val Glu Ile Lys
            100                 105

<210> SEQ ID NO 201
<211> LENGTH: 324
<212> TYPE: DNA
<213> ORGANISM: ARTIFICIAL SEQUENCE
<220> FEATURE:
<223> OTHER INFORMATION: VL11 coding sequence
<220> FEATURE:
<221> NAME/KEY: CDS
<222> LOCATION: (1)..(324)

<400> SEQUENCE: 201 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag ggt att agt aga agc      96
Glu Arg Ala Thr Leu Ser Cys Arg Ala Ser Gln Gly Ile Ser Arg Ser
            20                  25                  30 gaa tta gcc tgg tac cag cag aaa cct ggc cag gct ccc agc ctc ctc     144
Glu Leu Ala Trp Tyr Gln Gln Lys Pro Gly Gln Ala Pro Ser Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt caa caa ttt ggt agt tca ccg     288
Pro Glu Asp Phe Ala Val Tyr Tyr Cys Gln Gln Phe Gly Ser Ser Pro
            85                  90                  95 tgg acg ttc ggc caa ggg acc aag gtg gaa atc aaa                     324
Trp Thr Phe Gly Gln Gly Thr Lys Val Glu Ile Lys
            100                 105
```

```
<210> SEQ ID NO 202
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 202

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Glu Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys
            100                 105

<210> SEQ ID NO 203
<211> LENGTH: 324
<212> TYPE: DNA
<213> ORGANISM: ARTIFICIAL SEQUENCE
<220> FEATURE:
<223> OTHER INFORMATION: VL12 coding sequence
<220> FEATURE:
<221> NAME/KEY: CDS
<222> LOCATION: (1)..(324)

<400> SEQUENCE: 203 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag ggt att agt aga agc      96
Glu Arg Ala Thr Leu Ser Cys Arg Ala Ser Gln Gly Ile Ser Arg Ser
            20                  25                  30 aga tta gcc tgg tac cag cag aaa cct ggc cag gct ccc agc ctc ctc     144
Arg Leu Ala Trp Tyr Gln Gln Lys Pro Gly Gln Ala Pro Ser Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt caa caa ttt ggt agt tca ccg     288
Pro Glu Asp Phe Ala Val Tyr Tyr Cys Gln Gln Phe Gly Ser Ser Pro
                85                  90                  95 tgg acg ttc ggc caa ggg acc aag gtg gaa atc aaa                     324
Trp Thr Phe Gly Gln Gly Thr Lys Val Glu Ile Lys
            100                 105

<210> SEQ ID NO 204
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 204
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Arg Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys
            100                 105

<210> SEQ ID NO 205
<211> LENGTH: 324
<212> TYPE: DNA
<213> ORGANISM: ARTIFICIAL SEQUENCE
<220> FEATURE:
<223> OTHER INFORMATION: VL13 coding sequence
<220> FEATURE:
<221> NAME/KEY: CDS
<222> LOCATION: (1)..(324)

<400> SEQUENCE: 205 gaa att gtg ttg acg cag tct cca ggc acc ctg tct ttg tct cca ggg       48
Glu Ile Val Leu Thr Gln Ser Pro Gly Thr Leu Ser Leu Ser Pro Gly
1               5                   10                  15 gaa aga gcc acc ctc tcc tgc agg gcc agt cag ggt att agt aga agc       96
Glu Arg Ala Thr Leu Ser Cys Arg Ala Ser Gln Gly Ile Ser Arg Ser
            20                  25                  30 tac tta gcc tgg tac cag cag aaa cct ggc cag gct ccc agc ctc ctc      144
Tyr Leu Ala Trp Tyr Gln Gln Lys Pro Gly Gln Ala Pro Ser Leu Leu
        35                  40                  45 atc tat ggt gca tcc agc agg gcc act ggc atc cca gac agg ttc agt      192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
65                  70                  75                  80 cct gaa gat ttt gca gtg tat tac tgt caa caa gaa ggt agt tca ccg      288
Pro Glu Asp Phe Ala Val Tyr Tyr Cys Gln Gln Glu Gly Ser Ser Pro
                85                  90                  95 tgg acg ttc ggc caa ggg acc aag gtg gaa atc aaa                      324
Trp Thr Phe Gly Gln Gly Thr Lys Val Glu Ile Lys
            100                 105

<210> SEQ ID NO 206
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 206

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
```

```
                    35                  40                  45
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ser Ser Pro
                 85                  90                  95

Trp Thr Phe Gly Gln Gly Thr Lys Val Glu Ile Lys
            100                 105

<210> SEQ ID NO 207
<211> LENGTH: 324
<212> TYPE: DNA
<213> ORGANISM: ARTIFICIAL SEQUENCE
<220> FEATURE:
<223> OTHER INFORMATION: VL14 coding sequence
<220> FEATURE:
<221> NAME/KEY: CDS
<222> LOCATION: (1)..(324)

<400> SEQUENCE: 207 gaa att gtg ttg acg cag tct cca ggc acc ctg tct ttg tct cca ggg       48
Glu Ile Val Leu Thr Gln Ser Pro Gly Thr Leu Ser Leu Ser Pro Gly
 1               5                  10                  15 gaa aga gcc acc ctc tcc tgc agg gcc agt cag ggt att agt aga agc       96
Glu Arg Ala Thr Leu Ser Cys Arg Ala Ser Gln Gly Ile Ser Arg Ser
                20                  25                  30 tac tta gcc tgg tac cag cag aaa cct ggc cag gct ccc agc ctc ctc      144
Tyr Leu Ala Trp Tyr Gln Gln Lys Pro Gly Gln Ala Pro Ser Leu Leu
            35                  40                  45 atc tat ggt gca tcc agc agg gcc act ggc atc cca gac agg ttc agt      192
Ile Tyr Gly Ala Ser Ser Arg Ala Thr Gly Ile Pro Asp Arg Phe Ser
 50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
 65                  70                  75                  80 cct gaa gat ttt gca gtg tat tac tgt caa caa aga ggt agt tca ccg      288
Pro Glu Asp Phe Ala Val Tyr Tyr Cys Gln Gln Arg Gly Ser Ser Pro
                 85                  90                  95 tgg acg ttc ggc caa ggg acc aag gtg gaa atc aaa                      324
Trp Thr Phe Gly Gln Gly Thr Lys Val Glu Ile Lys
            100                 105

<210> SEQ ID NO 208
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 208

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Gly Ile Ser Arg Ser
                20                  25                  30

Tyr Leu Ala Trp Tyr Gln Gln Lys Pro Gly Gln Ala Pro Ser Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80
```

```
Pro Glu Asp Phe Ala Val Tyr Tyr Cys Gln Gln Arg Gly Ser Ser Pro
            85                  90                  95

Trp Thr Phe Gly Gln Gly Thr Lys Val Glu Ile Lys
            100                 105

<210> SEQ ID NO 209
<211> LENGTH: 324
<212> TYPE: DNA
<213> ORGANISM: ARTIFICIAL SEQUENCE
<220> FEATURE:
<223> OTHER INFORMATION: VL15 coding sequence
<220> FEATURE:
<221> NAME/KEY: CDS
<222> LOCATION: (1)..(324)

<400> SEQUENCE: 209 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag ggt att agt aga agc      96
Glu Arg Ala Thr Leu Ser Cys Arg Ala Ser Gln Gly Ile Ser Arg Ser
            20                  25                  30 gct tta gcc tgg tac cag cag aaa cct ggc cag gct ccc agc ctc ctc     144
Ala Leu Ala Trp Tyr Gln Gln Lys Pro Gly Gln Ala Pro Ser Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt caa caa gct ggt agt tca ccg     288
Pro Glu Asp Phe Ala Val Tyr Tyr Cys Gln Gln Ala Gly Ser Ser Pro
                85                  90                  95 tgg acg ttc ggc caa ggg acc aag gtg gaa atc aaa                     324
Trp Thr Phe Gly Gln Gly Thr Lys Val Glu Ile Lys
            100                 105

<210> SEQ ID NO 210
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 210

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Ala Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Ser Ser Pro
                85                  90                  95

Trp Thr Phe Gly Gln Gly Thr Lys Val Glu Ile Lys
            100                 105

<210> SEQ ID NO 211
```

```
<211> LENGTH: 324
<212> TYPE: DNA
<213> ORGANISM: ARTIFICIAL SEQUENCE
<220> FEATURE:
<223> OTHER INFORMATION: VL16 coding sequence
<220> FEATURE:
<221> NAME/KEY: CDS
<222> LOCATION: (1)..(324)

<400> SEQUENCE: 211 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
  1               5                  10                  15 gaa aga gcc acc ctc tcc tgc agg gcc agt cag agt gtt agt agt agc      96
Glu Arg Ala Thr Leu Ser Cys Arg Ala Ser Gln Ser Val Ser Ser Ser
             20                  25                  30 tac tta gcc tgg tac cag cag aaa cct ggc cag gct ccc agc ctc ctc     144
Tyr Leu Ala Trp Tyr Gln Gln Lys Pro Gly Gln Ala Pro Ser Leu Leu
         35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
 65                  70                  75                  80 cct gaa gat ttt gca gtg tat tac tgt caa caa ttt ggt agt tca ccg     288
Pro Glu Asp Phe Ala Val Tyr Tyr Cys Gln Gln Phe Gly Ser Ser Pro
                 85                  90                  95 tgg acg ttc ggc caa ggg acc aag gtg gaa atc aaa                      324
Trp Thr Phe Gly Gln Gly Thr Lys Val Glu Ile Lys
            100                 105

<210> SEQ ID NO 212
<211> LENGTH: 108
<212> TYPE: PRT
<213> ORGANISM: ARTIFICIAL SEQUENCE
<220> FEATURE:
<223> OTHER INFORMATION: Synthetic Construct

<400> SEQUENCE: 212

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Ser Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Pro
                 85                  90                  95

Trp Thr Phe Gly Gln Gly Thr Lys Val Glu Ile Lys
            100                 105

<210> SEQ ID NO 213
<211> LENGTH: 42
<212> TYPE: DNA
<213> ORGANISM: ARTIFICIAL SEQUENCE
<220> FEATURE:
<223> OTHER INFORMATION: 5152-98 primer sequence

<400> SEQUENCE: 213
```

```
gaaagtgagc ggccagttat cagcctgctg acagtaataa ac                              42

<210> SEQ ID NO 214
<211> LENGTH: 42
<212> TYPE: DNA
<213> ORGANISM: ARTIFICIAL SEQUENCE
<220> FEATURE:
<223> OTHER INFORMATION: 5152-97 primer sequence

<400> SEQUENCE: 214
gtttattact gtcagcaggc tgataactgg ccgctcactt tc                              42

<210> SEQ ID NO 215
<211> LENGTH: 39
<212> TYPE: DNA
<213> ORGANISM: ARTIFICIAL SEQUENCE
<220> FEATURE:
<223> OTHER INFORMATION: 5153-00 primer sequence

<400> SEQUENCE: 215
tccgccgaaa gtgagcggag cgttatcata ctgctgaca                                  39

<210> SEQ ID NO 216
<211> LENGTH: 39
<212> TYPE: DNA
<213> ORGANISM: ARTIFICIAL SEQUENCE
<220> FEATURE:
<223> OTHER INFORMATION: 5152-99 primer sequence

<400> SEQUENCE: 216
tgtcagcagt atgataacgc tccgctcact ttcggcgga                                  39

<210> SEQ ID NO 217
<211> LENGTH: 33
<212> TYPE: DNA
<213> ORGANISM: ARTIFICIAL SEQUENCE
<220> FEATURE:
<223> OTHER INFORMATION: 5153-02 primer sequence

<400> SEQUENCE: 217
cacccagctg ataccagctc tggtaaaggt gta                                        33

<210> SEQ ID NO 218
<211> LENGTH: 33
<212> TYPE: DNA
<213> ORGANISM: ARTIFICIAL SEQUENCE
<220> FEATURE:
<223> OTHER INFORMATION: 5153-01 primer sequence

<400> SEQUENCE: 218
tacaccttta ccagagctgg tatcagctgg gtg                                        33

<210> SEQ ID NO 219
<211> LENGTH: 33
<212> TYPE: DNA
<213> ORGANISM: ARTIFICIAL SEQUENCE
<220> FEATURE:
<223> OTHER INFORMATION: 5153-04 primer sequence

<400> SEQUENCE: 219
actgtaagtg ctgatagctc ccatccactc aag                                        33

<210> SEQ ID NO 220
<211> LENGTH: 33
<212> TYPE: DNA
<213> ORGANISM: ARTIFICIAL SEQUENCE
<220> FEATURE:
```

-continued

<223> OTHER INFORMATION: 5153-03 primer sequence

<400> SEQUENCE: 220
cttgagtgga tgggagctat cagcacttac agt                                    33

<210> SEQ ID NO 221
<211> LENGTH: 33
<212> TYPE: DNA
<213> ORGANISM: ARTIFICIAL SEQUENCE
<220> FEATURE:
<223> OTHER INFORMATION: 5153-06 primer sequence

<400> SEQUENCE: 221
gtttgtgtta ccactagcag tgctgatcca tcc                                    33

<210> SEQ ID NO 222
<211> LENGTH: 33
<212> TYPE: DNA
<213> ORGANISM: ARTIFICIAL SEQUENCE
<220> FEATURE:
<223> OTHER INFORMATION: 5153-05 primer sequence

<400> SEQUENCE: 222
ggatggatca gcactgctag tggtaacaca aac                                    33

<210> SEQ ID NO 223
<211> LENGTH: 33
<212> TYPE: DNA
<213> ORGANISM: ARTIFICIAL SEQUENCE
<220> FEATURE:
<223> OTHER INFORMATION: 5153-08 primer sequence

<400> SEQUENCE: 223
ctggagcttc tgtgcagcgt ttgtgttacc act                                    33

<210> SEQ ID NO 224
<211> LENGTH: 33
<212> TYPE: DNA
<213> ORGANISM: ARTIFICIAL SEQUENCE
<220> FEATURE:
<223> OTHER INFORMATION: 5153-07 primer sequence

<400> SEQUENCE: 224
agtggtaaca caaacgctgc acagaagctc cag                                    33

<210> SEQ ID NO 225
<211> LENGTH: 48
<212> TYPE: DNA
<213> ORGANISM: ARTIFICIAL SEQUENCE
<220> FEATURE:
<223> OTHER INFORMATION: 5153-10 primer sequence

<400> SEQUENCE: 225
cagggttccc tggccccagt agtcaaaagc aagctgccgt ctcgcaca                    48

<210> SEQ ID NO 226
<211> LENGTH: 48
<212> TYPE: DNA
<213> ORGANISM: ARTIFICIAL SEQUENCE
<220> FEATURE:
<223> OTHER INFORMATION: 5153-09 primer sequence

<400> SEQUENCE: 226
tgtgcgagac ggcagcttgc ttttgactac tggggccagg gaaccctg                    48

<210> SEQ ID NO 227

```
<211> LENGTH: 48
<212> TYPE: DNA
<213> ORGANISM: ARTIFICIAL SEQUENCE
<220> FEATURE:
<223> OTHER INFORMATION: 5153-12 primer sequence

<400> SEQUENCE: 227
cagggttccc tggccccagt agtcagcgta aagctgccgt ctcgcaca                 48

<210> SEQ ID NO 228
<211> LENGTH: 48
<212> TYPE: DNA
<213> ORGANISM: ARTIFICIAL SEQUENCE
<220> FEATURE:
<223> OTHER INFORMATION: 5153-11 primer sequence

<400> SEQUENCE: 228
tgtgcgagac ggcagcttta cgctgactac tggggccagg gaaccctg                 48

<210> SEQ ID NO 229
<211> LENGTH: 48
<212> TYPE: DNA
<213> ORGANISM: ARTIFICIAL SEQUENCE
<220> FEATURE:
<223> OTHER INFORMATION: 5153-14 primer sequence

<400> SEQUENCE: 229
cagggttccc tggccccaag cgtcaaagta aagctgccgt ctcgcaca                 48

<210> SEQ ID NO 230
<211> LENGTH: 48
<212> TYPE: DNA
<213> ORGANISM: ARTIFICIAL SEQUENCE
<220> FEATURE:
<223> OTHER INFORMATION: 5153-13 primer sequence

<400> SEQUENCE: 230
tgtgcgagac ggcagcttta ctttgacgct tggggccagg gaaccctg                 48

<210> SEQ ID NO 231
<211> LENGTH: 42
<212> TYPE: DNA
<213> ORGANISM: ARTIFICIAL SEQUENCE
<220> FEATURE:
<223> OTHER INFORMATION: 4634-64 primer sequence

<400> SEQUENCE: 231
aagctcgagg tcgactagac caccatggaa accccagcgc ag                       42

<210> SEQ ID NO 232
<211> LENGTH: 36
<212> TYPE: DNA
<213> ORGANISM: ARTIFICIAL SEQUENCE
<220> FEATURE:
<223> OTHER INFORMATION: 5153-20 primer sequence

<400> SEQUENCE: 232
ctggtaccag gctaaagcgc ttctactaat accctg                              36

<210> SEQ ID NO 233
<211> LENGTH: 36
<212> TYPE: DNA
<213> ORGANISM: ARTIFICIAL SEQUENCE
<220> FEATURE:
<223> OTHER INFORMATION: 5153-19 primer sequence

<400> SEQUENCE: 233
```

```
cagggtatta gtagaagcgc tttagcctgg taccag                                36
```

<210> SEQ ID NO 234
<211> LENGTH: 48
<212> TYPE: DNA
<213> ORGANISM: ARTIFICIAL SEQUENCE
<220> FEATURE:
<223> OTHER INFORMATION: 5153-22 primer sequence

<400> SEQUENCE: 234

```
ttggccgaac gtccacggtg aactaccagc ttgttgacag taatacac                   48
```

<210> SEQ ID NO 235
<211> LENGTH: 48
<212> TYPE: DNA
<213> ORGANISM: ARTIFICIAL SEQUENCE
<220> FEATURE:
<223> OTHER INFORMATION: 5153-21 primer sequence

<400> SEQUENCE: 235

```
gtgtattact gtcaacaagc tggtagttca ccgtggacgt tcggccaa                   48
```

<210> SEQ ID NO 236
<211> LENGTH: 48
<212> TYPE: DNA
<213> ORGANISM: ARTIFICIAL SEQUENCE
<220> FEATURE:
<223> OTHER INFORMATION: 5153-24 primer sequence

<400> SEQUENCE: 236

```
ttggccgaac gtagccggtg aactaccaaa ttgttgacag taatacac                   48
```

<210> SEQ ID NO 237
<211> LENGTH: 48
<212> TYPE: DNA
<213> ORGANISM: ARTIFICIAL SEQUENCE
<220> FEATURE:
<223> OTHER INFORMATION: 5153-23 primer sequence

<400> SEQUENCE: 237

```
gtgtattact gtcaacaatt tggtagttca ccggctacgt tcggccaa                   48
```

<210> SEQ ID NO 238
<211> LENGTH: 39
<212> TYPE: DNA
<213> ORGANISM: ARTIFICIAL SEQUENCE
<220> FEATURE:
<223> OTHER INFORMATION: 5153-26 primer sequence

<400> SEQUENCE: 238

```
ctggcggatc cagctccaga aagcatcacc actgctgat                             39
```

<210> SEQ ID NO 239
<211> LENGTH: 39
<212> TYPE: DNA
<213> ORGANISM: ARTIFICIAL SEQUENCE
<220> FEATURE:
<223> OTHER INFORMATION: 5153-25 primer sequence

<400> SEQUENCE: 239

```
atcagcagtg gtgatgcttt ctggagctgg atccgccag                             39
```

<210> SEQ ID NO 240
<211> LENGTH: 39
<212> TYPE: DNA
<213> ORGANISM: ARTIFICIAL SEQUENCE
<220> FEATURE:

```
<223> OTHER INFORMATION: 5153-28 primer sequence

<400> SEQUENCE: 240
ctggcggatc cagctccaag cgtaatcacc actgctgat                              39

<210> SEQ ID NO 241
<211> LENGTH: 39
<212> TYPE: DNA
<213> ORGANISM: ARTIFICIAL SEQUENCE
<220> FEATURE:
<223> OTHER INFORMATION: 5153-27 primer sequence

<400> SEQUENCE: 241
atcagcagtg gtgattacgc ttggagctgg atccgccag                              39

<210> SEQ ID NO 242
<211> LENGTH: 39
<212> TYPE: DNA
<213> ORGANISM: ARTIFICIAL SEQUENCE
<220> FEATURE:
<223> OTHER INFORMATION: 5153-30 primer sequence

<400> SEQUENCE: 242
ctggcggatc cagctagcga agtaatcacc actgctgat                              39

<210> SEQ ID NO 243
<211> LENGTH: 39
<212> TYPE: DNA
<213> ORGANISM: ARTIFICIAL SEQUENCE
<220> FEATURE:
<223> OTHER INFORMATION: 5153-29 primer sequence

<400> SEQUENCE: 243
atcagcagtg gtgattactt cgctagctgg atccgccag                              39

<210> SEQ ID NO 244
<211> LENGTH: 39
<212> TYPE: DNA
<213> ORGANISM: ARTIFICIAL SEQUENCE
<220> FEATURE:
<223> OTHER INFORMATION: 5153-32 primer sequence

<400> SEQUENCE: 244
cttgagggac ggattgtaag cggtggtccc actgttatg                              39

<210> SEQ ID NO 245
<211> LENGTH: 39
<212> TYPE: DNA
<213> ORGANISM: ARTIFICIAL SEQUENCE
<220> FEATURE:
<223> OTHER INFORMATION: 5153-31 primer sequence

<400> SEQUENCE: 245
cataacagtg ggaccaccgc ttacaatccg tccctcaag                              39

<210> SEQ ID NO 246
<211> LENGTH: 39
<212> TYPE: DNA
<213> ORGANISM: ARTIFICIAL SEQUENCE
<220> FEATURE:
<223> OTHER INFORMATION: 5153-24 primer sequence

<400> SEQUENCE: 246
cttgagggac ggattagcgt aggtggtccc actgttatg                              39

<210> SEQ ID NO 247
```

-continued

```
<211> LENGTH: 39
<212> TYPE: DNA
<213> ORGANISM: ARTIFICIAL SEQUENCE
<220> FEATURE:
<223> OTHER INFORMATION: 5153-33 primer sequence

<400> SEQUENCE: 247
cataacagtg ggaccaccta cgctaatccg tccctcaag                          39

<210> SEQ ID NO 248
<211> LENGTH: 48
<212> TYPE: DNA
<213> ORGANISM: ARTIFICIAL SEQUENCE
<220> FEATURE:
<223> OTHER INFORMATION: 5153-36 primer sequence

<400> SEQUENCE: 248
ccagacgtcc ataccatagt agtaagcacc ccctcgatct ctcgcaca               48

<210> SEQ ID NO 249
<211> LENGTH: 48
<212> TYPE: DNA
<213> ORGANISM: ARTIFICIAL SEQUENCE
<220> FEATURE:
<223> OTHER INFORMATION: 5153-35 primer sequence

<400> SEQUENCE: 249
tgtgcgagag atcgaggggg tgcttactac tatggtatgg acgtctgg               48

<210> SEQ ID NO 250
<211> LENGTH: 48
<212> TYPE: DNA
<213> ORGANISM: ARTIFICIAL SEQUENCE
<220> FEATURE:
<223> OTHER INFORMATION: 5153-38 primer sequence

<400> SEQUENCE: 250
ccagacgtcc ataccatagt aagcgtcacc ccctcgatct ctcgcaca               48

<210> SEQ ID NO 251
<211> LENGTH: 48
<212> TYPE: DNA
<213> ORGANISM: ARTIFICIAL SEQUENCE
<220> FEATURE:
<223> OTHER INFORMATION: 5153-37 primer sequence

<400> SEQUENCE: 251
tgtgcgagag atcgaggggg tgacgcttac tatggtatgg acgtctgg               48

<210> SEQ ID NO 252
<211> LENGTH: 48
<212> TYPE: DNA
<213> ORGANISM: ARTIFICIAL SEQUENCE
<220> FEATURE:
<223> OTHER INFORMATION: 5153-40 primer sequence

<400> SEQUENCE: 252
ccagacgtcc ataccataag cgtagtcacc ccctcgatct ctcgcaca               48

<210> SEQ ID NO 253
<211> LENGTH: 48
<212> TYPE: DNA
<213> ORGANISM: ARTIFICIAL SEQUENCE
<220> FEATURE:
<223> OTHER INFORMATION: 5153-39 primer sequence

<400> SEQUENCE: 253
```

```
tgtgcgagag atcgaggggg tgactacgct tatggtatgg acgtctgg          48

<210> SEQ ID NO 254
<211> LENGTH: 48
<212> TYPE: DNA
<213> ORGANISM: ARTIFICIAL SEQUENCE
<220> FEATURE:
<223> OTHER INFORMATION: 5153-42 primer sequence

<400> SEQUENCE: 254
ccagacgtcc ataccagcgt agtagtcacc ccctcgatct ctcgcaca          48

<210> SEQ ID NO 255
<211> LENGTH: 48
<212> TYPE: DNA
<213> ORGANISM: ARTIFICIAL SEQUENCE
<220> FEATURE:
<223> OTHER INFORMATION: 5153-41 primer sequence

<400> SEQUENCE: 255
tgtgcgagag atcgaggggg tgactactac gctggtatgg acgtctgg          48

<210> SEQ ID NO 256
<211> LENGTH: 48
<212> TYPE: DNA
<213> ORGANISM: ARTIFICIAL SEQUENCE
<220> FEATURE:
<223> OTHER INFORMATION: 5153-44 primer sequence

<400> SEQUENCE: 256
ccagacgtcc ataccatagt aagcagcacc ccctcgatct ctcgcaca          48

<210> SEQ ID NO 257
<211> LENGTH: 48
<212> TYPE: DNA
<213> ORGANISM: ARTIFICIAL SEQUENCE
<220> FEATURE:
<223> OTHER INFORMATION: 5153-43 primer sequence

<400> SEQUENCE: 257
tgtgcgagag atcgaggggg tgctgcttac tatggtatgg acgtctgg          48

<210> SEQ ID NO 258
<211> LENGTH: 48
<212> TYPE: DNA
<213> ORGANISM: ARTIFICIAL SEQUENCE
<220> FEATURE:
<223> OTHER INFORMATION: 5153-46 primer sequence

<400> SEQUENCE: 258
ccagacgtcc ataccagcag cagcgtcacc ccctcgatct ctcgcaca          48

<210> SEQ ID NO 259
<211> LENGTH: 48
<212> TYPE: DNA
<213> ORGANISM: ARTIFICIAL SEQUENCE
<220> FEATURE:
<223> OTHER INFORMATION: 5153-45 primer sequence

<400> SEQUENCE: 259
tgtgcgagag atcgaggggg tgacgctgct gctggtatgg acgtctgg          48

<210> SEQ ID NO 260
<211> LENGTH: 48
<212> TYPE: DNA
<213> ORGANISM: ARTIFICIAL SEQUENCE
<220> FEATURE:
```

```
<223> OTHER INFORMATION: 5245-87 primer sequence

<400> SEQUENCE: 260
ttggccgaac gtccacggtg aactaccttc ttgttgacag taatacac          48

<210> SEQ ID NO 261
<211> LENGTH: 48
<212> TYPE: DNA
<213> ORGANISM: ARTIFICIAL SEQUENCE
<220> FEATURE:
<223> OTHER INFORMATION: 5245-87 primer sequence

<400> SEQUENCE: 261
gtgtattact gtcaacaaga aggtagttca ccgtggacgt tcggccaa          48

<210> SEQ ID NO 262
<211> LENGTH: 48
<212> TYPE: DNA
<213> ORGANISM: ARTIFICIAL SEQUENCE
<220> FEATURE:
<223> OTHER INFORMATION: 5245-89 primer sequence

<400> SEQUENCE: 262
ttggccgaac gtccacggtg aactacctct tgttgacag taatacac          48

<210> SEQ ID NO 263
<211> LENGTH: 48
<212> TYPE: DNA
<213> ORGANISM: ARTIFICIAL SEQUENCE
<220> FEATURE:
<223> OTHER INFORMATION: 5245-88 primer sequence

<400> SEQUENCE: 263
gtgtattact gtcaacaaag aggtagttca ccgtggacgt tcggccaa          48

<210> SEQ ID NO 264
<211> LENGTH: 39
<212> TYPE: DNA
<213> ORGANISM: ARTIFICIAL SEQUENCE
<220> FEATURE:
<223> OTHER INFORMATION: 5245-91 primer sequence

<400> SEQUENCE: 264
ctggcggatc cagctccatt cgtaatcacc actgctgat             39

<210> SEQ ID NO 265
<211> LENGTH: 39
<212> TYPE: DNA
<213> ORGANISM: ARTIFICIAL SEQUENCE
<220> FEATURE:
<223> OTHER INFORMATION: 5245-90 primer sequence

<400> SEQUENCE: 265
atcagcagtg gtgattacga atggagctgg atccgccag             39

<210> SEQ ID NO 266
<211> LENGTH: 39
<212> TYPE: DNA
<213> ORGANISM: ARTIFICIAL SEQUENCE
<220> FEATURE:
<223> OTHER INFORMATION: 5245-93 primer sequence

<400> SEQUENCE: 266
ctggcggatc cagctccatc tgtaatcacc actgctgat             39

<210> SEQ ID NO 267
```

```
<211> LENGTH: 39
<212> TYPE: DNA
<213> ORGANISM: ARTIFICIAL SEQUENCE
<220> FEATURE:
<223> OTHER INFORMATION: 5245-92 primer sequence

<400> SEQUENCE: 267
atcagcagtg gtgattacag atggagctgg atccgccag                                  39

<210> SEQ ID NO 268
<211> LENGTH: 48
<212> TYPE: DNA
<213> ORGANISM: ARTIFICIAL SEQUENCE
<220> FEATURE:
<223> OTHER INFORMATION: 5245-95 primer sequence

<400> SEQUENCE: 268
ccagacgtcc ataccatatt cgtagtcacc ccctcgatct ctcgcaca                        48

<210> SEQ ID NO 269
<211> LENGTH: 48
<212> TYPE: DNA
<213> ORGANISM: ARTIFICIAL SEQUENCE
<220> FEATURE:
<223> OTHER INFORMATION: 5245-94 primer sequence

<400> SEQUENCE: 269
tgtgcgagag atcgaggggg tgactacgaa tatggtatgg acgtctgg                        48

<210> SEQ ID NO 270
<211> LENGTH: 48
<212> TYPE: DNA
<213> ORGANISM: ARTIFICIAL SEQUENCE
<220> FEATURE:
<223> OTHER INFORMATION: 5245-97 primer sequence

<400> SEQUENCE: 270
ccagacgtcc ataccatatc tgtagtcacc ccctcgatct ctcgcaca                        48

<210> SEQ ID NO 271
<211> LENGTH: 48
<212> TYPE: DNA
<213> ORGANISM: ARTIFICIAL SEQUENCE
<220> FEATURE:
<223> OTHER INFORMATION: 5245-97 primer sequence

<400> SEQUENCE: 271
tgtgcgagag atcgaggggg tgactacaga tatggtatgg acgtctgg                        48

<210> SEQ ID NO 272
<211> LENGTH: 48
<212> TYPE: DNA
<213> ORGANISM: ARTIFICIAL SEQUENCE
<220> FEATURE:
<223> OTHER INFORMATION: 5245-99 primer sequence

<400> SEQUENCE: 272
ccagacgtcc ataccttcgt agtagtcacc ccctcgatct ctcgcaca                        48

<210> SEQ ID NO 273
<211> LENGTH: 48
<212> TYPE: DNA
<213> ORGANISM: ARTIFICIAL SEQUENCE
<220> FEATURE:
<223> OTHER INFORMATION: 5245-98 primer sequence

<400> SEQUENCE: 273
```

```
tgtgcgagag atcgaggggg tgactactac gaaggtatgg acgtctgg          48
```

<210> SEQ ID NO 274
<211> LENGTH: 48
<212> TYPE: DNA
<213> ORGANISM: ARTIFICIAL SEQUENCE
<220> FEATURE:
<223> OTHER INFORMATION: 5246-01 primer sequence

<400> SEQUENCE: 274

```
ccagacgtcc atacctctgt agtagtcacc ccctcgatct ctcgcaca          48
```

<210> SEQ ID NO 275
<211> LENGTH: 48
<212> TYPE: DNA
<213> ORGANISM: ARTIFICIAL SEQUENCE
<220> FEATURE:
<223> OTHER INFORMATION: 5246-00 primer sequence

<400> SEQUENCE: 275

```
tgtgcgagag atcgaggggg tgactactac agaggtatgg acgtctgg          48
```

<210> SEQ ID NO 276
<211> LENGTH: 48
<212> TYPE: DNA
<213> ORGANISM: ARTIFICIAL SEQUENCE
<220> FEATURE:
<223> OTHER INFORMATION: 5245-81 primer sequence

<400> SEQUENCE: 276

```
ccagacgtcc ataccagcag cgtagtcacc ccctcgatct ctcgcaca          48
```

<210> SEQ ID NO 277
<211> LENGTH: 48
<212> TYPE: DNA
<213> ORGANISM: ARTIFICIAL SEQUENCE
<220> FEATURE:
<223> OTHER INFORMATION: 5245-80 primer sequence

<400> SEQUENCE: 277

```
tgtgcgagag atcgaggggg tgactacgct gctggtatgg acgtctgg          48
```

<210> SEQ ID NO 278
<211> LENGTH: 45
<212> TYPE: DNA
<213> ORGANISM: ARTIFICIAL SEQUENCE
<220> FEATURE:
<223> OTHER INFORMATION: 4647-89 primer sequence

<400> SEQUENCE: 278

```
aagctcgagg tcgactagac caccatgaag cacctgtggt tcttc             45
```

<210> SEQ ID NO 279

<400> SEQUENCE: 279

000

<210> SEQ ID NO 280

<400> SEQUENCE: 280

000

<210> SEQ ID NO 281

<400> SEQUENCE: 281

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 290

His Gly Glu Gly Thr Phe Thr Ser Asp Gln Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 291
<211> LENGTH: 31
<212> TYPE: PRT
<213> ORGANISM: ARTIFICIAL SEQUENCE

```
<220> FEATURE:
<223> OTHER INFORMATION: GLP-1 mimetic polypeptide

<400> SEQUENCE: 291

His Gly Glu Gly Thr Phe Thr Ser Asp Gln Ser Ser Tyr Leu Glu Gly
1               5                   10                  15

Gln Ala Ala Lys Glu Phe Ile Ala Trp Leu Gln Lys Gly Arg Gly
            20                  25                  30

<210> SEQ ID NO 292
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 292

His Gly Glu Gly Thr Phe Thr Ser Asp Val Ser Ser Tyr Gln Glu Gly
1               5                   10                  15

Gln Ala Ala Lys Glu Phe Ile Ala Trp Leu Val Lys Gly Arg Gly
            20                  25                  30

<210> SEQ ID NO 293
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 293

His Gly Glu Gly Thr Phe Thr Ser Asp Val Ser Ser Tyr Leu Glu Gly
1               5                   10                  15

Gln Ala Ala Lys Glu Phe Ile Ala Gln Leu Val Lys Gly Arg Gly
            20                  25                  30

<210> SEQ ID NO 294
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 294

His Gly Glu Gly Thr Phe Thr Ser Asp Val Ser Ser Tyr Leu Glu Gly
1               5                   10                  15

Gln Ala Ala Lys Glu Phe Ile Ala Gln Leu Gln Lys Gly Arg Gly
            20                  25                  30

<210> SEQ ID NO 295
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 295

His Gly Glu Gly Thr Phe Thr Ser Asp Val Ser Ser Tyr Leu Glu Gly
1               5                   10                  15

Gln Ala Ala Lys Glu Phe Ile Ala Trp Leu Gln Lys Gly Arg Gly
            20                  25                  30

<210> SEQ ID NO 296
<211> LENGTH: 31
<212> TYPE: PRT
<213> ORGANISM: ARTIFICIAL SEQUENCE
```

```
<220> FEATURE:
<223> OTHER INFORMATION: GLP-1 mimetic polypeptide

<400> SEQUENCE: 296

His Asn Glu Thr Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 297
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 297

His Gly Glu Gly Thr Phe Thr Ser Asp Val Ser Ser Tyr Leu Glu Asn
1               5                   10                  15

Gln Thr Ala Lys Glu Phe Ile Ala Trp Leu Val Lys Gly Arg Gly
            20                  25                  30

<210> SEQ ID NO 298
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 298

His Gly Glu Gly Thr Phe Thr Ser Asp Val Ser Ser Tyr Leu Glu Gly
1               5                   10                  15

Asn Ala Thr Lys Glu Phe Ile Ala Trp Leu Val Lys Gly Arg Gly
            20                  25                  30

<210> SEQ ID NO 299
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 299

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Asn Gly Thr Gly
            20                  25                  30

<210> SEQ ID NO 300
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 300

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Asn Arg Thr
            20                  25                  30

<210> SEQ ID NO 301
<211> LENGTH: 33
<212> TYPE: PRT
<213> ORGANISM: ARTIFICIAL SEQUENCE
```

-continued

<220> FEATURE:
<223> OTHER INFORMATION: GLP-1 mimetic polypeptide

<400> SEQUENCE: 301

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Asn Gly
            20                  25                  30

Thr

<210> SEQ ID NO 302
<211> LENGTH: 37
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 302

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Thr Gly Asn Gly Thr
        35

<210> SEQ ID NO 303
<211> LENGTH: 37
<212> TYPE: PRT
<213> ORGANISM: ARTIFICIAL SEQUENCE
<220> FEATURE:
<223> OTHER INFORMATION: GLP-1 mimetic polypeptide

<400> SEQUENCE: 303

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Ser Gly Asn Gly Thr
        35

<210> SEQ ID NO 304
<211> LENGTH: 348
<212> TYPE: DNA
<213> ORGANISM: ARTIFICIAL SEQUENCE
<220> FEATURE:
<223> OTHER INFORMATION: VH1 coding sequence
<220> FEATURE:
<221> NAME/KEY: CDS
<222> LOCATION: (1)..(348)

<400> SEQUENCE: 304 cag gtt cag ctg gtg cag tct gga gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc aga tat      96
Ser Val Lys Val Ser Cys Lys Ala Ser Gly Tyr Thr Phe Thr Arg Tyr
            20                  25                  30 ggt atc agc tgg gtg cga cag gcc cct gga caa ggg ctt gag tgg atg     144
Gly Ile Ser Trp Val Arg Gln Ala Pro Gly Gln Gly Leu Glu Trp Met
        35                  40                  45 gga tgg atc agc act tac agt ggt aac aca aac tat gca cag aag ctc     192
Gly Trp Ile Ser Thr Tyr Ser Gly Asn Thr Asn Tyr Ala Gln Lys Leu
    50                  55                  60

```
cag ggc aga gtc acc atg acc aca gac aca tcc acg agc aca gcc tac      240
Gln Gly Arg Val Thr Met Thr Thr Asp Thr Ser Thr Ser Thr Ala Tyr
 65                  70                  75                  80 atg gag ctg agg agc ctg aga tct gac gac acg gcc gtg tat tac tgt      288
Met Glu Leu Arg Ser Leu Arg Ser Asp Asp Thr Ala Val Tyr Tyr Cys
                 85                  90                  95 gcg aga cgg cag ctt tac ttt gac tac tgg ggc cag gga acc ctg gtc      336
Ala Arg Arg Gln Leu Tyr Phe Asp Tyr Trp Gly Gln Gly Thr Leu Val
            100                 105                 110 acc gtc tcc tca                                                      348
Thr Val Ser Ser
        115

<210> SEQ ID NO 305
<211> LENGTH: 116
<212> TYPE: PRT
<213> ORGANISM: ARTIFICIAL SEQUENCE
<220> FEATURE:
<223> OTHER INFORMATION: Synthetic Construct

<400> SEQUENCE: 305

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Arg Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Ser Gly Asn Thr Asn Tyr Ala Gln Lys Leu
        50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Arg Gln Leu Tyr Phe Asp Tyr Trp Gly Gln Gly Thr Leu Val
            100                 105                 110

Thr Val Ser Ser
        115

<210> SEQ ID NO 306
<211> LENGTH: 348
<212> TYPE: DNA
<213> ORGANISM: ARTIFICIAL SEQUENCE
<220> FEATURE:
<223> OTHER INFORMATION: VH2 coding sequence
<220> FEATURE:
<221> NAME/KEY: CDS
<222> LOCATION: (1)..(348)

<400> SEQUENCE: 306 cag gtt cag ctg gtg cag tct gga gct gag gtg aag aag cct ggg gcc       48
Gln Val Gln Leu Val Gln Ser Gly Ala Glu Val Lys Lys Pro Gly Ala
 1               5                  10                  15 tca gtg aag gtc tcc tgc aag gct tct ggt tac acc ttt acc aga tat       96
Ser Val Lys Val Ser Cys Lys Ala Ser Gly Tyr Thr Phe Thr Arg Tyr
                20                  25                  30 ggt atc agc tgg gtg cga cag gcc cct gga caa ggg ctt gag tgg atg      144
Gly Ile Ser Trp Val Arg Gln Ala Pro Gly Gln Gly Leu Glu Trp Met
            35                  40                  45 gga tgg atc agc act tac agt ggt aac aca aac tat gca cag aag ctc      192
Gly Trp Ile Ser Thr Tyr Ser Gly Asn Thr Asn Tyr Ala Gln Lys Leu
        50                  55                  60 cag ggc aga gtc acc atg acc aca gac aca tcc acg agc aca gcc tac      240
```

```
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt      288
Met Glu Leu Arg Ser Leu Arg Ser Asp Asp Thr Ala Val Tyr Tyr Cys
                85                  90                  95 gcg aga cgg cag ctt tac ttt gac gct tgg ggc cag gga acc ctg gtc      336
Ala Arg Arg Gln Leu Tyr Phe Asp Ala Trp Gly Gln Gly Thr Leu Val
            100                 105                 110 acc gtc tcc tca                                                      348
Thr Val Ser Ser
        115

<210> SEQ ID NO 307
<211> LENGTH: 116
<212> TYPE: PRT
<213> ORGANISM: ARTIFICIAL SEQUENCE
<220> FEATURE:
<223> OTHER INFORMATION: Synthetic Construct

<400> SEQUENCE: 307

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Tyr Phe Asp Ala Trp Gly Gln Gly Thr Leu Val
            100                 105                 110

Thr Val Ser Ser
        115

<210> SEQ ID NO 308
<211> LENGTH: 348
<212> TYPE: DNA
<213> ORGANISM: ARTIFICIAL SEQUENCE
<220> FEATURE:
<223> OTHER INFORMATION: VH3 coding sequence
<220> FEATURE:
<221> NAME/KEY: CDS
<222> LOCATION: (1)..(348)

<400> SEQUENCE: 308 cag gtt cag ctg gtg cag tct gga gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc aga tat      96
Ser Val Lys Val Ser Cys Lys Ala Ser Gly Tyr Thr Phe Thr Arg Tyr
            20                  25                  30 ggt atc agc tgg gtg cga cag gcc cct gga caa ggg ctt gag tgg atg     144
Gly Ile Ser Trp Val Arg Gln Ala Pro Gly Gln Gly Leu Glu Trp Met
        35                  40                  45 gga tgg atc agc act tac agt ggt aac aca aac tat gca cag aag ctc     192
Gly Trp Ile Ser Thr Tyr Ser Gly Asn Thr Asn Tyr Ala Gln Lys Leu
    50                  55                  60 cag ggc aga gtc acc atg acc aca gac aca tcc acg agc aca gcc tac     240
Gln Gly Arg Val Thr Met Thr Thr Asp Thr Ser Thr Ser Thr Ala Tyr
```

```
                                                                65                      70                      75                      80
atg gag ctg agg agc ctg aga tct gac gac acg gcc gtg tat tac tgt        288
Met Glu Leu Arg Ser Leu Arg Ser Asp Asp Thr Ala Val Tyr Tyr Cys
                85                      90                      95 gcg aga cgg cag ctt tac gct gac tac tgg ggc cag gga acc ctg gtc        336
Ala Arg Arg Gln Leu Tyr Ala Asp Tyr Trp Gly Gln Gly Thr Leu Val
            100                     105                     110 acc gtc tcc tca                                                        348
Thr Val Ser Ser
        115

<210> SEQ ID NO 309
<211> LENGTH: 116
<212> TYPE: PRT
<213> ORGANISM: ARTIFICIAL SEQUENCE
<220> FEATURE:
<223> OTHER INFORMATION: Synthetic Construct

<400> SEQUENCE: 309

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Tyr Ala Asp Tyr Trp Gly Gln Gly Thr Leu Val
            100                 105                 110

Thr Val Ser Ser
        115

<210> SEQ ID NO 310
<211> LENGTH: 348
<212> TYPE: DNA
<213> ORGANISM: ARTIFICIAL SEQUENCE
<220> FEATURE:
<223> OTHER INFORMATION: VH4 coding sequence
<220> FEATURE:
<221> NAME/KEY: CDS
<222> LOCATION: (1)..(348)

<400> SEQUENCE: 310 cag gtt cag ctg gtg cag tct gga gct gag gtg aag aag cct ggg gcc         48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc aga tat         96
Ser Val Lys Val Ser Cys Lys Ala Ser Gly Tyr Thr Phe Thr Arg Tyr
            20                  25                  30 ggt atc agc tgg gtg cga cag gcc cct gga caa ggg ctt gag tgg atg        144
Gly Ile Ser Trp Val Arg Gln Ala Pro Gly Gln Gly Leu Glu Trp Met
        35                  40                  45 gga tgg atc agc act tac agt ggt aac aca aac tat gca cag aag ctc        192
Gly Trp Ile Ser Thr Tyr Ser Gly Asn Thr Asn Tyr Ala Gln Lys Leu
    50                  55                  60 cag ggc aga gtc acc atg acc aca gac aca tcc acg agc aca gcc tac        240
Gln Gly Arg Val Thr Met Thr Thr Asp Thr Ser Thr Ser Thr Ala Tyr
65                  70                  75                  80
```

| | | |
|---|---|---|
| atg gag ctg agg agc ctg aga tct gac gac acg gcc gtg tat tac tgt<br>Met Glu Leu Arg Ser Leu Arg Ser Asp Asp Thr Ala Val Tyr Tyr Cys<br>                              85                           90                     95 | | 288 |
| gcg aga cgg cag ctt gct ttt gac tac tgg ggc cag gga acc ctg gtc<br>Ala Arg Arg Gln Leu Ala Phe Asp Tyr Trp Gly Gln Gly Thr Leu Val<br>                100                          105                       110 | | 336 |
| acc gtc tcc tca<br>Thr Val Ser Ser<br>        115 | | 348 |

<210> SEQ ID NO 311
<211> LENGTH: 116
<212> TYPE: PRT
<213> ORGANISM: ARTIFICIAL SEQUENCE
<220> FEATURE:
<223> OTHER INFORMATION: Synthetic Construct

<400> SEQUENCE: 311

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Ala Phe Asp Tyr Trp Gly Gln Gly Thr Leu Val
            100                 105                 110

Thr Val Ser Ser
        115

<210> SEQ ID NO 312
<211> LENGTH: 348
<212> TYPE: DNA
<213> ORGANISM: ARTIFICIAL SEQUENCE
<220> FEATURE:
<223> OTHER INFORMATION: VH5 coding sequence
<220> FEATURE:
<221> NAME/KEY: CDS
<222> LOCATION: (1)..(348)

<400> SEQUENCE: 312

| | | |
|---|---|---|
| cag gtt cag ctg gtg cag tct gga gct gag gtg aag aag cct ggg gcc<br>Gln Val Gln Leu Val Gln Ser Gly Ala Glu Val Lys Lys Pro Gly Ala<br>1                 5                   10                  15 | | 48 |
| tca gtg aag gtc tcc tgc aag gct tct ggt tac acc ttt acc aga tat<br>Ser Val Lys Val Ser Cys Lys Ala Ser Gly Tyr Thr Phe Thr Arg Tyr<br>           20                    25                    30 | | 96 |
| ggt atc agc tgg gtg cga cag gcc cct gga caa ggg ctt gag tgg atg<br>Gly Ile Ser Trp Val Arg Gln Ala Pro Gly Gln Gly Leu Glu Trp Met<br>        35                    40                    45 | | 144 |
| gga tgg atc agc act tac agt ggt aac aca aac gct gca cag aag ctc<br>Gly Trp Ile Ser Thr Tyr Ser Gly Asn Thr Asn Ala Ala Gln Lys Leu<br>    50                    55                    60 | | 192 |
| cag ggc aga gtc acc atg acc aca gac aca tcc acg agc aca gcc tac<br>Gln Gly Arg Val Thr Met Thr Thr Asp Thr Ser Thr Ser Thr Ala Tyr<br>65                70                  75                  80 | | 240 |

```
atg gag ctg agg agc ctg aga tct gac gac acg gcc gtg tat tac tgt      288
Met Glu Leu Arg Ser Leu Arg Ser Asp Asp Thr Ala Val Tyr Tyr Cys
                85                  90                  95 gcg aga cgg cag ctt tac ttt gac tac tgg ggc cag gga acc ctg gtc      336
Ala Arg Arg Gln Leu Tyr Phe Asp Tyr Trp Gly Gln Gly Thr Leu Val
            100                 105                 110 acc gtc tcc tca                                                      348
Thr Val Ser Ser
        115

<210> SEQ ID NO 313
<211> LENGTH: 116
<212> TYPE: PRT
<213> ORGANISM: ARTIFICIAL SEQUENCE
<220> FEATURE:
<223> OTHER INFORMATION: Synthetic Construct

<400> SEQUENCE: 313

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Ala Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Tyr Phe Asp Tyr Trp Gly Gln Gly Thr Leu Val
            100                 105                 110

Thr Val Ser Ser
        115

<210> SEQ ID NO 314
<211> LENGTH: 348
<212> TYPE: DNA
<213> ORGANISM: ARTIFICIAL SEQUENCE
<220> FEATURE:
<223> OTHER INFORMATION: VH6 coding sequence
<220> FEATURE:
<221> NAME/KEY: CDS
<222> LOCATION: (1)..(348)

<400> SEQUENCE: 314 cag gtt cag ctg gtg cag tct gga gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc aga tat       96
Ser Val Lys Val Ser Cys Lys Ala Ser Gly Tyr Thr Phe Thr Arg Tyr
            20                  25                  30 ggt atc agc tgg gtg cga cag gcc cct gga caa ggg ctt gag tgg atg      144
Gly Ile Ser Trp Val Arg Gln Ala Pro Gly Gln Gly Leu Glu Trp Met
        35                  40                  45 gga tgg atc agc act gct agt ggt aac aca aac tat gca cag aag ctc      192
Gly Trp Ile Ser Thr Ala Ser Gly Asn Thr Asn Tyr Ala Gln Lys Leu
    50                  55                  60 cag ggc aga gtc acc atg acc aca gac aca tcc acg agc aca gcc tac      240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt      288
```

```
Met Glu Leu Arg Ser Leu Arg Ser Asp Asp Thr Ala Val Tyr Tyr Cys
            85                  90                  95 gcg aga cgg cag ctt tac ttt gac tac tgg ggc cag gga acc ctg gtc      336
Ala Arg Arg Gln Leu Tyr Phe Asp Tyr Trp Gly Gln Gly Thr Leu Val
            100                 105                 110 acc gtc tcc tca                                                       348
Thr Val Ser Ser
        115

<210> SEQ ID NO 315
<211> LENGTH: 116
<212> TYPE: PRT
<213> ORGANISM: ARTIFICIAL SEQUENCE
<220> FEATURE:
<223> OTHER INFORMATION: Synthetic Construct

<400> SEQUENCE: 315

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Ala Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Tyr Phe Asp Tyr Trp Gly Gln Gly Thr Leu Val
            100                 105                 110

Thr Val Ser Ser
        115

<210> SEQ ID NO 316
<211> LENGTH: 342
<212> TYPE: DNA
<213> ORGANISM: ARTIFICIAL SEQUENCE
<220> FEATURE:
<223> OTHER INFORMATION: VH7 coding sequence
<220> FEATURE:
<221> NAME/KEY: CDS
<222> LOCATION: (1)..(342)

<400> SEQUENCE: 316 cag ctg gtg cag tct gga gct gag gtg aag aag cct ggg gcc tca gtg       48
Gln Leu Val Gln Ser Gly Ala Glu Val Lys Lys Pro Gly Ala Ser Val
1               5                   10                  15 aag gtc tcc tgc aag gct tct ggt tac acc ttt acc aga tat ggt atc       96
Lys Val Ser Cys Lys Ala Ser Gly Tyr Thr Phe Thr Arg Tyr Gly Ile
            20                  25                  30 agc tgg gtg cga cag gcc cct gga caa ggg ctt gag tgg atg gga gct      144
Ser Trp Val Arg Gln Ala Pro Gly Gln Gly Leu Glu Trp Met Gly Ala
        35                  40                  45 atc agc act tac agt ggt aac aca aac tat gca cag aag ctc cag ggc      192
Ile Ser Thr Tyr Ser Gly Asn Thr Asn Tyr Ala Gln Lys Leu Gln Gly
    50                  55                  60 aga gtc acc atg acc aca gac aca tcc acg agc aca gcc tac atg gag      240
Arg Val Thr Met Thr Thr Asp Thr Ser Thr Ser Thr Ala Tyr Met Glu
65                  70                  75                  80 ctg agg agc ctg aga tct gac gac acg gcc gtg tat tac tgt gcg aga      288
Leu Arg Ser Leu Arg Ser Asp Asp Thr Ala Val Tyr Tyr Cys Ala Arg
```

```
                         85                   90                   95
cgg cag ctt tac ttt gac tac tgg ggc cag gga acc ctg gtc acc gtc      336
Arg Gln Leu Tyr Phe Asp Tyr Trp Gly Gln Gly Thr Leu Val Thr Val
            100                 105                 110 tcc tca                                                              342
Ser Ser <210> SEQ ID NO 317
<211> LENGTH: 114
<212> TYPE: PRT
<213> ORGANISM: ARTIFICIAL SEQUENCE
<220> FEATURE:
<223> OTHER INFORMATION: Synthetic Construct

<400> SEQUENCE: 317

Gln Leu Val Gln Ser Gly Ala Glu Val Lys Lys Pro Gly Ala Ser Val
1               5                   10                  15

Lys Val Ser Cys Lys Ala Ser Gly Tyr Thr Phe Thr Arg Tyr Gly Ile
            20                  25                  30

Ser Trp Val Arg Gln Ala Pro Gly Gln Gly Leu Glu Trp Met Gly Ala
            35                  40                  45

Ile Ser Thr Tyr Ser Gly Asn Thr Asn Tyr Ala Gln Lys Leu Gln Gly
    50                  55                  60

Arg Val Thr Met Thr Thr Asp Thr Ser Thr Ser Thr Ala Tyr Met Glu
65                  70                  75                  80

Leu Arg Ser Leu Arg Ser Asp Asp Thr Ala Val Tyr Tyr Cys Ala Arg
                85                  90                  95

Arg Gln Leu Tyr Phe Asp Tyr Trp Gly Gln Gly Thr Leu Val Thr Val
            100                 105                 110

Ser Ser

<210> SEQ ID NO 318
<211> LENGTH: 348
<212> TYPE: DNA
<213> ORGANISM: ARTIFICIAL SEQUENCE
<220> FEATURE:
<223> OTHER INFORMATION: VH8 coding sequence
<220> FEATURE:
<221> NAME/KEY: CDS
<222> LOCATION: (1)..(348)

<400> SEQUENCE: 318 cag gtt cag ctg gtg cag tct gga gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc aga gct      96
Ser Val Lys Val Ser Cys Lys Ala Ser Gly Tyr Thr Phe Thr Arg Ala
            20                  25                  30 ggt atc agc tgg gtg cga cag gcc cct gga caa ggg ctt gag tgg atg     144
Gly Ile Ser Trp Val Arg Gln Ala Pro Gly Gln Gly Leu Glu Trp Met
            35                  40                  45 gga tgg atc agc act tac agt ggt aac aca aac tat gca cag aag ctc     192
Gly Trp Ile Ser Thr Tyr Ser Gly Asn Thr Asn Tyr Ala Gln Lys Leu
    50                  55                  60 cag ggc aga gtc acc atg acc aca gac aca tcc acg agc aca gcc tac     240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt     288
Met Glu Leu Arg Ser Leu Arg Ser Asp Asp Thr Ala Val Tyr Tyr Cys
                85                  90                  95 gcg aga cgg cag ctt tac ttt gac tac tgg ggc cag gga acc ctg gtc     336
Ala Arg Arg Gln Leu Tyr Phe Asp Tyr Trp Gly Gln Gly Thr Leu Val
```

```
                   100                 105                 110
acc gtc tcc tca                                                         348
Thr Val Ser Ser
          115

<210> SEQ ID NO 319
<211> LENGTH: 116
<212> TYPE: PRT
<213> ORGANISM: ARTIFICIAL SEQUENCE
<220> FEATURE:
<223> OTHER INFORMATION: Synthetic Construct

<400> SEQUENCE: 319

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ala
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Tyr Phe Asp Tyr Trp Gly Gln Gly Thr Leu Val
            100                 105                 110

Thr Val Ser Ser
          115

<210> SEQ ID NO 320
<211> LENGTH: 348
<212> TYPE: DNA
<213> ORGANISM: ARTIFICIAL SEQUENCE
<220> FEATURE:
<223> OTHER INFORMATION: VH9 coding sequence
<220> FEATURE:
<221> NAME/KEY: CDS
<222> LOCATION: (1)..(348)

<400> SEQUENCE: 320 cag gtt cag ctg gtg cag tct gga gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc aga tat        96
Ser Val Lys Val Ser Cys Lys Ala Ser Gly Tyr Thr Phe Thr Arg Tyr
            20                  25                  30 ggt atc agc tgg gtg cga cag gcc cct gga caa ggg ctt gag tgg atg       144
Gly Ile Ser Trp Val Arg Gln Ala Pro Gly Gln Gly Leu Glu Trp Met
        35                  40                  45 gga tgg atc agc act tac agt ggt aac aca aac tat gca cag aag ctc       192
Gly Trp Ile Ser Thr Tyr Ser Gly Asn Thr Asn Tyr Ala Gln Lys Leu
    50                  55                  60 cag ggc aga gtc acc atg acc aca gac aca tcc acg agc aca gcc tac       240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt       288
Met Glu Leu Arg Ser Leu Arg Ser Asp Asp Thr Ala Val Tyr Tyr Cys
                85                  90                  95 gcg aga cgg cag cag tac ttt gac tac tgg ggc cag gga acc ctg gtc       336
Ala Arg Arg Gln Gln Tyr Phe Asp Tyr Trp Gly Gln Gly Thr Leu Val
            100                 105                 110
```

```
acc gtc tcc tca                                                           348
Thr Val Ser Ser
        115

<210> SEQ ID NO 321
<211> LENGTH: 116
<212> TYPE: PRT
<213> ORGANISM: ARTIFICIAL SEQUENCE
<220> FEATURE:
<223> OTHER INFORMATION: Synthetic Construct

<400> SEQUENCE: 321

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Gln Tyr Phe Asp Tyr Trp Gly Gln Gly Thr Leu Val
            100                 105                 110

Thr Val Ser Ser
        115

<210> SEQ ID NO 322
<211> LENGTH: 348
<212> TYPE: DNA
<213> ORGANISM: ARTIFICIAL SEQUENCE
<220> FEATURE:
<223> OTHER INFORMATION: VH10 coding sequence
<220> FEATURE:
<221> NAME/KEY: CDS
<222> LOCATION: (1)..(348)

<400> SEQUENCE: 322 cag gtt cag ctg gtg cag tct gga gct gag gtg aag aag cct ggg gcc         48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc aga tat         96
Ser Val Lys Val Ser Cys Lys Ala Ser Gly Tyr Thr Phe Thr Arg Tyr
            20                  25                  30 ggt atc agc tgg gtg cga cag gcc cct gga caa ggg ctt gag tgg atg        144
Gly Ile Ser Trp Val Arg Gln Ala Pro Gly Gln Gly Leu Glu Trp Met
        35                  40                  45 gga tgg atc agc act tac agt ggt aac aca aac tat gca cag aag ctc        192
Gly Trp Ile Ser Thr Tyr Ser Gly Asn Thr Asn Tyr Ala Gln Lys Leu
    50                  55                  60 cag ggc aga gtc acc atg acc aca gac aca tcc acg agc aca gcc tac        240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt        288
Met Glu Leu Arg Ser Leu Arg Ser Asp Asp Thr Ala Val Tyr Tyr Cys
                85                  90                  95 gcg aga gct cag ctt tac ttt gac tac tgg ggc cag gga acc ctg gtc        336
Ala Arg Ala Gln Leu Tyr Phe Asp Tyr Trp Gly Gln Gly Thr Leu Val
            100                 105                 110
```

```
acc gtc tcc tca                                                    348
Thr Val Ser Ser
        115

<210> SEQ ID NO 323
<211> LENGTH: 116
<212> TYPE: PRT
<213> ORGANISM: ARTIFICIAL SEQUENCE
<220> FEATURE:
<223> OTHER INFORMATION: Synthetic Construct

<400> SEQUENCE: 323

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Gln Leu Tyr Phe Asp Tyr Trp Gly Gln Gly Thr Leu Val
            100                 105                 110

Thr Val Ser Ser
        115

<210> SEQ ID NO 324
<211> LENGTH: 348
<212> TYPE: DNA
<213> ORGANISM: ARTIFICIAL SEQUENCE
<220> FEATURE:
<223> OTHER INFORMATION: VH11 coding sequence
<220> FEATURE:
<221> NAME/KEY: CDS
<222> LOCATION: (1)..(348)

<400> SEQUENCE: 324 cag gtt cag ctg gtg cag tct gga gct gag gtg aag aag cct ggg gcc    48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc aga tat    96
Ser Val Lys Val Ser Cys Lys Ala Ser Gly Tyr Thr Phe Thr Arg Tyr
            20                  25                  30 ggt atc agc tgg gtg cga cag gcc cct gga caa ggg ctt gag tgg atg   144
Gly Ile Ser Trp Val Arg Gln Ala Pro Gly Gln Gly Leu Glu Trp Met
        35                  40                  45 gga tgg atc agc act tac agt ggt aac aca aac tat gca cag aag ctc   192
Gly Trp Ile Ser Thr Tyr Ser Gly Asn Thr Asn Tyr Ala Gln Lys Leu
    50                  55                  60 cag ggc aga gtc acc atg acc aca gac aca tcc acg agc aca gcc tac   240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt   288
Met Glu Leu Arg Ser Leu Arg Ser Asp Asp Thr Ala Val Tyr Tyr Cys
                85                  90                  95 gcg aga gct cag cag tac ttt gac tac tgg ggc cag gga acc ctg gtc   336
Ala Arg Ala Gln Gln Tyr Phe Asp Tyr Trp Gly Gln Gly Thr Leu Val
            100                 105                 110 acc gtc tcc tca                                                   348
```

Thr Val Ser Ser
        115

<210> SEQ ID NO 325
<211> LENGTH: 116
<212> TYPE: PRT
<213> ORGANISM: ARTIFICIAL SEQUENCE
<220> FEATURE:
<223> OTHER INFORMATION: Synthetic Construct

<400> SEQUENCE: 325

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Gln Gln Tyr Phe Asp Tyr Trp Gly Gln Gly Thr Leu Val
            100                 105                 110

Thr Val Ser Ser
        115
```

<210> SEQ ID NO 326
<211> LENGTH: 366
<212> TYPE: DNA
<213> ORGANISM: ARTIFICIAL SEQUENCE
<220> FEATURE:
<223> OTHER INFORMATION: VH12 coding sequence
<220> FEATURE:
<221> NAME/KEY: CDS
<222> LOCATION: (1)..(366)

<400> SEQUENCE: 326

```
cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac ttc tgg agc tgg atc cgc cag ctc cca ggg aag ggc ctg gag     144
Asp Tyr Phe Trp Ser Trp Ile Arg Gln Leu Pro Gly Lys Gly Leu Glu
        35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
                85                  90                  95 tgt gcg aga gat cga ggg ggt gac tac tac tat ggt atg gac gtc tgg     336
Cys Ala Arg Asp Arg Gly Gly Asp Tyr Tyr Tyr Gly Met Asp Val Trp
            100                 105                 110 ggc caa ggg acc acg gtc acc gtc tcc tca                             366
Gly Gln Gly Thr Thr Val Thr Val Ser Ser
```

<210> SEQ ID NO 327
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 327

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser
        115                 120
```

<210> SEQ ID NO 328
<211> LENGTH: 366
<212> TYPE: DNA
<213> ORGANISM: ARTIFICIAL SEQUENCE
<220> FEATURE:
<223> OTHER INFORMATION: VH13 coding sequence
<220> FEATURE:
<221> NAME/KEY: CDS
<222> LOCATION: (1)..(366)

<400> SEQUENCE: 328

```
cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac ttc tgg agc tgg atc cgc cag ctc cca ggg aag ggc ctg gag     144
Asp Tyr Phe Trp Ser Trp Ile Arg Gln Leu Pro Gly Lys Gly Leu Glu
        35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
                85                  90                  95 tgt gcg aga gat cga ggg ggt gct tac tac tat ggt atg gac gtc tgg     336
Cys Ala Arg Asp Arg Gly Gly Ala Tyr Tyr Tyr Gly Met Asp Val Trp
            100                 105                 110 ggc caa ggg acc acg gtc acc gtc tcc tca                             366
Gly Gln Gly Thr Thr Val Thr Val Ser Ser
        115                 120
```

<210> SEQ ID NO 329
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 329

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Ala Tyr Tyr Tyr Gly Met Asp Val Trp
            100                 105                 110

Gly Gln Gly Thr Thr Val Thr Val Ser Ser
        115                 120

<210> SEQ ID NO 330
<211> LENGTH: 366
<212> TYPE: DNA
<213> ORGANISM: ARTIFICIAL SEQUENCE
<220> FEATURE:
<223> OTHER INFORMATION: VH14 coding sequence
<220> FEATURE:
<221> NAME/KEY: CDS
<222> LOCATION: (1)..(366)

<400> SEQUENCE: 330 cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac ttc tgg agc tgg atc cgc cag ctc cca ggg aag ggc ctg gag     144
Asp Tyr Phe Trp Ser Trp Ile Arg Gln Leu Pro Gly Lys Gly Leu Glu
        35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
                85                  90                  95 tgt gcg aga gat cga ggg ggt gac gct tac tat ggt atg gac gtc tgg     336
Cys Ala Arg Asp Arg Gly Gly Asp Ala Tyr Tyr Gly Met Asp Val Trp
            100                 105                 110 ggc caa ggg acc acg gtc acc gtc tcc tca                             366
Gly Gln Gly Thr Thr Val Thr Val Ser Ser
        115                 120

<210> SEQ ID NO 331
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 331

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Ala Tyr Tyr Gly Met Asp Val Trp
            100                 105                 110

Gly Gln Gly Thr Thr Val Thr Val Ser Ser
        115                 120
```

<210> SEQ ID NO 332
<211> LENGTH: 366
<212> TYPE: DNA
<213> ORGANISM: ARTIFICIAL SEQUENCE
<220> FEATURE:
<223> OTHER INFORMATION: VH15 coding sequence
<220> FEATURE:
<221> NAME/KEY: CDS
<222> LOCATION: (1)..(366)

<400> SEQUENCE: 332

```
cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat gct ttc tgg agc tgg atc cgc cag ctc cca ggg aag ggc ctg gag     144
Asp Ala Phe Trp Ser Trp Ile Arg Gln Leu Pro Gly Lys Gly Leu Glu
        35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
                85                  90                  95 tgt gcg aga gat cga ggg ggt gac tac tac tat ggt atg gac gtc tgg     336
Cys Ala Arg Asp Arg Gly Gly Asp Tyr Tyr Tyr Gly Met Asp Val Trp
            100                 105                 110 ggc caa ggg acc acg gtc acc gtc tcc tca                             366
Gly Gln Gly Thr Thr Val Thr Val Ser Ser
        115                 120
```

<210> SEQ ID NO 333
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 333

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Ala Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser
        115                 120
```

<210> SEQ ID NO 334
<211> LENGTH: 366
<212> TYPE: DNA
<213> ORGANISM: ARTIFICIAL SEQUENCE
<220> FEATURE:
<223> OTHER INFORMATION: VH16 coding sequence
<220> FEATURE:
<221> NAME/KEY: CDS
<222> LOCATION: (1)..(366)

<400> SEQUENCE: 334

```
cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac gct tgg agc tgg atc cgc cag ctc cca ggg aag ggc ctg gag     144
Asp Tyr Ala Trp Ser Trp Ile Arg Gln Leu Pro Gly Lys Gly Leu Glu
        35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
                85                  90                  95 tgt gcg aga gat cga ggg ggt gac tac tac tat ggt atg gac gtc tgg     336
Cys Ala Arg Asp Arg Gly Gly Asp Tyr Tyr Tyr Gly Met Asp Val Trp
            100                 105                 110 ggc caa ggg acc acg gtc acc gtc tcc tca                              366
Gly Gln Gly Thr Thr Val Thr Val Ser Ser
        115                 120
```

<210> SEQ ID NO 335

```
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 335

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Ala Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser
        115                 120

<210> SEQ ID NO 336
<211> LENGTH: 366
<212> TYPE: DNA
<213> ORGANISM: ARTIFICIAL SEQUENCE
<220> FEATURE:
<223> OTHER INFORMATION: VH17 coding sequence
<220> FEATURE:
<221> NAME/KEY: CDS
<222> LOCATION: (1)..(366)

<400> SEQUENCE: 336 cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac gaa tgg agc tgg atc cgc cag ctc cca ggg aag ggc ctg gag     144
Asp Tyr Glu Trp Ser Trp Ile Arg Gln Leu Pro Gly Lys Gly Leu Glu
        35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
                85                  90                  95 tgt gcg aga gat cga ggg ggt gac tac tac tat ggt atg gac gtc tgg     336
Cys Ala Arg Asp Arg Gly Gly Asp Tyr Tyr Tyr Gly Met Asp Val Trp
            100                 105                 110 ggc caa ggg acc acg gtc acc gtc tcc tca                             366
Gly Gln Gly Thr Thr Val Thr Val Ser Ser
        115                 120

<210> SEQ ID NO 337
<211> LENGTH: 122
```

```
-continued

<212> TYPE: PRT
<213> ORGANISM: ARTIFICIAL SEQUENCE
<220> FEATURE:
<223> OTHER INFORMATION: Synthetic Construct

<400> SEQUENCE: 337

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Glu Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
            85                  90                  95

Cys Ala Arg Asp Arg Gly Gly Asp Tyr Tyr Tyr Gly Met Asp Val Trp
        100                 105                 110

Gly Gln Gly Thr Thr Val Thr Val Ser Ser
        115                 120

<210> SEQ ID NO 338
<211> LENGTH: 366
<212> TYPE: DNA
<213> ORGANISM: ARTIFICIAL SEQUENCE
<220> FEATURE:
<223> OTHER INFORMATION: VH18 coding sequence
<220> FEATURE:
<221> NAME/KEY: CDS
<222> LOCATION: (1)..(366)

<400> SEQUENCE: 338 cag gtg cag ctg cag gag tcg ggc cca gga ctg gtg aag cct tca cag     48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt     96
Thr Leu Ser Leu Thr Cys Thr Val Ser Gly Gly Ser Ile Ser Ser Gly
            20                  25                  30 gat tac tac tgg agc tgg atc cgc cag ctc cca ggg aag ggc ctg gag    144
Asp Tyr Tyr Trp Ser Trp Ile Arg Gln Leu Pro Gly Lys Gly Leu Glu
        35                  40                  45 tgg att ggg cac atc cat aac agt ggg acc acc tac tac aat ccg tcc    192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc    240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac    288
Ser Leu Arg Leu Ser Ser Val Thr Ala Ala Asp Thr Ala Val Tyr Tyr
            85                  90                  95 tgt gcg aga gat cga ggg ggt gac tac tac tat ggt atg gac gtc tgg    336
Cys Ala Arg Asp Arg Gly Gly Asp Tyr Tyr Tyr Gly Met Asp Val Trp
        100                 105                 110 ggc caa ggg acc acg gtc acc gtc tcc tca                             366
Gly Gln Gly Thr Thr Val Thr Val Ser Ser
        115                 120

<210> SEQ ID NO 339
<211> LENGTH: 122
<212> TYPE: PRT
```

<213> ORGANISM: ARTIFICIAL SEQUENCE
<220> FEATURE:
<223> OTHER INFORMATION: Synthetic Construct

<400> SEQUENCE: 339

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
            85                  90                  95

Cys Ala Arg Asp Arg Gly Gly Asp Tyr Tyr Tyr Gly Met Asp Val Trp
        100                 105                 110

Gly Gln Gly Thr Thr Val Thr Val Ser Ser
        115                 120
```

<210> SEQ ID NO 340
<211> LENGTH: 366
<212> TYPE: DNA
<213> ORGANISM: ARTIFICIAL SEQUENCE
<220> FEATURE:
<223> OTHER INFORMATION: VH19 coding sequence
<220> FEATURE:
<221> NAME/KEY: CDS
<222> LOCATION: (1)..(366)

<400> SEQUENCE: 340

```
cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac aga tgg agc tgg atc cgc cag ctc cca ggg aag ggc ctg gag     144
Asp Tyr Arg Trp Ser Trp Ile Arg Gln Leu Pro Gly Lys Gly Leu Glu
        35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
            85                  90                  95 tgt gcg aga gat cga ggg ggt gac tac tac tat ggt atg gac gtc tgg     336
Cys Ala Arg Asp Arg Gly Gly Asp Tyr Tyr Tyr Gly Met Asp Val Trp
        100                 105                 110 ggc caa ggg acc acg gtc acc gtc tcc tca                             366
Gly Gln Gly Thr Thr Val Thr Val Ser Ser
        115                 120
```

<210> SEQ ID NO 341
<211> LENGTH: 122
<212> TYPE: PRT
<213> ORGANISM: ARTIFICIAL SEQUENCE

<220> FEATURE:
<223> OTHER INFORMATION: Synthetic Construct

<400> SEQUENCE: 341

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Arg Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
            85                  90                  95

Cys Ala Arg Asp Arg Gly Gly Asp Tyr Tyr Tyr Gly Met Asp Val Trp
        100                 105                 110

Gly Gln Gly Thr Thr Val Thr Val Ser Ser
    115                 120
```

<210> SEQ ID NO 342
<211> LENGTH: 366
<212> TYPE: DNA
<213> ORGANISM: ARTIFICIAL SEQUENCE
<220> FEATURE:
<223> OTHER INFORMATION: VH20 coding sequence
<220> FEATURE:
<221> NAME/KEY: CDS
<222> LOCATION: (1)..(366)

<400> SEQUENCE: 342

```
cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac ttc gct agc tgg atc cgc cag ctc cca ggg aag ggc ctg gag     144
Asp Tyr Phe Ala Ser Trp Ile Arg Gln Leu Pro Gly Lys Gly Leu Glu
        35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
            85                  90                  95 tgt gcg aga gat cga ggg ggt gac tac tac tat ggt atg gac gtc tgg     336
Cys Ala Arg Asp Arg Gly Gly Asp Tyr Tyr Tyr Gly Met Asp Val Trp
        100                 105                 110 ggc caa ggg acc acg gtc acc gtc tcc tca                             366
Gly Gln Gly Thr Thr Val Thr Val Ser Ser
    115                 120
```

<210> SEQ ID NO 343
<211> LENGTH: 122
<212> TYPE: PRT
<213> ORGANISM: ARTIFICIAL SEQUENCE
<220> FEATURE:

<223> OTHER INFORMATION: Synthetic Construct

<400> SEQUENCE: 343

| Gln | Val | Gln | Leu | Gln | Glu | Ser | Gly | Pro | Gly | Leu | Val | Lys | Pro | Ser | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Thr Leu Ser Leu Thr Cys Thr Val Ser Gly Gly Ser Ile Ser Ser Gly
            20                  25                  30

Asp Tyr Phe Ala Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Tyr Gly Met Asp Val Trp
                100                 105                 110

Gly Gln Gly Thr Thr Val Thr Val Ser Ser
            115                 120

<210> SEQ ID NO 344
<211> LENGTH: 366
<212> TYPE: DNA
<213> ORGANISM: ARTIFICIAL SEQUENCE
<220> FEATURE:
<223> OTHER INFORMATION: VH21 coding sequence
<220> FEATURE:
<221> NAME/KEY: CDS
<222> LOCATION: (1)..(366)

<400> SEQUENCE: 344

```
cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac ttc tgg agc tgg atc cgc cag ctc cca ggg aag ggc ctg gag     144
Asp Tyr Phe Trp Ser Trp Ile Arg Gln Leu Pro Gly Lys Gly Leu Glu
        35                  40                  45 tgg att ggg cac atc cat aac agt ggg acc acc gct tac aat ccg tcc     192
Trp Ile Gly His Ile His Asn Ser Gly Thr Thr Ala Tyr Asn Pro Ser
    50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
                85                  90                  95 tgt gcg aga gat cga ggg ggt gac tac tac tat ggt atg gac gtc tgg     336
Cys Ala Arg Asp Arg Gly Gly Asp Tyr Tyr Tyr Gly Met Asp Val Trp
                100                 105                 110 ggc caa ggg acc acg gtc acc gtc tcc tca                             366
Gly Gln Gly Thr Thr Val Thr Val Ser Ser
            115                 120
```

<210> SEQ ID NO 345
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 345

| Gln | Val | Gln | Leu | Gln | Glu | Ser | Gly | Pro | Gly | Leu | Val | Lys | Pro | Ser | Gln |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Gly | Ser | Ile | Ser | Ser | Gly |
|---|---|---|---|---|---|---|---|---|---|---|---|---|---|---|---|
| | | | 20 | | | | | 25 | | | | | 30 | | |

| Asp | Tyr | Phe | Trp | Ser | Trp | Ile | Arg | Gln | Leu | Pro | Gly | Lys | Gly | Leu | Glu |
|---|---|---|---|---|---|---|---|---|---|---|---|---|---|---|---|
| | | | 35 | | | | | 40 | | | | | 45 | | |

| Trp | Ile | Gly | His | Ile | His | Asn | Ser | Gly | Thr | Thr | Tyr | Ala | Asn | Pro | Ser |
|---|---|---|---|---|---|---|---|---|---|---|---|---|---|---|---|
| | 50 | | | | | 55 | | | | | 60 | | | | |

| Leu | Lys | Ser | Arg | Val | Thr | Ile | Ser | Val | Asp | Thr | Ser | Lys | Lys | Gln | Phe |
|---|---|---|---|---|---|---|---|---|---|---|---|---|---|---|---|
| 65 | | | | | 70 | | | | | 75 | | | | | 80 |

| Ser | Leu | Arg | Leu | Ser | Ser | Val | Thr | Ala | Ala | Asp | Thr | Ala | Val | Tyr | Tyr |
|---|---|---|---|---|---|---|---|---|---|---|---|---|---|---|---|
| | | | | 85 | | | | | 90 | | | | | 95 | |

| Cys | Ala | Arg | Asp | Arg | Gly | Gly | Asp | Tyr | Tyr | Tyr | Gly | Met | Asp | Val | Trp |
|---|---|---|---|---|---|---|---|---|---|---|---|---|---|---|---|
| | | | 100 | | | | | 105 | | | | | 110 | | |

| Gly | Gln | Gly | Thr | Thr | Val | Thr | Val | Ser | Ser |
|---|---|---|---|---|---|---|---|---|---|
| | | | 115 | | | | 120 | | |

<210> SEQ ID NO 346
<211> LENGTH: 366
<212> TYPE: DNA
<213> ORGANISM: ARTIFICIAL SEQUENCE
<220> FEATURE:
<223> OTHER INFORMATION: VH22 coding sequence
<220> FEATURE:
<221> NAME/KEY: CDS
<222> LOCATION: (1)..(366)

<400> SEQUENCE: 346

| cag | gtg | cag | ctg | cag | gag | tcg | ggc | cca | gga | ctg | gtg | aag | cct | tca | cag | 48 |
|---|---|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Gln | |
| 1 | | | | 5 | | | | | 10 | | | | | 15 | | |

| acc | ctg | tcc | ctc | acc | tgc | act | gtc | tct | ggt | ggc | tcc | atc | agc | agt | ggt | 96 |
|---|---|---|---|---|---|---|---|---|---|---|---|---|---|---|---|---|
| Thr | Leu | Ser | Leu | Thr | Cys | Thr | Val | Ser | Gly | Gly | Ser | Ile | Ser | Ser | Gly | |
| | | | 20 | | | | | 25 | | | | | 30 | | | |

| gat | tac | ttc | tgg | agc | tgg | atc | cgc | cag | ctc | cca | ggg | aag | ggc | ctg | gag | 144 |
|---|---|---|---|---|---|---|---|---|---|---|---|---|---|---|---|---|
| Asp | Tyr | Phe | Trp | Ser | Trp | Ile | Arg | Gln | Leu | Pro | Gly | Lys | Gly | Leu | Glu | |
| | | | 35 | | | | | 40 | | | | | 45 | | | |

| tgg | att | ggg | cac | atc | cat | aac | agt | ggg | acc | acc | tac | gct | aat | ccg | tcc | 192 |
|---|---|---|---|---|---|---|---|---|---|---|---|---|---|---|---|---|
| Trp | Ile | Gly | His | Ile | His | Asn | Ser | Gly | Thr | Thr | Tyr | Ala | Asn | Pro | Ser | |
| | 50 | | | | | 55 | | | | | 60 | | | | | |

| ctc | aag | agt | cga | gtt | acc | ata | tca | gta | gac | acg | tct | aag | aag | cag | ttc | 240 |
|---|---|---|---|---|---|---|---|---|---|---|---|---|---|---|---|---|
| Leu | Lys | Ser | Arg | Val | Thr | Ile | Ser | Val | Asp | Thr | Ser | Lys | Lys | Gln | Phe | |
| 65 | | | | | 70 | | | | | 75 | | | | | 80 | |

| tcc | ctg | agg | ctg | agt | tct | gtg | act | gcc | gcg | gac | acg | gcc | gta | tat | tac | 288 |
|---|---|---|---|---|---|---|---|---|---|---|---|---|---|---|---|---|
| Ser | Leu | Arg | Leu | Ser | Ser | Val | Thr | Ala | Ala | Asp | Thr | Ala | Val | Tyr | Tyr | |
| | | | | 85 | | | | | 90 | | | | | 95 | | |

| tgt | gcg | aga | gat | cga | ggg | ggt | gac | tac | tac | tat | ggt | atg | gac | gtc | tgg | 336 |
|---|---|---|---|---|---|---|---|---|---|---|---|---|---|---|---|---|
| Cys | Ala | Arg | Asp | Arg | Gly | Gly | Asp | Tyr | Tyr | Tyr | Gly | Met | Asp | Val | Trp | |
| | | | 100 | | | | | 105 | | | | | 110 | | | |

| ggc | caa | ggg | acc | acg | gtc | acc | gtc | tcc | tca | 366 |
|---|---|---|---|---|---|---|---|---|---|---|
| Gly | Gln | Gly | Thr | Thr | Val | Thr | Val | Ser | Ser | |
| | | | 115 | | | | 120 | | | |

<210> SEQ ID NO 347
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 347

| Gln | Val | Gln | Leu | Gln | Glu | Ser | Gly | Pro | Gly | Leu | Val | Lys | Pro | Ser | Gln |
|---|---|---|---|---|---|---|---|---|---|---|---|---|---|---|---|
| 1 | | | | 5 | | | | | 10 | | | | | 15 | |

Thr Leu Ser Leu Thr Cys Thr Val Ser Gly Gly Ser Ile Ser Ser Gly
           20                    25               30

Asp Tyr Phe Trp Ser Trp Ile Arg Gln Leu Pro Gly Lys Gly Leu Glu
         35                    40                45

Trp Ile Gly His Ile His Asn Ser Gly Thr Thr Tyr Ala Asn Pro Ser
 50                     55                  60

Leu Lys Ser Arg Val Thr Ile Ser Val Asp Thr Ser Lys Lys Gln Phe
65                  70                  75               80

Ser Leu Arg Leu Ser Ser Val Thr Ala Ala Asp Thr Ala Val Tyr Tyr
         85                    90                95

Cys Ala Arg Asp Arg Gly Gly Asp Tyr Tyr Tyr Gly Met Asp Val Trp
        100                 105              110

Gly Gln Gly Thr Thr Val Thr Val Ser Ser
        115                120

<210> SEQ ID NO 348
<211> LENGTH: 366
<212> TYPE: DNA
<213> ORGANISM: ARTIFICIAL SEQUENCE
<220> FEATURE:
<223> OTHER INFORMATION: VH23 coding sequence
<220> FEATURE:
<221> NAME/KEY: CDS
<222> LOCATION: (1)..(366)

<400> SEQUENCE: 348

```
cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac ttc tgg agc tgg atc cgc cag ctc cca ggg aag ggc ctg gag     144
Asp Tyr Phe Trp Ser Trp Ile Arg Gln Leu Pro Gly Lys Gly Leu Glu
        35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
                85                  90                  95 tgt gcg aga gat cga ggg ggt gac tac gct tat ggt atg gac gtc tgg     336
Cys Ala Arg Asp Arg Gly Gly Asp Tyr Ala Tyr Gly Met Asp Val Trp
            100                 105                 110 ggc caa ggg acc acg gtc acc gtc tcc tca                             366
Gly Gln Gly Thr Thr Val Thr Val Ser Ser
        115                 120
```

<210> SEQ ID NO 349
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 349

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Ala Gly Met Asp Val Trp
            100                 105                 110

Gly Gln Gly Thr Thr Val Thr Val Ser Ser
        115                 120
```

<210> SEQ ID NO 350
<211> LENGTH: 366
<212> TYPE: DNA
<213> ORGANISM: ARTIFICIAL SEQUENCE
<220> FEATURE:
<223> OTHER INFORMATION: VH24 coding sequence
<220> FEATURE:
<221> NAME/KEY: CDS
<222> LOCATION: (1)..(366)

<400> SEQUENCE: 350

```
cag gtg cag ctg cag gag tcg ggc cca gga ctg gtg aag cct tca cag        48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt        96
Thr Leu Ser Leu Thr Cys Thr Val Ser Gly Gly Ser Ile Ser Ser Gly
            20                  25                  30 gat tac ttc tgg agc tgg atc cgc cag ctc cca ggg aag ggc ctg gag       144
Asp Tyr Phe Trp Ser Trp Ile Arg Gln Leu Pro Gly Lys Gly Leu Glu
        35                  40                  45 tgg att ggg cac atc cat aac agt ggg acc acc tac tac aat ccg tcc       192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc       240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac       288
Ser Leu Arg Leu Ser Ser Val Thr Ala Ala Asp Thr Ala Val Tyr Tyr
                85                  90                  95 tgt gcg aga gat cga ggg ggt gac tac tac gct ggt atg gac gtc tgg       336
Cys Ala Arg Asp Arg Gly Gly Asp Tyr Tyr Ala Gly Met Asp Val Trp
            100                 105                 110 ggc caa ggg acc acg gtc acc gtc tcc tca                                366
Gly Gln Gly Thr Thr Val Thr Val Ser Ser
        115                 120
```

<210> SEQ ID NO 351
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 351

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
            35                  40                  45

Trp Ile Gly His Ile His Asn Ser Gly Thr Thr Tyr Tyr Asn Pro Ser
50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
            85                  90                  95

Cys Ala Arg Asp Arg Gly Gly Asp Tyr Tyr Ala Gly Met Asp Val Trp
            100                 105                 110

Gly Gln Gly Thr Thr Val Thr Val Ser Ser
            115                 120
```

<210> SEQ ID NO 352
<211> LENGTH: 366
<212> TYPE: DNA
<213> ORGANISM: ARTIFICIAL SEQUENCE
<220> FEATURE:
<223> OTHER INFORMATION: VH25 coding sequence
<220> FEATURE:
<221> NAME/KEY: CDS
<222> LOCATION: (1)..(366)

<400> SEQUENCE: 352

```
cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac ttc tgg agc tgg atc cgc cag ctc cca ggg aag ggc ctg gag     144
Asp Tyr Phe Trp Ser Trp Ile Arg Gln Leu Pro Gly Lys Gly Leu Glu
            35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
            85                  90                  95 tgt gcg aga gat cga ggg ggt gac tac gaa tat ggt atg gac gtc tgg     336
Cys Ala Arg Asp Arg Gly Gly Asp Tyr Glu Tyr Gly Met Asp Val Trp
            100                 105                 110 ggc caa ggg acc acg gtc acc gtc tcc tca                             366
Gly Gln Gly Thr Thr Val Thr Val Ser Ser
            115                 120
```

<210> SEQ ID NO 353
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 353

Gln Val Gln Leu Gln Glu Ser Gly Pro Gly Leu Val Lys Pro Ser Gln

```
                    1               5                   10                  15
            Thr Leu Ser Leu Thr Cys Thr Val Ser Gly Gly Ser Ile Ser Ser Gly
                            20                  25                  30

Asp Tyr Phe Trp Ser Trp Ile Arg Gln Leu Pro Gly Lys Gly Leu Glu
                        35                  40                  45

Trp Ile Gly His Ile His Asn Ser Gly Thr Thr Tyr Tyr Asn Pro Ser
                    50                  55                  60

Leu Lys Ser Arg Val Thr Ile Ser Val Asp Thr Ser Lys Lys Gln Phe
             65                  70                  75                  80

Ser Leu Arg Leu Ser Ser Val Thr Ala Ala Asp Thr Ala Val Tyr Tyr
                            85                  90                  95

Cys Ala Arg Asp Arg Gly Gly Asp Tyr Glu Tyr Gly Met Asp Val Trp
                            100                 105                 110

Gly Gln Gly Thr Thr Val Thr Val Ser Ser
                            115                 120

<210> SEQ ID NO 354
<211> LENGTH: 366
<212> TYPE: DNA
<213> ORGANISM: ARTIFICIAL SEQUENCE
<220> FEATURE:
<223> OTHER INFORMATION: VH26 coding sequence
<220> FEATURE:
<221> NAME/KEY: CDS
<222> LOCATION: (1)..(366)

<400> SEQUENCE: 354 cag gtg cag ctg cag gag tcg ggc cca gga ctg gtg aag cct tca cag         48
Gln Val Gln Leu Gln Glu Ser Gly Pro Gly Leu Val Lys Pro Ser Gln
 1               5                   10                  15 acc ctg tcc ctc acc tgc act gtc tct ggt ggc tcc atc agc agt ggt         96
Thr Leu Ser Leu Thr Cys Thr Val Ser Gly Gly Ser Ile Ser Ser Gly
                 20                  25                  30 gat tac ttc tgg agc tgg atc cgc cag ctc cca ggg aag ggc ctg gag        144
Asp Tyr Phe Trp Ser Trp Ile Arg Gln Leu Pro Gly Lys Gly Leu Glu
             35                  40                  45 tgg att ggg cac atc cat aac agt ggg acc acc tac tac aat ccg tcc        192
Trp Ile Gly His Ile His Asn Ser Gly Thr Thr Tyr Tyr Asn Pro Ser
         50                  55                  60 ctc aag agt cga gtt acc ata tca gta gac acg tct aag aag cag ttc        240
Leu Lys Ser Arg Val Thr Ile Ser Val Asp Thr Ser Lys Lys Gln Phe
 65                  70                  75                  80 tcc ctg agg ctg agt tct gtg act gcc gcg gac acg gcc gta tat tac        288
Ser Leu Arg Leu Ser Ser Val Thr Ala Ala Asp Thr Ala Val Tyr Tyr
                 85                  90                  95 tgt gcg aga gat cga ggg ggt gac tac aga tat ggt atg gac gtc tgg        336
Cys Ala Arg Asp Arg Gly Gly Asp Tyr Arg Tyr Gly Met Asp Val Trp
            100                 105                 110 ggc caa ggg acc acg gtc acc gtc tcc tca                                366
Gly Gln Gly Thr Thr Val Thr Val Ser Ser
            115                 120

<210> SEQ ID NO 355
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 355

Gln Val Gln Leu Gln Glu Ser Gly Pro Gly Leu Val Lys Pro Ser Gln
 1               5                   10                  15
```

```
Thr Leu Ser Leu Thr Cys Thr Val Ser Gly Gly Ser Ile Ser Ser Gly
        20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
            85                  90                  95

Cys Ala Arg Asp Arg Gly Gly Asp Tyr Arg Tyr Gly Met Asp Val Trp
            100                 105                 110

Gly Gln Gly Thr Thr Val Thr Val Ser Ser
        115                 120
```

<210> SEQ ID NO 356
<211> LENGTH: 366
<212> TYPE: DNA
<213> ORGANISM: ARTIFICIAL SEQUENCE
<220> FEATURE:
<223> OTHER INFORMATION: VH27 coding sequence
<220> FEATURE:
<221> NAME/KEY: CDS
<222> LOCATION: (1)..(366)

<400> SEQUENCE: 356

```
cag gtg cag ctg cag gag tcg ggc cca gga ctg gtg aag cct tca cag    48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt    96
Thr Leu Ser Leu Thr Cys Thr Val Ser Gly Gly Ser Ile Ser Ser Gly
            20                  25                  30 gat tac gct tgg agc tgg atc cgc cag ctc cca ggg aag ggc ctg gag   144
Asp Tyr Ala Trp Ser Trp Ile Arg Gln Leu Pro Gly Lys Gly Leu Glu
        35                  40                  45 tgg att ggg cac atc cat aac agt ggg acc acc tac tac aat ccg tcc   192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc   240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac   288
Ser Leu Arg Leu Ser Ser Val Thr Ala Ala Asp Thr Ala Val Tyr Tyr
            85                  90                  95 tgt gcg aga gat cga ggg ggt gac tac gct tat ggt atg gac gtc tgg   336
Cys Ala Arg Asp Arg Gly Gly Asp Tyr Ala Tyr Gly Met Asp Val Trp
            100                 105                 110 ggc caa ggg acc acg gtc acc gtc tcc tca                           366
Gly Gln Gly Thr Thr Val Thr Val Ser Ser
        115                 120
```

<210> SEQ ID NO 357
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 357

```
Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Gly Ser Ile Ser Ser Gly
            20                  25                  30

Asp Tyr Ala Trp Ser Trp Ile Arg Gln Leu Pro Gly Lys Gly Leu Glu
            35                  40                  45

Trp Ile Gly His Ile His Asn Ser Gly Thr Thr Tyr Tyr Asn Pro Ser
 50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Ala Gly Met Asp Val Trp
            100                 105                 110

Gly Gln Gly Thr Thr Val Thr Val Ser Ser
            115                 120

<210> SEQ ID NO 358
<211> LENGTH: 366
<212> TYPE: DNA
<213> ORGANISM: ARTIFICIAL SEQUENCE
<220> FEATURE:
<223> OTHER INFORMATION: VH28 coding sequence
<220> FEATURE:
<221> NAME/KEY: CDS
<222> LOCATION: (1)..(366)

<400> SEQUENCE: 358 cag gtg cag ctg cag gag tcg ggc cca gga ctg gtg aag cct tca cag      48
Gln Val Gln Leu Gln Glu Ser Gly Pro Gly Leu Val Lys Pro Ser Gln
 1               5                  10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac gct tgg agc tgg atc cgc cag ctc cca ggg aag ggc ctg gag     144
Asp Tyr Ala Trp Ser Trp Ile Arg Gln Leu Pro Gly Lys Gly Leu Glu
            35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
 50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
                85                  90                  95 tgt gcg aga gat cga ggg ggt gac tac tac gct ggt atg gac gtc tgg     336
Cys Ala Arg Asp Arg Gly Gly Asp Tyr Tyr Ala Gly Met Asp Val Trp
            100                 105                 110 ggc caa ggg acc acg gtc acc gtc tcc tca                             366
Gly Gln Gly Thr Thr Val Thr Val Ser Ser
            115                 120

<210> SEQ ID NO 359
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 359

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
```

-continued

```
                    20                  25                  30
Asp Tyr Ala Trp Ser Trp Ile Arg Gln Leu Pro Gly Lys Gly Leu Glu
            35                  40                  45

Trp Ile Gly His Ile His Asn Ser Gly Thr Thr Tyr Tyr Asn Pro Ser
 50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Ala Gly Met Asp Val Trp
            100                 105                 110

Gly Gln Gly Thr Thr Val Thr Val Ser Ser
        115                 120

<210> SEQ ID NO 360
<211> LENGTH: 366
<212> TYPE: DNA
<213> ORGANISM: ARTIFICIAL SEQUENCE
<220> FEATURE:
<223> OTHER INFORMATION: VH29 coding sequence
<220> FEATURE:
<221> NAME/KEY: CDS
<222> LOCATION: (1)..(366)

<400> SEQUENCE: 360 cag gtg cag ctg cag gag tcg ggc cca gga ctg gtg aag cct tca cag     48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt     96
Thr Leu Ser Leu Thr Cys Thr Val Ser Gly Gly Ser Ile Ser Ser Gly
            20                  25                  30 gat tac ttc tgg agc tgg atc cgc cag ctc cca ggg aag ggc ctg gag    144
Asp Tyr Phe Trp Ser Trp Ile Arg Gln Leu Pro Gly Lys Gly Leu Glu
            35                  40                  45 tgg att ggg cac atc cat aac agt ggg acc acc tac tac aat ccg tcc    192
Trp Ile Gly His Ile His Asn Ser Gly Thr Thr Tyr Tyr Asn Pro Ser
 50                  55                  60 ctc aag agt cga gtt acc ata tca gta gac acg tct aag aag cag ttc    240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac    288
Ser Leu Arg Leu Ser Ser Val Thr Ala Ala Asp Thr Ala Val Tyr Tyr
                85                  90                  95 tgt gcg aga gat cga ggg ggt gac tac tac gaa ggt atg gac gtc tgg    336
Cys Ala Arg Asp Arg Gly Gly Asp Tyr Tyr Glu Gly Met Asp Val Trp
            100                 105                 110 ggc caa ggg acc acg gtc acc gtc tcc tca                            366
Gly Gln Gly Thr Thr Val Thr Val Ser Ser
        115                 120

<210> SEQ ID NO 361
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 361

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30
```

```
Asp Tyr Phe Trp Ser Trp Ile Arg Gln Leu Pro Gly Lys Gly Leu Glu
            35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Glu Gly Met Asp Val Trp
                100                 105                 110

Gly Gln Gly Thr Thr Val Thr Val Ser Ser
            115                 120
```

<210> SEQ ID NO 362
<211> LENGTH: 366
<212> TYPE: DNA
<213> ORGANISM: ARTIFICIAL SEQUENCE
<220> FEATURE:
<223> OTHER INFORMATION: VH30 coding sequence
<220> FEATURE:
<221> NAME/KEY: CDS
<222> LOCATION: (1)..(366)

<400> SEQUENCE: 362

```
cag gtg cag ctg cag gag tcg ggc cca gga ctg gtg aag cct tca cag       48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt       96
Thr Leu Ser Leu Thr Cys Thr Val Ser Gly Gly Ser Ile Ser Ser Gly
                20                  25                  30 gat tac ttc tgg agc tgg atc cgc cag ctc cca ggg aag ggc ctg gag      144
Asp Tyr Phe Trp Ser Trp Ile Arg Gln Leu Pro Gly Lys Gly Leu Glu
            35                  40                  45 tgg att ggg cac atc cat aac agt ggg acc acc tac tac aat ccg tcc      192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc      240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac      288
Ser Leu Arg Leu Ser Ser Val Thr Ala Ala Asp Thr Ala Val Tyr Tyr
                85                  90                  95 tgt gcg aga gat cga ggg ggt gac tac tac aga ggt atg gac gtc tgg      336
Cys Ala Arg Asp Arg Gly Gly Asp Tyr Tyr Arg Gly Met Asp Val Trp
                100                 105                 110 ggc caa ggg acc acg gtc acc gtc tcc tca                              366
Gly Gln Gly Thr Thr Val Thr Val Ser Ser
            115                 120
```

<210> SEQ ID NO 363
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 363

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30
```

```
Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
 50                  55                  60

Leu Lys Ser Arg Val Thr Ile Ser Val Asp Thr Ser Lys Lys Gln Phe
 65                  70                  75                  80

Ser Leu Arg Leu Ser Ser Val Thr Ala Ala Asp Thr Ala Val Tyr Tyr
                 85                  90                  95

Cys Ala Arg Asp Arg Gly Gly Asp Tyr Tyr Arg Gly Met Asp Val Trp
                100                 105                 110

Gly Gln Gly Thr Thr Val Thr Val Ser Ser
            115                 120

<210> SEQ ID NO 364
<211> LENGTH: 366
<212> TYPE: DNA
<213> ORGANISM: ARTIFICIAL SEQUENCE
<220> FEATURE:
<223> OTHER INFORMATION: VH31 coding sequence
<220> FEATURE:
<221> NAME/KEY: CDS
<222> LOCATION: (1)..(366)

<400> SEQUENCE: 364 cag gtg cag ctg cag gag tcg ggc cca gga ctg gtg aag cct tca cag    48
Gln Val Gln Leu Gln Glu Ser Gly Pro Gly Leu Val Lys Pro Ser Gln
 1               5                  10                  15 acc ctg tcc ctc acc tgc act gtc tct ggt ggc tcc atc agc agt ggt    96
Thr Leu Ser Leu Thr Cys Thr Val Ser Gly Gly Ser Ile Ser Ser Gly
             20                  25                  30 gat tac gct tgg agc tgg atc cgc cag ctc cca ggg aag ggc ctg gag   144
Asp Tyr Ala Trp Ser Trp Ile Arg Gln Leu Pro Gly Lys Gly Leu Glu
         35                  40                  45 tgg att ggg cac atc cat aac agt ggg acc acc tac tac aat ccg tcc   192
Trp Ile Gly His Ile His Asn Ser Gly Thr Thr Tyr Tyr Asn Pro Ser
 50                  55                  60 ctc aag agt cga gtt acc ata tca gta gac acg tct aag aag cag ttc   240
Leu Lys Ser Arg Val Thr Ile Ser Val Asp Thr Ser Lys Lys Gln Phe
 65                  70                  75                  80 tcc ctg agg ctg agt tct gtg act gcc gcg gac acg gcc gta tat tac   288
Ser Leu Arg Leu Ser Ser Val Thr Ala Ala Asp Thr Ala Val Tyr Tyr
                 85                  90                  95 tgt gcg aga gat cga ggg ggt gac tac gct gct ggt atg gac gtc tgg   336
Cys Ala Arg Asp Arg Gly Gly Asp Tyr Ala Ala Gly Met Asp Val Trp
                100                 105                 110 ggc caa ggg acc acg gtc acc gtc tcc tca                           366
Gly Gln Gly Thr Thr Val Thr Val Ser Ser
            115                 120

<210> SEQ ID NO 365
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 365

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Asp Tyr Ala Trp Ser Trp Ile Arg Gln Leu Pro Gly Lys Gly Leu Glu
```

-continued

```
                35                  40                  45
Trp Ile Gly His Ile His Asn Ser Gly Thr Thr Tyr Tyr Asn Pro Ser
 50                  55                  60

Leu Lys Ser Arg Val Thr Ile Ser Val Asp Thr Ser Lys Lys Gln Phe
 65                  70                  75                  80

Ser Leu Arg Leu Ser Ser Val Thr Ala Ala Asp Thr Ala Val Tyr Tyr
                 85                  90                  95

Cys Ala Arg Asp Arg Gly Gly Asp Tyr Ala Ala Gly Met Asp Val Trp
            100                 105                 110

Gly Gln Gly Thr Thr Val Thr Val Ser Ser
        115                 120

<210> SEQ ID NO 366
<211> LENGTH: 366
<212> TYPE: DNA
<213> ORGANISM: ARTIFICIAL SEQUENCE
<220> FEATURE:
<223> OTHER INFORMATION: VH32 coding sequence
<220> FEATURE:
<221> NAME/KEY: CDS
<222> LOCATION: (1)..(366)

<400> SEQUENCE: 366 cag gtg cag ctg cag gag tcg ggc cca gga ctg gtg aag cct tca cag      48
Gln Val Gln Leu Gln Glu Ser Gly Pro Gly Leu Val Lys Pro Ser Gln
 1               5                  10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
             20                  25                  30 gat tac ttc tgg agc tgg atc cgc cag ctc cca ggg aag ggc ctg gag     144
Asp Tyr Phe Trp Ser Trp Ile Arg Gln Leu Pro Gly Lys Gly Leu Glu
         35                  40                  45 tgg att ggg cac atc cat aac agt ggg acc acc tac tac aat ccg tcc     192
Trp Ile Gly His Ile His Asn Ser Gly Thr Thr Tyr Tyr Asn Pro Ser
 50                  55                  60 ctc aag agt cga gtt acc ata tca gta gac acg tct aag aag cag ttc     240
Leu Lys Ser Arg Val Thr Ile Ser Val Asp Thr Ser Lys Lys Gln Phe
 65                  70                  75                  80 tcc ctg agg ctg agt tct gtg act gcc gcg gac acg gcc gta tat tac     288
Ser Leu Arg Leu Ser Ser Val Thr Ala Ala Asp Thr Ala Val Tyr Tyr
                 85                  90                  95 tgt gcg aga gat cga ggg ggt gct gct tac tat ggt atg gac gtc tgg     336
Cys Ala Arg Asp Arg Gly Gly Ala Ala Tyr Tyr Gly Met Asp Val Trp
            100                 105                 110 ggc caa ggg acc acg gtc acc gtc tcc tca                             366
Gly Gln Gly Thr Thr Val Thr Val Ser Ser
        115                 120

<210> SEQ ID NO 367
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 367

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Asp Tyr Phe Trp Ser Trp Ile Arg Gln Leu Pro Gly Lys Gly Leu Glu
         35                  40                  45
```

```
Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Ala Ala Tyr Tyr Gly Met Asp Val Trp
            100                 105                 110

Gly Gln Gly Thr Thr Val Thr Val Ser Ser
        115                 120

<210> SEQ ID NO 368
<211> LENGTH: 366
<212> TYPE: DNA
<213> ORGANISM: ARTIFICIAL SEQUENCE
<220> FEATURE:
<223> OTHER INFORMATION: VH33 coding sequence
<220> FEATURE:
<221> NAME/KEY: CDS
<222> LOCATION: (1)..(366)

<400> SEQUENCE: 368 cag gtg cag ctg cag gag tcg ggc cca gga ctg gtg aag cct tca cag        48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt        96
Thr Leu Ser Leu Thr Cys Thr Val Ser Gly Gly Ser Ile Ser Ser Gly
            20                  25                  30 gat tac ttc tgg agc tgg atc cgc cag ctc cca ggg aag ggc ctg gag       144
Asp Tyr Phe Trp Ser Trp Ile Arg Gln Leu Pro Gly Lys Gly Leu Glu
        35                  40                  45 tgg att ggg cac atc cat aac agt ggg acc acc tac tac aat ccg tcc       192
Trp Ile Gly His Ile His Asn Ser Gly Thr Thr Tyr Tyr Asn Pro Ser
    50                  55                  60 ctc aag agt cga gtt acc ata tca gta gac acg tct aag aag cag ttc       240
Leu Lys Ser Arg Val Thr Ile Ser Val Asp Thr Ser Lys Lys Gln Phe
65                  70                  75                  80 tcc ctg agg ctg agt tct gtg act gcc gcg gac acg gcc gta tat tac       288
Ser Leu Arg Leu Ser Ser Val Thr Ala Ala Asp Thr Ala Val Tyr Tyr
                85                  90                  95 tgt gcg aga gat cga ggg ggt gac tac gct gct ggt atg gac gtc tgg       336
Cys Ala Arg Asp Arg Gly Gly Asp Tyr Ala Ala Gly Met Asp Val Trp
            100                 105                 110 ggc caa ggg acc acg gtc acc gtc tcc tca                               366
Gly Gln Gly Thr Thr Val Thr Val Ser Ser
        115                 120

<210> SEQ ID NO 369
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 369

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45
```

```
Trp Ile Gly His Ile His Asn Ser Gly Thr Thr Tyr Tyr Asn Pro Ser
     50                  55                  60

Leu Lys Ser Arg Val Thr Ile Ser Val Asp Thr Ser Lys Lys Gln Phe
 65                  70                  75                  80

Ser Leu Arg Leu Ser Ser Val Thr Ala Ala Asp Thr Ala Val Tyr Tyr
                 85                  90                  95

Cys Ala Arg Asp Arg Gly Gly Asp Tyr Ala Ala Gly Met Asp Val Trp
            100                 105                 110

Gly Gln Gly Thr Thr Val Thr Val Ser Ser
            115                 120
```

<210> SEQ ID NO 370
<211> LENGTH: 366
<212> TYPE: DNA
<213> ORGANISM: ARTIFICIAL SEQUENCE
<220> FEATURE:
<223> OTHER INFORMATION: VH34 coding sequence
<220> FEATURE:
<221> NAME/KEY: CDS
<222> LOCATION: (1)..(366)

<400> SEQUENCE: 370

```
cag gtg cag ctg cag gag tcg ggc cca gga ctg gtg aag cct tca cag        48
Gln Val Gln Leu Gln Glu Ser Gly Pro Gly Leu Val Lys Pro Ser Gln
 1               5                  10                  15 acc ctg tcc ctc acc tgc act gtc tct ggt ggc tcc atc agc agt ggt        96
Thr Leu Ser Leu Thr Cys Thr Val Ser Gly Gly Ser Ile Ser Ser Gly
             20                  25                  30 gat tac ttc tgg agc tgg atc cgc cag ctc cca ggg aag ggc ctg gag       144
Asp Tyr Phe Trp Ser Trp Ile Arg Gln Leu Pro Gly Lys Gly Leu Glu
         35                  40                  45 tgg att ggg cac atc cat aac agt ggg acc acc tac tac aat ccg tcc       192
Trp Ile Gly His Ile His Asn Ser Gly Thr Thr Tyr Tyr Asn Pro Ser
     50                  55                  60 ctc aag agt cga gtt acc ata tca gta gac acg tct aag aag cag ttc       240
Leu Lys Ser Arg Val Thr Ile Ser Val Asp Thr Ser Lys Lys Gln Phe
 65                  70                  75                  80 tcc ctg agg ctg agt tct gtg act gcc gcg gac acg gcc gta tat tac       288
Ser Leu Arg Leu Ser Ser Val Thr Ala Ala Asp Thr Ala Val Tyr Tyr
                 85                  90                  95 tgt gcg aga gat cga ggg ggt gac gct gct gct ggt atg gac gtc tgg       336
Cys Ala Arg Asp Arg Gly Gly Asp Ala Ala Ala Gly Met Asp Val Trp
            100                 105                 110 ggc caa ggg acc acg gtc acc gtc tcc tca                                366
Gly Gln Gly Thr Thr Val Thr Val Ser Ser
            115                 120
```

<210> SEQ ID NO 371
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 371

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Asp Tyr Phe Trp Ser Trp Ile Arg Gln Leu Pro Gly Lys Gly Leu Glu
         35                  40                  45

Trp Ile Gly His Ile His Asn Ser Gly Thr Thr Tyr Tyr Asn Pro Ser
```

```
                        50                  55                  60
Leu Lys Ser Arg Val Thr Ile Ser Val Asp Thr Ser Lys Lys Gln Phe
 65                  70                  75                  80

Ser Leu Arg Leu Ser Ser Val Thr Ala Ala Asp Thr Ala Val Tyr Tyr
                 85                  90                  95

Cys Ala Arg Asp Arg Gly Gly Asp Ala Ala Ala Gly Met Asp Val Trp
            100                 105                 110

Gly Gln Gly Thr Thr Val Thr Val Ser Ser
        115                 120

<210> SEQ ID NO 372
<211> LENGTH: 366
<212> TYPE: DNA
<213> ORGANISM: ARTIFICIAL SEQUENCE
<220> FEATURE:
<223> OTHER INFORMATION: VH35 coding sequence
<220> FEATURE:
<221> NAME/KEY: CDS
<222> LOCATION: (1)..(366)

<400> SEQUENCE: 372 cag gtg cag ctg cag gag tcg ggc cca gga ctg gtg aag cct tca cag       48
Gln Val Gln Leu Gln Glu Ser Gly Pro Gly Leu Val Lys Pro Ser Gln
 1               5                  10                  15 acc ctg tcc ctc acc tgc act gtc tct ggt ggc tcc atc agc agt ggt       96
Thr Leu Ser Leu Thr Cys Thr Val Ser Gly Gly Ser Ile Ser Ser Gly
             20                  25                  30 gat tac ttc tgg agc tgg atc cgc cag ctc cca ggg aag ggc ctg gag      144
Asp Tyr Phe Trp Ser Trp Ile Arg Gln Leu Pro Gly Lys Gly Leu Glu
         35                  40                  45 tgg att ggg tac atc tat tac agt ggg tcc acc tac tac aat ccg tcc      192
Trp Ile Gly Tyr Ile Tyr Tyr Ser Gly Ser Thr Tyr Tyr Asn Pro Ser
     50                  55                  60 ctc aag agt cga gtt acc ata tca gta gac acg tct aag aag cag ttc      240
Leu Lys Ser Arg Val Thr Ile Ser Val Asp Thr Ser Lys Lys Gln Phe
 65                  70                  75                  80 tcc ctg agg ctg agt tct gtg act gcc gcg gac acg gcc gta tat tac      288
Ser Leu Arg Leu Ser Ser Val Thr Ala Ala Asp Thr Ala Val Tyr Tyr
                 85                  90                  95 tgt gcg aga gat cga ggg ggt gac tac tac tat ggt atg gac gtc tgg      336
Cys Ala Arg Asp Arg Gly Gly Asp Tyr Tyr Tyr Gly Met Asp Val Trp
            100                 105                 110 ggc caa ggg acc acg gtc acc gtc tcc tca                              366
Gly Gln Gly Thr Thr Val Thr Val Ser Ser
        115                 120

<210> SEQ ID NO 373
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 373

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Asp Tyr Phe Trp Ser Trp Ile Arg Gln Leu Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60
```

```
Leu Lys Ser Arg Val Thr Ile Ser Val Asp Thr Ser Lys Lys Gln Phe
 65                  70                  75                  80

Ser Leu Arg Leu Ser Ser Val Thr Ala Ala Asp Thr Ala Val Tyr Tyr
                 85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser
        115                 120

<210> SEQ ID NO 374
<211> LENGTH: 366
<212> TYPE: DNA
<213> ORGANISM: ARTIFICIAL SEQUENCE
<220> FEATURE:
<223> OTHER INFORMATION: VH36 coding sequence
<220> FEATURE:
<221> NAME/KEY: CDS
<222> LOCATION: (1)..(366)

<400> SEQUENCE: 374 cag ctg cag gag tcg ggc cca gga ctg gtg aag cct tca cag acc ctg      48
Gln Leu Gln Glu Ser Gly Pro Gly Leu Val Lys Pro Ser Gln Thr Leu
 1               5                  10                  15 tcc ctc acc tgc act gtc tct ggt ggc tcc atc agc agt ggt gat tac      96
Ser Leu Thr Cys Thr Val Ser Gly Gly Ser Ile Ser Ser Gly Asp Tyr
             20                  25                  30 ttc tgg agc tgg atc cgc cag ctc cca ggg aag ggc ctg gag tgg att     144
Phe Trp Ser Trp Ile Arg Gln Leu Pro Gly Lys Gly Leu Glu Trp Ile
         35                  40                  45 ggg cac atc cat aac agt ggg acc acc tac tac aat ccg tcc ctc aag     192
Gly His Ile His Asn Ser Gly Thr Thr Tyr Tyr Asn Pro Ser Leu Lys
     50                  55                  60 agt cga gtt acc ata tca gta gac acg tct aag aag cag ttc tcc ctg     240
Ser Arg Val Thr Ile Ser Val Asp Thr Ser Lys Lys Gln Phe Ser Leu
 65                  70                  75                  80 agg ctg agt tct gtg act gcc gcg gac acg gcc gta tat tac tgt gcg     288
Arg Leu Ser Ser Val Thr Ala Ala Asp Thr Ala Val Tyr Tyr Cys Ala
                 85                  90                  95 aga gat tat ggg gac tac tat tac tac tat ggt atg gac gtc tgg         336
Arg Asp Tyr Gly Asp Tyr Tyr Tyr Tyr Tyr Gly Met Asp Val Trp
            100                 105                 110 ggc caa ggg acc acg gtc acc gtc tcc tca                             366
Gly Gln Gly Thr Thr Val Thr Val Ser Ser
        115                 120

<210> SEQ ID NO 375
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 375

Gln Leu Gln Glu Ser Gly Pro Gly Leu Val Lys Pro Ser Gln Thr Leu
 1               5                  10                  15

Ser Leu Thr Cys Thr Val Ser Gly Gly Ser Ile Ser Ser Gly Asp Tyr
             20                  25                  30

Phe Trp Ser Trp Ile Arg Gln Leu Pro Gly Lys Gly Leu Glu Trp Ile
         35                  40                  45

Gly His Ile His Asn Ser Gly Thr Thr Tyr Tyr Asn Pro Ser Leu Lys
     50                  55                  60
```

```
Ser Arg Val Thr Ile Ser Val Asp Thr Ser Lys Lys Gln Phe Ser Leu
 65                  70                  75                  80

Arg Leu Ser Ser Val Thr Ala Ala Asp Thr Ala Val Tyr Tyr Cys Ala
                 85                  90                  95

Arg Asp Tyr Gly Asp Tyr Tyr Tyr Tyr Tyr Gly Met Asp Val Trp
            100                 105                 110

Gly Gln Gly Thr Thr Val Thr Val Ser Ser
        115                 120

<210> SEQ ID NO 376
<211> LENGTH: 1458
<212> TYPE: DNA
<213> ORGANISM: ARTIFICIAL SEQUENCE
<220> FEATURE:
<223> OTHER INFORMATION: 16435 (3742) HC-ShK[1-35, Q16K] coding sequence
<220> FEATURE:
<221> NAME/KEY: CDS
<222> LOCATION: (1)..(1458)

<400> SEQUENCE: 376 cag gtt cag ctg gtg cag tct gga gct gag gtg aag aag cct ggg gcc      48
Gln Val Gln Leu Val Gln Ser Gly Ala Glu Val Lys Lys Pro Gly Ala
  1               5                  10                  15 tca gtg aag gtc tcc tgc aag gct tct ggt tac acc ttt acc aga tat      96
Ser Val Lys Val Ser Cys Lys Ala Ser Gly Tyr Thr Phe Thr Arg Tyr
             20                  25                  30 ggt atc agc tgg gtg cga cag gcc cct gga caa ggg ctt gag tgg atg     144
Gly Ile Ser Trp Val Arg Gln Ala Pro Gly Gln Gly Leu Glu Trp Met
         35                  40                  45 gga tgg atc agc act tac agt ggt aac aca aac tat gca cag aag ctc     192
Gly Trp Ile Ser Thr Tyr Ser Gly Asn Thr Asn Tyr Ala Gln Lys Leu
     50                  55                  60 cag ggc aga gtc acc atg acc aca gac aca tcc acg agc aca gcc tac     240
Gln Gly Arg Val Thr Met Thr Thr Asp Thr Ser Thr Ser Thr Ala Tyr
 65                  70                  75                  80 atg gag ctg agg agc ctg aga tct gac gac acg gcc gtg tat tac tgt     288
Met Glu Leu Arg Ser Leu Arg Ser Asp Asp Thr Ala Val Tyr Tyr Cys
                 85                  90                  95 gcg aga gct cag ctt tac ttt gac tac tgg ggc cag gga acc ctg gtc     336
Ala Arg Ala Gln Leu Tyr Phe Asp Tyr Trp Gly Gln Gly Thr Leu Val
            100                 105                 110 acc gtc tcc tca gct agc acc aag ggc cca tcg gtc ttc ccc ctg gcg     384
Thr Val Ser Ser Ala Ser Thr Lys Gly Pro Ser Val Phe Pro Leu Ala
        115                 120                 125 ccc tgc tcc agg agc acc tcc gag agc aca gcg gcc ctg ggc tgc ctg     432
Pro Cys Ser Arg Ser Thr Ser Glu Ser Thr Ala Ala Leu Gly Cys Leu
    130                 135                 140 gtc aag gac tac ttc ccc gaa ccg gtg acg gtg tcg tgg aac tca ggc     480
Val Lys Asp Tyr Phe Pro Glu Pro Val Thr Val Ser Trp Asn Ser Gly
145                 150                 155                 160 gct ctg acc agc ggc gtg cac acc ttc cca gct gtc cta cag tcc tca     528
Ala Leu Thr Ser Gly Val His Thr Phe Pro Ala Val Leu Gln Ser Ser
                165                 170                 175 gga ctc tac tcc ctc agc agc gtg gtg acc gtg ccc tcc agc aac ttc     576
Gly Leu Tyr Ser Leu Ser Ser Val Val Thr Val Pro Ser Ser Asn Phe
            180                 185                 190 ggc acc cag acc tac acc tgc aac gta gat cac aag ccc agc aac acc     624
Gly Thr Gln Thr Tyr Thr Cys Asn Val Asp His Lys Pro Ser Asn Thr
        195                 200                 205 aag gtg gac aag aca gtt gag cgc aaa tgt tgt gtc gag tgc cca ccg     672
Lys Val Asp Lys Thr Val Glu Arg Lys Cys Cys Val Glu Cys Pro Pro
    210                 215                 220
```

```
tgc cca gca cca cct gtg gca gga ccg tca gtc ttc ctc ttc ccc cca      720
Cys Pro Ala Pro Pro Val Ala Gly Pro Ser Val Phe Leu Phe Pro Pro
225                 230                 235                 240 aaa ccc aag gac acc ctc atg atc tcc cgg acc cct gag gtc acg tgc      768
Lys Pro Lys Asp Thr Leu Met Ile Ser Arg Thr Pro Glu Val Thr Cys
                245                 250                 255 gtg gtg gtg gac gtg agc cac gaa gac ccc gag gtc cag ttc aac tgg      816
Val Val Val Asp Val Ser His Glu Asp Pro Glu Val Gln Phe Asn Trp
            260                 265                 270 tac gtg gac ggc gtg gag gtg cat aat gcc aag aca aag cca cgg gag      864
Tyr Val Asp Gly Val Glu Val His Asn Ala Lys Thr Lys Pro Arg Glu
        275                 280                 285 gag cag ttc aac agc acg ttc cgt gtg gtc agc gtc ctc acc gtt gtg      912
Glu Gln Phe Asn Ser Thr Phe Arg Val Val Ser Val Leu Thr Val Val
    290                 295                 300 cac cag gac tgg ctg aac ggc aag gag tac aag tgc aag gtc tcc aac      960
His Gln Asp Trp Leu Asn Gly Lys Glu Tyr Lys Cys Lys Val Ser Asn
305                 310                 315                 320 aaa ggc ctc cca gcc ccc atc gag aaa acc atc tcc aaa acc aaa ggg     1008
Lys Gly Leu Pro Ala Pro Ile Glu Lys Thr Ile Ser Lys Thr Lys Gly
                325                 330                 335 cag ccc cga gaa cca cag gtg tac acc ctg ccc cca tcc cgg gag gag     1056
Gln Pro Arg Glu Pro Gln Val Tyr Thr Leu Pro Pro Ser Arg Glu Glu
            340                 345                 350 atg acc aag aac cag gtc agc ctg acc tgc ctg gtc aaa ggc ttc tac     1104
Met Thr Lys Asn Gln Val Ser Leu Thr Cys Leu Val Lys Gly Phe Tyr
        355                 360                 365 ccc agc gac atc gcc gtg gag tgg gag agc aat ggg cag ccg gag aac     1152
Pro Ser Asp Ile Ala Val Glu Trp Glu Ser Asn Gly Gln Pro Glu Asn
    370                 375                 380 aac tac aag acc aca cct ccc atg ctg gac tcc gac ggc tcc ttc ttc     1200
Asn Tyr Lys Thr Thr Pro Pro Met Leu Asp Ser Asp Gly Ser Phe Phe
385                 390                 395                 400 ctc tac agc aag ctc acc gtg gac aag agc agg tgg cag cag ggg aac     1248
Leu Tyr Ser Lys Leu Thr Val Asp Lys Ser Arg Trp Gln Gln Gly Asn
                405                 410                 415 gtc ttc tca tgc tcc gtg atg cat gag gct ctg cac aac cac tac acg     1296
Val Phe Ser Cys Ser Val Met His Glu Ala Leu His Asn His Tyr Thr
            420                 425                 430 cag aag agc ctc tcc ctg tct ccg ggt gga gga gga gga tcc gga gga     1344
Gln Lys Ser Leu Ser Leu Ser Pro Gly Gly Gly Gly Gly Ser Gly Gly
        435                 440                 445 gga gga agc cgc agc tgc atc gac acc atc ccc aag agc cgc tgc acc     1392
Gly Gly Ser Arg Ser Cys Ile Asp Thr Ile Pro Lys Ser Arg Cys Thr
    450                 455                 460 gcc ttc aag tgc aag cac agc atg aag tac cgc ctg agc ttc tgc cgc     1440
Ala Phe Lys Cys Lys His Ser Met Lys Tyr Arg Leu Ser Phe Cys Arg
465                 470                 475                 480 aag acc tgc ggc acc tgc                                             1458
Lys Thr Cys Gly Thr Cys
                485
```

<210> SEQ ID NO 377
<211> LENGTH: 486
<212> TYPE: PRT
<213> ORGANISM: ARTIFICIAL SEQUENCE
<220> FEATURE:
<223> OTHER INFORMATION: Synthetic Construct

<400> SEQUENCE: 377

Gln Val Gln Leu Val Gln Ser Gly Ala Glu Val Lys Lys Pro Gly Ala

-continued

```
1               5                   10                  15
Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
            35                  40                  45

Gly Trp Ile Ser Thr Tyr Ser Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Ala Gln Leu Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
            195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Phe Arg Val Val Ser Val Leu Thr Val Val
            290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
            325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
            420                 425                 430
```

-continued

Gln Lys Ser Leu Ser Leu Ser Pro Gly Gly Gly Gly Ser Gly Gly
        435                 440                 445

Gly Gly Ser Arg Ser Cys Ile Asp Thr Ile Pro Lys Ser Arg Cys Thr
    450                 455                 460

Ala Phe Lys Cys Lys His Ser Met Lys Tyr Arg Leu Ser Phe Cys Arg
465                 470                 475                 480

Lys Thr Cys Gly Thr Cys
            485

<210> SEQ ID NO 378
<211> LENGTH: 35
<212> TYPE: PRT
<213> ORGANISM: ARTIFICIAL SEQUENCE
<220> FEATURE:
<223> OTHER INFORMATION: ShK(1-35)

<400> SEQUENCE: 378

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 379
<211> LENGTH: 36
<212> TYPE: PRT
<213> ORGANISM: ARTIFICIAL SEQUENCE
<220> FEATURE:
<223> OTHER INFORMATION: [Lys16]ShK-Ala

<400> SEQUENCE: 379

Arg Ser Cys Ile Asp Thr Ile Pro Lys Ser Arg Cys Thr Ala Phe Lys
1               5                   10                  15

Cys Lys His Ser Met Lys Tyr Arg Leu Ser Phe Cys Arg Lys Thr Cys
            20                  25                  30

Gly Thr Cys Ala
        35

<210> SEQ ID NO 380
<211> LENGTH: 35
<212> TYPE: PRT
<213> ORGANISM: ARTIFICIAL SEQUENCE
<220> FEATURE:
<223> OTHER INFORMATION: 20kDa-PEG-ShK

<400> SEQUENCE: 380

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 381
<211> LENGTH: 35
<212> TYPE: PRT
<213> ORGANISM: ARTIFICIAL SEQUENCE
<220> FEATURE:
<223> OTHER INFORMATION: 20kDa-PEG-[Lys16]ShK

<400> SEQUENCE: 381

Arg Ser Cys Ile Asp Thr Ile Pro Lys Ser Arg Cys Thr Ala Phe Lys

```
                 1               5                  10                 15
Cys Lys His Ser Met Lys Tyr Arg Leu Ser Phe Cys Arg Lys Thr Cys
            20                  25                 30

Gly Thr Cys
        35

<210> SEQ ID NO 382
<211> LENGTH: 36
<212> TYPE: PRT
<213> ORGANISM: ARTIFICIAL SEQUENCE
<220> FEATURE:
<223> OTHER INFORMATION: 20kDa-PEG-[Lys16]ShK-Ala

<400> SEQUENCE: 382

Arg Ser Cys Ile Asp Thr Ile Pro Lys Ser Arg Cys Thr Ala Phe Lys
1               5                   10                  15

Cys Lys His Ser Met Lys Tyr Arg Leu Ser Phe Cys Arg Lys Thr Cys
            20                  25                  30

Gly Thr Cys Ala
        35

<210> SEQ ID NO 383
<211> LENGTH: 1911
<212> TYPE: DNA
<213> ORGANISM: ARTIFICIAL SEQUENCE
<220> FEATURE:
<223> OTHER INFORMATION: 16435 IgG2-HC (R118A)-huFGF21 (Ab 10162)
      coding sequence
<220> FEATURE:
<221> NAME/KEY: CDS
<222> LOCATION: (1)..(1911)

<400> SEQUENCE: 383
```

| | | | | | | | | | | | | | | | | |
|---|---|---|---|---|---|---|---|---|---|---|---|---|---|---|---|---|
| cag | gtt | cag | ctg | gtg | cag | tct | gga | gct | gag | gtg | aag | aag | cct | ggg | gcc | 48 |
| Gln | Val | Gln | Leu | Val | Gln | Ser | Gly | Ala | Glu | Val | Lys | Lys | Pro | Gly | Ala | |
| 1 | | | | 5 | | | | | 10 | | | | | 15 | | |
| tca | gtg | aag | gtc | tcc | tgc | aag | gct | tct | ggt | tac | acc | ttt | acc | aga | tat | 96 |
| Ser | Val | Lys | Val | Ser | Cys | Lys | Ala | Ser | Gly | Tyr | Thr | Phe | Thr | Arg | Tyr | |
| | | | 20 | | | | | 25 | | | | | 30 | | | |
| ggt | atc | agc | tgg | gtg | cga | cag | gcc | cct | gga | caa | ggg | ctt | gag | tgg | atg | 144 |
| Gly | Ile | Ser | Trp | Val | Arg | Gln | Ala | Pro | Gly | Gln | Gly | Leu | Glu | Trp | Met | |
| | | 35 | | | | | 40 | | | | | 45 | | | | |
| gga | tgg | atc | agc | act | tac | agt | ggt | aac | aca | aac | tat | gca | cag | aag | ctc | 192 |
| Gly | Trp | Ile | Ser | Thr | Tyr | Ser | Gly | Asn | Thr | Asn | Tyr | Ala | Gln | Lys | Leu | |
| | 50 | | | | | 55 | | | | | 60 | | | | | |
| cag | ggc | aga | gtc | acc | atg | acc | aca | gac | aca | tcc | acg | agc | aca | gcc | tac | 240 |
| Gln | Gly | Arg | Val | Thr | Met | Thr | Thr | Asp | Thr | Ser | Thr | Ser | Thr | Ala | Tyr | |
| 65 | | | | | 70 | | | | | 75 | | | | | 80 | |
| atg | gag | ctg | agg | agc | ctg | aga | tct | gac | gac | acg | gcc | gtg | tat | tac | tgt | 288 |
| Met | Glu | Leu | Arg | Ser | Leu | Arg | Ser | Asp | Asp | Thr | Ala | Val | Tyr | Tyr | Cys | |
| | | | | 85 | | | | | 90 | | | | | 95 | | |
| gcg | aga | gct | cag | ctt | tac | ttt | gac | tac | tgg | ggc | cag | gga | acc | ctg | gtc | 336 |
| Ala | Arg | Ala | Gln | Leu | Tyr | Phe | Asp | Tyr | Trp | Gly | Gln | Gly | Thr | Leu | Val | |
| | | | 100 | | | | | 105 | | | | | 110 | | | |
| acc | gtc | tcc | tca | gcc | tcc | acc | aag | ggc | cca | tcg | gtc | ttc | ccc | ctg | gcg | 384 |
| Thr | Val | Ser | Ser | Ala | Ser | Thr | Lys | Gly | Pro | Ser | Val | Phe | Pro | Leu | Ala | |
| | | 115 | | | | | 120 | | | | | 125 | | | | |
| ccc | tgc | tcc | agg | agc | acc | tcc | gag | agc | aca | gcg | gcc | ctg | ggc | tgc | ctg | 432 |
| Pro | Cys | Ser | Arg | Ser | Thr | Ser | Glu | Ser | Thr | Ala | Ala | Leu | Gly | Cys | Leu | |
| | 130 | | | | | 135 | | | | | 140 | | | | | |
| gtc | aag | gac | tac | ttc | ccc | gaa | ccg | gtg | acg | gtg | tcg | tgg | aac | tca | ggc | 480 |
| Val | Lys | Asp | Tyr | Phe | Pro | Glu | Pro | Val | Thr | Val | Ser | Trp | Asn | Ser | Gly | |
| 145 | | | | | 150 | | | | | 155 | | | | | 160 | |

| | |
|---|---|
| gct ctg acc agc ggc gtg cac acc ttc cca gct gtc cta cag tcc tca<br>Ala Leu Thr Ser Gly Val His Thr Phe Pro Ala Val Leu Gln Ser Ser<br>165                           170                     175 | 528 |
| gga ctc tac tcc ctc agc agc gtg gtg acc gtg ccc tcc agc aac ttc<br>Gly Leu Tyr Ser Leu Ser Ser Val Val Thr Val Pro Ser Ser Asn Phe<br>    180                       185                     190 | 576 |
| ggc acc cag acc tac acc tgc aac gta gat cac aag ccc agc aac acc<br>Gly Thr Gln Thr Tyr Thr Cys Asn Val Asp His Lys Pro Ser Asn Thr<br>195                           200                     205 | 624 |
| aag gtg gac aag aca gtt gag cgc aaa tgt tgt gtc gag tgc cca ccg<br>Lys Val Asp Lys Thr Val Glu Arg Lys Cys Cys Val Glu Cys Pro Pro<br>210                           215                     220 | 672 |
| tgc cca gca cca cct gtg gca gga ccg tca gtc ttc ctc ttc ccc cca<br>Cys Pro Ala Pro Pro Val Ala Gly Pro Ser Val Phe Leu Phe Pro Pro<br>225                   230                     235                     240 | 720 |
| aaa ccc aag gac acc ctc atg atc tcc cgg acc cct gag gtc acg tgc<br>Lys Pro Lys Asp Thr Leu Met Ile Ser Arg Thr Pro Glu Val Thr Cys<br>                   245                     250                     255 | 768 |
| gtg gtg gtg gac gtg agc cac gaa gac ccc gag gtc cag ttc aac tgg<br>Val Val Val Asp Val Ser His Glu Asp Pro Glu Val Gln Phe Asn Trp<br>    260                       265                     270 | 816 |
| tac gtg gac ggc gtg gag gtg cat aat gcc aag aca aag cca cgg gag<br>Tyr Val Asp Gly Val Glu Val His Asn Ala Lys Thr Lys Pro Arg Glu<br>275                           280                     285 | 864 |
| gag cag ttc aac agc acg ttc cgt gtg gtc agc gtc ctc acc gtt gtg<br>Glu Gln Phe Asn Ser Thr Phe Arg Val Val Ser Val Leu Thr Val Val<br>290                         295                     300 | 912 |
| cac cag gac tgg ctg aac ggc aag gag tac aag tgc aag gtc tcc aac<br>His Gln Asp Trp Leu Asn Gly Lys Glu Tyr Lys Cys Lys Val Ser Asn<br>305                   310                     315                     320 | 960 |
| aaa ggc ctc cca gcc ccc atc gag aaa acc atc tcc aaa acc aaa ggg<br>Lys Gly Leu Pro Ala Pro Ile Glu Lys Thr Ile Ser Lys Thr Lys Gly<br>                   325                     330                     335 | 1008 |
| cag ccc cga gaa cca cag gtg tac acc ctg ccc cca tcc cgg gag gag<br>Gln Pro Arg Glu Pro Gln Val Tyr Thr Leu Pro Pro Ser Arg Glu Glu<br>    340                       345                     350 | 1056 |
| atg acc aag aac cag gtc agc ctg acc tgc ctg gtc aaa ggc ttc tac<br>Met Thr Lys Asn Gln Val Ser Leu Thr Cys Leu Val Lys Gly Phe Tyr<br>355                           360                     365 | 1104 |
| ccc agc gac atc gcc gtg gag tgg gag agc aat ggg cag ccg gag aac<br>Pro Ser Asp Ile Ala Val Glu Trp Glu Ser Asn Gly Gln Pro Glu Asn<br>370                           375                     380 | 1152 |
| aac tac aag acc aca cct ccc atg ctg gac tcc gac ggc tcc ttc ttc<br>Asn Tyr Lys Thr Thr Pro Pro Met Leu Asp Ser Asp Gly Ser Phe Phe<br>385                   390                     395                     400 | 1200 |
| ctc tac agc aag ctc acc gtg gac aag agc agg tgg cag cag ggg aac<br>Leu Tyr Ser Lys Leu Thr Val Asp Lys Ser Arg Trp Gln Gln Gly Asn<br>                   405                     410                     415 | 1248 |
| gtc ttc tca tgc tcc gtg atg cat gag gct ctg cac aac cac tac acg<br>Val Phe Ser Cys Ser Val Met His Glu Ala Leu His Asn His Tyr Thr<br>                         420                     425                     430 | 1296 |
| cag aag agc ctc tcc ctg tct ccg ggt ggt gga ggt ggt ggt tct ggt<br>Gln Lys Ser Leu Ser Leu Ser Pro Gly Gly Gly Gly Gly Gly Ser Gly<br>435                           440                     445 | 1344 |
| ggt ggt agc gga ggc ggt tcc cac ccc atc cct gac tcc tct cca<br>Gly Gly Ser Gly Gly Gly Ser His Pro Ile Pro Asp Ser Ser Pro<br>450                           455                     460 | 1392 |
| ctc ctg caa ttc ggg ggc caa gtc cgg cag cgg tac ctc tac aca gat<br>Leu Leu Gln Phe Gly Gly Gln Val Arg Gln Arg Tyr Leu Tyr Thr Asp<br>465                           470                     475                     480 | 1440 |

```
gat gcc cag cag aca gaa gcc cac ctg gag atc agg gag gat ggg acg      1488
Asp Ala Gln Gln Thr Glu Ala His Leu Glu Ile Arg Glu Asp Gly Thr
            485                 490                 495 gtg ggg ggc gct gct gac cag agc ccc gaa agt ctc ctg cag ctg aaa      1536
Val Gly Gly Ala Ala Asp Gln Ser Pro Glu Ser Leu Leu Gln Leu Lys
        500                 505                 510 gcc ttg aag ccg gga gtt att caa atc ttg gga gtc aag aca tcc agg      1584
Ala Leu Lys Pro Gly Val Ile Gln Ile Leu Gly Val Lys Thr Ser Arg
    515                 520                 525 ttc ctg tgc cag cgg cca gat ggg gcc ctg tat gga tcg ctc cac ttt      1632
Phe Leu Cys Gln Arg Pro Asp Gly Ala Leu Tyr Gly Ser Leu His Phe
530                 535                 540 gac cct gag gcc tgc agc ttc cgg gag ctg ctt ctt gag gac gga tac      1680
Asp Pro Glu Ala Cys Ser Phe Arg Glu Leu Leu Leu Glu Asp Gly Tyr
545                 550                 555                 560 aat gtt tac cag tcc gaa gcc cac ggc ctc ccg ctg cac ctg cca ggg      1728
Asn Val Tyr Gln Ser Glu Ala His Gly Leu Pro Leu His Leu Pro Gly
                565                 570                 575 aac aag tcc cca cac cgg gac cct gca ccc cga gga cca gct cgc ttc      1776
Asn Lys Ser Pro His Arg Asp Pro Ala Pro Arg Gly Pro Ala Arg Phe
            580                 585                 590 ctg cca cta cca ggc ctg cca ccc gca ccc cgg gag cca ccc gga atc      1824
Leu Pro Leu Pro Gly Leu Pro Pro Ala Pro Pro Glu Pro Pro Gly Ile
        595                 600                 605 ctg gcc ccc cag ccc ccc gat gtg ggc tcc tcg gac cct ctg agc atg      1872
Leu Ala Pro Gln Pro Pro Asp Val Gly Ser Ser Asp Pro Leu Ser Met
    610                 615                 620 gtg gga cct tcc cag ggc cga agc ccc agc tac gct tcc                  1911
Val Gly Pro Ser Gln Gly Arg Ser Pro Ser Tyr Ala Ser
625                 630                 635

<210> SEQ ID NO 384
<211> LENGTH: 637
<212> TYPE: PRT
<213> ORGANISM: ARTIFICIAL SEQUENCE
<220> FEATURE:
<223> OTHER INFORMATION: Synthetic Construct

<400> SEQUENCE: 384

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Gln Leu Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Asn Phe
            180                 185                 190
Gly Thr Gln Thr Tyr Thr Cys Asn Val Asp His Lys Pro Ser Asn Thr
        195                 200                 205
Lys Val Asp Lys Thr Val Glu Arg Lys Cys Cys Val Glu Cys Pro Pro
    210                 215                 220
Cys Pro Ala Pro Pro Val Ala Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Gln Phe Asn Trp
            260                 265                 270
Tyr Val Asp Gly Val Glu Val His Asn Ala Lys Thr Lys Pro Arg Glu
        275                 280                 285
Glu Gln Phe Asn Ser Thr Phe Arg Val Val Ser Val Leu Thr Val Val
    290                 295                 300
His Gln Asp Trp Leu Asn Gly Lys Glu Tyr Lys Cys Lys Val Ser Asn
305                 310                 315                 320
Lys Gly Leu Pro Ala Pro Ile Glu Lys Thr Ile Ser Lys Thr Lys Gly
                325                 330                 335
Gln Pro Arg Glu Pro Gln Val Tyr Thr Leu Pro Pro Ser Arg Glu Glu
            340                 345                 350
Met Thr Lys Asn Gln Val Ser Leu Thr Cys Leu Val Lys Gly Phe Tyr
        355                 360                 365
Pro Ser Asp Ile Ala Val Glu Trp Glu Ser Asn Gly Gln Pro Glu Asn
    370                 375                 380
Asn Tyr Lys Thr Thr Pro Pro Met Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
            420                 425                 430
Gln Lys Ser Leu Ser Leu Ser Pro Gly Gly Gly Gly Gly Ser Gly
        435                 440                 445
Gly Gly Ser Gly Gly Gly Gly Ser His Pro Ile Pro Asp Ser Ser Pro
    450                 455                 460
Leu Leu Gln Phe Gly Gly Gln Val Arg Gln Arg Tyr Leu Tyr Thr Asp
465                 470                 475                 480
Asp Ala Gln Gln Thr Glu Ala His Leu Glu Ile Arg Glu Asp Gly Thr
                485                 490                 495
Val Gly Gly Ala Ala Asp Gln Ser Pro Glu Ser Leu Leu Gln Leu Lys
            500                 505                 510
Ala Leu Lys Pro Gly Val Ile Gln Ile Leu Gly Val Lys Thr Ser Arg
        515                 520                 525
Phe Leu Cys Gln Arg Pro Asp Gly Ala Leu Tyr Gly Ser Leu His Phe
    530                 535                 540
Asp Pro Glu Ala Cys Ser Phe Arg Glu Leu Leu Leu Glu Asp Gly Tyr
545                 550                 555                 560
Asn Val Tyr Gln Ser Glu Ala His Gly Leu Pro Leu His Leu Pro Gly
                565                 570                 575
Asn Lys Ser Pro His Arg Asp Pro Ala Pro Arg Gly Pro Ala Arg Phe
```

<210> SEQ ID NO 385
<211> LENGTH: 1929
<212> TYPE: DNA
<213> ORGANISM: ARTIFICIAL SEQUENCE
<220> FEATURE:
<223> OTHER INFORMATION: 4341 IgG2-HC-huFGF21 [1-181] (Ab 10163)
<220> FEATURE:
<221> NAME/KEY: CDS
<222> LOCATION: (1)..(1929)

<400> SEQUENCE: 385

```
cag gtg cag ctg cag gag tcg ggc cca gga ctg gtg aag cct tca cag    48
Gln Val Gln Leu Gln Glu Ser Gly Pro Gly Leu Val Lys Pro Ser Gln
 1               5                  10                  15 acc ctg tcc ctc acc tgc act gtc tct ggt ggc tcc atc agc agt ggt    96
Thr Leu Ser Leu Thr Cys Thr Val Ser Gly Gly Ser Ile Ser Ser Gly
             20                  25                  30 gat tac ttc tgg agc tgg atc cgc cag ctc cca ggg aag ggc ctg gag   144
Asp Tyr Phe Trp Ser Trp Ile Arg Gln Leu Pro Gly Lys Gly Leu Glu
         35                  40                  45 tgg att ggg cac atc cat aac agt ggg acc acc tac tac aat ccg tcc   192
Trp Ile Gly His Ile His Asn Ser Gly Thr Thr Tyr Tyr Asn Pro Ser
     50                  55                  60 ctc aag agt cga gtt acc ata tca gta gac acg tct aag aag cag ttc   240
Leu Lys Ser Arg Val Thr Ile Ser Val Asp Thr Ser Lys Lys Gln Phe
 65                  70                  75                  80 tcc ctg agg ctg agt tct gtg act gcc gcg gac acg gcc gta tat tac   288
Ser Leu Arg Leu Ser Ser Val Thr Ala Ala Asp Thr Ala Val Tyr Tyr
                 85                  90                  95 tgt gcg aga gat cga ggg ggt gac tac gct tat ggt atg gac gtc tgg   336
Cys Ala Arg Asp Arg Gly Gly Asp Tyr Ala Tyr Gly Met Asp Val Trp
            100                 105                 110 ggc caa ggg acc acg gtc acc gtc tcc tca gcc tcc acc aag ggc cca   384
Gly Gln Gly Thr Thr Val Thr Val Ser Ser Ala Ser Thr Lys Gly Pro
        115                 120                 125 tcg gtc ttc ccc ctg gcg ccc tgc tcc agg agc acc tcc gag agc aca   432
Ser Val Phe Pro Leu Ala Pro Cys Ser Arg Ser Thr Ser Glu Ser Thr
    130                 135                 140 gcg gcc ctg ggc tgc ctg gtc aag gac tac ttc ccc gaa ccg gtg acg   480
Ala Ala Leu Gly Cys Leu Val Lys Asp Tyr Phe Pro Glu Pro Val Thr
145                 150                 155                 160 gtg tcg tgg aac tca ggc gct ctg acc agc ggc gtg cac acc ttc cca   528
Val Ser Trp Asn Ser Gly Ala Leu Thr Ser Gly Val His Thr Phe Pro
                165                 170                 175 gct gtc cta cag tcc tca gga ctc tac tcc ctc agc agc gtg gtg acc   576
Ala Val Leu Gln Ser Ser Gly Leu Tyr Ser Leu Ser Ser Val Val Thr
            180                 185                 190 gtg ccc tcc agc aac ttc ggc acc cag acc tac acc tgc aac gta gat   624
Val Pro Ser Ser Asn Phe Gly Thr Gln Thr Tyr Thr Cys Asn Val Asp
        195                 200                 205 cac aag ccc agc aac acc aag gtg gac aag aca gtt gag cgc aaa tgt   672
His Lys Pro Ser Asn Thr Lys Val Asp Lys Thr Val Glu Arg Lys Cys
    210                 215                 220
```

```
tgt gtc gag tgc cca ccg tgc cca gca cca cct gtg gca gga ccg tca    720
Cys Val Glu Cys Pro Pro Cys Pro Ala Pro Pro Val Ala Gly Pro Ser
225             230                 235                 240 gtc ttc ctc ttc ccc cca aaa ccc aag gac acc ctc atg atc tcc cgg    768
Val Phe Leu Phe Pro Pro Lys Pro Lys Asp Thr Leu Met Ile Ser Arg
            245                 250                 255 acc cct gag gtc acg tgc gtg gtg gtg gac gtg agc cac gaa gac ccc    816
Thr Pro Glu Val Thr Cys Val Val Val Asp Val Ser His Glu Asp Pro
        260                 265                 270 gag gtc cag ttc aac tgg tac gtg gac ggc gtg gag gtg cat aat gcc    864
Glu Val Gln Phe Asn Trp Tyr Val Asp Gly Val Glu Val His Asn Ala
    275                 280                 285 aag aca aag cca cgg gag gag cag ttc aac agc acg ttc cgt gtg gtc    912
Lys Thr Lys Pro Arg Glu Glu Gln Phe Asn Ser Thr Phe Arg Val Val
290                 295                 300 agc gtc ctc acc gtt gtg cac cag gac tgg ctg aac ggc aag gag tac    960
Ser Val Leu Thr Val Val His Gln Asp Trp Leu Asn Gly Lys Glu Tyr
305                 310                 315                 320 aag tgc aag gtc tcc aac aaa ggc ctc cca gcc ccc atc gag aaa acc   1008
Lys Cys Lys Val Ser Asn Lys Gly Leu Pro Ala Pro Ile Glu Lys Thr
            325                 330                 335 atc tcc aaa acc aaa ggg cag ccc cga gaa cca cag gtg tac acc ctg   1056
Ile Ser Lys Thr Lys Gly Gln Pro Arg Glu Pro Gln Val Tyr Thr Leu
        340                 345                 350 ccc cca tcc cgg gag gag atg acc aag aac cag gtc agc ctg acc tgc   1104
Pro Pro Ser Arg Glu Glu Met Thr Lys Asn Gln Val Ser Leu Thr Cys
    355                 360                 365 ctg gtc aaa ggc ttc tac ccc agc gac atc gcc gtg gag tgg gag agc   1152
Leu Val Lys Gly Phe Tyr Pro Ser Asp Ile Ala Val Glu Trp Glu Ser
370                 375                 380 aat ggg cag ccg gag aac aac tac aag acc aca cct ccc atg ctg gac   1200
Asn Gly Gln Pro Glu Asn Asn Tyr Lys Thr Thr Pro Pro Met Leu Asp
385                 390                 395                 400 tcc gac ggc tcc ttc ttc ctc tac agc aag ctc acc gtg gac aag agc   1248
Ser Asp Gly Ser Phe Phe Leu Tyr Ser Lys Leu Thr Val Asp Lys Ser
            405                 410                 415 agg tgg cag cag ggg aac gtc ttc tca tgc tcc gtg atg cat gag gct   1296
Arg Trp Gln Gln Gly Asn Val Phe Ser Cys Ser Val Met His Glu Ala
        420                 425                 430 ctg cac aac cac tac acg cag aag agc ctc tcc ctg tct ccg ggt ggt   1344
Leu His Asn His Tyr Thr Gln Lys Ser Leu Ser Leu Ser Pro Gly Gly
    435                 440                 445 gga ggt ggt ggt tct ggt ggt ggt agc gga ggc ggc ggt tcc cac ccc   1392
Gly Gly Gly Gly Ser Gly Gly Gly Ser Gly Gly Gly Gly Ser His Pro
450                 455                 460 atc cct gac tcc tct cca ctc ctg caa ttc ggg ggc caa gtc cgg cag   1440
Ile Pro Asp Ser Ser Pro Leu Leu Gln Phe Gly Gly Gln Val Arg Gln
465                 470                 475                 480 cgg tac ctc tac aca gat gat gcc cag cag aca gaa gcc cac ctg gag   1488
Arg Tyr Leu Tyr Thr Asp Asp Ala Gln Gln Thr Glu Ala His Leu Glu
            485                 490                 495 atc agg gag gat ggg acg gtg ggg gct gct gac cag agc ccc gaa       1536
Ile Arg Glu Asp Gly Thr Val Gly Ala Ala Asp Gln Ser Pro Glu
        500                 505                 510 agt ctc ctg cag ctg aaa gcc ttg aag ccg gga gtt att caa atc ttg   1584
Ser Leu Leu Gln Leu Lys Ala Leu Lys Pro Gly Val Ile Gln Ile Leu
    515                 520                 525 gga gtc aag aca tcc agg ttc ctg tgc cag cgg cca gat ggg gcc ctg   1632
Gly Val Lys Thr Ser Arg Phe Leu Cys Gln Arg Pro Asp Gly Ala Leu
530                 535                 540
```

```
tat gga tcg ctc cac ttt gac cct gag gcc tgc agc ttc cgg gag ctg       1680
Tyr Gly Ser Leu His Phe Asp Pro Glu Ala Cys Ser Phe Arg Glu Leu
545                 550                 555                 560 ctt ctt gag gac gga tac aat gtt tac cag tcc gaa gcc cac ggc ctc       1728
Leu Leu Glu Asp Gly Tyr Asn Val Tyr Gln Ser Glu Ala His Gly Leu
                565                 570                 575 ccg ctg cac ctg cca ggg aac aag tcc cca cac cgg gac cct gca ccc       1776
Pro Leu His Leu Pro Gly Asn Lys Ser Pro His Arg Asp Pro Ala Pro
            580                 585                 590 cga gga cca gct cgc ttc ctg cca cta cca ggc ctg cca ccc gca ccc       1824
Arg Gly Pro Ala Arg Phe Leu Pro Leu Pro Gly Leu Pro Pro Ala Pro
        595                 600                 605 ccg gag cca ccc gga atc ctg gcc ccc cag ccc ccc gat gtg ggc tcc       1872
Pro Glu Pro Pro Gly Ile Leu Ala Pro Gln Pro Pro Asp Val Gly Ser
    610                 615                 620 tcg gac cct ctg agc atg gtg gga cct tcc cag ggc cga agc ccc agc       1920
Ser Asp Pro Leu Ser Met Val Gly Pro Ser Gln Gly Arg Ser Pro Ser
625                 630                 635                 640 tac gct tcc                                                            1929
Tyr Ala Ser <210> SEQ ID NO 386
<211> LENGTH: 643
<212> TYPE: PRT
<213> ORGANISM: ARTIFICIAL SEQUENCE
<220> FEATURE:
<223> OTHER INFORMATION: Synthetic Construct

<400> SEQUENCE: 386

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Ala Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240
```

```
Val Phe Leu Phe Pro Lys Pro Lys Asp Thr Leu Met Ile Ser Arg
            245                 250                 255

Thr Pro Glu Val Thr Cys Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Gly
            435                 440                 445

Gly Gly Gly Gly Ser Gly Gly Gly Ser Gly Gly Gly Ser His Pro
    450                 455                 460

Ile Pro Asp Ser Ser Pro Leu Leu Gln Phe Gly Gly Gln Val Arg Gln
465                 470                 475                 480

Arg Tyr Leu Tyr Thr Asp Asp Ala Gln Gln Thr Glu Ala His Leu Glu
                485                 490                 495

Ile Arg Glu Asp Gly Thr Val Gly Gly Ala Ala Asp Gln Ser Pro Glu
                500                 505                 510

Ser Leu Leu Gln Leu Lys Ala Leu Lys Pro Gly Val Ile Gln Ile Leu
            515                 520                 525

Gly Val Lys Thr Ser Arg Phe Leu Cys Gln Arg Pro Asp Gly Ala Leu
    530                 535                 540

Tyr Gly Ser Leu His Phe Asp Pro Glu Ala Cys Ser Phe Arg Glu Leu
545                 550                 555                 560

Leu Leu Glu Asp Gly Tyr Asn Val Tyr Gln Ser Glu Ala His Gly Leu
                565                 570                 575

Pro Leu His Leu Pro Gly Asn Lys Ser Pro His Arg Asp Pro Ala Pro
            580                 585                 590

Arg Gly Pro Ala Arg Phe Leu Pro Leu Pro Gly Leu Pro Pro Ala Pro
    595                 600                 605

Pro Glu Pro Pro Gly Ile Leu Ala Pro Gln Pro Pro Asp Val Gly Ser
    610                 615                 620

Ser Asp Pro Leu Ser Met Val Gly Pro Ser Gln Gly Arg Ser Pro Ser
625                 630                 635                 640

Tyr Ala Ser

<210> SEQ ID NO 387
```

-continued

```
<211> LENGTH: 1476
<212> TYPE: DNA
<213> ORGANISM: ARTIFICIAL SEQUENCE
<220> FEATURE:
<223> OTHER INFORMATION: 4341 IgG2-HC-ShK [1-35, Q16K] (Ab 10164)
<220> FEATURE:
<221> NAME/KEY: CDS
<222> LOCATION: (1)..(1476)

<400> SEQUENCE: 387
```

| | | | | | | | | | | | | | | | | |
|---|---|---|---|---|---|---|---|---|---|---|---|---|---|---|---|---|
| cag | gtg | cag | ctg | cag | gag | tcg | ggc | cca | gga | ctg | gtg | aag | cct | tca | cag | 48 |
| Gln | Val | Gln | Leu | Gln | Glu | Ser | Gly | Pro | Gly | Leu | Val | Lys | Pro | Ser | Gln | |
| 1 | | | | 5 | | | | | 10 | | | | | 15 | | |
| acc | ctg | tcc | ctc | acc | tgc | act | gtc | tct | ggt | ggc | tcc | atc | agc | agt | ggt | 96 |
| Thr | Leu | Ser | Leu | Thr | Cys | Thr | Val | Ser | Gly | Gly | Ser | Ile | Ser | Ser | Gly | |
| | | | 20 | | | | | 25 | | | | | 30 | | | |
| gat | tac | ttc | tgg | agc | tgg | atc | cgc | cag | ctc | cca | ggg | aag | ggc | ctg | gag | 144 |
| Asp | Tyr | Phe | Trp | Ser | Trp | Ile | Arg | Gln | Leu | Pro | Gly | Lys | Gly | Leu | Glu | |
| | | 35 | | | | | 40 | | | | | 45 | | | | |
| tgg | att | ggg | cac | atc | cat | aac | agt | ggg | acc | acc | tac | tac | aat | ccg | tcc | 192 |
| Trp | Ile | Gly | His | Ile | His | Asn | Ser | Gly | Thr | Thr | Tyr | Tyr | Asn | Pro | Ser | |
| 50 | | | | | 55 | | | | | 60 | | | | | | |
| ctc | aag | agt | cga | gtt | acc | ata | tca | gta | gac | acg | tct | aag | aag | cag | ttc | 240 |
| Leu | Lys | Ser | Arg | Val | Thr | Ile | Ser | Val | Asp | Thr | Ser | Lys | Lys | Gln | Phe | |
| 65 | | | | 70 | | | | | 75 | | | | | 80 | | |
| tcc | ctg | agg | ctg | agt | tct | gtg | act | gcc | gcg | gac | acg | gcc | gta | tat | tac | 288 |
| Ser | Leu | Arg | Leu | Ser | Ser | Val | Thr | Ala | Ala | Asp | Thr | Ala | Val | Tyr | Tyr | |
| | | | | 85 | | | | | 90 | | | | | 95 | | |
| tgt | gcg | aga | gat | cga | ggg | ggt | gac | tac | gct | tat | ggt | atg | gac | gtc | tgg | 336 |
| Cys | Ala | Arg | Asp | Arg | Gly | Gly | Asp | Tyr | Ala | Tyr | Gly | Met | Asp | Val | Trp | |
| | | | 100 | | | | | 105 | | | | | 110 | | | |
| ggc | caa | ggg | acc | acg | gtc | acc | gtc | tcc | tca | gct | agc | acc | aag | ggc | cca | 384 |
| Gly | Gln | Gly | Thr | Thr | Val | Thr | Val | Ser | Ser | Ala | Ser | Thr | Lys | Gly | Pro | |
| | | 115 | | | | | 120 | | | | | 125 | | | | |
| tcg | gtc | ttc | ccc | ctg | gcg | ccc | tgc | tcc | agg | agc | acc | tcc | gag | agc | aca | 432 |
| Ser | Val | Phe | Pro | Leu | Ala | Pro | Cys | Ser | Arg | Ser | Thr | Ser | Glu | Ser | Thr | |
| 130 | | | | | 135 | | | | | 140 | | | | | | |
| gcg | gcc | ctg | ggc | tgc | ctg | gtc | aag | gac | tac | ttc | ccc | gaa | ccg | gtg | acg | 480 |
| Ala | Ala | Leu | Gly | Cys | Leu | Val | Lys | Asp | Tyr | Phe | Pro | Glu | Pro | Val | Thr | |
| 145 | | | | 150 | | | | | 155 | | | | | 160 | | |
| gtg | tcg | tgg | aac | tca | ggc | gct | ctg | acc | agc | ggc | gtg | cac | acc | ttc | cca | 528 |
| Val | Ser | Trp | Asn | Ser | Gly | Ala | Leu | Thr | Ser | Gly | Val | His | Thr | Phe | Pro | |
| | | | 165 | | | | | 170 | | | | | 175 | | | |
| gct | gtc | cta | cag | tcc | tca | gga | ctc | tac | tcc | ctc | agc | agc | gtg | gtg | acc | 576 |
| Ala | Val | Leu | Gln | Ser | Ser | Gly | Leu | Tyr | Ser | Leu | Ser | Ser | Val | Val | Thr | |
| | | 180 | | | | | 185 | | | | | 190 | | | | |
| gtg | ccc | tcc | agc | aac | ttc | ggc | acc | cag | acc | tac | acc | tgc | aac | gta | gat | 624 |
| Val | Pro | Ser | Ser | Asn | Phe | Gly | Thr | Gln | Thr | Tyr | Thr | Cys | Asn | Val | Asp | |
| | 195 | | | | | 200 | | | | | 205 | | | | | |
| cac | aag | ccc | agc | aac | acc | aag | gtg | gac | aag | aca | gtt | gag | cgc | aaa | tgt | 672 |
| His | Lys | Pro | Ser | Asn | Thr | Lys | Val | Asp | Lys | Thr | Val | Glu | Arg | Lys | Cys | |
| 210 | | | | | 215 | | | | | 220 | | | | | | |
| tgt | gtc | gag | tgc | cca | ccg | tgc | cca | gca | cca | cct | gtg | gca | gga | ccg | tca | 720 |
| Cys | Val | Glu | Cys | Pro | Pro | Cys | Pro | Ala | Pro | Pro | Val | Ala | Gly | Pro | Ser | |
| 225 | | | | 230 | | | | | 235 | | | | | 240 | | |
| gtc | ttc | ctc | ttc | ccc | cca | aaa | ccc | aag | gac | acc | ctc | atg | atc | tcc | cgg | 768 |
| Val | Phe | Leu | Phe | Pro | Pro | Lys | Pro | Lys | Asp | Thr | Leu | Met | Ile | Ser | Arg | |
| | | | 245 | | | | | 250 | | | | | 255 | | | |
| acc | cct | gag | gtc | acg | tgc | gtg | gtg | gtg | gac | gtg | agc | cac | gaa | gac | ccc | 816 |
| Thr | Pro | Glu | Val | Thr | Cys | Val | Val | Val | Asp | Val | Ser | His | Glu | Asp | Pro | |
| | | 260 | | | | | 265 | | | | | 270 | | | | |
| gag | gtc | cag | ttc | aac | tgg | tac | gtg | gac | ggc | gtg | gag | gtg | cat | aat | gcc | 864 |

-continued

| | | | | | | | | | | | | |
|---|---|---|---|---|---|---|---|---|---|---|---|---|
| Glu | Val | Gln | Phe | Asn | Trp | Tyr | Val | Asp | Gly | Val | Glu | Val | His | Asn | Ala |
| | | 275 | | | | | 280 | | | | | 285 | | | |

```
aag aca aag cca cgg gag gag cag ttc aac agc acg ttc cgt gtg gtc      912
Lys Thr Lys Pro Arg Glu Glu Gln Phe Asn Ser Thr Phe Arg Val Val
290             295                 300 agc gtc ctc acc gtt gtg cac cag gac tgg ctg aac ggc aag gag tac      960
Ser Val Leu Thr Val Val His Gln Asp Trp Leu Asn Gly Lys Glu Tyr
305             310                 315                 320 aag tgc aag gtc tcc aac aaa ggc ctc cca gcc ccc atc gag aaa acc     1008
Lys Cys Lys Val Ser Asn Lys Gly Leu Pro Ala Pro Ile Glu Lys Thr
            325                 330                 335 atc tcc aaa acc aaa ggg cag ccc cga gaa cca cag gtg tac acc ctg     1056
Ile Ser Lys Thr Lys Gly Gln Pro Arg Glu Pro Gln Val Tyr Thr Leu
        340                 345                 350 ccc cca tcc cgg gag gag atg acc aag aac cag gtc agc ctg acc tgc     1104
Pro Pro Ser Arg Glu Glu Met Thr Lys Asn Gln Val Ser Leu Thr Cys
    355                 360                 365 ctg gtc aaa ggc ttc tac ccc agc gac atc gcc gtg gag tgg gag agc     1152
Leu Val Lys Gly Phe Tyr Pro Ser Asp Ile Ala Val Glu Trp Glu Ser
370                 375                 380 aat ggg cag ccg gag aac aac tac aag acc aca cct ccc atg ctg gac     1200
Asn Gly Gln Pro Glu Asn Asn Tyr Lys Thr Thr Pro Pro Met Leu Asp
385                 390                 395                 400 tcc gac ggc tcc ttc ttc ctc tac agc aag ctc acc gtg gac aag agc     1248
Ser Asp Gly Ser Phe Phe Leu Tyr Ser Lys Leu Thr Val Asp Lys Ser
            405                 410                 415 agg tgg cag cag ggg aac gtc ttc tca tgc tcc gtg atg cat gag gct     1296
Arg Trp Gln Gln Gly Asn Val Phe Ser Cys Ser Val Met His Glu Ala
        420                 425                 430 ctg cac aac cac tac acg cag aag agc ctc tcc ctg tct ccg ggt gga     1344
Leu His Asn His Tyr Thr Gln Lys Ser Leu Ser Leu Ser Pro Gly Gly
    435                 440                 445 gga gga gga tcc gga gga gga gga agc cgc agc tgc atc gac acc atc     1392
Gly Gly Gly Ser Gly Gly Gly Gly Ser Arg Ser Cys Ile Asp Thr Ile
450                 455                 460 ccc aag agc cgc tgc acc gcc ttc aag tgc aag cac agc atg aag tac     1440
Pro Lys Ser Arg Cys Thr Ala Phe Lys Cys Lys His Ser Met Lys Tyr
465                 470                 475                 480 cgc ctg agc ttc tgc cgc aag acc tgc ggc acc tgc                     1476
Arg Leu Ser Phe Cys Arg Lys Thr Cys Gly Thr Cys
            485                 490

<210> SEQ ID NO 388
<211> LENGTH: 492
<212> TYPE: PRT
<213> ORGANISM: ARTIFICIAL SEQUENCE
<220> FEATURE:
<223> OTHER INFORMATION: Synthetic Construct

<400> SEQUENCE: 388

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80
```

```
Ser Leu Arg Leu Ser Ser Val Thr Ala Ala Asp Thr Ala Val Tyr Tyr
                85                  90                  95

Cys Ala Arg Asp Arg Gly Gly Asp Tyr Ala Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Gly Ser Arg Ser Cys Ile Asp Thr Ile
    450                 455                 460

Pro Lys Ser Arg Cys Thr Ala Phe Lys Cys Lys His Ser Met Lys Tyr
465                 470                 475                 480

Arg Leu Ser Phe Cys Arg Lys Thr Cys Gly Thr Cys
                485                 490

<210> SEQ ID NO 389
```

<211> LENGTH: 511
<212> TYPE: PRT
<213> ORGANISM: ARTIFICIAL SEQUENCE
<220> FEATURE:
<223> OTHER INFORMATION: aKLH 120.6 IgG2-ShK[1-35, Q16K] fusion

<400> SEQUENCE: 389

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380
```

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Gly Gly Ser Gly Gly Gly Ser Arg Ser Cys Ile
465                 470                 475                 480

Asp Thr Ile Pro Lys Ser Arg Cys Thr Ala Phe Lys Cys Lys His Ser
                485                 490                 495

Met Lys Tyr Arg Leu Ser Phe Cys Arg Lys Thr Cys Gly Thr Cys
            500                 505                 510

<210> SEQ ID NO 390
<211> LENGTH: 181
<212> TYPE: PRT
<213> ORGANISM: Homo sapiens
<220> FEATURE:
<221> NAME/KEY: MISC_FEATURE
<223> OTHER INFORMATION: Human FGF21

<400> SEQUENCE: 390

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 391
<211> LENGTH: 38
<212> TYPE: DNA
<213> ORGANISM: ARTIFICIAL SEQUENCE
<220> FEATURE:
<223> OTHER INFORMATION: Forward primer sequence

<400> SEQUENCE: 391
```

```
ggttgagagg tgccagatgt cagggctgca gcagcggc                              38

<210> SEQ ID NO 392
<211> LENGTH: 42
<212> TYPE: DNA
<213> ORGANISM: ARTIFICIAL SEQUENCE
<220> FEATURE:
<223> OTHER INFORMATION: Reverse primer sequence

<400> SEQUENCE: 392
cagctgcacc tgaccaccac ctccaccgct atgctgagcg cg                        42
```

CARRIER IMMUNOGLOBULINS AND USES THEREOF

This application is a national stage application under 35 U.S.C. 371 of International Application No. PCT/US2011/052841, having an international filing date of Mar. 22, 2011, which claims the benefit of U.S. Provisional Application No. 61/385,460, filed Sep. 22, 2010, which is hereby incorporated by reference in its entirety.

The instant application contains an ASCII "txt" compliant sequence listing submitted via EFS-WEB on Sep. 22, 2011, which serves as both the computer readable form (CRF) and the paper copy required by 37 C.F.R. Section 1.821(c) and 1.821(e), and is hereby incorporated by reference in its entirety. The name of the "txt" file created on Sep. 22, 2011, is: A-1536-WO-PCTSeqList092211_ST25.txt, and is 501 kb in size.

Throughout this application various publications are referenced within parentheses or brackets. The disclosures of these publications in their entireties are hereby incorporated by reference in this application in order to more fully describe the state of the art to which this invention pertains.

BACKGROUND OF THE INVENTION

1. Field of the Invention

This invention relates to immunoglobulins to which one or more pharmacologically active chemical moieties can be conjugated for improved pharmacokinetic characteristics.

2. Discussion of the Related Art

A "carrier" moiety refers to a pharmacologically inactive molecule to which a pharmacologically active chemical moiety, such as a non-peptide organic moiety (i.e., "small molecule") or a polypeptide agent (e.g., the inventive immunoglublins), can be covalently conjugated or fused. Effective carriers have been sought to prevent or mitigate in vivo degradation of pharmacologically active moieties by proteolysis or other in vivo activity-diminishing chemical modifications of the pharmacologically active chemical moiety, or to reduce renal clearance, to enhance in vivo half-life or other pharmacokinetic properties of a therapeutic, such as increasing the rate of absorption, reducing toxicity or immunogenicity, improving solubility, and/or increasing manufacturability or storage stability, compared to an unconjugated form of the pharmacologically active moiety.

Examples of such carrier moieties that have been employed in the pharmaceutical industry include polyethylene glycol (see, e.g., Burg et al., Erythropoietin conjugates with polyethylene glycol, WO 01/02017), immunoglobulin Fc domain (see, e.g., Feige et al., Modified peptides as therapeutic agents, U.S. Pat. No. 6,660,843), human serum albumin (see, e.g., Rosen et al., Albumin fusion proteins, U.S. Pat. No. 6,926,898 and US 2005/0054051; Bridon et al., Protection of endogenous therapeutic peptides from peptidase activity through conjugation to blood components, U.S. Pat. No. 6,887,470), transthyretin (see, e.g., Walker et al., Use of transthyretin peptide/protein fusions to increase the serum half-life of pharmacologically active peptides/proteins, US 2003/0195154 A1; 2003/0191056 A1), or thyroxine-binding globulin, or a combination such as immunoglobulin (light chain+heavy chain) and Fc domain (the heterotrimeric combination a so-called "hemibody"), for example as described in Sullivan et al., Toxin Peptide Therapeutic Agents, PCT/US2007/022831, published as WO 2008/088422. Pharmacologically active moieties have also been conjugated to a peptide or small molecule that has an affinity for a long half-life serum protein. (See, e.g., Blaney et al., Method and compositions for increasing the serum half-life of pharmacologically active agents by binding to transthyretin-selective ligands, U.S. Pat. No. 5,714,142; Sato et al., Serum albumin binding moieties, US 2003/0069395 A1; Jones et al., Pharmaceutical active conjugates, U.S. Pat. No. 6,342,225).

Fischer et al. described a peptide-immunoglobulin-conjugate, in which the immunoglobulin consisted of two heavy chains or two heavy chains and two light chains, in which the immunoglobulin was not a functionable immunoglobulin (Fischer et al., A peptide-immunoglobulin conjugate, WO 2007/045463 A1).

The present invention provides immunoglobulins yielding exceptional uniformity and efficiency of recombinant expression, in vitro stability and non-aggregation, resistance to photodegradation and oxidation, non-cross-reactivity with human antigens, and good pharmacokinetic properties.

SUMMARY OF THE INVENTION

The invention relates to immunoglobulins, which are useful as carrier moieties. These immunoglobulins, including antibodies and antibody fragments, have reliable expression and purification characteristics, resulting in products that are stable and relatively uniform, and have outstanding pharmacokinetic (PK) properties in rats and cynomolgous monkeys. The inventive immunoglobulins have not been detected to bind to human proteins, cells or tissues. These immunoglobulins can also be used for many purposes, including, but not limited to, quality control or analytical standards for antibody-based drugs and as controls for biologically relevant isotype-matched antibodies.

Certain embodiments of the invention include an isolated immunoglobulin, comprising an immunoglobulin heavy chain variable region and an immunoglobulin light chain variable region, wherein:

the heavy chain variable region comprises the amino acid sequence of SEQ ID NO:323 [VH10] and the light chain variable region comprises the amino acid sequence of SEQ ID NO:188 [VL4] or SEQ ID NO:190 [VL5]; or the heavy chain variable region comprises the amino acid sequence of SEQ ID NO:321 [VH9] and the light chain variable region comprises the amino acid sequence of SEQ ID NO:188 [VL4] or SEQ ID NO:190 [VL5]; or the heavy chain variable region comprises the amino acid sequence of SEQ ID NO:325 [VH11] and the light chain variable region comprises the amino acid sequence of SEQ ID NO:182 [VL1], SEQ ID NO:188 [VL4], or SEQ ID NO:190 [VL5].

Examples include antibodies #16435, 16436, 16438, 16439, 16440, 16441, and 16444, disclosed in Table 2C. Typically, the inventive immunoglobulin at 30 micromolar concentration does not significantly bind soluble human IL-17R (SEQ ID NO:89) at 30 nanomolar concentration in an aqueous solution incubated under physiological conditions, e.g., as measured by a surface plasmon resonance binding assay, as described herein.

Other embodiments of the invention include an isolated immunoglobulin, comprising an immunoglobulin heavy chain variable region and an immunoglobulin light chain variable region, wherein:

the light chain variable region comprises the amino acid sequence of SEQ ID NO:196 [VL8] and the heavy chain variable region comprises the amino acid sequence of SEQ ID NO:335 [VH16], SEQ ID NO:349 [VH23], SEQ ID NO:351 [VH24], SEQ ID NO:353 [VH25], SEQ ID NO:355 [VH26], or SEQ ID NO:359 [VH28]; or the light chain variable region comprises the amino acid sequence of SEQ ID NO:204 [VL12] and the heavy chain variable region comprises the amino acid sequence of SEQ ID NO:349 [VH23] or SEQ ID NO:355 [VH26]; or the light chain variable region comprises the amino acid sequence of SEQ ID NO:202 [VL11] and the heavy chain variable region comprises the amino acid sequence of SEQ ID NO:349 [VH23]; or the light chain variable region comprises the amino acid sequence of SEQ ID NO:192 [VL6] and the heavy chain variable region comprises the amino acid sequence of SEQ ID NO:357 [VH27], SEQ ID NO:359 [VH28], or SEQ ID NO:369 [VH33]; or the light chain variable region comprises the amino acid sequence of SEQ ID NO:194 [VL7] and the heavy chain variable region comprises the amino acid sequence of SEQ ID NO:335 [VH16], SEQ ID NO:349 [VH23], or SEQ ID NO:351 [VH24].

Examples include antibodies #1961, 1962, 1963, 1964, 1965, 1966, 2323, 2324 2330, 4241, 4341, 10182, 10183, 10184, and 10188, disclosed in Table 2C. Typically, the inventive immunoglobulin at 10 micromolar concentration does not significantly bind soluble human TR2 (SEQ ID NO:82) at 10 nanomolar concentration in an aqueous solution incubated under physiological conditions, e.g., as measured by a surface plasmon resonance binding assay, as described herein.

In some embodiments, the immunoglobulin of the present invention is used as a carrier for pharmacologically active chemical moieties, e.g., small molecules, peptides, and/or proteins to enhance their PK properties. The pharmacologically active moieties can be conjugated, i.e., covalently bound, to the inventive immunoglobulin by a chemical conjugation reaction, or through recombinant genetic expression, they can be fused to the immunoglobulin.

The invention also provides materials and methods for producing such inventive immunoglobulins, including isolated nucleic acids that encode them, vectors and isolated host cells. Also provided are isolated nucleic acids encoding any of the immunoglobulin heavy and/or light chain sequences and/or VH and/or VL sequences. In a related embodiment, an expression vector comprising any of the aforementioned nucleic acids is provided. In still another embodiment, a host cell is provided comprising any of the aforementioned nucleic acids or expression vectors.

The inventive immunoglobulin can be used in the manufacture of a pharmaceutical composition or medicament. The inventive pharmaceutical composition or medicament comprises the immunoglobulin conjugated with a pharmacologically active agent, and a pharmaceutically acceptable diluent, carrier or excipient.

Numerous methods are contemplated in the present invention. For example, a method is provided involving culturing the aforementioned host cell comprising the expression vector of the invention such that the encoded immunoglobulin is expressed. Such methods can also comprise the step of recovering the immunoglobulin from the host cell culture. In a related embodiment, an isolated immunoglobulin produced by the aforementioned method is provided.

The foregoing summary is not intended to define every aspect of the invention, and additional aspects are described in other sections, such as the Detailed Description of Embodiments. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 1A represents a monovalent heterodimeric Fc-toxin peptide analog fusion with the toxin peptide analog fused to the C-terminal end of one of the immunoglobulin Fc domain monomers. FIG. 1N represents a monovalent antibody with a toxin peptide analog moiety inserted into an internal loop of the immun nM TRAIL. The decreased binding signal of TRAIL after the antibody incubation indicates the binding of the antibody to TRAIL in solution.

FIG. 20C shows results from an in vitro cell-based TRAIL activity assay. Samples of antibodies 4241 and 4341 were compared with positive control IgG1 anti-TR2 mAb 16449. The prepared antibody samples were added to TRAIL-sensitive human ascites colorectal adenocarcinoma cell line Colo205. The detection of TRAIL-mediated caspase-3 activation by measuring an increase in relative luminescence was used as a positive marker for apoptosis. Antibodies 4241 and 4341 failed to activate caspase-3, unlike positive control antibody 16449.

FIG. 22A-F shows size exclusion chromatography on 50 µg of antibodies 4241 (FIG. 22A), 4341 (FIG. 22B), 10182 (FIG. 22C), 10183 (FIG. 22D), 10184 (FIG. 22E), and 10185 (FIG. 22F), injected on to a Phenomenex BioSep SEC-3000 column (7.8×300 mm) in 50 mM $NaH_2PO_4$, 250 mM NaCl, and pH 6.9 at 1 mL/min, measuring the absorbance at 280 nm.

FIG. 23A) expression runs were conducted using a 6-day front-loaded process in CD 6-D assay media, while the large scale (3-L; FIG. 23B) runs were completed using an 11-day fed-batch process with peptone medium. Titer levels were measured using a protein A HPLC based assay.

FIG. 25 shows an overlay of the chomatograms of antibodies 4341 and 4241 on an SP—HP sepharose column (GE Life Sciences) eluted using a 20 column volume gradient to 50% S-Buffer B (20 mM acetic acid, 1 M NaCl, pH 5.0) at 7° C. observing the absorbance at 300 nm.

FIGS. 27A-B shows full scale (FIG. 27A) and zoomed (FIG. 27B) analysis, using two size exclusion columns (TSK-GEL G3000SWXL, 5 mm particle size, 7.8×300 mm, Toso-hBioscience, 08541) in series with a 100 mM sodium phosphate, 250 mM NaCl at pH 6.8 mobile phase flowed at 0.5 mL/min., of antibodies: 4241 (upper panels) and 4341 (lower panels).

FIG. 28 shows an analysis of antibodies 4341 and 4241 by DSC using a MicroCal VP-DSC where the samples were heated from 20° C. to 95° C. at a rate of 1° C. per minute. The protein concentration was 0.5 mg/ml in 10 mM sodium acetate, 9% sucrose, pH 5.0.

FIGS. 29A-D shows an analysis of 4241 (FIGS. 29A-B) and 4341 (FIGS. 29C-D) antibodies by reducing (FIG. 29A and FIG. 29C) and non-reducing (FIG. 29B and FIG. 29D) CE-SDS with detection of absorbance at 220 nm. A barefused silica capillary 50 µm×30.2 cm was used for the separation analysis.

FIG. 30 shows analysis of the 4241 (upper panel) and 4341 (lower panel) antibodies using ion exchange HPLC (SP-5PW, 10 µm particle, 7.5 mm ID×7.5 cm, TosohBioscience, 08541) using 20 mM acetic acid, pH 5.0 as buffer A and 20 mM acetic acid, 1 M NaCl, pH 5.0 as buffer B flowed at 1 mL/min with an 80 minute linear gradient from 0-40% buffer B.

FIGS. 31A-B shows HIC analysis of the 4241 (FIG. 31A) and 4341 (FIG. 31B) antibodies, before and after light exposure, using two Dionex ProPac HIC-10 columns in series with mobile phase A being 1 M ammonium sulfate, 20 mM sodium acetate, pH 5.0 and mobile phase B being 20 mM sodium acetate, 5% acetonitrile, pH 5.0. Samples were eluted at 0.8 ml/min with a 0-100% linear gradient over 50 minutes observing the absorbance at 220 nm.

FIGS. 37A-D shows reduced light chain LC-MS analysis of the final 3742 samples. The product was chromatographed through a Waters MassPREP micro desalting column using a Waters ACQUITY UPLC system. The column was set at 80° C. and the protein eluted using a linear gradient of increasing acetonitrile concentration in 0.1% formic acid. The column effluent was directed into a Waters LCT Premier ESI-TOF mass spectrometer for mass analysis. The instrument was run in the positive V mode. The capillary voltage was set at 3,200 V and the cone voltage at 80 V. The mass spectrum was acquired from 800 to 3000 m/z and deconvoluted using the MaxEnt1 software provided by the instrument manufacturer.

FIGS. 40A-C shows size exclusion chromatography on 50 µg of fusion antibodies 10162 (FIG. 40A), 10163 (FIG. 40B), and 10164 (FIG. 40C) injected on to a Phenomenex BioSep SEC-3000 column (7.8×300 mm) in 50 mM $NaH_2PO_4$, 250 mM NaCl, and pH 6.9 at 1 mL/min measuring the absorbance at 280 nm.

DETAILED DESCRIPTION OF EMBODIMENTS

Figure 1A:
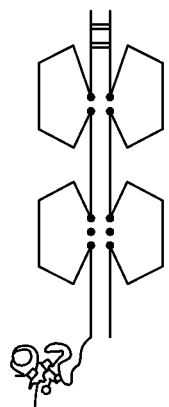
FIG. 1A-N shows schematic structures of some embodiments of a composition of the invention that include one or more units of a pharmacologically active toxin peptide analog (squiggle) fused, via an optional peptidyl linker moiety such as but not limited to L5 or L10 described herein, with one or more domains of an immunoglobulin. These schematics show a more typical IgG1, although they are intended to apply as well to IgG2s, which will have 4 disulfide bonds in the hinge and a different arrangement of the disulfide bond linking the heavy and light chain, and IgG3s and IgG4s.

The section headings used herein are for organizational purposes only and are not to be construed as limiting the subject matter described.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a cell" includes populations of a plurality of cells.

"Polypeptide" and "protein" are used interchangeably herein and include a molecular chain of two or more amino acids linked covalently through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be expressed recombinantly using known protein engineering techniques. In addition, fusion proteins can be derivatized as described herein by well-known organic chemistry techniques.

The term "isolated protein" referred means that a subject protein (1) is free of at least some other proteins with which it would normally be found in nature, (2) is essentially free of other proteins from the same source, e.g., from the same species, (3) is expressed recombinantly by a cell of a heterologous species or kind, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, and/or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an immunoglobulin, or an antibody) comprises an amino acid sequence wherein one or more amino acid residues are inserted into, deleted from and/or substituted into the amino acid sequence relative to another polypeptide sequence. Variants include fusion proteins.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

A "secreted" protein refers to those proteins capable of being directed to the ER, secretory vesicles, or the extracellular space as a result of a secretory signal peptide sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage. In some other embodiments of the inventive composition, the toxin peptide analog can be synthesized by the host cell as a secreted protein, which can then be further purified from the extracellular space and/or medium.

As used herein "soluble" when in reference to a protein produced by recombinant DNA technology in a host cell is a protein that exists in aqueous solution; if the protein contains a twin-arginine signal amino acid sequence the soluble protein is exported to the periplasmic space in gram negative bacterial hosts, or is secreted into the culture medium by eukaryotic host cells capable of secretion, or by bacterial host possessing the appropriate genes (e.g., the kil gene). Thus, a soluble protein is a protein which is not found in an inclusion body inside the host cell. Alternatively, depending on the context, a soluble protein is a protein which is not found integrated in cellular membranes; in contrast, an insoluble protein is one which exists in denatured form inside cytoplasmic granules (called an inclusion body) in the host cell, or again depending on the context, an insoluble protein is one which is present in cell membranes, including but not limited to, cytoplasmic membranes, mitochondrial membranes, chloroplast membranes, endoplasmic reticulum membranes, etc.

"Soluble human IL-17R" is a polypeptide (huIL-17R-FpH) having the following amino acid sequence:

SEQ ID NO: 89
LRLLDHRALVCSQPGLNCTVKNSTCLDDSWIHPRNLTPSSPKDLQIQLH

FAHTQQGDLFPVAHIEWTLQTDASILYLEGAELSVLQLNTNERLCVRFE

FLSKLRHHHRRWRFTFSHFVVDPDQEYEVTVHHLPKPIPDGDPNHQSKN

FLVPDCEHARMKVTTPCMSSGSLWDPNITVETLEAHOLRVSFTLWNEST

HYQILLTSFPHMENHSCFEHMHHIPAPRPEEFHQRSNVTLTLRNLKGCC

RHQVQIQPFFSSCLNDCLRHSATVSCPEMPDTPEPIPDYMPLWEPRSGS

SDYKDDDDKGSSHHHHHH//.

"Soluble human TR2" is a fusion polypeptide (huTR2 long-huFc (IgG1), in monomeric or dimeric form, having the following amino acid sequence:

SEQ ID NO: 82
MEQRGQNAPAASGARKRHGPGPREARGARPGPRVPKTLVLVVAAVLLLV

SAESALITQQDLAPQQRAAPQQKRSSPSEGLCPPGHHISEDGRDCISCK

YGQDYSTHWNDLLFCLRCTRCDSGEVELSPCTTTRNTVCQCEEGTFREE

DSPEMCRKCRTGCPRGMVKVGDCTPWSDIECVHKESGTKHSGEAPAVEE

TVTSSPGTPASPCSLSGVDKTHTCPPCPAPELLGGPSVFLFPPKPKDTL

MISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

K//.

"Under physiological conditions" with respect to incubating buffers and immunoglobulins, or other binding assay reagents means incubation under conditions of temperature, pH, and ionic strength, that permit a biochemical reaction, such as a non-covalent binding reaction, to occur. Typically, the temperature is at room or ambient temperature up to about 37° C. and at pH 6.5-7.5.

The term "recombinant" indicates that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well known molecular biological procedures. Examples of such molecular biological procedures are found in Maniatis et al., Molecular Cloning. A Laboratory Manual. Cold Spring Harbour Laboratory, Cold Spring Harbour, N.Y. (1982). A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid.

The term "polynucleotide" or "nucleic acid" includes both single-stranded and double-stranded nucleotide polymers containing two or more nucleotide residues. The nucleotide residues comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate.

The term "oligonucleotide" means a polynucleotide comprising 200 or fewer nucleotide residues. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

A "polynucleotide sequence" or "nucleotide sequence" or "nucleic acid sequence," as used interchangeably herein, is the primary sequence of nucleotide residues in a polynucleotide, including of an oligonucleotide, a DNA, and RNA, a nucleic acid, or a character string representing the primary sequence of nucleotide residues, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

As used herein, an "isolated nucleic acid molecule" or "isolated nucleic acid sequence" is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the immunoglobulin (e.g., antibody) where, for example, the nucleic acid molecule is in a chromosomal location different from that of natural cells.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. A "fusion gene" contains a coding region that encodes a toxin peptide analog. Genes also include non-expressed nucleic acid segments that, for example, form recognition sequences for other proteins. Non-expressed regulatory sequences including transcriptional control elements to which regulatory proteins, such as transcription factors, bind, resulting in transcription of adjacent or nearby sequences.

"Expression of a gene" or "expression of a nucleic acid" means transcription of DNA into RNA (optionally including modification of the RNA, e.g., splicing), translation of RNA into a polypeptide (possibly including subsequent post-translational modification of the polypeptide), or both transcription and translation, as indicated by the context.

As used herein the term "coding region" or "coding sequence" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

The term "control sequence" or "control signal" refers to a polynucleotide sequence that can, in a particular host cell, affect the expression and processing of coding sequences to which it is ligated. The nature of such control sequences may depend upon the host organism. In particular embodiments, control sequences for prokaryotes may include a promoter, a ribosomal binding site, and a transcription termination sequence. Control sequences for eukaryotes may include promoters comprising one or a plurality of recognition sites for transcription factors, transcription enhancer sequences or elements, polyadenylation sites, and transcription termination sequences. Control sequences can include leader sequences and/or fusion partner sequences. Promoters and enhancers consist of short arrays of DNA that interact specifically with cellular proteins involved in transcription (Maniatis, et al., Science 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 (1986) and Maniatis, et al., Science 236:1237 (1987)).

The term "vector" means any molecule or entity (e.g., nucleic acid, plasmid, bacteriophage or virus) used to transfer protein coding information into a host cell.

The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Such techniques are well known in the art. (E.g., Goodey, Andrew R.; et al., Peptide and DNA sequences, U.S. Pat. No. 5,302,697; Weiner et al., Compositions and methods for protein secretion, U.S. Pat. No. 6,022,952 and U.S. Pat. No. 6,335,178; Uemura et al., Protein expression vector and utilization thereof, U.S. Pat. No. 7,029,909; Ruben et al., 27 human secreted proteins, US 2003/0104400 A1).

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid and thereby expresses a gene of interest. The term includes the progeny of the parent cell, whether or not the progeny is identical in morphology or in genetic make-up to the original parent cell, so long as the gene of interest is present. Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, insect cells, plant cells, mammalian (including human) cells, e.g., CHO cells and HEK-293 cells. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired compounds are expressed. Such fermentation conditions are well known in the art.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

By "physiologically acceptable salt" of a composition of matter, for example a salt of the immunoglobulin, such as an antibody, is meant any salt or salts that are known or later discovered to be pharmaceutically acceptable. Some non-limiting examples of pharmaceutically acceptable salts are: acetate; trifluoroacetate; hydrohalides, such as hydrochloride and hydrobromide; sulfate; citrate; maleate; tartrate; glycolate; gluconate; succinate; mesylate; besylate; salts of gallic acid esters (gallic acid is also known as 3, 4, 5 trihydroxybenzoic acid) such as PentaGalloylGlucose (PGG) and epigallocatechin gallate (EGCG), salts of cholesteryl sulfate, pamoate, tannate and oxalate salts.

A "domain" or "region" (used interchangeably herein) of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane or extracellular domain).

"Treatment" or "treating" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. "Treatment" includes any indicia of success in the amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, self-reporting by a patient, neuropsychiatric exams, and/or a psychiatric evaluation.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with migraine headache. In some embodiments, the effective amount is a therapeutically effective amount or a prophylactically effective amount. A "therapeutically effective amount" is an amount sufficient to remedy a disease state (e.g., transplant rejection or GVHD, inflammation, multiple sclerosis, cancer, diabetes, neuropathy, pain) or symptom(s), particularly a state or symptom(s) associated with the disease state, or otherwise prevent, hinder, retard or reverse the progression of the disease state or any other undesirable symptom associated with the disease in any way whatsoever (i.e. that provides "therapeutic efficacy"). A "prophylactically effective amount" is an amount of a pharmaceutical composition that, when administered to a subject, will have the intended prophylactic effect, e.g., preventing or delaying the onset (or reoccurrence) of migraine headache or multiple sclerosis symptoms, or reducing the likelihood of the onset (or reoccurrence) of migraine headache, migraine headache symptoms, or multiple sclerosis symptoms. The full therapeutic or prophylactic effect does not necessarily occur by administration of one dose, and may occur only after administration of a series of doses. Thus, a therapeutically or prophylactically effective amount may be administered in one or more administrations.

"Mammal" for purposes of treatment refers to any animal classified as a mammal, including humans, domestic and farm animals, and zoo, sports, or pet animals, such as dogs, horses, cats, cows, rats, mice, monkeys, etc. Preferably, the mammal is human.

The term "naturally occurring" as used throughout the specification in connection with biological materials such as polypeptides, nucleic acids, host cells, and the like, refers to materials which are found in nature.

The term "antibody", or interchangeably "Ab", is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab, Fab', F(ab')$_2$, Fv, single chain antibodies, diabodies), comprising complementarity determining regions (CDRs) of the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity.

The term "antigen binding protein" (ABP) includes antibodies or antibody fragments, as defined above, and recombinant peptides or other compounds that contain sequences derived from CDRs having the desired antigen-binding properties such that they specifically bind a target antigen of interest.

In general, an antigen binding protein, e.g., an antibody or antibody fragment, "specifically binds" to an antigen of interest (e.g., IL-17R or TR2) when it has a significantly higher binding affinity for, and consequently is capable of distinguishing, that antigen, compared to its affinity for other unrelated proteins, under similar binding assay conditions. Typically, an antigen binding protein is said to "specifically bind" its target antigen when the dissociation constant ($K_D$) is $\leq 10^{-8}$ M. The antibody specifically binds antigen with "high affinity" when the $K_D$ is $\leq 5 \times 10^{-9}$ M, and with "very high affinity" when the $K_D$ is $\leq 5 \times 10^{-10}$ M. In one embodiment, the antibodies will bind to the antigen of interest with a $K_D$ of between about $10^{-8}$ M and $10^{-10}$ M, and in yet another embodiment the antibodies will bind with a $K_D \leq 5 \times 10^{-9}$.

"Antigen binding region" or "antigen binding site" means a portion of a protein, that specifically binds a specified antigen, e.g., IL-17R or TR2. For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs"). Certain antigen binding regions also include one or more "framework" regions ("FRs"). A "CDR" is an amino acid sequence that contributes to antigen binding specificity and affinity. "Framework" regions can aid in maintaining the proper conformation of the CDRs to promote binding between the antigen binding region and an antigen. In a traditional antibody, the CDRs are embedded within a framework in the heavy and light chain variable region where they constitute the regions responsible for antigen binding and recognition. A variable region of an immunoglobulin antigen binding protein comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra).

An "isolated" immunoglobulin, e.g., an antibody or antibody fragment, is one that has been identified and separated from one or more components of its natural environment or of a culture medium in which it has been secreted by a producing cell. "Contaminant" components of its natural environment or medium are materials that would interfere with diagnostic or therapeutic uses for the antibody, and may include enzymes, hormones, and other proteinaceous or nonproteinaceous solutes. In some embodiments, the antibody will be purified (1) to greater than 95% by weight of antibody, and most preferably more than 99% by weight, or (2) to homogeneity by SDS-PAGE under reducing or nonreducing conditions, optionally using a stain, e.g., Coomassie blue or silver stain. Isolated naturally occurring antibody includes the antibody in situ within recombinant cells since at least one component of the antibody's natural environment will not be present. Typically, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies that are antigen binding proteins are highly specific binders, being directed against an individual antigenic site or epitope, in contrast to polyclonal antibody preparations that typically include different antibodies directed against different epitopes. Nonlimiting examples of monoclonal antibodies include murine, rabbit, rat, chicken, chimeric, humanized, or human antibodies, fully assembled antibodies, multispecific antibodies (including bispecific antibodies), antibody fragments that can bind an antigen (including, Fab, Fab', F(ab)$_2$, Fv, single chain antibodies, diabodies), maxibodies, nanobodies, and recombinant peptides comprising CDRs of the foregoing as long as they exhibit the desired biological activity, or variants or derivatives thereof.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature, 352:624-628[1991] and Marks et al., J. Mol. Biol., 222:581-597 (1991), for example.

A "multispecific" binding agent or antigen binding protein or antibody is one that targets more than one antigen or epitope.

A "bispecific," "dual-specific" or "bifunctional" binding agent or antigen binding protein or antibody is a hybrid having two different antigen binding sites. Biantigen binding proteins, antigen binding proteins and antibodies are a species of multiantigen binding protein, antigen binding protein or multispecific antibody and may be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which may reside on the same or different protein targets.

The term "immunoglobulin" encompasses full antibodies comprising two dimerized heavy chains (HC), each covalently linked to a light chain (LC); a single undimerized immunoglobulin heavy chain and covalently linked light chain (HC+LC), or a chimeric immunoglobulin (light chain+heavy chain)-Fc heterotrimer (a so-called "hemibody"). An "immunoglobulin" is a protein, but is not necessarily an antigen binding protein.

In an "antibody", each tetramer is composed of two identical pairs of polypeptide chains, each pair having one "light" chain of about 220 amino acids (about 25 kDa) and one "heavy" chain of about 440 amino acids (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. The variable region differs among different antibodies. The constant region is the same among different antibodies. Within the variable region of each heavy or light chain, there are three hypervariable subregions that help determine the antibody's specificity for antigen in the case of an antibody that is an antigen binding protein. However, within the scope of the present invention, an embodiment of the immunoglobulin, e.g., an antibody, need not be an antigen binding protein, or need not be known to specifically bind to an antigen. The variable domain residues between the hypervariable regions are called the framework residues and generally are somewhat homologous among different antibodies. Immunoglobulins can be assigned to different classes depending on the amino acid sequence of the constant domain of their heavy chains. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)). Within the scope of the invention, an "antibody" also encompasses a recombinantly made antibody, and antibodies that are glycosylated or lacking glycosylation.

The term "light chain" or "immunoglobulin light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" or "immunoglobulin heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains are classified as mu (μ), delta (Δ), gamma (γ), alpha (α), and epsilon (ε), and define the antibody's isotype as IgM, IgD, IgG, IgA, and IgE, respectively. In separate embodiments of the invention, heavy chains may be of any isotype, including IgG (including IgG1, IgG2, IgG3 and IgG4 subtypes), IgA (including IgA1 and IgA2 subtypes), IgM and IgE. Several of these may be further divided into subclasses or isotypes, e.g. IgG1, IgG2, IgG3, IgG4, IgA1 and IgA2. Different IgG isotypes may have different effector functions (mediated by the Fc region), such as antibody-dependent cellular cytotoxicity (ADCC) and complement-dependent cytotoxicity (CDC). In ADCC, the Fc region of an antibody binds to Fc receptors (FcγRs) on the surface of immune effector cells such as natural killers and macrophages, leading to the phagocytosis or lysis of the targeted cells. In CDC, the antibodies kill the targeted cells by triggering the complement cascade at the cell surface.

An "Fc region", or used interchangeably herein, "Fc domain" or "immunoglobulin Fc domain", contains two heavy chain fragments, which in a full antibody comprise the $C_H1$ and $C_H2$ domains of the antibody. The two heavy chain fragments are held together by two or more disulfide bonds and by hydrophobic interactions of the $C_H3$ domains.

The term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

"Allotypes" are variations in antibody sequence, often in the constant region, that can be immunogenic and are encoded by specific alleles in humans. Allotypes have been identified for five of the human IGHC genes, the IGHG1, IGHG2, IGHG3, IGHA2 and IGHE genes, and are designated as G1m, G2m, G3m, A2m, and Em allotypes, respectively. At least 18 Gm allotypes are known: nG1m(1), nG1m(2), G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5). There are two A2m allotypes A2m(1) and A2m(2).

For a detailed description of the structure and generation of antibodies, see Roth, D. B., and Craig, N. L., *Cell*, 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "hypervariable" region refers to the amino acid residues of an antibody which are responsible for antigen-binding. The hypervariable region comprises amino acid residues from a complementarity determining region or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, $5^{th}$ Ed. Public Health Service, National Institutes of Health, Bethesda, Md. (1991)]. Even a single CDR may recognize and bind antigen, although with a lower affinity than the entire antigen binding site containing all of the CDRs.

An alternative definition of residues from a hypervariable "loop" is described by Chothia et al., *J. Mol. Biol.* 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or "FR" residues are those variable region residues other than the hypervariable region residues.

"Antibody fragments" comprise a portion of an intact full length antibody, preferably the antigen binding or variable region of the intact antibody. Examples of antibody fragments include Fab, Fab', F(ab')$_2$, and Fv fragments; diabodies; linear antibodies (Zapata et al., Protein Eng., 8(10):1057-1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment which contains the constant region. The Fab fragment contains all of the variable domain, as well as the constant domain of the light chain and the first constant domain (CH1) of the heavy chain. The Fc fragment displays carbohydrates and is responsible for many antibody effector functions (such as binding complement and cell receptors), that distinguish one class of antibody from another.

Pepsin treatment yields an F(ab')$_2$ fragment that has two "Single-chain Fv" or "scFv" antibody fragments comprising the VH and VL domains of antibody, wherein these domains are present in a single polypeptide chain. Fab fragments differ from Fab' fragments by the inclusion of a few additional residues at the carboxy terminus of the heavy chain CH1 domain including one or more cysteines from the antibody hinge region. Preferably, the Fv polypeptide further comprises a polypeptide linker between the VH and VL domains that enables the Fv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

A "Fab fragment" is comprised of one light chain and the $C_H1$ and variable regions of one heavy chain. The heavy chain of a Fab molecule cannot form a disulfide bond with another heavy chain molecule.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. A single variable domain (or half of an Fv comprising only three CDRs specific for an antigen) has the ability to recognize and bind antigen, although at a lower affinity than the entire binding site.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. No. 4,946,778 and No. 5,260,203, the disclosures of which are incorporated by reference in their entireties.

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., *Science* 242:423-426, 1988, and Huston et al., *Proc. Natl. Acad. Sci. USA* 85:5879-5883, 1988). An "Fd" fragment consists of the $V_H$ and $C_H1$ domains.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The term "compete" when used in the context of antigen binding proteins (e.g., neutralizing antigen binding proteins or neutralizing antibodies) that compete for the same epitope means competition between antigen binding proteins is determined by an assay in which the antigen binding protein (e.g., antibody or immunologically functional fragment thereof) under test prevents or inhibits specific binding of a reference antigen binding protein (e.g., a ligand, or a reference antibody) to a common antigen (e.g., IL-17R or a fragment thereof, or TR2 or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using I-125 label (see, e.g., Morel et al., 1988, Molec. Immunol. 25:7-15); solid phase direct biotin-avidin EIA (see, e.g., Cheung, et al., 1990, Virology 176:546-552); direct labeled RIA (Moldenhauer et al., 1990, Scand. J. Immunol. 32:77-82); and surface plasmon resonance (BIAcore®; e.g., Fischer et al., A peptide-immunoglobulin-conjugate, WO 2007/045463 A1, Example 10, which is incorporated herein by reference in its entirety), or KinExA. Typically, such an assay involves the use of purified antigen bound to a solid surface or cells bearing either of these, an unlabelled test immunoglobulin or antigen binding protein and a labeled reference antigen binding protein. Competitive inhibition is measured by determining the amount of label bound to the solid surface or cells in the presence of the test antigen binding protein. Usually the test immunoglobulin or antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 95%, or 97% or more.

When an immunoglobulin (e.g., an antibody or antibody fragment) "does not significantly bind" an antigen it means that the particular immunoglobulin, in excess, does not compete with a reference antigen binding protein, e.g., with a positive control antibody, to inhibit its binding to the target antigen by >39%, or >30%, or >20%, or >10%. As to specific binding to soluble human IL-17R, a positive control antibody is antibody 16429, described herein. As to specific binding to soluble human TR2, a positive control antibody is antibody 16449, described herein.

Antibody-antigen interactions can be characterized by the association rate constant in $M^{-1} s^{-1}$ ($k_a$), or the dissociation rate constant in $s^{-1}$ ($k_d$), or alternatively the dissociation equilibrium constant in M ($K_D$). Association rate constants, dissociation rate constants, or dissociation equilibrium constants may be readily determined using kinetic analysis techniques such as surface plasmon resonance (BIAcore®; e.g., Fischer et al., A peptide-immunoglobulin-conjugate, WO 2007/045463 A1, Example 10, which is incorporated herein by reference in its entirety), or KinExA using general procedures outlined by the manufacturer or other methods known in the art. The kinetic data obtained by BIAcore® or KinExA may be analyzed by methods described by the manufacturer.

"Measured by a surface plasmon resonance binding assay" with respect to determining whether a test immunoglobulin "does not significantly bind" means as measured in the solution equilibrium binding assay described herein to assess the binding activity of immunoglobulins based on surface plasmon resonance. A reference antigen binding protein (e.g., Antibody 16429 for human IL-17R or Antibody 16449 for human TR2) is immobilized to a BIACore® 2000, research grade sensor chip CM5 surface according to manufacturer's instructions (BIACore, Inc., Piscataway, N.J.). Carboxyl groups on the sensor chip surfaces are activated by injecting 60 µL of a mixture containing 0.2 M N-ethyl-N'-(dimethylaminopropyl) carbodiimide (EDC) and 0.05 M N-hydroxysuccinimide (NHS). The reference antigen binding protein is diluted in 10 mM sodium acetate, pH 4.0 and injected over the activated chip surface at 30 µL/min for 6 minutes. Excess reactive groups on the surfaces are deactivated by injecting 60 µL of 1 M ethanolamine. The final immobilized level is typically approximately 6600 resonance units (RU). Soluble target antigen (e.g., 10 nM of soluble human IL-17R or 30 nM of soluble human TR2) in the absence of soluble antigen binding protein (e.g., antibody) is used to establish the 100% binding signal to the fixed reference antigen binding protein (e.g., the positive control antibody). The decreased binding signal of the target antigen after incubation of the test immunoglobulin indicates its level of binding to the target antigen in solution.

The term "antigen" refers to a molecule or a portion of a molecule capable of being bound by a selective binding agent, such as an antigen binding protein (including, e.g., an antibody or immunological functional fragment thereof), and additionally capable of being used in an animal to produce antibodies capable of binding to that antigen. An antigen may possess one or more epitopes that are capable of interacting with different antigen binding proteins, e.g., antibodies.

The term "epitope" is the portion of a molecule that is bound by an antigen binding protein (for example, an antibody). The term includes any determinant capable of specifically binding to an antigen binding protein, such as an antibody or to a T-cell receptor. An epitope can be contiguous or non-contiguous (e.g., in a single-chain polypeptide, amino acid residues that are not contiguous to one another in the polypeptide sequence but that within the context of the molecule are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. For example, sequence identity can be determined by standard methods that are commonly used to compare the similarity in position of the amino acids of two polypeptides. Using a computer program such as BLAST or FASTA, two polypeptide or two polynucleotide sequences are aligned for optimal matching of their respective residues (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in *Atlas of Protein Sequence and Structure*, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences. In calculating percent identity, the sequences being compared are aligned in a way that gives the largest match between the sequences.

The GCG program package is a computer program that can be used to determine percent identity, which package includes GAP (Devereux et al., 1984, Nucl. Acid Res. 12:387; Genetics Computer Group, University of Wisconsin, Madison, Wis.). The computer algorithm GAP is used to align the two polypeptides or two polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program include the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps)
Gap Length Penalty: 4
Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

The term "modification" when used in connection with immunoglobulins, including antibodies and antibody fragments, of the invention, include, but are not limited to, one or more amino acid changes (including substitutions, insertions or deletions); chemical modifications; covalent modification by conjugation to therapeutic or diagnostic agents; labeling (e.g., with radionuclides or various enzymes); covalent polymer attachment such as PEGylation (derivatization with polyethylene glycol) and insertion or substitution by chemical synthesis of non-natural amino acids. Modified immunoglobulins of the invention will retain the binding (or non-binding) properties of unmodified molecules of the invention.

The term "derivative" when used in connection with immunoglobulins (including antibodies and antibody fragments) of the invention refers to immunoglobulins that are covalently modified by conjugation to therapeutic or diagnostic agents, labeling (e.g., with radionuclides or various enzymes), covalent polymer attachment such as PEGylation (derivatization with polyethylene glycol) and insertion or substitution by chemical synthesis of non-natural amino acids. Derivatives of the invention will retain the binding properties of underivatized molecules of the invention.

Embodiments of Immunoglobulins

In full-length immunoglobulin light and heavy chains, the variable and constant regions are joined by a "J" region of about twelve or more amino acids, with the heavy chain also including a "D" region of about ten more amino acids. See, e.g., Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site.

One example of a human IgG2 heavy chain (HC) constant domain has the amino acid sequence:

```
                                        SEQ. ID NO: 86
ASTKGPSVFPLAPCSRSTSESTAALGCLVKDYFPEPVTVSWNSGAL

TSGVHTFPAVLQSSGLYSLSSVVTVPSSNFGTQTYTCNVDHKPSNTKVD

KTVERKCCVECPPCPAPPVAGPSVFLFPPKPKDTLMISRTPEVTCVVVD

VSHEDPEVQFNWYVDGVEVHNAKTKPREEQFNSTFRVVSVLTVVHQDWL

NGKEYKCKVSNKGLPAPIEKTISKTKGQPREPQVYTLPPSREEMTKNQV

SLTCLVKGFYPSDIAVEWESNGQPENNYKTTPPMLDSDGSFFLYSKLTV

DKSRWQQGNVFSCSVMHEALHNHYTQKSLSLSPGK//.
```

Constant region sequences of other IgG isotypes are known in the art for making recombinant versions of the inventive immunoglobulin having an IgG1, IgG2, IgG3, or IgG4 immunoglobulin isotype, if desired. In general, human IgG2 can be used for targets where effector functions are not desired, and human IgG1 in situations where such effector functions (e.g., antibody-dependent cytotoxicity (ADCC)) are desired. Human IgG3 has a relatively short half life and human IgG4 forms antibody "half-molecules." There are four known allotypes of human IgG1. The preferred allotype is referred to as "hIgG1z", also known as the "KEEM" allotype. Human IgG1 allotypes "hIgG1za" (KDEL), "hIgG1f" (REEM), and "hIgG1fa" are also useful; all appear to have ADCC effector function.

Human hIgG1z heavy chain (HC) constant domain has the amino acid sequence:

```
                                           SEQ ID NO: 87
ASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVD

KKVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMT

KNQVSLTCLVKGFYPSDIAVEWESNGQPENNYKTTPPVLDSDGSFFLYS

KLTVDKSRWQQGNVFSCSVMHEALHNHYTQKSLSLSPGK//.
```

Human hIgG1za heavy chain (HC) constant domain has the amino acid sequence:

```
                                           SEQ ID NO: 88
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK//.
```

Human hIgG1f heavy chain (HC) constant domain has the amino acid sequence:

```
                                           SEQ ID NO: 127
ASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVD

KRVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMT

KNQVSLTCLVKGFYPSDIAVEWESNGQPENNYKTTPPVLDSDGSFFLYS

KLTVDKSRWQQGNVFSCSVMHEALHNHYTQKSLSLSPGK//.
```

Human hIgG1fa heavy chain (HC) constant domain has the amino acid sequence:

```
                                           SEQ ID NO: 90
ASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVD

KRVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYS

KLTVDKSRWQQGNVFSCSVMHEALHNHYTQKSLSLSPGK//.
```

One example of a human immunoglobulin light chain (LC) constant region sequence is the following (designated "CL-1"):

```
                                           SEQ ID NO: 91
GQPKANPTVTLFPPSSEELQANKATLVCLISDFYPGAVTVAWKAD

GSPVKAGVETTKPSKQSNNKYAASSYLSLTPEQWKSHRSYSCQVTHEGS

TVEKTVAPTECS//.
```

CL-1 is useful to increase the pI of antibodies and is convenient. There are three other human immunoglobulin light chain constant regions, designated "CL-2", "CL-3" and "CL-7", which can also be used within the scope of the present invention. CL-2 and CL-3 are more common in the human population.

CL-2 human light chain (LC) constant domain has the amino acid sequence:

```
                                                    SEQ ID NO: 92
Gqpkaapsvtlfppsseelqankativclisdfypgavtvawkadsspvkagvetttpskqsnnkyaassylsltpeq wkshrsyscqvthegstvektvaptecs//.
```

CL-3 human LC constant domain has the amino acid sequence:

```
                                                    SEQ ID NO: 93
gqpkaapsvtlfppsseelqankativelisdfypgavtvawkadsspvkagvetttpskqsnnkyaassylslipeq wkshksyscqvthegstvektvaptecs/.
```

CL-7 human LC constant domain has the amino acid sequence:

SEQ ID NO: 94
Gqpkaapsvtlfppsseelqankativelvsdfypgavtvawkadgspvkvgvettkpskqsnnky aassylsltpeqwkshrsyscrythegstvektvapaecs//.

Human LC kappa constant region has the amino acid sequence:

SEQ ID NO: 129
RTVAAPSVFIFPPSDEQLKSGTASVVCLLNNFYPREAKVQWKVDN

ALQSGNSQESVTEQDSKDSTYSLSSTLTLSKADYEKHKVYACEVTHQGL

SSPVTKSFNRGEC//.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope or domain on the target (e.g., human IL-17R or human TR2), however within the scope of the present invention, the original CDR sequences have been deliberately modified so as not significantly to bind to human IL-17R or TR2 targets. From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, *J. Mol. Biol.* 196:901-917; Chothia et al., 1989, *Nature* 342:878-883.

Specific examples of some of the full length light and heavy chains of the antibodies that are provided and their corresponding amino acid sequences are summarized in Table 1A and Table 1B below. Table 1A shows exemplary light chain sequences. Table 1B shows exemplary heavy chain sequences, some of which include constant region human IgG2 (SEQ ID NO:86) and some of which include constant region human IgG1f (SEQ ID NO:127). However, encompassed within the present invention are immunoglobulins with sequence changes in the constant or framework regions of those listed in Table 1A and/or Table 1B (e.g. IgG4 vs IgG2, CL2 vs CL1). Also, signal peptide (SP) sequences for all of the sequence in Table 1A and Table 1B are included, such as, the VK-1 SP signal peptide:

(SEQ ID NO: 103)
MDMRVPAQLLGLLLLWLRGARC, (SEQ ID NO: 104)
MEAPAQLLFLLLLWLPDTTG, (SEQ ID NO: 105)
MEWTWRVLFLVAAATGAHS, (SEQ ID NO: 106)
METPAQLLFLLLLWLPDTTG,

-continued (SEQ ID NO: 107)
MKHLWFFLLLVAAPRWVLS, but any other suitable signal peptide sequence may be employed within the scope of the invention. Another example of a useful signal peptide sequence is VH21 SP MEWSWVFLFFLSVTTGVHS (SEQ ID NO:95). Other exemplary signal peptide sequences are shown in Table 1A-B.

TABLE 1A

Immunoglobulin Light Chain Sequences. Signal peptide sequences are indicated by underline.

| SEQ ID NO: | Designation | Sequence |
|---|---|---|
| 109 | 16435 (LC: P66L, D90E) | MEAPAQLLFLLLLWLPDTTGEIVMTQSPATLSV SPGERATLSCRASQSVSSNLAWFQQKPGQAPR LLIYDASTRATGVPARFSGSGSGTEFTLTISSLQ SEDFAVYYCQQYDNWPLTFGGGTKVEIKRTVA APSVFIFPPSDEQLKSGTASVVCLLNNFYPREAK VQWKVDNALQSGNSQESVTEQDSKDSTYSLSS TLTLSKADYEKHKVYACEVTHQGLSSPVTKSF NRGEC |
| 110 | 16435 (LC: P66L, D90E) | EIVMTQSPATLSVSPGERATLSCRASQSVSSNL AWFQQKPGQAPRLLIYDASTRATGVPARFSGS GSGTEFTLTISSLQSEDFAVYYCQQYDNWPLTF GGGTKVEIKRTVAAPSVFIFPPSDEQLKSGTASV VCLLNNFYPREAKVQWKVDNALQSGNSQESV TEQDSKDSTYSLSSTLTLSKADYEKHKVYACE VTHQGLSSPVTKSFNRGEC |
| 121 | 16444 (LC: P66L, D90E, W114A) | MEAPAQLLFLLLLWLPDTTGEIVMTQSPATLSV SPGERATLSCRASQSVSSNLAWFQQKPGQAPR LLIYDASTRATGVPARFSGSGSGTEFTLTISSLQ SEDFAVYYCQQYDNAPLTFGGGTKVEIKRTVA APSVFIFPPSDEQLKSGTASVVCLLNNFYPREAK VQWKVDNALQSGNSQESVTEQDSKDSTYSLSS TLTLSKADYEKHKVYACEVTHQGLSSPVTKSF NRGEC |
| 122 | 16444 (LC: P66L, D90E, W114A) | EIVMTQSPATLSVSPGERATLSCRASQSVSSNL AWFQQKPGQAPRLLIYDASTRATGVPARFSGS GSGTEFTLTISSLQSEDFAVYYCQQYDNAPLTF GGGTKVEIKRTVAAPSVFIFPPSDEQLKSGTASV VCLLNNFYPREAKVQWKVDNALQSGNSQESV TEQDSKDSTYSLSSTLTLSKADYEKHKVYACE VTHQGLSSPVTKSFNRGEC |
| 97 | 4241 (LC:Y53A) | METPAQLLFLLLLWLPDTTGEIVLTQSPGTLSLS PGERATLSCRASQGISRSALAWYQQKPGQAPSL LIYGASSRATGIPDRFSGSGSGTDFTLTISRLEPE DFAVYYCQQFGSSPWTFGQGTKVEIKRTVAAP SVFIFPPSDEQLKSGTASVVCLLNNFYPREAKV QWKVDNALQSGNSQESVTEQDSKDSTYSLSST LTLSKADYEKHKVYACEVTHQGLSSPVTKSFN RGEC |
| 98 | 4241 (LC:Y53A) | EIVLTQSPGTLSLSPGERATLSCRASQGISRSAL AWYQQKPGQAPSLLIYGASSRATGIPDRFSGSG SGTDFTLTISRLEPEDFAVYYCQQFGSSPWTFG QGTKVEIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |

TABLE 1A-continued

Immunoglobulin Light Chain Sequences. Signal peptide sequences are indicated by underline.

| SEQ ID NO: | Designation | Sequence |
|---|---|---|
| 115 | 4341 (LC:Y53E) | METPAQLLFLLLLWLPDTTGEIVLTQSPGTLSLS PGERATLSCRASQGISRSELAWYQQKPGQAPSL LIYGASSRATGIPDRFSGSGSGTDFTLTISRLEPE DFAVYYCQQFGSSPWTFGQGTKVEIKRTVAAP SVFIFPPSDEQLKSGTASVVCLLNNFYPREAKV QWKVDNALQSGNSQESVTEQDSKDSTYSLSST LTLSKADYEKHKVYACEVTHQGLSSPVTKSFN RGEC |
| 116 | 4341 (LC:Y53E) | EIVLTQSPGTLSLSPGERATLSCRASQGISRSELA WYQQKPGQAPSLLIYGASSRATGIPDRFSGSGS GTDFTLTISRLEPEDFAVYYCQQFGSSPWTFGQ GTKVEIKRTVAAPSVFIFPPSDEQLKSGTASVVC LLNNFYPREAKVQWKVDNALQSGNSQESVTE QDSKDSTYSLSSTLTLSKADYEKHKVYACEVT HQGLSSPVTKSFNRGEC |

TABLE 1B

Immunoglobulin Heavy Chain Sequences. Signal peptide sequences are indicated by underline.

| SEQ ID NO: | Designation | Sequence |
|---|---|---|
| 112 | 16435 (HC:R118A) | MEWTWRVLFLVAAATGAHSQVQLVQSGA EVKKPGASVKVSCKASGYTFTRYGISWVRQ APGQGLEWMGWISTYSGNTNYAQKLQGRV TMTTDTSTSTAYMELRSLRSDDTAVYYCAR AQLYFDYWGQGTLVTVSSASTKGPSVFPLA PCSRSTSESTAALGCLVKDYFPEPVTVSWNS GALTSGVHTFPAVLQSSGLYSLSSVVTVPSS NFGTQTYTCNVDHKPSNTKVDKTVERKCC VECPPCPAPPVAGPSVFLFPPKPKDTLMISRT PEVTCVVVDVSHEDPEVQFNWYVDGVEVH NAKTKPREEQFNSTFRVVSVLTVVHQDWL NGKEYKCKVSNKGLPAPIEKTISKTKGQPRE PQVYTLPPSREEMTKNQVSLTCLVKGFYPS DIAVEWESNGQPENNYKTTPPMLDSDGSFF LYSKLTVDKSRWQQGNVFSCSVMHEALHN HYTQKSLSLSPGK |
| 113 | 16435 (HC:R118A) | QVQLVQSGAEVKKPGASVKVSCKASGYTF TRYGISWVRQAPGQGLEWMGWISTYSGNT NYAQKLQGRVTMTTDTSTSTAYMELRSLRS DDTAVYYCARAQLYFDYWGQGTLVTVSSA STKGPSVFPLAPCSRSTSESTAALGCLVKDY FPEPVTVSWNSGALTSGVHTFPAVLQSSGL YSLSSVVTVPSSNFGTQTYTCNVDHKPSNT KVDKTVERKCCVECPPCPAPPVAGPSVFLFP PKPKDTLMISRTPEVTCVVVDVSHEDPEVQ FNWYVDGVEVHNAKTKPREEQFNSTFRVV SVLTVVHQDWLNGKEYKCKVSNKGLPAPI EKTISKTKGQPREPQVYTLPPSREEMTKNQV SLTCLVKGFYPSDIAVEWESNGQPENNYKT TPPMLDSDGSFFLYSKLTVDKSRWQQGNVF SCSVMHEALHNHYTQKSLSLSPGK |
| 124 | 16444 (HC: R118A, L120Q) | MEWTWRVLFLVAAATGAHSQVQLVQSGA EVKKPGASVKVSCKASGYTFTRYGISWVRQ APGQGLEWMGWISTYSGNTNYAQKLQGRV TMTTDTSTSTAYMELRSLRSDDTAVYYCAR AQQYFDYWGQGTLVTVSSASTKGPSVFPLA PCSRSTSESTAALGCLVKDYFPEPVTVSWNS GALTSGVHTFPAVLQSSGLYSLSSVVTVPSS NFGTQTYTCNVDHKPSNTKVDKTVERKCC VECPPCPAPPVAGPSVFLFPPKPKDTLMISRT PEVTCVVVDVSHEDPEVQFNWYVDGVEVH NAKTKPREEQFNSTFRVVSVLTVVHQDWL NGKEYKCKVSNKGLPAPIEKTISKTKGQPRE PQVYTLPPSREEMTKNQVSLTCLVKGFYPS DIAVEWESNGQPENNYKTTPPMLDSDGSFF LYSKLTVDKSRWQQGNVFSCSVMHEALHN HYTQKSLSLSPGK |
| 125 | 16444 (HC: R118A, L120Q) | QVQLVQSGAEVKKPGASVKVSCKASGYTF TRYGISWVRQAPGQGLEWMGWISTYSGNT NYAQKLQGRVTMTTDTSTSTAYMELRSLRS DDTAVYYCARAQQYFDYWGQGTLVTVSS ASTKGPSVFPLAPCSRSTSESTAALGCLVKD YFPEPVTVSWNSGALTSGVHTFPAVLQSSG LYSLSSVVTVPSSNFGTQTYTCNVDHKPSNT KVDKTVERKCCVECPPCPAPPVAGPSVFLFP PKPKDTLMISRTPEVTCVVVDVSHEDPEVQ FNWYVDGVEVHNAKTKPREEQFNSTFRVV SVLTVVHQDWLNGKEYKCKVSNKGLPAPI EKTISKTKGQPREPQVYTLPPSREEMTKNQV SLTCLVKGFYPSDIAVEWESNGQPENNYKT TPPMLDSDGSFFLYSKLTVDKSRWQQGNVF SCSVMHEALHNHYTQKSLSLSPGK |
| 100 | 4241 (HC: Y125E) | MKHLWFFLLLVAAPRWVLSQVQLQESGPG LVKPSQTLSLTCTVSGGSISSGDYFWSWIRQ LPGKGLEWIGHIHNSGTTYYNPSLKSRVTIS VDTSKKQFSLRLSSVTAADTAVYYCARDRG GDYEYGMDVWGQGTTVTVSSASTKGPSVF PLAPSSKSTSGGTAALGCLVKDYFPEPVTVS WNSGALTSGVHTFPAVLQSSGLYSLSSVVT VPSSSLGTQTYICNVNHKPSNTKVDKRVEP KSCDKTHTCPPCPAPELLGGPSVFLFPPKPK DTLMISRTPEVTCVVVDVSHEDPEVKFNWY VDGVEVHNAKTKPREEQYNSTYRVVSVLT VLHQDWLNGKEYKCKVSNKALPAPIEKTIS KAKGQPREPQVYTLPPSREEMTKNQVSLTC LVKGFYPSDIAVEWESNGQPENNYKTTPPV LDSDGSFFLYSKLTVDKSRWQQGNVFSCSV MHEALHNHYTQKSLSLSPGK |
| 101 | 4241 (HC:Y125E) | QVQLQESGPGLVKPSQTLSLTCTVSGGSISS GDYFWSWIRQLPGKGLEWIGHIHNSGTTYY NPSLKSRVTISVDTSKKQFSLRLSSVTAADT AVYYCARDRGGDYEYGMDVWGQGTTVTV SSASTKGPSVFPLAPSSKSTSGGTAALGCLV KDYFPEPVTVSWNSGALTSGVHTFPAVLQS SGLYSLSSVVTVPSSSLGTQTYICNVNHKPS NTKVDKRVEPKSCDKTHTCPPCPAPELLGG PSVFLFPPKPKDTLMISRTPEVTCVVVDVSH EDPEVKFNWYVDGVEVHNAKTKPREEQYN STYRVVSVLTVLHQDWLNGKEYKCKVSNK ALPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| 118 | 4341 (HC:Y125A) | MKHLWFFLLLVAAPRWVLSQVQLQESGPG LVKPSQTLSLTCTVSGGSISSGDYFWSWIRQ LPGKGLEWIGHIHNSGTTYYNPSLKSRVTIS VDTSKKQFSLRLSSVTAADTAVYYCARDRG GDYAYGMDVWGQGTTVTVSSASTKGPSVF PLAPSSKSTSGGTAALGCLVKDYFPEPVTVS WNSGALTSGVHTFPAVLQSSGLYSLSSVVT VPSSSLGTQTYICNVNHKPSNTKVDKRVEP KSCDKTHTCPPCPAPELLGGPSVFLFPPKPK DTLMISRTPEVTCVVVDVSHEDPEVKFNWY VDGVEVHNAKTKPREEQYNSTYRVVSVLT VLHQDWLNGKEYKCKVSNKALPAPIEKTIS KAKGQPREPQVYTLPPSREEMTKNQVSLTC LVKGFYPSDIAVEWESNGQPENNYKTTPPV LDSDGSFFLYSKLTVDKSRWQQGNVFSCSV MHEALHNHYTQKSLSLSPGK |

TABLE 1B-continued

Immunoglobulin Heavy Chain Sequences. Signal peptide sequences are indicated by underline.

| SEQ ID NO: | Designation | Sequence |
|---|---|---|
| 119 | 4341 (HC:Y125A) | QVQLQESGPGLVKPSQTLSLTCTVSGGSISS GDYFWSWIRQLPGKGLEWIGHIHNSGTTYY NPSLKSRVTISVDTSKKQFSLRLSSVTAADT AVYYCARDRGGDYAYGMDVWGQGTTVT VSSASTKGPSVFPLAPSSKSTSGGTAALGCL VKDYFPEPVTVSWNSGALTSGVHTFPAVLQ SSGLYSLSSVVTVPSSSLGTQTYICNVNHKP SNTKVDKRVEPKSCDKTHTCPPCPAPELLG GPSVFLFPPKPKDTLMISRTPEVTCVVVDVS HEDPEVKFNWYVDGVEVHNAKTKPREEQY NSTYRVVSVLTVLHQDWLNGKEYKCKVSN KALPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |

Some useful embodiments of the isolated immunoglobulin comprising an antibody or antibody fragment, comprise:

(a) an immunoglobulin heavy chain comprising the amino acid sequence of SEQ ID NO:113, or comprising the foregoing sequence from which one, two, three, four or five amino acid residues are lacking from the N-terminal or C-terminal, or both; and an immunoglobulin light chain comprising the amino acid sequence of SEQ ID NO:110, or comprising the foregoing sequence from which one, two, three, four or five amino acid residues are lacking from the N-terminal or C-terminal, or both; or (b) an immunoglobulin heavy chain comprising the amino acid sequence of SEQ ID NO:125, or comprising the foregoing sequence from which one, two, three, four or five amino acid residues are lacking from the N-terminal or C-terminal, or both; and an immunoglobulin light chain comprising the amino acid sequence of SEQ ID NO:122, or comprising the foregoing sequence from which one, two, three, four or five amino acid residues are lacking from the N-terminal or C-terminal, or both; or (c) an immunoglobulin heavy chain comprising the amino acid sequence of SEQ ID NO:101, or comprising the foregoing sequence from which one, two, three, four or five amino acid residues are lacking from the N-terminal or C-terminal, or both; and an immunoglobulin light chain comprising the amino acid sequence of SEQ ID NO:98, or comprising the foregoing sequence from which one, two, three, four or five amino acid residues are lacking from the N-terminal or C-terminal, or both; or (d) an immunoglobulin heavy chain comprising the amino acid sequence of SEQ ID NO:119, or comprising the foregoing sequence from which one, two, three, four or five amino acid residues are lacking from the N-terminal or C-terminal, or both; and an immunoglobulin light chain comprising the amino acid sequence of SEQ ID NO:116, or comprising the foregoing sequence from which one, two, three, four or five amino acid residues are lacking from the N-terminal or C-terminal, or both.

In some instances, such antibodies include at least one heavy chain and one light chain, whereas in other instances the variant forms contain two identical light chains and two identical heavy chains. It is within the scope of the invention that the heavy chain(s) and/or light chain(s) may have one, two, three, four or five amino acid residues lacking from the N-terminal or C-terminal, or both, in relation to any one of the heavy and light chains set forth in Tables 1A and Table 1B, e.g., due to post-translational modifications. For example, CHO cells typically cleave off a C-terminal lysine. As described herein, certain embodiments comprising conjugates with one or more pharmacologically active chemical moieties, such as a phramacologically active polypeptide can comprise heteromultimers, such as monovalent heterodimers, heterotrimers, or heterotetramers, as illustrated schematically in FIGS. 1F-1N (see, also Table 2D).

Variable Domains of Immunogloblins, e.g., Antibodies

The various heavy chain and light chain variable regions provided herein are depicted in Table 2A-B. Each of these variable regions may be attached to the above heavy and light chain constant regions to form a complete antibody heavy and light chain, respectively. Further, each of the so generated heavy and light chain sequences may be combined to form a complete antibody structure. It should be understood that the heavy chain and light chain variable regions provided herein can also be attached to other constant domains having different sequences than the exemplary sequences listed above.

Also provided are immunoglobulins, including antibodies or antibody fragments, that contain or include at least one immunoglobulin light chain variable region selected from $V_L2$, $V_L3$, $V_L4$, and $V_L5$, as shown in Table 2A below, and at least one immunoglobulin heavy chain variable region selected from $V_H2$, $V_H3$, $V_H4$, $V_H5$, $V_H6$, $V_H7$, $V_H8$, $V_H9$, $V_H10$, and $V_H11$, as shown in Table 2B below, and immunologically functional fragments, derivatives, muteins and variants of these light chain and heavy chain variable regions. Examples of such embodiments are found in Table 2C and Table 2D below.

Also provided are immunoglobulins, including antibodies or antibody fragments, that contain or include at least one immunoglobulin light chain variable region selected from $V_L7$, $V_L8$, $V_L9$, $V_L10$, $V_L11$, $V_L12$, $V_L13$, $V_L14$, $V_L15$ and $V_L16$, as shown in Table 2A below, and at least one immunoglobulin heavy chain variable region selected from $V_H13$, $V_H14$, $V_H15$, $V_H16$, $V_H17$, $V_H18$, $V_H19$, $V_H20$, $V_H21$, $V_H22$, $V_H23$, $V_H24$, $V_H25$, $V_H26$, $V_H27$, $V_H28$, $V_H29$, $V_H30$, $V_H31$, $V_H32$, $V_H33$, $V_H34$, $V_H35$, and $V_H36$, as shown in Table 2B below, and immunologically functional fragments, derivatives, muteins and variants of these light chain and heavy chain variable regions. Examples of such embodiments are found in Table 2C and Table 2D below.

Exemplary embodiments of the inventive immunoglobulin include those, in which:

the heavy chain variable region comprises the amino acid sequence of SEQ ID NO:323 [VH10]; and the light chain variable region comprises the amino acid sequence of SEQ ID NO:188 [VL4]; or the light chain variable region comprises the amino acid sequence of SEQ ID NO:196 [VL8]; and the heavy chain variable region comprises the amino acid sequence of SEQ ID NO:353 [VH25]; or the light chain variable region comprises the amino acid sequence of SEQ ID NO:202 [VL11]; and the heavy chain variable region comprises the amino acid sequence of SEQ ID NO:349 [VH23]; or the heavy chain variable region comprises the amino acid sequence of SEQ ID NO:325 [VH11]; and the light chain variable region comprises the amino acid sequence of SEQ ID NO:190 [VL5].

Immunoglobulins of this type can generally be designated by the formula "$V_Hx/V_Ly$," where "x" corresponds to the number of heavy chain variable regions included in the immunoglobulin and "y" corresponds to the number of the light chain variable regions included in the immunoglobulin (in general, x and y are each 1 or 2).

TABLE 2A

Exemplary V_L Chains. Optional N-terminal signal sequences are not shown, but may be reflected in the arbitrary "description" of the V_L.

| Designation | Description | SEQ ID NO | Amino Acid Sequence |
|---|---|---|---|
| VL1 | Anti-IL-17R Wild type (WT) | 182 | EIVMTQSPATLSVSPGERATLSCRASQSVSSNLAWFQQKPGQAPRPLIYDASTRATGVPARFSGSGSGTDFTLTISSLQSEDFAVYYCQQYDNWPLTFGGGTKVEIK |
| VL2 | W114A | 184 | EIVMTQSPATLSVSPGERATLSCRASQSVSSNLAWFQQKPGQAPRPLIYDASTRATGVPARFSGSGSGTDFTLTISSLQSEDFAVYYCQQYDNAPLTFGGGTKVEIK |
| VL3 | Y111A | 186 | EIVMTQSPATLSVSPGERATLSCRASQSVSSNLAWFQQKPGQAPRPLIYDASTRATGVPARFSGSGSGTDFTLTISSLQSEDFAVYYCQQADNWPLTFGGGTKVEIK |
| VL4 | P66L, D90E | 188 | EIVMTQSPATLSVSPGERATLSCRASQSVSSNLAWFQQKPGQAPRLLIYDASTRATGVPARFSGSGSGTEFTLTISSLQSEDFAVYYCQQYDNWPLTFGGGTKVEIK |
| VL5 | P66L, D90E, W114A | 190 | EIVMTQSPATLSVSPGERATLSCRASQSVSSNLAWFQQKPGQAPRLLIYDASTRATGVPARFSGSGSGTEFTLTISSLQSEDFAVYYCQQYDNAPLTFGGGTKVEIK |
| VL6 | Anti-huTR2 Wild type (WT) | 192 | EIVLTQSPGTLSLSPGERATLSCRASQGISRSYLAWYQQKPGQAPSLLIYGASSRATGIPDRFSGSGSGTDFTLTISRLEPEDFAVYYCQQFGSSPWTFGQGTKVEIK |
| VL7 | F112A | 194 | EIVLTQSPGTLSLSPGERATLSCRASQGISRSYLAWYQQKPGQAPSLLIYGASSRATGIPDRFSGSGSGTDFTLTISRLEPEDFAVYYCQQAGSSPWTFGQGTKVEIK |
| VL8 | Y53A | 196 | EIVLTQSPGTLSLSPGERATLSCRASQGISRSYLAWYQQKPGQAPSLLIYGASSRATGIPDRFSGSGSGTDFTLTISRLEPEDFAVYYCQQFGSSPWTFGQGTKVEIK |
| VL9 | W117A | 198 | EIVLTQSPGTLSLSPGERATLSCRASQGISRSYLAWYQQKPGQAPSLLIYGASSRATGIPDRFSGSGSGTDFTLTISRLEPEDFAVYYCQQFGSSPWTFGQGTKVEIK |
| VL10 | F112Y | 200 | EIVLTQSPGTLSLSPGERATLSCRASQGISRSYLAWYQQKPGQAPSLLIYGASSRATGIPDRFSGSGSGTDFTLTISRLEPEDFAVYYCQQYGSSPWTFGQGTKVEIK |
| VL11 | Y53E | 202 | EIVLTQSPGTLSLSPGERATLSCRASQGISRSELAWYQQKPGQAPSLLIYGASSRATGIPDRFSGSGSGTDFTLTISRLEPEDFAVYYCQQFGSSPWTFGQGTKVEIK |
| VL12 | Y53R | 204 | EIVLTQSPGTLSLSPGERATLSCRASQGISRSRLAWYQQKPGQAPSLLIYGASSRATGIPDRFSGSGSGTDFTLTISRLEPEDFAVYYCQQFGSSPWTFGQGTKVEIK |
| VL13 | F112E | 206 | EIVLTQSPGTLSLSPGERATLSCRASQGISRSYLAWYQQKPGQAPSLLIYGASSRATGIPDRFSGSGSGTDFTLTISRLEPEDFAVYYCQQEGSSPWTFGQGTKVEIK |

TABLE 2A-continued

Exemplary V_L Chains. Optional N-terminal signal sequences are not shown, but may be reflected in the arbitrary "description" of the V_L.

| Designation | Description | SEQ ID NO | Amino Acid Sequence |
|---|---|---|---|
| VL14 | F112R | 208 | EIVLTQSPGTLSLSPGERATLSCRASQGISRSYLAWYQQKPGQAPSLLIYGASSRATGIPDRFSGSGSGTDFTLTISRLEPEDFAVYYCQQRGSSPWTFGQGTKVEIK |
| VL15 | Y53A, F112A | 210 | EIVLTQSPGTLSLSPGERATLSCRASQGISRSYLAWYQQKPGQAPSLLIYGASSRATGIPDRFSGSGSGTDFTLTISRLEPEDFAVYYCQQAGSSPWTFGQGTKVEIK |
| VL16 | G48S, I49V, R51S | 212 | EIVLTQSPGTLSLSPGERATLSCRASQSVSSSYLAWYQQKPGQAPSLLIYGASSRATGIPDRFSGSGSGTDFTLTISRLEPEDFAVYYCQQAGSSPWTFGQGTKVEIK |

TABLE 2B

Exemplary V_H Chains. Optional N-terminal signal sequences are not shown, but may be reflected in the arbitrary "description" of the V_H.

| Designation | Description | SEQ ID NO | Amino Acid Sequence |
|---|---|---|---|
| VH1 | Anti-IL-17R Wild type (WT) | 305 | QVQLVQSGAEVKKPGASVKVSCKASGYTFTRYGISWVRQAPGQGLEWMGWISTYSGNTNYAQKLQGRVTMTTDTSTSTAYMELRSLRSDDTAVYYCARRQLYFDYWGQGTLVTVSS |
| VH2 | Y124A | 307 | QVQLVQSGAEVKKPGASVKVSCKASGYTFTRYGISWVRQAPGQGLEWMGWISTYSGNTNYAQKLQGRVTMTTDTSTSTAYMELRSLRSDDTAVYYCARRQLYFDAWGQGTLVTVSS |
| VH3 | F122A | 309 | QVQLVQSGAEVKKPGASVKVSCKASGYTFTRYGISWVRQAPGQGLEWMGWISTYSGNTNYAQKLQGRVTMTTDTSTSTAYMELRSLRSDDTAVYYCARRQLYADYWGQGTLVTVSS |
| VH4 | Y121A | 311 | QVQLVQSGAEVKKPGASVKVSCKASGYTFTRYGISWVRQAPGQGLEWMGWISTYSGNTNYAQKLQGRVTMTTDTSTSTAYMELRSLRSDDTAVYYCARRQLAFDYWGQGTLVTVSS |
| VH5 | Y79A | 313 | QVQLVQSGAEVKKPGASVKVSCKASGYTFTRYGISWVRQAPGQGLEWMGWISTYSGNTNAAQKLQGRVTMTTDTSTSTAYMELRSLRSDDTAVYYCARRQLYFDYWGQGTLVTVSS |
| VH6 | Y73A | 315 | QVQLVQSGAEVKKPGASVKVSCKASGYTFTRYGISWVRQAPGQGLEWMGWISTASGNTNYAQKLQGRVTMTTDTSTSTAYMELRSLRSDDTAVYYCARRQLYFDYWGQGTLVTVSS |
| VH7 | W69A | 317 | QVQLVQSGAEVKKPGASVKVSCKASGYTFTRYGISWVRQAPGQGLEWMGAISTYSGNTNYAQKLQGRVTMTTDTSTSTAYMELRSLRSDDTAVYYCARRQLYFDYWGQGTLVTVSS |

TABLE 2B-continued

Exemplary V_H Chains. Optional N-terminal signal sequences are not shown, but may be reflected in the arbitrary "description" of the V_H.

| Designation | Description | SEQ ID NO | Amino Acid Sequence |
|---|---|---|---|
| VH8 | Y51A | 319 | QVQLVQSGAEVKKPGASVKVSCKASG YTFTRAGISWVRQAPGQGLEWMGWIS TYSGNTNYAQKLQGRVTMTTDTSTST AYMELRSLRSDDTAVYYCARRQLYFD YWGQGTLVTVSS |
| VH9 | L12Q | 321 | QVQLVQSGAEVKKPGASVKVSCKASG YTFTRYGISWVRQAPGQGLEWMGWIS TYSGNTNYAQKLQGRVTMTTDTSTST AYMELRSLRSDDTAVYYCARRQQYFD YWGQGTLVTVSS |
| VH10 | R118A | 323 | QVQLVQSGAEVKKPGASVKVSCKASG YTFTRYGISWVRQAPGQGLEWMGWIS TYSGNTNYAQKLQGRVTMTTDTSTST AYMELRSLRSDDTAVYYCARAQLYFD YWGQGTLVTVSS |
| VH11 | R118A, L120Q | 325 | QVQLVQSGAEVKKPGASVKVSCKASG YTFTRYGISWVRQAPGQGLEWMGWIS TYSGNTNYAQKLQGRVTMTTDTSTST AYMELRSLRSDDTAVYYCARAQQYFD YWGQGTLVTVSS |
| VH12 | Anti-huTR2 Wild type (WT) | 327 | QVQLQESGPGLVKPSQTLSLTCTVSGG SISSGDYFWSWIRQLPGKGLEWIGHIHN SGTTYYNPSLKSRVTISVDTSKKQFSLR LSSVTAADTAVYYCARDRGGDYYYG MDVWGQGTTVTVSS |
| VH13 | D123A | 329 | QVQLQESGPGLVKPSQTLSLTCTVSGG SISSGDYFWSWIRQLPGKGLEWIGHIHN SGTTYYNPSLKSRVTISVDTSKKQFSLR LSSVTAADTAVYYCARDRGGAYYYG MDVWGQGTTVTVSS |
| VH14 | Y124A | 331 | QVQLQESGPGLVKPSQTLSLTCTVSGG SISSGDYFWSWIRQLPGKGLEWIGHIHN SGTTYYNPSLKSRVTISVDTSKKQFSLR LSSVTAADTAVYYCARDRGGDAYYG MDVWGQGTTVTVSS |
| VH15 | Y53A | 333 | QVQLQESGPGLVKPSQTLSLTCTVSGG SISSGDAFWSWIRQLPGKGLEWIGHIHN SGTTYYNPSLKSRVTISVDTSKKQFSLR LSSVTAADTAVYYCARDRGGDYYYG MDVWGQGTTVTVSS |
| VH16 | F54A | 335 | QVQLQESGPGLVKPSQTLSLTCTVSGG SISSGDYAWSWIRQLPGKGLEWIGHIHN SGTTYYNPSLKSRVTISVDTSKKQFSLR LSSVTAADTAVYYCARDRGGDYYYG MDVWGQGTTVTVSS |
| VH17 | F54E | 337 | QVQLQESGPGLVKPSQTLSLTCTVSGG SISSGDYEWSWIRQLPGKGLEWIGHIHN SGTTYYNPSLKSRVTISVDTSKKQFSLR LSSVTAADTAVYYCARDRGGDYYYG MDVWGQGTTVTVSS |
| VH18 | F54Y | 339 | QVQLQESGPGLVKPSQTLSLTCTVSGG SISSGDYYWSWIRQLPGKGLEWIGHIH NSGTTYYNPSLKSRVTISVDTSKKQFSL RLSSVTAADTAVYYCARDRGGDYYYG MDVWGQGTTVTVSS |
| VH19 | F54R | 341 | QVQLQESGPGLVKPSQTLSLTCTVSGG SISSGDYRWSWIRQLPGKGLEWIGHIHN SGTTYYNPSLKSRVTISVDTSKKQFSLR LSSVTAADTAVYYCARDRGGDYYYG MDVWGQGTTVTVSS |
| VH20 | W55A | 343 | QVQLQESGPGLVKPSQTLSLTCTVSGG SISSGDYFASWIRQLPGKGLEWIGHIHN SGTTYYNPSLKSRVTISVDTSKKQFSLR LSSVTAADTAVYYCARDRGGDYYYG MDVWGQGTTVTVSS |
| VH21 | Y79A | 345 | QVQLQESGPGLVKPSQTLSLTCTVSGG SISSGDYFWSWIRQLPGKGLEWIGHIHN SGTTAYNPSLKSRVTISVDTSKKQFSLR LSSVTAADTAVYYCARDRGGDYYYG MDVWGQGTTVTVSS |
| VH22 | Y80A | 347 | QVQLQESGPGLVKPSQTLSLTCTVSGG SISSGDYFWSWIRQLPGKGLEWIGHIHN SGTTYANPSLKSRVTISVDTSKKQFSLR LSSVTAADTAVYYCARDRGGDYYYG MDVWGQGTTVTVSS |
| VH23 | Y125A | 349 | QVQLQESGPGLVKPSQTLSLTCTVSGG SISSGDYFWSWIRQLPGKGLEWIGHIHN SGTTYYNPSLKSRVTISVDTSKKQFSLR LSSVTAADTAVYYCARDRGGDYAYG MDVWGQGTTVTVSS |
| VH24 | Y126A | 351 | QVQLQESGPGLVKPSQTLSLTCTVSGG SISSGDYFWSWIRQLPGKGLEWIGHIHN SGTTYYNPSLKSRVTISVDTSKKQFSLR LSSVTAADTAVYYCARDRGGDYYAG MDVWGQGTTVTVSS |
| VH25 | Y125E | 353 | QVQLQESGPGLVKPSQTLSLTCTVSGG SISSGDYFWSWIRQLPGKGLEWIGHIHN SGTTYYNPSLKSRVTISVDTSKKQFSLR LSSVTAADTAVYYCARDRGGDYEYGM DVWGQGTTVTVSS |
| VH26 | Y125R | 355 | QVQLQESGPGLVKPSQTLSLTCTVSGG SISSGDYFWSWIRQLPGKGLEWIGHIHN SGTTYYNPSLKSRVTISVDTSKKQFSLR LSSVTAADTAVYYCARDRGGDYRYGM DVWGQGTTVTVSS |
| VH27 | F54A, Y125A | 357 | QVQLQESGPGLVKPSQTLSLTCTVSGG SISSGDYAWSWIRQLPGKGLEWIGHIH NSGTTYYNPSLKSRVTISVDTSKKQFSL RLSSVTAADTAVYYCARDRGGDYAYG MDVWGQGTTVTVSS |
| VH28 | F54A, Y126A | 359 | QVQLQESGPGLVKPSQTLSLTCTVSGG SISSGDYAWSWIRQLPGKGLEWIGHIH NSGTTYYNPSLKSRVTISVDTSKKQFSL RLSSVTAADTAVYYCARDRGGDYYAG MDVWGQGTTVTVSS |
| VH29 | Y126E | 361 | QVQLQESGPGLVKPSQTLSLTCTVSGG SISSGDYFWSWIRQLPGKGLEWIGHIHN SGTTYYNPSLKSRVTISVDTSKKQFSLR LSSVTAADTAVYYCARDRGGDYYEGM DVWGQGTTVTVSS |
| VH30 | Y126R | 363 | QVQLQESGPGLVKPSQTLSLTCTVSGG SISSGDYFWSWIRQLPGKGLEWIGHIHN SGTTYYNPSLKSRVTISVDTSKKQFSLR LSSVTAADTAVYYCARDRGGDYYRGM DVWGQGTTVTVSS |
| VH31 | F54A, Y125A, Y126A | 365 | QVQLQESGPGLVKPSQTLSLTCTVSGG SISSGDYAWSWIRQLPGKGLEWIGHIH NSGTTYYNPSLKSRVTISVDTSKKQFSL RLSSVTAADTAVYYCARDRGGDYAAG MDVWGQGTTVTVSS |

TABLE 2B-continued

Exemplary V_H Chains. Optional N-terminal signal sequences are not shown, but may be reflected in the arbitrary "description" of the V_H.

| Designation | Description | SEQ ID NO | Amino Acid Sequence |
|---|---|---|---|
| VH32 | D123A, Y124A | 367 | QVQLQESGPGLVKPSQTLSLTCTVSGGSISSGDYFWSWIRQLPGKGLEWIGHIHNSGTTYYNPSLKSRVTISVDTSKKQFSLRLSSVTAADTAVYYCARDRGGAAYYGMDVWGQGTTVTVSS |
| VH33 | Y125A, Y126A | 369 | QVQLQESGPGLVKPSQTLSLTCTVSGGSISSGDYFWSWIRQLPGKGLEWIGHIHNSGTTYYNPSLKSRVTISVDTSKKQFSLRLSSVTAADTAVYYCARDRGGDYAAGMDVWGQGTTVTVSS |
| VH34 | Y124A, Y125A, Y126A | 371 | QVQLQESGPGLVKPSQTLSLTCTVSGGSISSGDYFWSWIRQLPGKGLEWIGHIHNSGTTYYNPSLKSRVTISVDTSKKQFSLRLSSVTAADTAVYYCARDRGGDAAAGMDVWGQGTTVTVSS |
| VH35 | H71Y, H73Y, N74Y, T77S | 373 | QVQLQESGPGLVKPSQTLSLTCTVSGGSISSGDYFWSWIRQLPGKGLEWIGYIYYSGSTYYNPSLKSRVTISVDTSKKQFSLRLSSVTAADTAVYYCARDRGGDYYYGMDVWGQGTTVTVSS |
| VH36 | R120Y, G122D, D125Y | 375 | QVQLQESGPGLVKPSQTLSLTCTVSGGSISSGDYFWSWIRQLPGKGLEWIGHIHNSGTTYYNPSLKSRVTISVDTSKKQFSLRLSSVTAADTAVYYCARDYGDYYYYYGMDVWGQGTTVTVSS |

TABLE 2C

Embodiments of the immunoglobulins containing the indicated V_L and V_H (or multimers thereof), as disclosed in Tables 2A and 2B above. Antibodies 16429 and 16449, also listed here, are positive control antibodies for human IL-17R and TR2, respectively.

| Antibody # | V_L | V_H |
|---|---|---|
| 1869 | VL6 | VH13 |
| 1870 | VL6 | VH14 |
| 1910 | VL7 | VH12 |
| 1911 | VL9 | VH12 |
| 1912 | VL6 | VH15 |
| 1913 | VL6 | VH16 |
| 1914 | VL6 | VH20 |
| 1915 | VL6 | VH21 |
| 1916 | VL6 | VH22 |
| 1919 | VL6 | VH23 |
| 1920 | VL6 | VH24 |
| 1921 | VL6 | VH32 |
| 1922 | VL6 | VH34 |
| 1961 | VL8 | VH16 |
| 1962 | VL8 | VH23 |
| 1963 | VL8 | VH24 |
| 1964 | VL7 | VH24 |
| 1965 | VL7 | VH23 |
| 1966 | VL7 | VH16 |
| 2281 | VL16 | VH12 |
| 2301 | VL10 | VH12 |
| 2302 | VL15 | VH12 |
| 2303 | VL11 | VH12 |
| 2304 | VL12 | VH12 |
| 2305 | VL13 | VH12 |
| 2306 | VL14 | VH12 |
| 2307 | VL6 | VH18 |
| 2321 | VL6 | VH35 |
| 2322 | VL6 | VH36 |
| 2323 | VL6 | VH27 |
| 2324 | VL6 | VH28 |
| 2325 | VL6 | VH19 |
| 2326 | VL6 | VH25 |
| 2327 | VL6 | VH26 |
| 2328 | VL6 | VH29 |
| 2329 | VL6 | VH30 |
| 2330 | VL6 | VH33 |
| 2331 | VL6 | VH31 |
| 2332 | VL6 | VH17 |
| 4241 | VL8 | VH25 |
| 4341 | VL11 | VH23 |
| 10182 | VL8 | VH26 |
| 10183 | VL12 | VH23 |
| 10184 | VL12 | VH26 |
| 10185 | VL11 | VH25 |
| 10186 | VL7 | VH28 |
| 10187 | VL7 | VH27 |
| 10188 | VL8 | VH28 |
| 10189 | VL8 | VH27 |
| 10190 | VL15 | VH24 |
| 10191 | VL15 | VH23 |
| 10192 | VL15 | VH16 |
| 16429 | VL1 | VH1 |
| 16430 | VL4 | VH1 |
| 16433 | VL5 | VH1 |
| 16434 | VL1 | VH10 |
| 16435 | VL4 | VH10 |
| 16436 | VL5 | VH10 |
| 16437 | VL1 | VH9 |
| 16438 | VL4 | VH9 |
| 16439 | VL5 | VH9 |
| 16440 | VL1 | VH11 |
| 16441 | VL4 | VH11 |
| 16444 | VL5 | VH11 |
| 16449 | VL6 | VH12 |
| 16613 | VL8 | VH12 |
| 16629 | VL3 | VH1 |
| 16630 | VL2 | VH1 |
| 16631 | VL1 | VH8 |
| 16632 | VL1 | VH7 |
| 16633 | VL1 | VH6 |
| 16634 | VL1 | VH5 |
| 16635 | VL1 | VH4 |
| 16636 | VL1 | VH3 |
| 16637 | VL1 | VH2 |

TABLE 2D

Embodiments of the carrier antibodies containing the indicated V_L and V_H (or multimers thereof), as disclosed in Tables 2A and 2B above, and a fusion partner as described in greater detail in Examples 5-6 herein.

| Antibody # | V_L | V_H | Fusion partner |
|---|---|---|---|
| 3742 | VL1 | VH1 | ShK(1-35, Q16K) |
| 10162 | VL4 | VH10 | FGF21 |
| 10163 | VL11 | VH23 | FGF21 |
| 10164 | VL11 | VH23 | ShK(1-35, Q16K) |

In some embodiments, the immunoglobulin (including antibodies and antibody fragments) can be useful as a therapeutic molecule which can be used singularly or in combination with other therapeutics to achieve the desired effects. In such embodiments, the inventive immunoglobulin (including antibodies and antibody fragments) further comprises one to twenty-four, one to sixteen, one to eight, or one to four, pharmacologically active chemical moieties conjugated thereto, whether a small molecule or a polypeptide. The pharmacologically active small molecule or polypeptide chemical moieties can be conjugated at or via the N-terminal or C-terminal residue of the immunoglobulin immunoglobulin monomers (e.g., LC or HC monomers), chemical reactions known in the art and further described herein. Alternatively encompassed by the invention, is conjugation of the pharmacologically active chemical moiety, or moieties, at or via functional groups on one or more side chains of the amino acid residue(s) within the primary chain of the inventive immunoglobulin. Useful methods and internal conjugation sites (e.g., particular cysteine residues) within immunoglobulin chains are known in the art (e.g., Gegg et al., Modified Fc Molecules, published in WO 2007/022070 and US 20070269369, which are incorporated herein by reference in their entireties).

In other embodiments of the invention, in which the pharmacologically active chemical moiety is a polypeptide, a recombinant fusion protein can be produced with the pharmacologically active polypeptide being inserted in the primary amino acid sequence of the of the immunoglobulin heavy chain within an internal loop of the Fc domain of the immunoglobulin heavy chain, instead of at the N- and/or C-terminus, as further described in the Examples herein and in the art (e.g., Gegg et al., U.S. Pat. No. 7,442,778; U.S. Pat. No. 7,655,765; U.S. Pat. No. 7,655,764; U.S. Pat. No. 7,662,931; U.S. Pat. No. 7,645,861; published U.S. Patent Applications US 2009/0281286; and US 2009/0286964, each of which are incorporated herein by reference in their entireties).

"Conjugated" means that at least two chemical moieties are covalently linked, or bound to each other, either directly, or optionally, via a peptidyl or non-peptidyl linker moiety that is itself covalently linked to both of the moieties. For example, covalent linkage can be via an amino acid residue of a peptide or protein, including via an alpha amino group, an alpha carboxyl group, or via a side chain. The method by which the covalent linkage is achieved is not critical, for example, whether "conjugation" is by chemical synthetic means or by recombinant expression of fused (i.e., conjugated) partners in a fusion protein.

As stated above, some embodiments of the inventive compositions involve at least one pharmacologically active polypeptide moiety conjugated to the pharmacologically inactive immunoglobulin of the invention, for example constituting a recombinant fusion protein of the pharmacologically active polypeptide moiety conjugated to the pharmacologically inactive immunoglobulin of the invention. The term "pharmacologically active" means that a substance so described is determined to have activity that affects a medical parameter (e.g., blood pressure, blood cell count, cholesterol level, pain perception) or disease state (e.g., cancer, autoimmune disorders, chronic pain), excluding mere immunogenicity, if any, of the substance. Conversely, the term "pharmacologically inactive" means that no activity affecting a medical parameter or disease state can be determined for that substance, excluding mere immunogenicity, if any, of the substance. Thus, pharmacologically active peptides or proteins comprise agonistic or mimetic and antagonistic peptides as defined below. The present invention encompasses the use of any pharmacologically active protein, which has an amino acid sequence ranging from about 5 to about 80 amino acid residues in length, and which is amenable to recombinant expression. In some useful embodiments of the invention, the pharmacologically active protein is modified in one or more ways relative to a native sequence of interest, including amino acid additions or insertions, amino acid deletions, peptide truncations, amino acid substitutions, or chemical derivatization of amino acid residues (accomplished by known chemical techniques), so long as the requisite bioactivity is maintained.

The terms "-mimetic peptide," "peptide mimetic," and "-agonist peptide" refer to a peptide or protein having biological activity comparable to a naturally occurring protein of interest, for example, but not limited to, a toxin peptide molecule, e.g., ShK or OSK1 toxin peptides, or peptide analogs thereof. These terms further include peptides that indirectly mimic the activity of a naturally occurring peptide molecule, such as by potentiating the effects of the naturally occurring molecule.

The term "-antagonist peptide," "peptide antagonist," and "inhibitor peptide" refer to a peptide that blocks or in some way interferes with the biological activity of a receptor of interest, or has biological activity comparable to a known antagonist or inhibitor of a receptor of interest (such as, but not limited to, an ion channel or a G-Protein Coupled Receptor (GPCR)).

Examples of pharmacologically active proteins that can be used within the present invention include, but are not limited to, a toxin peptide (e.g., OSK1 or an OSK1 peptide analog; ShK or an ShK peptide analog), an IL-6 binding peptide, a CGRP peptide antagonist, a bradykinin B1 receptor peptide antagonist, a parathyroid hormone (PTH) agonist peptide, a parathyroid hormone (PTH) antagonist peptide, an ang-1 binding peptide, an ang-2 binding peptide, a myostatin binding peptide, an erythropoietin-mimetic (EPO-mimetic) peptide, a FGF21 peptide, a thrombopoietin-mimetic (TPO-mimetic) peptide (e.g., AMP2 or AMP5), a nerve growth factor (NGF) binding peptide, a B cell activating factor (BAFF) binding peptide, and a glucagon-like peptide (GLP)-1 or a peptide mimetic thereof or GLP-2 or a peptide mimetic thereof.

Glucagon-like peptide 1 (GLP-1) and the related peptide glucagon are produced via differential processing of proglucagon and have opposing biological activities. Proglucagon itself is produced in α-cells of the pancreas and in the enteroendocrine L-cells, which are located primarily in the distal small intestine and colon. In the pancreas, glucagon is selectively cleaved from proglucagon. In the intestine, in contrast, proglucagon is processed to form GLP-1 and glucagon-like peptide 2 (GLP-2), which correspond to amino acid residues 78-107 and 126-158 of proglucagon, respectively (see, e.g., Irwin and Wong, 1995, *Mol. Endocrinol.* 9:267-277 and Bell et al., 1983, *Nature* 304:368-371). By convention, the numbering of the amino acids of GLP-1 is based on the GLP-1 (1-37) formed from cleavage of proglucagon. The biologically active forms are generated from further processing of this peptide, which, in one numbering convention, yields GLP-1 (7-37)-OH and GLP-1 (7-36)-$NH_2$. Both GLP-1 (7-37)-OH (or simply GLP-1 (7-37)) and GLP-1 (7-36)-$NH_2$ have the same activities. For convenience, the term "GLP-1", is used to refer to both of these forms. The first amino acid of these processed peptides is His7 in this numbering convention. Another numbering convention recognized in the art, however, assumes that the numbering of the processed peptide begins with His as position 1 rather than position 7. Thus, in this numbering scheme, GLP-1 (1-31) is the same as GLP-1(7-37), and GLP-1(1-30) is the same as GLP-1 (7-36). Examples of GLP-1 mimetic polypeptide sequences include:

(SEQ ID NO: 290)
HGEGTFTSDQSSYLEGQAAKEFIAWLVKGRG//;

-continued

HGEGTFTSDQSSYLEGQAAKEFIAWLQKGRG// ; (SEQ ID NO: 291)

HGEGTFTSDVSSYQEGQAAKEFIAWLVKGRG// ; (SEQ ID NO: 292)

HGEGTFTSDVSSYLEGQAAKEFIAQLVKGRG// ; (SEQ ID NO: 293)

HGEGTFTSDVSSYLEGQAAKEFIAQLQKGRG// ; (SEQ ID NO: 294)

HGEGTFTSDVSSYLEGQAAKEFIAWLQKGRG// ; (SEQ ID NO: 295)

HNETTFTSDVSSYLEGQAAKEFIAWLVKGRG// (SEQ ID NO: 296)

HGEGTFTSDVSSYLENQTAKEFIAWLVKGRG// ; (SEQ ID NO: 297)

HGEGTFTSDVSSYLEGNATKEFIAWLVKGRG// ; (SEQ ID NO: 298)

HGEGTFTSDVSSYLEGQAAKEFIAWLVNGTG// ; (SEQ ID NO: 299)

HGEGTFTSDVSSYLEGQAAKEFIAWLVKNRT// ; (SEQ ID NO: 300)

HGEGTFTSDVSSYLEGQAAKEFIAWLVKGRNGT// ; (SEQ ID NO: 301)

HGEGTFTSDVSSYLEGQAAKEFIAWLVKGRGGTGNGT// ; and (SEQ ID NO: 302)

HGEGTFTSDVSSYLEGQAAKEFIAWLVKGRGGSGNGT//. (SEQ ID NO: 303)

Human GLP-2 and GLP-2-mimetic analogs are also known in the art. (See, e.g., Prasad et al., Glucagonlike peptide-2 analogue enhances intestinal mucosal mass after ischemia and reperfusion, J. Pediatr. Surg. 2000 February; 35(2):357-59 (2000); Yusta et al., Glucagon-like peptide-2 receptor activation engages bad and glycogen synthase kinase-3 in a protein kinase A-dependent manner and prevents apoptosis following inhibition of phosphatidylinositol 3-kinase, J. Biol. Chem. 277(28):24896-906 (2002)).

"Toxin peptides" include peptides and polypeptides having the same amino acid sequence of a naturally occurring pharmacologically active peptide or polypeptide that can be isolated from a venom, and also include modified peptide analogs of such naturally occurring molecules. (See, e.g., Kalman et al., ShK-Dap22, a potent Kv1.3-specific immunosuppressive polypeptide, J. Biol. Chem. 273(49):32697-707 (1998); Kem et al., U.S. Pat. No. 6,077,680; Mouhat et al., OsK1 derivatives, WO 2006/002850 A2; Chandy et al., Analogs of SHK toxin and their uses in selective inhibition of Kv1.3 potassium channels, WO 2006/042151; Sullivan et al., Toxin Peptide therapeutic agents, WO 2006/116156 A2, all of which are incorporated herein by reference in their entirety). Snakes, scorpions, spiders, bees, snails and sea anemone are a few examples of organisms that produce venom that can serve as a rich source of small bioactive toxin peptides or "toxins" that potently and selectively target ion channels and receptors. An example of a toxin peptide is OSK1 (also known as OsK1), a toxin peptide isolated from *Orthochirus scrobiculosus* scorpion venom. (e.g., Mouhat et al., K+ channel types targeted by synthetic OSK1, a toxin from *Orthochirus scrobiculosus* scorpion venom, Biochem. J. 385:95-104 (2005); Mouhat et al., Pharmacological profiling of *Orthochirus scrobiculosus* toxin 1 analogs with a trimmed N-terminal domain, Molec. Pharmacol. 69:354-62 (2006); Mouhat et al., OsK1 derivatives, WO 2006/002850 A2). Another example is ShK, isolated from the venom of the sea anemone *Stichodactyla helianthus*. (E.g., Tudor et al., Ionisation behaviour and solution properties of the potassium-channel blocker ShK toxin, Eur. J. Biochem. 251(1-2):133-41 (1998); Pennington et al., Role of disulfide bonds in the structure and potassium channel blocking activity of ShK toxin, Biochem. 38(44): 14549-58 (1999); Kem et al., ShK toxin compositions and methods of use, U.S. Pat. No. 6,077,680; Lebrun et al., Neuropeptides originating in scorpion, U.S. Pat. No. 6,689,749; Beeton et al., Targeting effector memory T cells with a selective peptide inhibitor of Kv1.3 channnels for therapy of autoimmune diseases, Molec. Pharmacol. 67(4):1369-81 (2005)).

The toxin peptides are usually between about 20 and about 80 amino acids in length, contain 2-5 disulfide linkages and form a very compact structure. Toxin peptides (e.g., from the venom of scorpions, sea anemones and cone snails) have been isolated and characterized for their impact on ion channels. Such peptides appear to have evolved from a relatively small number of structural frameworks that are particularly well suited to addressing the critical issues of potency and stability. The majority of scorpion and Conus toxin peptides, for example, contain 10-40 amino acids and up to five disulfide bonds, forming extremely compact and constrained structure (microproteins) often resistant to proteolysis. The conotoxin and scorpion toxin peptides can be divided into a number of superfamilies based on their disulfide connections and peptide folds. The solution structure of many of these has been determined by NMR spectroscopy, illustrating their compact structure and verifying conservation of their family fold. (E.g., Tudor et al., Ionisation behaviour and solution properties of the potassium-channel blocker ShK toxin, Eur. J. Biochem. 251(1-2):133-41 (1998); Pennington et al., Role of disulfide bonds in the structure and potassium channel blocking activity of ShK toxin, Biochem. 38(44): 14549-58 (1999); Jaravine et al., Three-dimensional structure of toxin OSK1 from *Orthochirus scrobiculosus* scorpion venom, Biochem. 36(6):1223-32 (1997); del Rio-Portillo et al.; NMR solution structure of Cn12, a novel peptide from the Mexican scorpion Centruroides noxius with a typical beta-toxin sequence but with alpha-like physiological activity, Eur. J. Biochem. 271 (12): 2504-16 (2004); Prochnicka-Chalufour et al., Solution structure of discrepin, a new K+-channel blocking peptide from the alpha-KTx15 subfamily, Biochem. 45(6):1795-1804 (2006)). Examples of pharmacologically active toxin peptides for which the practice of the present invention can be useful include, but are not limited to ShK, OSK1, charybdotoxin (ChTx), kaliotoxin1 KTX1), or maurotoxin, or toxin peptide analogs of any of these, modified from the native sequences at one or more amino acid residues. Other examples are known in the art, or can be found in Sullivan et al., WO06116156 A2 or U.S. patent application Ser. No. 11/406,454 (titled: Toxin Peptide Therapeutic Agents, published as US 2007/0071764); Mouhat et al., OsK1 derivatives, WO 2006/002850 A2; Sullivan et al., U.S. patent application Ser. No. 11/978,076 (titled: Conjugated Toxin Peptide Therapeutic Agents, filed 25 Oct. 2007, and published as US20090291885 on Nov. 26, 2009), Sullivan et al., WO 2008/088422; Lebrun et al., U.S. Pat. No. 6,689,749, and Sullivan et al., Selective and Potent Peptide Inhibitors of Kv1.3, U.S. Provisional Application No. 61/210,594, filed Mar. 20, 2009, which are each incorporated by reference in their entireties.

The term "peptide analog" refers to a peptide having a sequence that differs from a peptide sequence existing in nature by at least one amino acid residue substitution, internal addition, or internal deletion of at least one amino acid, and/or amino- or carboxy-terminal end truncations, or additions). An "internal deletion" refers to absence of an amino acid from a sequence existing in nature at a position other than the N- or C-terminus. Likewise, an "internal addition" refers to presence of an amino acid in a sequence existing in nature at a position other than the N- or C-terminus. "Toxin peptide analogs", such as, but not limited to, an OSK1 peptide analog, ShK peptide analog, or ChTx peptide analog, contain modifications of a native toxin peptide sequence of interest (e.g., amino acid residue substitutions, internal additions or insertions, internal deletions, and/or amino- or carboxy-terminal end truncations, or additions as previously described above) relative to a native toxin peptide sequence of interest.

A "CGRP peptide antagonist" is a peptide that preferentially binds the $CGRP_1$ receptor, such as, but not limited to, a CGRP peptide analog, and that antagonizes, blocks, decreases, reduces, impedes, or inhibits $CGRP_1$ receptor activation by full length native human αCGRP or βCGRP under physiological conditions of temperature, pH, and ionic strength. CGRP peptide antagonists include full and partial antagonists. Such antagonist activity can be detected by known in vitro methods or in vivo functional assay methods. (See, e.g., Smith et al., Modifications to the N-terminus but not the C-terminus of calcitonin gene-related peptide (8-37) produce antagonists with increased affinity, J. Med. Chem., 46:2427-2435 (2003)). Examples of useful CGRP peptide antagonists are disclosed in Gegg et al., CGRP peptide antagonists and conjugates, WO 2007/048026 A2 and U.S. Ser. No. 11/584,177, filed on Oct. 19, 2006, published as US 2008/0020978 A1, which is incorporated herein by reference in its entirety.

The terms "parathyroid hormone (PTH) agonist" and "PTH agonist" refer to a molecule that binds to PTH-1 or PTH-2 receptor and increases or decreases one or more PTH activity assay parameters as does full-length native human parathyroid hormone. Examples of useful PTH agonist peptides are disclosed in Table 1 of U.S. Pat. No. 6,756,480, titled Modulators of receptors for parathyroid hormone and parathyroid hormone-related protein, which is incorporated herein by reference in its entirety. An exemplary PTH activity assay is disclosed in Example 1 of U.S. Pat. No. 6,756,480.

The term "parathyroid hormone (PTH) antagonist" refers to a molecule that binds to PTH-1 or PTH-2 receptor and blocks or prevents the normal effect on those parameters by full length native human parathyroid hormone. Examples of useful PTH antagonist peptides are disclosed in Table 2 of U.S. Pat. No. 6,756,480, which is incorporated herein by reference in its entirety. An exemplary PTH activity assay is disclosed in Example 2 of U.S. Pat. No. 6,756,480.

The terms "bradykinin B1 receptor antagonist peptide" and "bradykinin B1 receptor peptide antagonist" mean a peptide with antagonist activity with respect to human bradykinin B1 receptor (hB1). Useful bradykinin B1 receptor antagonist peptides can be identified or derived as described in Ng et al., Antagonist of the bradykinin B1 receptor, US 2005/0215470 A1, published Sep. 29, 2005, which issued as U.S. Pat. No. 7,605,120; U.S. Pat. No. 5,834,431 or 5,849,863. An exemplary B1 receptor activity assays are disclosed in Examples 6-8 of US 2005/0215470 A1.

The terms "thrombopoietin (TPO)-mimetic peptide" and "TPO-mimetic peptide" refer to peptides that can be identified or derived as described in Cwirla et al. (1997), *Science* 276: 1696-9, U.S. Pat. Nos. 5,869,451 and 5,932,946, which are incorporated by reference in their entireties; U.S. Pat. App. No. 2003/0176352, published Sep. 18, 2003, which is incorporated by reference in its entirety; WO 03/031589, published Apr. 17, 2003; WO 00/24770, published May 4, 2000; and any peptides appearing in Table 5 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that each of these references enables one to select different peptides than actually disclosed therein by following the disclosed procedures with different peptide libraries.

The terms "EPO-mimetic peptide" and "erythropoietin-mimetic peptide" refers to peptides that can be identified or derived as described in Wrighton et al. (1996), Science 273: 458-63, and Naranda et al. (1999), Proc. Natl. Acad. Sci. USA 96: 7569-74, both of which are incorporated herein by reference in their entireties. Useful EPO-mimetic peptides include EPO-mimetic peptides listed in Table 5 of published U.S. patent application US 2007/0269369 A1 and in U.S. Pat. No. 6,660,843, which are both hereby incorporated by reference in their entireties.

The term "ang-2-binding peptide" comprises peptides that can be identified or derived as described in U.S. Pat. App. No. 2003/0229023, published Dec. 11, 2003; WO 03/057134, published Jul. 17, 2003; U.S. 2003/0236193, published Dec. 25, 2003 (each of which is incorporated herein by reference in its entirety); and any peptides appearing in Table 6 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that each of these references enables one to select different peptides than actually disclosed therein by following the disclosed procedures with different peptide libraries.

The terms "nerve growth factor (NGF) binding peptide" and "NGF-binding peptide" comprise peptides that can be identified or derived as described in WO 04/026329, published Apr. 1, 2004 and any peptides identified in Table 7 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that this reference enables one to select different peptides than actually disclosed therein by following the disclosed procedures with different peptide libraries.

The term "myostatin-binding peptide" comprises peptides that can be identified or derived as described in U.S. Ser. No. 10/742,379, filed Dec. 19, 2003, which is incorporated herein by reference in its entirety, and peptides appearing in Table 8 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that each of these references enables one to select different peptides than actually disclosed therein by following the disclosed procedures with different peptide libraries.

The terms "BAFF-antagonist peptide" and "BAFF binding peptide" comprise peptides that can be identified or derived as described in U.S. Pat. Appln. No. 2003/0195156 A1, which is incorporated herein by reference in its entirety and those peptides appearing in Table 9 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that the foregoing references enable one to select different peptides than actually disclosed therein by following the disclosed procedures with different peptide libraries.

The foregoing are intended merely as non-limiting examples of the pharmacologically active polypeptides that can be usefully conjugated or fused to the inventive immunoglobulins (including antibodies and antibody fragements). Any include pharmacologically active polypeptide moiety can be used within the scope of the invention, including a polypeptide having a so-called avimer structure (see, e.g., Kolkman et al., Novel Proteins with Targeted Binding, US 2005/0089932; Baker et al., IL-6 Binding Proteins, US 2008/0281076; Stemmer et al., Protein Scaffolds and Uses Thereof, US 2006/0223114 and US 2006/0234299).

Useful preclinical animal models are known in the art for use in validating a drug in a therapeutic indication of interest (e.g., an adoptive-transfer model of periodontal disease by Valverde et al., J. Bone Mineral Res. 19:155 (2004); an ultrasonic perivascular Doppler flow meter-based animal model of arterial thrombosis in Gruner et al., Blood 105:1492-99 (2005); pulmonary thromboembolism model, aorta occlusion model, and murine stroke model in Braun et al., WO 2009/115609 A1). For example, an adoptive transfer experimental autoimmune encephalomyelitis (AT-EAE) model of multiple sclerosis has been described for investigations concerning immune diseases, such as multiple sclerosis (Beeton et al., J. Immunol. 166:936 (2001); Beeton et al., PNAS 98:13942 (2001); Sullivan et al., Example 45 of WO 2008/088422 A2, incorporated herein by reference in its entirety). In the AT-EAE model, significantly reduced disease severity and increased survival are expected for animals treated with an effective amount of the inventive pharmaceutical composition, while untreated animals are expected to develop severe disease and/or mortality. For running the AT-EAE model, the encephalomyelogenic CD4+ rat T cell line, PAS, specific for myelin-basic protein (MBP) originated from Dr. Evelyne Beraud. The maintenance of these cells in vitro and their use in the AT-EAE model has been described earlier [Beeton et al. (2001) PNAS 98, 13942]. PAS T cells are maintained in vitro by alternating rounds of antigen stimulation or activation with MBP and irradiated thymocytes (2 days), and propagation with T cell growth factors (5 days). Activation of PAS T cells ($3 \times 10^5$/ml) involves incubating the cells for 2 days with 10 µg/ml MBP and $15 \times 10^6$/ml syngeneic irradiated (3500 rad) thymocytes. On day 2 after in vitro activation, $10-15 \times 10^6$ viable PAS T cells are injected into 6-12 week old female Lewis rats (Charles River Laboratories) by tail IV. Daily subcutaneous injections of vehicle (2% Lewis rat serum in PBS) or test pharmaceutical composition are given from days −1 to 3, where day −1 represent 1 day prior to injection of PAS T cells (day 0). In vehicle treated rats, acute EAE is expected to develop 4 to 5 days after injection of PAS T cells. Typically, serum is collected by tail vein bleeding at day 4 and by cardiac puncture at day 8 (end of the study) for analysis of levels of inhibitor. Rats are typically weighed on days −1, 4, 6, and 8. Animals may be scored blinded once a day from the day of cell transfer (day 0) to day 3, and twice a day from day 4 to day 8. Clinical signs are evaluated as the total score of the degree of paresis of each limb and tail. Clinical scoring: 0=No signs, 0.5=distal limp tail, 1.0=limp tail, 2.0=mild paraparesis, ataxia, 3.0=moderate paraparesis, 3.5=one hind leg paralysis, 4.0=complete hind leg paralysis, 5.0=complete hind leg paralysis and incontinence, 5.5=tetraplegia, 6.0=moribund state or death. Rats reaching a score of 5.0 are typically euthanized.

Production of Antibody Embodiments of the Immunoglobulins

Polyclonal Antibodies.

Polyclonal antibodies are preferably raised in animals by multiple subcutaneous (sc) or intraperitoneal (ip) injections of the relevant antigen and an adjuvant. Alternatively, antigen may be injected directly into the animal's lymph node (see Kilpatrick et al., Hybridoma, 16:381-389, 1997). An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 µg of the protein or conjugate (for mice) with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies.

The inventive immunoglobulins that are provided include monoclonal antibodies. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. For example, monoclonal antibodies may be made using the hybridoma method first described by Kohler et al., Nature, 256:495 (1975), or may be made by recombinant DNA methods from predetermined sequences as is useful in the present invention (e.g., Cabilly et al., Methods of producing immunoglobulins, vectors and transformed host cells for use therein, U.S. Pat. No. 6,331,415), including methods, such as the "split DHFR" method, that facilitate the generally equimolar production of light and heavy chains, optionally using mammalian cell lines (e.g., CHO cells) that can glycosylate the antibody (See, e.g., Page, Antibody production, EP0481790 A2 and U.S. Pat. No. 5,545,403).

Generally, in the hybridoma method, which is not useful in the production of the inventive immunoglobulins, but is useful to produce antigen binding proteins, a mouse or other appropriate host mammal, such as rats, hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

In some instances, a hybridoma cell line is produced by immunizing a transgenic animal having human immunoglobulin sequences with an immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds to an tigen of interest. Such hybridoma cell lines, and monoclonal antibodies produced by them, are aspects of the present invention.

The hybridoma cells, once prepared, are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)). Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by BIAcore® or Scatchard analysis (Munson et al., Anal. Biochem., 107:220 (1980); Fischer et al., A peptide-immunoglobulin-conjugate, WO 2007/045463 A1, Example 10, which is incorporated herein by reference in its entirety).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

Hybridomas or mAbs may be further screened to identify mAbs with particular properties, such as the ability to inhibit $K^{1+}$ flux though Kv1.x channels. Examples of such screens are provided in the examples below. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, affinity chromatography, or any other suitable purification technique known in the art.

Recombinant Production of Antibodies.

The present invention provides isolated nucleic acids encoding any of the antibodies (polyclonal and monoclonal), including antibody fragments, of the invention described herein, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium. Similar materials and methods apply to production of polypeptide-based immunoglobulins.

Relevant amino acid sequences from an immunoglobulin or polypeptide of interest may be determined by direct protein sequencing, and suitable encoding nucleotide sequences can be designed according to a universal codon table. Alternatively, genomic or cDNA encoding the monoclonal antibodies may be isolated and sequenced from cells producing such antibodies using conventional procedures (e.g., by using oligonucleotide probes that are capable of binding specifically to genes encoding the heavy and light chains of the monoclonal antibodies).

Cloning of DNA is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

The sequence encoding an entire variable region of the immunoglobulin polypeptide may be determined; however, it will sometimes be adequate to sequence only a portion of a variable region, for example, the CDR-encoding portion. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoman immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Isolated DNA can be operably linked to control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the antibody; e.g., ATG-GACATGAGGGTGCCCGCTCAGCTC-CTGGGGCTCCTGCTGCTGTGGCT GAGAGGT-GCGCGCTGT//SEQ ID NO:102, which encodes the VK-1 signal peptide sequence MDMRVPAQLLGLLLLWLR-GARC//SEQ ID NO:103), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Exemplary host cells include prokaryote, yeast, or higher eukaryote cells. Prokaryotic host cells include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacillus* such as *B. subtilis* and *B. licheniformis, Pseudomonas*, and *Streptomyces*. Eukaryotic microbes such as filamentous fungi or yeast are suitable cloning or expression hosts for recombinant polypeptides or antibodies. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluvveromyces, Yarrowia; Candida; Trichoderma reesia; Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Host cells for the expression of glycosylated immunoglobulin, including antibody, can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

Vertebrate host cells are also suitable hosts, and recombinant production of antigen binding protein (including antibody) from such cells has become routine procedure. Examples of useful mammalian host cell lines are Chinese hamster ovary cells, including CHOK1 cells (ATCC CCL61), DXB-11, DG-44, and Chinese hamster ovary cells/–DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Virol.* 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y. Acad. Sci. 383: 44-68 (1982)); MRC 5 cells or FS4 cells; or mammalian myeloma cells.

Host cells are transformed or transfected with the above-described nucleic acids or vectors for production immunoglobulins and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of immunoglobulins.

The host cells used to produce the immunoglobulins of the invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. No. 4,767,704; 4,657,866; 4,927,762; 4,560,655; or 5,122,469; WO90103430; WO 87/00195; or U.S. patent Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the immunoglobulin can be produced intracellularly, in the periplasmic space, or directly secreted into the medium. If the immunoglobulin is produced intracellularly, as a first step, the particulate debris, either host cells or lysed fragments, is removed, for example, by centrifugation or ultrafiltration.

The immunoglobulin (e.g., an antibody or antibody fragment) can be purified using, for example, hydroxylapatite chromatography, cation or anion exchange chromatography, or preferably affinity chromatography, using the antigen of interest or protein A or protein G as an affinity ligand. Protein A can be used to purify proteins that include polypeptides are based on human γ1, γ2, or γ4 heavy chains (Lindmark et al., J. Immunol. Meth. 62: 1-13 (1983)). Protein G is recommended for all mouse isotypes and for human γ3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a $C_H3$ domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered.

Chimeric, Humanized and Human Engineered™ Monoclonal Antibodies.

Chimeric monoclonal antibodies, in which the variable Ig domains of a rodent monoclonal antibody are fused to human constant Ig domains, can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). A number of techniques have been described for humanizing or modifying antibody sequence to be more human-like, for example, by (1) grafting the non-human complementarity determining regions (CDRs) onto a human framework and constant region (a process referred to in the art as humanizing through "CDR grafting") or (2) transplanting the entire non-human variable domains, but "cloaking" them with a human-like surface by replacement of surface residues (a process referred to in the art as "veneering") or (3) modifying selected non-human amino acid residues to be more human, based on each residue's likelihood of participating in antigen-binding or antibody structure and its likelihood for immunogenicity. See, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991); Co, M. S., et al. (1994), J. Immunol. 152, 2968-2976); Studnicka et al. Protein Engineering 7: 805-814 (1994); each of which is incorporated herein by reference in its entirety.

A number of techniques have been described for humanizing or modifying antibody sequence to be more human-like, for example, by (1) grafting the non-human complementarity determining regions (CDRs) onto a human framework and constant region (a process referred to in the art as humanizing through "CDR grafting") or (2) transplanting the entire non-human variable domains, but "cloaking" them with a human-like surface by replacement of surface residues (a process referred to in the art as "veneering") or (3) modifying selected non-human amino acid residues to be more human, based on each residue's likelihood of participating in antigen-binding or antibody structure and its likelihood for immunogenicity. See, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991); Co, M. S., et al. (1994), J. Immunol. 152, 2968-2976); Studnicka et al. Protein Engineering 7: 805-814 (1994); each of which is incorporated herein by reference in its entirety.

In one aspect of the invention, the light and heavy chain variable regions of the antibodies provided herein (see, Table 2A-B) are grafted to framework regions (FRs) from antibodies from the same, or a different, phylogenetic species. To create consensus human FRs, FRs from several human heavy chain or light chain amino acid sequences may be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of the antibody are not replaced, while the rest of the FR amino acids are replaced. A "rare amino acid" is a specific amino acid that is in a position in which this particular amino acid is not usually found in an FR. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

Antibodies can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein. See also Jakobovits et al., Proc. Natl. Acad. Sci. USA, 90:2551 (1993); Jakobovits et al., Nature, 362:255-258 (1993); Bruggermann et al., Year in Immuno., 7:33 (1993); Mendez et al., *Nat. Genet.* 15:146-156 (1997); and U.S. Pat. No. 5,591,669, U.S. Pat. No. 5,589,369, U.S. Pat. No. 5,545,807; and U.S Patent Application No. 20020199213. U.S. Patent Application No. and 20030092125 describes methods for biasing the immune response of an animal to the desired epitope. Human antibodies may also be generated by in vitro activated B cells (see U.S. Pat. Nos. 5,567,610 and 5,229,275).

Antibody Production by Phage Display Techniques

The development of technologies for making repertoires of recombinant human antibody genes, and the display of the encoded antibody fragments on the surface of filamentous bacteriophage, has provided another means for generating human-derived antibodies. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning Antibody fragments specific for the antigen are enriched and finally isolated.

Phage display techniques can also be used in an approach for the humanization of rodent monoclonal antibodies, called "guided selection" (see Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); and, Winter, G., et al., Annu Rev. Immunol. 12, 433-455 (1994); U.S. patent application no. 20020004215 and WO92/01047; U.S. patent application no. 20030190317 published Oct. 9, 2003 and U.S. Pat. No. 6,054,287; U.S. Pat. No. 5,877,293.

Watkins, "Screening of Phage-Expressed Antibody Libraries by Capture Lift," Methods in Molecular Biology, Antibody Phage Display: Methods and Protocols 178: 187-193, and U.S. Patent Application Publication No. 20030044772 published Mar. 6, 2003 describes methods for screening phage-expressed antibody libraries or other binding molecules by capture lift, a method involving immobilization of the candidate binding molecules on a solid support.

Other Embodiments of Immunoglobulins: Antibody Fragments

As noted above, antibody fragments comprise a portion of an intact full length antibody, preferably an antigen binding or variable region of the intact antibody, and include linear antibodies and multispecific antibodies formed from antibody fragments. Nonlimiting examples of antibody fragments include Fab, Fab', F(ab')2, Fv, Fd, domain antibody (dAb), complementarity determining region (CDR) fragments, single-chain antibodies (scFv), single chain antibody fragments, maxibodies, diabodies, triabodies, tetrabodies, minibodies, linear antibodies, chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity. Such antigen fragments may be produced by the modification of whole antibodies or synthesized de novo using recombinant DNA technologies or peptide synthesis.

Additional antibody fragments include a domain antibody (dAb) fragment (Ward et al., Nature 341:544-546, 1989) which consists of a $V_H$ domain.

"Linear antibodies" comprise a pair of tandem Fd segments ($V_H$-$C_H1$-$V_H$-$C_H1$) which form a pair of antigen binding regions. Linear antibodies can be bispecific or monospecific (Zapata et al. Protein Eng. 8:1057-62 (1995)).

A "minibody" consisting of scFv fused to CH3 via a peptide linker (hingeless) or via an IgG hinge has been described in Olafsen, et al., Protein Eng Des Sel. 2004 April; 17(4):315-23.

The term "maxibody" refers to bivalent scFvs covalently attached to the Fc region of an immunoglobulin, see, for example, Fredericks et al, Protein Engineering, Design & Selection, 17:95-106 (2004) and Powers et al., Journal of Immunological Methods, 251:123-135 (2001).

Functional heavy-chain antibodies devoid of light chains are naturally occurring in certain species of animals, such as nurse sharks, wobbegong sharks and Camelidae, such as camels, dromedaries, alpacas and llamas. The antigen-binding site is reduced to a single domain, the $VH_H$ domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelized $V_{HH}$ reportedly recombines with IgG2 and IgG3 constant regions that contain hinge, CH2, and CH3 domains and lack a CH1 domain. Classical $V_H$-only fragments are difficult to produce in soluble form, but improvements in solubility and specific binding can be obtained when framework residues are altered to be more $VH_H$-like. (See, e.g., Reichman, et al., J Immunol Methods 1999, 231:25-38.) Camelized $V_{HH}$ domains have been found to bind to antigen with high affinity (Desmyter et al., J. Biol. Chem. 276:26285-90, 2001) and possess high stability in solution (Ewert et al., Biochemistry 41:3628-36, 2002). Methods for generating antibodies having camelized heavy chains are described in, for example, in U.S. Patent Publication Nos. 2005/0136049 and 2005/0037421. Alternative scaffolds can be made from human variable-like domains that more closely match the shark V-NAR scaffold and may provide a framework for a long penetrating loop structure.

Because the variable domain of the heavy-chain antibodies is the smallest fully functional antigen-binding fragment with a molecular mass of only 15 kDa, this entity is referred to as a nanobody (Cortez-Retamozo et al., Cancer Research 64:2853-57, 2004). A nanobody library may be generated from an immunized dromedary as described in Conrath et al., (*Antimicrob Agents Chemother* 45: 2807-12, 2001).

Intrabodies are single chain antibodies which demonstrate intracellular expression and can manipulate intracellular protein function (Biocca, et al., *EMBO J.* 9:101-108, 1990; Colby et al., *Proc Natl Acad Sci USA*. 101:17616-21, 2004). Intrabodies, which comprise cell signal sequences which retain the antibody contruct in intracellular regions, may be produced as described in Mhashilkar et al (*EMBO J.* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med Hypotheses*. 64:1105-8, 2005).

Further encompassed by the invention are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

Various techniques have been developed for the production of antibody fragments. Traditionally, these fragments were derived via proteolytic digestion of intact antibodies, but can also be produced directly by recombinant host cells. See, for example, Better et al., Science 240: 1041-1043 (1988); Skerra et al. Science 240: 1038-1041 (1988); Carter et al., Bio/Technology 10:163-167 (1992).

Other Embodiments of Immunoglobulins: Multivalent Antibodies

In some embodiments, it may be desirable to generate multivalent or even a multispecific (e.g. bispecific, trispecific, etc.) monoclonal antibody. Such antibody may have binding specificities for at least two different epitopes of the target antigen, or alternatively it may bind to two different molecules, e.g. to the target antigen and to a cell surface protein or receptor. For example, a bispecific antibody may include an arm that binds to the target and another arm that binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the target-expressing cell. As another example, bispecific antibodies may be used to localize cytotoxic agents to cells which express target antigen. These antibodies possess a target-binding arm and an arm which binds the cytotoxic agent (e.g., saporin, anti-interferon-60, vinca alkaloid, ricin A chain, methotrexate or radioactive isotope hapten). Multispecific antibodies can be prepared as full length antibodies or antibody fragments.

Additionally, the immunoglobulins (e.g., antibodies and antibody fragments) and conjugates of the present invention can also be constructed to fold into multivalent forms, which may improve half-life in blood. Multivalent forms can be prepared by techniques known in the art.

Bispecific or multispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques. Another method is designed to make tetramers by adding a streptavidin-coding sequence at the C-terminus of the scFv. Streptavidin is composed of four subunits, so when the scFv-streptavidin is folded, four subunits associate to form a tetramer (Kipriyanov et al., Hum Antibodies Hybridomas 6(3): 93-101 (1995), the disclosure of which is incorporated herein by reference in its entirety).

According to another approach for making bispecific antibodies, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO 96/27011 published Sep. 6, 1996.

Techniques for generating bispecific or multispecific antibodies from antibody fragments have also been described in the literature. For example, bispecific or trispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. Better et al., Science 240: 1041-1043 (1988) disclose secretion of functional antibody fragments from bacteria (see, e.g., Better et al., Skerra et al. Science 240: 1038-1041 (1988)). For example, Fab'-SH fragments can be directly recovered from *E. coli* and chemically coupled to form bispecific antibodies (Carter et al., Bio/Technology 10:163-167 (1992); Shalaby et al., J. Exp. Med. 175:217-225 (1992)).

Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecfic antibody.

Various techniques for making and isolating bispecific or multispecific antibody fragments directly from recombinant cell culture have also been described. For example, bispecific antibodies have been produced using leucine zippers, e.g. GCN4. (See generally Kostelny et al., J. Immunol. 148(5): 1547-1553 (1992).) The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

Diabodies, described above, are one example of a bispecific antibody. See, for example, Hollinger et al., Proc. Natl. Acad. Sci. USA, 90:6444-6448 (1993). Bivalent diabodies can be stabilized by disulfide linkage.

Stable monospecific or bispecific Fv tetramers can also be generated by noncovalent association in (scFv$_2$)$_2$ configuration or as bis-tetrabodies. Alternatively, two different scFvs can be joined in tandem to form a bis-scFv.

Another strategy for making bispecific antibody fragments by the use of single-chain Fv (sFv) dimers has also been reported. See Gruber et al., J. Immunol. 152: 5368 (1994). One approach has been to link two scFv antibodies with linkers or disulfide bonds (Mallender and Voss, J. Biol. Chem. 269:199-2061994, WO 94/13806, and U.S. Pat. No. 5,989, 830, the disclosures of which are incorporated herein by reference in their entireties).

Alternatively, the bispecific antibody may be a "linear antibody" produced as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are also contemplated. For example, trispecific antibodies can be prepared. (Tutt et al., J. Immunol. 147:60 (1991)).

A "chelating recombinant antibody" is a bispecific antibody that recognizes adjacent and non-overlapping epitopes of the target antigen, and is flexible enough to bind to both epitopes simultaneously (Neri et al., *J Mol Biol.* 246:367-73, 1995).

Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-$CH_1$ (Fd) chains, e.g., to produce a tribody two scFvs are fused to C-term of Fab while in a bibody one scFv is fused to C-term of Fab.

In yet another method, dimers, trimers, and tetramers are produced after a free cysteine is introduced in the parental protein. A peptide-based cross linker with variable numbers (two to four) of maleimide groups was used to cross link the protein of interest to the free cysteines (Cochran et al., Immunity 12(3): 241-50 (2000), the disclosure of which is incorporated herein in its entirety).

Other Embodiments of Immunoglobulins

Inventive immunoglobulins also include peptibodies. The term "peptibody" refers to a molecule comprising an antibody Fc domain attached to at least one peptide. The production of peptibodies is generally described in PCT publication WO 00/24782, published May 4, 2000. Any of these peptides may be linked in tandem (i.e., sequentially), with or without linkers. Peptides containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized, for example the carboxyl terminus may be capped with an amino group, cysteines may be cappe, or amino acid residues may substituted by moieties other than amino acid residues (see, e.g., Bhatnagar et al., J. Med. Chem. 39: 3814-9 (1996), and Cuthbertson et al., J. Med. Chem. 40: 2876-82 (1997), which are incorporated by reference herein in their entirety). The peptide sequences may be optimized, analogous to affinity maturation for antibodies, or otherwise altered by alanine scanning or random or directed mutagenesis followed by screening to identify the best binders. Lowman, Ann. Rev. Biophys. Biomol. Struct. 26: 401-24 (1997). Various molecules can be inserted into the immunoglobulin structure, e.g., within the peptide portion itself or between the peptide and vehicle portions of the immunoglobulins, while retaining the desired activity of immunoglobulin. One can readily insert, for example, molecules such as an Fc domain or fragment thereof, polyethylene glycol or other related molecules such as dextran, a fatty acid, a lipid, a cholesterol group, a small carbohydrate, a peptide, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of, for example, a desired molecule in between two consecutive amino acids, optionally joined by a suitable linker.

Linkers.

A "linker" or "linker moiety", as used interchangeably herein, refers to a biologically acceptable peptidyl or non-peptidyl organic group that is covalently bound to an amino acid residue of a polypeptide chain (e.g., an immunoglobulin HC or immunoglobulin LC or immunoglobulin Fc domain) contained in the inventive composition, which linker moiety covalently joins or conjugates the polypeptide chain to another peptide or polypeptide chain in the molecule, or to a therapeutic moiety, such as a biologically active small molecule or oligopeptide, or to a half-life extending moiety, e.g., see, Sullivan et al., Toxin Peptide Therapeutic Agents, US2007/0071764; Sullivan et al., Toxin Peptide Therapeutic Agents, PCT/US2007/022831, published as WO 2008/088422; and U.S. Provisional Application Ser. No. 61/210, 594, filed Mar. 20, 2009, which are all incorporated herein by reference in their entireties.

The presence of any linker moiety in the immunoglobulins of the present invention is optional. When present, the linker's chemical structure is not critical, since it serves primarily as a spacer to position, join, connect, or optimize presentation or position of one functional moiety in relation to one or more other functional moieties of a molecule of the inventive immunoglobulin. The presence of a linker moiety can be useful in optimizing pharmcologial activity of some embodiments of the inventive immunoglobulin (including antibodies and antibody fragments). The linker is preferably made up of amino acids linked together by peptide bonds. The linker moiety, if present, can be independently the same or different from any other linker, or linkers, that may be present in the inventive immunoglobulin.

As stated above, the linker moiety, if present (whether within the primary amino acid sequence of the immunoglobulin, or as a linker for attaching a therapeutic moiety or half-life extending moiety to the inventive immunoglobulin), can be "peptidyl" in nature (i.e., made up of amino acids linked together by peptide bonds) and made up in length, preferably, of from 1 up to about 40 amino acid residues, more preferably, of from 1 up to about 20 amino acid residues, and most preferably of from 1 to about 10 amino acid residues. Preferably, but not necessarily, the amino acid residues in the linker are from among the twenty canonical amino acids, more preferably, cysteine, glycine, alanine, proline, asparagine, glutamine, and/or serine. Even more preferably, a peptidyl linker is made up of a majority of amino acids that are sterically unhindered, such as glycine, serine, and alanine linked by a peptide bond. It is also desirable that, if present, a peptidyl linker be selected that avoids rapid proteolytic turnover in circulation in vivo. Some of these amino acids may be glycosylated, as is well understood by those in the art. For example, a useful linker sequence constituting a sialylation site is $X_1X_2NX_4X_5G$ (SEQ ID NO:148), wherein $X_1$, $X_2$, $X_4$ and $X_5$ are each independently any amino acid residue.

In other embodiments, the 1 to 40 amino acids of the peptidyl linker moiety are selected from glycine, alanine, proline, asparagine, glutamine, and lysine. Preferably, a linker is made up of a majority of amino acids that are sterically unhindered, such as glycine and alanine. Thus, preferred linkers include polyglycines, polyserines, and polyalanines, or combinations of any of these. Some exemplary peptidyl linkers are poly(Gly)$_{1-8}$, particularly (Gly)$_3$, (Gly)$_4$ (SEQ ID NO:149), (Gly)$_5$ (SEQ ID NO:150) and (Gly)$_7$ (SEQ ID NO:151), as well as, poly(Gly)$_4$Ser (SEQ ID NO:152), poly (Gly-Ala)$_{2-4}$ and poly(Ala)$_{1-8}$. Other specific examples of peptidyl linkers include (Gly)$_5$Lys (SEQ ID NO:154), and (Gly)$_5$LysArg (SEQ ID NO:155). Other examples of useful peptidyl linkers are: Other examples of useful peptidyl linkers are:

```
                                  (SEQ ID NO: 159);
(Gly)₃Lys(Gly)₄

(SEQ ID NO: 156);
(Gly)₃AsnGlySer(Gly)₂

(SEQ ID NO: 157);
(Gly)₃Cys(Gly)₄
and
                                  (SEQ ID NO: 158)
GlyProAsnGlyGly
```

To explain the above nomenclature, for example, (Gly)$_3$Lys(Gly)$_4$ means Gly-Gly-Gly-Lys-Gly-Gly-Gly-Gly (SEQ ID NO:159). Other combinations of Gly and Ala are also useful.

Commonly used linkers include those which may be identified herein as "L5" (GGGGS; or "G$_4$S"; SEQ ID NO:152), "L10" (GGGGSGGGGS; SEQ ID NO:153), "L25" (GGGGSGGGGSGGGGSGGGGSGGGGS; SEQ ID NO:146) and any linkers used in the working examples hereinafter.

In some embodiments of the compositions of this invention, which comprise a peptide linker moiety, acidic residues, for example, glutamate or aspartate residues, are placed in the amino acid sequence of the linker moiety. Examples include the following peptide linker sequences:

```
                                  (SEQ ID NO: 160)
GGEGGG;

(SEQ ID NO: 161)
GGEEEGGG;

(SEQ ID NO: 162)
GEEEG;

(SEQ ID NO: 163)
GEEE;

(SEQ ID NO: 164)
GGDGGG;

(SEQ ID NO: 165)
GGDDDGG;

(SEQ ID NO: 166)
GDDDG;

(SEQ ID NO: 167)
GDDD;

(SEQ ID NO: 168)
GGGGSDDSDEGSDGEDGGGGS;
```

```
                                  (SEQ ID NO: 169)
WEWEW;

(SEQ ID NO: 170)
FEFEF;

(SEQ ID NO: 171)
EEEWWW;

(SEQ ID NO: 172)
EEEFFF;

(SEQ ID NO: 173)
WWEEEWW;
or
                                  (SEQ ID NO: 174)
FFEEEFF.
```

In other embodiments, the linker constitutes a phosphorylation site, e.g., $X_1X_2YX_4X_5G$ (SEQ ID NO:175), wherein $X_1$, $X_2$, $X_4$, and $X_5$ are each independently any amino acid residue; $X_1X_2SX_4X_5G$ (SEQ ID NO:176), wherein $X_1$, $X_2$, $X_4$ and $X_5$ are each independently any amino acid residue; or $X_1X_2TX_4X_5G$ (SEQ ID NO:177), wherein $X_1$, $X_2$, $X_4$ and $X_5$ are each independently any amino acid residue.

The linkers shown here are exemplary; peptidyl linkers within the scope of this invention may be much longer and may include other residues. A peptidyl linker can contain, e.g., a cysteine, another thiol, or nucleophile for conjugation with a half-life extending moiety. In another embodiment, the linker contains a cysteine or homocysteine residue, or other 2-amino-ethanethiol or 3-amino-propanethiol moiety for conjugation to maleimide, iodoacetaamide or thioester, functionalized half-life extending moiety.

Another useful peptidyl linker is a large, flexible linker comprising a random Gly/Ser/Thr sequence, for example: GSGSATGGSGSTASSGSGSATH (SEQ ID NO:178) or HGSGSATGGSGSTASSGSGSAT (SEQ ID NO:179), that is estimated to be about the size of a 1 kDa PEG molecule. Alternatively, a useful peptidyl linker may be comprised of amino acid sequences known in the art to form rigid helical structures (e.g., Rigid linker: -AEAAAKEAAAKEAAAK-AGG-) (SEQ ID NO:180). Additionally, a peptidyl linker can also comprise a non-peptidyl segment such as a 6 carbon aliphatic molecule of the formula —CH$_2$—CH$_2$—CH$_2$—CH$_2$—CH$_2$—CH$_2$—. The peptidyl linkers can be altered to form derivatives as described herein.

Optionally, a non-peptidyl linker moiety is also useful for conjugating the half-life extending moiety to the peptide portion of the half-life extending moiety-conjugated toxin peptide analog. For example, alkyl linkers such as —NH—(CH$_2$)$_s$—C(O)—, wherein s=2-20 can be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. Exemplary non-peptidyl linkers are polyethylene glycol (PEG) linkers (e.g., shown below):

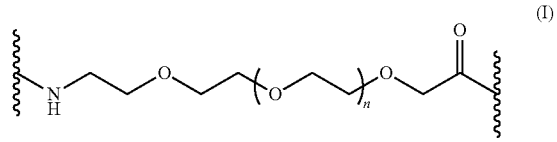

(I)

wherein n is such that the linker has a molecular weight of about 100 to about 5000 Daltons (Da), preferably about 100 to about 500 Da.

In one embodiment, the non-peptidyl linker is aryl. The linkers may be altered to form derivatives in the same manner as described in the art, e.g., in Sullivan et al., Toxin Peptide Therapeutic Agents, US2007/0071764; Sullivan et al., Toxin Peptide Therapeutic Agents, PCT/US2007/022831, published as WO 2008/088422; and U.S. Provisional Application Ser. No. 61/210,594, filed Mar. 20, 2009, which are all incorporated herein by reference in their entireties.

In addition, PEG moieties may be attached to the N-terminal amine or selected side chain amines by either reductive alkylation using PEG aldehydes or acylation using hydroxysuccinimido or carbonate esters of PEG, or by thiol conjugation.

"Aryl" is phenyl or phenyl vicinally-fused with a saturated, partially-saturated, or unsaturated 3-, 4-, or 5 membered carbon bridge, the phenyl or bridge being substituted by 0, 1, 2 or 3 substituents selected from $C_{1-8}$ alkyl, $C_{1-4}$ haloalkyl or halo.

"Heteroaryl" is an unsaturated 5, 6 or 7 membered monocyclic or partially-saturated or unsaturated 6-, 7-, 8-, 9-, 10- or 11 membered bicyclic ring, wherein at least one ring is unsaturated, the monocyclic and the bicyclic rings containing 1, 2, 3 or 4 atoms selected from N, O and S, wherein the ring is substituted by 0, 1, 2 or 3 substituents selected from $C_{1-8}$ alkyl, $C_{1-4}$ haloalkyl and halo.

Non-peptide portions of the inventive composition of matter, such as non-peptidyl linkers or non-peptide half-life extending moieties can be synthesized by conventional organic chemistry reactions.

The above is merely illustrative and not an exhaustive treatment of the kinds of linkers that can optionally be employed in accordance with the present invention.

Production of Immunoglobulin Variants.

As noted above, recombinant DNA- and/or RNA-mediated protein expression and protein engineering techniques, or any other methods of preparing peptides, are applicable to the making of the inventive compositions. For example, polypeptides can be made in transformed host cells. Briefly, a recombinant DNA molecule, or construct, coding for the peptide is prepared. Methods of preparing such DNA molecules are well known in the art. For instance, sequences encoding the peptides can be excised from DNA using suitable restriction enzymes. Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial host cells in culture include bacteria (such as Escherichia coli sp.), yeast (such as Saccharomyces sp.) and other fungal cells, insect cells, plant cells, mammalian (including human) cells, e.g., CHO cells and HEK-293 cells, and others noted herein or otherwise known in the art. Modifications can be made at the DNA level, as well. The peptide-encoding DNA sequence may be changed to codons more compatible with the chosen host cell. For E. coli, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired compounds are expressed. Such fermentation conditions are well known in the art. In addition, the DNA optionally further encodes, 5' to the coding region of a fusion protein, a signal peptide sequence (e.g., a secretory signal peptide) operably linked to the expressed immunoglobulin. For further examples of appropriate recombinant methods and exemplary DNA constructs useful for recombinant expression of the inventive compositions by mammalian cells, including dimeric Fc fusion proteins ("peptibodies") or chimeric immunoglobulin (light chain+heavy chain)-Fc heterotrimers ("hemibodies"), conjugated to specific binding agents of the invention, see, e.g., Sullivan et al., Toxin Peptide Therapeutic Agents, US2007/0071764; Sullivan et al., Toxin Peptide Therapeutic Agents, PCT/US2007/022831, published as WO 2008/088422; and U.S. Provisional Application Ser. No. 61/210,594, filed Mar. 20, 2009, which are all incorporated herein by reference in their entireties.

Amino acid sequence variants of the desired immunoglobulin may be prepared by introducing appropriate nucleotide changes into the encoding DNA, or by peptide synthesis. Such variants include, for example, deletions and/or insertions and/or substitutions of residues within the amino acid sequences of the immunoglobulins or antibodies. Any combination of deletion, insertion, and substitution is made to arrive at the final construct, provided that the final construct possesses the desired characteristics. The amino acid changes also may alter post-translational processes of the immunoglobulin, such as changing the number or position of glycosylation sites. In certain instances, immunoglobulin variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated. Covariance analysis techniques can be employed by the skilled artisan to design useful modifications in the amino acid sequence of the immunoglobulin, including an antibody or antibody fragment. (E.g., Choulier, et al., Covariance Analysis of Protein Families: The Case of the Variable Domains of Antibodies, Proteins: Structure, Function, and Genetics 41:475-484 (2000); Demarest et al., Optimization of the Antibody $C_H3$ Domain by Residue Frequency Analysis of IgG Sequences, J. Mol. Biol. 335:41-48 (2004); Hugo et al., VL position 34 is a key determinant for the engineering of stable antibodies with fast dissociation rates, Protein Engineering 16(5):381-86 (2003); Aurora et al., Sequence covariance networks, methods and uses thereof, US 2008/0318207 A1; Glaser et al., Stabilized polypeptide compositions, US 2009/0048122 A1; Urech et al., Sequence based engineering and optimization of single chain antibodies, WO 2008/110348 A1; Borras et al., Methods of modifying antibodies, and modified antibodies with improved functional properties, WO 2009/000099 A2). Such modifications determined by covariance analysis can improve potency, pharmacokinetic, pharmacodynamic, and/or manufacturability characteristics of an immunoglobulin.

Nucleic acid molecules encoding amino acid sequence variants of the immunoglobulin or antibody are prepared by a variety of methods known in the art. Such methods include oligonucleotide-mediated (or site-directed) mutagenesis, PCR mutagenesis, and cassette mutagenesis of an earlier prepared variant or a non-variant version of the immunoglobulin.

Substitutional mutagenesis within any of the hypervariable or CDR regions or framework regions is contemplated. A useful method for identification of certain residues or regions of the immunoglobulin that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed variants are screened for the desired activity.

Some embodiments of the immunoglobulins of the present invention can also be made by synthetic methods. Solid phase synthesis is the preferred technique of making individual peptides since it is the most cost-effective method of making small peptides. For example, well known solid phase synthesis techniques include the use of protecting groups, linkers, and solid phase supports, as well as specific protection and deprotection reaction conditions, linker cleavage conditions, use of scavengers, and other aspects of solid phase peptide synthesis. Suitable techniques are well known in the art. (E.g., Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527; "Protecting Groups in Organic Synthesis," 3rd Edition, T. W. Greene and P. G. M. Wuts, Eds., John Wiley & Sons, Inc., 1999; NovaBiochem Catalog, 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; "Protecting Groups," P. J. Kocienski, Ed., Georg Thieme Verlag, Stuttgart, Germany, 1994; "Fmoc Solid Phase Peptide Synthesis, A Practical Approach," W. C. Chan and P. D. White, Eds., Oxford Press, 2000, G. B. Fields et al., Synthetic Peptides: A User's Guide, 1990, 77-183). For further examples of synthetic and purification methods known in the art, which are applicable to making the inventive compositions of matter, see, e.g., Sullivan et al., Toxin Peptide Therapeutic Agents, US2007/0071764 and Sullivan et al., Toxin Peptide Therapeutic Agents, PCT/US2007/022831, published as WO 2008/088422 A2, which are both incorporated herein by reference in their entireties.

In further describing any of the immunoglobulins herein, as well as variants, a one-letter abbreviation system is frequently applied to designate the identities of the twenty "canonical" amino acid residues generally incorporated into naturally occurring peptides and proteins (Table 3). Such one-letter abbreviations are entirely interchangeable in meaning with three-letter abbreviations, or non-abbreviated amino acid names. Within the one-letter abbreviation system used herein, an upper case letter indicates a L-amino acid, and a lower case letter indicates a D-amino acid. For example, the abbreviation "R" designates L-arginine and the abbreviation "r" designates D-arginine.

TABLE 3

One-letter abbreviations for the canonical amino acids.
Three-letter abbreviations are in parentheses.

| | |
|---|---|
| Alanine (Ala) | A |
| Glutamine (Gln) | Q |
| Leucine (Leu) | L |
| Serine (Ser) | S |
| Arginine (Arg) | R |
| Glutamic Acid (Glu) | E |
| Lysine (Lys) | K |
| Threonine (Thr) | T |
| Asparagine (Asn) | N |
| Glycine (Gly) | G |
| Methionine (Met) | M |
| Tryptophan (Trp) | W |
| Aspartic Acid (Asp) | D |
| Histidine (His) | H |
| Phenylalanine (Phe) | F |
| Tyrosine (Tyr) | Y |
| Cysteine (Cys) | C |
| Isoleucine (Ile) | I |
| Proline (Pro) | P |
| Valine (Val) | V |

An amino acid substitution in an amino acid sequence is typically designated herein with a one-letter abbreviation for the amino acid residue in a particular position, followed by the numerical amino acid position relative to an original sequence of interest, which is then followed by the one-letter symbol for the amino acid residue substituted in. For example, "T30D" symbolizes a substitution of a threonine residue by an aspartate residue at amino acid position 30, relative to the original sequence of interest. Another example, "W101F" symbolizes a substitution of a tryptophan residue by a phenylalanine residue at amino acid position 101, relative to the original sequence of interest.

Non-canonical amino acid residues can be incorporated into a polypeptide within the scope of the invention by employing known techniques of protein engineering that use recombinantly expressing cells. (See, e.g., Link et al., Non-canonical amino acids in protein engineering, Current Opinion in Biotechnology, 14(6):603-609 (2003)). The term "non-canonical amino acid residue" refers to amino acid residues in D- or L-form that are not among the 20 canonical amino acids generally incorporated into naturally occurring proteins, for example, β-amino acids, homoamino acids, cyclic amino acids and amino acids with derivatized side chains. Examples include (in the L-form or D-form) β-alanine, β-aminopropionic acid, piperidinic acid, aminocaprioic acid, aminoheptanoic acid, aminopimelic acid, desmosine, diaminopimelic acid, $N^\alpha$-ethylglycine, $N^\alpha$-ethylaspargine, hydroxylysine, allo-hydroxylysine, isodesmosine, allo-isoleucine, ω-methylarginine, $N^\alpha$-methylglycine, $N^\alpha$-methylisoleucine, $N^\alpha$-methylvaline, γ-carboxyglutamate, ε-N,N,N-trimethyllysine, ε-N-acetyllysine, O-phosphoserine, $N^\alpha$-acetylserine, $N^\alpha$-formylmethionine, 3-methylhistidine, 5-hydroxylysine, and other similar amino acids, and those listed in Table 4 below, and derivatized forms of any of these as described herein. Table 4 contains some exemplary non-canonical amino acid residues that are useful in accordance with the present invention and associated abbreviations as typically used herein, although the skilled practitioner will understand that different abbreviations and nomenclatures may be applicable to the same substance and appear interchangeably herein.

TABLE 4

Useful non-canonical amino acids for amino acid addition, insertion, or substitution into peptide sequences in accordance with the present invention. In the event an abbreviation listed in Table 4 differs from another abbreviation for the same substance disclosed elsewhere herein, both abbreviations are understood to be applicable. The amino acids listed in Table 4 can be in the L-form or D-form.

| Amino Acid | Abbreviation(s) |
|---|---|
| Acetamidomethyl | Acm |
| Acetylarginine | acetylarg |
| α-aminoadipic acid | Aad |
| aminobutyric acid | Abu |
| 6-aminohexanoic acid | Ahx; εAhx |
| 3-amino-6-hydroxy-2-piperidone | Ahp |
| 2-aminoindane-2-carboxylic acid | Aic |
| α-amino-isobutyric acid | Aib |
| 3-amino-2-naphthoic acid | Anc |
| 2-aminotetraline-2-carboxylic acid | Atc |
| Aminophenylalanine | Aminophe; Amino-Phe |
| 4-amino-phenylalanine | 4AmP |
| 4-amidino-phenylalanine | 4AmPhe |
| 2-amino-2-(1-carbamimidoylpiperidin-4-yl)acetic acid | 4AmPig |
| Arg ψ(CH$_2$NH) -reduced amide bond | rArg |
| β-homoarginine | bhArg |
| β-homolysine | bhomoK |
| β-homo Tic | BhTic |
| β-homophenylalanine | BhPhe |
| β-homoproline | BhPro |
| β-homotryptophan | BhTrp |
| 4,4'-biphenylalanine | Bip |
| β,β-diphenyl-alanine | BiPhA |
| β-phenylalanine | BPhe |
| p-carboxyl-phenylalanine | Cpa |
| Citrulline | Cit |
| Cyclohexylalanine | Cha |
| Cyclohexylglycine | Chg |
| Cyclopentylglycine | Cpg |
| 2-amino-3-guanidinopropanoic acid | 3G-Dpr |
| α,γ-diaminobutyric acid | Dab |
| 2,4-diaminobutyric acid | Dbu |
| diaminopropionic acid | Dap |
| α,β-diaminopropionoic acid (or 2,3-diaminopropionic acid) | Dpr |
| 3,3-diphenylalanine | Dip |
| 4-guanidino phenylalanine | Guf |
| 4-guanidino proline | 4GuaPr |
| Homoarginine | hArg; hR |
| Homocitrulline | hCit |
| Homoglutamine | hQ |
| Homolysine | hLys; hK; homoLys |
| Homophenylalanine | hPhe; homoPhe |
| 4-hydroxyproline (or hydroxyproline) | Hyp |
| 2-indanylglycine (or indanylglycine) | IgI |
| indoline-2-carboxylic acid | Idc |
| Iodotyrosine | I-Tyr |
| Lys ψ(CH$_2$NH)-reduced amide bond | rLys |
| methinine oxide | Met[O] |
| methionine sulfone | Met[O]$_2$ |
| N$^α$-methylarginine | NMeR |
| Nα-[(CH$_2$)$_3$NHCH(NH)NH$_2$] substituted glycine | N-Arg |
| N$^α$-methylcitrulline | NMeCit |
| N$^α$-methylglutamine | NMeQ |
| N$^α$-methylhomocitrulline | N$^α$-MeHoCit |
| N$^α$-methylhomolysine | NMeHoK |
| N$^α$-methylleucine | N$^α$-MeL; NMeL; NMeLeu; NMe-Leu |
| N$^α$-methyllysine | NMe-Lys |
| Nε-methyl-lysine | N-εMe-K |
| Nε-ethyl-lysine | N-εEt-K |
| Nε-isopropyl-lysine | N-εiPr-K |
| N$^α$-methylnorleucine | NMeNle; NMe-Nle |
| N$^α$-methylornithine | N$^α$-MeOrn; NMeOrn |
| N$^α$-methylphenylalanine | NMe-Phe |
| 4-methyl-phenylalanine | MePhe |
| α-methylphenylalanine | AMeF |
| N$^α$-methylthreonine | NMe-Thr; NMeThr |
| N$^α$-methylvaline | NMeVal; NMe-Val |
| Nε-(O-(aminoethyl)-O'-(2-propanoyl)-undecaethyleneglycol)-Lysine | K(NPeg11) |
| Nε-(O-(aminoethyl)-O'-(2-propanoyl)-(ethyleneglycol)27-Lysine | K(NPeg27) |
| 3-(1-naphthyl)alanine | 1-Nal; 1Nal |
| 3-(2-naphthyl)alanine | 2-Nal; 2Nal |
| nipecotic acid | Nip |
| Nitrophenylalanine | nitrophe |
| norleucine | Nle |
| norvaline | Nva or Nvl |
| O-methyltyrosine | Ome-Tyr |
| octahydroindole-2-carboxylic acid | Oic |
| Ornithine | Orn |
| Orn ψ(CH2NH)-reduced amide bond | rOrn |
| 4-piperidinylalanine | 4PipA |
| 4-pyridinylalanine | 4Pal |
| 3-pyridinylalanine | 3Pal |
| 2-pyridinylalanine | 2Pal |
| para-aminophenylalanine | 4AmP; 4-Amino-Phe |
| para-iodophenylalanine (or 4-iodophenylalanine) | pI-Phe |
| Phenylglycine | Phg |
| 4-phenyl-phenylalanine (or biphenylalanine) | 4Bip |
| 4,4'-biphenyl alanine | Bip |
| pipecolic acid | Pip |
| 4-amino-1-piperidine-4-carboxylic acid | 4Pip |
| Sarcosine | Sar |
| 1,2,3,4-tetrahydroisoquinoline | Tic |
| 1,2,3,4-tetrahydroisoquinoline-1-carboxylic acid | Tiq |
| 1,2,3,4-tetrahydroisoquinoline-7-hydroxyl-3-carboxylic acid | Hydroxyl-Tic |
| 1,2,3,4-tetrahydronorharman-3-carboxylic acid | Tpi |
| thiazolidine-4-carboxylic acid | Thz |
| 3-thienylalanine | Thi |

Nomenclature and Symbolism for Amino Acids and Peptides by the UPAC-IUB Joint Commission on Biochemical Nomenclature (JCBN) have been published in the following documents: Biochem. J., 1984, 219, 345-373; Eur. J. Biochem., 1984, 138, 9-37; 1985, 152, 1; 1993, 213, 2; Internat. J. Pept. Prot. Res., 1984, 24, following p 84; J. Biol. Chem., 1985, 260, 14-42; Pure Appl. Chem., 1984, 56, 595-624; Amino Acids and Peptides, 1985, 16, 387-410; Biochemical Nomenclature and Related Documents, 2nd edition, Portland Press, 1992, pages 39-69.

The one or more useful modifications to peptide domains of the inventive immunoglobulin can include amino acid additions or insertions, amino acid deletions, peptide truncations, amino acid substitutions, and/or chemical derivatization of amino acid residues, accomplished by known chemical techniques. For example, the thusly modified amino acid sequence includes at least one amino acid residue inserted or substituted therein, relative to the amino acid sequence of the native sequence of interest, in which the inserted or substituted amino acid residue has a side chain comprising a nucleophilic or electrophilic reactive functional group by which the peptide is conjugated to a linker and/or half-life extending moiety. In accordance with the invention, useful examples of such a nucleophilic or electrophilic reactive functional group include, but are not limited to, a thiol, a primary amine, a seleno, a hydrazide, an aldehyde, a carboxylic acid, a ketone, an aminooxy, a masked (protected) aldehyde, or a masked (protected) keto functional group. Examples of amino acid residues having a side chain comprising a nucleophilic reactive functional group include, but are not limited to, a lysine residue, a homolysine, an α,β-diaminopropionic acid residue, an α,γ-diaminobutyric acid residue, an ornithine residue, a cysteine, a homocysteine, a glutamic acid residue, an aspartic acid residue, or a selenocysteine residue.

Amino acid residues are commonly categorized according to different chemical and/or physical characteristics. The term "acidic amino acid residue" refers to amino acid residues in D- or L-form having side chains comprising acidic groups. Exemplary acidic residues include aspartatic acid and glutamatic acid residues. The term "alkyl amino acid residue" refers to amino acid residues in D- or L-form having $C_{1-6}$alkyl side chains which may be linear, branched, or cyclized, including to the amino acid amine as in proline, wherein the $C_{1-6}$alkyl is substituted by 0, 1, 2 or 3 substituents selected from $C_{1-4}$haloalkyl, halo, cyano, nitro, —C(=O)$R^b$, —C(=O)O$R^a$, —C(=O)N$R^aR^a$, —C(=N$R^a$)N$R^aR^a$, —N$R^a$C(=N$R^a$)N$R^aR^a$, —O$R^a$, —OC(=O)$R^b$, —OC(=O)N$R^aR^a$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$; wherein $R^a$ is independently, at each instance, H or $R^b$; and $R^b$ is independently, at each instance $C_{1-6}$alkyl substituted by 0, 1, 2 or 3 substituents selected from halo, $C_{1-4}$alk, $C_{1-3}$haloalk, —O$C_{1-4}$alk, —NH$_2$, —NH$C_{1-4}$alk, and —N($C_{1-4}$alk)$C_{1-4}$alk; or any protonated form thereof, including alanine, valine, leucine, isoleucine, proline, serine, threonine, lysine, arginine, histidine, aspartate, glutamate, asparagine, glutamine, cysteine, methionine, hydroxyproline, but which residues do not contain an aryl or aromatic group. The term "aromatic amino acid residue" refers to amino acid residues in D- or L-form having side chains comprising aromatic groups. Exemplary aromatic residues include tryptophan, tyrosine, 3-(1-naphthyl)alanine, or phenylalanine residues. The term "basic amino acid residue" refers to amino acid residues in D- or L-form having side chains comprising basic groups. Exemplary basic amino acid residues include histidine, lysine, homolysine, ornithine, arginine, N-methyl-arginine, ω-aminoarginine, ω-methyl-arginine, 1-methyl-histidine, 3-methyl-histidine, and homoarginine (hR) residues. The term "hydrophilic amino acid residue" refers to amino acid residues in D- or L-form having side chains comprising polar groups. Exemplary hydrophilic residues include cysteine, serine, threonine, histidine, lysine, asparagine, aspartate, glutamate, glutamine, and citrulline (Cit) residues. The terms "lipophilic amino acid residue" refers to amino acid residues in D- or L-form having sidechains comprising uncharged, aliphatic or aromatic groups. Exemplary lipophilic sidechains include phenylalanine, isoleucine, leucine, methionine, valine, tryptophan, and tyrosine. Alanine (A) is amphiphilic—it is capable of acting as a hydrophilic or lipophilic residue. Alanine, therefore, is included within the definition of both "lipophilic residue" and "hydrophilic residue." The term "nonfunctional amino acid residue" refers to amino acid residues in D- or L-form having side chains that lack acidic, basic, or aromatic groups. Exemplary neutral amino acid residues include methionine, glycine, alanine, valine, isoleucine, leucine, and norleucine (Nle) residues.

Additional useful embodiments of can result from conservative modifications of the amino acid sequences of the polypeptides disclosed herein. Conservative modifications will produce half-life extending moiety-conjugated peptides having functional, physical, and chemical characteristics similar to those of the conjugated (e.g., PEG-conjugated) peptide from which such modifications are made. Such conservatively modified forms of the conjugated polypeptides disclosed herein are also contemplated as being an embodiment of the present invention.

In contrast, substantial modifications in the functional and/or chemical characteristics of peptides may be accomplished by selecting substitutions in the amino acid sequence that differ significantly in their effect on maintaining (a) the structure of the molecular backbone in the region of the substitution, for example, as an α-helical conformation, (b) the charge or hydrophobicity of the molecule at the target site, or (c) the size of the molecule.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., Acta Physiol. Scand. Suppl., 643:55-67 (1998); Sasaki et al., 1998, Adv. Biophys. 35:1-24 (1998), which discuss alanine scanning mutagenesis).

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the peptide or vehicle-conjugated peptide molecules described herein.

Naturally occurring residues may be divided into classes based on common side chain properties:
1) hydrophobic: norleucine (Nor or Nle), Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced into regions of the toxin peptide analog.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Examples of conservative substitutions include the substitution of one non-polar (hydrophobic) amino acid residue such as isoleucine, valine, leucine norleucine, alanine, or methionine for another, the substitution of one polar (hydrophilic) amino acid residue for another such as between arginine and lysine, between glutamine and asparagine, between glycine and serine, the substitution of one basic amino acid residue such as lysine, arginine or histidine for another, or the substitution of one acidic residue, such as aspartic acid or glutamic acid for another. The phrase "conservative amino acid substitution" also includes the use of a chemically derivatized residue in place of a non-derivatized residue, provided that such polypeptide displays the requisite bioactivity. Other exemplary amino acid substitutions that can be useful in accordance with the present invention are set forth in Table 5 below.

TABLE 5

Some Useful Amino Acid Substitutions.

| Original Residues | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |

TABLE 5-continued

Some Useful Amino Acid Substitutions.

| Original Residues | Exemplary Substitutions |
| --- | --- |
| Leu | Norleucine, Ile, Val, Met, Ala, Phe |
| Lys | Arg, 1,4-Diamino-butyric Acid, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

Ordinarily, amino acid sequence variants of the immunoglobulin will have an amino acid sequence having at least 60% amino acid sequence identity with the original immunoglobulin or antibody amino acid sequences of either the heavy or the light chain variable region, or at least 65%, or at least 70%, or at least 75% or at least 80% identity, more preferably at least 85% identity, even more preferably at least 90% identity, and most preferably at least 95% identity, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the original sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the immunoglobulin or antibody sequence shall be construed as affecting sequence identity or homology.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an immunoglobulin with an N-terminal methionyl residue or the immunoglobulin (including antibody or antibody fragment) fused to an epitope tag or a salvage receptor binding epitope. Other insertional variants of the immunoglobulin or antibody molecule include the fusion to a polypeptide which increases the serum half-life of the immunoglobulin, e.g. at the N-terminus or C-terminus.

Examples of epitope tags include the flu HA tag polypeptide and its antibody 12CA5 [Field et al., Mol. Cell. Biol. 8: 2159-2165 (1988)]; the c-myc tag and the 8F9, 3C7, 6E10, G4, B7 and 9E10 antibodies thereto [Evan et al., Mol. Cell. Biol. 5(12): 3610-3616 (1985)]; and the Herpes Simplex virus glycoprotein D (gD) tag and its antibody [Paborsky et al., Protein Engineering 3(6): 547-553 (1990)]. Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.) are well known and routinely used in the art.

Some particular, non-limiting, embodiments of amino acid substitution variants of the inventive immunoglobulins, including antibodies and antibody fragments are exemplified below.

Any cysteine residue not involved in maintaining the proper conformation of the immunoglobulin also may be substituted, generally with serine, to improve the oxidative stability of the molecule and prevent aberrant crosslinking Conversely, cysteine bond(s) may be added to the immunoglobulin to improve its stability (particularly where the immunoglobulin is an antibody fragment such as an Fv fragment).

In certain instances, immunoglobulin variants are prepared with the intent to modify those amino acid residues which are directly involved in epitope binding in a starting sequence. In other embodiments, modification of residues which are not directly involved in epitope binding or residues not involved in epitope binding in any way, is desirable, for purposes discussed herein. Mutagenesis within any of the CDR regions and/or framework regions is contemplated.

In order to determine which antigen binding protein amino acid residues are important for epitope recognition and binding, alanine scanning mutagenesis can be performed to produce substitution variants. See, for example, Cunningham et al., Science, 244:1081-1085 (1989), the disclosure of which is incorporated herein by reference in its entirety. In this method, individual amino acid residues are replaced one-at-a-time with an alanine residue and the resulting antibody is screened for its ability to bind its specific epitope relative to the unmodified polypeptide. Modified antigen binding proteins with reduced binding capacity are sequenced to determine which residue was changed, indicating its significance in binding or biological properties.

Substitution variants of antigen binding proteins can be prepared by affinity maturation wherein random amino acid changes are introduced into the parent polypeptide sequence. See, for example, Ouwehand et al., Vox Sang 74 (Suppl 2):223-232, 1998; Rader et al., Proc. Natl. Acad. Sci. USA 95:8910-8915, 1998; Dall'Acqua et al., Curr. Opin. Struct. Biol. 8:443-450, 1998, the disclosures of which are incorporated herein by reference in their entireties. Affinity maturation involves preparing and screening the antigen binding proteins, or variants thereof and selecting from the resulting variants those that have modified biological properties, such as increased binding affinity relative to the parent antigen binding protein. A convenient way for generating substitutional variants is affinity maturation using phage display. Briefly, several hypervariable region sites are mutated to generate all possible amino substitutions at each site. The variants thus generated are expressed in a monovalent fashion on the surface of filamentous phage particles as fusions to the gene III product of M13 packaged within each particle. The phage-displayed variants are then screened for their biological activity (e.g., binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., *J. Mol. Biol.* 260, 359-68, 1996), and saturation mutagenesis (Nishimiya et al., *J. Biol. Chem.* 275:12813-20, 2000; Chowdhury, P. S. *Methods Mol. Biol.* 178, 269-85, 2002) are typical examples of stochastic mutagenesis methods (Rajpal et al., *Proc Natl Acad Sci USA.* 102:8466-71, 2005). Nonstochastic techniques often use alanine-scanning or site-directed mutagenesis to generate limited collections of specific muteins. Some methods are described in further detail below.

Affinity Maturation Via Panning Methods

Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (*Cancer Immunol Immunother.* 50:163-71, 2001). Methods of affinity maturation using phage display technologies are described elsewhere herein and known in the art (see e.g., Daugherty et al., *Proc Natl Acad Sci USA.* 97:2029-34, 2000).

Look-through mutagenesis—Look-through mutagenesis (LTM) (Rajpal et al., Proc Natl Acad Sci USA. 102:8466-71, 2005) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all muteins. After positive selection, clones with improved binding are sequenced, and beneficial mutations are mapped.

Error-prone PCR—Error-prone PCR involves the randomization of nucleic acids between different selection rounds. The randomization occurs at a low rate by the intrinsic error rate of the polymerase used but can be enhanced by error-prone PCR (Zaccolo et al., J. Mol. Biol. 285:775-783, 1999) using a polymerase having a high intrinsic error rate during transcription (Hawkins et al., J Mol. Biol. 226:889-96, 1992). After the mutation cycles, clones with improved affinity for the antigen are selected using routine methods in the art.

Techniques utilizing gene shuffling and directed evolution may also be used to prepare and screen antigen binding proteins, or variants thereof, for desired activity. For example, Jermutus et al., Proc Natl Acad Sci USA., 98(1):75-80 (2001) showed that tailored in vitro selection strategies based on ribosome display were combined with in vitro diversification by DNA shuffling to evolve either the off-rate or thermodynamic stability of scFvs; Fermer et al., Tumour Biol. 2004 January-April; 25(1-2):7-13 reported that use of phage display in combination with DNA shuffling raised affinity by almost three orders of magnitude. Dougherty et al., Proc Natl Acad Sci USA. 2000 Feb. 29; 97(5):2029-2034 reported that (i) functional clones occur at an unexpectedly high frequency in hypermutated libraries, (ii) gain-of-function mutants are well represented in such libraries, and (iii) the majority of the scFv mutations leading to higher affinity correspond to residues distant from the binding site.

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, they are subjected to screening as described herein and antibodies with superior properties in one or more relevant assays may be selected for further development.

Immunoglobulins with Modified Carbohydrate

Immunoglobulin variants can also be produced that have a modified glycosylation pattern relative to the parent polypeptide, for example, adding or deleting one or more of the carbohydrate moieties bound to the immunoglobulin, and/or adding or deleting one or more glycosylation sites in the immunoglobulin.

Glycosylation of polypeptides, including antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an immunoglobulin by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an immunoglobulin by inserting or substituting one or more serine or threonine residues to the sequence of the original immunoglobulin or antibody.

Altered Effector Function

Cysteine residue(s) may be removed or introduced in the Fc region of an antibody or Fc-containing polypeptide, thereby eliminating or increasing interchain disulfide bond formation in this region. A homodimeric immunoglobulin thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric immunoglobulins or antibodies may also be prepared using heterobifunctional cross-linkers as described in Wolff et al., Cancer Research 53: 2560-2565 (1993). Alternatively, an immunoglobulin can be engineered which has dual Fc regions and may thereby have enhanced complement lysis and ADCC capabilities. See Stevenson et al., Anti-CancerDrug Design 3: 219-230 (1989).

It is also contemplated that one or more of the N-terminal 20 amino acid residues (e.g., a signal sequence) of the heavy or light chain are removed.

Modifications to increase serum half-life also may desirable, for example, by incorporation of or addition of a salvage receptor binding epitope (e.g., by mutation of the appropriate region or by incorporating the epitope into a peptide tag that is then fused to the immunoglobulin at either end or in the middle, e.g., by DNA or peptide synthesis) (see, e.g., WO96/32478) or adding molecules such as PEG or other water soluble polymers, including polysaccharide polymers.

The salvage receptor binding epitope preferably constitutes a region wherein any one or more amino acid residues from one or two loops of a Fc domain are transferred to an analogous position of the immunoglobulin or fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the immunoglobulin or antibody. Alternatively, the epitope is taken from the CH2 domain of the Fc region and transferred to the $C_L$ region or $V_L$ region, or both, of the immunoglobulin fragment. See also International applications WO 97/34631 and WO 96/32478 which describe Fc variants and their interaction with the salvage receptor.

Other sites and amino acid residue(s) of the constant region have been identified that are responsible for complement dependent cytotoxicity (CDC), such as the Clq binding site, and/or the antibody-dependent cellular cytotoxicity (ADCC) [see, e.g., Molec. Immunol. 29 (5): 633-9 (1992); Shields et al., J. Biol. Chem., 276(9):6591-6604 (2001); Lazar et al., Proc. Nat'l. Acad. Sci. 103(11): 4005 (2006) which describe the effect of mutations at specific positions, each of which is incorporated by reference herein in its entirety]. Mutation of residues within Fc receptor binding sites can result in altered (i.e. increased or decreased) effector function, such as altered affinity for Fc receptors, altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different subclass (e.g. replacing an IgG1 residue with a corresponding IgG2 residue at that position).

The invention also encompasses production of immunoglobulin molecules, including antibodies and antibody fragments, with altered carbohydrate structure resulting in altered effector activity, including antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., Biotechnol Bioeng. 2004 Sep. 5; 87(5):614-22). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., Mol. Immunol. 1989 December; 26(12):1113-23). Some host cell strains, e.g. Lec13 or rat hybridoma YB2/0 cell line naturally produce antibodies with lower fucosylation levels. Shields et al., J Biol. Chem. 2002 Jul. 26; 277(30):26733-40; Shinkawa et al., J Biol. Chem. 2003 Jan. 31; 278(5):3466-73. An increase in the level of bisected carbohydrate, e.g. through recombinantly producing antibody in cells that overexpress GnTIII enzyme, has also been determined to increase ADCC activity. Umana et al., Nat. Biotechnol. 1999 February; 17(2):176-80. It has been predicted that the absence of only one of the two fucose residues may be sufficient to increase ADCC activity. (Ferrara et al., J Biol. Chem. 2005 Dec. 5).

Other Covalent Modifications of Immunoglobulins

Other particular covalent modifications of the immunoglobulin, are also included within the scope of this invention. They may be made by chemical synthesis or by enzymatic or chemical cleavage of the immunoglobulin or antibody, if applicable. Other types of covalent modifications can be introduced by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK$_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R—N.dbd..C.dbd.N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the immunoglobulin (e.g., antibody or antibody fragment). These procedures are advantageous in that they do not require production of the immunoglobulin in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine.

These methods are described in WO87/05330 published 11 Sep. 1987, and in Aplin and Wriston, CRC Crit. Rev. Biochem., pp. 259-306 (1981).

Removal of any carbohydrate moieties present on the immunoglobulin may be accomplished chemically or enzymatically. Chemical deglycosylation requires exposure of the immunoglobulin to the compound trifluoromethanesulfonic acid, or an equivalent compound. This treatment results in the cleavage of most or all sugars except the linking sugar (N-acetylglucosamine or N-acetylgalactosamine), while leaving the immunoglobulin intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on an immunoglobulin can be achieved by the use of a variety of endo- and exo-glycosidases as described by Thotakura et al. Meth. Enzymol. 138: 350 (1987).

Another type of covalent modification of the immunoglobulins of the invention (including antibodies and antibody fragments) comprises linking the immunoglobulin to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Isolated Nucleic Acids

Another aspect of the present invention is an isolated nucleic acid that encodes an immunoglobulin of the invention, such as, but not limited to, an isolated nucleic acid that encodes an antibody or antibody fragment of the invention. Such nucleic acids are made by recombinant techniques known in the art and/or disclosed herein.

In other embodiments the isolated nucleic acid encodes an immunoglobulin comprising an immunoglobulin heavy chain variable region and an immunoglobulin light chain variable region, wherein:

(a) the heavy chain variable region comprises the amino acid sequence of SEQ ID NO:323 and the light chain variable region comprises the amino acid sequence of SEQ ID NO:188 or SEQ ID NO:190; or (b) the heavy chain variable region comprises the amino acid sequence of SEQ ID NO:321 and the light chain variable region comprises the amino acid sequence of SEQ ID NO:188 or SEQ ID NO:190; or (c) the heavy chain variable region comprises the amino acid sequence of SEQ ID NO:325 and the light chain variable region comprises the amino acid sequence of SEQ ID NO:182, SEQ ID NO:188, or SEQ ID NO:190.

And in some embodiments the isolated nucleic acid encodes an immunoglobulin comprising an immunoglobulin heavy chain variable region and an immunoglobulin light chain variable region, wherein:

(a) the light chain variable region comprises the amino acid sequence of SEQ ID NO:196 and the heavy chain variable region comprises the amino acid sequence of SEQ ID NO:335, SEQ ID NO:349, SEQ ID NO:351, SEQ ID NO:353, SEQ ID NO:355, or SEQ ID NO:359; or (b) the light chain variable region comprises the amino acid sequence of SEQ ID NO:204 and the heavy chain variable region comprises the amino acid sequence of SEQ ID NO:349 or SEQ ID NO:355; or (c) the light chain variable region comprises the amino acid sequence of SEQ ID NO:202 and the heavy chain variable region comprises the amino acid sequence of SEQ ID NO:349; or (d) the light chain variable region comprises the amino acid sequence of SEQ ID NO:192 and the heavy chain variable region comprises the amino acid sequence of SEQ ID NO:357, SEQ ID NO:359, or SEQ ID NO:369; or (e) the light chain variable region comprises the amino acid sequence of SEQ ID NO:194 and the heavy chain variable region comprises the amino acid sequence of SEQ ID NO:335, SEQ ID NO:349, or SEQ ID NO:351.

In other examples, the isolated nucleic acid encodes an immunoglobulin comprising an immunoglobulin heavy chain and an immunoglobulin light chain wherein:

(a) the heavy chain variable region comprises the amino acid sequence of SEQ ID NO:323; and the light chain variable region comprises the amino acid sequence of SEQ ID NO:188; or (b) the light chain variable region comprises the amino acid sequence of SEQ ID NO:196; and the heavy chain variable region comprises the amino acid sequence of SEQ ID NO:353; or (c) the light chain variable region comprises the amino acid sequence of SEQ ID NO:202; and the heavy chain variable region comprises the amino acid sequence of SEQ ID NO:349; or (d) the heavy chain variable region comprises the amino acid sequence of SEQ ID NO:325; and the light chain variable region comprises the amino acid sequence of SEQ ID NO:190.

Or in some embodiments, the isolated nucleic acid encodes an immunoglobulin comprising:

an immunoglobulin heavy chain comprising the amino acid sequence of SEQ ID NO:113, or comprising the foregoing sequence from which one, two, three, four or five amino acid residues are lacking from the N-terminal or C-terminal, or both; and an immunoglobulin light chain comprising the amino acid sequence of SEQ ID NO:110, or comprising the foregoing sequence from which one, two, three, four or five amino acid residues are lacking from the N-terminal or C-terminal, or both; or an immunoglobulin heavy chain comprising the amino acid sequence of SEQ ID NO:125, or comprising the foregoing sequence from which one, two, three, four or five amino acid residues are lacking from the N-terminal or C-terminal, or both; and an immunoglobulin light chain comprising the amino acid sequence of SEQ ID NO:122, or comprising the foregoing sequence from which one, two, three, four or five amino acid residues are lacking from the N-terminal or C-terminal, or both; or an immunoglobulin heavy chain comprising the amino acid sequence of SEQ ID NO:101, or comprising the foregoing sequence from which one, two, three, four or five amino acid residues are lacking from the N-terminal or C-terminal, or both; and an immunoglobulin light chain comprising the amino acid sequence of SEQ ID NO:98, or comprising the foregoing sequence from which one, two, three, four or five amino acid residues are lacking from the N-terminal or C-terminal, or both; or an immunoglobulin heavy chain comprising the amino acid sequence of SEQ ID NO:119, or comprising the foregoing sequence from which one, two, three, four or five amino acid residues are lacking from the N-terminal or C-terminal, or both; and an immunoglobulin light chain comprising the amino acid sequence of SEQ ID NO:116, or comprising the foregoing sequence from which one, two, three, four or five amino acid residues are lacking from the N-terminal or C-terminal, or both.

The present invention is also directed to vectors, including expression vectors that comprise any of the inventive isolated nucleic acids. An isolated host cell that comprises the expression vector is also encompassed by the present invention, which is made by molecular biological techniques known in the art and/or disclosed herein.

The invention is also directed to a method involving:

culturing the host cell in a culture medium under conditions permitting expression of the immunoglobulin encoded by the expression vector; and recovering the immunoglobulin from the culture medium. Recovering the immunoglobulin is accomplished by known methods of antibody purification, such as but not limited to, antibody purification techniques disclosed in Example 1 and elsewhere herein.

Gene Therapy

Delivery of a therapeutic immunoglobulin to appropriate cells can be effected via gene therapy ex vivo, in situ, or in vivo by use of any suitable approach known in the art. For example, for in vivo therapy, a nucleic acid encoding the desired immunoglobulin or antibody, either alone or in conjunction with a vector, liposome, or precipitate may be injected directly into the subject, and in some embodiments, may be injected at the site where the expression of the immunoglobulin compound is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, chemical treatments, DEAE-dextran, and calcium phosphate precipitation. Other in vivo nucleic acid transfer techniques include transfection with viral vectors (such as adenovirus, Herpes simplex I virus, adeno-associated virus or retrovirus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL)) (Felgner et al, (1987) Proc. Natl. Acad. Sci. USA 84, 7413-7417; Malone et al. (1989) Proc. Natl. Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES) (J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2,3-dioleoyloxy]propyl)-N,N,N-trimethylammonium methylsulfate (DOTAP)(Boehringer Mannheim), polyethyleneimine (PEI), dioleoyl esters, ChoTB, ChoSC, DOSC)(Leventis et al. (1990) Biochim. Inter. 22, 235-241); 3beta[N—(N',N'-dimethylaminoethane)-carbamoyl]cholesterol (DC-Chol), dioleoylphosphatidyl ethanolamine (DOPE)/3beta[N—(N',N'- dimethylaminoethane)-carbamoyl]cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1,1,3,3-tetramethylbutyl)cresoxy] ethoxy]ethyl]dimethylbenzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 235(3):726-9), chondroitan-based proteoglycans, sulfated proteoglycans, polyethylenimine, polylysine (Pollard H et al. J Biol Chem, 1998 273 (13):7507-11), integrin-binding peptide CYGGRGDTP (SEQ ID NO:235), linear dextran nonasaccharide, glycerol, cholesteryl groups tethered at the 3'-terminal internucleoside link of an oligonucleotide (Letsinger, R. L. 1989 Proc Natl Acad Sci USA 86: (17):6553-6), lysophosphatide, lysophosphatidylcholine, lysophosphatidylethanolamine, and 1-oleoyl lysophosphatidylcholine.

In some situations it may be desirable to deliver the nucleic acid with an agent that directs the nucleic acid-containing vector to target cells. Such "targeting" molecules include antigen binding proteins specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antigen binding proteins for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. For additional reviews of gene therapy technology, see Friedmann, Science, 244: 1275-1281 (1989); Anderson, Nature, supplement to vol. 392, no 6679, pp. 25-30 (1998); Verma, Scientific American: 68-84 (1990); and Miller, Nature, 357: 455460 (1992).

Administration and Preparation of Pharmaceutical Formulations

The immunoglobulins or antibodies used in the practice of a method of the invention may be formulated into pharmaceutical compositions and medicaments comprising a carrier suitable for the desired delivery method. Suitable carriers include any material which, when combined with the immunoglobulin or antibody, and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary immunoglobulin concentrations in the formulation may range from about 0.1 mg/ml to about 180 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the immunoglobulin may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the immunoglobulin, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the immunoglobulin formulation to reduce aggregation of the formulated immunoglobulin and/or minimize the formation of particulates in the formulation and/or reduce adsorption. Exemplary surfactants include nonionic surfactants such as polysorbates (e.g. polysorbate 20, or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. immunoglobulin, buffer, polyol and surfactant) and is essentially free of one or more preservatives, such as benzyl alcohol, phenol, m-cresol, chlorobutanol and benzethonium Cl. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

Therapeutic formulations of the immunoglobulin are prepared for storage by mixing the immunoglobulin having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In one embodiment, a suitable formulation of the claimed invention contains an isotonic buffer such as a phosphate, acetate, or Tris buffer in combination with a tonicity agent such as a polyol, Sorbitol, sucrose or sodium chloride which tonicifies and stabilizes. One example of such a tonicity agent is 5% Sorbitol or sucrose. In addition, the formulation could optionally include a surfactant such as to prevent aggregation and for stabilization at 0.01 to 0.02% wt/vol. The pH of the formulation may range from 4.5-6.5 or 4.5 to 5.5. Other exemplary descriptions of pharmaceutical formulations for antibodies may be found in US 2003/0113316 and U.S. Pat. No. 6,171,586, each incorporated herein by reference in its entirety.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Suspensions and crystal forms of immunoglobulins are also contemplated. Methods to make suspensions and crystal forms are known to one of skill in the art.

The formulations to be used for in vivo administration must be sterile. The compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, Journal of Parenteral Science and Technology, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, Drug Development and Industrial Pharmacy, Volume 18, Numbers 11 and 12, pages 1311-1354 (1992).

Excipients have been noted in some cases to act as stabilizers for freeze-dried products; Carpenter et al., Developments in Biological Standardization, Volume 74, pages 225-239 (1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and di-saccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the immunoglobulin, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The immunoglobulin is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the immunoglobulin is suitably administered by pulse infusion, particularly with declining doses of the immunoglobulin or antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. Most preferably, the immunoglobulin of the invention is administered intravenously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

Embodiments or aspects of the invention can include but are not limited to the following:

Aspect 1. An isolated immunoglobulin, comprising an immunoglobulin heavy chain variable region and an immunoglobulin light chain variable region, wherein:

(a) the heavy chain variable region comprises the amino acid sequence of SEQ ID NO:323 and the light chain variable region comprises the amino acid sequence of SEQ ID NO:188 or SEQ ID NO:190; or (b) the heavy chain variable region comprises the amino acid sequence of SEQ ID NO:321 and the light chain variable region comprises the amino acid sequence of SEQ ID NO:188 or SEQ ID NO:190; or (c) the heavy chain variable region comprises the amino acid sequence of SEQ ID NO:325 and the light chain variable region comprises the amino acid sequence of SEQ ID NO:182, SEQ ID NO:188, or SEQ ID NO:190.

Aspect 2. An isolated immunoglobulin, comprising an immunoglobulin heavy chain variable region and an immunoglobulin light chain variable region, wherein:

(a) the light chain variable region comprises the amino acid sequence of SEQ ID NO:196 and the heavy chain variable region comprises the amino acid sequence of SEQ ID NO:335, SEQ ID NO:349, SEQ ID NO:351, SEQ ID NO:353, SEQ ID NO:355, or SEQ ID NO:359; or (b) the light chain variable region comprises the amino acid sequence of SEQ ID NO:204 and the heavy chain variable region comprises the amino acid sequence of SEQ ID NO:349 or SEQ ID NO:355; or (c) the light chain variable region comprises the amino acid sequence of SEQ ID NO:202 and the heavy chain variable region comprises the amino acid sequence of SEQ ID NO:349; or (d) the light chain variable region comprises the amino acid sequence of SEQ ID NO:192 and the heavy chain variable region comprises the amino acid sequence of SEQ ID NO:357, SEQ ID NO:359, or SEQ ID NO:369; or (e) the light chain variable region comprises the amino acid sequence of SEQ ID NO:194 and the heavy chain variable region comprises the amino acid sequence of SEQ ID NO:335, SEQ ID NO:349, or SEQ ID NO:351.

Aspect 3. The isolated immunoglobulin of Aspect 1, wherein the heavy chain variable region comprises the amino acid sequence of SEQ ID NO:323; and the light chain variable region comprises the amino acid sequence of SEQ ID NO:188.

Aspect 4. The isolated immunoglobulin of Aspect 2, wherein the light chain variable region comprises the amino acid sequence of SEQ ID NO:196; and the heavy chain variable region comprises the amino acid sequence of SEQ ID NO:353.

Aspect 5. The isolated immunoglobulin of Aspect 2, wherein the light chain variable region comprises the amino acid sequence of SEQ ID NO:202; and the heavy chain variable region comprises the amino acid sequence of SEQ ID NO:349.

Aspect 6. The isolated immunoglobulin of Aspect 1, wherein the heavy chain variable region comprises the amino acid sequence of SEQ ID NO:325; and the light chain variable region comprises the amino acid sequence of SEQ ID NO:190.

Aspect 7. The isolated immunoglobulin of Aspect 1 or Aspect 2, wherein the isolated immunoglobulin comprises an antibody or antibody fragment.

Aspect 8. The isolated immunoglobulin of any of Aspects 1-7, comprising an IgG1, IgG2, IgG3 or IgG4.

Aspect 9. The isolated immunoglobulin of any of Aspects 1-8, comprising a monoclonal antibody.

Aspect 10. The isolated immunoglobulin of any of Aspects 1-9, comprising a human antibody.

Aspect 11. The isolated immunoglobulin of Aspect 10, comprising:

(a) an immunoglobulin heavy chain comprising the amino acid sequence of SEQ ID NO:113, or comprising the foregoing sequence from which one, two, three, four or five amino acid residues are lacking from the N-terminal or C-terminal, or both; and an immunoglobulin light chain comprising the amino acid sequence of SEQ ID NO:110, or comprising the foregoing sequence from which one, two, three, four or five amino acid residues are lacking from the N-terminal or C-terminal, or both; or (b) an immunoglobulin heavy chain comprising the amino acid sequence of SEQ ID NO:125, or comprising the foregoing sequence from which one, two, three, four or five amino acid residues are lacking from the N-terminal or C-terminal, or both; and an immunoglobulin light chain comprising the amino acid sequence of SEQ ID NO:122, or comprising the foregoing sequence from which one, two, three, four or five amino acid residues are lacking from the N-terminal or C-terminal, or both; or (c) an immunoglobulin heavy chain comprising the amino acid sequence of SEQ ID NO:101, or comprising the foregoing sequence from which one, two, three, four or five amino acid residues are lacking from the N-terminal or C-terminal, or both; and an immunoglobulin light chain comprising the amino acid sequence of SEQ ID NO:98, or comprising the foregoing sequence from which one, two, three, four or five amino acid residues are lacking from the N-terminal or C-terminal, or both; or (d) an immunoglobulin heavy chain comprising the amino acid sequence of SEQ ID NO:119, or comprising the foregoing sequence from which one, two, three, four or five amino acid residues are lacking from the N-terminal or C-terminal, or both; and an immunoglobulin light chain comprising the amino acid sequence of SEQ ID NO:116, or comprising the foregoing sequence from which one, two, three, four or five amino acid residues are lacking from the N-terminal or C-terminal, or both.

Aspect 12. The isolated immunoglobulin of any of Aspects 1-11, further comprising one to twenty-four pharmacologically active chemical moieties conjugated thereto.

Aspect 13. The isolated immunoglobulin of any of Aspects 1-12, wherein the pharmacologically active chemical moiety is a pharmacologically active polypeptide.

Aspect 14. The isolated immunoglobulin of any of Aspect 1-13, wherein the immunoglobulin is recombinantly produced.

Aspect 15. The isolated immunoglobulin of Aspect 14, wherein the immunoglobulin comprises at least one immunoglobulin heavy chain and at least one immunoglobulin light chain, and wherein the pharmacologically active polypeptide is inserted in the primary amino acid sequence of the of the immunoglobulin heavy chain within an internal loop of the Fc domain of the immunoglobulin heavy chain.

Aspect 16. The isolated immunoglobulin of Aspect 13 or 14, wherein the immunoglobulin comprises at least one immunoglobulin heavy chain and at least one immunoglobulin light chain, and wherein the pharmacologically active polypeptide is conjugated at the N-terminal or C-terminal of the immunoglobulin heavy chain.

Aspect 17. The isolated immunoglobulin of Aspect 13 or 14, wherein the immunoglobulin comprises at least one immunoglobulin heavy chain and at least one immunoglobulin light chain, and wherein the pharmacologically active polypeptide is conjugated at the N-terminal or C-terminal of the immunoglobulin light chain.

Aspect 18. The isolated immunoglobulin of Aspect 13 or 14, wherein the pharmacologically active polypeptide is a toxin peptide, an IL-6 binding peptide, a CGRP peptide antagonist, a bradykinin B1 receptor peptide antagonist, a PTH agonist peptide, a PTH antagonist peptide, an ang-1 binding peptide, an ang-2 binding peptide, a myostatin binding peptide, an EPO-mimetic peptide, a FGF21 peptide, a TPO-mimetic peptide, a NGF binding peptide, a BAFF antagonist peptide, a GLP-1 or peptide mimetic thereof, or a GLP-2 or peptide mimetic thereof.

Aspect 19. The isolated immunoglobulin of Aspect 18, wherein the toxin peptide is ShK or a ShK peptide analog.

Aspect 20. A pharmaceutical composition comprising the immunoglobulin of any of Aspects 1-19; and a pharmaceutically acceptable diluent, excipient or carrier.

Aspect 21. An isolated nucleic acid that encodes the immunoglobulin of any of Aspects 1-11.

Aspect 22. An isolated nucleic acid that encodes the immunoglobulin of Aspect 3.

Aspect 23. An isolated nucleic acid that encodes the immunoglobulin of Aspect 4.

Aspect 24. An isolated nucleic acid that encodes the immunoglobulin of claim Aspect 5.

Aspect 25. An isolated nucleic acid that encodes the immunoglobulin of Aspect 6.

Aspect 26. An isolated nucleic acid that encodes the immunoglobulin of Aspect 11.

Aspect 27. An isolated nucleic acid that encodes the immunoglobulin of any of Aspects 13-19.

Aspect 28. A vector comprising the isolated nucleic acid of Aspect 21.

Aspect 29. A vector comprising the isolated nucleic acid of any of Aspects 22-26.

Aspect 30. A vector comprising the isolated nucleic acid of Aspect 27.

Aspect 31. The vector of Aspect 28, comprising an expression vector.

Aspect 32. The vector of Aspect 29, comprising an expression vector.

Aspect 33. The vector of Aspect 30, comprising an expression vector.

Aspect 34. An isolated host cell, comprising the expression vector of any of Aspects 31-33.

Aspect 35. A method, comprising:
(a) culturing the host cell of Aspect 34 in a culture medium under conditions permitting expression of the immunoglobulin encoded by the expression vector; and
(b) recovering the immunoglobulin from the culture medium.

Aspect 36. The immunoglobulin of Aspect 1, wherein the immunoglobulin at 30 micromolar concentration does not significantly bind soluble human IL-17R (SEQ ID NO:89) at 30 nanomolar concentration in an aqueous solution incubated under physiological conditions, as measured by a surface plasmon resonance binding assay.

Aspect 37. The immunoglobulin of Aspect 2, wherein the immunoglobulin at 10 micromolar concentration does not significantly bind soluble human TR2 (SEQ ID NO:82) at 10 nanomolar concentration in an aqueous solution incubated under physiological conditions, as measured by a surface plasmon resonance binding assay.

The invention is illustrated by the following further examples, which are not intended to be limiting in any way.

EXAMPLES

Example 1

Generation of Antibodies to Human IL-17R and Screening

Cloning and Engineering.

The Antibody 16429 DNA sequences encoding immunoglobulin heavy chain (comprising VH1) and light chain (comprising VL1) subunits for anti-huIL-17R antibodies were obtained from Tocker et al. (WO 2008/054603 A2) and were cloned using standard recombinant technology. In order to eliminate the binding ability of these antibodies a series of site directed mutagenesis clones were generated using polymerase chain reaction (PCR) amplification. The amino acids to be changed were selected on the basis of location in the complementarity determining regions (CDRs), change from germline sequence, estimated solvent exposure, and aromatic and charge nature. The initial set of mutants was germlining and alanine scanning mutants. Subsequently, mutations were combined and in several cases the alanine scanning mutants were mutated to introduce negative charge, by replacing the alanine with glutamic acid, or positive charge, by replacing the alanine with arginine.

A representative example of the PCR site direct mutation procedure is the introduction of an alanine in place of a tryptophan the CDR3 of the anti-IL17 light chain.

PCR amplification was done as a three step process with a 5' and 3' PCR used to introduce the mutation and a final overlap PCR to join the two ends of the mutated anti-IL17R light chain. The 5' PCR use the forward primer, 5'-AAG CTC GAG GTC GAC TAG ACC ACC ATG GAA GCC CCA GCG CAG-3' (SEQ ID NO:31) and the reverse primer, 5'-GAA AGT GAG CGG AGC GTT ATC ATA CTG CTG ACA-3' (SEQ ID NO:32). The 3' PCR use the forward primer, 5'-TGT CAG CAG TAT GAT AAC GCT CCG CTC ACT TTC-3' (SEQ ID NO:33) and the reverse primer, 5'-AAC CGT TTA AAC GCG GCC GCT CAA CAC TCT CCC CTG TTG AA-3' (SEQ ID NO:34). The overlap PCR use the forward primer, 5'-AAG CTC GAG GTC GAC TAG ACC ACC ATG GAA GCC CCA GCG CAG-3' (SEQ ID NO:31) and the reverse primer, 5'-AAC CGT TTA AAC GCG GCC GCT CAA CAC TCT CCC CTG TTG AA-3' (SEQ ID NO:34).

The PCRs were performed with Phusion HF DNA polymerase (Finnzyme). The PCR reaction cycles for the 5' and 3' PCRs consisted of a 20 second denaturation of the anti-IL-17R light chain DNA at 94° C., followed by three cycles of amplification with each cycle consisting of 20 seconds at 94° C.; 30 seconds at 55° C.; and 30 seconds at 72° C. plus an additional 27 cycles consisting of 20 seconds at 94° C.; 30 seconds at 60° C.; and 30 seconds at 72° C. The reactions were then incubated for 7 minutes at 72° C. following the last PCR cycle to insure complete elongation. The PCR reaction cycles for the overlap PCR consisted of a 20 second denaturation of the 5' and 3' PCR DNAs at 94° C., followed by three cycles of amplification with each cycles consisting of 20 seconds at 94° C.; 60 seconds at 55° C.; and 40 seconds at 72° C. plus an additional 27 cycles consisting of 20 seconds at 94° C.; 30 seconds at 60° C.; and 40 seconds at 72° C. The reaction was then incubated for 7 minutes at 72° C. following the last PCR cycle to insure complete elongation. The overlap PCR product was cloned into pTT5 expression vector (NRCC) and its sequences determined using ABI DNA sequencing instrument (Perkin Elmer). Further detail about construct development is found in Example 5 and Example 6 herein. Table 6 (below) contains details about the primers and templates used in cloning the component subunits of various embodiments of the inventive immunoglobulins and conjugates, based on the same PCR cycling conditions described in this paragraph.

Transient Expression to Generate Recombinant Monoclonal Antibodies.

Transient transfections were carried out in HEK 293-6E cells as follows. The human embryonic kidney 293 cell line stably expressing Epstein Barr virus Nuclear Antigen-1 (293-6E cells) was obtained from the National Research Council (Montreal, Canada). Cells were maintained as serum-free suspension cultures using F17 medium (Invitrogen, Carlsbad, Calif.) supplemented with 6 mM L-glutamine (Invitrogen, Carlsbad, Calif.), 1.1% F-68 Pluronic (Invitrogen, Carlsbad, Calif.) and 250 µg/µl Geneticin (Invitrogen, Carlsbad, Calif.). The suspension cell cultures were maintained in Erlenmeyer shake flask cultures. The culture flasks were shaken at 65 rpm at 37° C. in a humidified, 5% $CO_2$ atmosphere. A stock solution (1 mg/ml) of 25-kDa linear PEI (Polysciences, Warrington, Pa.) was prepared in water, acidified with HCl to pH 2.0 until dissolved, then neutralized with NaOH, sterilized by filtration (0.2 µm), aliquoted, and stored at −20° C. until used. Tryptone N1 was obtained from OrganoTechni S.A. (Tekni-Science, QC, Canada). A stock solution (20%, w/v) was prepared in Freestyle medium (Invitrogem, Carlsbad, Calif.), sterilized by filtration through 0.2 µm filters, and stored at 4° C. until use. Typically, transfections were performed at the 1 L scale. Cells (293-6E) were grown too a viable cell density of $1.1×10^6$ cells/ml then transfection complexes were prepared in ¹⁄₁₀th volume of the final culture volume. For a 1-L transfection culture, transfection complexes were prepared in 100 ml F17 basal medium, and 500 µg plasmid DNA (heavy chain and light chain DNA, 1:1 ratio) was first diluted in 100 ml F17 medium. After a 5-minute incubation at room temperature, 1.5 ml of PEI solution was added. The complexes were vortexed mildly, then incubated for 15 minutes at room temperature. The cells were transfected by adding the transfection complex mix to the cells in the shale flask culture. 24 hours post-transfection, Tryptone N1 was added to the transfected culture to a final concentration of 0.5%, and the transfected cultures were maintained on a shaker at 65 rpm at 37° C. in a humidified, 5% $CO_2$ atmosphere for another 5 days after which they were harvested. The conditioned medium was harvested by centrifugation at 4000 rpm, and then sterile filtered through 0.2 µm filter (Corning Inc.).

Purification of Antibodies.

The transiently expressed antibodies were purified using recombinant protein A sepharose (GE Healthcare) directly loading the conditioned media on the column at 5 ml/min at 7° C. The column was then washed with 10 column volumes of Dulbecco's PBS without divalent cations and then eluted with 100 mM acetic acid, pH 3.5. The eluted antibody was pooled based on the chromatographic profile and the pH was adjusted to 5.0 using 2 M Tris base. The pool was then filtered through a 0.8/0.22 µm syringe filter and then dialyzed against 10 mM acetic acid, 9% sucrose, pH 5.0. The buffer exchanged antibody was then concentrated using a Vivaspin 30 kDa centrifugal concentration (Sartorius), and the concentrated product was filtered through a 0.22 µm cellulose acetate filter.

BIAcore® Binding Assays.

The lead candidates were then selected based on lack of binding to the IL-17R extracellular domain as determined by BIAcore analysis. Antibody 16429 is a human antibody that specifically binds to huIL-17R. A solution equilibrium binding assay was developed to assess the binding activity of a set of antibodies to huIL-17R. Antibody 16429 was immobilized to a BIACore® 2000, research grade sensor chip CM5 surface according to manufacturer's instructions (BIACore, Inc., Piscataway, N.J.). Briefly, carboxyl groups on the sensor chip surfaces were activated by injecting 60 µL of a mixture containing 0.2 M N-ethyl-N'-(dimethylaminopropyl)carbodiimide (EDC) and 0.05 M N-hydroxysuccinimide (NHS). Antibody 16429 was diluted in 10 mM sodium acetate, pH 4.0 and injected over the activated chip surface at 30 µL/min for 6 minutes. Excess reactive groups on the surfaces were deactivated by injecting 60 µL of 1 M ethanolamine. The final immobilized level was approximately 6600 resonance units (RU). As represented in FIG. 2A, 10 nM of IL-17R in the absence of soluble antibody was used to establish the 100% binding signal of IL-17R to the fixed 16429 antibody. To determine antibody binding in solution, 10 nM, 100 nM and 1000 nM of the antibody samples were incubated with the 10 nM IL-17R. The decreased binding signal of IL-17R after the antibody incubation indicates the binding of the antibody to IL-17R in solution. Based on this assay, the 16435, 16438, 16439, 16440, 16441, and 16444 antibodies demonstrated substantial reduction in IL-17R binding capability. As represented in FIG. 2B, 30 nM IL-17R and 30 µM antibody samples were used to further demonstrate that the selected antibodies lost their IL-17R binding activity. Based on this assay, all six antibodies examined (16435, 16438, 16439, 16440, 16441, and 16444) showed no signficant IL-17R binding activity at up to 30 µM antibody.

Cell Based Activity Assay.

Interaction of IL-17 with the IL-17R on cells induces the production of various factors, including growth-related oncogene alpha (GRO-α), from these cells. A cell-based characterization assay was developed to measure GRO-α released using sandwich ELISA. In this ELISA, a GRO-α capture antibody is utilized to bind GRO-α, and then a biotinylated GRO-α detection antibody is used to detect the captured protein. Streptavidin conjugated to horseradish peroxidise (HRP) is then added to detect the amount of biotinylated GRO-α detection antibody bound. The amount of HRP bound is measured by evaluation of absorbance at 450 nm. An increase in absorbance at 450 nm is indicative of an increase in the amount of GRO-α produced. In this assay, human foreskin fibroblasts (HFF) are incubated with 5 ng/ml IL-17 and 0.1 µM, 1 µM and 10 µM of antibody samples. The conditioned cell medium is then harvested and processed for assessment of GRO-α levels using a GRO-α sandwich ELISA. All six experimental carrier antibodies (16435, 16438, 16439, 16440, 16441, and 16444) showed no significant blocking activity in this assay at up to 10 µM antibody (FIG. 3).

Analysis of Homogeneity.

Figure 4A:
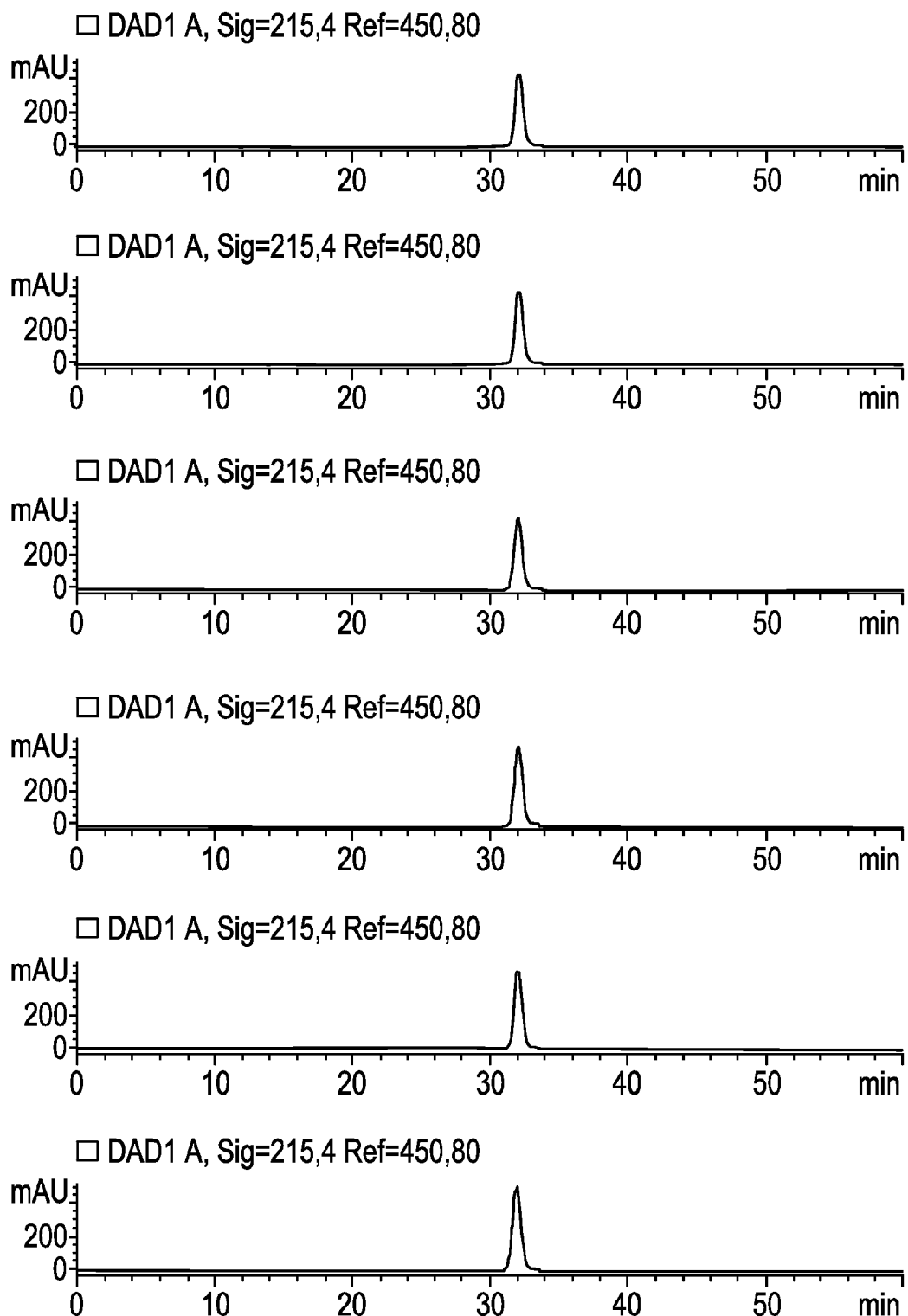
Figure 4B:
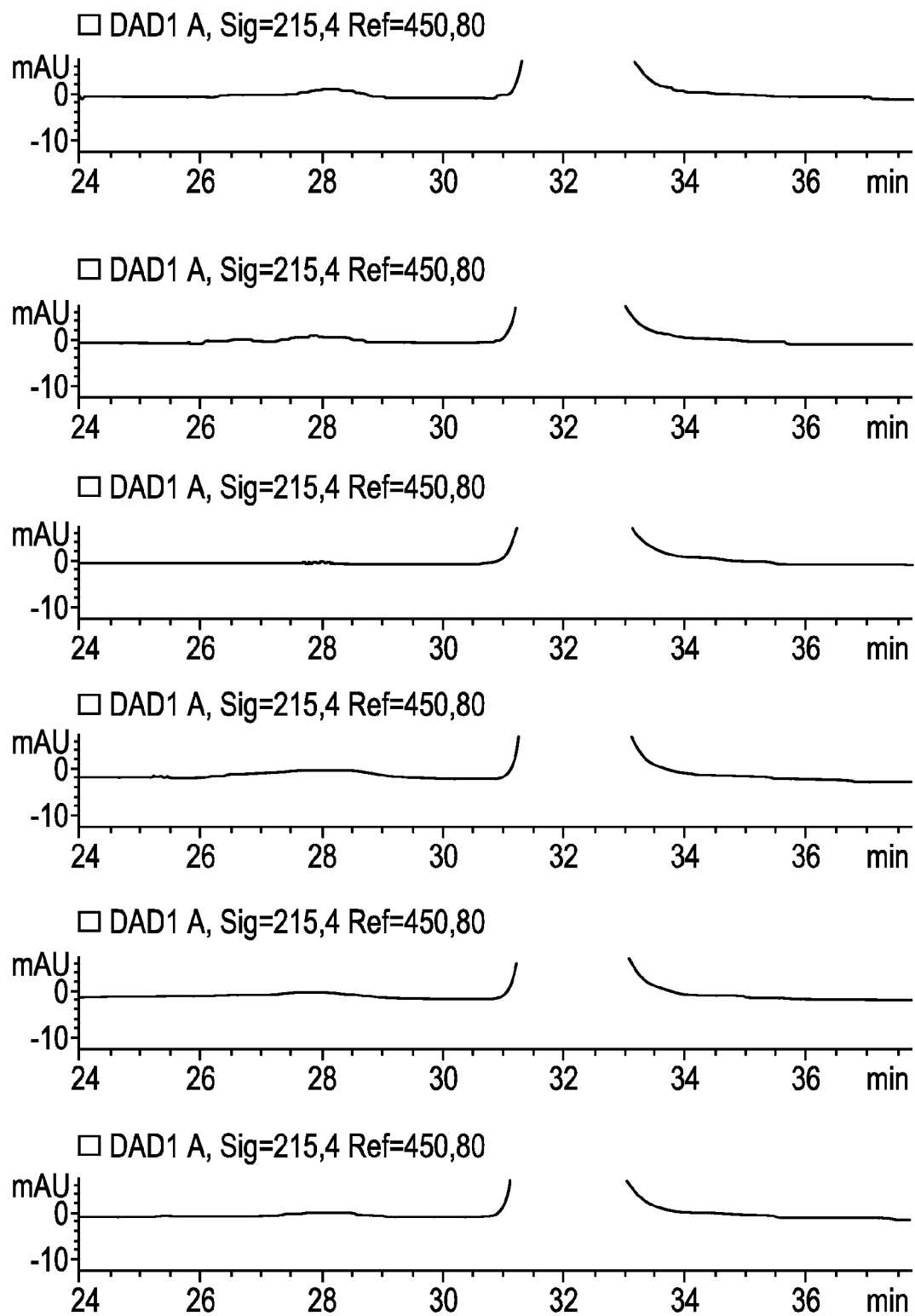
Figure 5:
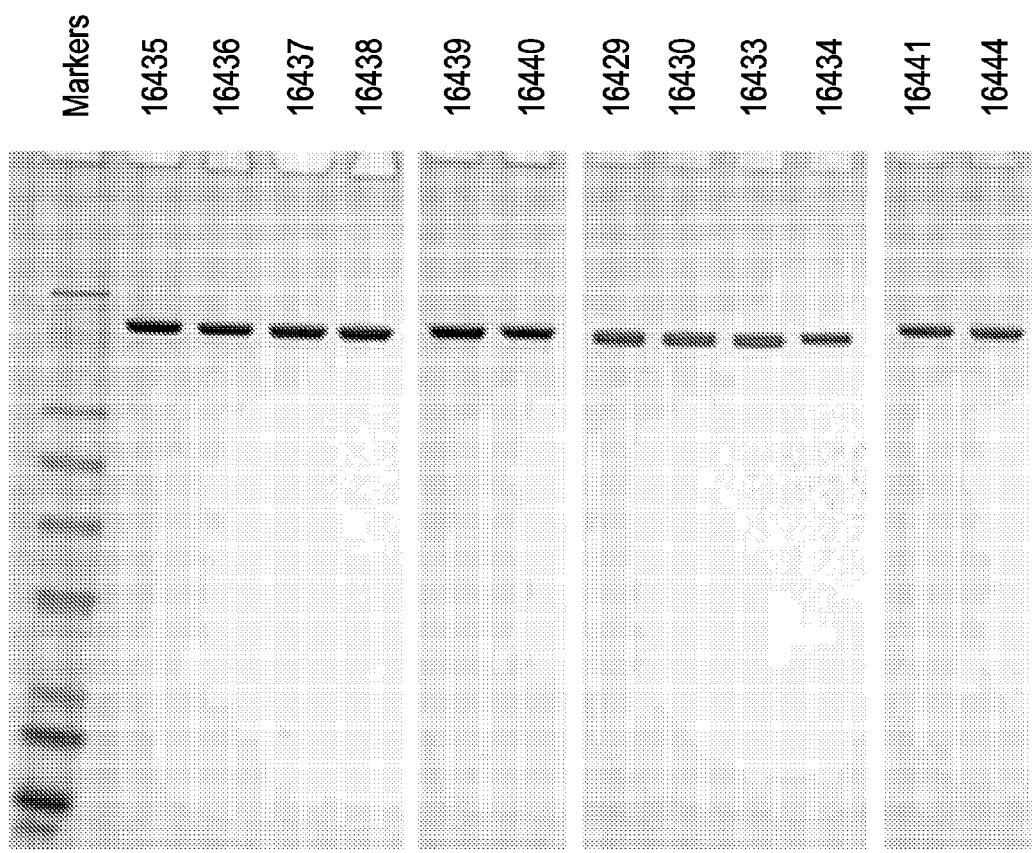
Figure 6:
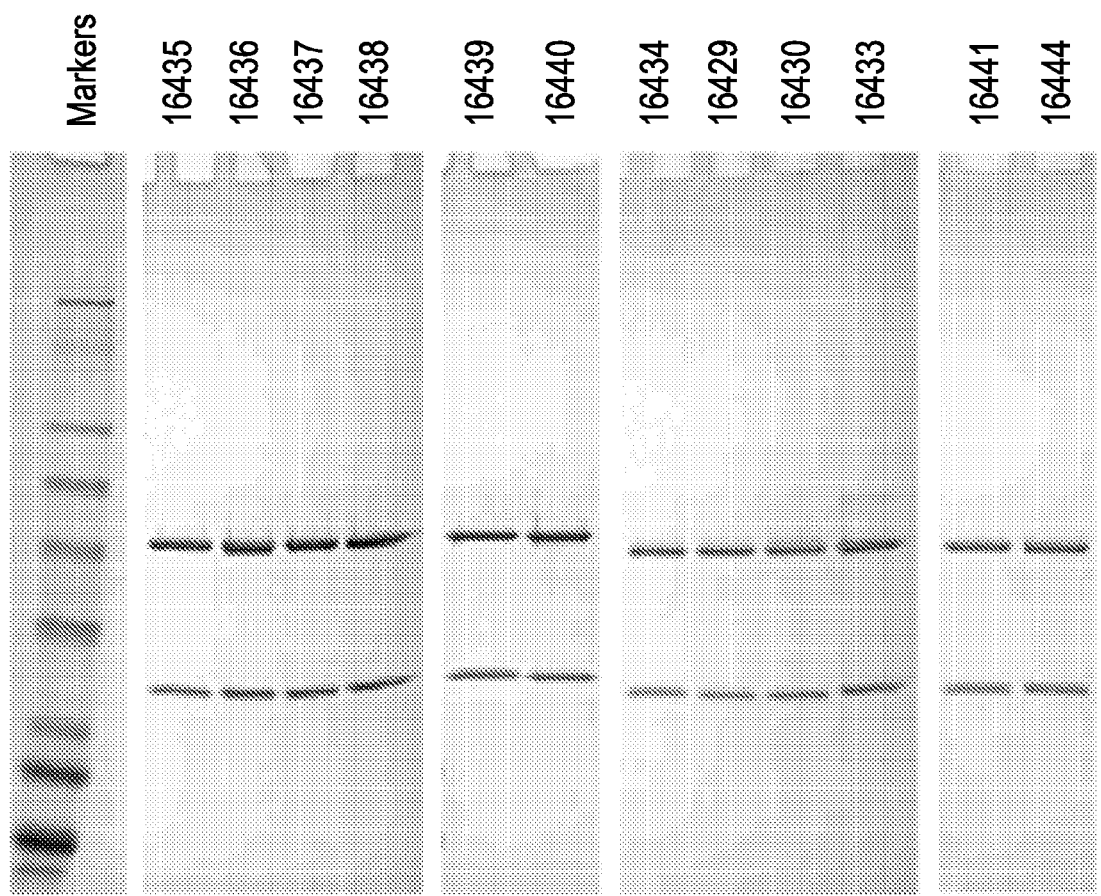

Antibodies produced by transient expression were analyzed for homogeneity using two size exclusion columns (TSK-GEL G3000SWXL, 5 mm particle size, 7.8×300 mm, TosohBioscience, 08541) in series with a 100 mM sodium phosphate, 250 mM NaCl, pH 6.8, mobile phase flowed at 0.5 mL/min (FIGS. 4A-B). While all the antibodies showed relatively low levels of high molecular weight species, 16439 and 16435 had the least, while 16440 had the most. The lead antibodies were further analyzed for product quality on a 1.0-mm Tris-glycine 4-20% SDS-PAGE (Novex) using reducing (FIG. 6) and non-reducing loading buffer (FIG. 5). All candidates appeared quite similar by both non-reducing and reducing SDS-PAGE; however, 16433 did show some additional high molecular mass material on the reducing SDS-PAGE. Lead candidates were further selected based on SEC behavior, SDS-PAGE uniformity, BIAcore binding analysis, cell based assay results and expression levels. Based on these criteria, 16435 and 16444 were chosen for further evaluation.

Stable Expression of Antibodies.

Antibody 16435 and 16444 expressing pools were created by transfecting CHO DHFR(−) host cells with corresponding HC and LC expression plasmid set using a standard electroporation procedure. Per each antibody molecule, 3-4 different transfections were performed to generate multiple pools. After transfection the cells were grown as a pool in a serum free, (−) GHT (selective growth media to allow for selection and recovery of the plasmid containing cells. Cell pools grown in (−) GHT selective media were cultured until they reached >85% viability. The selected cell pools were amplified with 150 nm MTX. When the viability of the MTX amplified pools reached >85% viability, the pools were screened using an abbreviated six day batch production assay with an enriched production media to assess expression. The best pool was chosen based on the six day assay titer and correct mass confirmation. Subsequently, scale-up production using 11-day fed-batch process was performed for the antibody generation, followed by harvest and purification.

Figure 7A:
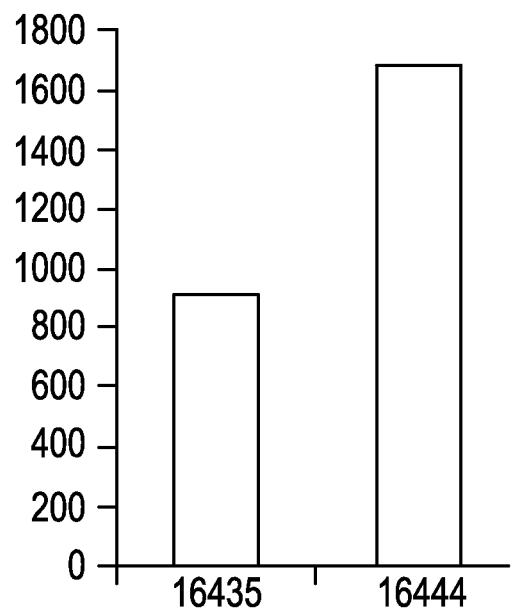
Figure 7B:
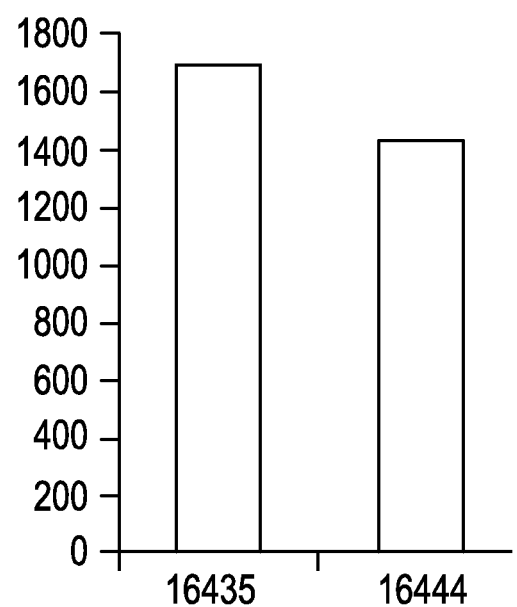

Titers were determined by HPLC assay (FIGS. 7A-B) using a Poros A column, 20 µm, 2.1×30 mm (Applied Biosystems, part #1-5024-12). Briefly, Antibodies in conditioned media were filtered using Spin-X columns (Corning, part #8160) prior to analysis by HPLC, and a blank injection of 1×PBS (Invitrogen, part #14190-144) was performed prior to injection of test antibodies and after each analysis run. In addition, conditioned media without antibody was injected prior to analysis to condition the column, and new columns were conditioned by triplicate injection of 100 µg of control antibody. After a 9-minute wash with PBS at 0.6 ml/min, the antibody was eluted with ImmunoPure IgG Elution Buffer (Pierce, part #21009) and the absorbance at 280 nm was observed. Antibody titers were quantified against a standard plot of control antibody concentration versus peak area. A control antibody stock was prepared at a concentration of 4 mg/ml, and five standard antibody concentrations were prepared by dilution of the antibody control stock in a volume of PBS (0.1 µg/µl to 1.6 µg/µl). By extending the standard curve, the lower limit of detection is 0.02 µg/µl of antibody, and the higher limit of quantification is 4 µg/µl. An assumption was made that test antibodies have similar absorbance characteristics as the control; however titers can be adjusted by multiplying titer an extinction coefficient ratio of the control antibody over the extinction coefficient of the test antibody. The titer assay results show that after scale up to the fed batch process, the 16435 antibody demonstrated marginally better expression than the 16444 carrier antibody.

Purification of Stably Expressed Antibodies.

Figure 8A:
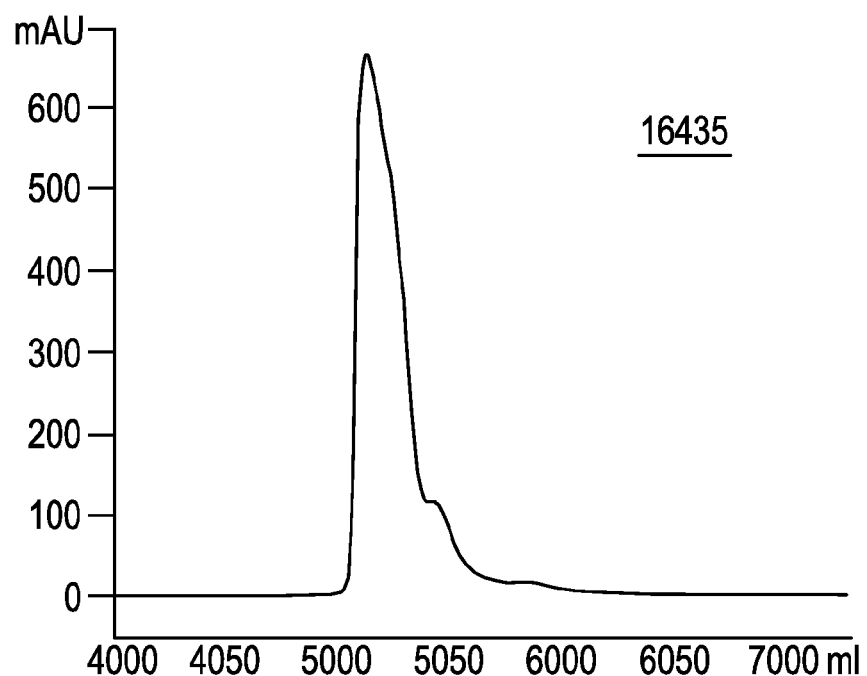
Figure 8B:
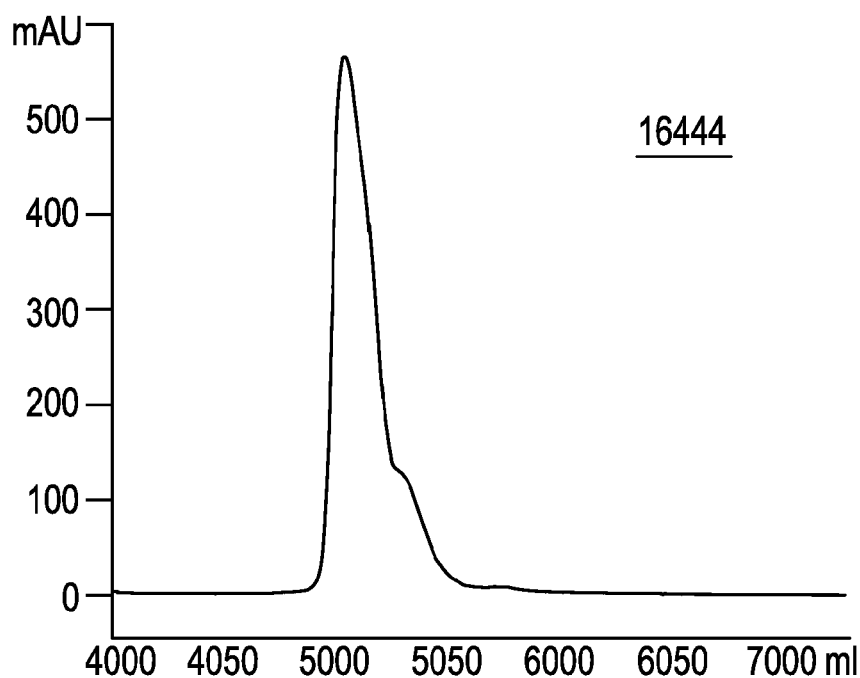

Stably expressed antibodies were purified by Mab Select Sure chromatography (GE Life Sciences) using 8 column volumes of Dulbecco's PBS without divalent cations as the wash buffer and 100 mM acetic acid, pH 3.5, as the elution buffer at 7° C. The elution peak was pooled based on the chromatogram, and the pH was raised to about 5.0 using 2 M Tris base. The pool was then diluted with at least 3 volumes of water, filtered through a 0.22-µm cellulose acetate filter and then loaded on to an SP-HP sepharose column (GE Life Sciences) and washed with 10 column volumes of S-Buffer A (20 mM acetic acid, pH 5.0) followed by elution using a 20 column volume gradient to 50% S-Buffer B (20 mM acetic acid, 1 M NaCl, pH 5.0) at 7° C. A pool was made based on the chromatogram and SDS-PAGE analysis, then the material was concentrated about 6-fold and diafiltered against about 5 volumes of 10 mM acetic acid, 9% sucrose, pH 5.0 using a VivaFlow TFF cassette with a 30 kDa membrane. The dialyzed material was then filtered through a 0.8/0.2-µm cellulose acetate filter and the concentration was determined by the absorbance at 280 nm. Comparison of the ion exchange chromatographic profiles of the 16435 and 16444 variants showed no significant differences (FIGS. 8A-B).

Analysis of Stably Expressed Antibodies.

Figure 9A:
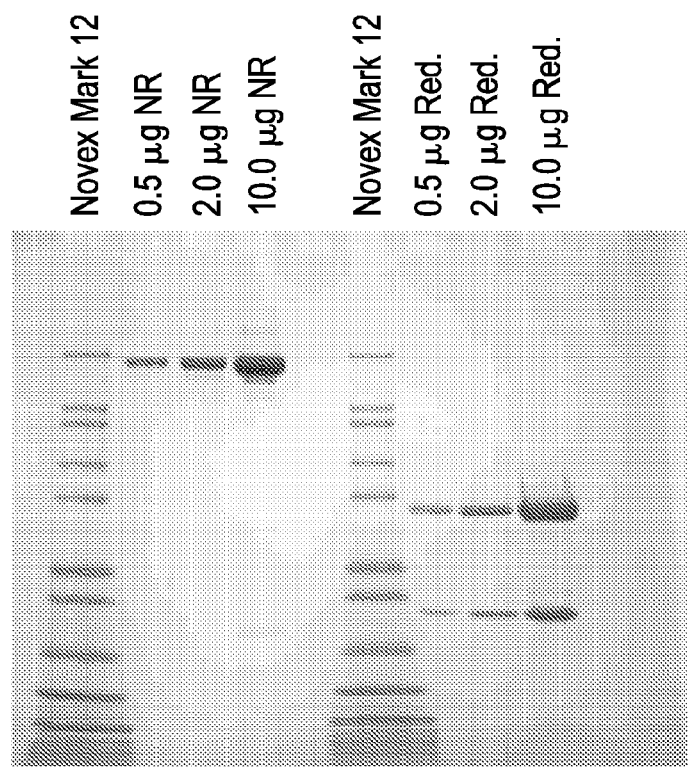
Figure 9B:
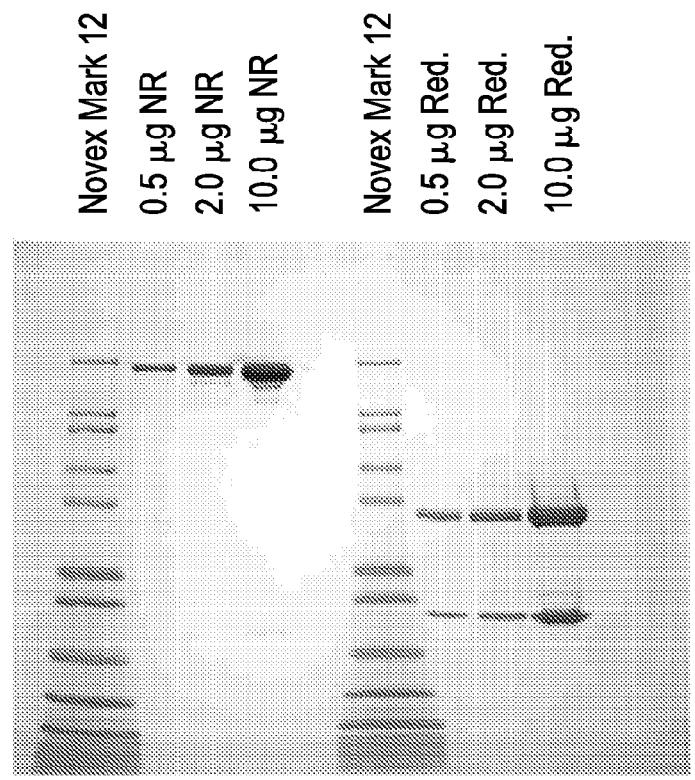

Analysis of the variants using 1.0-mm Tris-glycine 4-20% SDS-PAGE (Novex) with reducing and non-reducing loading buffer also showed no significant difference between the variants (FIGS. 9A-B). However analysis using two size exclusion columns (TSK-GEL G3000SWXL, 5 mm particle size, 7.8×300 mm, TosohBioscience, 08541) in series with a 100 mM sodium phosphate, 250 mM NaCl, pH 6.8, mobile phase flowed at 0.5 mL/min showed that 16444 possessed more high molecular weight species, and 16435 had a more prominent pre-peak (FIG. 10).

Antibodies were also analyzed for thermoresistance by DSC using a MicroCal VP-DSC where the samples were heated from 20° C. to 95° C. at a rate of 1° C. per minute. DSC directly measures heat changes that occur in biomolecules during controlled increase or decrease in temperature, making it possible to study materials in their native state.

Figure 11:
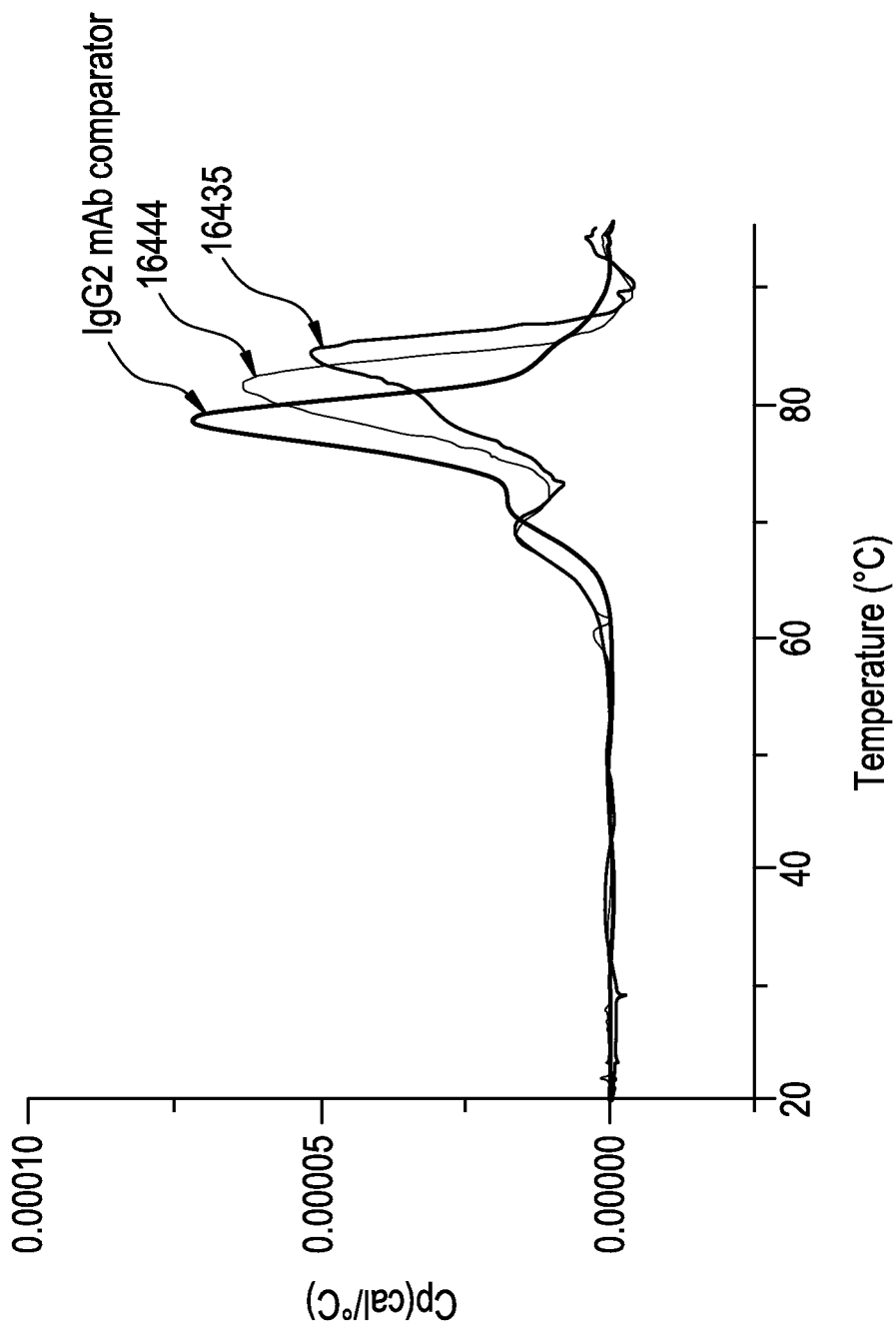
Figure 12A:
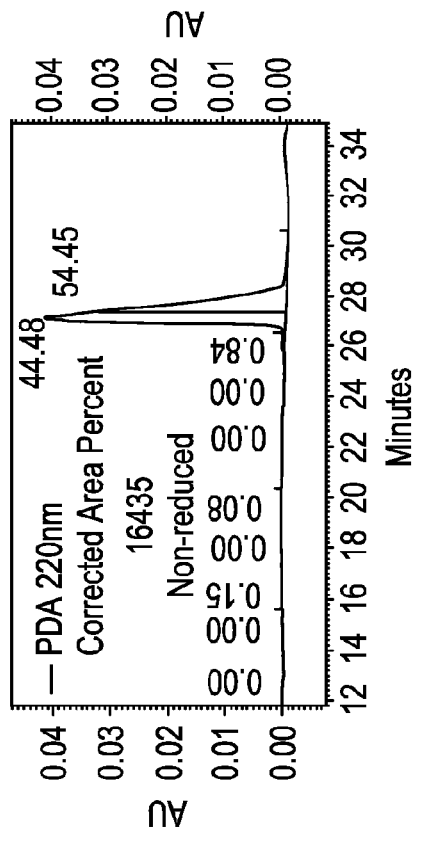
Figure 12B:
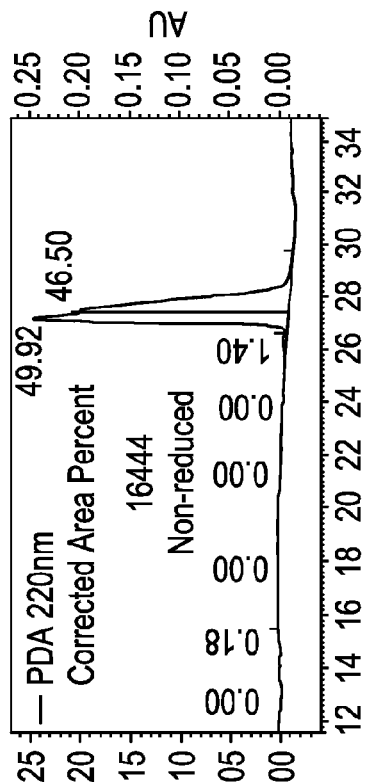
Figure 12C:
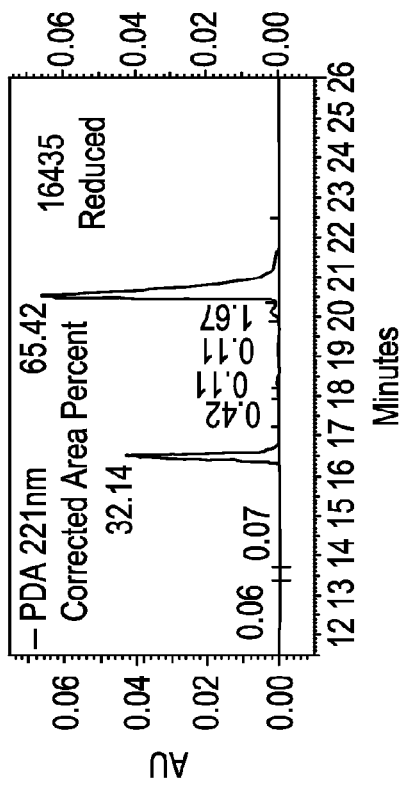
Figure 12D:
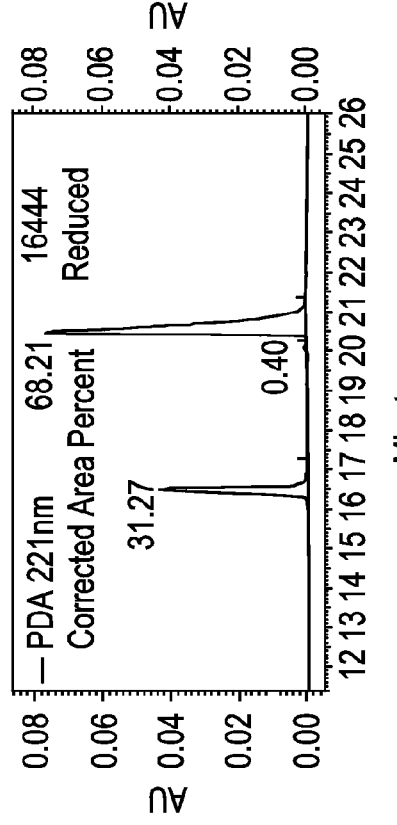

DSC measures the enthalpy (ΔH) of unfolding due to heat denaturation. A biomolecule in solution is in equilibrium between the native (folded) conformation and its denatured (unfolded) state. The higher the thermal transition midpoint (Tm), when 50% of the biomolecules are unfolded, the more stable the molecule. DSC is also used to determine the change in heat capacity (ΔCp) of denaturation (see, FIG. 11). The proteins were incubated at 0.5 mg/ml in 10 mM sodium acetate, 9% sucrose, pH 5.0 (FIG. 11). The 16435 antibody produced the most desirable melting profile, with a higher temperature for the secondary transition.

The antibodies were analyzed by reducing and non-reducing CE-SDS (FIGS. 12A-D). All CE SDS experiments were performed using Beckman PA800 CE system (Fullerton, Calif.) equipped with UV diode detector employing 221 nm and 220 nm wavelength. A bare-fused silica capillary 50 µm×30.2 cm was used for the separation analysis. Buffer vial preparation and loading as well as capillary cartridge installation were conducted as described in the Beckman Coulter manual for IgG Purity/Heterogeneity. The running conditions for reduced and non-reduced CE-SDS were similar to those described in Beckman Coulter manual for IgG Purity/Heterogeneity with some modifications which are briefly described below. For non-reducing conditions, the antibody sample (150 μg) was added to 20 μl of SDS reaction buffer and 5 μl of 70 mM N-ethylmaleimide. Water was then added to make final volume 35 μl and the protein concentration was brought to 4.3 mg/ml. The SDS reaction buffer was made of 4% SDS, 0.01 M citrate phosphate buffer (Sigma) and 0.036 M sodium phosphate dibasic. The preparation was vortexed thoroughly, and heated at 45° C. for 5 min. The preparation was then combined with an additional 115 μl of 4% SDS. After being vortexed and centrifuged, the preparation was placed in a 200 μL PCR vial and then loaded onto the PA800 instrument. The sample was injected at the anode with reverse polarity using −10 kV for 30 sec, and was then separated at −15 kV with 20 psi pressure at both ends of capillary during the 35 min separation. For reducing conditions, the antibody sample was diluted to 2.1 mg/ml by adding purified H$_2$O, and 95 μl of the antibody was added to 105 μL of SDS sample buffer (Beckman) with 5.6% beta mercaptoethanol. The preparation was then vortexed thoroughly and then heated at 70° C. for 10 min. After being centrifuged, the supernatant was placed in a 200 μl PCR vial and then loaded onto the PA800 instrument. The sample was injected at the anode with reverse polarity using −5 kV for 20 sec, and was then separated at −15 kV with 20 psi pressure at both ends of capillary during 30 min separation. Both 16435 and 16444 antibodies produced very similar profiles with both reducing and non-reducing CE-SDS (FIGS. 12A-D).

Figure 13:
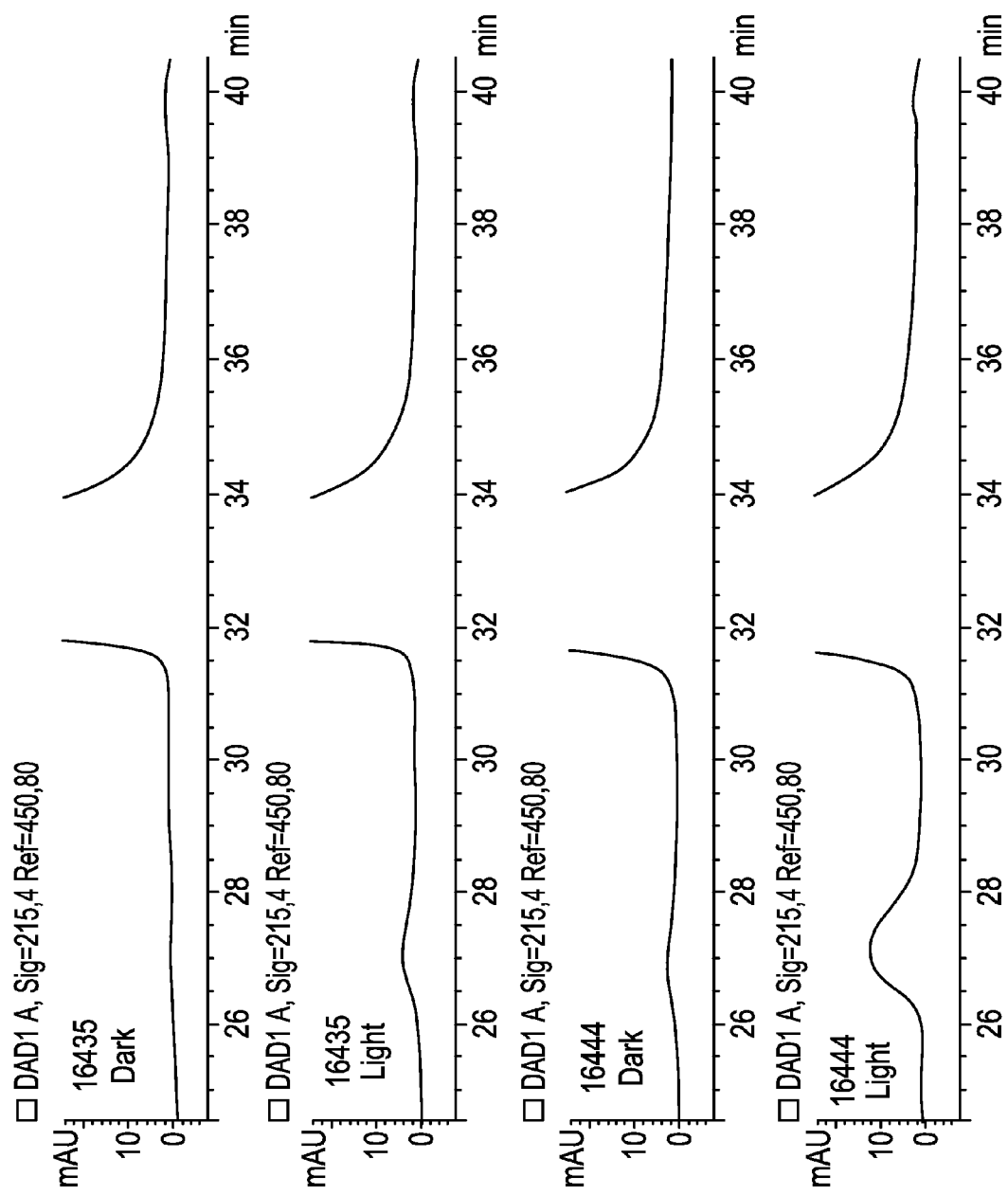

To measure the light sensitivity of the antibodies, they were incubated in ambient lab fluorescent lighting or covered in aluminum foil for 3 days at room temperature. Light exposed and dark control antibodies were then analyzed using two size exclusion columns (TSK-GEL G3000SWXL, 5 mm particle size, 7.8×300 mm, TosohBioscience, 08541) in series with a 100 mM sodium phosphate, 250 mM NaCl, pH 6.8, mobile phase flowed at 0.5 mL/min. Based on the SEC chromatograms, 16444 showed significantly more light sensitivity than 16435 (FIG. 13). The antibodies were then analyzed by hydrophobic interaction chromatography (HIC) using two Dionex ProPac HIC-10 columns in series with mobile phase A being 1 M ammonium sulfate, 20 mM sodium acetate, pH 5.0 and mobile phase B being 20 mM sodium acetate, 5% acetonitrile, pH 5.0. Samples were eluted at 0.8 ml/min with a 0-100% linear gradient over 50 minutes observing the absorbance at 220 nm. Based on the HIC chromatograms, 16435 had a narrower main peak, indicating more product uniformity (FIG. 14). Based on the lower light sensitivity, better purification yield (1219 mg/L vs. 1008 mg/L), better DSC profile, better SEC profile and fewer mutations from the parental antibody, 16435 was chosen as the primary lead for this family of antibodies.

TABLE 6

PCR primer sets and templates used to clone the indicated products.

| Primer Sets SEQ ID NOS: | With Template SEQ ID NO: | Product + Primer Set SEQ ID NOS: | Final Product SEQ ID NO: |
|---|---|---|---|
| Round One Cloning | | | |
| (31, 32)(33, 34) | 187 | (31, 34) | 189 |
| (35, 37)(38, 36) | 304 | (35, 36) | 322 |
| (35, 39)(40, 36) | 304 | (35, 36) | 320 |
| (35, 41)(42, 36) | 304 | (35, 36) | 324 |
| (278, 43)(44, 36) | 326 | (278, 36) | 328 |
| (278, 45)(46, 36) | 326 | (278, 36) | 330 |
| Round Two Cloning | | | |
| (31, 213)(214, 34) | 181 | (31, 34) | 185 |
| (31, 215)(216, 34) | 181 | (31, 34) | 183 |
| (35, 217)(218, 36) | 304 | (35, 36) | 318 |
| (35, 219)(220, 36) | 304 | (35, 36) | 316 |
| (35, 221)(222, 36) | 304 | (35, 36) | 314 |
| (35, 223)(224, 36) | 304 | (35, 36) | 312 |
| (35, 225)(226, 36) | 304 | (35, 36) | 310 |
| (35, 227)(228, 36) | 304 | (35, 36) | 308 |
| (35, 229)(230, 36) | 304 | (35, 36) | 306 |
| (231, 232)(233, 34) | 191 | (231, 34) | 195 |
| (231, 234)(235, 34) | 191 | (231, 34) | 193 |
| (231, 236)(237, 34) | 191 | (231, 34) | 197 |
| (278, 238)(239, 36) | 326 | (278, 36) | 332 |
| (278, 240)(241, 36) | 326 | (278, 36) | 334 |
| (278, 242)(243, 36) | 326 | (278, 36) | 342 |
| (278, 244)(245, 36) | 326 | (278, 36) | 344 |
| (278, 246)(247, 36) | 326 | (278, 36) | 346 |
| (278, 248)(249, 36) | 326 | (278, 36) | 328 |
| (278, 250)(251, 36) | 326 | (278, 36) | 330 |
| (278, 252)(253, 36) | 326 | (278, 36) | 348 |
| (278, 254)(255, 36) | 326 | (278, 36) | 350 |
| (278, 256)(257, 36) | 326 | (278, 36) | 366 |
| (278, 258)(259, 36) | 326 | (278, 36) | 370 |
| Round Three Cloning (double mutants & germlining) | | | |
| (231, 132)(133, 34) | 191 | (231, 34) | 211 |
| (231, 134)(135, 34) | 191 | (231, 34) | 199 |
| (278, 136)(137, 36) | 326 | (278, 36) | 338 |
| (278, 138)(139, 36) | 326 | (278, 36) | 372 |
| (278, 140)(141, 36) | 326 | (278, 36) | 374 |
| (231, 234)(235, 34) | 195 | (231, 34) | 209 |
| (278, 240)(241, 36) | 348 | (278, 36) | 356 |
| (278, 240)(241, 36) | 350 | (278, 36) | 358 |
| Round Four Cloning (charge mutants [A to E or R] and triple mutants) | | | |
| (231, 142)(143, 34) | 191 | (231, 34) | 201 |
| (231, 144)(145, 34) | 191 | (231, 34) | 203 |
| (231, 260)(261, 34) | 191 | (231, 34) | 205 |
| (231, 262)(263, 34) | 191 | (231, 34) | 207 |
| (278, 264)(265, 36) | 326 | (278, 36) | 336 |
| (278, 266)(267, 36) | 326 | (278, 36) | 340 |
| (278, 268)(269, 36) | 326 | (278, 36) | 352 |
| (278, 270)(271, 36) | 326 | (278, 36) | 354 |
| (278, 272)(273, 36) | 326 | (278, 36) | 360 |
| (278, 274)(275, 36) | 326 | (278, 36) | 362 |
| (278, 276)(277, 36) | 326 | (278, 36) | 368 |
| (278, 276)(277, 36) | 334 | (278, 36) | 364 |

Example 2

Generation of Antibodies to Human TRAIL R2 and Screening

Cloning and Engineering.

The Antibody 16449 DNA sequences encoding immunoglobulin heavy chain (comprising VH12) and light chain (comprising VL6) subunits for anti-huTR2 antibodies were obtained from Gliniak et al. (U.S. Pat. No. 7,521,048) and were cloned using standard recombinant technology. In order to eliminate the binding ability of these antibodies a series of site directed mutagenesis clones were generated using polymerase chain reaction (PCR) amplification. The amino acids to be changed were selected on the basis of location in the complementarity determining regions (CDRs), change from germline sequence, estimated solvent exposure, and aromatic and charge nature. The initial set of mutants was germlining and alanine scanning mutants. Subsequently, mutations were combined and in several cases the alanine scanning mutants were mutated to introduce negative charge, by replacing the alanine with glutamic acid, or positive charge, by replacing the alanine with arginine. Further detail about construct development is found in Example 5 and Table 6 herein.

Transient Expression to Generate Recombinant Monoclonal Antibodies.

Transient transfections were carried out in HEK 293-6E cells as follows. The human embryonic kidney 293 cell line stably expressing Epstein Barr virus Nuclear Antigen-1 (293-6E cells) was obtained from the National Research Council (Montreal, Canada). Cells were maintained as serum-free suspension cultures using F17 medium (Invitrogen, Carlsbad, Calif.) supplemented with 6 mM L-glutamine (Invitrogen, Carlsbad, Calif.), 1.1% F-68 Pluronic (Invitrogen, Carlsbad, Calif.) and 250 μg/ul Geneticin (Invitrigen, Carlsbad, Calif.). The suspension cell cultures were maintained in Erlenmeyer shake flask cultures. The culture flasks were shaken at 65 rpm at 37° C. in a humidified, 5% $CO_2$ atmosphere. A stock solution (1 mg/ml) of 25-kDa linear PEI (Polysciences, Warrington, Pa.) was prepared in water, acidified with HCl to pH 2.0 until dissolved, then neutralized with NaOH, sterilized by filtration (0.2 μm), aliquoted, and stored at −20° C. until used. Tryptone N1 was obtained from OrganoTechni S.A. (Tekni-Science, QC, Canada). A stock solution (20%, w/v) was prepared in Freestyle medium (Invitrogem, Carlsbad, Calif.), sterilized by filtration through 0.2 μm filters, and stored at 4° C. until use. Typically, transfections were performed at the 1 L scale. Cells (293-6E) were grown too a viable cell density of $1.1 \times 10^6$ cells/ml then transfection complexes were prepared in ⅟₁₀th volume of the final culture volume. For a 1-L transfection culture, transfection complexes were prepared in 100 ml F17 basal medium, and 500 μg plasmid DNA (heavy chain and light chain DNA, 1:1 ratio) was first diluted in 100 ml F17 medium. After a 5-minute incubation at room temperature, 1.5 ml of PEI solution was added. The complexes were vortexed mildly, then incubated for 15 minutes at room temperature. The cells were transfected by adding the transfection complex mix to the cells in the shale flask culture. 24 hours post-transfection, Tryptone N1 was added to the transfected culture to a final concentration of 0.5%, and the transfected cultures were maintained on a shaker at 65 rpm at 37° C. in a humidified, 5% $CO_2$ atmosphere for another 5 days after which they were harvested. The conditioned medium was harvested by centrifugation at 4000 rpm, and then sterile filtered through 0.2 μm filter (Corning Inc.).

Purification of Antibodies.

The transiently expressed antibodies were purified using recombinant protein A sepharose (GE Healthcare) directly loading the conditioned media on the column at 5 ml/min at 7° C. The column was then washed with 10 column volumes of Dulbecco's PBS without divalent cations and then eluted with 100 mM acetic acid, pH 3.5. The eluted antibody was pooled based on the chromatographic profile and the pH was adjusted to 5.0 using 2 M tris base. The pool was then filtered through a 0.8/0.22 μm syringe filter and then dialyzed against 10 mM acetic acid, 9% sucrose, pH 5.0. The buffer exchanged antibody was then concentrated using a Vivaspin 30 kDa centrifugal concentrator (Sartorius), and the concentrated product was filtered through a 0.22 μm cellulose acetate filter.

BIAcore Binding Assays.

Figure 15:
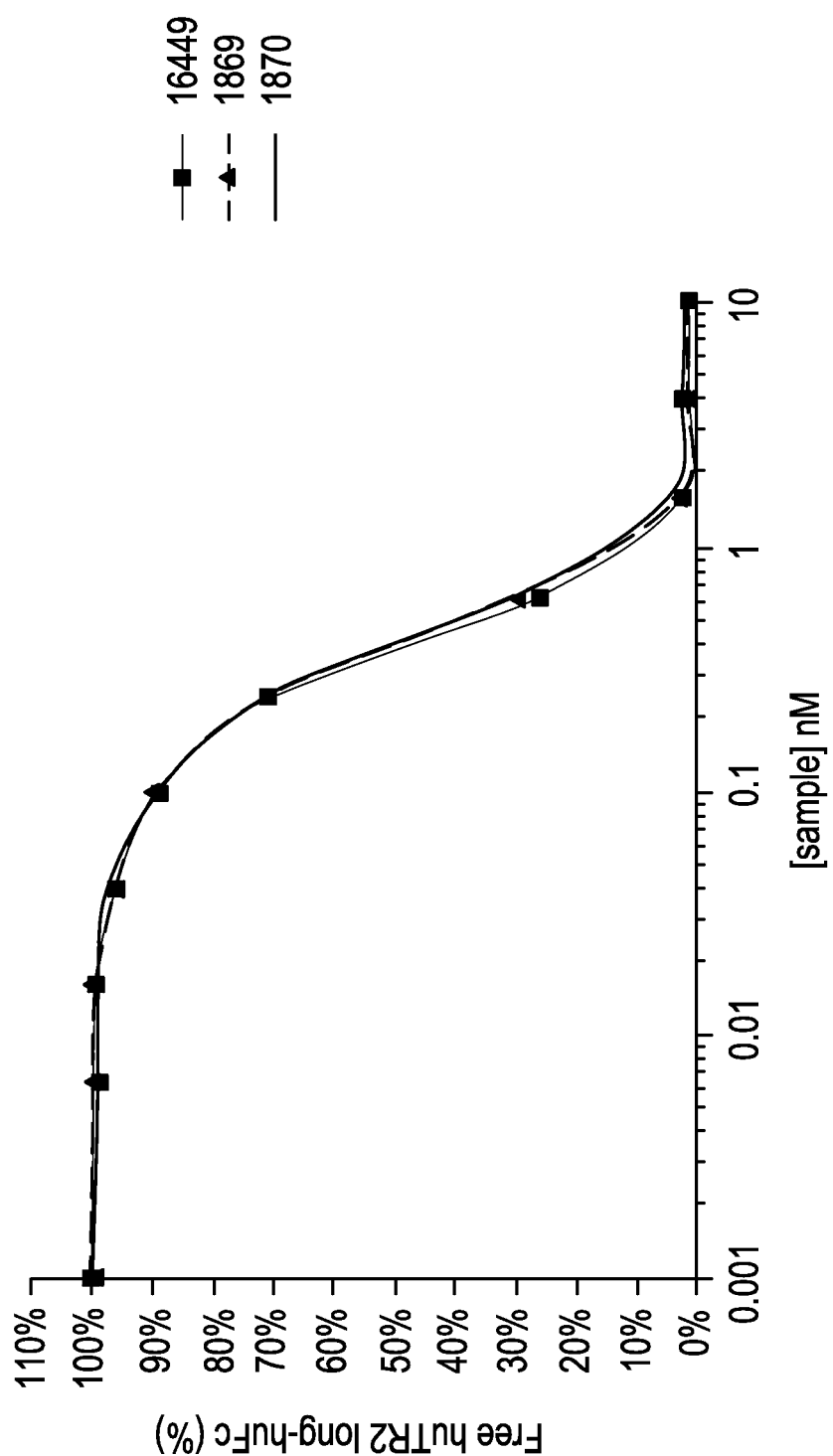

Antibody 16449 is a human antibody that specifically binds to Trail Receptor 2 (TR2). A solution equilibrium binding assay was developed to assess the binding activity of a set of antibodies to TR2. Antibody 16449 was immobilized to a CM5 sensor chip surface as described in Example 1 above. Final immobilized level was approximately 8000 resonance units (RU). TR2 (1 nM) in the absence of antibody was used to establish the 100% binding signal of TR2 that is free of antibody binding in solution. To determine antibody binding in solution, serial diluted antibody samples in a range of 7 pM to 10 nM were incubated with the 1 nM TR2. The decreased binding signal of TR2 after the antibody incubation indicates the binding of the antibody to TR2 in solution. The results in FIG. 15 indicate that all three new antibody constructs (16449, 1869, and 1870) retained TR2 binding activity similar to that of the original construct.

Figure 16:
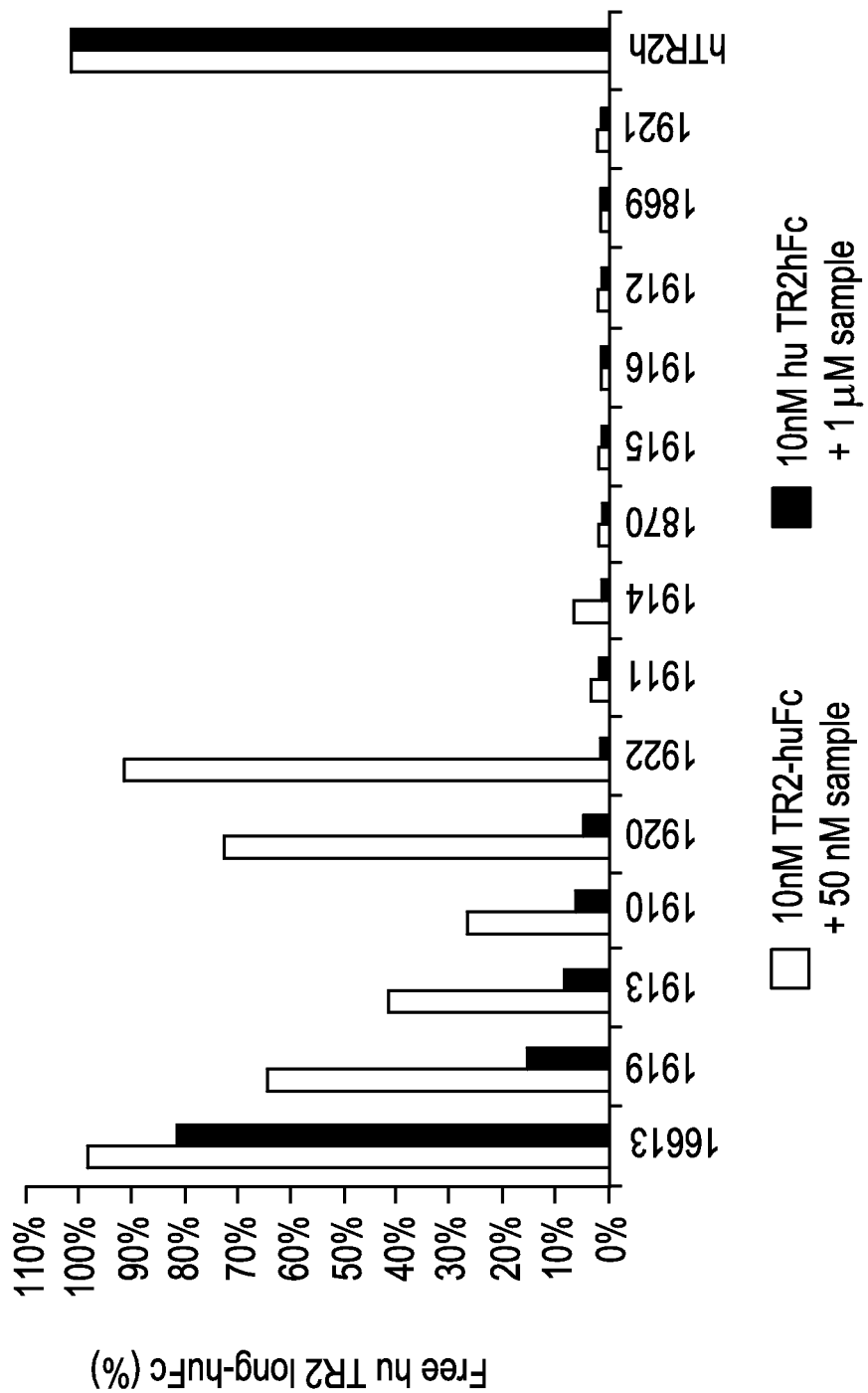
Figure 17:
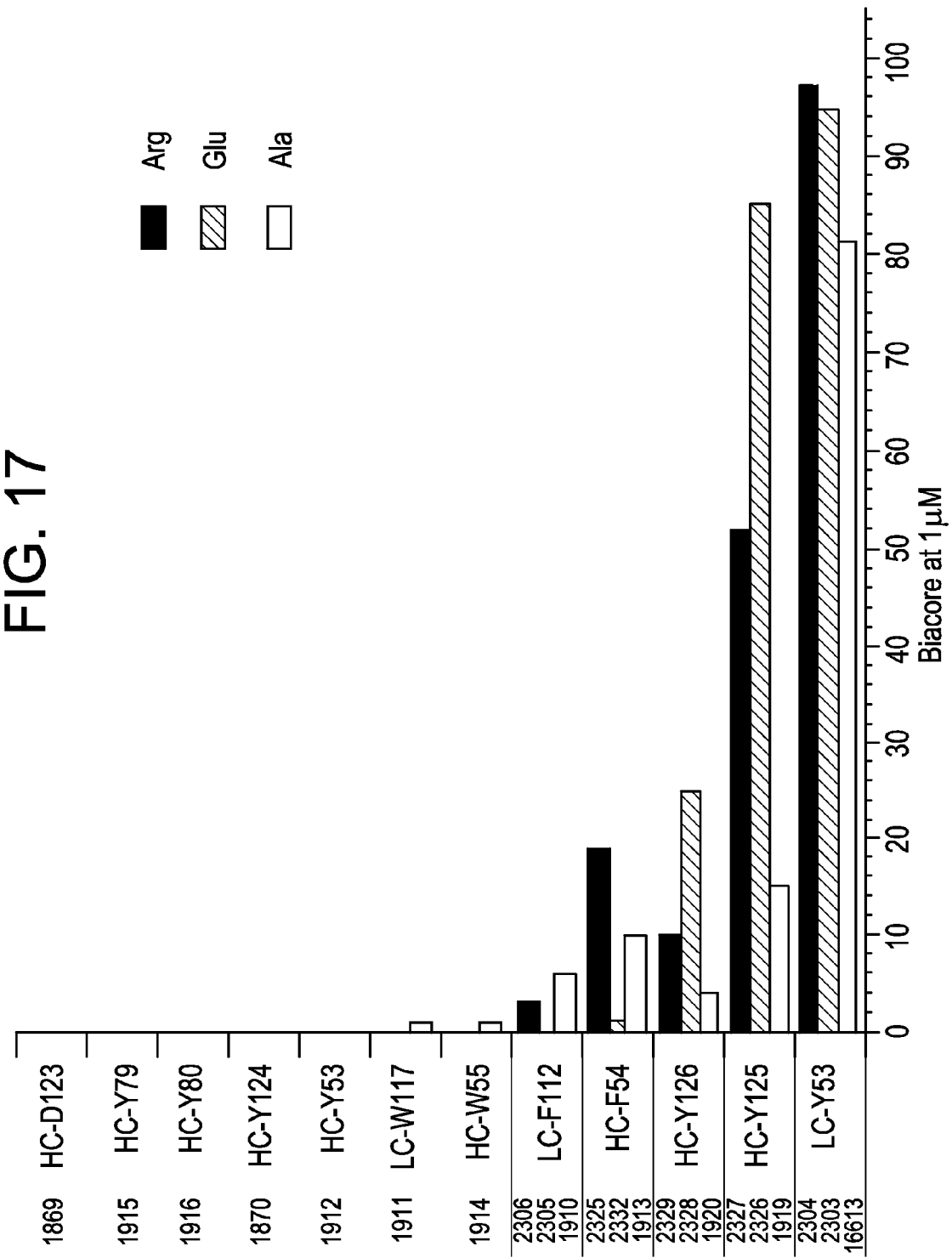
FIG. 17 shows non-binding to TRAIL (huTR2) by antibody embodiments of the present invention. Antibody 16449 was immobilized to a CM5 sensor chip, and 10 nM of TRAIL in the absence of antibody was used to establish the 100% binding signal of TRAIL that is free of antibody binding in solution. To determine antibody binding in solution, 1000 nM of the antibody samples were incubated with the 10 nM TRAIL. The decreased binding signal of TRAIL after the antibody incubation indicates the binding of the antibody to TRAIL in solution.
Figure 18:
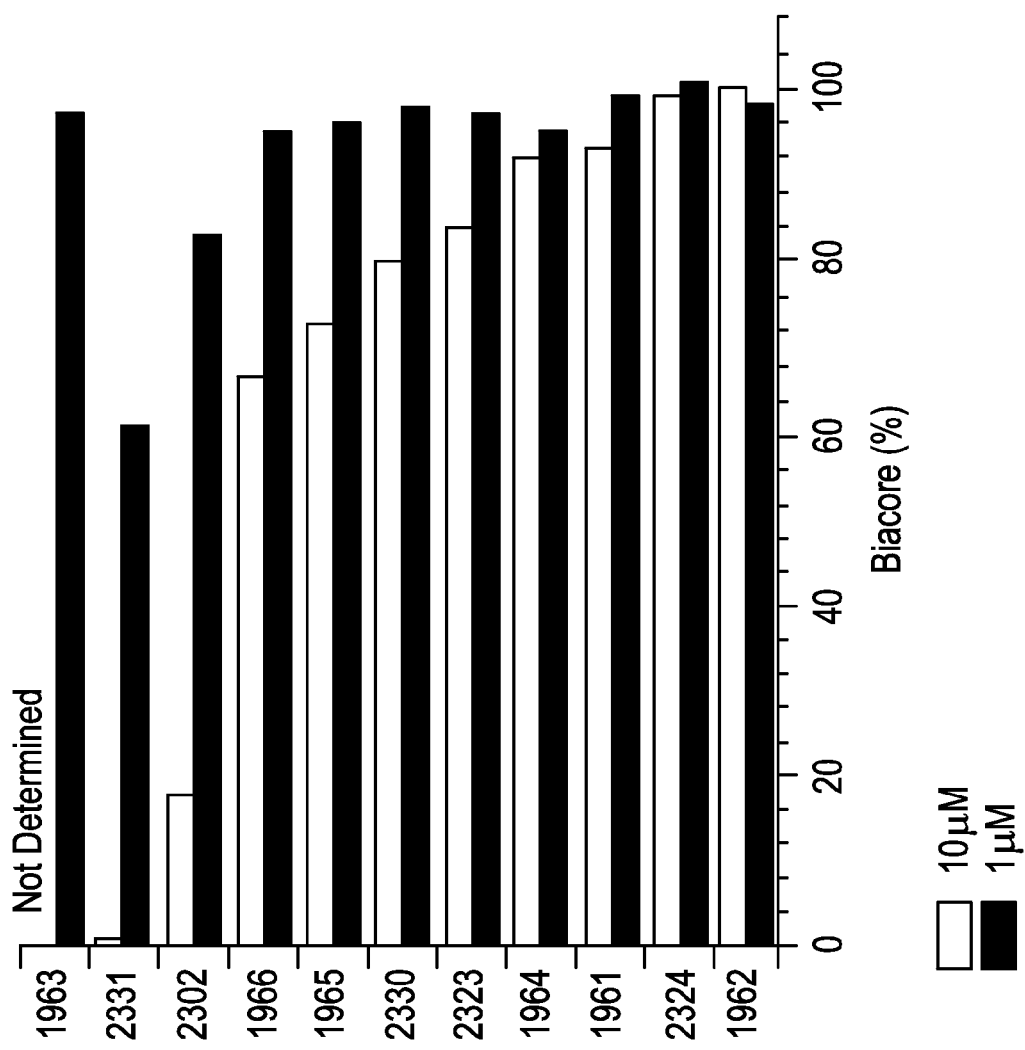
FIG. 18 shows non-binding to TRAIL (huTR2) by antibody embodiments of the present invention, listed on the y-axis. Antibody 16449 was immobilized to a CM5 sensor chip, and 10 nM of TRAIL in the absence of antibody was used to establish the 100% binding signal of TRAIL that is free of antibody binding in solution. To determine antibody binding in solution, 1000 and 10000 nM of the antibody samples were incubated with the 10 nM TRAIL. The decreased binding signal of TRAIL after the antibody incubation indicates the binding of the antibody to TRAIL in solution.
Figure 19:
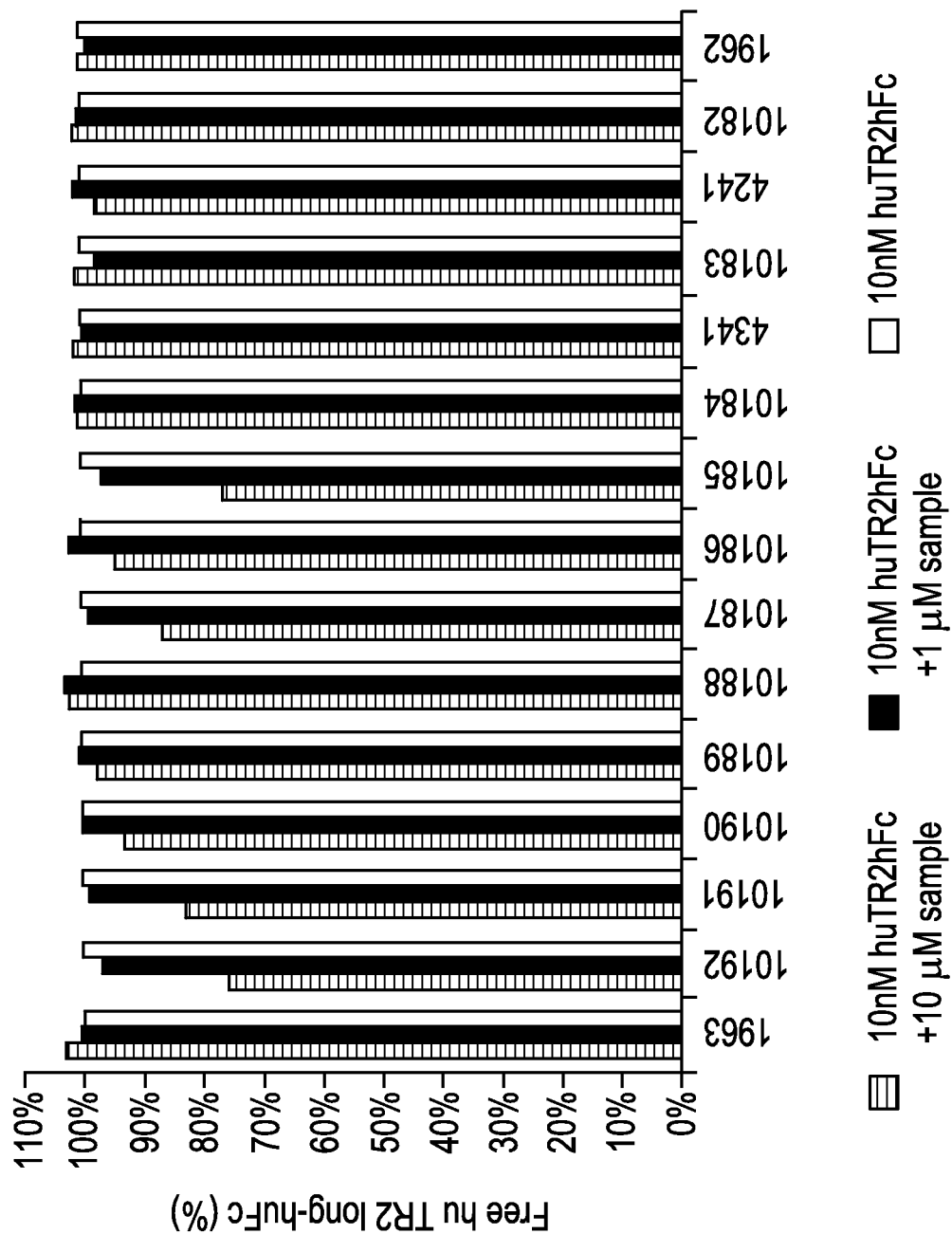
FIG. 19 shows non-binding to TRAIL (huTR2) by antibody embodiments of the present invention, listed on the x-axis. Antibody 16449 was immobilized to a CM5 sensor chip, and 10 nM of TRAIL in the absence of antibody was used to establish the 100% binding signal of TRAIL that is free of antibody binding in solution. To determine antibody binding in solution, 50000 nM of the antibody samples were incubated with the 10 nM TRAIL. The decreased binding signal of TRAIL after the antibody incubation indicates the binding of the antibody to TRAIL in solution.
Figure 20A:
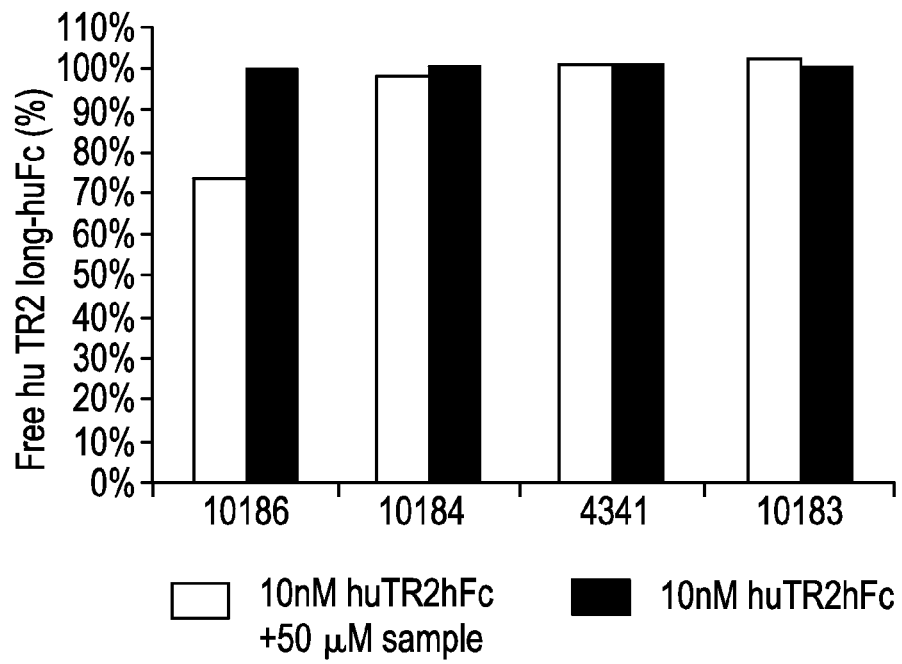
FIGS. 20A-B shows non-binding to TRAIL (huTR2) by antibody embodiments of the present invention, listed on the x-axis. Antibody 16449 was immobilized to a CM5 sensor chip, and 10 nM of TRAIL in the absence of antibody was used to establish the 100% binding signal of TRAIL that is free of antibody binding in solution. To determine antibody binding in solution, 1000, 10000 and 50000 nM of the antibody samples were incubated with the 10 nM TRAIL. The decreased binding signal of TRAIL after the antibody incubation indicates the binding of the antibody to TRAIL in solution.
Figure 20B:
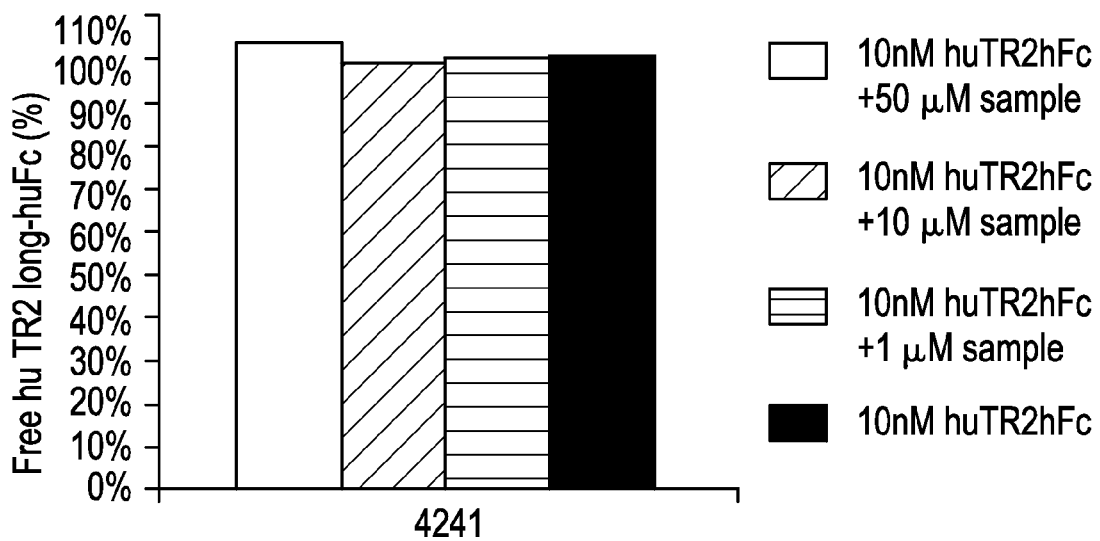

In other experiments, 10 nM TR2 was incubated with 50 nM and 1 μM antibody samples in the assay as described above. 10 nM TR2 was used to define the 100% binding signal. Although several of the antibodies showed significant lack of binding at 50 nM (16613, 1919, 1913, 1910, 1920 and 1922), none showed complete lack of binding at 1000 nM (results shown in FIG. 16). Additional point mutagenesis yielded antibodies with lower affinity for TR2 (FIG. 17). Two sites (heavy chain Y125 and light chain Y53) showed exceptional sensitivity to mutagenesis, particularly with charged substitutions at position Y125. Double alanine substitutions produced variants with even further decreased binding affinity for TR2 (FIG. 18). Combining the alanine mutations with charged mutations in a pairwise, or greater order, fashion produced several molecules that did not show significant binding to TR2 even at 10 μM antibody (FIG. 19). From these data, five of the best variants (10186, 10184, 4341, 10183, and 4241) were advanced for binding studies at 50 μM antibody (FIGS. 20A-B). All but 10186 showed no significant binding to TR2 even at 50 μM.

Cell Based Activity Assay.

Colo205 is a human colon carcinoma cell line that is sensitive to the presence of TRAIL. Binding of positive control IgG1 anti-TR2 mAb molecules (antibody 16449) to TR2 on the surface of Colo205 results in cell apoptosis. A Colo205 based cell assay was developed to verify the cell killing efficacy of antibodies. The in vitro biological activity of the Antibody 16449 (anti-TRAIL-R2 antibody) is analyzed by its ability to induce apoptosis in human ascites colorectal adenocarcinoma cell line Colo205. The detection of caspase-3 activation is used as a positive marker for apoptosis, using the Apo-One™ Homogeneous Caspase™-3/7 assay kit (PromegaCorporation, Madison, Wis.), according to the manufacturer's instruction. (see, Niles et al., The Apo-One™. Homogeneous Caspase™-3/7 assay: a simplified "solution" for apoptosis detection, Cell Notes 2:2-3 (2001)). In this method, luminescent caspase-3/7 reagent provides a sensitive and robust monitoring of anti-TRAIL-R2 induced caspase activation in Colo205 cells. Luminescence produced is proportional to the amount of caspase activity present. The luminescence of each sample is measured in a plate-reading luminometer. Biological activity of the test sample is determined by comparing test sample response to Reference Standard response. To compare the samples with standard control antibody, 200 nM and 10 μM of antibody samples were preincubated with 1 or 100 μg/ml of protein G. The mixtures were then added to Colo205 cultures. FIG. 20C indicates that, unlike the control anti-TR2 mAb molecules, the antibody samples do not have the ability to kill the cells even at very high concentrations (e.g., 30 µg/mL of antibody).

Analysis of Homogeneity.

Figure 21A:
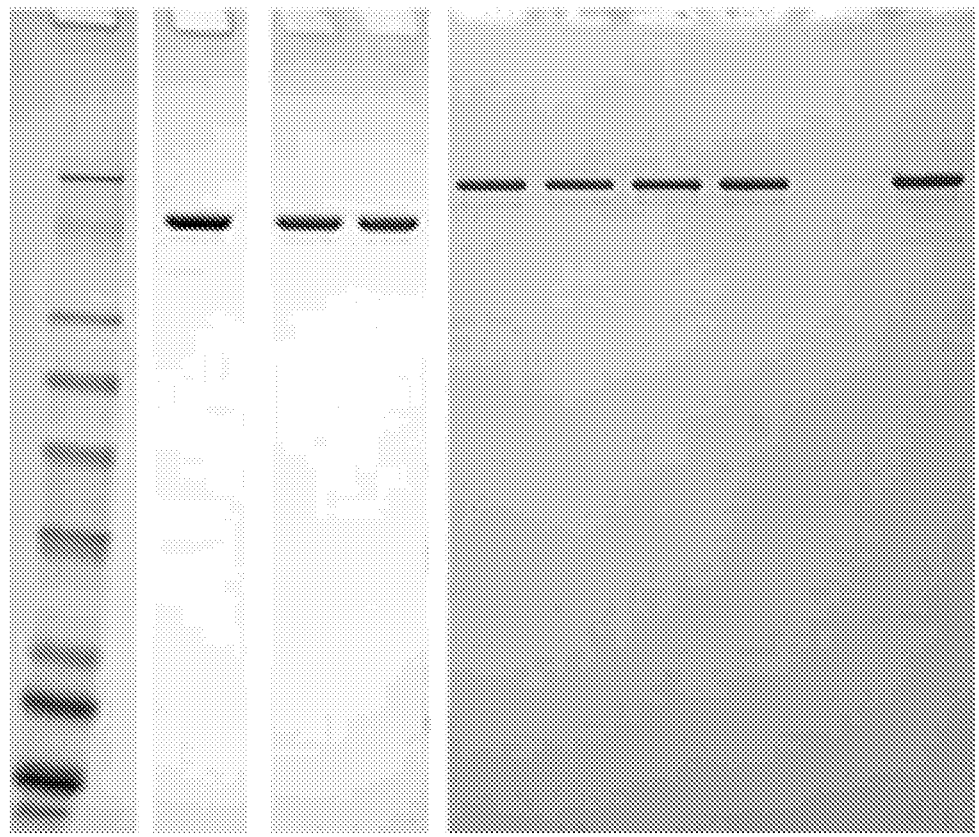
FIG. 21A shows non-reducing analysis of 2 µg of antibodies 1870 [aka 16451], 16449, 16450, 10185, 10184, 4341, 10183 and 10182 on 1.0 mm Tris-glycine 4-20% SDS-PAGEs (Novex) developed at 220V using non-reducing loading buffer and staining with QuickBlue (Boston Biologicals). Molecular weight markers are Novex SeeBlue pre-stained standards. Molecular weight markers are Novex SeeBlue® pre-stained standards.
Figure 21B:
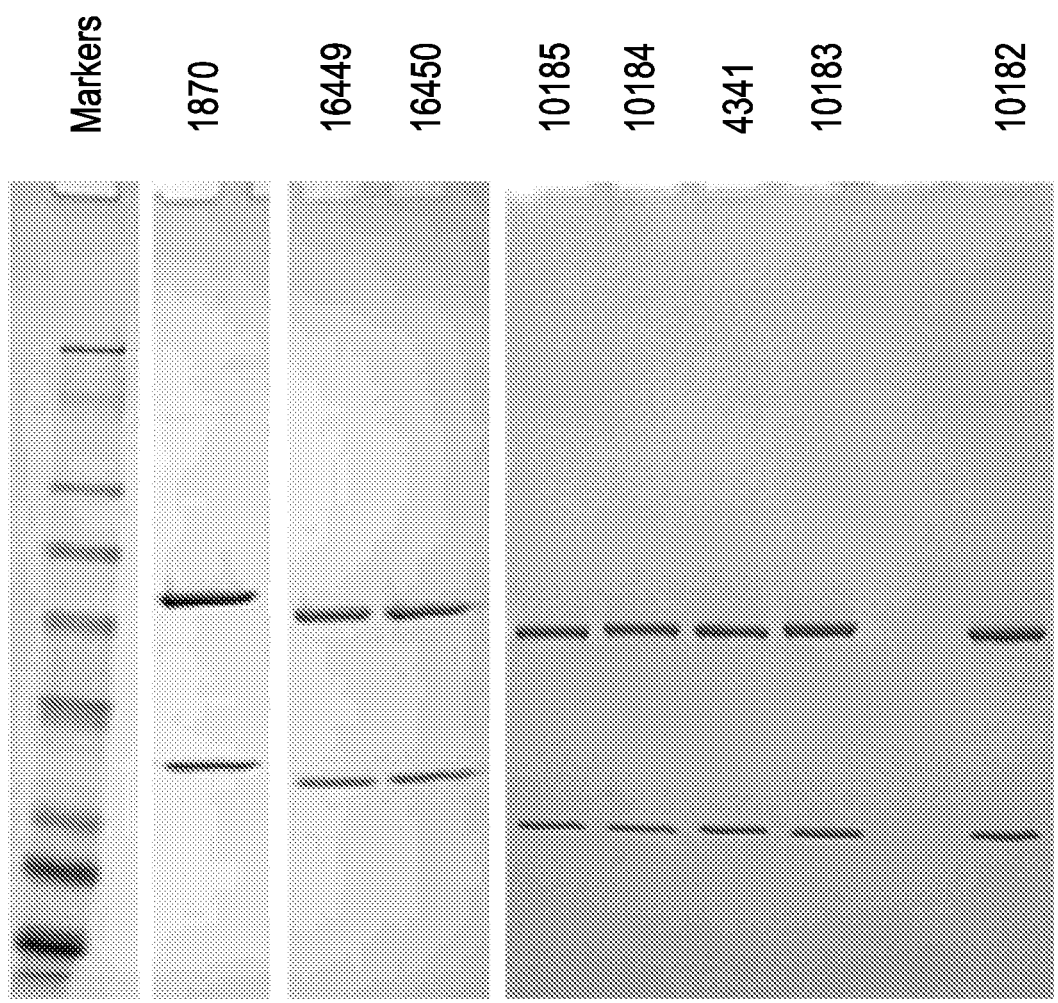
FIG. 21B shows reducing analysis of 2 µg of antibodies 1870 [aka16451], 16449, 16450, 10185, 10184, 4341, 10183 and 10182 on 1.0 mm Tris-glycine 4-20% SDS-PAGEs (Novex) developed at 220V using non-reducing loading buffer and staining with QuickBlue (Boston Biologicals). Molecular weight markers are Novex SeeBlue® pre-stained standards.

The lead antibodies were analyzed for product quality on a 1.0-mm Tris-glycine 4-20% SDS-PAGE (Novex) using reducing (FIG. 21B) and non-reducing loading buffer (FIG. 21A). All candidates appeared quite similar by both non-reducing and reducing SDS-PAGE. Antibodies were further analyzed for homogeneity using one size exclusion column (Phenomenex SEC3000, 7.8×300 mm) with a 50 mM sodium phosphate, 250 mM NaCl, pH 6.8, mobile phase flowed at 1.0 mL/min (representative results are shown in FIG. 22). While all the antibodies showed relatively low levels of high molecular weight species, 10185 and 10184 showed slightly more high molecular mass material. Lead candidates were selected based on SEC behavior, BIAcore binding analysis, cell based assay results, estimated proteolytic vulnerability and lower shift in the calculated isoelectric point. Based on these criteria, 4241 and 4341 were chosen for further evaluation.

Construct Development for Stable Expression.

Pools of stably expressed antibodies 4241 and 4341 were created by transfecting CHO DHFR(−) host cells with corresponding HC and LC expression plasmid set using a standard electroporation procedure. Per each antibody molecule, 3-4 different transfections were performed to generate multiple pools. After transfection, the cells were grown as a pool in a serum free (−)GHT selective growth media to allow for selection and recovery of the plasmid containing cells. Cell pools grown in (−)GHT selective media were cultured until they reached >85% viability. The selected cell pools were amplified with 150 nm methotrexate (MTX). When the viability of the MTX-amplified pools reached >85% viability, the pools were screened using an abbreviated six-day batch production assay with an enriched production media to assess expression. The best pool was chosen based on the six-day assay titer and correct mass confirmation. Subsequently, scale-up production using 11-day fed-batch process was performed for the antibody generation, followed by harvest and purification.

Titers were determined by HPLC assay using a Poros A column, 20 µm, 2.1×30 mm (Applied Biosystems, part #1-5024-12). Briefly, Antibodies in conditioned media were filtered using Spin-X columns (Corning, part #8160) prior to analysis by HPLC, and a blank injection of 1×PBS (Invitrogen, part #14190-144) was performed prior to injection of test antibodies and after each analysis run. In addition, conditioned media without antibody was injected prior to analysis to condition the column, and new columns were conditioned by triplicate injection of 100 µg of control antibody. After a 9-minute wash with PBS at 0.6 ml/min, the antibody was eluted with ImmunoPure IgG Elution Buffer (Pierce, part #21009) and the absorbance at 280 nm was measured.

Figure 23A:
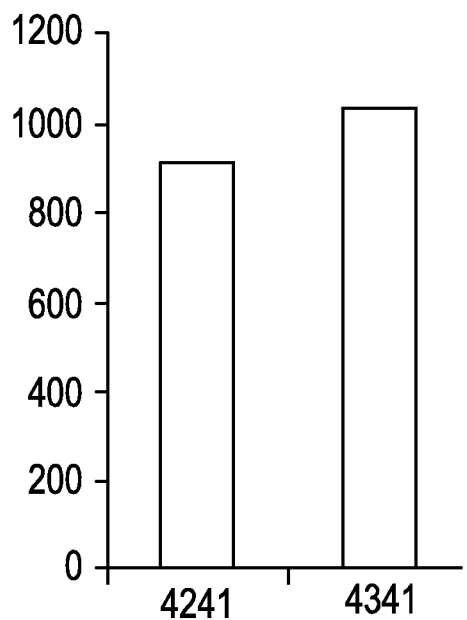
FIGS. 23A-B shows titers for antibodies 4241 and 4341, respectively. Expressing pools were created by transfecting CHO DHFR(−) host cells with corresponding HC and LC expression plasmid. Small scale (5-mL.
Figure 23B:
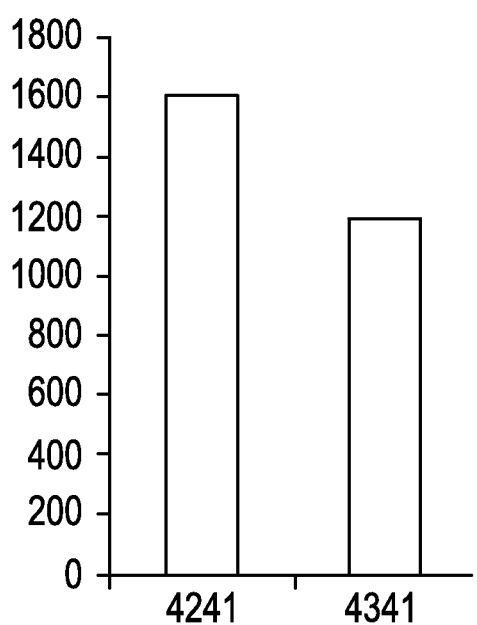

Antibody titers were quantified against a standard plot of control antibody concentration versus peak area. A control antibody stock was prepared at a concentration of 4 mg/ml, and five standard antibody concentrations were prepared by dilution of the antibody control stock in a volume of PBS (0.1 µg/µl to 1.6 µg/µl). By extending the standard curve, the lower limit of detection is 0.02 µg/µl of antibody, and the higher limit of quantification is 4 µg/µl. An assumption is made that test antibodies have similar absorbance characteristics as the control; however Titers can be adjusted by multiplying titer an extinction coefficient ratio of the control antibody over the extinction coefficient of the test antibody. The titer assay results show that after scale up to the fed batch process, the 4241 antibody demonstrated marginally better expression than the 4341 antibody (FIGS. 23A-B).

Purification of Stably Expressed Antibodies.

Figure 24A:
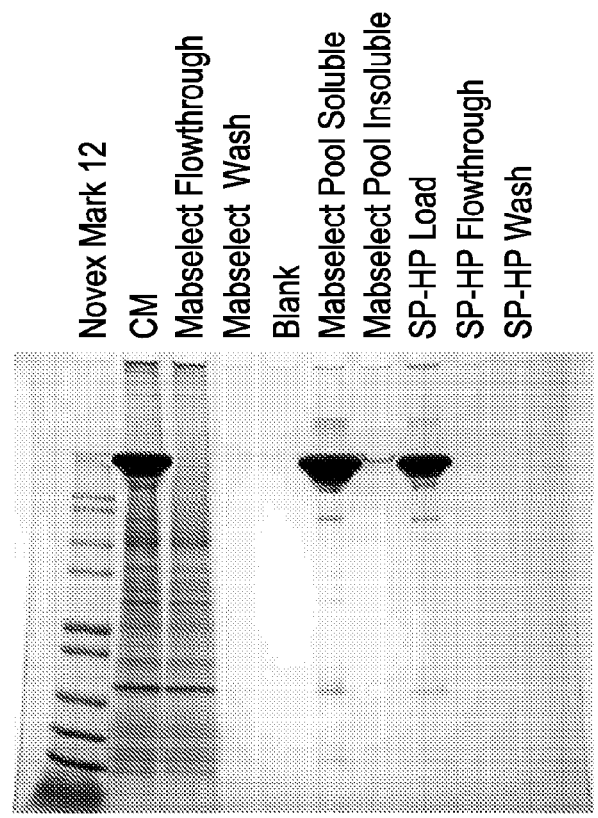
FIGS. 24A-B shows reducing analysis of the in process samples for antibodies 4241 (FIG. 24A) and 4341 (FIG. 24B) on 1.0 mm Tris-glycine 4-20% SDS-PAGEs (Novex) developed at 220V using non-reducing loading buffer and staining with QuickBlue (Boston Biologicals).
Figure 24B:
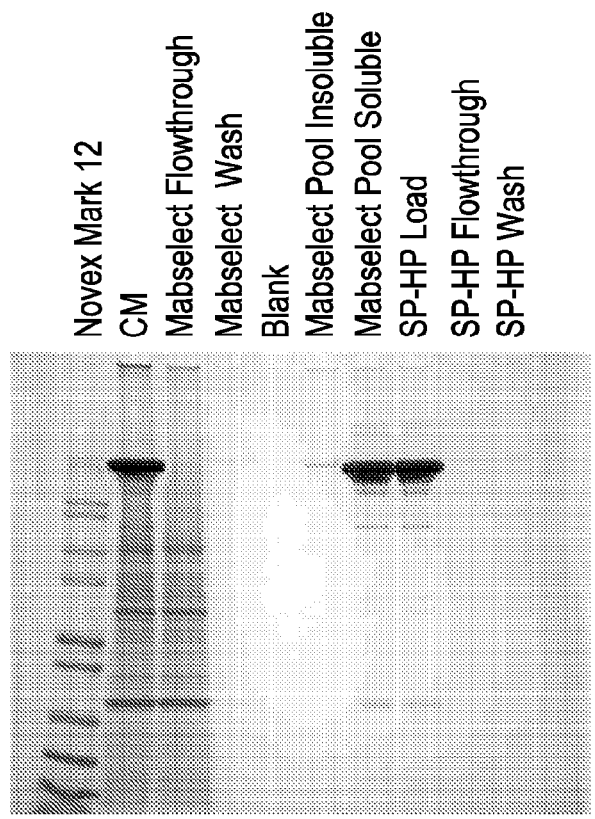

Stably expressed antibodies were purified by Mab Select Sure chromatography (GE Life Sciences) using 8 column volumes of Dulbecco's PBS without divalent cations as the wash buffer and 100 mM acetic acid, pH 3.5, as the elution buffer at 7° C. The elution peak was pooled based on the chromatogram, and the pH was raised to about 5.0 using 2 M Tris base. The pool was then diluted with at least 3 volumes of water, filtered through a 0.22-µm cellulose acetate filter and then loaded on to an SP-HP sepharose column (GE Life Sciences) and washed with 10 column volumes of S-Buffer A (20 mM acetic acid, pH 5.0) followed by elution using a 20 column volume gradient to 50% S-Buffer B (20 mM acetic acid, 1 M NaCl, pH 5.0) at 7° C. A pool was made based on the chromatogram and SDS-PAGE analysis, then the material was concentrated about 6-fold and diafiltered against about 5 volumes of 10 mM acetic acid, 9% sucrose, pH 5.0 using a VivaFlow TFF cassette with a 30 kDa membrane. The dialyzed material was then filtered through a 0.8/0.2-µm cellulose acetate filter and the concentration was determined by the absorbance at 280 nm. The purification processed samples were analyzed using a 1.0-mm Tris-glycine 4-20% SDS-PAGE (Novex) reducing loading buffer (FIGS. 24A-B). These data showed that both 4241 and 4341 antibodies had similar purification characteristics, with no steps producing unexpected sample losses.

Analysis of Stably Expressed Antibodies.

Figure 26A:
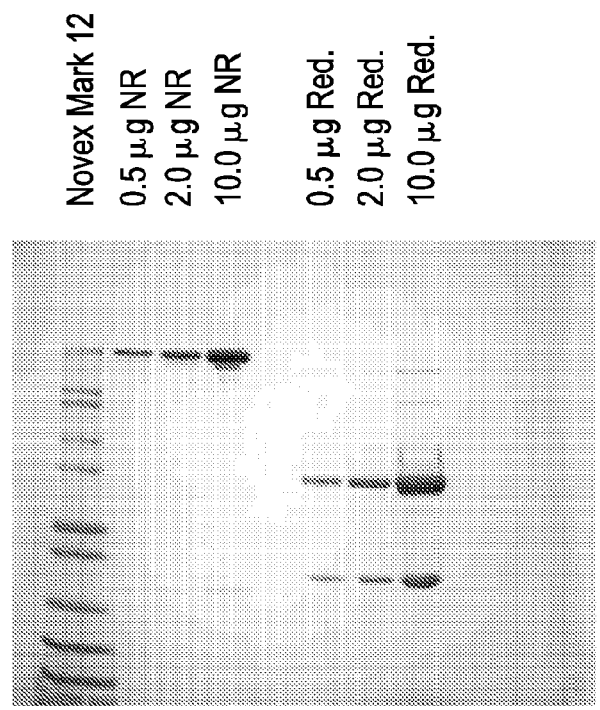
FIGS. 26A-B shows analysis of the 4241 (FIG. 26A) and 4341 (FIG. 26B) antibodies on 1.0 mm Tris-glycine 4-20% SDS-PAGEs (Novex) developed at 220V staining with QuickBlue (Boston Biologicals). The lanes marked "NR" contained non-reducing sample buffer, while those in lanes marked "Red." contained reducing sample buffer.
Figure 26B:
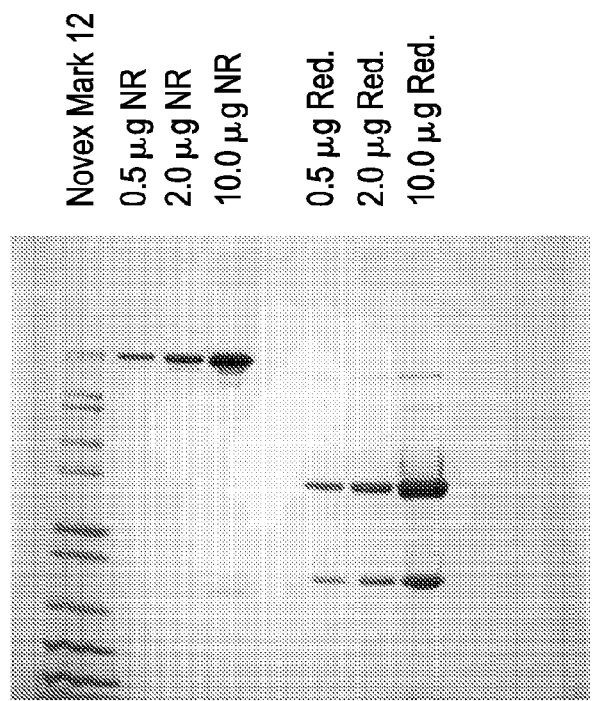

Comparison of the ion exchange chromatographic profiles of the 4241 and 4341 variants (FIG. 25) showed that 4341 has a narrower main peak indicating less heterogeneity than 4241. Analysis of the variants using 1.0-mm Tris-glycine 4-20% SDS-PAGE (Novex) with reducing and non-reducing loading buffer showed no significant difference between the variants (FIGS. 26A-B). Analysis using two size exclusion columns (TSK-GEL G3000SWXL, 5 mm particle size, 7.8× 300 mm, TosohBioscience, 08541) in series with a 100 mM sodium phosphate, 250 mM NaCl, pH 6.8, mobile phase flowed at 0.5 mL/min also showed no significant difference between the 4241 and 4341 variants (FIGS. 27A-B). The antibodies were analyzed for thermoresistance by DSC using a MicroCal VP-DSC where the samples were heated from 20° C. to 95° C. at a rate of 1° C. per minute. The proteins were at 0.5 mg/ml in 10 mM sodium acetate, 9% sucrose, pH 5.0 (FIG. 28). The 4241 antibody produced the most desirable melting profile, with a higher temperature for the secondary transition, compared to antibody 4341.

The 4241 and 4341 antibodies were analyzed by reducing and non-reducing CE-SDS (FIGS. 29A-D). All CE SDS experiments were performed using Beckman PA800 CE system (Fullerton, Calif.) equipped with UV diode detector employing 221 nm and 220 nm wavelength. A bare-fused silica capillary 50 µm×30.2 cm was used for the separation analysis. Buffer vial preparation and loading as well as capillary cartridge installation were conducted as described in the Beckman Coulter manual for IgG Purity/Heterogeneity. The running conditions for reduced and non-reduced CE-SDS were similar to those described in Beckman Coulter manual for IgG Purity/Heterogeneity with some modifications which are briefly described below. For non-reducing conditions, the antibody sample (150 µg) was added to 20 µl of SDS reaction buffer and 5 µl of 70 mM N-ethylmaleimide. Water was then added to make final volume 35 µl and the protein concentration was brought to 4.3 mg/ml. The SDS reaction buffer was made of 4% SDS, 0.01 M citrate phosphate buffer (Sigma) and 0.036 M sodium phosphate dibasic. The preparation was vortexed thoroughly, and heated at 45° C. for 5 min. The preparation was then combined with an additional 115 µl of 4% SDS. After being vortexed and centrifuged, the preparation was placed in a 200 µl PCR vial and then loaded onto the PA800 instrument. The sample was injected at the anode with reverse polarity using −10 kV for 30 sec, and was then separated at −15 kV with 20 psi pressure at both ends of capillary during the 35-min separation. For reducing conditions, the antibody sample was diluted to 2.1 mg/ml by adding purified $H_2O$, and 95 µl of the antibody was added to 105 µl of SDS sample buffer (Beckman) with 5.6% beta mercaptoethanol. The preparation was then vortexed thoroughly and then heated at 70° C. for 10 min. After being centrifuged, the supernatant was placed in a 200 µl PCR vial and then loaded onto the PA800 instrument. The sample was injected at the anode with reverse polarity using −5 kV for 20 sec, and was then separated at −15 kV with 20 psi pressure at both ends of capillary during 30 min separation. Neither of the antibodies showed significant differenced by CE-SDS analysis (FIGS. 29A-D).

Figure 31B:
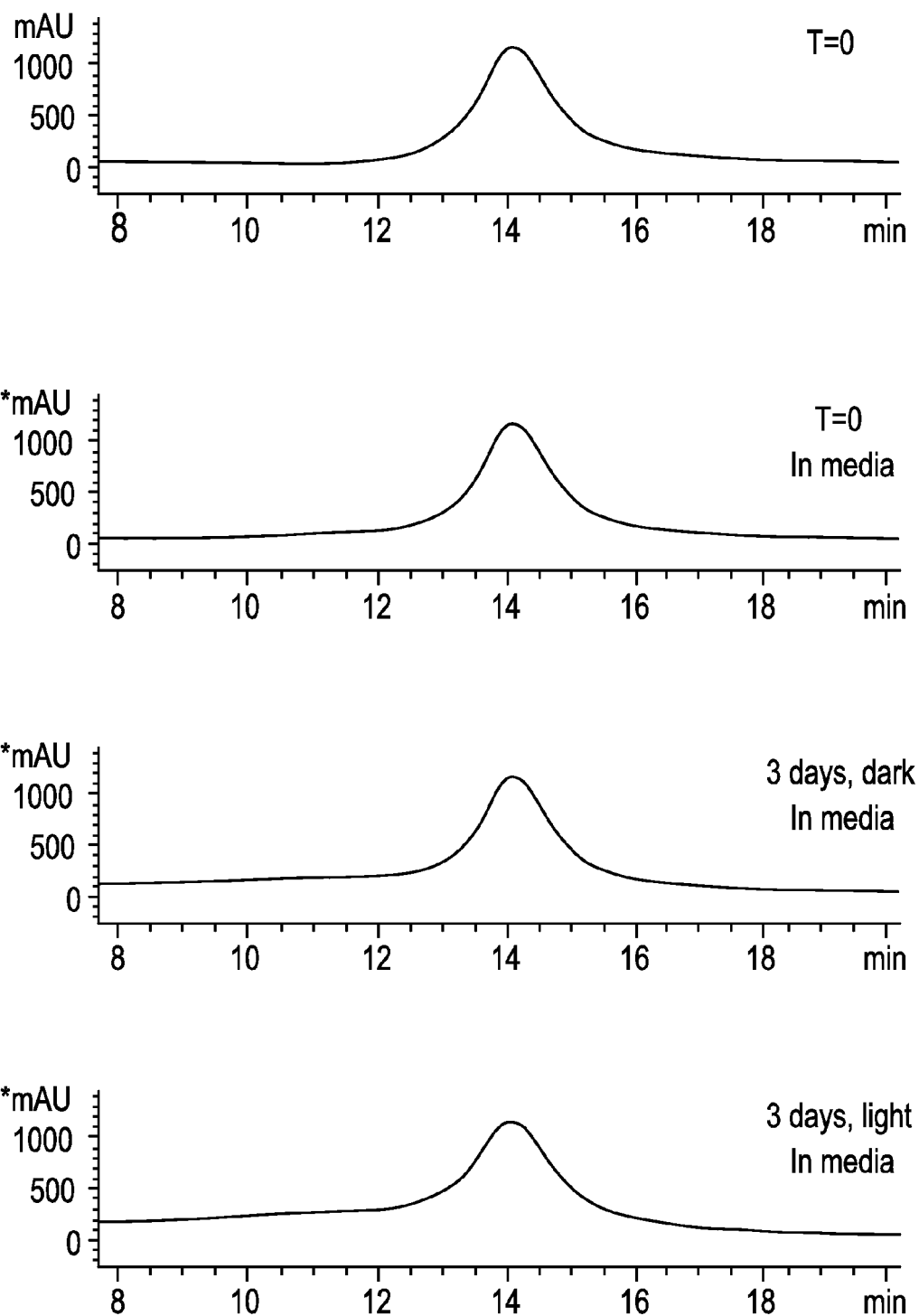

Antibodies were also analyzed for homogeneity using high performance ion exchange chromotography (SP-5PW, 10 µm particle, 7.5 mm ID×7.5 cm, TosohBioscience, 08541) using 20 mM acetic acid, pH 5.0 as buffer A and 20 mM acetic acid, 1 M NaCl, pH 5.0 as buffer B flowed at 1 mL/min with an 80 minute linear gradient from 0-40% buffer B. Neither purified 4241 or 4341 antibody showed significant difference in the high performance ion exchange profiles with this method (FIG. 30). To measure the light sensitivity of the antibodies, they were incubated in ambient lab fluorescent lighting or covered in aluminum foil for 3 days at room temperature. The antibodies were then analyzed by hydrophobic interaction chromatography using two Dionex ProPac HIC-10 columns in series with mobile phase A being 1 M ammonium sulfate, 20 mM sodium acetate, pH 5.0 and mobile phase B being 20 mM sodium acetate, 5% acetonitrile, pH 5.0. Samples were eluted at 0.8 ml/min with a 0-100% linear gradient over 50 minutes observing the absorbance at 220 nm. Based on the HIC chromatograms both with and without light exposure, neither antibody displayed significant differences (FIGS. 31A-B). Based primarily on the more uniform ion exchange chromatography peak during purification 4341 was chosen as the primary lead for this family of antibodies.

Example 3

Human Tissue Cross-Reactivity Assessment

In general accordance with the guidance laid out in Points to Consider in the Manufacture and Testing of Monoclonal Antibody Products for Human Use (U.S. Department of Health and Human Services, Food and Drug Administraton, Center for Biologics Evaluation and Research (1997)), a preliminary non-GLP study was carried out to determine cross-reactivity of inventive antibodies with a variety of human tissues. If an antibody is intended for drug development, a more extensive testing under GLP conditions is required. The tissue cross-reactivity of antibodies 16435 and 4341 was evaluated (Charles River Laboratories, Preclinical Services, Reno, Nev.) with cryosections of selected human tissues using Alexa Fluor 488 labeled forms of the test articles. Normal human tissues from two unique individuals (unless otherwise indicated) were obtained from the Special Pathology Services Human Tissue Bank collected by the National Disease Research Interchange (NDRI, Philadelphia, Pa.), Cureline, Inc. (Burlingame, Calif.), Cybrdi (Rockville, Md.), or Rocky Mountain Lions Eye Bank (Aurora, Colo.). Tissues tested included human cerebellum, lung, cerebral cortex, ovary (from mature female), eye, placenta, gastrointestinal tract (small intestine), skin (1 individual), heart, spleen, kidney (1 individual), thyroid, liver, testis. Sections of fresh-frozen human tissues and control bead blocks (human serum albumin [HSA] beads) were cut on the cryostat and thaw mounted onto capillary gap slides. The tissue and control bead slides were fixed in cold acetone for approximately 10 minutes at −10° C. to −25° C. The fixed slides were allowed to dry for at least one hour (to overnight). If stored frozen, fixed slides were removed from the freezer on the day prior to an experiment and allowed to thaw overnight prior to use. All the following steps were performed at room temperature unless otherwise specified. The slides were incubated with 1× Morphosave™ for approximately 15 minutes to preserve tissue morphology then washed two times for approximately 5 minutes each in 1× phosphate-buffered saline (PBS). To block endogenous peroxidase, the slides were incubated in a glucose oxidase solution for approximately 1 hour at approximately 37° C. The slides were washed two times in 1×PBS for approximately 5 minutes each. Endogenous biotin was blocked by sequential incubation (approximately 15 minutes each) in avidin and biotin solutions. Following the incubation in biotin, the tissue sections were blocked with a blocking antibody solution for approximately 25 minutes. Alexa Fluor 488-Ab 16435, and Alexa Fluor 488 anti-Ab 4341 were applied to sections at the optimal concentration (2.0 µg/mL) or 5 times the optimal concentration (10.0 µg/mL) for approximately 25 minutes. Slides were washed 3 times with wash buffer and then incubated with the secondary antibody (rabbit anti-Alexa Fluor 488) for approximately 25 minutes. Following incubation with the secondary antibody, slides were washed 4 times with wash buffer then incubated with the tertiary antibody (horseradish peroxidase conjugated goat anti-rabbit IgG antibody) for approximately 25 minutes and binding visualized with a diaminobenzidine (DAB) chromogen substrate. HSA beads were used as a negative control. Tissues were qualified as adequate for immunohistochemistry via staining with an antibody against CD31 (anti-CD31) i.e., platelet endothelial cell adhesion molecule (PECAM-1). There was no specific staining in any human tissue examined at either 2.0 or 10.0 µg/mL concentration for any of the tested antibodies.

Example 4

Figure 32:
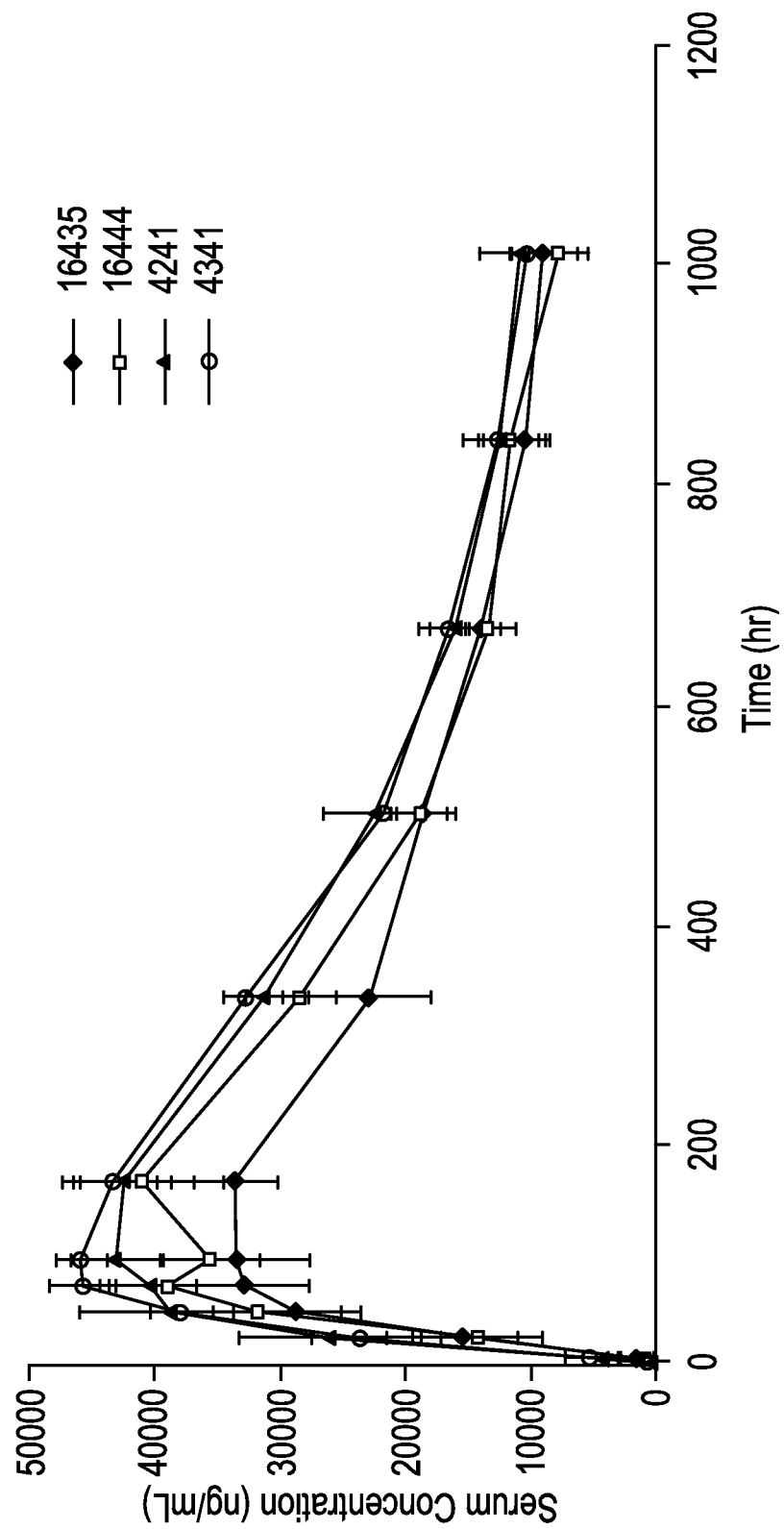
FIG. 32 shows representative pharmacokinetic profiles of the 16435, 16444, 4241, and 4341 antibodies, as determined in adult Sprague-Dawley rats (8-12 weeks old) by injecting 5 mg/kg subcutaneously and collecting blood at 0, 0.25, 1, 4, 24, 48, 72, 96, 168, 336, 504, 672, 840 and 1008 hours post-dose from the lateral tail vein. Serum concentrations were then determined using an anti-human Fc based ELISA.

Pharmacokinetic (PK) Studies of Antibody Embodiments of the Invention in Rats and Cynomolgus Monkeys The pharmacokinetic profile of the 16435, 16444, 4241, and 4341 carrier antibodies was determined in adult Sprague-Dawley rats (8-12 weeks old) by injecting 5 mg/kg subcutaneously and collecting approximately 250 µL of blood in Microtainer® serum separator tubes at 0, 0.25, 1, 4, 24, 48, 72, 96, 168, 336, 504, 672, 840 and 1008 hours post-dose from the lateral tail vein. Each sample was maintained at room temperature following collection, and following a 30-40 minute clotting period, samples were centrifuged at 2-8° C. at 11,500 rpm for about 10 minutes using a calibrated Eppendorf 5417R Centrifuge System (Brinkmann Instruments, Inc., Westbury, N.Y.). The collected serum was then transferred into a pre-labeled (for each rat), cryogenic storage tube and stored at −60° C. to −80° C. for future analysis. To measure the serum sample concentrations from the PK study samples, the following method was used: ½ area black plate (Corning 3694) was coated with 2 µg/ml of anti-hu Fc, antibody 1.35.1 in PBS and then incubated overnight at 4° C. The plate was then washed and blocked with I-Block™ (Applied Biosystems) overnight at 4° C. If samples needed to be diluted, then they were diluted in Rat SD control serum. The standards and samples were then diluted 1:20 in I-Block™+ 5% BSA into 380 μl of diluting buffer. The plate was washed and 50-μl samples of pretreated standards and samples were transferred into an antibody 1.35.1 coated plate and incubated for 1.5 h at room temperature. The plate was washed, then 50 μl of 100 ng/ml of anti-hu Fc antibody 21.1-HRP conjugate in I-Block™+5% BSA was added and incubated for 1.5 h. The plate was washed, then 50 μl of Pico substrate were added, after which the plate was immediately analyzed with a luminometer. The pharmacokentic profile was not significantly different for any of the four antibodies (FIG. 32) with $AUC_{0-t}\pm SD$ of 18,492±2,104; 21,021±2,832; 24,045±2,480 and 24,513±972 μg/h/mL for antibodies 16435, 16444, 4241 and 4341, respectively.

Figure 33:
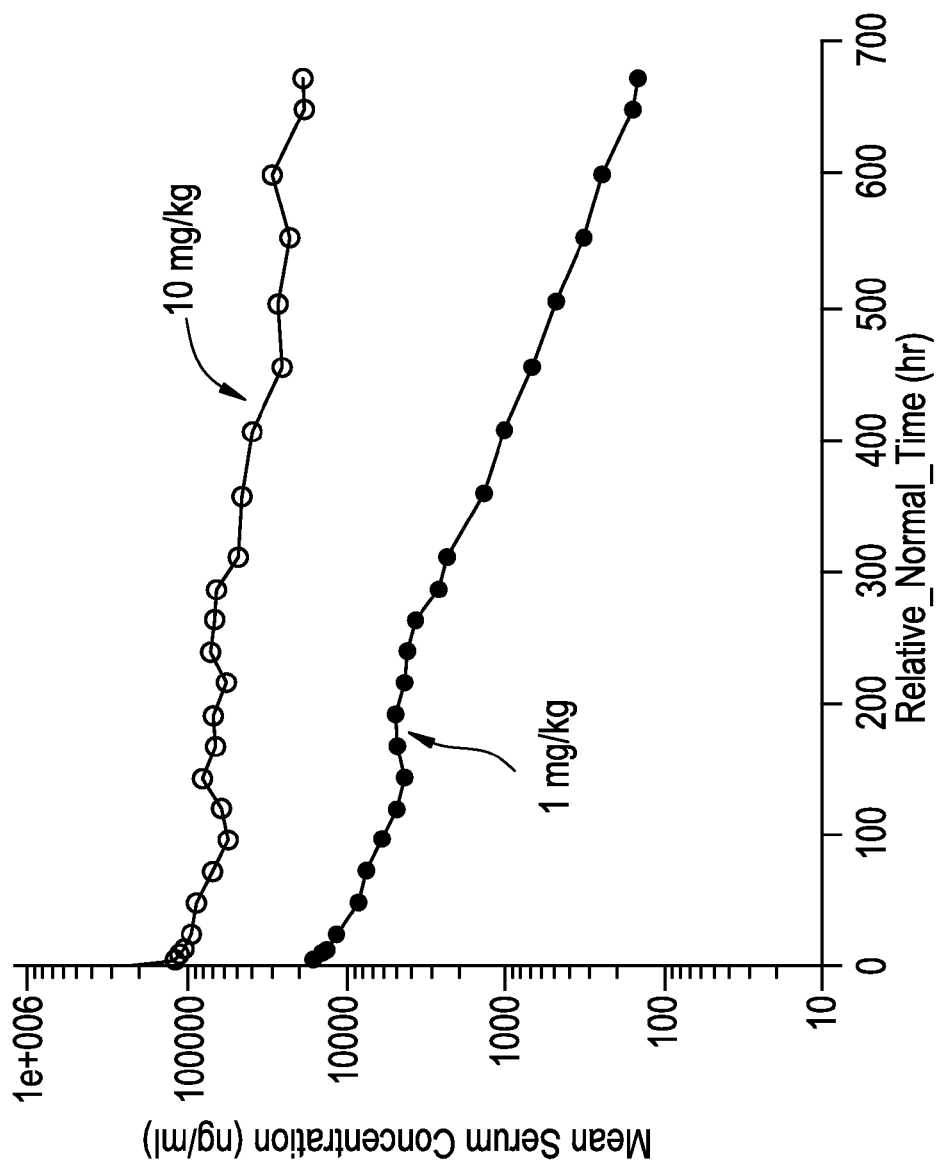
FIG. 33 shows representative pharmacokinetic profiles of the 16435 antibody, as determined in male cynomolgus monkeys using a single IV dose at either 1 mg/kg or 10 mg/kg. Serum samples were collected pre-dose and at 0.25, 0.5, 1, 4, 8, 12, 24, 48, 72, 96, 120, 144, 168, 192, 216, 240, 264, 288, 312, 360, 408, 456, 504, 552, 600, 648 and 672 hours after administration. Samples were assayed for 16435 antibody levels using an anti-IgG sandwich ELISA.

The pharmacokinetic profile of the 16435 antibody was determined in cynomolgus monkeys (*Macaca fascicularis*) to assess the in vivo parameters. Briefly, a single IV bolus dose of 16435, either 1 mg/kg or 10 mg/kg, was administered to mature male cynomolgus monkeys (n=2 per group). Serum samples were collected pre-dose and at timepoints 0.25, 0.5, 1, 4, 8, 12, 24, 48, 72, 96, 120, 144, 168, 192, 216, 240, 264, 288, 312, 360, 408, 456, 504, 552, 600, 648 and 672 hours after antibody administration. Samples were assayed for 16435 antibody levels by using an anti-IgG sandwich ELISA. Time concentration data were analyzed using non-compartmental methods with WinNonLin® (Enterprise version 5.1.1, 2006, Pharsight® Corp. Mountain View, Calif.). The resulting pharmacokinetic profile did not show any significant abnormalities (FIG. 33).

Example 5

Antibody 16435-ShK[1-35, Q16K] Fusion Cloning, Purification & Analysis

Cloning and Expression.

The components of the monovalent 16435-ShK fusion (Antibody 3742) include:
(a) 16435 kappa LC (SEQ ID NO:109);
(b) 16435 IgG2 HC (SEQ ID NO:112); and
(c) 16435 IgG2-ShK[1-35, Q16K] (SEQ ID NO:377):

```
                                          SEQ ID NO: 377
QVQLVQSGAEVKKPGASVKVSCKASGYTFTRYGISWVRQAPGQG

LEWMGWISTYSGNTNYAQKLQGRVTMTTDTSTSTAYMELRSLRSDDTAV

YYCARAQLYFDYWGQGTLVTVSSASTKGPSVFPLAPCSRSTSESTAALG

CLVKDYFPEPVTVSWNSGALTSGVHTFPAVLQSSGLYSLSSVVTVPSSN

FGTQTYTCNVDHKPSNTKVDKTVERKCCVECPPCPAPPVAGPSVFLFPP

KPKDTLMISRTPEVTCVVVDVSHEDPEVQFNWYVDGVEVHNAKTKPREE

QFNSTFRVVSVLTVVHQDWLNGKEYKCKVSNKGLPAPIEKTISKTKGQP

REPQVYTLPPSREEMTKNQVSLTCLVKGFYPSDIAVEWESNGQPENNYK

TTPPMLDSDGSFFLYSKLTVDKSRWQQGNVFSCSVMHEALHNHYTQKSL

SLSPGGGGSGGGGSRSCIDTIPKSRCTAFKCKHSMKYRLSFCRKTCGT
C//.
```

Figure 34:
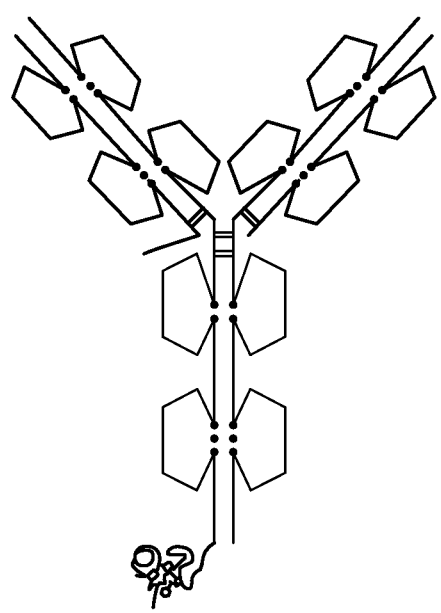
FIG. 34 shows a schematic structural representation of one embodiment of a composition of the invention that includes one unit of a pharmacologically active toxin peptide analog (squiggle) fused, via an optional peptidyl linker moiety with one immunoglobulin.

The desired product antibody fusion (3742) was a full antibody with the ShK[1-35, Q16K] peptide (SEQ ID NO:76) fused to the C-terminus of one heavy chain (see, schematic representation in FIG. 34). With two different heavy chains sharing one variety of light chain, the ratio of heavy chain: light chain:heavy chain-ShK[1-35, Q16K] was 1:2:1. The expected expression products are 16435 IgG2, monovalent 16435 IgG2-ShK[1-35, Q16K], and divalent 16435 IgG2-ShK[1-35, Q16K]. The monovalent 16435 IgG2-Shk fusion protein was isolated from the mix using cation exchange chromatography, as described herein.

The ShK[1-35, Q16K] fragment was generated using construct pTT5-aKLH120.6-IgG2-HC-L10-ShK[1-35, Q16K], encoding (SEQ ID NO:389), as a template, which was digested with StuI and NotI and purified with the PCR Purification Kit (Qiagen). At the same time, pDC324 (SEQ ID NO:111) was digested with StuI and NotI, treated with Calf Intestine Phosphatase (CIP) and run out on a 1% agarose gel. The larger fragment was cut out and gel purified by Qiagen's Gel Purification Kit. The purified Shk[1-35, Q16K] fragment was ligated to the large vector fragment and transformed into OneShot Top10 bacteria. DNAs from transformed bacterial colonies were isolated and submitted for sequencing. Although analysis of several sequences of clones yielded a 100% percent match with the above sequence, only one clone was selected for large scaled plasmid purification. The final pDC324-16435-IgG2-HC-L10-ShK[1-35, Q16K] construct encoded an IgG2-HC-L10-ShK[1-35, Q16K] fusion polypeptide (SEQ ID:377).

Purification.

Initial purification of the 3742 conditioned media was done by affinity FPLC capture of the Fc region using Protein A Sepharose (GE Healthcare) followed by a column wash with Dulbecco's PBS without divalent cations (Invitrogen) and step elution with 100 mM acetic acid, pH 3.5. Protein containing fractions were pooled and neutralized to pH 5.0 with 10 N NaOH and diluted 5-times volume with water. The material was filtered through a 0.45 μm cellulose acetate filter (Corning) and further purified by cation exchange FPLC (SP Sepharose High Performance; GE Healthcare). Samples were loaded onto a column equilibrated with 100% buffer A (50 mM acetic acid, pH 5.0) and eluted with a gradient of 0 to 800 mM NaCl over 30 column volumes. Peaks containing monovalent species were pooled and formulated into 10 mM sodium acetate, 9% sucrose, pH 5.0.

Analysis.

Figure 35:
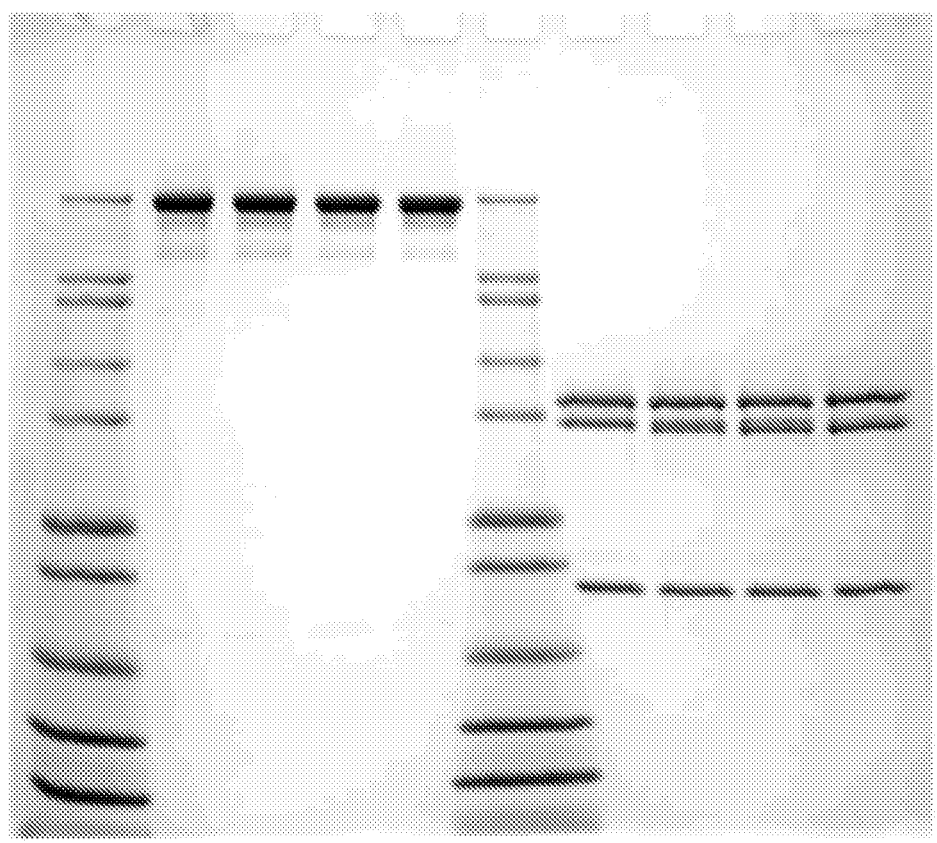
FIG. 35 shows a Coomassie brilliant blue-stained Tris-glycine 4-20% SDS-PAGE of final monovalent 16435 IgG2-L10-Shk[1-35, Q16K] products. Products were isolated from four different expression pools. Lanes 1-10 were loaded as follows: Novex Mark12 wide range protein standards (10 µl), 2 µg pool 1 product non-reduced, 2 µg pool 2 product non-reduced, 2 µg pool 3 product non-reduced, 2 µg pool 4 product non-reduced, Novex Mark12 wide range protein standards (10 µl), 2 µg pool 1 product reduced, 2 µg pool 2 product reduced, 2 µg pool 3 product reduced, 2 µg pool 4 product reduced.
Figure 36A:
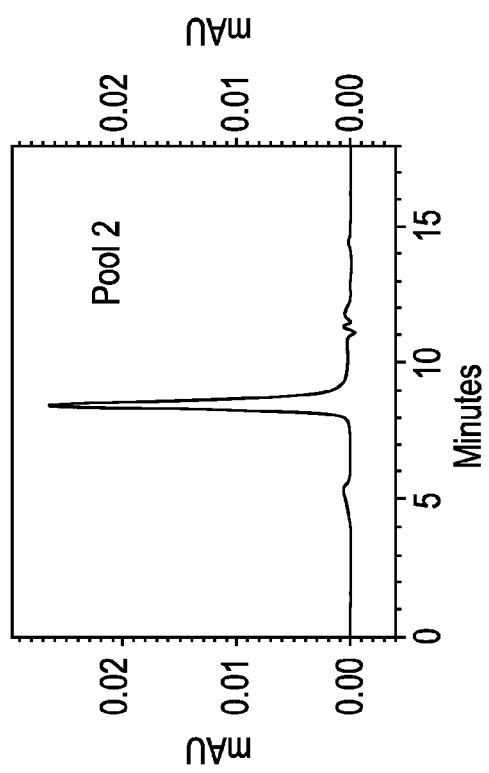
FIGS. 36A-D shows size exclusion chromatography on 30 µg of the final pool 1, 2, 3 & 4 of the 3742 product injected onto a Phenomenex BioSep SEC-3000 column (7.8×300 mm) equilibrated in 50 mM NaH2PO4, 250 mM NaCl, pH 6.9 at 1 ml/min, measuring the absorbance at 280 nm.
Figure 36B:
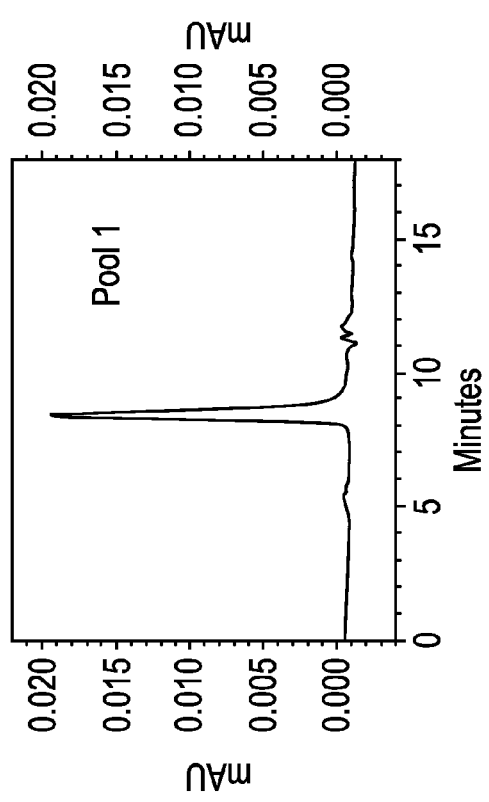
Figure 36C:
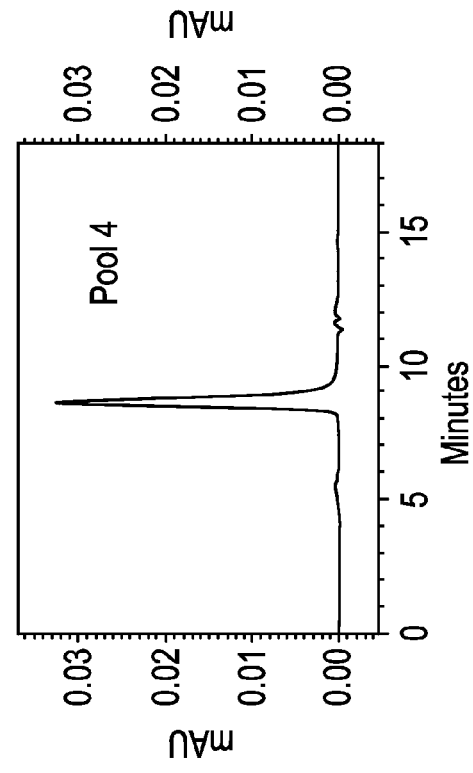
Figure 36D:
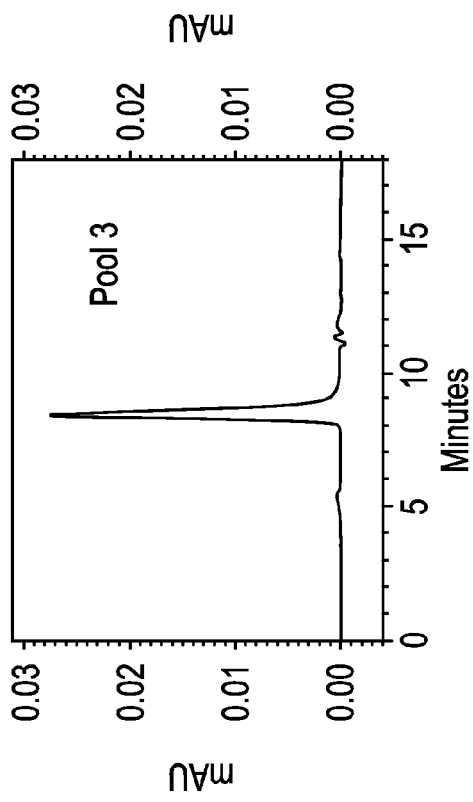
Figure 38A:
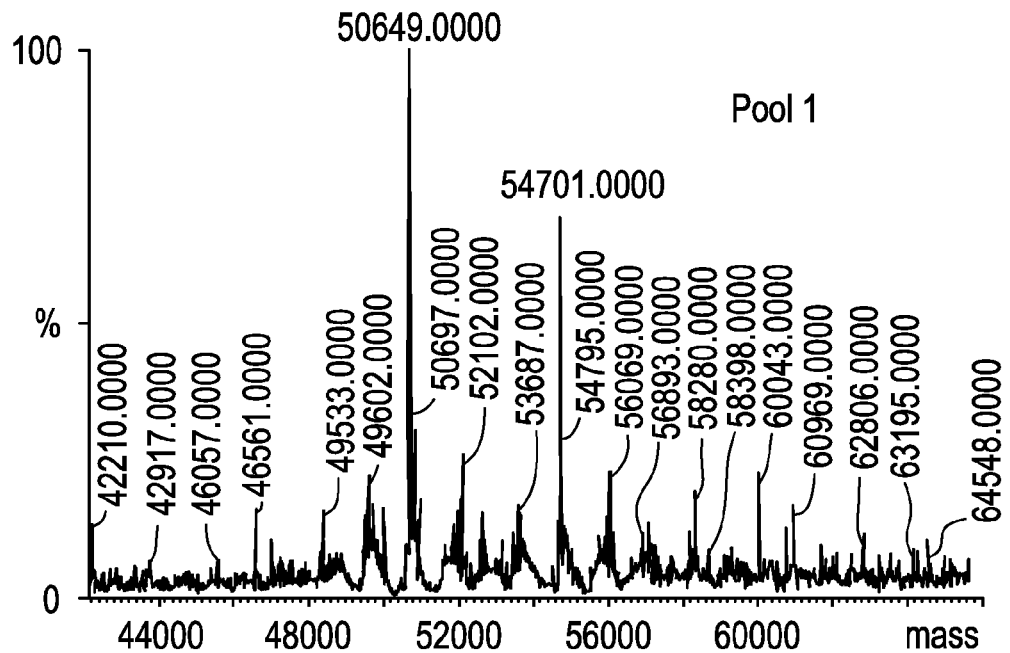
FIGS. 38A-D shows reduced heavy chain LC-MS analysis of the final 3742 samples. The product was chromatographed through a Waters MassPREP micro desalting column using a Waters ACQUITY UPLC system. The column was set at 80° C. and the protein eluted using a linear gradient of increasing acetonitrile concentration in 0.1% formic acid. The column effluent was directed into a Waters LCT Premier ESI-TOF mass spectrometer for mass analysis. The instrument was run in the positive V mode. The capillary voltage was set at 3,200 V and the cone voltage at 80 V. The mass spectrum was acquired from 800 to 3000 m/z and deconvoluted using the MaxEnt1 software provided by the instrument manufacturer.
Figure 38B:
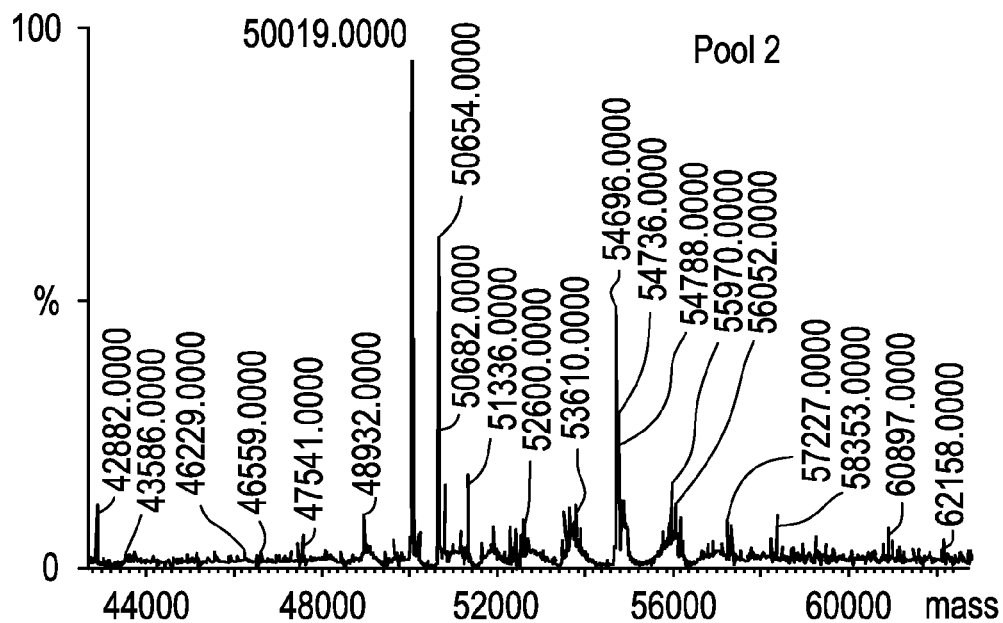
Figure 38C:
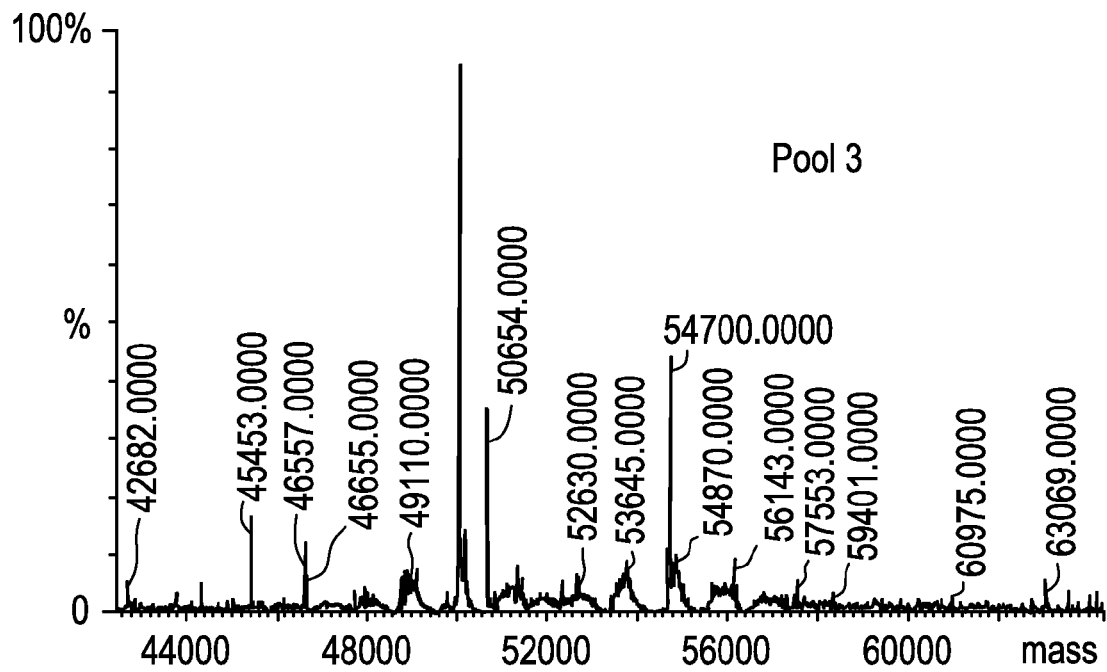
Figure 38D:
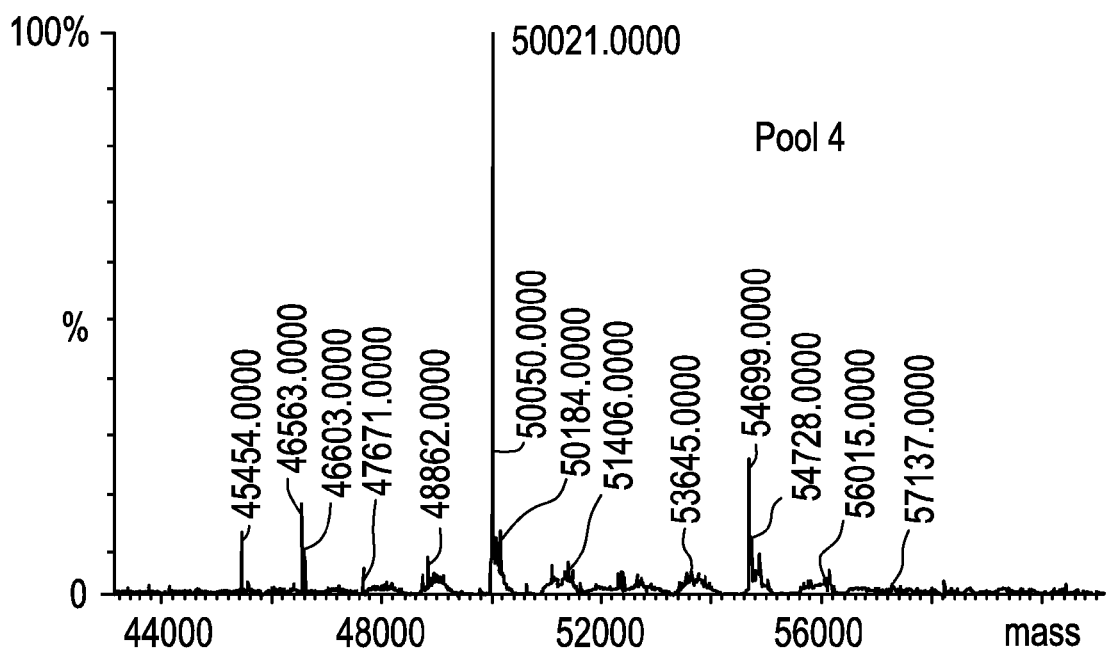

Reducing and non-reducing SDS-PAGE analysis was done on 3742 pools using 4-12% tris-glycine gels (Invitrogen) with 2 μg of protein, stained with QuickBlue (Boston Biologicals). Based on the SDS-PAGE there were no significant differences between the pools (FIG. 35). Analytical SEC was done using a Biosep SEC-53000 column (Phenomenex) with an isocratic elution using 50 mM sodium phosphate, 250 mM NaCl, pH 6.9 as the mobile phase at 1 ml/min (FIGS. 36A-D). All four pools showed relatively low levels of aggregate based on the SEC data; however, pool 1 showed somewhat higher levels than the other pools.

The final 3742 samples were characterized by LC-MS analysis of reduced heavy chain (FIGS. 38A-D) and light chain (FIGS. 37A-D). The product was chromatographed through a Waters MassPREP micro desalting column using a Waters ACQUITY UPLC system. The column was set at 80° C. and the protein eluted using a linear gradient of increasing acetonitrile concentration in 0.1% formic acid. The column effluent was directed into a Waters LCT Premier ESI-TOF mass spectrometer for mass analysis. The instrument was run in the positive V mode. The capillary voltage was set at 3,200 V and the cone voltage at 80 V. The mass spectrum was acquired from 800 to 3000 m/z and deconvoluted using the MaxEnt1 software provided by the instrument manufacturer.

All four pools yielded the expected mass within the error of the instrument, indicating all pools were producing the expected product (FIGS. 37A-D and FIGS. 38A-D).

Whole Blood Assay.

An ex vivo assay was employed to examine impact of toxin peptide analog Kv1.3 inhibitors on secretion of IL-2 and IFN-γ. The potency of ShK analogs and conjugates in blocking T cell inflammation in human whole blood was examined using an ex vivo assay that has been described earlier (see Example 46 of WO 2008/088422 A2, incorporated herein by reference in its entirety). In brief, 50% human whole blood was stimulated with thapsigargin to induce store depletion, calcium mobilization and cytokine secretion. To assess the potency of molecules in blocking T cell cytokine secretion, various concentrations of Kv1.3 blocking peptides and peptide-conjugates were pre-incubated with the human whole blood sample for 30-60 min prior to addition of the thapsigargin stimulus. After 48 hours at 37° C. and 5% $CO_2$, conditioned medium was collected and the level of cytokine secretion was determined using a 4-spot electrochemiluminescent immunoassay from MesoScale Discovery. Using thapsigargin stimulus, the cytokines IL-2 and IFN-g were secreted robustly from blood isolated from multiple donors. The IL-2 and IFN-g produced in human whole blood following thapsigargin stimulation were produced from T cells, as revealed by intracellular cytokine staining and fluorescence-activated cell sorting (FACS) analysis. Kv1.3 is the major voltage-gated potassium channel present on T cells. Allowing for $K^+$ efflux, Kv1.3 provides the driving force for continued $Ca^{2+}$ influx which is necessary for the sustained elevation in intracellular calcium needed for efficient T cell activation and cytokine secretion. Kv1.3 inhibitors have been shown earlier to suppress this calcium flux induced by TCR ligation (G. C. Koo et al., 1999, Cell. Immunol. 197, 99-107). Thapsigargin-induced store-depletion and TCR ligation elicits similar patterns of $Ca^{2+}$ mobilization in isolated T cells (E. Donnadieu et al., 1991, J. Biol. Chem. 267, 25864-25872), but we have found thapsigargin gives a more robust response in whole blood. Therefore, we employed a bioassay whereby the bioactivity of Kv1.3 inhibitors is assessed by examining their ability to block thapsigargin-induced cytokine secretion from T cells in human whole blood. Since whole blood is a complex fluid containing high protein levels, the activity of peptides and peptide conjugates in this whole blood assay has an additional advantage in assessing the molecules stability over 48 hours in a biologically relevant fluid. The whole blood assay provides important confirmation of the Kv1.3 potency of molecules determined by electrophysiology (ePhys), since ePhys assays are generally of short duration (<1-2 hours) and use physiological saline containing no protein. The longer duration of the whole blood assay may allow for more effective determination of equilibrium binding kinetics relative to ePhys studies which are of short duration. As seen in Table 7A (below), all four pools of 3742-ShK(1-35, Q16K) showed good potency in the human whole blood assay, indicating the isolated molecules have obtained the proper tertiary structure and are reasonably stable in serum for 48 hours. Table 7B (below) shows that the potency was comparable to other ShK-conjugated molecules.

TABLE 7A

Human whole blood ("WB") assays of four pools of 3742 (SEQ ID NOS: 377; 109, 112; 109) of IL-2 and interferon-gamma ("IFNγ") were conducted as described in Example 5 herein.

| Pool | $IC_{50}$ IFNγ (pM) | $IC_{50}$ IL-2 (pM) |
|---|---|---|
| 1 | 708 | 2220 |
| 2 | 599 | 2461 |
| 3 | 598 | 1649 |
| 4 | 412 | 909 |

TABLE 7B

Data demonstrating potency of various conjugates of [Lys16]ShK in the Whole Blood Assay. Toxin peptides and toxin peptide analogs were PEGylated as described in Example 9 herein. Immunoglobulin-containing compounds were recombinantly expressed and purified as described in Example 8. Human whole blood ("WB") assays of IL-2 and interferon-gamma ("IFNg") were conducted as described in Example 5 herein).

| SEQ ID NO or citation | Conjugate Type | Designation | WB (IL-2) IC50 (nM) | WB (IFNg) IC50 (nM) | Potency Relative to ShK (WB, IL2) |
|---|---|---|---|---|---|
| 378 | none | ShK(1-35) | 0.067 | 0.078 | 1.00 |
| 76 | none | [Lys16]ShK | 0.110 | 0.158 | 1.64 |
| 379 | none | [Lys16]ShK-Ala | 0.138 | 0.266 | 2.06 |
| 380 | PEG | 20 kDa-PEG-ShK | 0.380 | 0.840 | 5.67 |
| 381 | PEG | 20 kDa-PEG-[Lys16]ShK | 0.092 | 0.160 | 1.37 |
| 382 | PEG | 20 kDa-PEG-[Lys16]ShK-Ala | 0.754 | 1.187 | 11.25 |
| 377; 109; 112; 109 | IgG2 | Monovalent antibody # 3742-ShK(1-35, Q16K), Pool 4 | 0.412 | 0.909 | 6.15 |
| Example 1, WO2008/088422 A2 | IgG1 | Bivalent Fc-L10-ShK[1-35] homodimer | 0.386 | 0.320 | 5.76 |
| Example 2, WO2008/088422 A2 | IgG1 | Bivalent Fc-L10-ShK[2-35] homodimer | 0.585 | 2.285 | 8.73 |

TABLE 7B-continued

Data demonstrating potency of various conjugates of [Lys16]ShK in the Whole Blood Assay. Toxin peptides and toxin peptide analogs were PEGylated as described in Example 9 herein. Immunoglobulin-containing compounds were recombinantly expressed and purified as described in Example 8. Human whole blood ("WB") assays of IL-2 and interferon-gamma ("IFNg") were conducted as described in Example 5 herein).

| SEQ ID NO or citation | Conjugate Type | Designation | WB (IL-2) IC50 (nM) | WB (IFNg) IC50 (nM) | Potency Relative to ShK (WB, IL2) |
|---|---|---|---|---|---|
| Example 2, WO2008/088422 A2 | IgG1 | Monovalent Fc/Fc-L10-ShK[2-35] heterodimer | 2.149 | 5.199 | 32.07 |
| 1; 26 | IgG2 | Monovalent Fc/Fc-ShK(1-35 Q16K) heterodimer | 0.160 | 0.499 | 2.39 |
| 26; 26 | IgG2 | Bivalent Fc-ShK(1-35, Q16K) homodimer | 1.850 | 3.140 | 27.61 |

Example 6

Ab 4341-ShK(1-35, Q16K), 4341-FGF21 and 16435-FGF21 Fusion Construct Generation Antibody 16435-huFGF21 Fusion (Ab 10162).
The components of the 16435-huFGF21 fusion include:
(a) 16435 kappa LC (SEQ ID NO:109);
(b) 16435 HC(R118A; SEQ ID NO:112); and
(c) 16435 IgG2-HC-huFGF21 [1-181] (SEQ ID NO:384):

```
                                              SEQ ID NO: 384
QVQLVQSGAEVKKPGASVKVSCKASGYTFTRYGISWVRQAPGQG

LEWMGWISTYSGNTNYAQKLQGRVTMTTDTSTSTAYMELRSLRSDDTAVY

YCARAQLYFDYWGQGTLVTVSSASTKGPSVFPLAPCSRSTSESTAALGCL

VKDYFPEPVTVSWNSGALTSGVHTFPAVLQSSGLYSLSSVVTVPSSNFGT

QTYTCNVDHKPSNTKVDKTVERKCCVECPPCPAPPVAGPSVFLFPPKPKD

TLMISRTPEVTCVVVDVSHEDPEVQFNWYVDGVEVHNAKTKPREEQFNST

FRVVSVLTVVHQDWLNGKEYKCKVSNKGLPAPIEKTISKTKGQPREPQVY

TLPPSREEMTKNQVSLTCLVKGFYPSDIAVEWESNGQPENNYKTTPPMLD

SDGSFFLYSKLTVDKSRWQQGNVFSCSVMHEALHNHYTQKSLSLSPGGGG

GGSGGGSGGGGSHPIPDSSPLLQFGGQVRQRYLYTDDAQQTEAHLEIRED

GTVGGAADQSPESLLQLKALKPGVIQILGVKTSRFLCQRPDGALYGSLHF

DPEACSFRELLLEDGYNVYQSEAHGLPLHLPGNKSPHRDPAPRGPARFLP

LPGLPPAPPEPPGILAPQPPDVGSSDPLSMVGPSQGRSPSYAS//.
```

The 16435 huIgG2-HC-L15-huFGF21 [1-181] fragment was generated using construct pTT5-aKLH120.6-IgG2-HC-L15-huFGF21 [1-181] (SEQ ID NO:130) as a template, which was digested with BsmBI and NotI and purified with the Qiagen Gel Purification Kit. At the same time, pTT5-16435 IgG2 HC was digested with BsmBI and NotI, and run out on a 1% agarose gel. The vector fragments, which contained the 16435 heavy chain variable region, were cut out and gel purified by Qiagen Gel Purification Kit. The purified huIgG2-HC-L15-huFGF21 [1-181] fragment was ligated to the vector fragments containing the 16435 heavy chain variable region and transformed into DH10b bacteria. DNAs from transformed bacterial colonies were isolated and submitted for sequencing. Although analysis of several sequences of clones yielded a 100% percent match with the above sequence, only one clone was selected for large scaled plasmid purification. The final pTT5-16435-IgG2-HC-L15-huFGF21 [1-181] construct encoded an IgG2-HC-L15-huFGF21 [1-181] fusion polypeptide (SEQ ID:384)

Antibody 4341-huFGF21 Fusion (Ab 10163).
The components of the 4341-ShK[1-35, Q16K] fusion (Ab 10163) include:
(a) 4341 kappa LC (SEQ ID NO:115);
(b) 4341 HC (Y125A; SEQ ID NO:118); and
(c) 4341 IgG2-HC-huFGF21 [1-181] (SEQ ID NO:386):

```
                                              SEQ ID NO: 386
QVQLQESGPGLVKPSQTLSLTCTVSGGSISSGDYFWSWIRQLP

GKGLEWIGHIHNSGTTYYNPSLKSRVTISVDTSKKQFSLRLSSVTAADTA

VYYCARDRGGDYAYGMDVWGQGTTVTVSSASTKGPSVFPLAPCSRSTSES

TAALGCLVKDYFPEPVTVSWNSGALTSGVHTFPAVLQSSGLYSLSSVVTV

PSSNFGTQTYTCNVDHKPSNTKVDKTVERKCCVECPPCPAPPVAGPSVFL

FPPKPKDTLMISRTPEVTCVVVDVSHEDPEVQFNWYVDGVEVHNAKTKPR

EEQFNSTFRVVSVLTVVHQDWLNGKEYKCKVSNKGLPAPIEKTISKTKGQ

PREPQVYTLPPSREEMTKNQVSLTCLVKGFYPSDIAVEWESNGQPENNYK

TTPPMLDSDGSFFLYSKLTVDKSRWQQGNVFSCSVMHEALHNHYTQKSLS

LSPGGGGGSGGGSGGGGSHPIPDSSPLLQFGGQVRQRYLYTDDAQQTEA

HLEIREDGTVGGAADQSPESLLQLKALKPGVIQILGVKTSRFLCQRPDGA

LYGSLHFDPEACSFRELLLEDGYNVYQSEAHGLPLHLPGNKSPHRDPAPR

GPARFLPLPGLPPAPPEPPGILAPQPPDVGSSDPLSMVGPSQGRSPSYAS

//.
```

The huIgG2-HC-L15-huFGF21 [1-181] fragment was generated using construct pTT5-aKLH120.6-IgG2-HC-L15-huFGF21 [1-181] as a template, which was digested with BsmBI and NotI and purified with the Qiagen Gel Purification Kit. At the same time, pTT5-4341 IgG2 HC was digested with BsmBI and NotI, and run out on a 1% agarose gel. The larger fragment, which contained the 4341 heavy chain variable region, was cut out and gel purified by Qiagen Gel Purification Kit. The purified huIgG2-HC-L15-huFGF21 [1-181] fragment was ligated to the large vector fragment containing the 4341 heavy chain variable region and transformed into DH10b bacteria. DNAs from transformed bacterial colonies were isolated and submitted for sequencing. Although analysis of several sequences of clones yielded a 100% percent match with the above sequence, only one clone was selected for large scaled plasmid purification. The final pTT5-4341-IgG2-HC-L15-huFGF21 [1-181] construct encoded an IgG2-HC-L15-huFGF21 [1-181] fusion polypeptide (SEQ ID:386).

4341-ShK[1-35, Q16K] Fusion (Antibody 10164).

The components of the 4341-ShK[1-35, Q16K] fusion (Ab 10164) include:

(a) 4341 kappa LC (SEQ ID NO:115);
(b) 4341 HC (Y125A; SEQ ID NO:118); and
(c) 4341 IgG2-HC-ShK [1-35, Q16K] (SEQ ID NO:388):

```
                                           SEQ ID NO: 388
QVQLQESGPGLVKPSQTLSLTCTVSGGSISSGDYFWSWIRQLP

GKGLEWIGHIHNSGTTYYNPSLKSRVTISVDTSKKQFSLRLSSVTAADTA

VYYCARDRGGDYAYGMDVWGQGTTVTVSSASTKGPSVFPLAPCSRSTSES

TAALGCLVKDYFPEPVTVSWNSGALTSGVHTFPAVLQSSGLYSLSSVVTV

PSSNFGTQTYTCNVDHKPSNTKVDKTVERKCCVECPPCPAPPVAGPSVFL

FPPKPKDTLMISRTPEVTCVVVDVSHEDPEVQFNWYVDGVEVHNAKTKPR

EEQFNSTFRVVSVLTVVHQDWLNGKEYKCKVSNKGLPAPIEKTISKTKGQ

PREPQVYTLPPSREEMTKNQVSLTCLVKGFYPSDIAVEWESNGQPENNYK

TTPPMLDSDGSFFLYSKLTVDKSRWQQGNVFSCSVMHEALHNHYTQKSLS

LSPGGGGSGGGGSRSCIDTIPKSRCTAFKCKHSMKYRLSFCRKTCGTC/
/.
```

The huIgG2-HC-L10-ShK [1-35, Q16K] fragment was generated using construct pDC324-16435-HC-L10-IgG2-ShK [1-35, Q16K] (SEQ ID NO:376) as a template, which was digested with BsmBI and NotI and purified with the Qiagen Gel Purification Kit. At the same time, pTT5-4341 IgG2 HC was digested with BsmBI and NotI, and run out on a 1% agarose gel. The larger fragment, which contained the 4341 heavy chain variable region, was cut out and gel purified by Qiagen Gel Purification Kit. The purified huIgG2-HC-L10-ShK [1-35, Q16K] fragment was ligated to the large vector fragment containing the 4341 heavy chain variable region and transformed into DH10b bacteria. DNAs from transformed bacterial colonies were isolated and submitted for sequencing. Although analysis of several sequences of clones yielded a 100% percent match with the above sequence, only one clone was selected for large scaled plasmid purification. The final pTT5-4341-IgG2-HC-L10-ShK [1-35, Q16K] construct encoded an IgG2-HC-L10-ShK [1-35, Q16K] fusion polypeptide (SEQ ID NO:388).

Example 7

Ab 4341-ShK, 4341-FGF21 and 16435-FGF21 Fusion Expression, Purification & Analysis Transient transfections were carried out in HEK 293-6E cells as follows. The human embryonic kidney 293 cell line stably expressing Epstein Barr virus Nuclear Antigen-1 (293-6E cells) was obtained from the National Research Council (Montreal, Canada). Cells were maintained as serum-free suspension cultures using F17 medium (Invitrogen, Carlsbad, Calif.) supplemented with 6 mM L-glutamine (Invitrogen, Carlsbad, Calif.), 1.1% F-68 Pluronic (Invitrogen, Carlsbad, Calif.) and 250 µg/ul Geneticin (Invitrogen, Carlsbad, Calif.). The suspension cell cultures were maintained in Erlenmeyer shake flask cultures. The culture flasks were shaken at 65 rpm at 37° C. in a humidified, 5% $CO_2$ atmosphere. A stock solution (1 mg/ml) of 25-kDa linear PEI (Polysciences, Warrington, Pa.) was prepared in water, acidified with HCl to pH 2.0 until dissolved, then neutralized with NaOH, sterilized by filtration (0.2 µm), aliquoted, and stored at −20° C. until used. Tryptone N1 was obtained from OrganoTechni S.A. (Tekni-Science, QC, Canada). A stock solution (20%, w/v) was prepared in F17 medium, sterilized by filtration through 0.2 µm filters, and stored at 4° C. until use. Typically, transfections were performed at the 1 L scale. Cells (293-6E) were grown too a viable cell density of $1.1 \times 10^6$ cells/ml then transfection complexes were prepared in 1/10th volume of the final culture volume. For a 1-L transfection culture, transfection complexes were prepared in 100 ml F17 basal medium, and 500 µg plasmid DNA (heavy chain and light chain DNA, 1:1 ratio) was first diluted in 100 ml F17 medium. After a 5-minute incubation at room temperature, 1.5 ml of PEI solution was added. The complexes were vortexed mildly, then incubated for 15 minutes at room temperature. The cells were transfected by adding the transfection complex mix to the cells in the shake flask culture. 24 hours post-transfection, Tryptone N1 was added to the transfected culture to a final concentration of 0.5%, and the transfected cultures were maintained on a shaker at 65 rpm at 37° C. in a humidified, 5% $CO_2$ atmosphere for another 5 days after which they were harvested. The conditioned medium was harvested by centrifugation at 4000 rpm, and then sterile filtered through 0.2 µm filter (Corning Inc.).

Figure 39A:
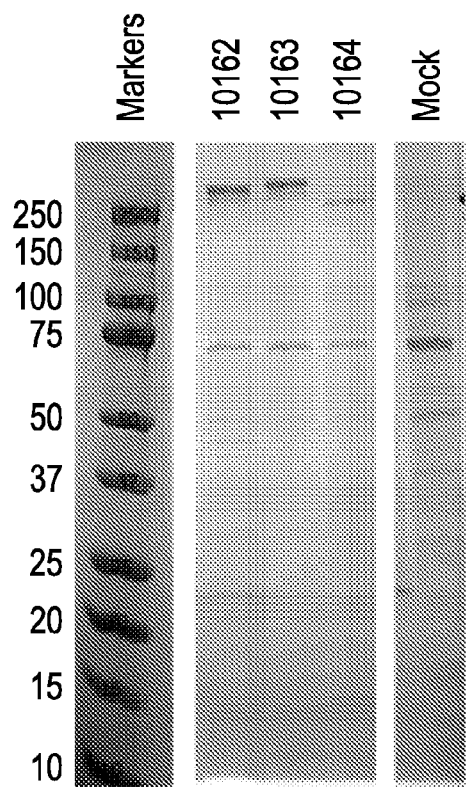
FIG. 39A shows non-reducing analysis of the conditioned media of antibody fusions 10162, 10163 and 10164, along with the conditioned media from a mock transfection, on 1.0 mm Tris-glycine 4-20% SDS-PAGEs (Novex) developed at 220V using non-reducing loading buffer and staining with QuickBlue (Boston Biologicals). Molecular weight markers are indicated in kDa.

The transiently expressed antibodies were purified using recombinant protein A sepharose (GE Healthcare) directly loading the conditioned media on the column at 5 ml/min at 7° C. The column was then washed with 10 column volumes of Dulbecco's PBS without divalent cations and then eluted with 100 mM acetic acid, pH 3.5. The eluted antibodies were pooled based on the chromatographic profile and the pH was adjusted to 5.0 using 2 M tris base. The pools were then filtered through a 0.8/0.22 um syringe filter and then dialyzed against 10 mM acetic acid, 9% sucrose, pH 5.0. The buffer exchanged antibodies were then concentrated using a Vivaspin 30 kDa centrifugal concentration (Sartorius), and the concentrated products were filtered through a 0.22 um cellulose acetate filter. All conditioned media, including a mock transfection, were analyzed using a 1.0 mm Tris-glycine 4-20% SDS-PAGE run at 35 mA/1000V/250W for 55 min (FIG. 39A) loading 10 µl conditioned media. The band above the 250 molecular weight marker not observed in the mock transfection sample is likely the expressed product. All three experimental transfections showed a signficant quantity of the expected product on the SDS-PAGE.

Figure 39B:
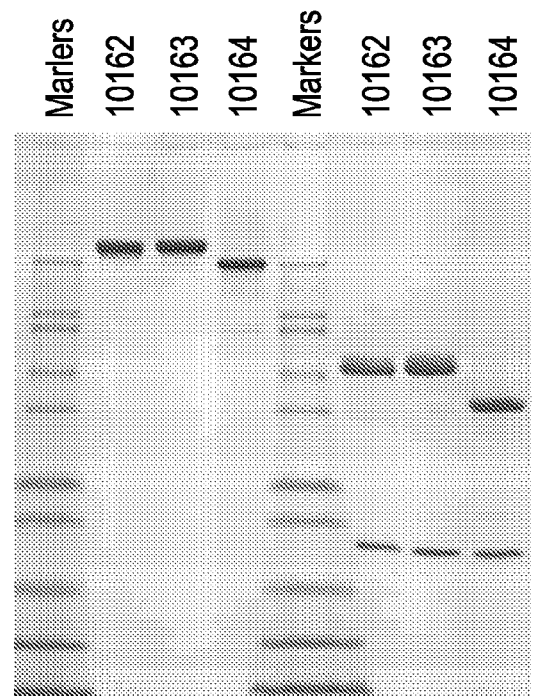
FIG. 39B shows a Coomassie brilliant blue stained Tris-glycine 4-20% SDS-PAGE of final 10162, 10163 & 10164 products. In lanes 1 & 5, Novex Mark 12 standards were loaded. For lanes 2-4 (non-reducing) and 6-8 (reducing), 2 µg of product was loaded.

Antibody fusions were analyzed for product quality on a 1.0-mm Tris-glycine 4-20% SDS-PAGE (Novex) using reducing and non-reducing loading buffer (FIG. 39B). All candidates electrophoresed as expected by both non-reducing and reducing SDS-PAGE; however, 10162 and 10163 show some slower migrating than expected bands, possibly indicating partial glycosylation. Antibodies were further analyzed for homogeneity using one size exclusion column (Phenomenex SEC3000, 7.8×300 mm) with a 50 mM sodium phosphate, 250 mM NaCl, pH 6.8, mobile phase flowed at 1.0 mL/min (FIG. 40). The 10162 and 10163 fusions eluted as expected and showed relatively low levels of high molecular weight species; however, the 10164 fusion eluted earlier than expected, possibly indicating aggregation.

Figure 41A:
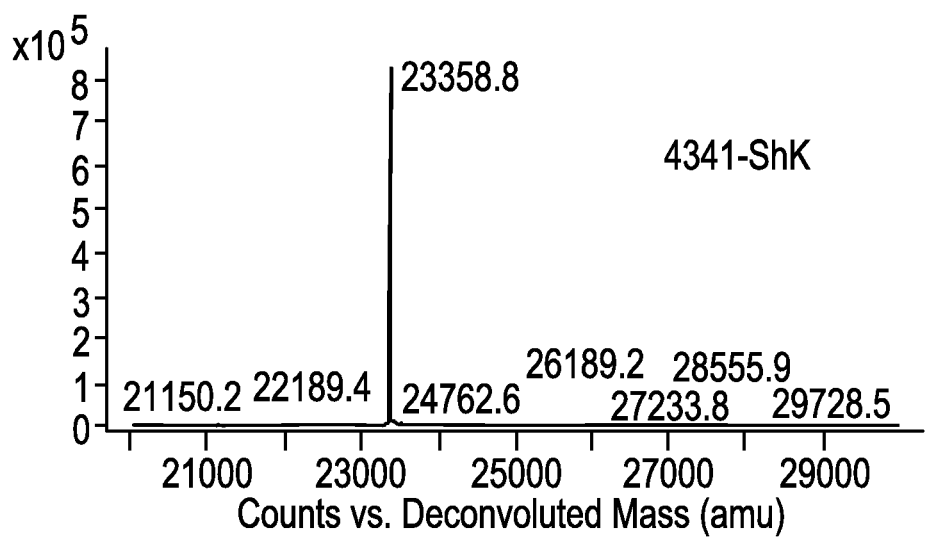
FIGS. 41A-C shows reduced light chain LC-MS analysis of the final 4341-ShK(1-35, Q16K) (FIG. 41A), 4341-FGF21 (FIG. 41B), and 16435-FGF21 (FIG. 41C) samples. The product was chromatographed through a Waters MassPREP micro desalting column using a Waters ACQUITY UPLC system. The column was set at 80° C. and the protein eluted using a linear gradient of increasing acetonitrile concentration in 0.1% formic acid. The column effluent was directed into a Waters LCT Premier ESI-TOF mass spectrometer for mass analysis. The instrument was run in the positive V mode. The capillary voltage was set at 3,200 V and the cone voltage at 80 V. The mass spectrum was acquired from 800 to 3000 m/z and deconvoluted using the MaxEnt1 software provided by the instrument manufacturer.
Figure 41B:
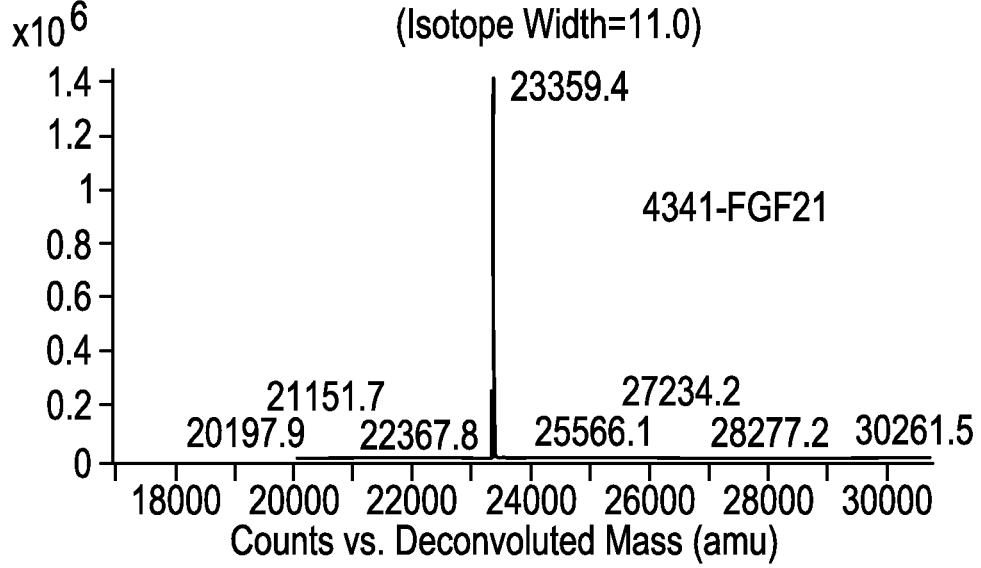
Figure 41C:
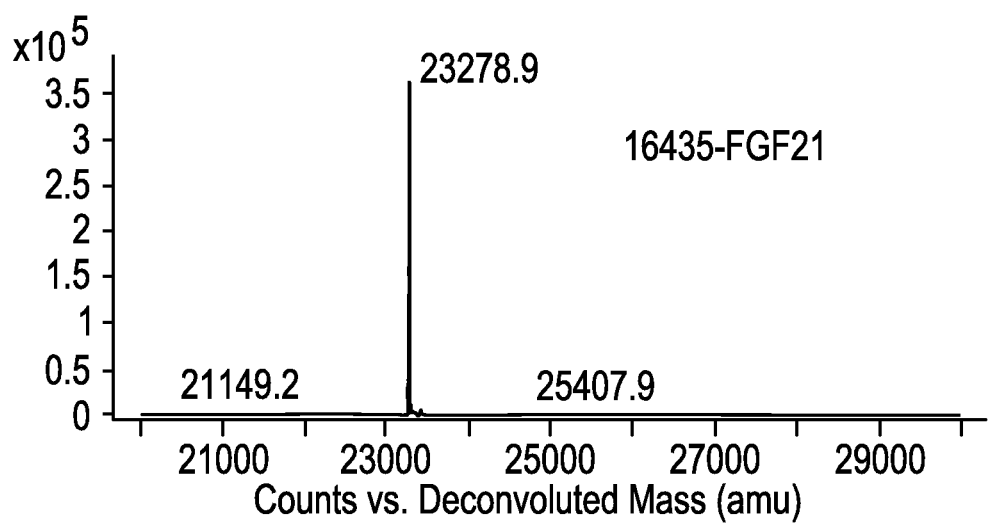

LC-MS analysis was conducted of reduced light chain (FIGS. 41A-C) and heavy chain (FIGS. 42A-C), respectively, of the final 4341-ShK, 4341-FGF21, and 16435-FGF21 samples. The FGF21 fusion samples were deglycosylated prior to reduction using the PNGase F technique as described by the manufacturer (QA Bio, LLC, Palm Desert, Calif.), except that the substrate to enzyme ratio was 10 μg substrate to 1 μL enzyme. The product was chromatographed through a Zorbax SB300 C8 50×1 mm 3 micron column using an Agilent 1100 capillary HPLC system. The column was set at 75° C. and the protein eluted using a gradient of increasing n-propanol concentration in 0.1% trifluoroacetic acid. The column effluent was directed into an Agilent-TOF mass spectrometer for mass analysis. The capillary voltage was set at 3,200 V and the fragmentor voltage at 225 V. The mass spectrum was acquired from 800 to 3000 m/z and deconvoluted using the MassHunter software provided by the instrument manufacturer. All samples possessed the expected mass within the error of the instrument, indicating all pools contained the expected product.

Example 8

Expression and Purification of Monovalent or Multivalent Immunoglobulin- and/or Fc Domain-Toxin Peptide Analog Fusions An assortment of monovalent, bivalent and trivalent structures were expressed and purified for comparison, including exemplary embodiments of the invention, as illustrated in Table 7B in Example 5. Those included antibody IgG2- or IgG1-ShK fusion variants (see FIG. 1F-L). For example, bivalent Fc-L10-ShK[1-35], monovalent immunoglobulin heavy chain-[Lys16]ShK fusion antibody; see FIG. 1F). IgG2 Fc/Fc-ShK variants (see FIG. 1A), bivalent Fc-L10-ShK[2-35], monovalent Fc/Fc-L10-ShK[2-35] were also made for comparison, by recombinant methods as described in Sullivan et al., WO 2008/088422 A2, and in particular Examples 1, 2, and 56 therein, incorporated by reference in its entirety, or as modified herein.

Transient expression system used to generate toxin peptide analog-Fc fusions ("peptibodies") or other immunoglobulin fusion embodiments. HEK 293-6E cells were maintained in 3 L Fernbach Erlenmeyer Flasks between 2e5 and 1.2e6 cells/ml in F17 medium supplemented with L-Glutamine (6 mM) and Geneticin (25 μg/ml) at 37° C., 5% CO$_2$, and shaken at 65 RPM. At the time of transfection, cells were diluted to 1.1× 10$^6$ cells/mL in the F17 medium mentioned above at 90% of the final culture volume. DNA complex was prepared in Freestyle 293 medium at 10% of the final culture volume. DNA complex includes 500 ug total DNA per liter of culture and 1.5 ml PEImax per liter of culture. DNA complex is briefly shaken once ingredients are added and incubated at room temperature for 10 to 20 minutes before being added to the cell culture and placed back in the incubator. The day after transfection, Tryptone N1 (5 g/L) was added to the culture from liquid 20% stock. Six days after transfection, culture was centrifuged at 4,000 RPM for 40 minutes to pellet the cells and the cultured medium was harvested through a 0.45 um filter.

In preparing the DNA complex, the ratio of plasmids was proportional to the desired molar ratio of the peptides needed to generate the intended product. The components of the IgG2 Fc/Fc-ShK include IgG2 Fc and IgG2 Fc-ShK at a 1:1 ratio. During expression these assemble into IgG2 Fc homodimers, IgG2 Fc/Fc-ShK heterodimers, and IgG2 Fc-ShK homodimers. The IgG2 Fc/Fc-ShK heterodimer (monovalent form) was isolated during purification using cation exchange chromatography.

IgG2 Fc-ShK[2-35]; IgG2 Fc Shk[2-35, Q16K]; IgG2 Fc-Shk[1-35]; IgG2 Fc-ShK[1-35, Q16K] mammalian expression. DNA sequences coding for the immunoglobulin Fc domain of human IgG2:

```
                                             SEQ ID NO: 1
MEWSWVFLFFLSVTTGVHSERKVECPPCPAPPVAGPSVFLFPP

KPKDTLMISRTPEVTCVVVDVSHEDPEVQFNWYVDGVEVHNAKTKPREEQ

FNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTP

PMLDSDGSFFLYSKLTVDKSRWQQGNVFSCSVMHEALHNHYTQKSLSLSP

GK//,
``` fused in-frame to a monomer of the Kvl 3 inhibitor peptide ShK[2-35] or a mutated ShK[2-35, Q16K] were constructed using standard PCR technology. The ShK[2-35] or ShK[2-35, Q16K] and the 10 amino acid linker portion of the molecule were generated in a PCR reaction using the original Fc-2xL-ShK[2-35] in pcDNA3.1(+)CMVi as a template (see Sullivan et al., WO 2008/088422 A2, Example 2, FIGS. 15A-B therein). The ShK[1-35] was generated in a PCR reaction using the original Fc-2xL-ShK[1-35] in pcDNA3.1(+)CMVi as a template (Sullivan et al., WO 2008/088422 A2, Example 1, FIGS. 14A-B therein). These ShK constructs have the following modified VH21 Signal peptide amino acid sequence of MEWSWVFLFFLSVTTGVHS//SEQ ID NO:2 generated from a pSelexis-Vh21-hIgG2-Fc template with the following oligos:

```
                                             (SEQ ID NO: 3)
5'- CAT GAA TTC CCC ACC ATG GAA TGG AGC

TGG -3';
and
                                             (SEQ ID NO: 4)
5'- CA CGG TGG GCA CTC GAC TTT GCG CTC

GGA GTG GAC ACC -3'.
```

Wild Type ShK[2-35] with N-terminal linker extension (amino acid sequence GGGGSGGGGSSCIDTIPK-SRCTAFQCKHSMKYRLSFCRKTCGTC//SEQ ID NO:6) was encoded by the DNA sequence below:

```
                                             SEQ ID NO: 5
GGAGGAGGAGGATCCGGAGGAGGAGGAAGCAGCTGCATCGACACCATC

CCCAAGAGCCGCTGCACCGCCTTCCAGTGCAAGCACAGCATGAAGTACC

GCCTGAGCTTCTGCCGCAAGACCTGCGGCACCTGC//.
```

A fragment containing this coding sequence (SEQ ID NO:5) was generated using the oligos below (SEQ ID NO:7 and SEQ ID NO:8)- and the original Fc-L10-ShK[2-35] in pcDNA3.1(+)CMVi as a template (Sullivan et al., WO 2008/088422 A2, Example 2, FIGS. 15A-B therein, incorporated by reference):

```
                                          (SEQ ID NO: 7)
5'-GTC CAC TCC GAG CGC AAA GTC GAG TGC CCA

CCG TGC C-3';
and (SEQ ID NO: 8)
5'- TCC TCC TCC TTT ACC CGG AGA CAG GGA

GAG -3'//.
```

Mutant ShK[2-35, Q16K] was generated using site directed mutagenesis with Stratagene's QuikChange Multi site-Directed Mutagenesis kit cat#200531 per the manufacterer's instruction. Oligos used to generate the mutagenesis were:

```
                                          (SEQ ID NO: 9)
5'-GCT GCA CCG CCT TCA AGT GCA AGC ACA GC 3';
and (SEQ ID NO: 10)
5'- GCT GTG CTT GCA CTT GAA GGC GGT GCA

GC -3';
``` and using the original Fc-L10-ShK[2-35] in pcDNA3.1(+) CMVi as a template (Sullivan et al., WO 2008/088422 A2, Example 2, FIGS. 15A-B therein) resulting in the DNA coding sequence

```
                                         (SEQ ID NO: 11)
Ggaggaggaggatccggaggaggaggaagcagctgcatcgacaccatccccaagagccgctgcacc gccttcaagtgcaagcacagcatgaagtaccgcctgagcttctgccgcaagacctgcggcacctgc//
``` which encodes the amino acid sequence Shk(2-35, K16) with a N-terminal linker extension:

```
                                         SEQ ID NO: 12)
ggggsggggsscidtipksrctafkckhsmkyrlsfcrktcgtc//.
```

ShK[1-35]WT fragment was generated using the original Fc-2xL-ShK[1-35] in pcDNA3.1(+)CMVi as a template (Sullivan et al., WO 2008/088422 A2, Example 1, FIGS. 14A-B therein) and oligos:

```
                                          (SEQ ID NO: 7)
5'-GTC CAC TCC GAG CGC AAA GTC GAG TGC CCA

CCG TGC C-3';
and (SEQ ID NO: 8)
5'- TCC TCC TCC TTT ACC CGG AGA CAG GGA

GAG -3'.
```

The IgG2Fc region was generated using oligos:

```
                                         (SEQ ID NO: 13)
5'-CCG GGT AAA GGA GGA GGA GGA TCC GGA G-3';
and (SEQ ID NO: 14)
5'- CAT GCG GCC GCT CAT TAG CAG GTG -3',
``` and the pSelexis Vh21-hIgG2-Fc template resulting in a fragment containing the following DNA coding sequence:

```
                                         SEQ ID NO: 15
gcaccacctgtggcaggaccgtcagtcttcctcttcccccaaaacccaaggacaccctcatgatctcccg gaccctgaggtcacgtgcgtggtggtggacgtgagccacgaagaccccgaggtccagttcaactggtacgtggacgg cgtggaggtgcataatgccaagacaaagccacgggaggagcagttcaacagcacgttccgtgtggtcagcgtcctcac cgttgtgcaccaggactggctgaacggcaaggagtacaagtgcaaggtctccaacaaaggcctcccagcccccatcga gaaaaccatctccaaaaccaaagggcagccccgagaaccacaggtgtacaccctgcccccatcccgggaggagatga ccaagaaccaggtcagcctgacctgcctggtcaaaggcttctaccccagcgacatcgccgtggagtgggagagcaatg ggcagccggagaacaactacaagaccacacctcccatgctggactccgacggctccttcttcctctacagcaagctcacc gtggacaagagcaggtggcagcaggggaacgtcttctcatgctccgtgatgcatgaggctctgcacaaccactacacgc agaagagcctctccctgtctccgggtaaa //,
``` which encodes the amino acid sequence (SEQ ID NO: 16)
appvagpsvflfppkpkdtlmisrtpevtcvvvdvshedpevqfnwyvdgvevhnaktkpreeqfnstfrvvsylt vvhqdwlngkeykckvsnkglpapiektisktkgqprepqvytlppsreemtknqvsltclvkgfypsdiavewes ngqpennykttppmldsdgsfflyskltvdksrwqqgnvfscsvmhealhnhytqkslslspgk.

The PCR fragments were generated and the products were run out on a gel. After gel purification, the DNA fragments were put together in a PCR tube and sewn together with outside primers:

(SEQ ID NO: 3)
5'- CAT GAA TTC CCC ACC ATG GAA TGG AGC TGG -3';
and (SEQ ID NO: 14)
5'- CAT GCG GCC GCT CAT TAG CAG GTG -3'.

The PCR products were digested with EcoRI and NotI (Roche) restriction enzymes and agarose gel purified by Gel Purification Kit. At the same time, the pTT14 vector (an Amgen vector containing a CMV promoter, Poly A tail and a Puromycin resistance gene) was digested with EcoRI and NotI restriction enzymes and the large fragment was purified by Gel Purification Kit. Each purified PCR product was ligated to the large fragment and transformed into OneShot Top10 bacteria. DNAs from transformed bacterial colonies were isolated and subjected to EcoRI and NotI restriction enzyme digestions and resolved on a one percent agarose gel. DNAs resulting in an expected pattern were submitted for sequencing. Although, analysis of several sequences of clones yielded a 100% percent match with the above sequence, only one clone of each construct was selected for large scaled plasmid purification. The final pTT14-VH1SP-IgG2-Fc construct encoded IgG2-Fc-L10-ShK(2-35) fusion polypeptide having the following sequence:

(SEQ ID NO: 17)
Mewswvflfflsvttgvhserkvecppcpappvagpsvflfppkpkdtlmisrtpevtcvvvdvshe dpevqfnwyvdgvevhnaktkpreeqfnstfrvvsyltvvhqdwlngkeykckvsnkglpapiektisktkgqpr epqvytlppsreemtknqvsltclvkgfypsdiavewesngqpennykttppmldsdgsfflyskltvdksrwqqg nvfscsvmhealhnhytqkslslspgkggggsggggsscidtipksrctafqckhsmkyrlsfcrktcgtc//.

The pTT14-VH21SP-IgG2-Fc-L10-ShK(2-35,Q16K) construct encoded a IgG2-Fc L10-ShK(2-35, Q16K) fusion polypeptide sequence:

SEQ ID NO: 18
Mewswvflfflsvttgvhserkvecppcpappvagpsvflfppkpkdtlmisrtpevtcvvvdvshe dpevqfnwyvdgvevhnaktkpreeqfnstfrvvsvltvvhqdwlngkeykckvsnkglpapiektisktkgqpr epqvytlppsreemtknqvsltclvkgfypsdiavewesngqpennykttppmldsdgsfflyskltvdksrwqqg nvfscsvmhealhnhytqkslslspgkggggsggggsscidtipksrctafKckhsmkyrlsfcrktcgtc//;

and pTT14-VH21SP-IgG2-Fc ShK1-35 construct contained a coding sequence for IgG2 Fc-L10-ShK(1-35) fusion polypeptide having the following sequence:

(SEQ ID NO: 19)
mewswvflfflsvttgvhserkvecppcpappvagpsvflfppkpkdtlmisrtpevtcvvvdvshe dpevqfnwyvdgvevhnaktkpreeqfnstfrvvsyltvvhqdwlngkeykckvsnkglpapiektisktkgqpr epqvytlppsreemtknqvsltclvkgfypsdiavewesngqpennykttppmldsdgsfflyskltvdksrwqqg nvfscsvmhealhnhytqkslslspgkggggsggggsrscidtipksrctafqckhsmkyrlsfcrktcgtc//.

Generating the VH21SP-IgG2-Fc-only construct in pYD16 (an Amgen vector containing a CMV promoter, Poly A tail and a Hygromycin resistance gene) occurred as follows: The VH21 signal peptide was generated using the following oligos:

(SEQ ID NO: 20)
5'-CAT AAG CTT CCC ACC ATG GAA TGG AGC TGG-3';
and (SEQ ID NO: 4)
5'-CA CGG TGG GCA CTC GAC TTT GCG CTC GGA GTG GAC ACC-3', and using the pSelexis template as noted above.

The Fc region was generated using the pSelexis template described above and following oligos:

(SEQ ID NO: 7)
5'-GTC CAC TCC GAG CGC AAA GTC GAG TGC CCA CCG

-continued

TGC C-3';
and (SEQ ID NO: 21)
5'-CAT GGA TCC TCA TTT ACC CGG AGA CAG GGA G-3'.

The PCR fragments were gel purified and sewn together in single PCR reaction using outside primers GGT TGA GAG GTG CCA GAT GTC AGG GCT GCA GCA GCG GC//SEQ ID NO:391 and CAG CTG CAC CTG ACC ACC ACC TCC ACC GCT ATG CTG AGC GCG//SEQ ID NO:392. The resulting PCR fragment was gel purified, and digested by HindIII and BamHI. Concurrently, pYD16 vector (an Amgen vector containing a CMV promoter, Poly A tail and a Hygromycin resistance gene) was also cut by HindIII and BamHI and the large vector fragment was purified by Qiagen's Gel Purification Kit. The purified PCR product was ligated to the large fragment and transformed into OneShot Top10 bacteria. DNA from transformed bacterial colonies were isolated and subjected to HindIII and BamHI restriction enzyme digestions and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final pYD16-VH21SP-IgG2-Fc construct encoded human IgG2-Fc (SEQ ID NO:1 above).

IgG2-Fc ShK[1-35, Q16K] Mammalian Expression.

Using the DNA pTT5-aKLH120.6-VK1SP-IgG2-HC-L10-ShK[1-35, Q16K] construct, the fragment containing the DNA coding sequence (SEQ ID NO: 22)
ggatccggaggaggaggaagccgcagctgcatcgacaccatccccaagagccgctgcaccgccttca agtgcaagcacagcatgaagtaccgcctgagcttctgccgcaagacctgcggcacctgctaatgagcggccgctcgag gccggcaaggccggatcc// was cut out using BamHI/BamHI. This coding sequence (SEQ ID NO:23) encodes ShK(1-35, Q16K) with an N-terminal linker sequence:

(SEQ ID NO: 23)
GSGGGGSRSCIDTIPKSRCTAFKCKHSMKYRLSFCRKTCGTC//.

At the same time, pTT14-hIgG2-Fc-ShK[1-35]WT construct, was also digested by BamHI/BamHI, thereby removing the Shk[1-35] coding region to yield the coding sequence (SEQ ID NO: 24)
Atggaatggagctgggtctttctcttcttcctgtcagtaacgactggtgtccactccgagcgcaaagtcga gtgcccaccgtgcccagcaccacctgtggcaggaccgtcagtcttcctcttcccccaaaacccaaggacaccctcatga tctcccggacccctgaggtcacgtgcgtggtggtggacgtgagccacgaagaccccgaggtccagttcaactggtacgt ggacggcgtggaggtgcataatgccaagacaaagccacgggaggagcagttcaacagcacgttccgtgtggtcagcg tcctcaccgttgtgcaccaggactggctgaacggcaaggagtacaagtgcaaggtctccaacaaaggcctcccagcccc catcgagaaaaccatctccaaaaccaaagggcagccccgagaaccacaggtgtacaccctgcccccatcccgggagg agatgaccaagaaccaggtcagcctgacctgcctggtcaaaggcttctacccagcgacatcgccgtggagtgggaga gcaatgggcagccggagaacaactacaagaccacacctcccatgctggactccgacggctccttcttcctctacagcaa

```
gctcaccgtggacaagagcaggtggcagcaggggaacgtatctcatgctccgtgatgcatgaggctctgcacaaccac tacacgcagaagagcctctccctgtctccgggtaaaggaggagga//,
``` encoding the amino acid sequence (SEQ ID NO: 25)
```
mewswvflfflsvttgvhserkvecppcpappvagpsvflfppkpkdtlmisrtpevtcvvvdvshedpevqfnw yvdgvevhnaktkpreeqfnstfrvvsyltvvhqdwlngkeykckvsnkglpapiektisktkgqprepqvytlpps reemtknqvsltclvkgfypsdiavewesngqpennykttppmldsdgsfflyskltvdksrwqqgnvfscsvmh ealhnhytqkslslspgkggg//.
```

The pTT14-hIgG2-Fc vector with the ShK removed was treated with Calf Intestine Phosphatase (CIP) to remove the 5' Phosphate group and Phenol/Chloroform extracted to prevent religation of the vector upon itself. The insert ShK[1-35, Q16K] fragment was gel purified away from its vector and cleaned up with Qiagen Gel Purification Kit. The purified insert was ligated to the large vector fragment and transformed into OneShot Top10 bacteria. DNAs from transformed bacterial colonies were isolated and subjected to BamHI restriction enzyme digestion and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final pTT14-IgG2-Fc-ShK[1-35, Q16K] construct encoded the following IgG2 Fc-L10-ShK (1-35, Q16K) fusion protein sequence:

(SEQ ID NO: 26)

mewswvflfflsvttgvhserkvecppcpappvagpsvflfppkpkdtlmisrtpevtcvvvdvshe dpevqfnwyvdgvevhnaktkpreeqfnstfrvvsyltvvhqdwlngkeykckvsnkglpapiektisktkgqpr epqvytlppsreemtknqvsltclvkgfypsdiavewesngqpennykttppmldsdgsfflyskltvdksrwqqg nvfscsvmhealhnhytqkslslspgkggggsggggsrscidtipksrctafkckhsmkyrlsfcrktcgtc//.

The amino acid sequence for IgG2 Fc-L10-ShK(1-35) is: -

(SEQ ID NO: 30)

mewswvflfflsvttgvhserkvecppcpappvagpsvflfppkpkdtlmisrtpevtcvvvdvshe dpevqfnwyvdgvevhnaktkpreeqfnstfrvvsyltvvhqdwlngkeykckvsnkglpapiektisktkgqpr epqvytlppsreemtknqvsltclvkgfypsdiavewesngqpennykttppmldsdgsfflyskltvdksrwqqg nvfscsvmhealhnhytqkslslspgkggggsggggsrscidtipksrctafqckhsmkyrlsfcrktcgtC//.

The desired aKLH IgG2/Fc-ShK product contained one copy of each of components (a)-(c), immediately above, configured as in FIG. 1E. Because of this, the ratio was 1:1:1. This product can be described as half antibody and half Fc fusion ("hemibody"), coupled together at the Fc domain. Additional peptide assemblies that had to be removed from the culture were the aKLH Ab and the Fc-ShK homodimer.

The ShK[1-35]WT fragment was generated using the original Fc-L10-ShK[1-35] in pcDNA3.1(+)CMVi as a template (described in Example 1, FIG. 14A-14B in Sullivan et al., Toxin Peptide Therapeutic Agents, PCT/US2007/022831, published as WO 2008/088422, which is incorporated herein by reference in its entirety) and the oligos:

(SEQ ID NO: 47)

5'-TCC CTG TCT CCG GGT GGA GGA GGA GGA TCC GGA

G-3';

and (SEQ ID NO: 14)

5'-CAT GCG GCC GCT CAT TAG CAG GTG-3'.

The PCR products were run on a 1% agarose gel. The bands were punched for an agarose plug and the plugs were placed in a fresh PCR reaction tube. The agarose plugs were then amplified by PCR using the outside primers SEQ ID NO:357 and SEQ ID NO:330. The PCR product was then digested by XbaI and NotI and PCR clean up kit (Qiagen) purified. At the same time, pTT5 Vector (an Amgen vector containing a CMV promoter and Poly A tail) was cut by XbaI and NotI. The pTT5 vector was run out on a 1% agarose gel and the larger fragment was cut out and gel purified by Qiagen's Gel Purification Kit. The purified PCR product was ligated to the large vector fragment and transformed into OneShot Top10 bacteria. DNAs from transformed bacterial colonies were isolated and subjected to XbaI and NotI restriction enzyme digestions and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final pTT5-aKLH 120.6-VK1SP-IgG2-HC-L10-ShK[1-35] construct encoded an IgG2-HC-L10-ShK[1-35] fusion polypeptide with the amino acid sequence:

(SEQ ID NO: 48)
Mdmrvpaqllglllllwlrgarcqvqlvqsgaevkkpgasvkvsckasgytftgyhmhwyrqapgq glewmgwinpnsggtnyaqkfqgrytmtrdtsistaymelsrlrsddtavyycardrgsyywfdpwgqgtlvtvss astkgpsvfplapcsrstsestaalgclykdyfpepvtvswnsgaltsgvhdpavlqssglyslssvvtvpssnfgtqty tcnvdhkpsntkvdktverkccvecppcpappvagpsvflfppkpkdtlmisrtpevtcvvvdvshedpevqthw yvdgvevhnaktkpreeqfnstfrvvsyltvvhqdwlngkeykckvsnkglpapiektisktkgqprepqvytlpps reemtknqvsltclvkgfypsdiavewesngqpennykttppmldsdgsfflyskltvdksrwqqgnvfscsvmh ealhnhytqkslslspgggggsggggsrscidtipksrctafqckhsmkyrlsfcrktcgtc//.

To generate the ShK[1-35, Q16K] mutant version of this construct, site-directed mutagenesis was performed using the Stratagene Quikchange Multi site Directed Mutagenesis Kit (Cat#200531), per manufacturer's instructions, and oligos:

(SEQ ID NO: 9)
5'-GCT GCA CCG CCT TCA AGT GCA AGC ACA GC 3';
and (SEQ ID NO: 10)
5'-GCT GTG CTT GCA CTT GAA GGC GGT GCA GC-3'.

The final construct pTT5-aKLH120.6-VK1SP-IgG2-HC-L10-ShK[1-35, Q16K] encoded IgG2-HC-L10-ShK[1-35, Q16K] fusion polypeptide with the following amino acid sequence:

(SEQ ID NO: 49)
Mdmrvpaqllglllllwlrgarcqvqlvqsgaevkkpgasvkvsckasgytftgyhmhwyrqapgq glewmgwinpnsggtnyaqkfqgrvtmtrdtsistaymelsrlrsddtavyycardrgsyywfdpwgqgtlvtvss astkgpsvfplapcsrstsestaalgclvkdyfpepvtvswnsgaltsgvhtfpavlqssglyslssvvtvpssnfgtqty tcnvdhkpsntkvdktverkccvecppcpappvagpsvflfppkpkdtlmisrtpevtcvvvdvshedpevqfnw yvdgvevhnaktkpreeqfnstfrvvsyltvvhqdwingkeykckvsnkglpapiektisktkgqprepqvytlpps reemtknqvsltclvkgfypsdiavewesngqpennykttppmldsdgsfflyskltvdksrwqqgnvfscsvmh ealhnhytqkslslspgggggsggggsrscidtipksrctafkckhsmkyrlsfcrktcgtc//.

aKLH-IgG2 Heavy Chain-L10-ShK[2-35, Q16K] Mammalian Expression.

Using DNA construct pTT5-aKLH 120.6-VK1SP-IgG2-HC-L10-ShK[1-35] as the vector, the ShK[1-35] was cut out using BamHI/BamHI. The vector fragment from pTT5-aKLH 120.6-VK1SP-IgG2-HC without ShK[1-35] contained the coding sequence:

(SEQ ID NO: 50)
atggacatgagggtgcccgctcagctcctggggctcctgctgctgtggctgagaggtgccagatgtcag gtgcagctggtgcagtctggggctgaggtgaagaagcctggggcctcagtgaaggtctcctgcaaggcttctggataca ccttcaccggctaccacatgcactgggtgcgacaggcccctggacaagggcttgagtggatgggatggatcaaccctaa cagtggtggcacaaactatgcacagaagtttcagggcagggtcaccatgaccagggacacgtccatcagcacagccta catggagctgagcaggctgagatctgacgacacggccgtgtattactgtgcgagagatcgtgggagctactactggttcg acccctggggccagggaaccctggtcaccgtctcctcagcctccaccaagggcccatcggtcttccccctggcgccctg ctccaggagcacctccgagagcacagcggccctgggctgcctggtcaaggactacttccccgaaccggtgacggtgtc -continued

```
gtggaactcaggcgctctgaccagcggcgtgcacaccttcccagctgtcctacagtcctcaggactctactccctcagca gcgtggtgaccgtgccctccagcaacttcggcacccagacctacacctgcaacgtagatcacaagcccagcaacacca aggtggacaagacagttgagcgcaaatgttgtgtcgagtgcccaccgtgcccagcaccacctgtggcaggaccgtcagt cttcctcttccccccaaaacccaaggacaccctcatgatctcccggacccctgaggtcacgtgcgtggtggtggacgtga gccacgaagaccccgaggtccagttcaactggtacgtggacggcgtggaggtgcataatgccaagacaaagccacgg gaggagcagttcaacagcacgttccgtgtggtcagcgtcctcaccgttgtgcaccaggactggctgaacggcaaggagt acaagtgcaaggtctccaacaaaggcctcccagcccccatcgagaaaaccatctccaaaaccaaagggcagccccga gaaccacaggtgtacaccctgcccccatcccgggaggagatgaccaagaaccaggtcagcctgacctgcctggtcaaa ggcttctaccccagcgacatcgccgtggagtgggagagcaatgggcagccggagaacaactacaagaccacacctcc catgctggactccgacggctccttcttcctctacagcaagctcaccgtggacaagagcaggtggcagcaggggaacgtc ttctcatgctccgtgatgcatgaggctctgcacaaccactacacgcagaagagcctctccctgtctccgggtggaggagg a//,
``` encoding the amino acid sequence (SEQ ID NO: 51)
```
mdmrvpaqllglllllwlrgarcqvqlvqsgaevkkpgasvkvsckasgytftgyhmhwyrqapgq glewmgwinpnsggtnyaqkfqgrvtmtrdtsistaymelsrlrsddtavyycardrgsyywfdpwgqgtlvtvss astkgpsvfplapcsrstsestaalgclvkdyfpepvtvswnsgaltsgvhtfpavlqssglyslssvvtvpssnfgtqty tcnvdhkpsntkvdktverkccvecppcpappvagpsvflfppkpkdtlmisrtpevtcvvvdvshedpevqfnw yvdgvevhnaktkpreeqfnstfrvvsyltvvhqdwlngkeykckvsnkglpapiektisktkgqprepqvytlpps reemtknqvsltclvkgfypsdiavewesngqpennykttppmldsdgsfflyskltvdksrwqqgnvfscsvmh ealhnhytqkslslspgggg//.
```

The vector fragment was then treated with Calf Intestine Phosphatase (CIP) to remove the 5' Phosphate group and Phenol/Chloroform extracted to prevent religation of the vector upon itself. The insert came from pTT14-VH21SP-IgG2-Fc-ShK[2-35, Q16K] encoding IgG2 Fc-L10-ShK(2-35, Q16K):

(SEQ ID NO: 18)
```
mewswvflfflsvttgvhserkvecppcpappvagpsvflfppkpkdtlmisrtpevtcvvvdvshe dpevqfnwpidgvevhnaktkpreeqfnstfrvvsyltvvhqdwingkeykekvsnkglpapiektisktkgqpr epqvytlppsreemtknqvsltclvkgfypsdiavewesngqpennykttppmldsdgsfflyskltvdksrwqqg nvfscsvmhealhnhytqkslslspgkggggsggggscidtipksrctafkckhsmkyrlsfcrktcgtc//,
``` and the insert was also digested out using BamHI/BamHI. The insert ShK[2-35, Q16K] fragment was gel purified away from its vector and cleaned up with Qiagen Gel Purification Kit. A purified DNA insert containing the coding sequence (SEQ ID NO: 52)
```
gga tcc gga gga gga gga agc agc tgc atc gac acc atc ccc aag agc cgc tgc acc gcc ttc aag tgc aag cac agc atg aag tac cgc ctg agc ttc tgc cgc aag acc tgc ggc acc tgc taa tga //,
``` encoding the amino acid sequence

GSGGGGSSCIDTIPKSRCTAFKCKHSMKYRLSFCRKTCGTC, (SEQ ID NO: 53)

was ligated to the large vector fragment and transformed into OneShot Top10 bacteria. DNAs from transformed bacterial colonies were isolated and subjected to BamHI restriction enzyme digestion and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final construct pTT5-aKLH-IgG2 HC-L10-ShK[2-35,Q16K] encoded an IgG2 HC-L10-ShK [2-35,Q16K] fusion polypeptide:

(SEQ ID NO: 54)

Mdmrvpaqllglllllwlrgarcqvqlvqsgaevkkpgasvkvsckasgytftgyhmhwyrqapgq glewmgwinpnsggtnyaqkfqgrvtmtrdtsistaymelsrlrsddtavyycardrgsyywfdpwgqgtlvtvss astkgpsvfplapcsrstsestaalgclykdyfpepvtvswnsgaltsgvhtfpavlqssglyslssvvtvpssnfgtqty tcnvdhkpsntkvdktverkccvecppcpappvagpsvflfppkpkdtlmisrtpevtcvvvdvshedpevqthw yvdgvevhnaktkpreeqfnstfrvvsyltvvhqdwlngkeykekvsnkglpapiektisktkgqprepqvytlpps reemtknqvsltelvkgfypsdiavewesngqpennykttppmldsdgsfflyskltvdksrwqqgnvfscsvmh ealhnhytqkslslspgggggsgggggscidtipksrctafkckhsmkyrlsfcrktcgtc//.

VH21SP-N-terminus ShK[1-35] Wild Type-IgG1-Fc Mammalian Expression.

A DNA sequence coding for a monomer of the Kv1.3 inhibitor peptide ShK[1-35] fused in-frame to the N-terminal Fc region of human IgG1 was constructed as described below.

Figure 42A:
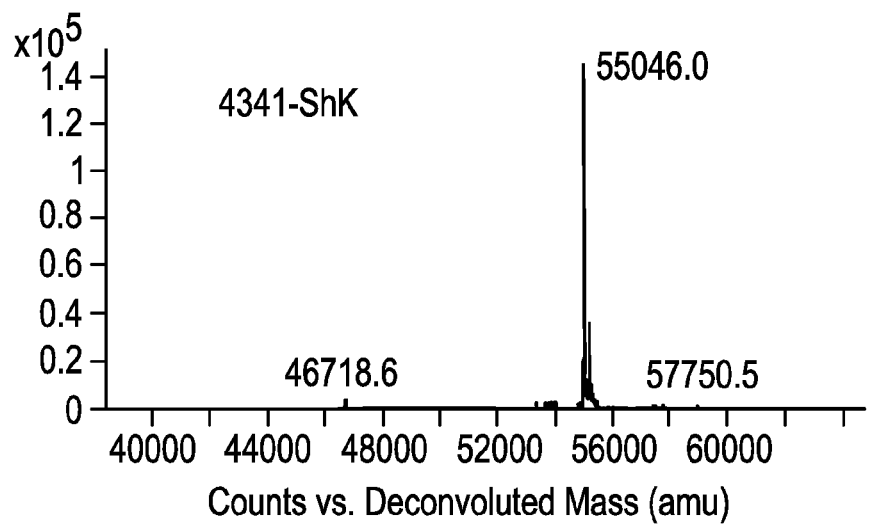
FIGS. 42A-C shows reduced heavy chain LC-MS analysis of the final 4341-ShK (1-35, Q16K) (FIG. 42A), 4341-FGF21 (FIG. 42B), and 16435-FGF21 (FIG. 42C) samples. The product was chromatographed through a Waters MassPREP micro desalting column using a Waters ACQUITY UPLC system. The column was set at 80° C. and the protein eluted using a linear gradient of increasing acetonitrile concentration in 0.1% formic acid. The column effluent was directed into a Waters LCT Premier ESI-TOF mass spectrometer for mass analysis. The instrument was run in the positive V mode. The capillary voltage was set at 3,200 V and the cone voltage at 80 V. The mass spectrum was acquired from 800 to 3000 m/z and deconvoluted using the MaxEnt1 software provided by the instrument manufacturer.
Figure 42B:
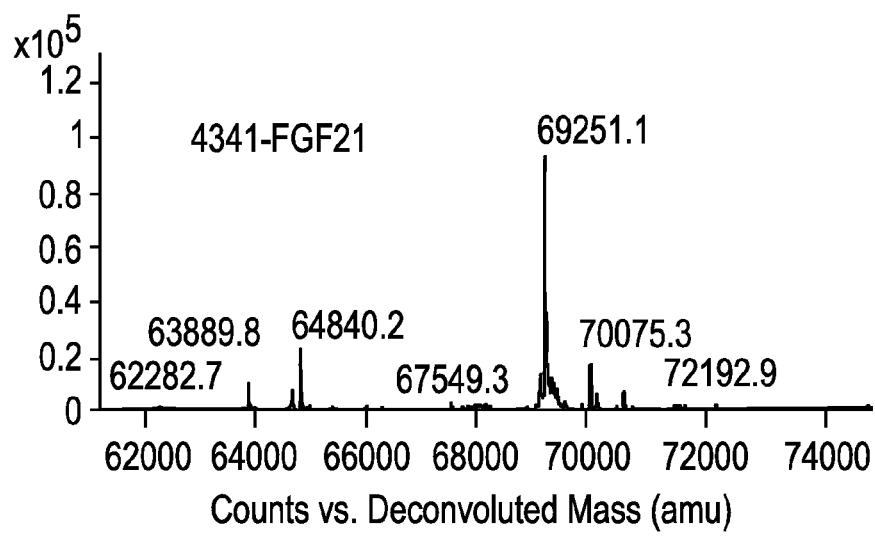
Figure 42C:
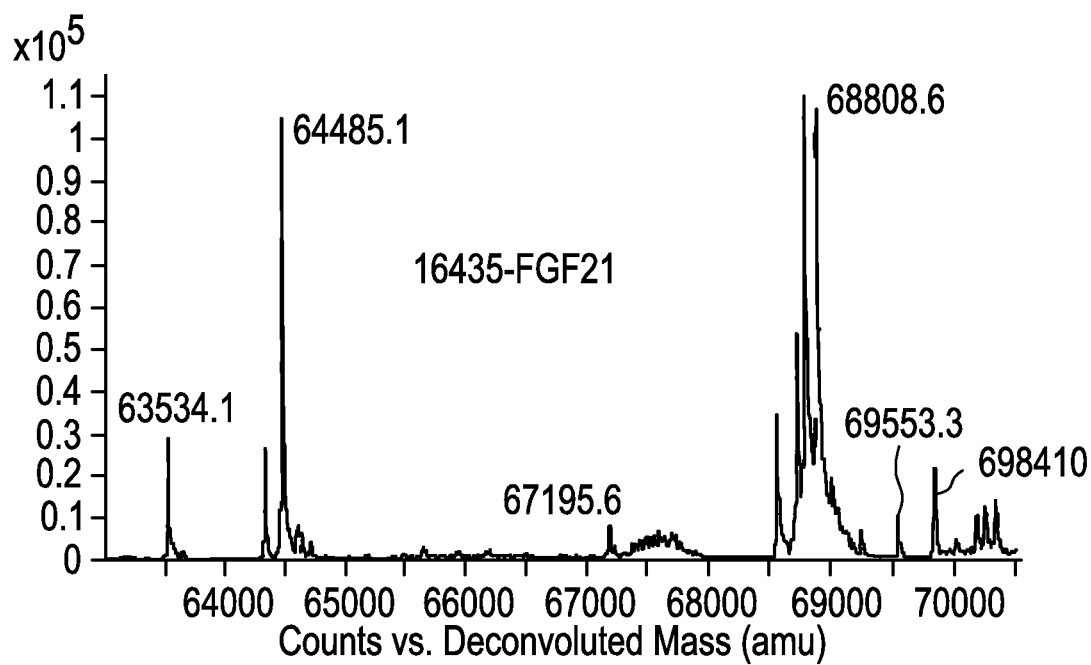

For construction of VH21 SP-ShK(1-35)-L10-IgG1 Fc expression vector, a PCR strategy was employed to generate the VH21 signal peptide ShK(1-35) gene linked to a four glycine and one serine amino acid flanked by HindIII and BamHI restriction sites and a four glycine and one serine amino acid linked to IgG1 Fc fragment flanked by BamHI and NotI restriction sites was generated in a PCR reaction using the Fc-L10-OSK1 in pcDNA3.1(+)CMVi as a template (described in Example 41 and FIGS. 42A-B of Sullivan et al., WO 2008/088422A2, incorporated by reference).

To generate VH21 SP-ShK(1-35)-G₄S, two oligos with the sequence as depicted below were used in a PCR reaction with PfuTurbo HotStart DNA polymerase (Stratagene) at 95° C.-30 sec, 55° C.-30 sec, 75° C.-45 sec for 35 cycles; HindIII (aagctt) and BamHI (ggatcc) restriction sites are underlined:

Forward primer:

(SEQ ID NO: 55)
tgcagaagcttctagaccaccatggaatggagctgggtctttctcttcttcctgtcagtaacgactggtgtccactcccgcag ctgcatcgacaccatccccaagagccgctgcaccgccttccagt//;
and Reverse primer:

(SEQ ID NO: 56)
Ctccggatcctcctcctccgcaggtgccgcaggtcttgcggcagaagctcaggcggtacttcatgctgtg cttgcactggaaggcggtgcagcggctcttggggatggtgtcgat//.

The resulting PCR products were resolved as the 202 bp bands on a two percent agarose gel. The 202 bp PCR product was purified using PCR Purification Kit (Qiagen), then digested with HindIII and BamHI (Roche) restriction enzymes, and agarose gel was purified by Gel Extraction Kit (Qiagen).

To generate G₄S-IgG1 Fc, two oligos with the sequence as depicted below were used in a PCR reaction with PfuTurbo HotStart DNA polymerase (Stratagene) at 95° C.-30 sec, 55° C.-30 sec, 75° C.-1 min for 30 cycles; BamHI (ggatcc) and NotI (gcggccgc) restriction sites are underlined:

Forward primer:

(SEQ ID NO: 57)
gtaggatccggaggaggaggaagcgacaaaactcacac//;
and

Reverse primer:

(SEQ ID NO: 58)
Cgagcggccgcttactatttacccggagacaggga//.

The resulting PCR products were resolved as the 721-bp bands on a one percent agarose gel. The 721-bp PCR product was purified using PCR Purification Kit (Qiagen), then digested with BamHI and NotI (Roche) restriction enzymes, and agarose gel was purified by Gel Extraction Kit (Qiagen).

The pcDNA3.1(+)CMVi-Fc-L10-OSK1 vector was digested with BamHI and NotI restriction enzymes and the large fragment was purified by Gel Extraction Kit. The gel purified 4GS-IgG1 Fc fragment was ligated to the purified large fragment and transformed into One Shot® Top10 (Invitrogen) to create a pCMVi-Fc-L10-IgG1 Fc vector. Subsequently, pCMVi-Fc-L10-IgG1 Fc vector was digested with HindIII and BamHI restriction enzymes and the large fragment was purified by Gel Extraction Kit. The gel purified VH21 SP-ShK(1-35)-4GS fragment was ligated to the purified large fragment and transformed into One Shot® Top10 (Invitrogen) resulting in a pCMV1-VH21 SP-ShK(1-35)-L10-IgG1 Fc construct. DNAs from transformed bacterial colonies were isolated and digested with BamHI and NotI restriction enzymes and resolved on a one percent agarose gel. DNAs resulting in an expected pattern were submitted for sequencing. Although, analysis of several sequences of clones yielded a 100% percent match with the above sequences, only one clone from each gene was selected for large scaled plasmid purification. The DNA from VH21 SP-ShK(1-35)-L10-IgG1 Fc in pCMVi vector was resequenced to confirm the Fc and linker regions and the sequence was 100% identical to the above sequence. Fragment VH21 SP-ShK(1-35)-L10-IgG1 Fc contained the coding sequence (SEQ ID NO: 59)

```
atggaatggagctgggtctttctcttcttcctgtcagtaacgactggtgtccactcccgcagctgcatcgaca ccatccccaagagccgctgcaccgccttccagtgcaagcacagcatgaagtaccgcctgagcttctgccgcaagacctg cggcacctgcggaggaggaggatccggaggaggaggaagcgacaaaactcacacatgcccaccgtgcccagcacct gaactctggggggaccgtcagtatcctcttccccccaaaacccaaggacaccctcatgatctcccggacccctgaggt cacatgcgtggtggtggacgtgagccacgaagaccctgaggtcaagttcaactggtacgtggacggcgtggaggtgca taatgccaagacaaagccgcgggaggagcagtacaacagcacgtaccgtgtggtcagcgtcctcaccgtcctgcacca ggactggctgaatggcaaggagtacaagtgcaaggtctccaacaaagcccctcccagccccatcgagaaaaccatctc caaagccaaagggcagccccgagaaccacaggtgtacaccctgcccccatcccgggatgagctgaccaagaaccag gtcagcctgacctgcctggtcaaaggcttctatcccagcgacatcgccgtggagtgggagagcaatgggcagccggag aacaactacaagaccacgcctcccgtgctggactccgacggctccttcttcctctacagcaagctcaccgtggacaagag caggtggcagcaggggaacgtcttctcatgctccgtgatgcatgaggctctgcacaaccactacacgcagaagagcctc tccctgtctccgggtaaatagtaa//,
``` encoding VH21 SP-ShK(1-35)-L10-IgG1 Fc amino acid sequence (SEQ ID NO: 60)

```
mewswvflfflsyttgvhsrscidtipksrctafqckhsmkyrlsfcrktcgtcggggsggggsdkthtcppcpapell ggpsvflfppkpkdtlmisrtpevtcvvvdvshedpvevkfnwyvdgvevhnaktkpreeqynstyrvvsvltvlhq dwlngkeykckvsnkalpapiektiskakgqprepqvytlppsrdeltknqvsltclvkgfypsdiavewesngqpe nnykttppvldsdgsfflyskltvdksrwqqgnvfscsvmhealhnhytqkslslspgkll.
```

Mammalian Expression of N-terminus ShK[1-35, Q16K]-aKLH HC; and N-terminus ShK[1-35Q16K]-aKLH LC.

Using a construct encoding N-terminus ShK[1-35]Wild Type-L10-IgG1-Fc, site directed mutagenesis was performed using the following oligos to produce a Q16K mutation in the ShK region:

(SEQ ID NO: 9)

```
5'-GCT GCA CCG CCT TCA AGT GCA AGC ACA GC-37//;
``` and (SEQ ID NO: 10)

```
5'-GCT GTG CTT GCA CTT GAA GGC GGT GCA GC-3'.
```

The Stratagene QuikChange Multi Site Directed Mutagenesis Kit was used according to the manufacturer's instructions. The final construct for pCMVi-N-terminus-ShK[1-35Q16K]-L10-IgG1-Fc encoded the following Signal peptide (VH21 SP)-ShK[1-35, Q16K]-L10-IgG1-Fc fusion polypeptide:

(SEQ ID NO: 61)
Mewswvflfflsvttgvhsrscidtipksrctafkckhsmkyrlsfcrktcgtcggggsggggsdktht cppcpapellggpsvflfppkpkdtlmisrtpevtcvvvdvshedpevkfnwyvdgvevhnaktkpreeqynstyr vvsyltvlhqdwingkeykekvsnkalpapiektiskakgqprepqvytlppsrdeltknqvsltclvkgfypsdiav ewesngqpennykttppvldsdgsfflyskltvdksrwqqgnvfscsvmhealhnhytqkslslspgk//.

To generate the N-terminus ShK[1-35, Q16K]-aKLH HC construct, a PCR product containing the Signal peptide-ShK[1-35Q16K]-L10 linker was produced using the following oligos:

(SEQ ID NO: 62)
5'-CAT TCT AGA CCA CCA TGG AAT GG-3';

(SEQ ID NO: 63)
5'-CAG CTG CAC CTG GCT TCC TCC TCC TCC GG-3';

and template pCMVi-N-terminus-ShK[1-35, Q16K]-L10-IgG1-Fc, resulted in a fragment containing the coding sequence (SEQ ID NO: 64)
atggaatggagagggtctttctcttcttcctgtcagtaacgactggtgtccactcccgcagctgcatcgacaccatccccaa gagccgctgcaccgccttcaagtgcaagcacagcatgaagtaccgcctgagcttctgccgcaagacctgcggcacctg cggaggaggaggatccggaggaggaggaagc//, encoding the VH21 SP-ShK(1-35, Q16K)-L10 amino acid sequence (SEQ ID NO: 65)
MEWSWVFLFFLSVTTGVHSRSCIDTIPKSRCTAFKCKHSMKYRLSFCRK

TCGTCGGGGSGGGGS//.

To generate the aKLH-HC fragment, a PCR product was created using oligos:

(SEQ ID NO: 66)
5'-GGA GGA GGA AGC CAG GTG CAG CTG GTG CAG-3';

(SEQ ID NO: 67)
5'-CAT GCG GCC GCT CAT TTA CCC-3';

and template pTT5-aKLH 120.6-HC, resulting in a DNA fragment containing the coding sequence (SEQ ID NO: 68)
caggtgcagctggtgcagtctggggctgaggtgaagaagcctggggcctcagtgaaggtctcctgcaa ggcttctggatacaccttcaccggctaccacatgcactgggtgcgacaggcccctggacaagggcttgagtggatggga tggatcaaccctaacagtggtggcacaaactatgcacagaagtttcagggcagggtcaccatgaccagggacacgtcca tcagcacagcctacatggagctgagcaggctgagatctgacgacacggccgtgtattactgtgcgagagatcgtgggag ctactactggttcgaccctggggccagggaaccctggtcaccgtctcctcagcctccaccaagggcccatcggtcttcc ccctggcgccctgctccaggagcacctccgagagcacagcggccctgggctgcctggtcaaggactacttccccgaac cggtgacggtgtcgtggaactcaggcgctctgaccagcggcgtgcacaccttcccagctgtcctacagtcctcaggactc -continued

```
tactccctcagcagcgtggtgaccgtgccctccagcaacttcggcacccagacctacacctgcaacgtagatcacaagc ccagcaacaccaaggtggacaagacagttgagcgcaaatgttgtgtcgagtgcccaccgtgcccagcaccacctgtgg caggaccgtcagtcttcctatccccccaaaacccaaggacaccctcatgatctcccggacccctgaggtcacgtgcgtg gtggtggacgtgagccacgaagaccccgaggtccagttcaactggtacgtggacggcgtggaggtgcataatgccaag acaaagccacgggaggagcagttcaacagcacgttccgtgtggtcagcgtcctcaccgttgtgcaccaggactggctga acggcaaggagtacaagtgcaaggtctccaacaaaggcctcccagccccatcgagaaaaccatctccaaaaccaaag ggcagccccgagaaccacaggtgtacaccctgcccccatcccgggaggagatgaccaagaaccaggtcagcctgacc tgcctggtcaaaggcttctaccccagcgacatcgccgtggagtgggagagcaatgggcagccggagaacaactacaag accacacctcccatgctggactccgacggctccttcttcctctacagcaagctcaccgtggacaagagcaggtggcagca ggggaacgtcttctcatgctccgtgatgcatgaggctctgcacaaccactacacgcagaagagcctctccctgtctccgg gtaaatga//,
```

20 encoding amino acid sequence (SEQ ID NO: 69)
qvqlvqsgaevkkpgasvkvsckasgytftgyhmhwvrqapgqglewmgwinpnsggtnyaqkfqgrvtmtr dtsistaymelsrlrsddtavyycardrgsyywfdpwgqgtlvtvssastkgpsvfplapcsrstsestaalgclvkdyf pepvtvswnsgaltsgvhtfpavlqssglyslssvvtvpssnfgtqtytcnvdhkpsntkvdktverkccvecppcpa ppvagpsvflfppkpkdtlmisrtpevtcvvvdvshedpevqthwyvdgvevhnaktkpreeqfnstfrvvsvltv vhqdwlngkeykckvsnkglpapiektisktkgqprepqvytlppsreemtknqvsltclvkgfypsdiavewesn gqpennykttppmldsdgsfflyskltvdksrwqqgnvfscsvmhealhnhytqkslslspgk//.

The two PCR products were run out on a gel and the appropriate sized band was punched for an agarose plug. The agarose plugs were placed in a single new PCR reaction, and the fragments were sewn together using outer most primers (SEQ ID NO:62) and (SEQ ID NO:67). The PCR fragment was cut using XbaI and NotI and cleaned with Qiagen PCR Cleanup Kit. At the same time, pTT5 vector was also cut by XbaI and NotI and gel purified. The purified insert was ligated to the large vector fragment and transformed into OneShot Top10 bacteria. DNAs from transformed bacterial colonies were isolated and subjected to XbaI and NotI restriction enzyme digestions and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final construct pTT5-N-terminus ShK[1-35Q16K]-L10-aKLH120.6-HC encoded a VH21 SP-ShK[1-35, Q16K]-L10-aKLH120.6-HC fusion polypeptide:

Mewswvflfflsvttgvhsrscidtipk-srctafkckhsmkyrlsfcrktcgtcggggsggggsqvqlv qsgaevkkpgas-vkvsckasgytftgyhmhwvrqapgq-glewmgwinpnsggtnyaqkfqgrvtmtrdtsista ymelsrlrsddtavyycardrgsyywfd-pwgqgtlvtvssastkgpsvfplapcsrstsestaalgclvkdyfpepvtv swnsgaltsgvhtfpavlqssglyslss-vvtvpssnfgtqtytcnvdhkpsntkvdktverkccvecppcpappvag psv-flfppkpkdtlmisrtpevtcvvvd-vshedpevqfnwyvdgvevhnaktkpreeqfnstfrvvsvltvvhqdw lngkeykckvsnkglpapiektiskt-kgqprepqvytlppsreemtknqvsltclvkgfypsdiavewesngqpen nykttppmldsdgsfflyskltvdksr-wqqgnvfscsvmhealhnhytqkslslspgk//(SEQ ID NO:70).

Lastly, the N-terminus-ShK[1-35, Q16K]-L10-aKLH120.6 Light Chain (LC) was generated in the same manner as above. A PCR product containing the signal peptide-ShK[1-35, Q16K]-L10 was created using oligos:

(SEQ ID NO: 62)
5'-CAT TCT AGA CCA CCA TGG AAT GG-3';
and (SEQ ID NO: 71)
5'-CAT CTG GAT GTC GCT TCC TCC TCC TCC GG-3';

and template pCMVi-N-terminus-ShK[1-35Q16K]-L10-IgG1-Fc, resulting in a DNA fragment containing the coding sequence (SEQ ID NO: 64)
atggaatggagagggtctttctcttcttcctgtcagtaacgactggtgtccactcccgcagctgcatcgacaccatccccaa gagccgctgcaccgccttcaagtgcaagcacagcatgaagtaccgcctgagcttctgccgcaagacctgggcacctg cggaggaggaggatccggaggaggaggaagc//, encoding the amino acid sequence for a signal peptide (VH21 SP)-ShK(1-35, Q16K)-L10 linker:

(SEQ ID NO: 65)
mewswvflfflsvttgvhsrscidtipksrctafkckhsmkyrlsferktegteggggsggggs//.

Using template and oligos:

(SEQ ID NO: 72)
5'-GGA GGA GGA AGC GAC ATC CAG ATG ACC CAG TC-3';
and (SEQ ID NO: 73)
5'-CAT CTC GAG CGG CCG CTC AAC-3'.

The resulting cloned PCR fragment contained the coding sequence (SEQ ID NO: 74)
atggaatggagctgggtctttctcttcttcctgtcagtaacgactggtgtccactcccgcagctgcatcgacaccatccccaa gagccgctgcaccgccttcaagtgcaagcacagcatgaagtaccgcctgagcttctgccgcaagacctgcggcacctg cggaggaggaggatccggaggaggaggaagcgacatccagatgacccagtctccatcctccctgtctgcatctgtagg agacagagtcaccatcacttgccgggcaagtcagggcattagaaatgatttaggctggtatcagcagaaaccagggaaa gcccctaaacgcctgatctatgctgcatccagtttgcaaagtggggtcccatcaaggttcagcggcagtggatctgggac agaattcactctcacaatcagcagcctgcagcctgaagattttgcaacttattactgtctacagcataatagttacccgctcac tttcggcggagggaccaaggtggagatcaaacgaactgtggctgcaccatctgtcttcatcttcccgccatctgatgagca gttgaaatctggaactgcctctgttgtgtgcctgctgaataacttctatcccagagaggccaaagtacagtggaaggtggat aacgccctccaatcgggtaactcccaggagagtgtcacagagcaggacagcaaggacagcacctacagcctcagcag caccctgacgctgagcaaagcagactacgagaaacacaaagtctacgcctgcgaagtcacccatcagggcctgagctc gcccgtcacaaagagcttcaacaggggagagtgttga// was generated, encoding the amino acid sequence for N-terminus VH21 SP-ShK[1-35, Q16K]-L10-aKLH120.6 Light Chain (LC) with an N-terminal signal peptide:

(SEQ ID NO: 75)
mewswvflfflsvttgvhsrscidtipksrctafkckhsmkyrlsfcrktcgtcggggsggggsdiqmt qspsslsasvgdrvtitcrasqgirndlgwyqqkpgkapkrliyaasslqsgvpsrfsgsgsgteftltisslqpedfatyy clqhnsypltfgggtkveikrtvaapsvfifppsdeqlksgtasvvcllnnfypreakvqwkvdnalqsgnsqesvte qdskdstyslsstltlskadyekhkvyacevthqglsspvtksfnrgec//.

Both PCR fragments (DNA fragment containing the coding sequence (SEQ ID NO:64) and aKLH 120.6 Light Chain LC fragment containing the coding sequence (SEQ ID NO:74) were run out on a gel, and the appropriate sized band was punched for an agarose plug. The agarose plugs were placed in a single new PCR reaction, and the fragments were sewn together using outer most primers (SEQ ID NO:62) and (SEQ ID NO:73). The resulting PCR fragment was cut using XbaI and NotI and cleaned with Qiagen PCR Cleanup Kit.

At the same time, pTT14 vector (an Amgen vector containing a CMV promoter, Poly A tail and a Puromycin resistance gene) was also cut by XbaI and NotI and gel purified. The purified insert was ligated to the large vector fragment and transformed into OneShot Top10 bacteria. DNAs from transformed bacterial colonies were isolated and subjected to XbaI and NotI restriction enzyme digestions and resolved on a one percent agarose gel. DNAs resulting in an expected pattern were submitted for sequencing. The final construct pTT14-N-terminus ShK[1-35Q16K]-L10-aKLH120.6-LC encoding a Signal Peptide-ShK[1-35, Q16K]-L10-aKLH120.6-LC fusion polypeptide sequence (i.e., SEQ ID NO:75).

Example 9

Purifications and Evaluation of Comparator Molecules: Monovalent Fc/Fc-L10-ShK[2-35] Heterodimers and Monovalent or Bivalent Fc/Fc-ShK(1-35 Q16K)(IgG2) Heterodimers and Other Polypeptide Molecules Monovalent or bivalent Fc-L10-ShK[2-35], monovalent or bivalent Fc-L10-ShK[1-35], monovalent or bivalent Fc-L10-ShK(1-35, Q16K), and other ShK-related polypeptide molecules molecules listed in Table 7B (in Example 5 herein), were expressed, isolated and purified by methods described herein. PEGylated and un-PEGylated toxin peptide comparators in Table 7B were prepared synthetically as follows:

Peptide Synthesis.

$N^\alpha$-Fmoc, side-chain protected amino acids and H-Cys(Trt)-2Cl-Trt resin were purchased from Novabiochem, Bachem, or Sigma Aldrich. The following side-chain protection strategy was employed: Asp(OtBu), Arg(Pbf), Cys(Trt), Glu(OtBu), His(Trt), Lys($N^\epsilon$-Boc), Ser(OtBu), Thr(OtBu) and Tyr(OtBu). ShK (RSCIDTIPKSRCTAFQCKHSMKYRLSFCRKTCGTC//SEQ ID NO:378), [Lys16]ShK (RSCIDTIPKSRCTAFKCKHSMKYRLSFCRKTCGTC//SEQ ID NO:76), or other toxin peptide analog amino acid sequences, were synthesized in a stepwise manner on an CS Bio peptide synthesizer by SPPS using DIC/HOBt coupling chemistry at 0.2 mmol equivalent scale using H-Cys(Trt)-2Cl-Trt resin (0.2 mmol, 0.32 mmol/g loading). For each coupling cycle, 1 mmol $N^\alpha$-Fmoc-amino acid was dissolved in 2.5 mL of 0.4 M 1-hydroxybenzotriazole (HOBt) in N,N-dimethylformamide (DMF). To the solution was added 1.0 mL of 1.0 M N,N'-diisopropylcarbodiimide (DIC) in DMF. The solution was agitated with nitrogen bubbling for 15 min to accomplish pre-activation and then added to the resin. The mixture was shaken for 2 h. The resin was filtered and washed three times with DMF, twice with dichloromethane (DCM), and three times with DMF. Fmoc deprotections were carried out by treatment with 20% piperidine in DMF (5 mL, 2×15 min). The first 23 residues were single coupled through repetition of the Fmoc-amino acid coupling and Fmoc removal steps described above. The remaining residues were double coupled by performing the coupling step twice before proceeding with Fmoc-removal.

Following synthesis, the resin was then drained, and washed sequentially with DCM, DMF, DCM, and then dried in vacuo. The peptide-resin was transferred to a 250-mL plastic round bottom flask. The peptide was deprotected and released from the resin by treatment with triisopropylsilane (1.5 mL), 3,6-dioxa-1,8-octane-dithiol (DODT, 1.5 mL), water (1.5 mL), trifluoroacetic acid (TFA, 20 mL), and a stir bar, and the mixture was stirred for 3 h. The mixture was filtered through a 150-mL sintered glass funnel into a 250-mL plastic round bottom flask. The mixture was filtered through a 150-mL sintered glass funnel into a 250-mL plastic round bottom flask, and the filtrate was concentrated in vacuo. The crude peptide was precipitated with the addition of cold diethyl ether, collected by centrifugation, and dried under vacuum.

Peptide Folding.

The dry crude linear peptide (about 600 mg), for example [Lys16]ShK peptide (SEQ ID NO:76) or [Lys16]ShK-Ala (also known as [Lys16, Ala36]-ShK; SEQ ID NO:379) peptide, was dissolved in 16 mL acetic acid, 64 mL water, and 40 mL acetonitrile. The mixture was stirred rapidly for 15 min to complete dissolution. The peptide solution was added to a 2-L plastic bottle that contained 1700 mL of water and a large stir bar. To the thus diluted solution was added 20 mL of concentrated ammonium hydroxide to raise the pH of the solution to 9.5. The pH was adjusted with small amounts of acetic acid or $NH_4OH$ as necessary. The solution was stirred at 80 rpm overnight and monitored by LC-MS. Folding was usually judged to be complete in 24 to 48 h, and the solution was quenched by the addition of acetic acid and TFA (pH=2.5). The aqueous solution was filtered (0.45 μm cellulose membrane).

Reversed-Phase HPLC Purification.

Reversed-phase high-performance liquid chromatography was performed on an analytical (C18, 5 μm, 0.46 cm×25 cm) or a preparative (C18, 10 μm, 2.2 cm×25 cm) column. Chromatographic separations were achieved using linear gradients of buffer B in A (A=0.1% aqueous TFA; B=90% aq. ACN containing 0.09% TFA) typically 5-95% over 35 min at a flow rate of 1 mL/min for analytical analysis and 5-65% over 90 min at 20 mL/min for preparative separations. Analytical and preparative HPLC fractions were characterized by ESMS and photodiode array (PDA) HPLC, combined and lyophilized.

Mass Spectrometry.

Mass spectra were acquired on a single quadrupole mass spectrometer equipped with an Ionspray atmospheric pressure ionization source. Samples (25 μL) were injected into a moving solvent (10 μL/min; 30:50:20 ACN/MeOH containing 0.05% TFA) coupled directly to the ionization source via a fused silica capillary interface (50 μm i.d.). Sample droplets were ionized at a positive potential of 5 kV and entered the analyzer through an interface plate and subsequently through an orifice (100-120 μm diameter) at a potential of 60 V. Full scan mass spectra were acquired over the mass range 400-2200 Da with a scan step size of 0.1 Da. Molecular masses were derived from the observed m/z values.

PEGylation, Purification and Analysis.

Peptide, e.g., [Lys16]ShK (SEQ ID NO:76) or [Lys16]ShK-Ala (SEQ ID NO:379), was selectively PEGylated by reductive alkylation at its N-terminus, using activated linear or branched PEG. Conjugation was performed at 2 mg/ml in 50 mM $NaH_2PO_4$, pH 4.5 reaction buffer containing 20 mM sodium cyanoborohydride and a 2 molar excess of 20 kDa monomethoxy-PEG-aldehyde (NOF, Japan). Conjugation reactions were stirred for approximately 5 hrs at room temperature, and their progress was monitored by RP-HPLC. Completed reactions were quenched by 4-fold dilution with 20 mM NaOAc, pH 4 and chilled to 4° C. The PEG-peptides were then purified chromatographically at 40 C; using SP Sepharose HP columns (GE Healthcare, Piscataway, N.J.) eluted with linear 0-1M NaCl gradients in 20 mM NaOAc, pH 4.0. Eluted peak fractions were analyzed by SDS-PAGE and RP-HPLC and pooling determined by purity >97%. Principle contaminants observed were di-PEGylated toxin peptide analog. Selected pools were concentrated to 2-5 mg/ml by centrifugal filtration against 3 kDa MWCO membranes and dialyzed into 10 mM NaOAc, pH 4 with 5% sorbitol. Dialyzed pools were then sterile filtered through 0.2 micron filters and purity determined to be >97% by SDS-PAGE (data not shown). Reverse-phase HPLC was performed on an Agilent 1100 model HPLC running a Zorbax® 5 μm 300SB-C8 4.6× 50 mm column (Agilent) in 0.1% TFA/$H_2O$ at 1 ml/min and column temperature maintained at 40° C. Samples of PEG-peptide (20 μg) were injected and eluted in a linear 6-60% gradient while monitoring wavelength 215 nm.

Fusion Proteins.

Figure 1B:
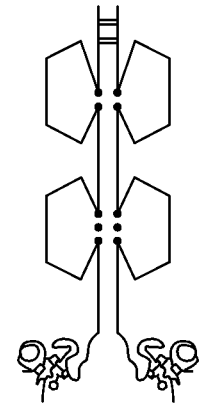
FIG. 1B represents a bivalent homodimeric Fc-toxin peptide analog fusion, with toxin peptide analogs fused to the C-terminal ends of both of the immunoglobulin Fc domain monomers.
Figure 1C:
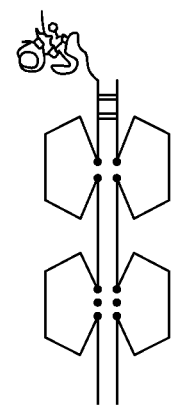
FIG. 1C represents a monovalent heterodimeric toxin peptide analog-Fc fusion with the toxin peptide analog fused to the N-terminal end of one of the immunoglobulin Fc domain monomers.
Figure 1D:
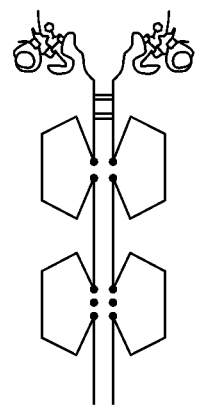
FIG. 1D represents a bivalent homodimeric toxin peptide analog-Fc fusion, with toxin peptide analogs fused to the N-terminal ends of both of the immunoglobulin Fc domain monomers.
Figure 1E:
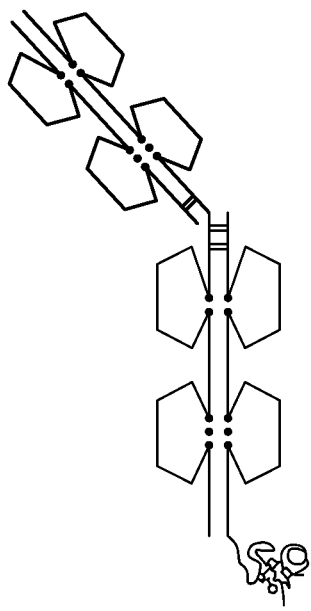
FIG. 1E represents a monovalent heterotrimeric Fc-toxin peptide analog/Ab comprising an immunoglobulin heavy chain (HC)+immunoglobulin light chain (LC)+an immunoglobulin Fc monomer with a toxin peptide analog fused to its C-terminal end.
Figure 1F:
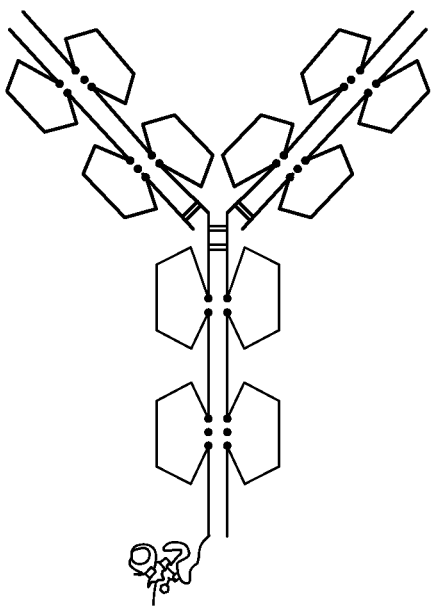
FIG. 1F represents a monovalent heterotetrameric (HT) antibody HC-toxin peptide analog fusion, with a toxin peptide analog fused to the C-terminal end of one of the HC monomers.
Figure 1G:
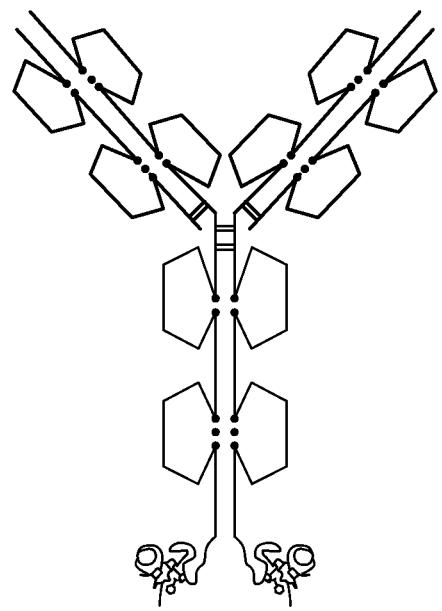
FIG. 1G represents a bivalent HT antibody Ab HC-toxin peptide analog fusion having toxin peptide analogs on the C-terminal ends of both HC monomers.
Figure 1H:
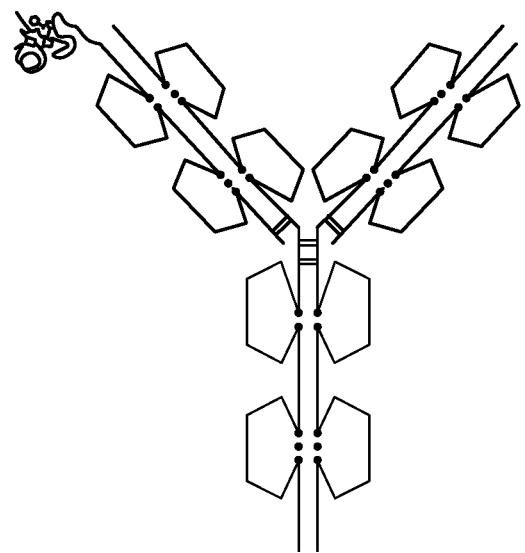
FIG. 1H represents a monovalent HT toxin peptide analog-LC Ab, with the toxin peptide analog fused to the N-terminal end of one of the LC monomers.
Figure 1I:
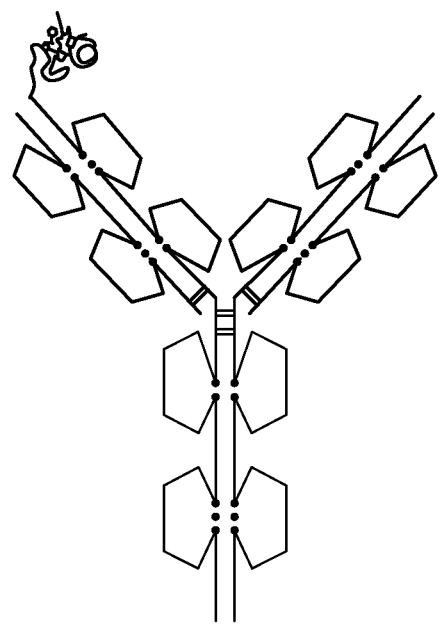
FIG. 1I represents a monovalent HT toxin peptide analog-HC Ab, with the toxin peptide analog fused to the N-terminal end of one of the HC monomers.
Figure 1J:
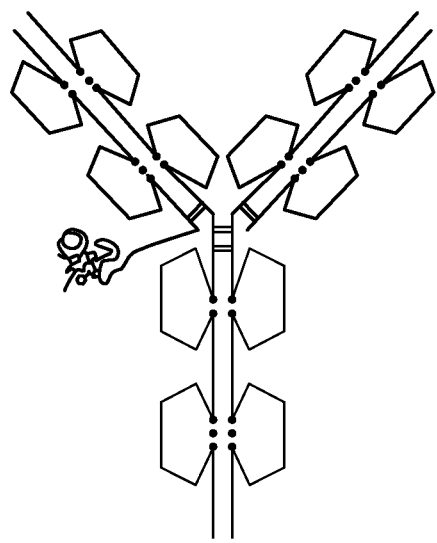
FIG. 1J represents a monovalent HT Ab LC-toxin peptide analog fusion (i.e., LC-toxin peptide analog fusion+LC+2(HC)), with the toxin peptide analog fused to the C-terminal end of one of the LC monomers.
Figure 1K:
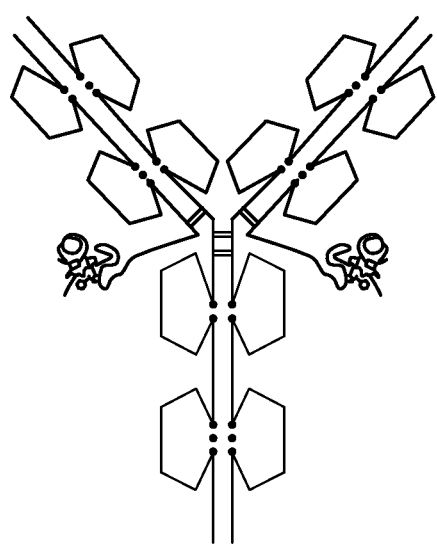
FIG. 1K represents a bivalent HT Ab LC-toxin peptide analog fusion (i.e., 2(LC-toxin peptide analog fusion)+2(HC)), with toxin peptide analogs fused to the C-terminal end of both of the LC monomers.
Figure 1L:
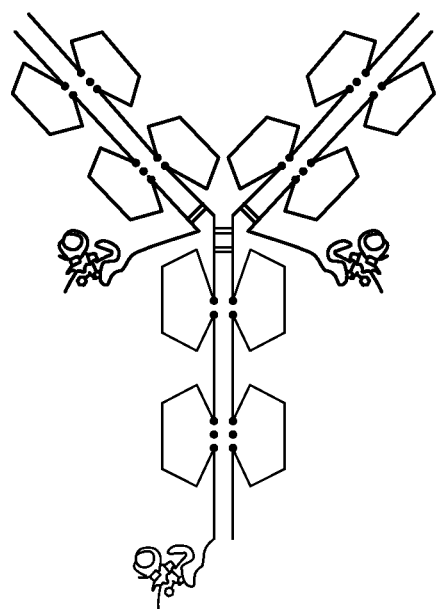
FIG. 1L represents a trivalent HT Ab LC-toxin peptide analog/HC-toxin peptide analog (i.e., 2(LC-toxin peptide analog fusion)+HC-toxin peptide analog fusion+HC), with the toxin peptide analogs fused to the C-terminal ends of both of the LC monomers and one of the HC monomers.
Figure 1M:
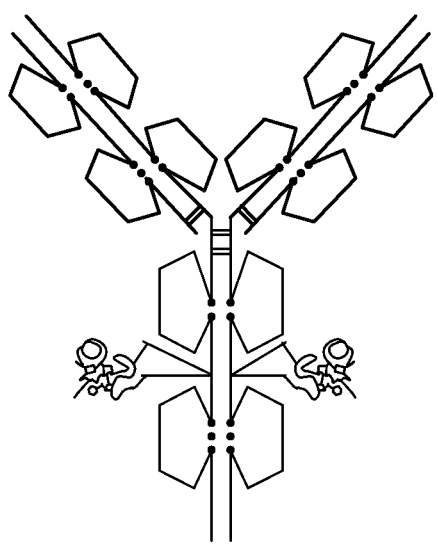
FIG. 1M represents a bivalent antibody with a toxin peptide analog moiety inserted into an internal loop of the immunoglobulin Fc domain of each HC monomer.
Figure 1N:
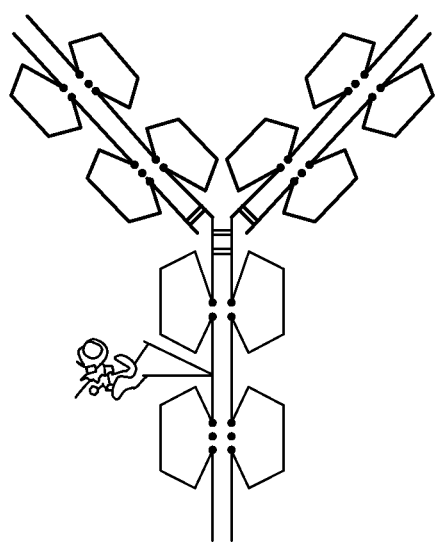

Generally, FIG. 1A and FIG. 1B show a schematic representation of monovalent and bivalent Fc-toxin peptide (or toxin peptide analog) fusion proteins (or "peptibodies"), respectively. The bivalent Fc-ShK molecule is a homodimer containing two Fc-ShK chains. The monovalent Fc-ShK toxin peptide (or toxin peptide analog) molecule is a heterodimer containing one Fc chain and one Fc-ShK (or analog) chain. Since the monovalent Fc-ShK molecule contains just a single ShK peptide per dimer, it is considered monovalent. Constructs or chains referred to as Fc-(toxin peptide analog), contain an N-terminal Fc region and an optional flexible linker sequence (e.g., L10 peptidyl linker GGGGSGGGGS; SEQ ID NO:153) covalently attached to the toxin peptide or toxin peptide analog, such that the orientation from N- to C-terminus would be: Fc-linker-toxin peptide or toxin peptide analog.

In Examples 1 and 2 of Sullivan et al., WO 2008/088422A2, were described the activity of bivalent Fc-ShK peptibodies, Fc-L10-ShK(1-35) and Fc-L10-ShK(2-35) expressed from mammalian cells. In Example 1 of WO 2008/088422A2, was also described isolation of a monovalent Fc-L10-ShK(1-35) molecule, formed as a small by-product during expression. The monovalent antibody #3742-ShK(1-35, Q16K) conjugate provided potent blockade of T cell cytokine secretion in human whole blood (see, Table 7A-B, in Example 5 herein).

Example 10

Pharmacokinetic (PK) Studies in Rats and Cynomolgus Monkeys

Rat PK.

Figure 43:
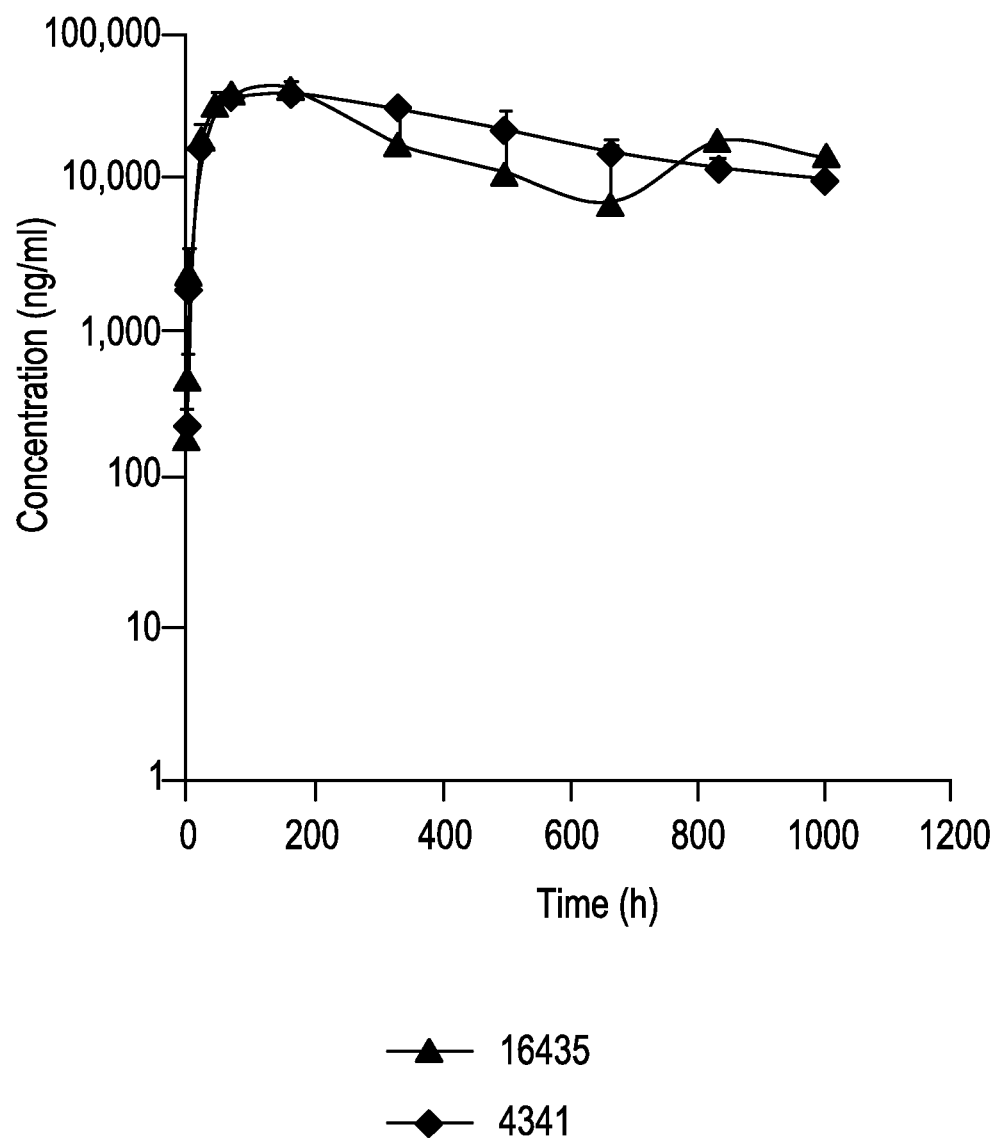
FIG. 43 shows representative PK profiles of antibodies 16435 and 4341 (both at 5 mg/kg dose) in SD rats.

The pharmacokinetic profiles of the 16435 and 4341 antibodies were determined in adult Sprague-Dawley (SD) rats (n=3 per group) by injecting 5 mg/kg subcutaneously and collecting approximately 250 µL of blood in Microtainer® serum separator tubes at 0, 0.25, 1, 4, 24, 48, 72, 168, 336, 504, 672, 840 and 1008 hours post-dose from the lateral tail vein. Each sample was maintained at room temperature following collection, and following a 30-40 minute clotting period, samples were centrifuged at 2-8° C. at 11,500 rpm for about 10 minutes using a calibrated Eppendorf 5417R Centrifuge System (Brinkmann Instruments, Inc., Westbury, N.Y.). The collected serum was then transferred into a pre-labeled (for each rat), cryogenic storage tube and stored at −60° C. to −80° C. for future analysis. To measure the serum sample concentrations from the PK study samples, the following method was used: ½ area black plate (Corning 3694) was coated with 2 µg/ml of anti-hu Fc, antibody 1.35.1 in PBS and then incubated overnight at 4° C. The plate was then washed and blocked with I-Block™ (Applied Biosystems) overnight at 4° C. If samples needed to be diluted, then they were diluted in Rat SD serum. The standards and samples were then diluted 1:20 in 1×PBS+1M NaCl+0.5% Tween 20 and 1% BSA buffer (5% serum). The plate was washed and 50-µl samples of diluted standards and samples were transferred into an antibody 1.35.1 coated plate and incubated for 1.5 h at room temperature. The plate was washed, then 50 µl of 100 ng/ml of anti-hu Fc antibody 21.1-HRP conjugate in I-Block™+5% BSA was added and incubated for 1.5 h. The plate was washed, then 50 µl of Pico substrate were added, after which the plate was immediately analyzed with a luminometer. Time concentration data were analyzed using non-compartmental methods with WinNonLin® (Enterprise version 5.1.1, 2006, Pharsight® Corp. Mountain View, Calif.) (FIG. 34.0). The pharmacokentic profiles of these two antibodies in Sprague-Dawley rat are shown in FIG. 43. The PK parameters of 16435 and 4341 antibodies in SD Rats are summarized in the Table 8 (below). Both molecules have good PK profile in rats with half life of over 10 days.

Cynomolgus PK.

Figure 44:
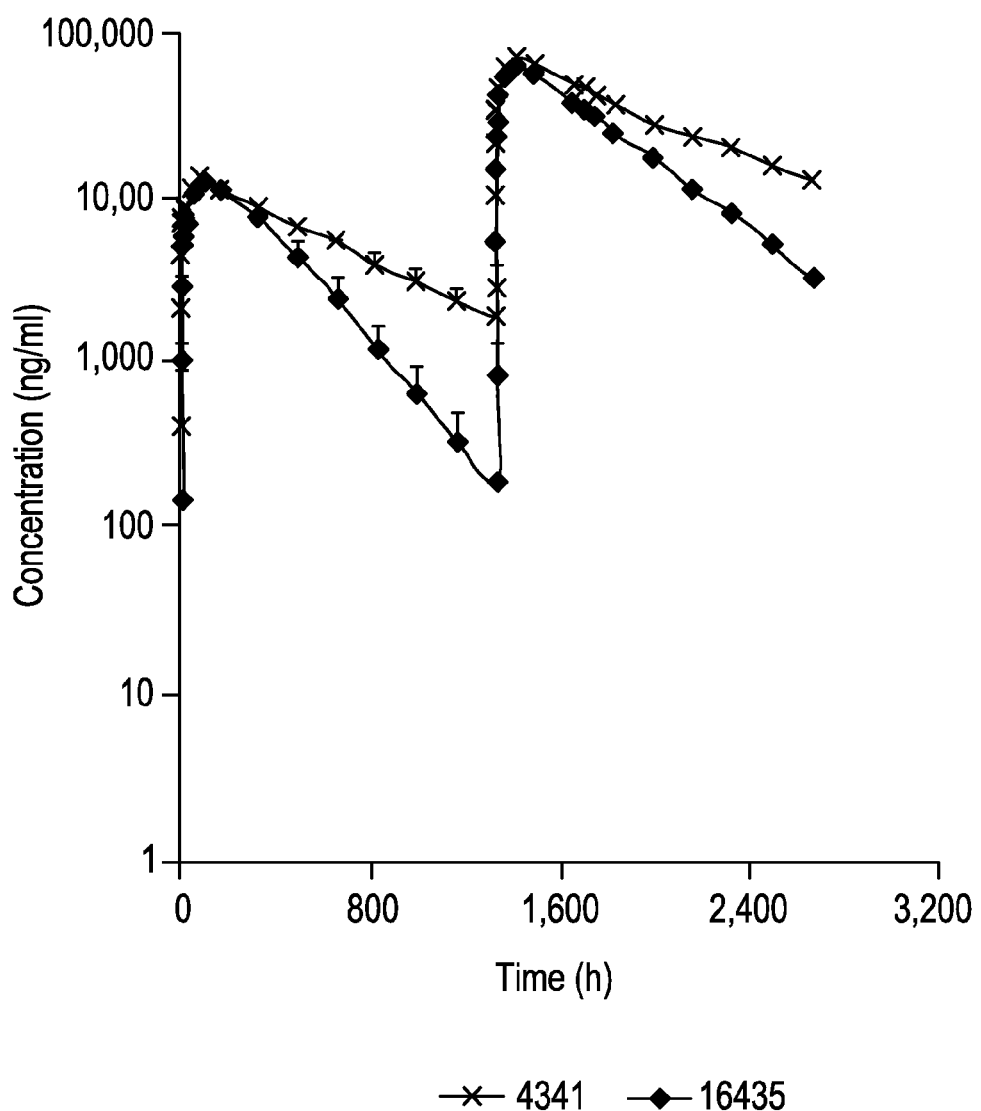
FIG. 44 shows representative PK profiles for sequential doses (5 mg/kg) of antibodies 16435 or 4341 in cynomolgus monkeys.

The pharmacokinetic profiles of the 16435 and 4341 antibodies were also determined in cynomolgus monkeys (n=2 per group) by injecting of two subsequent subcutaneous doses of 1 mg/kg at day 0 and 5 mg/kg at day 57. Serum samples were collected at pre-dose, 0.5, 2, 4, 8, 12, 24, 48, 96, 168, 336, 504, 672, 840, 1008, 1176, 1344 (prior to second dose) hours post $1^{st}$ dose at 1 mg/kg and 0.5, 2, 4, 8, 12, 24, 48, 96, 168, 336, 360, 384, 432, 504, 672, 840, 1008, 1176, 1344 following post $2^{nd}$ dose at 5 mg/kg. The samples were assayed for the 16435 and 4341 antibody levels by using an anti-IgG sandwich ELISA as described above. Time concentration data were analyzed using non-compartmental methods with WinNonLin®. The pharmacokentic profiles of these two antibodies in cynomolgus monkey are shown in FIG. 44. The PK parameters of 16435 and 4341 antibodies in cynomolgus monkeys are summarized in the Table 9 (below). Both molecules exhibited a good PK profile in cynos, with half life of about 12 and 21 days for 16435 and 4341, respectively. The 4341 antibody has better PK attributes than 16435 and has shown normal hu IgG clearance in monkey based on FcRn binding and in the absence of any target mediated drug disposition (TMDD) clearance mechanism. In addition, the results in FIG. 44 show that even with multiple dosing in the cynos, both antibodies 16435 and 4341 had no indication of a signficant change in the clearance mediated by an immune response in the cynos. If there had been a significant immune response causing abnormal antibody clearance, it would have been expected after the second dose, due to immune system priming by the first dose.

TABLE 9

PK parameters of antibodies 16435 and 4341 in cynomolgus monkeys.

| Compound | SC Dose (mg/kg) | $T_{1/2}$ (h) | Tmax (h) | Cmax (ng/mL) | MRT (h) | CL/F (mL/h/kg) | $AUC_{0-t}$ (ng · h/mL) | $AUC_{0-inf}$ (ng · h/mL) |
|---|---|---|---|---|---|---|---|---|
| 16435 | 5 | 285 | 96 | 58,682 | 450 | 0.161 | 29,924,604 | 31,230,285 |
| 4341 | 5 | 502 | 96 | 68,166 | 740 | 0.096 | 43,578,088 | 51,909,826 |

ABBREVIATIONS

Abbreviations used throughout this specification are as defined below, unless otherwise defined in specific circumstances.

Ac acetyl (used to refer to acetylated residues)
AcBpa acetylated p-benzoyl-L-phenylalanine
ACN acetonitrile
AcOH acetic acid
ADCC antibody-dependent cellular cytotoxicity
Aib aminoisobutyric acid
bA beta-alanine
Bpa p-benzoyl-L-phenylalanine
BrAc bromoacetyl ($BrCH_2C(O)$)
BSA Bovine serum albumin

TABLE 8

PK parameters of antibodies 16435 and 4341 in SD Rats.

| Compound | SC Dose (mg/kg) | $T_{1/2}$ (h) | Tmax (h) | Cmax (ng/mL) | MRT (h) | CL/F (mL/h/kg) | $AUC_{0-t}$ (ng · h/mL) | $AUC_{0-inf}$ (ng · h/mL) |
|---|---|---|---|---|---|---|---|---|
| 16435 | 5 | 226 | 104 | 44,080 | 395 | 0.368 | 16,038,601 | 20,048,353 |
| 4341 | 5 | 365 | 136 | 38,963 | 580 | 0.190 | 22,280,335 | 26,661,802 |

Bzl Benzyl
Cap Caproic acid
CBC complete blood count
COPD Chronic obstructive pulmonary disease
CTL Cytotoxic T lymphocytes
DCC Dicylcohexylcarbodiimide
Dde 1-(4,4-dimethyl-2,6-dioxo-cyclohexylidene)ethyl
DNP 2,4-dinitrophenol
DOPC 1,2-Dioleoyl-sn-Glycero-3-phosphocholine
DOPE 1,2-Dioleoyl-sn-Glycero-3-phosphoethanolamine
DPPC 1,2-Dipalmitoyl-sn-Glycero-3-phosphocholine
DSPC 1,2-Distearoyl-sn-Glycero-3-phosphocholine
DTT Dithiothreitol
EAE experimental autoimmune encephalomyelitis
ECL enhanced chemiluminescence
ESI-MS Electron spray ionization mass spectrometry
FACS fluorescence-activated cell sorting
Fmoc fluorenylmethoxycarbonyl
GHT glycine, hypoxanthine, thymidine
HOBt 1-Hydroxybenzotriazole
HPLC high performance liquid chromatography
HSL homoserine lactone
IB inclusion bodies
KCa calcium-activated potassium channel (including IKCa, BKCa, SKCa)
KLH Keyhole Limpet Hemocyanin
Kv voltage-gated potassium channel
Lau Laurie acid
LPS lipopolysaccharide
LYMPH lymphocytes
MALDI-MS Matrix-assisted laser desorption ionization mass spectrometry
Me methyl
MeO methoxy
MeOH methanol
MHC major histocompatibility complex
MMP matrix metalloproteinase
MW Molecular Weight
MWCO Molecular Weight Cut Off
1-Nap 1-napthylalanine
NEUT neutrophils
Nle norleucine
NMP N-methyl-2-pyrrolidinone
OAc acetate
PAGE polyacrylamide gel electrophoresis
PBMC peripheral blood mononuclear cell
PBS Phosphate-buffered saline
Pbf 2,2,4,6,7-pendamethyldihydrobenzofuran-5-sulfonyl
PCR polymerase chain reaction
PD pharmacodynamic
Pec pipecolic acid
PEG Poly(ethylene glycol)
pGlu pyroglutamic acid
Pic picolinic acid
PK pharmacokinetic
pY phosphotyrosine
RBS ribosome binding site
RT room temperature (about 25° C.)
Sar sarcosine
SDS sodium dodecyl sulfate
STK serine-threonine kinases
t-Boc tert-Butoxycarbonyl
tBu tert-Butyl
TCR T cell receptor
TFA trifluoroacetic acid
THF thymic humoral factor
Trt trityl

What is claimed is:

1. An isolated immunoglobulin, comprising an immunoglobulin heavy chain variable region and an immunoglobulin light chain variable region, wherein:
the heavy chain variable region comprises the amino acid sequence of SEQ ID NO:323 and the light chain variable region comprises the amino acid sequence of SEQ ID NO:188.

2. The isolated immunoglobulin of claim 1, wherein the isolated immunoglobulin comprises an antibody or antibody fragment.

3. The isolated immunoglobulin of claim 2, comprising an IgG1, IgG2, IgG3 or IgG4.

4. The isolated immunoglobulin of claim 2, comprising a monoclonal antibody.

5. The isolated immunoglobulin of claim 4, comprising a human antibody.

6. The isolated immunoglobulin of claim 5, comprising:
an immunoglobulin heavy chain comprising the amino acid sequence of SEQ ID NO:113, or comprising the foregoing sequence from which one, two, three, four or five amino acid residues are lacking from the N-terminal or C-terminal, or both; and an immunoglobulin light chain comprising the amino acid sequence of SEQ ID NO:110, or comprising the foregoing sequence from which one, two, three, four or five amino acid residues are lacking from the N-terminal or C-terminal, or both.

7. The isolated immunoglobulin of claim 1, further comprising at least one pharmacologically active chemical moieties conjugated thereto.

8. The isolated immunoglobulin of claim 7, wherein the pharmacologically active chemical moiety is a pharmacologically active polypeptide.

9. The isolated immunoglobulin of claim 8, wherein the immunoglobulin is recombinantly produced.

10. The isolated immunoglobulin of claim 9, wherein the immunoglobulin comprises at least one immunoglobulin heavy chain and at least one immunoglobulin light chain, and wherein the pharmacologically active polypeptide is inserted in the primary amino acid sequence of the of the immunoglobulin heavy chain within an internal loop of the Fc domain of the immunoglobulin heavy chain.

11. The isolated immunoglobulin of claim 8, wherein the immunoglobulin comprises at least one immunoglobulin heavy chain and at least one immunoglobulin light chain, and wherein the pharmacologically active polypeptide is conjugated at the N-terminal or C-terminal of the immunoglobulin heavy chain.

12. The isolated immunoglobulin of claim 8, wherein the immunoglobulin comprises at least one immunoglobulin heavy chain and at least one immunoglobulin light chain, and wherein the pharmacologically active polypeptide is conjugated at the N-terminal or C-terminal of the immunoglobulin light chain.

13. The isolated immunoglobulin of claim 8, wherein the pharmacologically active polypeptide is a toxin peptide, an IL-6 binding peptide, a calcitonin gene related peptide (CGRP) peptide antagonist, a bradykinin B1 receptor peptide antagonist, a parathyroid hormone (PTH) agonist peptide, a PTH antagonist peptide, an angiopoietin-1 (ang-1) binding peptide, an angiopoietin-2 (ang-2) binding peptide, a myostatin binding peptide, an erythropoietin (EPO)-mimetic peptide, a fibroblast growth factor 21 (FGF21) peptide, a thombopoietin (TPO)-mimetic peptide, a nerve growth factor (NGF) binding peptide, a B-cell activating factor (BAFF) antagonist peptide, a glucagon-like peptide-1 (GLP-1) or peptide mimetic thereof, or a glucagon-like peptide-2 (GLP-2) or peptide mimetic thereof.

14. The isolated immunoglobulin of claim 13, wherein the toxin peptide is stichodactyla toxin (ShK) or a ShK peptide analog.

15. A pharmaceutical composition comprising the immunoglobulin of claim 1; and a pharmaceutically acceptable diluent, excipient or carrier.

16. The immunoglobulin of claim 1, wherein the immunoglobulin at 30 micromolar concentration does not significantly bind soluble human IL-17R (SEQ ID NO:89) at 30 nanomolar concentration in an aqueous solution incubated under physiological conditions, as measured by a surface plasmon resonance binding assay.

* * * * *